US009944913B2

(12) United States Patent
Aehle et al.

(10) Patent No.: US 9,944,913 B2
(45) Date of Patent: *Apr. 17, 2018

(54) GLUCOAMYLASE VARIANTS WITH ALTERED PROPERTIES

(71) Applicant: Danisco US Inc., Palo Alto, CA (US)

(72) Inventors: Wolfgang Aehle, Zwingenberg (DE); Piet Van Solingen, Naaldwijk (NL); Martijn Scheffers, Leiden (NL); Richard Bott, Burlingame, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/230,036

(22) Filed: Aug. 5, 2016

(65) Prior Publication Data

US 2017/0114336 A1 Apr. 27, 2017

Related U.S. Application Data

(62) Division of application No. 12/443,255, filed as application No. PCT/US2007/021683 on Oct. 9, 2007, now Pat. No. 9,447,397.

(60) Provisional application No. 60/850,431, filed on Oct. 10, 2006.

(51) Int. Cl.
| C12N 9/34 | (2006.01) |
| C12N 15/00 | (2006.01) |
| C07H 21/04 | (2006.01) |
| C12N 15/09 | (2006.01) |

(52) U.S. Cl.
CPC .... C12N 9/2428 (2013.01); C12Y 302/01003 (2013.01); C12N 15/09 (2013.01)

(58) Field of Classification Search
None
See application file for complete search history.

(56) References Cited

U.S. PATENT DOCUMENTS

| 4,247,637 A | 1/1981 | Tamura et al. |
| 4,514,496 A | 4/1985 | Yoshizumi et al. |
| RE32,153 E | 5/1986 | Tamura et al. |
| 4,618,579 A | 10/1986 | Dwiggins et al. |
| 4,794,175 A | 12/1988 | Nunberg et al. |
| 4,863,864 A | 9/1989 | Ashikari et al. |
| 5,024,941 A | 6/1991 | Maine |
| 5,246,853 A | 9/1993 | Clarkson et al. |
| 5,475,101 A | 12/1995 | Ward et al. |
| 5,874,276 A | 2/1999 | Fowler et al. |
| 6,022,725 A | 2/2000 | Fowler et al. |
| 6,254,914 B1 | 7/2001 | Singvay et al. |
| 6,255,084 B1 | 7/2001 | Nielsen et al. |
| 6,268,328 B1 | 7/2001 | Mitchinson et al. |
| 6,352,851 B1 | 3/2002 | Nielsen et al. |
| 6,537,792 B1 | 3/2003 | Allen et al. |
| 6,582,914 B1 | 6/2003 | Caldwell |
| 6,620,924 B2 | 9/2003 | Nielsen et al. |
| 6,777,589 B1 | 8/2004 | Lundquist et al. |
| 6,803,499 B1 | 10/2004 | Anderson et al. |
| 6,899,910 B2 | 5/2005 | Johnston et al. |
| 7,037,704 B2 | 5/2006 | Dunn-Coleman et al. |
| 7,494,685 B2 | 2/2009 | Dunn-Coleman et al. |
| 8,058,033 B2 | 11/2011 | Aehle et al. |
| 2006/0015342 A1 | 1/2006 | Kurzweil et al. |
| 2006/0094080 A1 | 5/2006 | Dunn-Coleman et al. |

FOREIGN PATENT DOCUMENTS

| EP | 0215594 | 3/1987 |
| EP | 0238023 | 9/1987 |
| EP | 0244234 | 11/1987 |
| WO | WO1988/09795 | 12/1988 |
| WO | WO1992/06184 | 4/1992 |
| WO | WO1992/06209 | 4/1992 |
| WO | WO1996/00787 | 1/1996 |
| WO | WO2000/04136 | 1/2000 |
| WO | WO2002/14490 | 2/2002 |
| WO | WO2002/46429 | 6/2002 |
| WO | WO2003/049550 | 6/2003 |
| WO | WO2004/080923 | 9/2004 |
| WO | WO2004/081193 | 9/2004 |
| WO | WO2005/001036 | 1/2005 |
| WO | WO2005/052148 | 6/2005 |
| WO | WO2005/117756 | 12/2005 |
| WO | WO2006/043178 | 4/2006 |
| WO | WO2006/060062 | 6/2006 |

OTHER PUBLICATIONS

Aleshin, et al., "Refined crystal structures of glucoamylase from *Aspergillus awamori* var. X100," *J Mol Biol*, 238: 575-591, 1994.
Aleshin, et al., "Crystal Structure of Glucoamylase from *Aspergillus awamori* var. X100 to 2.2-A Resolution," *J. of Biological Chem.*, V. 267:27, pp. 19291-19298, 1992.
Altschul et al., [27] Local Alignment Statistics, *Meth. Enzymol.*, 266:460-480, 1993.
Altschul, Stephen F. et al., "Basic Local Alignment Search Tool," *J. Mol. Biol.*, 215:403-410, 1990.
Anagnostopoulos, C. et al., "Requirements for Transformation in *Bacillus Subtilis*," *J. Bacteriol.*, 81:741-746, 1961.
Ashikari et al., "Direct fermentation of raw corn to ethanol by yeast transformants containing a modified *Rhizopus* glucoamylase gene," *Appl. Microbiol. Biotechnol.*, (1989) 32:129-133.
Ashikari, et al., "*Rhizopus* Raw-Starch-Degrading Glucoamylase: Its Cloning and Expression in Yeast," *Agric. Biol. Chem.*, vol. 50, No. 4, pp. 957-964, 1986.
Ausubel et al., *Current Protocols in Molecular Biology*, V: 2 (1987), supra, chapter 9, pp. 9.01-9.17.3, suppl. 45.

(Continued)

*Primary Examiner* — Yong Pak

(57) ABSTRACT

The present invention relates to variants of a parent glucoamylase having altered properties (e.g., improved thermostability and/or specific activity). In particular, the present invention provides compositions comprising the variant glucoamylases, including starch hydrolyzing compositions, animal feed compositions and cleaning compositions. The invention also relates to DNA constructs encoding the variants and methods of producing the glucoamylase variants in host cells.

5 Claims, 12 Drawing Sheets

(56) References Cited

OTHER PUBLICATIONS

Bajar, Aslam, et al., "Identification of a fungal cutinase promoter that is inducible by a plant signal via a phosphorylated trans-acting factor," *Proc. Natl. Acad. Sci. USA*, vol. 88, pp. 8208-8212, Sep. 1991.

Bennett and Lasure, More Gene Manipulations in Fungi, Academic Press, San Diego, pp. 70-76. Timberlake, "Cloning and Analysis of Fungi Genes," Chapter 3, (1991).

Bergés, T. et al., "Isolation of uridine auxotrophs from Trichoderma reesei and efficient transformation with the cloned ura3 and ura5 genes," *Curr. Genet.*, vol. 19, No. 5, pp. 359-365, 1991.

Berka, et al., "*Aspergillus niger* var. *awamori* as a Host for the Expression of Heterologous Genes," Kelly and Baldwin (eds.) *Applications of Enzyme Biotechnology*, New York: Plenum Press, 1991, pp. 273-292.

Boel, et al., "Glucoamylases G1 and G2 from *Aspergillus niger* are synthesized from two different but closely related mRNAs," *The EMBO Journal*, vol. 3, No. 5, pp. 1097-1102, 1984.

Boel, E. et al., "Two different types of intervening sequences in the glucoamylase gene from *Aspergillus niger*," *The EMBO Journal*, vol. 3, No. 7, pp. 1581-1585, 1984.

Campbell, et al., "Improved transformation efficiency of *Aspergillus niger* using the homologous niaD gene for nitrate reductase," *Current Genetics*, 16:53-56, 1989.

Cao, et al., "Penicillopepsin-JT2, a recombinant enzyme from *Penicillium janthinellum* and the contribution of a hydrogen bond in subsite $S_3$ to $k_{cat}$," *Protein Science*, vol. 9, pp. 991-1001, 2000.

Chen, et al., "Effect of replacing helical glycine residues with alanines on reversible and irreversible stability and production of Aspergillus awamori glucoamylase," *Protein Engineering*, vol. 9, No. 6, pp. 499-505, 1996.

Chen, et al., "Identification and elimination by site-directed mutagenesis of thermolabile aspartyl bonds in *Aspergillus awamori* glucoamylase," *Protein Engineering*, vol. 8, No. 6, pp. 575-582, 1995.

Coutinho et al., "Structural similarities in glucoamylases by hydrophobic cluster analysis," *Protein Eng.*, 7: 749-760, 1994.

Coutinho et al., "Structure—function relationships in the catalytic and starch binding domains of glucoamylase," *Protein Eng.*, 7:393-400, 1994.

Database EMBL [Online] Feb. 2, 2001 (Feb. 2, 2001), "Talaromyces emersonii ga gene for glucoamylase, exons 1-5" XP002495030 retrieved from EBI accession No. EMBL:AJ304803 Database accession No. AJ304803.

de Groot, et al., "*Agrobacterium tumefaciens*-mediated transformation of filamentous fungi," *Nature Biotechnology*, vol. 16, 1998, pp. 839-842.

Devereux et al., "A Comprehensive set of sequence analysis programs for the VAX," *Nucl. Acids Res.*, vol. 12, p. 387-395, 1984.

Elder et al., "Glucoamylase activity in industrial enzyme preparations using colorimetric enzymatic method," *Journal of AOAC International*, vol. 78(2), pp. 398-401, 1995.

Emsley, P., et al., "Coot: model-building tools for molecular graphics." Acta Crystallogr D Biol Crystallogr 60:2126-2132, 2004.

Fagerstrom, R., et al., "Characterization, Subsite Mapping and Partial Amino Acid Sequence of Glucoamylase from the Filamentous Fungus Trichoderma reesei." Biotechnol. Appl. Biochem. 21(2):223-231, 1995.

Feng et al., "Progressive Sequence Alignment as a Prerequisite to Correct Phylogenetic Tress," *J. Mol Evol.* vol. 25, pp. 351-360, 1987.

Fierobe, et al. "Mutational Modulation of Substrate Bond-Type Specificity and Thermostability of Glucoamylase from Aspergillus awamori by Replacement with Short Homologue Active Site Sequences and Thiol/Disulfide Engineering." *Biochemistry* 35(26): 8696-8704, Jan. 1, 1996.

Finkelstein et al., chapter 6 in Biotechnology of Filamentous Fungi, Finkelstein et al. Eds. Butterworth-Heinemann, Boston, MA (1992).

Fromm et al., "Inheritance and Expression of Chimeric Genes in the Progency of Transcgenic Maize Plants," *Biotechnology*, V. 8 pp. 833-839, Sep. 1990.

Goedegebuur, et al., "Cloning and relational analysis of 15 novel fungal endoglucanases from family 12 glycosyl hydrolase," *Current Genetics*, vol. 41, pp. 89-98, 2002.

Goto, et al., "The Mechanism of Binding of Glucoamylase I from *Aspergillus awamori* var. *kawachi* to Cyclodextrins and Raw Starch," *Biosci. Biotech. Biochem.*, vol. 58, No. 1, pp. 49-54, 1994.

Harkki, et al., "A Novel Fungal Expression System : Secretion of Active Calf Chymosin from the Filamentous Fungus *Trichoderma Reesei*," *Bio/Technology*, vol. 7, pp. 596-603, Jun. 1989.

Harkki, et al., "Genetic engineering of *Trichoderma* to produce strains with novel cellulase profiles," *Enzyme Microb. Technol.*, vol. 13, pp. 227-233, Mar. 1991.

Hayashida, et al., "Molecular Cloning of the Glucoamylase I Gene of *Aspergillus awamori* var. *kawachi* for Localization of the Raw-starch-affinity Site," *Agric. Biol. Chem.*, vol. 53, No. 4, pp. 923-929, 1989.

Higgins et al., "Fast and sensitive multiple sequence alignments on microcomputer," *CABIOS*, vol. 5, 1989, p. 151-153.

Houghton-Larsen et al., "Cloning and characterisation of a glucoamylase gene (GlaM) from the dimorphic zygomycete Mucor circinelloides," *Appl. Microbiol. Biotechnol.*, 2003, v. 62, pp. 210-217.

Ilmen, Marja, et al., "Regulation of Cellulase Gene Expression in the Filamentous Fungus *Trichoderma reesei*," *Appl. and Envir. Micro.*, vol. 63, No. 4, pp. 1298-1306, Apr. 1997.

Innis, M. A. et al., "Expression, Glycosylation, and Secretion of an *Aspergillus* Glucoamylase by *Saccharomyces cerevisiae*," *Science*, vol. 228, pp. 21-26, 1985.

International Preliminary Report on Patentability for International Application No. PCT/US2007/021683 dated Apr. 15, 2009.

International Search Report and the Written Opinion of the International Searching Authority for International Application No. PCT/US2007/021683 dated Aug. 22, 2008.

Karlin, et al., "Applications and statistics for multiple high-scoring segments in molecular sequences," *Proc. Natl. Acad. Sci. USA*, 90:5873-5877, 1993.

Kelly, et al., "Transformation of *Aspergillus niger* by the amdS gene of *Aspergillus nidulans*," *The EMBO Journal*, vol. 4, No. 2, pp. 475-479, 1985.

Li, et al. "Effect of introducing proline residues on the stability of Aspergillus awamori." *Protein Eng.* 10(10): 1199-1204, Oct. 1, 1997.

Matthews, B. W., "Solvent Content of Protein Crystals," *J Mol Biol*, 33:491-497, 1968.

Minshull J. et al., "Engineering protein function by selective amino acid diversification," (2004) *Methods*, 32(4):416-427.

Murshudov, G.N., et al. "Refinement of Macromolecular Structures by the Maximum-Likelihood Method." Acta Crystallogr. D53: 240-255, 1997.

Needleman, Saul B., "A General Method Applicable to the Search for Similarities in the Amino Acid Sequence of Two Proteins," *J. Mol. Biol.*, 48:443-453, 1970.

Nevalainen et al., "*The Molecular Biology of Trichoderma and its Application to the Expression of Both Homologous and Heterologous Genes*", Molecular Industrial Mycology, Eds. Leong and Berka, Marcel Dekker Inc., NY (1992) pp. 129-148.

Nielsen, B.R., et al., "Cloning, heterologous expression, and enzymatic characterization of a thermostable glucoamylase from Talaromyces emersonii." Protein Expression and Purification 26(1): 1-8, 2002.

Nunberg, et al., "Molecular Cloning and Characterization of the Glucoamylase Gene of *Aspergillus awamori*," *Molecular and Cellular Biology*, pp. 2306-2315, Nov. 1984.

Pearson, et al., "Improved tools for biological sequence comparison," *Proc. Natl. Acad. Sci. USA*, vol. 85, pp. 2444-2448, Apr. 1988.

Pentillä et al., "A versatile transformation system for the cellulolytic filamentous fungus *Trichoderma reesei*," *Gene*, vol. 61, pp. 155-164, 1987.

(56) References Cited

OTHER PUBLICATIONS

Potrykus et al., "Molecular and general genetics of a hybrid foreign gene introduced into tobacco by direct gene transfer," *Mol. Gen. Genet.*, V. 199 :169-177 (1985).

Pourquie, et al., "Scale Up of Cellulase Production and Utilization," Biochemistry and Genetics of Cellulose Degradation, *Academic Press Ltd.*, pp. 71-86, 1988.

Punt et al., "Transformation of *Asperghillus* based on the hygromycin B resistance marker from *Escherichia coli,*" *Gene* 56:117-124, 1987.

Reilly, P.J., et al. "Protein engineering of glucoamylase to improve industrial performance a review." Starch/Stärke, 51 (8-9): 269-274, 1991.

Sauer, J., et al., "Glucoamylase: Structure/function relationships, and protein engineering." Biochimica et Biophysica Acta 1543(2): 275-293, 2000.

Sheir-Neiss, et al., "Characterization of the secreted cellulases of *Trichoderma reesei* wild type and mutants during controlled fermentations," *Appl. Microbiol. Biotechnol.*, vol. 20, pp. 46-53, 1984.

Smith, et al., "Comparison of Biosequences," *Advances in Applied Mathematics,* vol. 2, pp. 482-489, 1981.

Svensson et al., "Amino Acid Sequence Studies of a Novel Subtilisin," *Carlsberg Res. Commun.*, 48:583-591, 1983.

Van den Hondel et al., "Heterologous Gene Expression in Filamentous Fungi," *More Gene Manipulations in Fungi,* Chapter 18, pp. 396-428, 1991, Academic Press, Inc.

van Hartingsveldt, et al., "Development of a homologous transformation system for *Aspergillus niger* based on the pyrG gene," *Mol. Gen. Genet.*, 206:71-75, 1987.

Ward, et al., "Use of *Aspergillus* overproducing mutants, cured for integrated plasmid, to overproduce heterologous proteins," *Appl. Microbiol. Biotechnol.,* vol. 39, pp. 738-743, 1993.

Yelton, et al, "Transformation of *Aspergillus nidulans* by using a trpC plasmid," *Proc. Natl. Acad. Sci.,* vol. 81, pp. 1470-1474, 1984.

TrGA Parent Protein (632 Amino Acids) (SEQ ID NO: 1)

```
  1 MHVLSTAVLL GSVAVQKVLG RPGSSGLSDV TKRSVDDFIS TETPIALNNL
 51 LCNVGPDGCR AFGTSAGAVI ASPSTIDPDY YYMWTRDSAL VFKNLIDRFT
101 ETYDAGLQRR IEQYITAQVT LQGLSNPSGS LADGSGLGEP KFELTLKPFT
151 GNWGRPQRDG PALRAIALIG YSKWLINNNY QSTVSNVIWP IVRNDLNYVA
201 QYWNQTGFDL WEEVNGSSFF TVANQHRALV EGATLAATLG QSGSAYSSVA
251 PQVLCFLQRF WVSSGGYVDS NINTNEGRTG KDVNSVLTSI HTFDPNLGCD
301 AGTFQPCSDK ALSNLKVVVD SFRSIYGVNK GIPAGAAVAI GRYAEDVYYN
351 GNPWYLATFA AAEQLYDAIY VWKKTGSITV TATSLAFFQE LVPGVTAGTY
401 SSSSSTFTNI INAVSTYADG FLSEAAKYVP ADGSLAEQFD RNSGTPLSAL
451 HLTWSYASFL TATARRAGIV PPSWANSSAS TIPSTCSGAS VVGSYSRPTA
501 TSFPPSQTPK PGVPSGTPYT PLPCATPTSV AVTFHELVST QFGQTVKVAG
551 NAAALGNWST SAAVALDAVN YADNHPLWIG TVNLEAGDVV EYKYINVGQD
601 GSVTWESDPN HTYTVPAVAC VTQVVKEDTW QS
```

FIG. 1A

DNA Coding Sequence of TrGA (1899 bp) (SEQ ID NO: 4)

```
   1 ATGCACGTCC TGTCGACTGC GGTGCTGCTC GGCTCCGTTG CCGTTCAAAA
  51 GGTCCTGGGA AGACCAGGAT CAAGCGGTCT GTCCGACGTC ACCAAGAGGT
 101 CTGTTGACGA CTTCATCAGC ACCGAGACGC CTATTGCACT GAACAATCTT
 151 CTTTGCAATG TTGGTCCTGA TGGATGCCGT GCATTCGGCA CATCAGCTGG
 201 TGCGGTGATT GCATCTCCCA GCACAATTGA CCCGGACTAC TATTACATGT
 251 GGACGCGAGA TAGCGCTCTT GTCTTCAAGA ACCTCATCGA CCGCTTCACC
 301 GAAACGTACG ATGCGGGCCT GCAGCGCCGC ATCGAGCAGT ACATTACTGC
 351 CCAGGTCACT CTCCAGGGCC TCTCTAACCC CTCGGGCTCC CTCGCGGACG
 401 GCTCTGGTCT CGGCGAGCCC AAGTTTGAGT TGACCCTGAA GCCTTTCACC
 451 GGCAACTGGG GTCGACCGCA GCGGGATGGC CCAGCTCTGC GAGCCATTGC
 501 CTTGATTGGA TACTCAAAGT GGCTCATCAA CAACAACTAT CAGTCGACTG
 551 TGTCCAACGT CATCTGGCCT ATTGTGCGCA ACGACCTCAA CTATGTTGCC
 601 CAGTACTGGA ACCAAACCGG CTTTGACCTC TGGGAAGAAG TCAATGGGAG
 651 CTCATTCTTT ACTGTTGCCA ACCAGCACCG AGCACTTGTC GAGGGCGCCA
 701 CTCTTGCTGC CACTCTTGGC CAGTCGGGAA GCGCTTATTC ATCTGTTGCT
 751 CCCCAGGTTT TGTGCTTTCT CCAACGATTC TGGGTGTCGT CTGGTGGATA
 801 CGTCGACTCC AACATCAACA CCAACGAGGG CAGGACTGGC AAGGATGTCA
 851 ACTCCGTCCT GACTTCCATC CACACCTTCG ATCCCAACCT TGGCTGTGAC
 901 GCAGGCACCT TCCAGCCATG CAGTGACAAA GCGCTCTCCA ACCTCAAGGT
 951 TGTTGTCGAC TCCTTCCGCT CCATCTACGG CGTGAACAAG GGCATTCCTG
1001 CCGGTGCTGC CGTCGCCATT GGCCGGTATG CAGAGGATGT GTACTACAAC
1051 GGCAACCCTT GGTATCTTGC TACATTTGCT GCTGCCGAGC AGCTGTACGA
1101 TGCCATCTAC GTCTGGAAGA AGACGGGCTC CATCACGGTG ACCGCCACCT
1151 CCCTGGCCTT CTTCCAGGAG CTTGTTCCTG GCGTGACGGC CGGGACCTAC
1201 TCCAGCAGCT CTTCGACCTT TACCAACATC ATCAACGCCG TCTCGACATA
1251 CGCCGATGGC TTCCTCAGCG AGGCTGCCAA GTACGTCCCC GCCGACGGTT
1301 CGCTGGCCGA GCAGTTTGAC CGCAACAGCG GCACTCCGCT GTCTGCGCTT
1351 CACCTGACGT GGTCGTACGC CTCGTTCTTG ACAGCCACGG CCCGTCGGGC
1401 TGGCATCGTG CCCCCCTCGT GGGCCAACAG CAGCGCTAGC ACGATCCCCT
1451 CGACGTGCTC CGGCGCGTCC GTGGTCGGAT CCTACTCGCG TCCCACCGCC
1501 ACGTCATTCC CTCCGTCGCA GACGCCCAAG CCTGGCGTGC CTTCCGGTAC
1551 TCCCTACACG CCCCTGCCCT GCGCGACCCC AACCTCCGTG GCCGTCACCT
1601 TCCACGAGCT CGTGTCGACA CAGTTTGGCC AGACGGTCAA GGTGGCGGGC
1651 AACGCCGCGG CCCTGGGCAA CTGGAGCACG AGCGCCGCCG TGGCTCTGGA
1701 CGCCGTCAAC TATGCCGATA ACCACCCCCT GTGGATTGGG ACGGTCAACC
1751 TCGAGGCTGG AGACGTCGTG GAGTACAAGT ACATCAATGT GGGCCAAGAT
1801 GGCTCCGTGA CCTGGGAGAG TGATCCCAAC CACACTTACA CGGTTCCTGC
1851 GGTGGCTTGT GTGACGCAGG TTGTCAAGGA GGACACCTGG CAGTCGTAA
```

FIG. 1B

```
AaGA    (1)    -ATLDSWLSNEATVARTAILNNIGADGAWVSGADSGIVVASPSTDNPDYF
AnGA    (1)    -ATLDSWLSNEATVARTAILNNIGADGAWVSGADSGIVVASPSTDNPDYF
AoGA    (1)    QSDLNAFIEAQTPIAKQGYLNNIGADGKLVEGAAAGIVYASPSKSNPDYF
HgGA    (1)    -AAVDTFINTEKPIAWNKLLANIGPNGKAAPGAAAGVVIASPSRTDPPYF
HvGA    (1)    --SVDDFINTQTPIALNNLLCNVGPDGCRAFGTSAGAVIASPSTTDPDYY
TrGA    (1)    --SVDDFISTETPIALNNLLCNVGPDGCRAFGTSAGAVIASPSTIDPDYY
                    *    *   *   *    *   * * ****    * *

AaGA    (50)   YTWTRDSGLVIKTLVDLFRNGDTD-LLSTIENYISSQAIVQGISNPSGDL
AnGA    (50)   YTWTRDSGLVLKTLVDLFRNGDTS-LLSTIENYISAQAIVQGISNPSGDL
AoGA    (51)   YTWTRDAGLTMEEYIEQFIGGDAT-LESTIQNYVDSQANEQAVSNPSGGL
HgGA    (50)   FTWTPDAALVLTGIIESLGHNYNT---------------TLQQVSNPSGTF
HvGA    (49)   YMWTRDSALVFKNIVDRFTQQYDAGLQRRIEQYISAQVTLQGISNPSGSL
TrGA    (49)   YMWTRDSALVFKNLIDRFTETYDAGLQRRIEQYITAQVTLQGLSNPSGSL
                ** *  *                               *   *****

AaGA    (99)   SSGG-LGEPKFNVDETAYTGSWGRPQRDGPALRATAMIGFRQWLLDNGYT
AnGA    (99)   SSGAGLGEPKFNVDETAYTGSWGRPQRDGPALRATAMIGFGQWLLDNGYT
AoGA    (100)  SDGSGLAEPKFYYNISQFTDSWGRPQRDGPALRASALIAYGNSLISSDKQ
HgGA    (86)   ADGSGLGEAKFNVDLTAFTGEWGRPQRDGPPLRAIALIQYAKWLIANGYK
HvGA    (99)   SDGSGLGEPKFELTLSQFTGNWGRPQRDGPALRAIALIGYSKWLINNNYQ
TrGA    (99)   ADGSGLGEPKFELTLKPFTGNWGRPQRDGPALRAIALIGYSKWLINNNYQ
                *  *   *  **       *   ******** ***   *        *

AaGA    (148)  SAATEIVWPLVRNDLSYVAQYWNQTGYDLWEEVNGSSFFTIAVQHRALVE
AnGA    (149)  STATDIVWPLVRNDLSYVAQYWNQTGYDLWEEVNGSSFFTIAVQHRALVE
AoGA    (150)  SVVKANIWPIYQNDLSYVGQYWNQTGFDLWEEVQGSSFFTVAVQHKALVE
HgGA    (136)  STAKSVVWPVVKNDLAYTAQYWNETGFDLWEEVPGSSFFTIASSHRALTE
HvGA    (149)  STVSNIIWPIVRNDLNYVAQYWNQTGFDLWEEVNGSSFFTVANQHRALVE
TrGA    (149)  STVSNVIWPIVRNDLNYVAQYWNQTGFDLWEEVNGSSFFTVANQHRALVE
                *    **   *** *    **** ** ******  ****** *  ** *

AaGA    (198)  GSAFATAVGSSCSWCDSQAPQILCYLQSFWTG--EYILANFDSS--RSGK
AnGA    (199)  GSAFATAVGSSCSWCDSQAPEILCYLQSFWTG--SFILANFDSS--RSGK
AoGA    (200)  GDAFAKALGEECQACS-VAPQILCHLQDFWNG--SAVLSNLPTNG-RSGL
HgGA    (186)  GAYLAAQLDTECPPCTTVAPQVLCFQQAFWNSKGNYVVSTSTAGEYRSGK
HvGA    (199)  GATLAATLGQSGSTYSSVAPQILCFLQRFWVS--GGYIDSNINTNEGRTGK
TrGA    (199)  GATLAATLGQSGSAYSSVAPQVLCFLQRFWVSSGGYVDSNINTNEGRTGK
                *   *          ** ** *  **            *         * *

AaGA    (244)  DTNTLLGSIHTFDPEAGCDDSTFQPCSPRALANHKEVVDSFRSIYTLNDG
AnGA    (245)  DANTLLGSIHTFDPEACDDSTFQPCSPRALANHKEVVDSFRSIYTLNDG
AoGA    (246)  DTNSLLGSIHTFDPAAACDDTTFQPCSSRALSNHKLVVDSFRSVYGINNG
HgGA    (236)  DANSILASIHNFDPEAGCDNLTFQPCSERALANHKAYVDSFRNLYAINKG
HvGA    (248)  DANSLLASIHTFDPSLGCDASTFQPCSDKALSNLKVVVDSFRSIYGVNKG
TrGA    (249)  DVNSVLTSIHTFDPNLGCDAGTFQPCSDKALSNLKVVVDSFRSIYGVNKG
                *  *   * *** ***  **    **  *** *   * *  *****     *    *
```

FIG. 4A

```
AaGA    (294)   LSDSEAVAVGRYPKDSYYNGNPWFLCTLAAAEQLYDALYQWDKQGSLEIT
AnGA    (295)   LSDSEAVAVGRYPEDTYYNGNPWFLCTLAAAEQLYDALYQWDKQGSLEVT
AoGA    (296)   RGAGKAAAVGPYAEDTYQGGNPWYLTTLVAAELLYDALYQWDKQGQVNVT
HgGA    (286)   IAQGKAVAVGRYSEDVYYNGNPWYLANFAAAEQLYDAIYVWNKQGSITVT
HvGA    (298)   IPAGSAVAIGRYPEDVYFNGNPWYLATFAAAEQLYDSVYVWKKTGSITVT
TrGA    (299)   IPAGAAVAIGRYAEDVYYNGNPWYLATFAAAEQLYDAIYVWKKTGSITVT
                  * *     * *   ****  *   *** ***    * * *       *

AaGA    (344)   DVSLDFFQALYSDAATGTYSSSSSTYSSIVDAVKTFADGFVSIVETHAAS
AnGA    (345)   DVSLDFFKALYSDAATGTYSSSSSTYSSIVDAVKTFADGFVSIVETHAAS
AoGA    (346)   ETSLPFFKDLSSNVTTGSYAKSSSAYESLTSAVKTYADGFISVVQEYTPD
HgGA    (336)   SVSLPFFRDLVSSVSTGTYSKSSSTFTNIVNAVKAYADGFIEVAAKYTPS
HvGA    (348)   STSSAFFQELVPGVAAGTYSSSQSTFTSIINAISTYADGFLSEAAKYVPA
TrGA    (349)   ATSLAFFQELVPGVTAGTYSSSSSTFTNIINAVSTYADGFLSEAAKYVPA
                  *  **  *         * *   *    *     ****

AaGA    (394)   NGSLSEQYDKSDGDELSARDLTWSYAALLTANNRRNSVMPPSWGETSAS-
AnGA    (395)   NGSMSEQYDKSDGEQLSARDLTWSYAALLTANNRRNSVVPASWGETSAS-
AoGA    (396)   GGALAEQYSRDQGTPVSASDLTWSYAAFLSAVGRRNGTVPASWGSSTAN-
HgGA    (386)   NGALAEQYDRNTGKPDSAADLTWSYSAFLSAIDRRAGLVPPSWRASVAKS
HvGA    (398)   DGSLAEQFDRNTGTPLSAVHLTWSYASFLTAAARRAGVVPPSWASSGAN-
TrGA    (399)   DGSLAEQFDRNSGTPLSALHLTWSYASFLTATARRAGIVPPSWANSSAS-
                   * **       *   ** *****   *  **    *  **     *

AaGA    (443)   SVPGTC
AnGA    (444)   SVPGTC
AoGA    (445)   AVPSQC
HgGA    (436)   QLPSTC
HvGA    (447)   TVPSSC
TrGA    (448)   TIPSTC
                   *  *
```

*FIG. 4B*

GLUCOAMYLASE VARIANTS WITH ALTERED PROPERTIES

CROSS REFERENCE TO RELATED APPLICATIONS

The present application is a divisional application of U.S. patent application Ser. No. 12/443,255, filed May 25, 2010, now U.S. Pat. No. 9,447,397, which claims priority under 35 U.S.C. § 371 to International Application No. PCT/US2007/021683, filed Oct. 9, 2007, which claims the benefit of U.S. Provisional Application Ser. No. 60/850,431, filed on Oct. 10, 2006, which are hereby incorporated by reference.

FIELD OF THE INVENTION

The present invention relates to variants of a parent glucoamylase having altered properties (e.g., improved thermostability and/or specific activity). In particular, the present invention provides compositions comprising the variant glucoamylases, including starch hydrolyzing compositions, animal feed compositions and cleaning compositions. The invention also relates to DNA constructs encoding the variants and methods of producing the glucoamylase variants in host cells.

BACKGROUND OF THE INVENTION

Glucoamylase enzymes (glucan 1,4-α-glucohydrolases, EC 3.2.1.3) are starch hydrolyzing exo-acting carbohydrases, which catalyze the removal of successive glucose units from the non-reducing ends of starch or related oligo and polysaccharide molecules. Glucoamylases can hydrolyze both the linear and branched glucosidic linkages of starch (e.g., amylose and amylopectin).

Glucoamylases are produced by numerous strains of bacteria, fungi, yeast and plants. Particularly interesting, and commercially important, glucoamylases are fungal enzymes that are extracellularly produced, for example from strains of *Aspergillus* (Svensson et al. (1983) *Carlsberg Res. Commun.* 48:529-544; Boel et al., (1984) *EMBO J.* 3:1097-1102; Hayashida et al., (1989) *Agric. Biol. Chem.* 53:923-929; U.S. Pat. No. 5,024,941; U.S. Pat. No. 4,794,175 and WO 88/09795); *Talaromyces* (U.S. Pat. No. 4,247,637; U.S. Pat. No. 6,255,084 and U.S. Pat. No. 6,620,924); *Rhizopus* (Ashikari et al., (1986) *Agric. Biol. Chem.* 50:957-964; Ashikari et al., (1989) *App. Microbiol. and Biotech.* 32:129-133 and U.S. Pat. No. 4,863,864); *Humicola* (WO 05/052148 and U.S. Pat. No. 4,618,579) and *Mucor* (Houghton-Larsen et al., (2003) *Appl. Microbiol. Biotechnol.* 62:210-217). Many of the genes that code for these enzymes have been cloned and expressed in yeast, fungal and/or bacterial cells.

Commercially, glucoamylases are very important enzymes and have been used in a wide variety of applications that require the hydrolysis of starch (e.g. for producing glucose and other monosaccharides from starch). Glucoamylases are used to produce high fructose corn sweeteners, which comprise over 50% of the sweetener market in the United States. In general, glucoamylases may be, and commonly are, used with alpha amylases in starch hydrolyzing processes to hydrolyze starch to dextrins and then glucose. The glucose may then be converted to fructose by other enzymes (e.g. glucose isomerases); crystallized; or used in fermentations to produce numerous end products (e.g., ethanol, citric acid, lactic acid, succinate, ascorbic acid intermediates, glutamic acid, glycerol and 1, 3 propanediol). Ethanol produced by using glucoamylases in the fermentation of starch and/or cellulose containing material may be used as a source of fuel or for alcoholic consumption.

Although glucoamylases have been used successfully in commercial applications for many years, a need still exists for new glucoamylases with altered properties, such as improved specific activity and increased thermostability.

While different mutations have been made in glucoamylases of *Aspergillus*, which enhance thermal stability and specific activity and reference is made to U.S. Pat. No. 6,537,792; U.S. Pat. No. 6,352,851; Chen et al. (1996) *Prot. Eng.* 9:499-505, Chen et al., (1995) *Prot Eng.* 8:575-582; Fierobe et al. (1996) *Biochem.* 35:8698-8704; and Li et al., (1997) *Prot. Eng.* 10:1199-1204, the need still exists for providing glucoamylase variants with altered properties relative to their parent.

SUMMARY OF THE INVENTION

In one aspect, the present invention relates to glucoamylase variants having one or more amino acid substitutions at residues positions corresponding to positions 4, 5, 12, 24, 43, 44, 45, 46, 47, 49, 51, 70, 75, 6, 94, 100, 108, 114, 116, 119, 122, 124, 125, 137, 141, 143, 146, 148, 169, 171, 172, 175, 178, 180, 181, 208, 211, 228, 242, 243, 245, 292, 294,197, 309, 310, 313, 314, 315, 316, 317, 321, 340, 341, 350, 353, 356, 363, 368, 369, 375, 376, 395, 398, 401, 408, 409, 412, 415, 418, 421, 433, 436 and 451 of SEQ ID NO: 2 or 3 and/or an equivalent position in a parent glucoamylase. The equivalent position can be determined by sequence identity such that the parent glucoamylase has at least 80% sequence identity and less than 100% sequence identity with SEQ ID NOs: 1, 2, 3, 4, 5, 6, 7, 8, or 9. The parent glucoamylase can be one of SEQ ID NO: 1, 2 or 3. The equivalent position can be determined by structural identity to SEQ ID NO:3. A further aspect of the present invention is a glucoamylase variant having one or more amino acid substitutions corresponding to a position selected from positions 4, 5, 24, 29, 43, 49, 70, 75, 76, 100, 108, 119, 124, 137, 146, 148, 169, 171, 172, 175, 178, 181, 208, 211, 243, 292, 294, 297, 314, 316, 317, 340, 341, 350, 356, 363, 368, 369, 376, 395, 401, 412, 433, 436 and 451 and having at least 90% sequence identity to SEQ ID NO. 2. In some aspects, the one or more amino acid substitutions correspond to the following positions: 5, 24, 43, 49, 70, 75, 76, 94, 119, 141, 146, 148, 172, 175, 178, 180, 181, 208, 211, 243, 294, 309, 314, 353, 369, 375, 409. The parent glucoamylase can be any one of: a *Trichoderma* spp., an *Aspergillus* spp., a *Humicola* spp., a *Penicillium* spp., a *Talaromycese* spp., or a *Schizosaccharmyces* spp. In some aspects, the glucoamylase variant is preferably a *Trichoderma* spp. or an *Aspergillus* spp.

In further aspects of the invention, the glucoamylase variant includes a substitution in a position corresponding to at least one of the following positions: D4L/E/R/S/C/A/Q/W, F5C/M/N/R/S/T/V/W, I12L/R, D24E/L/Y/T, F29L/I/D/C/S/V/W, I43F/R/D/Y/S, D44E/H/K/S/N/Y/F/R, Y47W, Y49N, Q70R/K/M/P/G/L/F, Q75R/K/A, R76L/M/K/T/P, P94L, D100W/I/Q/M/P/A/N, N119P/T/Y/D/E, N146S/G/C/H/E/D/T/W/L/M, Q148V/Y/H/A/C/D/G/M/R/S/T, Y169D/F, Q172C/A/D/R/E/F/H/V/L/M/N/S/T/V, E180A/C/G/H/I/L/N/P/Q/R/S/T/V/Y, V181E/C/D/G/H/I/P/T/Y/S/K/F/A, Q208L/A/C/E/N/F/H/T, S211C/R/E/A/Y/W/M/H/L/I/R/Q/T, E243S/R/N/M/Y/A/L, R245A/E/M/I/P/V, I292D/H/P/R/T/N/V/F/L, G294D/E/T/Q/I/A, K297F/L/P/T/M/D/N/Q/A/Y/H/S/R/W, R309A/C/G/H/I/N/P/Q/S/T/W/Y/L, Y310E/G/L/P/S/W/R/Q, D313Q, V314A/R/N/D/C/E/Q/G/H/I/K/L/M/

F/P/S/T/W/Y, Y315F, Y316Q/R, N317T/H, K340D/T, K341F/D/P/V/G/S, T350S/E/A/N, Q356H/D/E, T363L/R/C/H/W, S368W/D/F/L, S369F, N376Q/T/H/S/V, Y395Q/R/S, A398S/I/T, S401C/V, R408S, N409W/T/K, T412A/h/K/G, R433H/Q, I436A/T, and S451M/T/H. some preferred variants have substitutions at position 172. Other preferred variants have substitutions at position 208 or 211. Other preferred variants have substitutions corresponding to Q172F, Q208N or S221R. Other preferred variants have at least one substitution at position 314. In some aspects, the variants have at least one substitution at position 24, 181, 208, 243, 292, 294, 353, 375 or 409. Some preferred substitutions are at positions D24E/L/Y, V181K/L, Q208C, E243Y I292V, G294A/Q, T353R, N375N/Q and/or N409K/W. In one aspect, the variant glucoamylase exhibits increased thermostability as compared to the parent glucoamylase. Alternatively, or in addition, the variant exhibits increased specific activity compared to the parent glucoamylase.

A further aspect of the invention is a polynucleotide encoding the variant described herein. A further aspect is a host cell containing the polynucleotide. A further aspect of the invention is an enzyme composition including the glucoamylase variant described herein. In one aspect, the enzyme composition is used in a starch conversion process or an animal feed formulation. In other aspects, the enzyme composition is used in an alcohol fermentation process.

A further aspect of the invention is a method of producing a variant glucoamylase in a host cell by transforming a host cell with a DNA construct comprising the polynucleotide encoding the variant glucoamylase; culturing the host cell under conditions suitable for the expression and production of the glucoamylase variant and producing the variant. The method may also include the step of recovering the glucoamylase variant from the culture.

BRIEF DESCRIPTION OF THE DRAWINGS

FIG. 1A illustrates the *Trichoderma reesei* glucoamylase (TrGA) parent glucoamylase having 632 amino acids (SEQ ID NO: 1). The signal peptide is underlined, the catalytic region (SEQ ID NO:3) starting with amino acid residues SVDDFI (SEQ ID NO:160) and having 453 amino acid residues is in bold; the linker region is in italics and the binding domain is both italics and underlined. The mature protein which includes the catalytic domain (SEQ ID NO:3), linker region and starch binding domain is represented by SEQ ID NO:2. FIG. 1B illustrates the cDNA (SEQ ID NO:4) which codes for the TrGA.

FIG. 4A and FIG. 4B illustrate an alignment comparison of the catalytic domains of parent glucoamylases including glucoamylase derived from *Aspergillus awamori* (AaGA) (SEQ ID NO:5); *Aspergillus niger* (AnGA) (SEQ ID NO:6); *Aspergillus orzyae* (AoGA) (SEQ ID NO:7); *Trichoderma reesei* (TrGA) (SEQ ID NO:3); *Humicola grisea* (HgGA) (SEQ ID NO:8); and *Hypocrea vinosa* (HvGA) (SEQ ID NO:9). Identical amino acids are indicated by an asterisk (*).

DETAILED DESCRIPTION OF THE INVENTION

I. Definitions

Figure 2:
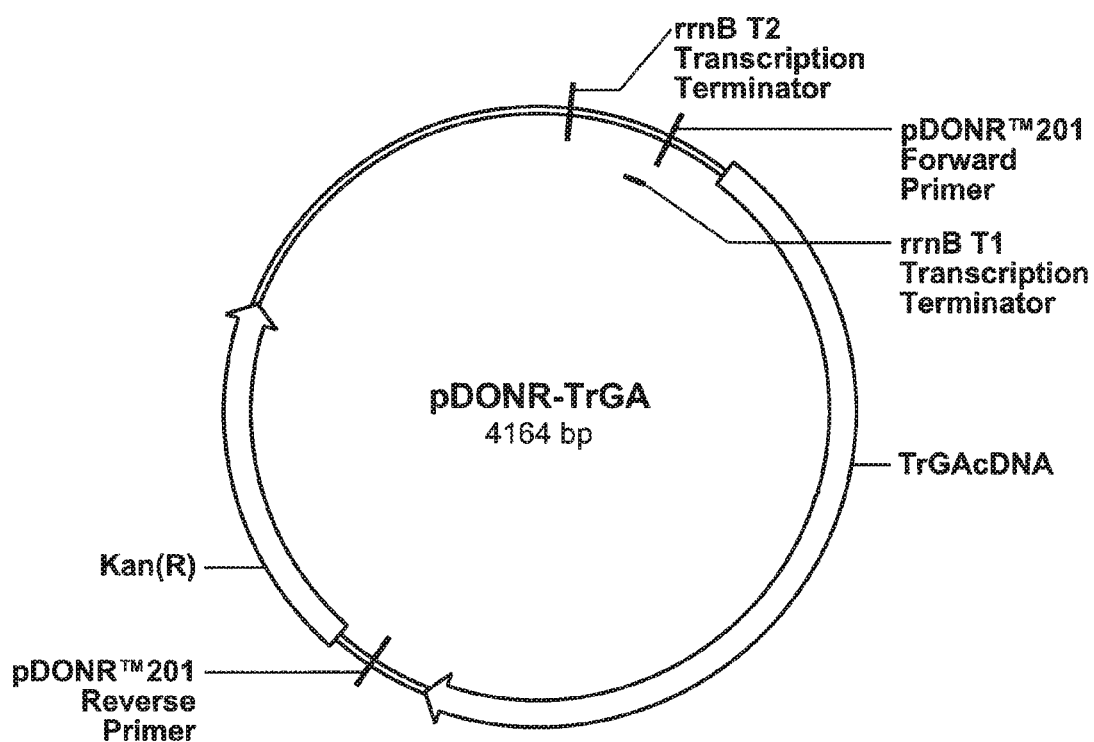
FIG. 2 illustrates the plasmid pDONR-TrGA which includes the cDNA (SEQ ID NO:4) of the parent TrGA.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "glucoamylase (EC 3.2.1.3)" refers to an enzyme that catalyzes the release of D-glucose from the non-reducing ends of starch and related oligo- and polysaccharides.

The term "parent" or "parent sequence" refers to a sequence that is native or naturally occurring in a host cell.

The term "TrGA" refers to a parent *Trichoderma reesei* glucoamylase sequence having the mature protein sequence illustrated in SEQ ID NO:2 which includes the catalytic domain having the sequence illustrated in SEQ ID NO:3. The isolation, cloning and expression of the TrGA are described in WO 2006/060062 and U.S. Pat. Pub. No. 2006/0094080 published May 4, 2006 which are incorporated herein by reference. In some embodiments, the parent sequence refers to a TrGA that is the starting point for protein engineering. The numbering of the glucoamylase amino acids herein is based on the sequence of the TrGA (SEQ ID NO: 2 and SEQ ID NO: 3).

The phrase "mature form of a protein or polypeptide" refers to the final functional form of the protein or polypeptide. To exemplify, a mature form of the TrGA includes the catalytic domain, linker region and starch binding domain having the amino acid sequence of SEQ ID NO:2.

The term "*Trichoderma* glucoamylase homologues" refers to parent glucoamylases having at least 80% amino acid sequence identity to the TrGA sequence (SEQ ID NO:1, SEQ ID NO:2 or SEQ ID NO:3) and which glucoamylases retain the functional characteristics of a glucoamylase.

As used herein, a "homologous sequence" means a nucleic acid or polypeptide sequence having at least 100%, at least 99%, at least 98%, at least 97%, at least 96%, at least 95%, at least 94%, at least 93%, at least 92%, at least 91%, at least 90%, at least 88%, at least 85%, at least 80%, at least 75%, at least 70%, at least 65%, at least 60%, at least 55%, at least 50%, or at least 45% sequence identity to a nucleic acid sequence or polypeptide sequence when optimally aligned for comparison, wherein the function of the candidate nucleic acid sequence or polypeptide sequence is essentially the same as the nucleic acid sequence or polypeptide sequence said candidate homologous sequence is being compared with. In some embodiments, homologous sequences have between 85% and 100% sequence identity, while in other embodiments there is between 90% and 100% sequence identity, and in other embodiments, there is 95% and 100% sequence identity. In some embodiments the candidate homologous sequence is compared with the TrGA nucleic acid sequence or mature protein sequence.

As used herein, the terms "glucoamylase variant", "variant" and "TrGA variant" are used in reference to glucoamylases that are similar to a parent glucoamylase sequence (e.g., the TrGA or *Trichoderma* glucoamylase homologues) but have at least one substitution, deletion or insertion in their amino acid sequence that makes them different in sequence from a parent glucoamylase.

As used herein the term "catalytic domain" refers to a structural region of a polypetide, which contains the active site for substrate hydrolysis.

The term "linker" refers to a short amino acid sequence generally having between 3 and 40 amino acids residues that covalently bind an amino acid sequence comprising a starch binding domain with an amino acid sequence comprising a catalytic domain.

The term "starch binding domain" refers to an amino acid sequence that binds preferentially to a starch substrate.

As used herein, the terms "mutant sequence" and "mutant gene" are used interchangeably and refer to a polynucleotide sequence that has an alteration in at least one codon occurring in a host cell's parent sequence. The expression product of the mutant sequence is a variant protein with an altered amino acid sequence relative to the parent. The expression product may have an altered functional capacity (e.g., enhanced enzymatic activity).

The term "property" or grammatical equivalents thereof in the context of a polypeptide, as used herein, refers to any characteristic or attribute of a polypeptide that can be selected or detected. These properties include, but are not limited to oxidative stability, substrate specificity, catalytic activity, thermal stability, pH activity profile, resistance to proteolytic degradation, $K_M$, $K_{CAT}$, $K_{CAT}/K_M$ ratio, protein folding, ability to bind a substrate and ability to be secreted.

The term "property" of grammatical equivalent thereof in the context of a nucleic acid, as used herein, refers to any characteristic or attribute of a nucleic acid that can be selected or detected. These properties include, but are not limited to, a property affecting gene transcription (e.g., promoter strength or promoter recognition), a property affecting RNA processing (e.g., RNA splicing and RNA stability), a property affecting translation (e.g., regulation, binding of mRNA to ribosomal proteins).

The terms "thermally stable" and "thermostable" refer to glucoamylase variants of the present invention that retain a specified amount of enzymatic activity after exposure to identified temperatures over a given period of time under conditions prevailing during the hydrolysis of starch substrates, for example while exposed to altered temperatures.

The term "enhanced stability" in the context of a property such as thermostability refers to a higher retained starch hydrolytic activity over time as compared to other glucoamylases, variants and/or wild-type glucoamylases.

The term "diminished stability" in the context of a property such as thermostability refers to a lower retained starch hydrolytic activity over time as compared to other glucoamylases, variants and/or wild-type glucoamylase.

The terms "active" and "biologically active" refer to a biological activity associated with a particular protein. It follows that the biological activity of a given protein refers to any biological activity typically attributed to that protein by those skilled in the art. For example, an enzymatic activity associated with a glucoamylase is hydrolytic and, thus an active glucoamylase has hydrolytic activity.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases.

As used herein, the terms "DNA construct," "transforming DNA" and "expression vector" are used interchangeably to refer to DNA used to introduce sequences into a host cell or organism. The DNA may be generated in vitro by PCR or any other suitable technique(s) known to those in the art. The DNA construct, transforming DNA or recombinant expression cassette can be incorporated into a plasmid, chromosome, mitochondrial DNA, plastid DNA, virus, or nucleic acid fragment. Typically, the recombinant expression cassette portion of an expression vector, DNA construct or transforming DNA includes, among other sequences, a nucleic acid sequence to be transcribed and a promoter. In preferred embodiments, expression vectors have the ability to incorporate and express heterologous DNA fragments in a host cell.

As used herein, the term "vector" refers to a polynucleotide construct designed to introduce nucleic acids into one or more cell types. Vectors include cloning vectors, expression vectors, shuttle vectors, plasmids, cassettes and the like.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction.

As used herein, the terms "transformed" and "stably transformed" refers to a cell that has a non-native (heterologous) polynucleotide sequence integrated into its genome or as an episomal plasmid that is maintained for at least two generations.

As used herein, the terms "selectable marker" and "selective marker" refer to a nucleic acid (e.g., a gene) capable of expression in host cells which allows for ease of selection of those hosts containing the vector. Typically, selectable markers are genes that confer antimicrobial resistance or a metabolic advantage on the host cell to allow cells containing the exogenous DNA to be distinguished from cells that have not received any exogenous sequence during the transformation.

As used herein, the term "promoter" refers to a nucleic acid sequence that functions to direct transcription of a downstream gene. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide. Generally, "operably linked" means that the DNA sequences being linked are contiguous, and, in the case of a secretory leader, contiguous and in reading phase.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

The "percent (%) nucleic acid sequence identity" or "percent (%) amino acid sequence identity" is defined as the percentage of nucleotide residues or amino acid residues in a candidate sequence that are identical with the nucleotide residues or amino acid residues of the starting sequence (i.e., TrGA).

Homologous sequences are determined by known methods of sequence alignment. A commonly used alignment method is BLAST described by Altschul et al., (Altschul et al., *J. Mol. Biol.*, 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Other methods find use in aligning sequences. One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

The term "optimal alignment" refers to the alignment giving the highest percent identity score.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm–5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous or homologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

In an embodiment of the invention, mutated DNA sequences are generated with site saturation mutagenesis in at least one codon. In another preferred embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the parent sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, "heterologous protein" refers to a protein or polypeptide that does not naturally occur in the host cell.

As used herein, "homologous protein" refers to a protein or polypeptide native or naturally occurring in a cell and includes native proteins that are over-expressed in the cell whether by recombinant DNA technology or naturally.

An enzyme is "over-expressed" in a host cell if the enzyme is expressed in the cell at a higher level than the level at which it is expressed in a corresponding wild-type cell.

The terms "protein" and "polypeptide" are used interchangeability herein. In the present disclosure and claims, the conventional one-letter and three-letter codes for amino acid residues are used. The 3-letter code for amino acids as defined in conformity with the IUPAC-IUB Joint Commission on Biochemical Nomenclature (JCBN). It is also understood that a polypeptide may be coded for by more than one nucleotide sequence due to the degeneracy of the genetic code.

Variants of the invention are described by the following nomenclature: [original amino acid residue/position/substituted amino acid residue]. For example the substitution of leucine for arginine at position 76 is represented as R76L. When more than one amino acid is substituted at a given position, the substitution is represented as 1) Q172C, Q172D or Q172R; 2) Q172C, D, or R or c) Q172C/D/R. When a position suitable for substitution is identified herein without a specific amino acid suggested, it is to be understood that any amino acid residue may be substituted for the amino acid residue present in the position. Where a variant glucoamylase contains a deletion in comparison with other glucoamylases the deletion is indicated with "*". For example, a deletion at position R76 is represented as R76*. A deletion of two or more consecutive amino acids is indicated for example as (76-78)*.

A "prosequence" is an amino acid sequence between the signal sequence and mature protein that is necessary for the secretion of the protein. Cleavage of the pro sequence will result in a mature active protein.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., glucoamylase), or may be from a gene encoding another secreted protein.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Host strain" or "host cell" refers to a suitable host for an expression vector comprising DNA according to the present invention.

The terms "derived from" and "obtained from" refer to not only a glucoamylase produced or producible by a strain of the organism in question, but also a glucoamylase encoded by a DNA sequence isolated from such strain and produced in a host organism containing such DNA sequence. Additionally, the term refers to a glucoamylase which is encoded by a DNA sequence of synthetic and/or cDNA origin and which has the identifying characteristics of the glucoamylase in question.

A "derivative" within the scope of this definition generally retains the characteristic hydrolyzing activity observed in the wild-type, native or parent form to the extent that the derivative is useful for similar purposes as the wild-type, native or parent form. Functional derivatives of glucoamylases encompass naturally occurring, synthetically or recombinantly produced peptides or peptide fragments which have the general characteristics of the glucoamylases of the present invention.

The term "isolated" or "purified" refers to a material that is removed from its original environment (e.g., the natural environment if it is naturally occurring).

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations which were not members of the predefined set of mutations. In some embodiments, the methods include those set forth in U.S. Pat. No. 6,582,914, hereby incorporated by reference. In alternative embodiments, combinatorial mutagenesis methods encompass commercially available kits (e.g., QuikChange® Multisite, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein the term "dry solids content (DS or ds)" refers to the total solids of a slurry in % on a dry weight basis.

As used herein, the term "initial hit" refers to a variant that was identified by screening a combinatorial consensus mutagenesis library. In preferred embodiments, initial hits have improved performance characteristics, as compared to the starting gene.

As used herein, the term "improved hit" refers to a variant that was identified by screening an enhanced combinatorial consensus mutagenesis library.

As used herein, the term "target property" refers to the property of the starting gene that is to be altered. It is not intended that the present invention be limited to any particular target property. However, in some preferred embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention.

Other definitions of terms may appear throughout the specification

Before the exemplary embodiments are described in more detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Although any methods and materials similar or equivalent to those described herein can be used in the practice or testing of the present invention, exemplary and preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

Preferred Embodiments

An objective of the present invention was to alter properties, such as improve the thermal stability and/or specific activity of parent glucoamylases and in particular *Trichoderma reesei* glucoamylase (TrGA), wherein the glucoamylase variants having altered, such as improved, properties would be useful, for example in starch conversion or alcohol fermentation processes.

Parent Glucoamylases:

In some embodiments, the present invention provides a glucoamylase variant. The glucoamylase variant is a variant of a parent glucoamylase, said parent glucoamylase comprising an amino acid sequence as illustrated in SEQ ID NO:1, 2, 3, 5, 6, 7, 8 or 9 or said parent glucoamylase comprising a catalytic domain having an amino acid sequence displaying at least 80% sequence identity with one or more of the amino acid sequences illustrated in SEQ ID NO:1, 2, 3, 5, 6, 7, or 8 and/or encoded by a DNA sequence which hybridizes under medium, high or stringent conditions with a DNA encoding a glucoamylase having one of the amino acid sequences of SEQ ID NO: 1, 2 or 3.

Predicted structure and known sequences of glucoamylases are conserved among fungal species (Coutinho et al., 1994 Protein Eng., 7:393-400 and Coutinho et al., 1994, Protein Eng., 7: 749-760). In some embodiments, the parent glucoamylase is a filamentous fungal glucoamylase. In some embodiments, the parent glucoamylase is obtained from a *Trichoderma* strain (e.g., *T. reesei, T. longibrachiatum, T. strictipilis, T. asperellum, T. konilangbra* and *T. hazianum*), an *Aspergillus* strain (e.g. *A. niger, A. nidulans, A. kawachi, A. awamori* and *A. orzyae*), a *Talaromyces* strain (e.g. *T. emersonii, T. thermophilus*, and *T. duponti*), a Hypocrea strain (e.g. *H. gelatinosa, H. orientalis, H. vinosa*, and *H. citrina*), a *Fusarium* strain (e.g., *F. oxysporum, F. roseum*, and *F. venenatum*), a *Neurospora* strain (e.g., *N. crassa*) and a *Humicola* strain (e.g., *H. grisea, H. insolens* and *H. lanuginose*), a *Penicillium* strain (e.g. *P. notatum* or *P. chrysogenum*), or a *Saccharomycopsis* strain (e.g. *S. fibuligera*).

In some embodiments, the parent glucoamylase may be a bacterial glucoamylase. For example, the polypeptide may be obtained from a gram positive bacterial strain such as *Bacillus* (e.g., *B. alkalophilus, B. amyloliquefaciens, B. lentus, B. licheniformis, B. stearothermophilus, B. subtilis* and *B. thuringiensis*) or a *Streptomyces* strain (e.g., *S. lividans*).

In some embodiments, the parent glucoamylase will have at least 80% sequence identity, at least 85% sequence identity, at least 88% sequence identity, at least 90% sequence identity, at least 93% sequence identity, at least 95% sequence identity, at least 96% sequence identity, at least 97% sequence identity, at least 98% sequence identity and also at least 99% sequence identity with the TrGA amino acid sequence of SEQ ID NO: 2.

In other embodiments, the parent glucoamylase will have at least 80% sequence identity, at least 85% sequence identity, at least 90% sequence identity, at least 95% sequence identity, at least 97% sequence identity and also at least 98% sequence identity with the catalytic domain of the TrGA amino acid sequence of SEQ ID NO:3.

In yet other embodiments, the parent glucoamylase will comprise an amino acid sequence having at least 90% sequence identity, at least 93% sequence identity, at least 95% sequence identity, at least 96% sequence identity, at least 97% sequence identity, at least 98% sequence identity and also at least 99% sequence identity with the catalytic domain of the *Aspergillus* parent glucoamylase of SEQ ID NO:5 or SEQ ID NO:6.

In other embodiments, the parent glucoamylase will comprise an amino acid sequence having at least 90% sequence identity, at least 95% sequence identity, at least 97% sequence identity and also at least 99% sequence identity with the catalytic domain of the *Humicola grisea* (HgGA) parent glucoamylase of SEQ ID NO:8.

In further embodiments, a *Trichoderma* glucoamylase homologue will be obtained from a *Trichoderma* or *Hypocrea* strain. Some preferred *Trichoderma* glucoamylase homologues are described in US Pat. Pub. No. 2006/0094080 and reference is made specifically to amino acid sequences set forth in SEQ ID NOs: 17-22 and 43-47 of said reference.

In some preferred embodiments, the parent glucoamylase is TrGA comprising the amino acid sequence of SEQ ID NO:2 or a *Trichoderma* glucoamylase homologue having at least 80%, at least 85%, at least 88%, at least 90%, at least 93%, at least 95%, at least 96%, at least 97%, at least 98%, at least 99% sequence identity to the TrGA sequence.

Glucoamylase Structural Homology:

The central dogma of molecular biology is that the sequence of DNA encoding a gene for a particular enzyme, determines the amino acid sequence of the protein, this sequence in turn determines the three-dimensional folding of the enzyme. This folding brings together disparate residues that create a catalytic center and substrate binding surface and this results in the high specificity and activity of the enzymes in question.

Figure 12:
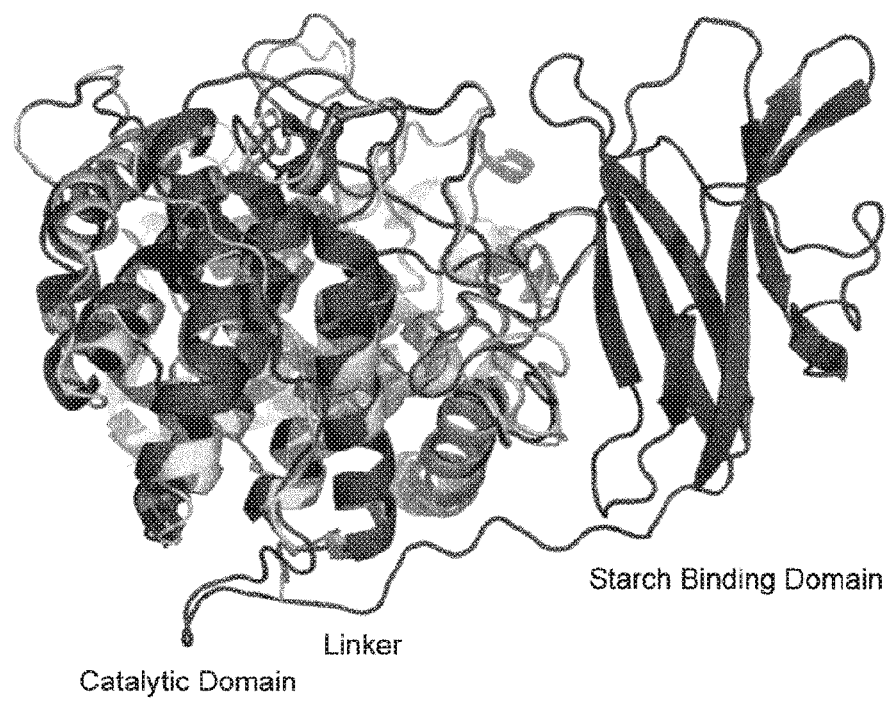
FIG. 12 is a comparison of the three dimensional structures of *Trichoderma glucoamylase* (black) (SEQ ID NO:2) and *Aspergillus awamorii* glucoamylase (grey) viewed from the side.
Figure 13:
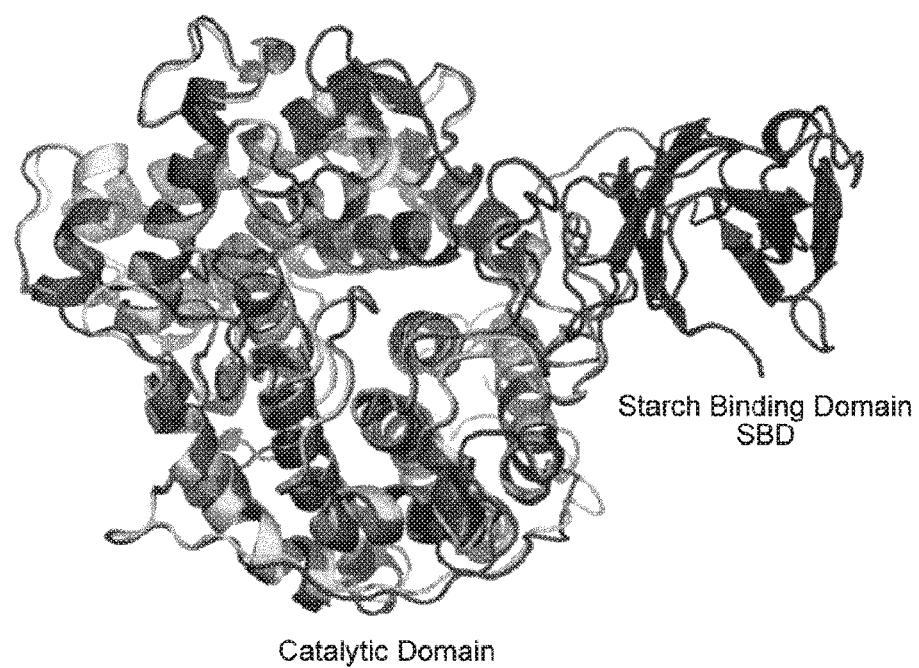
FIG. 13 is a comparison of the three dimensional structures of *Trichoderma glucoamylase* (black) and *Aspergillus awamorii* glucoamylase (grey) viewed from the top.

Glucoamylases consist of as many as three distinct structural domains, a catalytic domain of approximately 450 residues which is structurally conserved in all glucoamylases, generally followed by a linker region consisting of between 30 and 80 residues which are connected to a starch binding domain of approximately 100 residues. The structure of the *Trichoderma reesei* glucoamylase with all three regions intact was determined to 1.8 Angstrom resolution herein (see Table 15 and Example 11). Using the coordinates (see Table 15) the structure was aligned with the coordinates of the catalytic domain from *Aspergillus awamorii* strain X100 that was determined previously (Aleshin, A. E., Hoffman, C., Firsov, L. M., and Honzatko, R. B. 1994 Refined crystal structures of glucoamylase from *Aspergillus awamori* var. X100. *J Mol Biol* 238: 575-591.). The *Aspergillus awamori* crystal structure only included the catalytic domain. As seen in FIGS. 12 and 13 the structure of the catalytic domains overlap very closely and it is possible to identify equivalent residues based on this structural superposition. The inventors believe that all glucoamylases share the basic structure depicted in FIGS. 12 and 13.

FIG. 12 is a comparison of the three dimensional structures of the *Trichoderma* Glucoamylase (black) of SEQ ID NO:1 (see FIG. 1 for amino acid sequence) and of *Aspergillus awamorii* (grey) viewed from the side. In this view the relationship between the catalytic domain and the linker region and the starch binding domain can be seen.

FIG. 13 is a comparison of the three dimensional structures of the *Trichoderma* glucoamylase (black) and of *Aspergillus awamorii* (grey) viewed from the top. The glucoamylases shown here and indeed all known glucoamylases to date share this structural homology. The conservation of structure correlates with the conservation of activity and a conserved mechanism of action for all glucoamylases. Given this high homology, changes resulting from site specific variants of the *Trichoderma glucoamylase* resulting in altered function would also have similar structural and therefore functional consequences in other glucoamylases. Therefore, the teachings of which variants result in desirable benefits can be applied to other glucoamylases.

Thus, the amino acid position numbers discussed herein refer to those assigned to the mature *Trichoderma reesei* glucoamylase sequence presented in FIG. 1. The present invention, however, is not limited to the variants of *Trichoderma* glucoamylase, but extends to glucoamylases containing amino acid residues at positions which are "equivalent" to the particular identified residues in *Trichoderma reesei* glucoamylase (SEQ ID NO:2). In a preferred embodiment of the present invention, the parent glucoamylase is *Taleromyces* GA and the substitutions are made at the equivalent amino acid residue positions in *Taleromyces* glucoamylase as those described herein. In other embodiments, the parent glucoamylase is one of those listed in Table 1. In further embodiments, the parent glucoamylase is a *Penicillium* glucoamylase, such as *Penicillium chrysogenum*, Structural identity determines whether the amino acid residues are equivalent. Structural identity is a one-to-one topological equivalent when the two structures (three dimensional and amino acid structures) are aligned. A residue (amino acid) position of a glucoamylase is equivalent to a residue of *T. reesei* glucoamylase if it is either homologous (i.e., corresponding in position in either primary or tertiary structure) or analogous to a specific residue or portion of that residue in *T. reesei* glucoamylase (having the same or similar functional capacity to combine, react, or interact chemically).

In order to establish identity to the primary structure, the amino acid sequence of a glucoamylase can be directly compared to *Trichoderma reesei* glucoamylase primary sequence and particularly to a set of residues known to be invariant in glucoamylases for which sequence is known. For example, FIGS. 4A and B herein shows the conserved residues between glucoamylases. After aligning the conserved residues, allowing for necessary insertions and deletions in order to maintain alignment (i.e. avoiding the elimination of conserved residues through arbitrary deletion and insertion), the residues equivalent to particular amino acids in the primary sequence of *Trichoderma reesei* glucoamylase are defined. Alignment of conserved residues preferably should conserve 100% of such residues. However, alignment of greater than 75% or as little as 50% of conserved residues is also adequate to define equivalent residues.

For example, in FIG. 4, glucoamylases from six organisms are aligned to provide the maximum amount of homology between amino acid sequences. A comparison of these sequences shows that there are a number of conserved residues contained in each sequence as designated by an asterisk. These conserved residues, thus, may be used to define the corresponding equivalent amino acid residues of *Trichoderma reesei* glucoamylase in other glucoamylases such as glucoamylase from *Aspergillus niger*.

Structural identity involves the identification of equivalent residues between the two structures. "Equivalent residues" can be defined by determining homology at the level of tertiary structure (structural identity) for an enzyme whose tertiary structure has been determined by x-ray crystallography. Equivalent residues are defined as those for which the atomic coordinates of two or more of the main chain atoms of a particular amino acid residue of the *Trichoderma reesei* glucoamylase (N on N, CA on CA, C on C and 0 on 0) are within 0.13 nm and preferably 0.1 nm after alignment. Alignment is achieved after the best model has been oriented and positioned to give the maximum overlap of atomic coordinates of non-hydrogen protein atoms of the glucoamylase in question to the *Trichoderma reesei* glucoamylase. The best model is the crystallographic model giving the lowest R factor for experimental diffraction data at the highest resolution available.

$$R \text{ factor} = \frac{\sum_{h} |Fo(h)| - |Fc(h)|}{\sum_{h} |Fo(h)|}$$

Equivalent residues which are functionally analogous to a specific residue of *Trichoderma reesei* glucoamylase are defined as those amino acids of the enzyme which may adopt a conformation such that they either alter, modify or contribute to protein structure, substrate binding or catalysis in a manner defined and attributed to a specific residue of the Trichoderma reesei glucoamylase. Further, they are those residues of the enzyme (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of Trichoderma reesei glucoamylase. The coordinates of the three dimensional structure of Trichoderma reesei glucoamylase are set forth in Table 15 and can be used as outlined above to determine equivalent residues on the level of tertiary structure.

Some of the residues identified for substitution are conserved residues whereas others are not. In the case of residues which are not conserved, the substitution of one or more amino acids is limited to substitutions which produce a variant which has an amino acid sequence that does not correspond to one found in nature. In the case of conserved residues, such substitutions should not result in a naturally-occurring sequence.

Variants:

The variants according to the invention include at least one substitution, deletion or insertion in the amino acid sequence of a parent glucoamylase that makes the variant different in sequence from the parent glucoamylase. In some embodiments, the variants of the invention will have at least 20%, at least 40%, at least 60%, at least 80%, at least 85%, at least 90%, at least 95% and also at least 100% of the glucoamylase activity of the TrGA activity of SEQ ID NO:2.

In some embodiments, the variants according to the invention will comprise a substitution, deletion or insertion in at least one amino acid position of the parent TrGA (SEQ ID NO:2), or in an equivalent position in the sequence of another parent glucoamylase having at least 90% sequence identity to the TrGA sequence, including but not limited to; at least 93% sequence identity, at least 95%, at least 97%, and at least 99%.

In other embodiments, the variant according to the invention will comprise a substitution, deletion or insertion in at least one amino acid position of a fragment of the parent TrGA, wherein the fragment comprises the catalytic domain of the TrGA sequence (SEQ ID NO:3) or in an equivalent position in a fragment comprising the catalytic domain of a parent glucoamylase having at least 80% sequence identity to the fragment of the TrGA sequence, at least 90%, at least 95%, at least 97%, and at least 99%. In some embodiments, the fragment will comprise at least 400, 425, 450, and/or 500 amino acid residues. In some embodiments when the parent glucoamylase includes not only a catalytic domain, linker region and starch binding domain, the fragment may include part of the linker region. In a particularly preferred embodiment, the variant will comprise a substitution, deletion or insertion in the amino acid sequence of a fragment of the TrGA sequence (SEQ ID NO: 2 or SEQ ID NO: 3).

Structural identity with reference to an amino acid substitution, means that the substitution occurs at the equivalent amino acid position in the homologous glucoamylase or parent glucoamylase. The term equivalent position means a position that is common to two parent sequences which is based on an alignment of the amino acid sequence of the parent glucoamylase in question as well as alignment of the three-dimensional structure of the parent glucoamylase in question with the TrGA reference glucoamylase amino acid sequence and three-dimensional sequence. For example, with reference to FIG. 4, position 24 in TrGA (SEQ ID NO: 3) is D24 and the equivalent position for Aspergillus niger (SEQ ID NO. 6) is position D25 and the equivalent position for Aspergillus oryzea (SEQ ID NO: 7) is position D26. See FIGS. 12 and 13 for an exemplary alignment of the three-dimensional sequence.

In some embodiments, the glucoamylase variant will include at least one substitution in the amino acid sequence of a parent. In further embodiments, the variant may have more than one substitution (e.g. two, three or four substitutions).

In some embodiments, a glucoamylase variant comprises a substitution, deletion or insertion, and preferably a substitution in at least one amino acid position in a position corresponding to the regions of non-conserved amino acids as illustrated in FIG. 4 (e.g. amino acid positions corresponding to those positions which are not designated by"*" in FIG. 4).

While the variants can be in any position in the mature protein sequence (SEQ ID NOS: 2 or 3), in one embodiment, a glucoamylase variant comprises one or more substitutions in the following positions in the amino acid sequence set forth in SEQ ID NO: 2 or 3: 4, 5, 12, 24, 29, 43, 44, 45, 46, 47, 49, 51, 70, 75, 76, 94, 100, 108, 114, 116, 119, 122, 124, 125, 137, 143, 146, 148, 169, 171, 172, 175, 178, 180, 181, 208, 211, 228, 242, 243, 245, 292, 294, 297, 309, 310, 313, 314, 315, 316, 317, 321, 340, 341, 350, 353, 356, 363, 368, 369, 375, 376, 395, 398, 401, 408, 409, 412, 415, 418, 421, 433, 436, and 451; and/or in an equivalent position in a parent glucoamylase. In some embodiments, the parent glucoamylase will have at least 90%, at least 95%, at least 96%, at least 97% at least 98%, and at least 99% identity with SEQ ID NO: 2 or SEQ ID NO: 3. In other embodiments the parent glucoamylase will be a Trichoderma glucoamylase homologue.

In some embodiments, the glucoamylase variant comprises one or more substitutions in the following positions in the amino acid sequence set forth in SEQ ID NO: 2 or 3: D4, F5, 112, D24, F29, 143, D44, P45, D46, Y47, Y49, W51, Y70, Q75, R76, P94, D100, K108, K114, F116, N119, R122, Q124, R125, G137, N146, Q148, Y169, N171, Q172, F175, W178, E180, V181, Q208, 5211, W228, N242, E243, R245, 1292, G294, K297, R309, Y310, D3B, V314, Y315, Y316, N317, W321, K340, K341, T350, Q356, T363, S368, 5369, N376, Y395, A398, 5401, R408, N409, T412, H418, W421, R433, 1436, and/or 5451 and/or an equivalent position in parent glucoamylase (e.g. a Trichoderma glucoamylase homologue).

In other embodiments, the variant of a glucoamylase parent comprises one or more substitutions in the following positions in the amino acid sequence set forth in SEQ ID NO:2 or 3: 4, 5, 24, 29, 43, 44, 49, 70, 75, 76, 100, 108, 119, 124, 137, 146, 148, 169, 171, 172, 175, 178, 181, 208, 211, 243, 292, 294, 297, 314, 316, 317, 340, 341, 350, 356, 363, 368, 369, 376, 395, 401, 409, 412, 433, 436, and/or 451 and/or an equivalent position in a parent glucoamylase (e.g., Trichoderma glucoamylase homologue).

In further embodiments, the variant of a glucoamylase parent comprises at least one of the following substitutions in the following positions in an amino acid sequence set forth in SEQ ID NO:2 or 3: D4L/E/R/S/C/A/Q/W, F5C/M/ N/R/S/T/V/W, I12L/R, D24E/L/Y/T, F29L/I/D/C/S/V/W, I43F/R/D/Y/S, D44E/H/K/S/N/Y/F/R, Y47W,Y49N, Q70R/ K/M/P/G/L/F, Q75R/K/A, R76L/M/K/T/P, P94L, D100W/ I/Q/M/P/A/N, N119P/T/Y/D/E, N146S/G/C/H/E/D/T/W/L/ F/M, Q148V/Y/H/A/C/D/G/M/R/S/T, Y169D/F, Q172C/A/

D/R/E/F/H/V/L/M/N/S/T/V, F175H/A/G/R/S/T/C/W/Y, W178A/C/D/E/F/G/H/K/N/R/S/T/V/Y, E180A/C/G/H/I/L/ N/P/Q/R/S/T/V/Y/, V181E/C/D/G/H/I/P/T/Y/S/L/K/F/A, Q208L/A/C/E/N/F/H/T, S211C/R/E/A/Y/W/M/H/L/I/R/Q/ T, E243S/R/N/M/Y/A/L, R245A/E/M/I/P/V, I292D/H/P/R/ T/N/V/F/L, G294D/E/T/Q/I/A, K297F/L/P/T/M/D/N/Q/A/ Y/H/S/R/W, R309A/C/G/H/I/N/P/Q/S/T/W/Y/L, Y310E/G/ L/P/S/W/R/Q, D313Q, V314A/R/N/D/C/E/Q/G/H/I/L/K/M/ F/P/S/T/W/Y, Y315F, Y316Q/R, N317T/H, K340D/T, K341F/D/P/V/G/S, T350S/E/A/N, Q356H/D/E, T363L/R/ C/H/W, S368W/D/F/L, S369F, N376Q/T/H/S/V, Y395Q/R/ S, A398S/I/T, S401C/V, R408S, N409W/T/K, T412A/H/K/ G, R433H/Q, I436A/T, S451M/T/H/and/or a substitution in an equivalent position in a parent glucoamylase homologue.

In some preferred embodiments, the glucoamylase variant comprises at least one substitution in a position corresponding to the amino acid residue position set forth in SEQ ID NO:2: of 5, 24, 43, 49, 70, 75, 76, 94, 119, 146, 148, 172, 175, 178, 180, 181, 208, 211, 245, 294, 353, 315, 375, 409, 309, 314, 369, 412 and/or an equivalent position in a homologous parent glucoamylase.

In some particularly preferred embodiments, the glucoamylase variant comprises at least one substitution selected from the group consisting of FSW, D24E, I43R, I43Y, I43S, I43F, Y47W, Y49N, Q70K, Q75R, R76L, P94L, N119P/T/Y/D, N146S/D/T/E/W/L, Q148V N171D, Q172C/ D/R/E/F/V/L/T, F175R/W/Y, W178K/N/Y, E180H/N/V/R, V181E/F/G/I/H, Q208A/T/N, S211H/M/L/R, R245E, R245M, R309W, V314F/G/H/K/P/R/Y, Y315F, S369F, T412K corresponding to the position set forth in SEQ ID NO:2 or 3 and/or an equivalent position in a homologous parent glucoamylase.

In further particular embodiments, the glucoamylase variant comprises at least one substitution of an amino acid residue selected from the positions corresponding to position 5, 43, 75, 76, 94, 108, 119, 124, 146, 148, 171, 172, 175, 178, 180, 181, 208, 211, 297, 314, 316, or 412 of SEQ ID NO: 2 or 3 and/or an equivalent position in a Trichoderma glucoamylase homologue. In some preferred embodiments, the substitution is at a position corresponding to position number 148, 172, 175, 178, 180, 208, 211, 314, 412 or 297 of SEQ ID NO:2 or 3 and/or an equivalent position in a Trichoderma glucoamylase homologue.

In some particularly preferred embodiments, the substitution is at a position corresponding to position number 108, 124, 171, 172, 208, 211, 314 or 316 of SEQ ID NO:2 or a homologous parent glucoamylase (e.g., Trichoderma glucoamylase homologue).

In some embodiments, the glucoamylase variants comprise multiple substitutions. Some of the multiple substitutions will include a substitution at one or more of the positions equivalent to and including the positions 24, 43, 44, 108, 124, 171, 175, 181, 208, 243, 292, 294, 297, 310, 314 and 363 of SEQ ID NO:2 or 3. Some preferred multiple substitutions will include one or more of the positions equivalent to and corresponding to positions 108, 124, 171, 208, 211 and 314 of SEQ ID NO:2 or 3. In some embodiments, the glucoamylase variants comprise multiple substitutions, such as Y47W and Y315F or Y47F and Y315W.

Some examples of multiple substitutions include substitutions at positions:
D24/I43/D44/F175/V181/V314/T363;
D24/Q208/I292/G294/K297/Y310;
V181/E243/I292/k297/N317/Y395;
D24/V181/Q208/G294/T363/N376/N409;
D24/V181/I292/G294/E243/N409; and
I43R/E243/I292/G294/K297 of SEQ ID NO:2 or 3 and equivalent positions in parent glucoamylases and particularly Trichoderma glucoamylase homologues.

Some preferred multiple substitutions include the substitutions:
D24E,L/I43F,R/D44H,N/F175H/V181K,L/V314D,H,K/ T363R;
D24L,W,Y/Q208F/I292F,N,V/G294A,I,Q/K297A/ Y310F,Q,R;
V181F,K,L/E243A,N,M,R,Y/I292F,L,N,V/K297A,D,H, M,N,Q/N317H/Y395Q,R
D24E,L,Y/V181F,K,L/Q208C,F/G294A,I,Q/T363R/ N376Q/N409K,W;
D24E,L,Y/V181F,K,L/I292F,L,N,V/G294A,I,Q/E243A, M,N,R,Y/N409K,W; and I43R/E243A,M,N,R,Y/I292F,L, N,V/G294A/K297A,D,H,M,N,Q,S,R,W,Y of SEQ ID NO:2 or 3 and equivalent positions in parent glucoamylases and particularly Trichoderma glucoamylase homologue.

A number of parent glucoamylases have been aligned with the amino acid sequence of TrGA. FIG. 4 includes the catalytic domain of the following parent glucoamylases Aspergillus awamori (AaGA) (SEQ ID NO:5); Aspergillus niger (AnGA) (SEQ ID NO:6); Aspergillus orzyae (AoGA) (SEQ ID NO:7), Humicola grisea (HgGA) (SEQ ID NO:8) and Hypocrea vinosa (HvGA) (SEQ ID NO:9). The % identity of the catalytic domains is represented in Table 1 below. In some embodiments, for example, the variant glucoamylase will be derived from a parent glucoamylase which is an Aspergillus glucoamylase and the variant will include at least one substitution in a position equivalent to a position set forth in SEQ ID NO:2 or 3 and particularly in a position corresponding to D4, F5, I12, D24, F29, I43, D44, P45, D46, Y47, Y49, W51, Y70, Q75, R76, P94, D100, K108, K114, F116, N119, R122, Q124, R125, G137, N146, Q148, Y169, N171, Q172, F175, W178, E180, V181, Q208, S211, W228, N242, E243, R245, I292, G294, K297, R309, Y310, D313, V314, Y315, Y316, N317, W321, K340, K341, T350, Q356, T363, S368, S369, N376, Y395, A398, S401, R408, N409, T412, H418, W421, R433, I436, and/or S451.

Endo-H removal of N-linked sugars in the Trichoderma reesei glucoamylase had a stabilizing effect (when looking at Tm). Thus, variants having an N171D substitution can have increased thermostability as compared to wildtype. In some embodiments, variants having one or more substitutions at sites having N-linked sugars are provided, including N171D in Trichoderma reesei (SEQ ID NO:2).

TABLE 1

|  | AaGA | AnGA | AoGA | HgGA | HvGA | TrGA |
|---|---|---|---|---|---|---|
| AaGA | 100 | 95 | 58 | 53 | 57 | 56 |
| AnGA |  | 100 | 59 | 53 | 57 | 56 |
| AoGA |  |  | 100 | 55 | 56 | 56 |
| HgGA |  |  |  | 100 | 61 | 63 |
| HvGA |  |  |  |  | 100 | 91 |
| TrGA |  |  |  |  |  | 100 |

The present invention also provides glucoamylase variants having at least one altered property (e.g., improved property) as compared to a parent glucoamylase and particularly to the TrGA. In some preferred embodiments, at least one altered property (e.g. improved property) is selected from the group consisting of acid stability, thermal stability and specific activity. Preferably, the altered property is increased acid stability, increased thermal stability and/or increased specific activity. Preferably, the increased thermal stability is at higher temperatures. In one embodiment, the increased pH stability is at high pH. In a further embodiment, the increased pH stability is at low pH.

The glucoamylase variants of the invention may also provide higher rates of starch hydrolysis at low substrate concentrations as compared to the parent glucoamylase. The variant may have a higher Vmax or lower Km than a parent glucoamylase when tested under the same conditions. For example the variant glucoamylase may have a higher Vmax at a temperature range of 25° C. to 70° C. (e.g. at 25° C. to 35° C.; 30° C.-35° C.; 40° C. to 50° C.; at 50° C. to 55° C. and at 55° C. to 62° C.). The Michaelis-Menten constant, Km and Vmax values can be easily determined using standard known procedures.

Thermal Stability (Thermostabile Variants):

In one aspect, the invention relates to a variant glucoamylase having altered thermal stability at altered temperatures as compared to a parent or wild type. Altered temperatures include increased or decreased temperatures. In some embodiments, the glucoamylase variant will have improved thermostability such as retaining at least 50%, 60%, 70%, 75%, 80%, 85%, 90%, 92%, 95%, 96%, 97%, 98% or 99% enzymatic activity after exposure to altered temperatures over a given time period, for example, at least 60 minutes, 120 minutes, 180 minutes, 240 minutes, 300 minutes, etc. In some embodiments, the variant has increased thermal stability compared to the parent glucoamylase at selected temperatures in the range of 40 to 80° C., also in the range of 50 to 75° C. and in the range of 60 to 70° C., and preferably at a pH range of 4.0 to 6.0. In some embodiments, the thermostability is determined as described in the Examples.

In some embodiments, particularly interesting variants in connection with an improvement in thermostability include one or more deletions, substitutions or insertions and particularly substitutions in the following positions in the amino acid sequence set forth in SEQ ID NO:2 or 3: D4, F5, I12, D24, F29, 143, D44, P45, D46, Y47, Y49, W51, Y70, Q75, R76, P94, D100, K108, K114, F116, N119, R122, Q124, R125, G137, N146, Q148, Y169, N171, Q172, F175, W178, E180, V181, Q208, S211, W228, N242, E243, R245, I292, G294, K297, R309, Y310, D313, V314, Y315, Y316, N317, W321, K340, K341, T350, Q356, T363, S368, S369, N376, Y395, A398, S401, R408, N409, T412, H418, W421, R433, I436, and/or S451 and/or an equivalent position in a parent glucoamylase. In some preferred embodiments, the parent glucoamylase will be a *Trichoderma* glucoamylase homologue and in further preferred embodiments, the parent glucoamylase will have at least 90%, at least 95% and at least 98% sequence identity to SEQ ID NO:2 or 3.

Chimeric Glucoamylases:

Glucoamylase variants of the invention may also include chimeric or hybrid glucoamylases with, for example a starch binding domain (SBD) from one glucoamylase and a catalytic domain and linker from another. For example, a hybrid glucoamylase can be made by swapping the SBD from AnGA with the SBD from TrGA, making a hybrid with the AnGA SBD and the TrGA catalytic domain and linker. Alternatively, the SBD and linker from AnGA can be swapped for the SBD and linker of TrGA.

Specific Activity:

In another aspect, the invention relates to a variant glucoamylase having altered specific activity as compared to a parent or wildtype glucoamylase.

In some embodiments, particularly interesting variants in connection with an improvement in specific activity include one or more deletions, substitutions or insertions and particularly substitutions in the following positions in the amino acid sequence set forth in SEQ ID NO:2 or 3: D4, F5, I12, D24, F29, 143, D44, P45, D46, Y47, Y49, W51, Y70, Q75, R76, P94, D100, K108, K114, F116, N119, R122, Q124, R125, G137, N146, Q148, Y169, N171, Q172, F175, W178, E180, V181, Q208, S211, W228, N242, E243, R245, I292, G294, K297, R309, Y310, D313, V314, Y315, Y316, N317, W321, K340, K341, T350, Q356, T363, S368, S369, N376, Y395, A398, S401, R408, N409, T412, H418, W421, R433, I436, and/or S451 and/or an equivalent position in a parent glucoamylase. In some embodiments, variants of the invention having improved specific activity include a substitution in the following positions in the amino acid sequence set forth in SEQ ID NO: 2 or 3: D4, D24, 143, D44, Y70, Q75, R76, D100, K108, N119, Q124, N146, Q148, N171, Q172, F175, V181, Q208, S211, E243, R245, I292, G294, K297, V314, Y316, N317, K340, K341, T350, Q356, T363, S368, N376, Y395, A398, S401, N409, T412, I436, and/or S451 and/or an equivalent position in a parent glucoamylase. In some preferred embodiments, the parent glucoamylase will comprise a sequence having at least 90% or 95% sequence identity to the sequence of SEQ ID NO:2 or 3.

Polynucleotides:

The present invention also relates to isolated polynucleotides encoding a variant glucoamylase of the invention. The polynucleotides encoding a variant glucoamylase may be prepared by established techniques known in the art. The polynucleotides may be prepared synthetically, such as by an automatic DNA synthesizer. The DNA sequence may be of mixed genomic (or cDNA) and synthetic origin prepared by ligating fragments together. The polynucleotides may also be prepared by polymerase chain reaction (PCR) using specific primers. In general, reference is made to Minshull J., et al., (2004), Engineered protein function by selective amino acid diversification, Methods 32(4):416-427). Also a number of companies now synthesize DNA such as Geneart AG, Regensburg, Germany.

The present invention also provides isolated polynucleotides comprising a nucleotide sequence (i) having at least 70% identity to SEQ ID NO:4, or (ii) being capable of hybridizing to a probe derived from the nucleotide sequence set forth in SEQ ID NO:4, under conditions of intermediate to high stringency, or (iii) being complementary to a nucleotide sequence having at least 90% sequence identity to the sequence set forth in SEQ ID NO:4. Probes useful according to the invention may include at least 50, 100, 150, 200, 250, 300 or more contiguous nucleotides of SEQ ID NO:4.

The present invention further provides isolated polynucleotides that encode variant glucoamylases which comprise an amino acid sequence comprising at least 80% amino acid sequence identity to SEQ ID NO:2 or 3. In some embodiments, the variant glucoamylases have at least 80% amino acid sequence identity to SEQ ID NO:2 or 3. In some embodiments, the variant glucoamylases have at least 90% amino acid sequence identity to SEQ ID NO:2. In some embodiments, the variant glucoamylases have at least 93% amino acid sequence identity to SEQ ID NO:2. In some embodiments, the variant glucoamylases have at least 95% amino acid sequence identity to SEQ ID NO:2. In some embodiments, the variant glucoamylases have at least 97% amino acid sequence identity to SEQ ID NO:2. In some embodiments, the variant glucoamylases have at least 98% amino acid sequence identity to SEQ ID NO:2. In some embodiments, the variant glucoamylases have at least 99% amino acid sequence identity to SEQ ID NO:2. The present invention also provides expression vectors comprising any of the polynucleotides provided above.

The present invention also provides fragments (i.e., portions) of the DNA encoding the variant glucoamylases provided herein. These fragments find use in obtaining partial length DNA fragments capable of being used to isolate or identify polynucleotides encoding mature glucoamylase enzymes described herein from filamentous fungal cells (e.g., *Trichoderma, Aspergillus, Fusarium, Penicillium, Schizosaccharomyces,* and *Humicola*), or a segment thereof having glucoamylase activity. In some embodiments, fragments of the DNA may comprise at least 50, 100, 150, 200, 250 300 or more contiguous nucleotides. In some embodiments, portions of the DNA provided in SEQ ID NO:4 find use in obtaining parent glucoamylase and particularly *Trichoderma* glucoamylase homologues from other species, such as filamentous fungi which encode a glucoamylase.

DNA Constructs and Vectors:

According to one embodiment of the invention, a DNA construct comprising a polynucleotide as described above encoding a variant glucoamylase encompassed by the invention and operably linked to a promoter sequence is assembled to transfer into a host cell.

The DNA construct may be introduced into a host cell using a vector. The vector may be any vector which when introduced into a host cell is preferably integrated into the host cell genome and is replicated. Vectors include cloning vectors, expression vectors, shuttle vectors, plasmids, phage particles, cassettes and the like. In some preferred embodiments, the vector is an expression vector that comprises regulatory sequences operably linked to the glucoamylase coding sequence.

Examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396-428 and U.S. Pat. No. 5,874,276. Reference is also made to the Fungal Genetics Stock Center Catalogue of Strains (FGSC, <www.fgsc.net>) for a list of vectors. Particularly useful vectors include vectors obtained from for example Invitrogen and Promega.

Specific vectors suitable for use in fungal host cells include vectors such as pFB6, pBR322, pUC18, pUC100, pDONR™201, pDONR™221, pENTR™, pGEM®3Z and pGEM®4Z. A general purpose expression vector useful in *Aspergillus* includes pRAX with a glaA promoter, and in *Hypocrea/Trichoderma* includes pTrex3g with a cbh1 promoter.

Suitable plasmids for use in bacterial cells include pBR322 and pUC19 permitting replication in *E. coli* and pE194 for example permitting replication in *Bacillus*.

In some preferred embodiments, the promoter shows transcriptional activity in a bacterial or a fungal host cell and may be derived from genes encoding proteins either homologous or heterologous to the host cell. The promoter may be a mutant, a truncated and/or a hybrid promoter. The above-mentioned promoters are known in the art.

Examples of suitable promoters useful in fungal cells and particularly filamentous fungal cells such as *Trichoderma* or *Aspergillus* cells include such exemplary promoters as the *T. reesei* promoters cbh1, cbh2, egl1, egl2, eg5, xln1 and xln2. Other examples of useful promoters include promoters from *A. awamori* and *A. niger* glucoamylase genes (glaA) (See, Nunberg et al., (1984) *Mol. Cell Biol.* 4:2306-2315 and Boel et al., (1984) *EMBO J.* 3:1581-1585), *A. oryzae* TAKA amylase promoter, the TPI (triose phosphate isomerase) promoter from *S. cerevisiae*, the promoter from *Aspergillus nidulans* acetamidase genes and *Rhizomucor miehei* lipase genes.

Examples of suitable promoters useful in bacterial cells include those obtained from the *E. coli* lac operon; *Bacillus licheniformis* alpha amylase gene (amyL), *B. stearothermophilus* amylase gene (amyM); *Bacillus subtilis* xylA and xylB genes, the beta-lactamase gene, and the tac promoter.

In one embodiment, the promoter is one that is native to the host cell. For example, when *T. reesei* is the host, the promoter is a native *T. reesei* promoter. In another embodiment, the promoter is one that is heterologous to the fungal host cell. In some embodiments the promoter will be the parent glucoamylase promoter such as the TrGA promoter.

In some embodiments, the DNA construct includes nucleic acids coding for a signal sequence that is an amino acid sequence linked to the amino terminus of the polypeptide which directs the encoded polypeptide into the cell's secretory pathway. The 5' end of the coding sequence of the nucleic acid sequence may naturally include a signal peptide coding region which is naturally linked in translation reading frame with the segment of the glucoamylase coding sequence which encodes the secreted glucoamylase or the 5' end of the coding sequence of the nucleic acid sequence may include a signal peptide which is foreign to the coding sequence. In some embodiments, the DNA construct includes a signal sequence that is naturally associated with a parent glucoamylase gene from which a variant glucoamylase has been obtained. In some embodiments the signal sequence will be the sequence depicted in SEQ ID NO:1 or a sequence having at least 90%, at least 94% and at least 98% sequence identity thereto. Effective signal sequences may include the signal sequences obtained from glucoamylases of other filamentous fungal enzymes, such as from *Trichoderma* (*T. reesei* glucoamylase), *Humicola* (*H. insolens* cellulase or *H. grisea* glucoamylase), *Aspergillus* (*A. niger* glucoamylase and *A. oryzae* TAKA amylase), and *Rhizopus*.

In additional embodiments, a DNA construct or vector comprising a signal sequence and a promoter sequence to be introduced into a host cell are derived from the same source. In some embodiments, the native glucoamylase signal sequence of a *Trichoderma* glucoamylase homologue, such as a signal sequence from a *Hypocrea* strain may be used.

In some embodiments, the expression vector also includes a termination sequence. Any terminator sequence functional in the host cell may be used in the present invention. In one embodiment, the termination sequence and the promoter sequence are derived from the same source. In another embodiment, the termination sequence is homologous to the host cell. Useful terminator sequence include terminator sequences obtained from the genes of *Trichoderma reesei* cbh1; *A. niger* or *A. awamori* glucoamylase (Nunberg et al. (1984) supra, and Boel et al., (1984) supra), *Aspergillus nidulans* anthranilate synthase, *Aspergillus oryzae* TAKA amylase, or *A. nidulans* trpC (Punt et al., (1987) *Gene* 56:117-124).

In some embodiments, an expression vector includes a selectable marker. Examples of preferred selectable markers include ones which confer antimicrobial resistance (e.g., hygromycin and phleomycin). Nutritional selective markers also find use in the present invention including those markers known in the art as amdS (acetamidase), argB (ornithine carbamoyltransferase) and pyrG (orotidine-5'phosphate decarboxylase). Markers useful in vector systems for transformation of *Trichoderma* are known in the art (See, e.g., Finkelstein, chapter 6 in BIOTECHNOLOGY OF FILAMENTOUS FUNGI, Finkelstein et al. Eds. Butterworth-Heinemann, Boston, Mass. (1992); Kinghorn et al. (1992) APPLIED MOLECULAR GENETICS OF FILAMENTOUS FUNGI, Blackie Academic and Professional, Chapman and Hall, London; Berges and Barreau (1991) Curr. Genet. 19:359-365; and van Hartingsveldt et al., (1987) Mol. Gen. Genet. 206:71-75). In a preferred embodiment, the selective marker is the amdS gene, which encodes the enzyme acetamidase, allowing transformed cells to grow on acetamide as a nitrogen source. The use of *A. nidulans* amdS gene as a selective marker is described in Kelley et al., (1985) *EMBO J.* 4:475-479 and Penttilä et al., (1987) *Gene* 61:155-164.

Methods used to ligate the DNA construct comprising a nucleic acid sequence encoding a variant glucoamylase, a promoter, a terminator and other sequences and to insert them into a suitable vector are well known in the art. Linking is generally accomplished by ligation at convenient restriction sites. If such sites do not exist, synthetic oligonucleotide linkers are used in accordance with conventional practice. (See, Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology).

Host Cells:

The present invention also relates to host cells comprising a polynucleotide encoding a variant glucoamylase of the invention, which are used to produce the glucoamylases of the invention. In some preferred embodiments, the host cells are selected from bacterial, fungal, plant and yeast cells. The term host cell includes both the cells, progeny of the cells and protoplasts created from the cells which are used to produce a variant glucoamylase according to the invention.

In some embodiments, the host cells are fungal cells and preferably filamentous fungal host cells. The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., (1984) Appl. Microbiol. Biotechnol 20:46-53; ATCC No. 56765 and ATCC No. 26921); *Penicillium* sp., *Humicola* sp. (e.g., *H. insolens*, *H. lanuginosa* and *H. grisea*); *Chrysosporium* sp. (e.g., *C. lucknowense*), *Gliocladium* sp., *Aspergillus* sp. (e.g., *A. oryzae*, *A. niger*, *A sojae*, *A. japonicus*, *A. nidulans*, and *A. awamori*) (Ward et al., (1993) Appl. Microbiol. Biotechnol. 39:738-743 and Goedegebuur et al., (2002) Genet 41:89-98), *Fusarium* sp., (e.g. *F. roseum*, *F. graminum F. cerealis*, *F. oxysporuim* and *F. venenatum*), *Neurospora* sp., (*N. crassa*), *Hypocrea* sp., *Mucor* sp., (*M. miehei*), *Rhizopus* sp. and *Emericella* sp. (See also, Innis et al., (1985) *Sci.* 228:21-26). The term "*Trichoderma*" or "*Trichoderma* sp." or "*Trichoderma* spp." refer to any fungal genus previously or currently classified as *Trichoderma*.

In some embodiments, the host cells will be gram-positive bacterial cells. Non-limiting examples include strains of *Streptomyces*, (e.g., *S. lividans*, *S. coelicolor* and *S. griseus*) and *Bacillus*. As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*."

In some embodiments the host cell is a gram-negative bacterial strain, such as *E. coli* or *Pseudomonas* sp. In other embodiments, the host cells may be yeast cells such as *Saccharomyces* sp., *Schizosaccharomyces* sp., *Pichia* sp., or *Candida* sp.

In other embodiments, the host cell will be a genetically engineered host cell wherein native genes have been inactivated, for example by deletion in bacterial or fungal cells. Where it is desired to obtain a fungal host cell having one or more inactivated genes known methods may be used (e.g. methods disclosed in U.S. Pat. No. 5,246,853, U.S. Pat. No. 5,475,101 and WO 92/06209). Gene inactivation may be accomplished by complete or partial deletion, by insertional inactivation or by any other means which renders a gene nonfunctional for its intended purpose (such that the gene is prevented from expression of a functional protein). In some preferred embodiments, when the host cell is a *Trichoderma* cell and particularly a *T. reesei* host cell, the cbh1, cbh2, egl1 and egl2 genes will be inactivated and preferably deleted. Particularly preferred *Trichoderma reesei* host cells having quad-deleted proteins are set forth and described in U.S. Pat. No. 5,847,276 and WO 05/001036. In other embodiments, the host cell is a protease deficient or protease minus strain.

Transformation of Host Cells:

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (See, e.g., Ausubel et al., (1987), supra, chapter 9; and Sambrook (1989) supra, and Campbell et al., (1989) *Curr. Genet.* 16:53-56).

Transformation methods for *Bacillus* are disclosed in numerous references including Anagnostopoulos C and J. Spizizen (1961) J. Bacteriol. 81:741-746 and WO 02/14490.

Transformation methods for *Aspergillus* are described in Yelton et al (1984) Proc. Natl. Acad. Sci. USA 81:1470-1474; Berka et al., (1991) in Applications of Enzyme Biotechnology, Eds. Kelly and Baldwin, Plenum Press (NY); Cao et al., (2000) *Sci.* 9:991-1001; Campbell et al., (1989) *Curr. Genet.* 16:53-56 and EP 238 023. The expression of heterologous protein in *Trichoderma* is described in U.S. Pat. No. 6,022,725; U.S. Pat. No. 6,268,328; Harkki et al. (1991); Enzyme Microb. Technol. 13:227-233; Harkki et al., (1989) *Bio Technol*. 7:596-603; EP 244,234; EP 215,594; and Nevalainen et al., "*The Molecular Biology of Trichoderma and its Application to the Expression of Both Homologous and Heterologous Genes*", in MOLECULAR INDUSTRIAL MYCOLOGY, Eds. Leong and Berka, Marcel Dekker Inc., NY (1992) pp. 129-148). Reference is also made to WO96/00787 and Bajar et al., (1991) Proc. Natl. Acad. Sci. USA 88:8202-28212 for transformation of *Fusarium* strains.

In one specific embodiment, the preparation of *Trichoderma* sp. for transformation involves the preparation of protoplasts from fungal mycelia (See, Campbell et al., (1989) *Curr. Genet.* 16:53-56; Pentilla et al., (1987) *Gene* 61:155-164). *Agrobacterium tumefaciens*-mediated transformation of filamentous fungi is known (See, de Groot et al., (1998) *Nat. Biotechnol.* 16:839-842). Reference is also made to U.S. Pat. No. 6,022,725 and U.S. Pat. No. 6,268,328 for transformation procedures used with filamentous fungal hosts.

Preferably, genetically stable transformants are constructed with vector systems whereby the nucleic acid encoding the variant glucoamylase is stably integrated into a host strain chromosome. Transformants are then purified by known techniques.

In some further embodiments, the host cells are plant cells, such as cells from a monocot plant (e.g. corn, wheat and sorghum) or cells from a dicot plant (e.g. soybean). Methods for making DNA constructs useful in transformation of plants and methods for plant transformation are known. Some of these methods include *Agrobacterium tumefaciens* mediate gene transfer; microprojectile bombardment, PEG mediated transformation of protoplasts, electroporation and the like. Reference is made to (U.S. Pat. No. 6,803,499, U.S. Pat. No. 6,777,589; Fromm et al (1990) *Biotechnol.* 8:833-839; Potrykus et al (1985) *Mol. Gen. Genet.* 199:169-177.

Production of Proteins:

The present invention further relates to methods of producing the variant glucoamylases comprising transforming a host cell with an expression vector comprising a polynucleotide encoding a variant glucoamylase according to the invention, optionally culturing the host cell under conditions suitable for production of the variant glucoamylase and optionally recovering the glucoamylase.

In the expression and production methods of the present invention the host cells are cultured under suitable conditions in shake flask cultivation, small scale or large scale fermentations (including continuous, batch and fed batch fermentations) in laboratory or industrial fermentors, with suitable medium containing physiological salts and nutrients (See, e.g., Pourquie, J. et al., BIOCHEMISTRY AND GENETICS OF CELLULOSE DEGRADATION, eds. Aubert, J. P. et al., Academic Press, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth) find use in the present invention. Preferred culture conditions for bacterial and filamentous fungal cells are known in the art and may be found in the scientific literature and/or from the source of the fungi such as the American Type Culture Collection and Fungal Genetics Stock Center. In cases where a glucoamylase coding sequence is under the control of an inducible promoter, the inducing agent (e.g., a sugar, metal salt or antimicrobial), is added to the medium at a concentration effective to induce glucoamylase expression.

In some embodiments, the present invention relates to methods of producing the variant glucoamylase comprising cultivating a plant or plant cell comprising a polynucleotide encoding a variant glucoamylase according to the invention under conditions suitable for the production of the variant and optionally recovering the glucoamylase.

In some embodiments, in order to evaluate the expression of a variant glucoamylase by a cell line that has been transformed with a polynucleotide encoding a variant glucoamylase encompassed by the invention, assays are carried out at the protein level, the RNA level and/or by use of functional bioassays particular to glucoamylase activity and/or production. Some of these assays include Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a variant glucoamylase may be measured in a sample directly, for example, by assays directly measuring reducing sugars such as glucose in the culture medium and by assays for measuring glucoamylase activity, expression and/or production. In particular, glucoamylase activity may be assayed by the 3,5-dinitrosalicylic acid (DNS) method (See, Goto et al., (1994) *Biosci. Biotechnol. Biochem.* 58:49-54). In additional embodiments, protein expression, is evaluated by immunological methods, such as immunohistochemical staining of cells, tissue sections or immunoassay of tissue culture medium, (e.g., by Western blot or ELISA). Such immunoassays can be used to qualitatively and quantitatively evaluate expression of a glucoamylase. The details of such methods are known to those of skill in the art and many reagents for practicing such methods are commercially available.

The glucoamylases of the present invention may be recovered or purified from culture media by a variety of procedures known in the art including centrifugation, filtration, extraction, precipitation and the like.

Compositions:

The variant glucoamylases may be used in enzyme compositions including but not limited to starch hydrolyzing and saccharifying compositions, cleaning and detergent compositions (e.g., laundry detergents, dish washing detergents, and hard surface cleaning compositions), alcohol fermentation compositions, and in animal feed compositions. Further the variant glucoamylases may be used in baking applications, such as bread and cake production, brewing, healthcare, textile, environmental waste conversion processes, biopulp processing, and biomass conversion applications.

In some embodiments, an enzyme composition including a variant glucoamylase encompassed by the invention obtained in culture media or recovered and purified from the culture medium will be optionally used in combination with any one or combination of the following enzymes—alpha amylases, proteases, pullulanases, isoamylases, cellulases, hemicellulases, xylanases, cyclodextrin glycotransferases, lipases, phytases, laccases, oxidases, esterases, cutinases, xylanases, granular starch hydrolyzing enzyme and other glucoamylases. In one embodiment, the proteases are acid fungal proteases (AFP). In a further embodiment, the acid fungal proteases are from *Trichoderma* (e.g., NSP-24, see also US 2006/015342, published Jul. 13, 2006, SEQ ID NO:10, incorporated by reference). In a further embodiment, the phytase is from Buttiauxiella.spp. (e.g., BP-17, see also variants disclosed in PCT patent publication WO 2006/043178).

In some particularly preferred compositions the variant glucoamylases of the invention will be combined with an alpha amylase, such as fungal alpha amylases (e.g. *Aspergillus* sp.) or bacterial alpha amylases (e.g. *Bacillus* sp. such as *B. stearothermophilus, B. amyloliquefaciens* and *B. licheniformis*) and variants and hybrids thereof. In one embodiment the alpha amylase is an acid stable alpha amylase. In one embodiment, the alpha amylase is a granular starch hydrolyzing enzyme (GSHE). In one embodiment, the alpha amylase is *Aspergillus* kawachi alpha amylase (AKAA), see U.S. Pat. No. 7,037,704. Commercially available alpha amylases contemplated for use in the compositions of the invention are known and include GZYME G997, SPEZYME FRED, SPEZYME XTRA, STARGEN (Danisco US, Inc, Genencor Division), TERMAMYL 120-L and SUPRA (Novozymes, Biotech.) and VIRIDIUM (Diversa).

In other preferred embodiments, the variant glucoamylases of the invention may be combined with other glucoamylases. In some embodiments, the glucoamylases of the invention will be combined with one or more glucoamylases derived from strains of *Aspergillus* or variants thereof, such as *A. oryzae, A. niger, A. kawachi,* and *A. awamori*; glucoamylases derived from strains of *Humicola* or variants thereof, particularly *H. grisea,* such as the glucoamylase having at least 90%, 93%, 95%, 96%, 97%, 98% and 99% sequence identity to SEQ ID NO: 3 disclosed in WO 05/052148; glucoamylases derived from strains of *Talaromyces* or variants thereof, particularly *T. emersonii*; glucoamylases derived from strains of *Athelia* and particularly *A. rolfsii*; glucoamylases derived from strains of *Penicillium*, particularly *P. chrysogenum*.

Uses:

In particular, the variant glucoamylases may be used for starch conversion processes, and particularly in the production of dextrose for fructose syrups, specialty sugars and in alcohol and other end-product (e.g. organic acid, ascorbic acid, and amino acids) production from fermentation of starch containing substrates (G.M.A van Beynum et al., Eds. (1985) STARCH CONVERSION TECHNOLOGY, Marcel Dekker Inc. NY). Dextrins produced using variant glucoamylase compositions of the invention may result in glucose yields of at least 80%, at least 85%, at least 90% and at least 95%. Production of alcohol from the fermentation of starch substrates using glucoamylases encompassed by the invention may include the production of fuel alcohol or portable alcohol. In some embodiments, the production of alcohol will be greater when the variant glucoamylase is used under the same conditions as the parent glucoamylase. In some embodiments, the production of alcohol will be between about 0.5% and 2.5% better, including but not limited to 0.6%, 0.7%, 0.8%, 0.9%, 1.0%, 1.1%, 1.2%, 1.3%, 1.4%, 1.5%, 1.6%. 1.7%, 1.8%, 1.9%, 2.0%, 2.1%, 2.2%, 2.3%, and 2.4% more alcohol than the parent glucoamylase.

In one preferred embodiment, the variant glucoamylases of the invention will find use in the hydrolysis of starch from various plant-based substrates, which are used for alcohol production. In some preferred embodiments, the plant-based substrates will include corn, wheat, barley, rye, milo, rice, sugar cane, potatoes and combinations thereof. In some embodiments, the plant-based substrate will be fractionated plant material, for example a cereal grain such as corn, which is fractionated into components such as fiber, germ, protein and starch (endosperm) (U.S. Pat. No. 6,254,914 and U.S. Pat. No. 6,899,910). Methods of alcohol fermentations are described in THE ALCOHOL TEXTBOOK, A REFERENCE FOR THE BEVERAGE, FUEL AND INDUSTRIAL ALCOHOL INDUSTRIES, 3$^{rd}$ Ed., Eds K. A. Jacques et al., 1999, Nottingham University Press, UK. In certain preferred embodiments, the alcohol will be ethanol. In particular, alcohol fermentation production processes are characterized as wet milling or dry milling processes. In some embodiments, the variant glucoamylase will be used in a wet milling fermentation process and in other embodiments the variant glucoamylase will find use in a dry milling process.

Dry grain milling involves a number of basic steps, which generally include: grinding, cooking, liquefaction, saccharification, fermentation and separation of liquid and solids to produce alcohol and other co-products. Plant material and particularly whole cereal grains, such as corn, wheat or rye are ground. In some cases the grain may be first fractionated into component parts. The ground plant material may be milled to obtain a coarse or fine particle. The ground plant material is mixed with liquid (e.g. water and/or thin stillage) in a slurry tank. The slurry is subjected to high temperatures (e.g. 90° C. to 105° C. or higher) in a jet cooker along with liquefying enzymes (e.g. alpha amylases) to solublize and hydrolyze the starch in the grain to dextrins. The mixture is cooled down and further treated with saccharifying enzymes, such as glucoamylases encompassed by the instant invention, to produce glucose. The mash containing glucose may then be fermented for approximately 24 to 120 hours in the presence of fermentation microorganisms, such as ethanol producing microorganism and particularly yeast (*Saccharomyces* spp). The solids in the mash are separated from the liquid phase and alcohol such as ethanol and useful co-products such as distillers' grains are obtained.

In some embodiments, the saccharification step and fermentation step are combined and the process is referred to as simultaneous saccharification and fermentation or simultaneous saccharification, yeast propagation and fermentation.

In other embodiments, the variant glucoamylase is used in a process for starch hydrolysis wherein the temperature of the process is carried out at a temperature of between 30° C. and 75° C. and also at a temperature of between 40° C. and 65° C. at a pH range of between pH 3.0 and pH 6.5. The fermentation processes in some embodiments include milling of a cereal grain or fractionated grain and combining the ground cereal grain with liquid to form a slurry which is then mixed in a single vessel with a variant glucoamylase according to the invention and optionally other enzymes such as but not limited to alpha amylases, other glucoamylases, phytases, proteases, pullulanases, isoamylases or other enzymes having granular starch hydrolyzing activity and yeast to produce ethanol and other co-products (U.S. Pat. No. 4,514,496, WO 04/081193 and WO 04/080923).

In some embodiments, the invention pertains to a method of saccharifying a liquid starch solution, which comprises an enzymatic saccharification step using a variant glucoamylase of the invention.

The present invention also provides an animal feed comprising at least one variant glucoamylase encompassed by the invention. Methods of using a glucoamylase enzyme in the production of feeds comprising starch are provided in WO 03/049550, filed Dec. 13, 2002 (herein incorporated by reference in its entirety. Briefly, the glucoamylase variant is admixed with a feed comprising starch. The glucoamylase is capable of degrading resistant starch for use by the animal.

Other objects and advantages of the present invention are apparent from the present Specification.

EXPERIMENTAL

In the disclosure and experimental section which follows, the following abbreviations apply: GA (glucoamylase); GAU (glucoamylase unit); wt % (weight percent); ° C. (degrees Centigrade); rpm (revolutions per minute); $H_2O$ (water); $dH_2O$ (deionized water); $dIH_2O$ (deionized water, Milli-Q filtration); aa or AA (amino acid); bp (base pair); kb (kilobase pair); kD (kilodaltons); g or gm (grams); µg (micrograms); mg (milligrams); µL (microliters); ml and mL (milliliters); mm (millimeters); µm (micrometer); M (molar); mM (millimolar); µM (micromolar); U (units); V (volts); MW (molecular weight); sec(s) or s(s) (second/seconds); min(s) or m(s) (minute/minutes); hr(s) or h(s) (hour/hours); DO (dissolved oxygen); ABS (Absorbance); EtOH (ethanol); PSS (physiological salt solution; m/v (mass/volume); and MTP (microtiter plate); N (Normal); DP1 (monosaccharides); DP2 (disaccharides); DP>3 (oligosaccharides, sugars having a degree of polymerization greater than 3); ppm (parts per million).

The methods used to provide variants are described below. However, it should be noted that different methods may be used to provide variants of a parent molecule and the invention is not limited to the methods used in the examples. It is intended that any suitable means for making variants and selection of variants may be used.

pNPG Glucoamylase Activity Assay for 96-Well Microtiter Plates:

The reagent solutions were: NaAc buffer: 200 mM sodium acetate buffer pH 4.5; Substrate: 50 mM p-nitrophenyl-α-D-glucopyranoside (Sigma N-1377) in NaAc buffer (0.3 g/20 ml) and stop solution: 800 mM glycine-NaOH buffer pH 10. 30 µl filtered supernatant was placed in a fresh 96-well flat bottom MTP. To each well 50 µl NaAc buffer and 120 µl substrate was added and incubated for 30 minutes at 50° C. (Thermolab systems iEMS Incubator/shaker HT). The reaction was terminated by adding 100 µl stop solution. The absorbance was measured at 405 nm in a MTP-reader (Molecular Devices Spectramax 384 plus) and the activity was calculated using a molar extinction coefficient of 0.011 µM/cm.

Thermal Stability Assay:

Crude supernatant (100 µl) was added to 100 µl 50 mM NaAc buffer pH 4.5. the sample was equally divided over 2 MTP. One MTP (initial plate) was incubated for 1 hr at 4° C. and the other MTP (residual plate) was incubated at 60° C. (Thermolab systems iEMS Incubator/Shaker HT) for 1 hr. The residual plate was chilled for 15 min on ice. Activity is measured on both plates using the ethanol application assay described below, with the following modification: the amount of sample taken for the thermostability assay is 25 µl and the amount of 30 mM NaAc buffer pH 4.0 is 350.

Thermostability is calculated as % residual activity as follows:

$$\frac{\text{ABS (340) residual} - \text{blank}}{\text{ABS (340) initial} - \text{blank}} \times 100\%.$$

The crude supernatant material is tested for remaining glucose in the culture medium after the growth period. If remaining glucose is found, the absorbance value is subtracted from the measured absorbance values of both the initial activity as the residual activity.

Bradford Assay for Protein Quantification in 96-Well Microtiter Plates:

The reagent solution was Bradford Quickstart work solution (BioRad cat#500-0205). 100 µl of 10 kD-filtered supernatant was placed in a fresh 96-well flat bottom plate. To each well 200 µl reagent was added and incubated for 5 minutes at room temperature. The absorbance was measured at 595 nm in a MTP-reader (Molecular Devices Spectramax 384 plus). Protein concentrations were calculated according to a Bovine Serum Albumin (BSA) (0-50 µg/ml) standard curve.

Hexokinase Activity Assay:

Hexokinase cocktail: 10-15 minutes prior to use, 90 ml water was added to a BoatlL container glucose HK R1 (IL test glucose (HK) kit, Instrument Laboratory #182507-40) and gently mixed. 85 µl of Hexokinase cocktail was added to 100 µl of dH$_2$O. 150 of sample was added to the mixtures and incubated for 5 mins in the dark at room temperature. Absorbance was read at 340 nm in a MTP-reader. Glucose concentrations were calculated according to a glucose (0-1 mg/ml) standard curve.

Assay Conditions Ethanol Application:

8% stock solution: 8 g of soluble corn starch (Sigma #S4180) was suspended in 40 ml dH$_2$O at room temperature. 50 ml of boiling dH$_2$O was added to the slurry in a 250 ml flask and cooked for 5 mins. The starch solution was cooled to 25° C. and the volume adjusted to 100 ml with dH$_2$O.

Stop Solution: 800 mM Glycine-NaOH Buffer, pH 10.0.

4% (m/v) soluble starch working solution: stock solution was diluted (1:1) with 100 mM sodium acetate buffer pH 4.0.

50 µl 30 mM NaAc buffer pH 4.0 was placed in a fresh 96-well flat bottom plate. To each well 120 µl 4% soluble corn starch and 100 10 kD-filtered supernatant was added and incubated for 2 hrs at 32° C. 900 rpm (Thermolabsystems iEMS Incubator/Shaker HT). The reaction was stopped by adding 90 µl 4° C.-cold Stop Solution. The sample was placed on ice. Starch was spun down at 716×g at 15° C. for 5 mins (SIGMA 6K15) and 15 µl supernatant was used in the Hexokinase activity assay described above to determine the glucose content.

Assay Conditions Sweetener Application:

8% stock solution: 8 g of soluble starch (Sigma #S4180) was suspended in 40 ml water at room temperature. 50 ml of boiling dH$_2$O was added to the slurry in a 250 ml flask and cooked for 5 mins. The starch solution was cooled to 25° C. and the volume adjusted to 100 ml with dH$_2$O.

Stop solution: 800 mM Glycine-NaOH buffer, pH 10.0.

4% (m/v) soluble starch working solution: stock solution was diluted (1:1) with 100 mM sodium acetate buffer pH 4.5.

50 µl 80 mM NaAc buffer pH 4.5 was placed in a fresh 96-well flat bottom plate. To each well 120 µl 4% soluble cornstarch and 5 µl 10 kD-filtered supernatant was added and incubated for 1 hr at 60° C. The reaction was stopped by adding 90 µl 4° C. cold Stop Solution. The sample was placed on ice for 30 mins. Starch was spun down at 716 rpm at 15° C. for 5 minutes (Sigma 6K15, centrifuge) and 15 µl of the supernatant was used in the Hexokinase activity assay described herein to determine glucose content.

EXAMPLES

The following examples are provided in order to demonstrate and further illustrate certain preferred embodiments and aspect of the present invention and are not to be construed as limiting the scope thereof.

Example 1

Construction of the pREP3Y-TrGA Vector

Figure 3A:
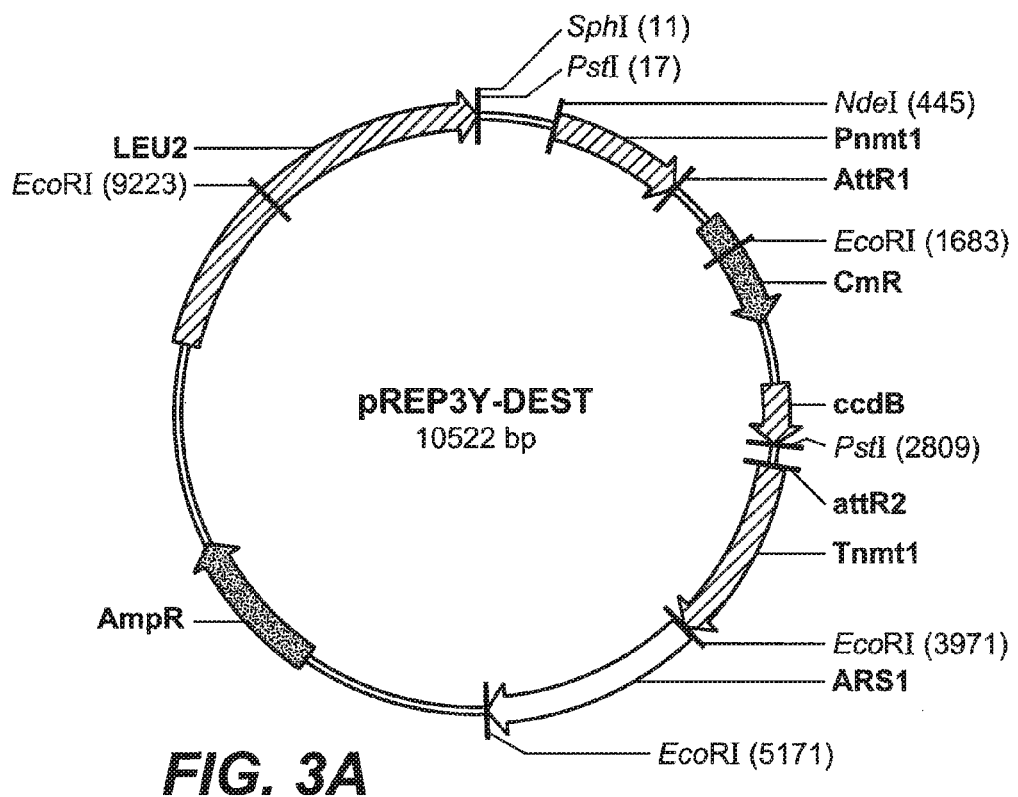
FIG. 3A illustrates the plasmids pREP3Y-DEST and FIG. 3B illustrates the plasmids pREP3Y-TrGA.
Figure 3B:
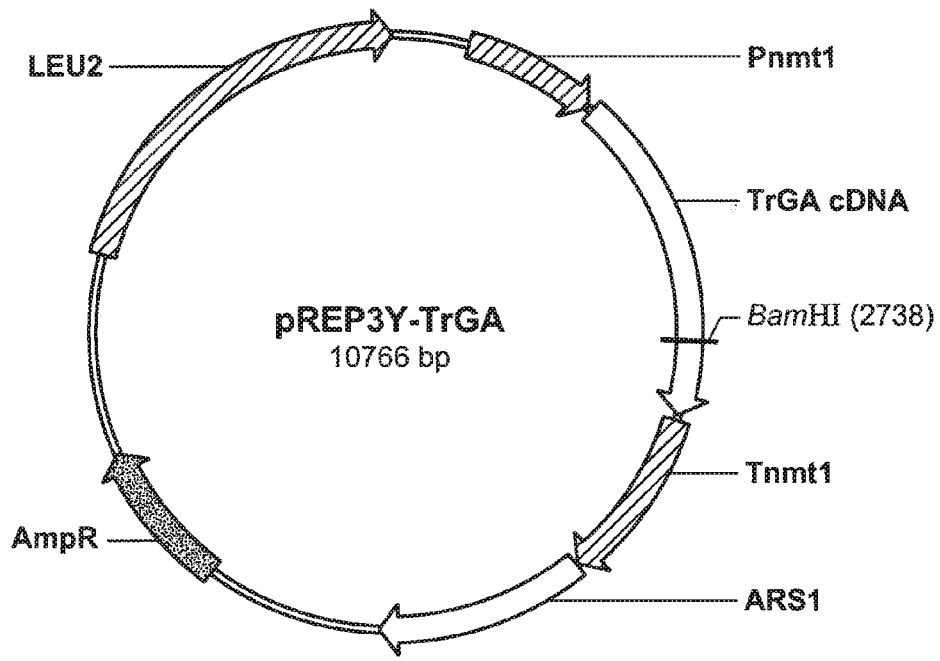

The TrGA expression cassette composed of the DNA sequence (SEQ ID NO: 4) encoding the TrGA signal peptide, the pro-sequence, and the mature protein, including the catalytic domain, linker region and starch binding domain, was cloned into pDONR™201, a Gateway® Entry vector (Invitrogen, Carlsbad, Calif., USA). The TrGA expression cassette was cloned into the Gateway compatible destination vector pREP3Y-DEST (FIG. 3) by the Gateway® LR recombination reaction.

The pRep3Y-TrGA expression vector (FIG. 3B) enabled the expression of the TrGA protein (SEQ ID NO:2) in *Schizosaccharomyces pombe*.

Sixty-five TrGA site saturated mutagenesis (SSM) libraries were constructed using the pDONR-TrGA entry vector (FIG. 2) as a template and the primers listed in Table 2. The mutagenesis primers used in the experiments all contain the triple DNA sequence code NNS (N=A,C,T,G and S=C or G) at the position that corresponds with the codon of the TrGA sequence to be mutated (SEQ ID NO:2) and initiated random incorporation of nucleotides at that position. Construction of each SSM library started with two PCR amplifications using the Gateway forward (pDONR201—FW) and a specific reverse mutagenesis primer (Table 3), and Gateway reversed (pDONR201—RV) primer and a specific forward mutagenesis primer (Table 2) (equal positions for the mutagenesis primers). Phusion high fidelity DNA polymerase (Finnzymes OY, Espoo, Finland) was used for PCR amplification (0.204 primers, 25 cycles) according to the protocol provided by Finnzymes. Briefly, 1 µl (SEQ ID NO:1), DNA fragment of both specific PCR mixes, both targeted at the same codon were added to 48 µl of fresh PCR reaction solution together with primers Gateway FW and Gateway RV (Invitrogen) and mixed. This fusion PCR amplification (22 cycles) resulted in a linear expression cassette DNA fragment with a specific TrGA codon randomly mutated and unique Gateway recombination sites on both ends. Purification of this DNA fragment (ChargeSwitch® PCR clean-up, Invitrogen, Carlsbad USA) and a BP recombination reaction (Invitrogen, Carlsbad, USA) with pDONR201 (Invitrogen) generated a circular multimeric DNA (entry vector) that was subsequently transformed to *E. coli* Max efficiency DH5α, (Invitrogen) and plated on 2×TY medium [Bacto Tryptone (Difco) 16 g/L, Bacto Yeast Extract (Difco) 10 g/L, NaCL 5 g/L] supplemented with 50 µg/mL kanamycin.

TABLE 2

Forward primers used to generate TrGA SSM Libraries

| Primers | DNA SEQUENCE 5' TO 3' | SEQ ID NO: |
|---|---|---|
| pDON R201-FW | TCGCGTTAACGCTAGCATGGATCTC | 10 |
| D4F | TCTGTTGACNNSTTCATCAGCACCGAGACGC | 11 |
| F5F | TCTGTTGACGACNNSATCAGCACCGAGACGCCTA | 12 |
| I12F | ATCAGCACCGAGACGCCTNNSGCACTGAACAATCTTCTTT | 13 |
| D24F | CTTTGCAATGTTGGTCCTNNSGGATGCCGTGCATTCGGCA | 14 |
| F29F | CCTGATGGATGCCGTGCANNSGGCACATCAGCTGGTGCGG | 15 |
| I43F | ATTGCATCTCCCAGCACANNSGACCCGGACTACTATTACA | 16 |
| D44F | GCATCTCCCAGCACAATTNNSCCGGACTACTATTACATGT | 17 |
| P45F | TCTCCCAGCACAATTGACNNSGACTACTATTACATGTGGA | 18 |
| D46F | CCCAGCACAATTGACCCGNNSTACTATTACATGTGGACGC | 19 |
| Y47F | AGCACAATTGACCCGGACNNSTATTACATGTGGACGCGAG | 20 |
| Y49F | ATTGACCCGGACTACTATNNSATGTGGACGCGAGATAGCG | 21 |
| W51F | CCGGACTACTATTACATGNNSACGCGAGATAGCGCTCTTG | 22 |
| Y70F | GACCGCTTCACCGAAACGNNSGATGCGGGCCTGCAGCGCC | 23 |
| Q75F | ACGTACGATGCGGGCCTGNNSCGCCGCATCGAGCAGTACA | 24 |
| R76F | TACGATGCGGGCCTGCAGNNSCGCATCGAGCAGTACATTA | 25 |
| P94F | CTCCAGGGCCTCTCTAACNNSTCGGGCTCCCTCGCGGACG | 26 |
| D100F | CCCTCGGGCTCCCTCGCGNNSGGCTCTGGTCTCGGCGAGC | 27 |
| K114F | AAGTTTGAGTTGACCCTGNNSCCTTTCACCGGCAACTGGG | 28 |
| F116F | GAGTTGACCCTGAAGCCTNNSACCGGCAACTGGGGTCGAC | 29 |
| N119F | CTGAAGCCTTTCACCGGCNNSTGGGGTCGACCGCAGCGGG | 30 |
| R122F | TTCACCGGCAACTGGGGTNNSCCGCAGCGGGATGGCCCAG | 31 |
| R125F | AACTGGGGTCGACCGCAGNNSGATGGCCCAGCTCTGCGAG | 32 |
| N146F | AAGTGGCTCATCAACAACNNSTATCAGTCGACTGTGTCCA | 33 |
| Q148F | CTCATCAACAACAACTATNNSTCGACTGTGTCCAACGTCA | 34 |
| Y169F | CTCAACTATGTTGCCCAGNNSTGGAACCAAACCGGCTTTG | 35 |

TABLE 2-continued

Forward primers used to generate TrGA SSM Libraries

| Primers | DNA SEQUENCE 5' TO 3' | SEQ ID NO: |
|---|---|---|
| Q172F | GTTGCCCAGTACTGGAACNNSACCGGCTTTGACCTCTGGG | 36 |
| F175F | TACTGGAACCAAACCGGCNNSGACCTCTGGGAAGAAGTCA | 37 |
| W178F | CAAACCGGCTTTGACCTCNNSGAAGAAGTCAATGGGAGCT | 38 |
| E180F | GGCTTTGACCTCTGGGAANNSGTCAATGGGAGCTCATTCT | 39 |
| V181F | TTTGACCTCTGGGAAGAANNSAATGGGAGCTCATTCTTTA | 40 |
| Q208F | CTTGCTGCCACTCTTGGCNNSTCGGGAAGCGCTTATTCAT | 41 |
| S211F | ACTCTTGGCCAGTCGGGANNSGCTTATTCATCTGTTGCTC | 42 |
| W228F | TGCTTTCTCCAACGATTCNNSGTGTCGTCTGGTGGATACG | 43 |
| N242F | GACTCCAACATCAACACCNNSGAGGGCAGGACTGGCAAGG | 44 |
| E243F | TCCAACATCAACACCAACNNSGGCAGGACTGGCAAGGATG | 45 |
| R245F | ATCAACACCAACGAGGGCNNSACTGGCAAGGATGTCAACT | 46 |
| I292F | GTCGACTCCTTCCGCTCCNNSTACGGCGTGAACAAGGGCA | 47 |
| G294F | TCCTTCCGCTCCATCTACNNSGTGAACAAGGGCATTCCTG | 48 |
| K297F | TCCATCTACGGCGTGAACNNSGGCATTCCTGCCGGTGCTG | 49 |
| R309F | GCTGCCGTCGCCATTGGCNNSTATGCAGAGGATGTGTACT | 50 |
| Y310F | GCCGTCGCCATTGGCCGGNNSGCAGAGGATGTGTACTACA | 51 |
| D313F | ATTGGCCGGTATGCAGAGNNSGTGTACTACAACGGCAACC | 52 |
| V314F | GGCCGGTATGCAGAGGATNNSTACTACAACGGCAACCCTT | 53 |
| Y315F | CGGTATGCAGAGGATGTGNNSTACAACGGCAACCCTTGGT | 54 |
| Y316F | TATGCAGAGGATGTGTACNNSAACGGCAACCCTTGGTATC | 55 |
| N317F | GCAGAGGATGTGTACTACNNSGGCAACCCTTGGTATCTTG | 56 |
| W321F | TACTACAACGGCAACCCTNNSTATCTTGCTACATTTGCTG | 57 |
| K340F | GATGCCATCTACGTCTGGNNSAAGACGGGCTCCATCACGG | 58 |
| K341F | GCCATCTACGTCTGGAAGNNSACGGGCTCCATCACGGTGA | 59 |
| T350F | TCCATCACGGTGACCGCCNNSTCCCTGGCCTTCTTCCAGG | 60 |
| Q356F | ACCTCCCTGGCCTTCTTCNNSGAGCTTGTTCCTGGCGTGA | 61 |
| T363F | GAGCTTGTTCCTGGCGTGNNSGCCGGGACCTACTCCAGCA | 62 |
| S368F | GTGACGGCCGGGACCTACNNSAGCAGCTCTTCGACCTTTA | 63 |
| S369F | ACGGCCGGGACCTACTCCNNSAGCTCTTCGACCTTTACCA | 64 |
| N376F | AGCTCTTCGACCTTTACCNNSATCATCAACGCCGTCTCGA | 65 |
| Y395F | CTCAGCGAGGCTGCCAAGNNSGTCCCCGCCGACGGTTCGC | 66 |
| A398F | GCTGCCAAGTACGTCCCCNNSGACGGTTCGCTGGCCGAGC | 67 |
| S401F | TACGTCCCCGCCGACGGTNNSCTGGCCGAGCAGTTTGACC | 68 |
| R408F | CTGGCCGAGCAGTTTGACNNSAACAGCGGCACTCCGCTGT | 69 |
| N409F | GCCGAGCAGTTTGACCGCNNSAGCGGCACTCCGCTGTCTG | 70 |
| T412F | TTTGACCGCAACAGCGGCNNSCCGCTGTCTGCGCTTCACC | 71 |
| H418F | ACTCCGCTGTCTGCGCTTNNSCTGACGTGGTCGTACGCCT | 72 |
| W421F | TCTGCGCTTCACCTGACGNNSTCGTACGCCTCGTTCTTGA | 73 |

TABLE 2-continued

Forward primers used to generate TrGA SSM Libraries

| Primers | DNA SEQUENCE 5' TO 3' | SEQ ID NO: |
|---|---|---|
| R433F | TTGACAGCCACGGCCCGTNNSGCTGGCATCGTGCCCCCCT | 74 |
| I436F | ACGGCCCGTCGGGCTGGCNNSGTGCCCCCCTCGTGGGCCA | 75 |
| S451F | AGCGCTAGCACGATCCCCNNSACGTGCTCCGGCGCGTCCG | 76 |

TABLE 3

Primers used to Generate TrGA SSM Libraries

| Primer | DNA sequence 5' to 3' | SEQ ID NO: |
|---|---|---|
| pDON201-RV | GTAACATCAGAGATTTTGAGACAC | 77 |
| D4R | GCGTCTCGGTGCTGATGAASNNGTCAACAGA | 78 |
| F5R | TAGGCGTCTCGGTGCTGATSNNGTCGTCAACAGA | 79 |
| I12R | AAAGAAGATTGTTCAGTGCSNNAGGCGTCTCGGTGCTGAT | 80 |
| D24R | TGCCGAATGCACGGCATCCSNNAGGACCAACATTGCAAAG | 81 |
| F29R | CCGCACCAGCTGATGTGCCSNNTGCACGGCATCCATCAGG | 82 |
| I43R | TGTAATAGTAGTCCGGGTCSNNTGTGCTGGGAGATGCAAT | 83 |
| D44R | ACATGTAATAGTAGTCCGGSNNAATTGTGCTGGGAGATGC | 84 |
| P45R | TCCACATGTAATAGTAGTCSNNGTCAATTGTGCTGGGAGA | 85 |
| D46R | GCGTCCACATGTAATAGTASNNCGGGTCAATTGTGCTGGG | 86 |
| Y47R | CTCGCGTCCACATGTAATASNNGTCCGGGTCAATTGTGCT | 87 |
| Y49R | CGCTATCTCGCGTCCACATSNNATAGTAGTCCGGGTCAAT | 88 |
| W51R | CAAGAGCGCTATCTCGCGTSNNCATGTAATAGTAGTCCGG | 89 |
| Y70R | GGCGCTGCAGGCCCGCATCSNNCGTTTCGGTGAAGCGGTC | 90 |
| Q75R | TGTACTGCTCGATGCGGCGSNNCAGGCCCGCATCGTACGT | 91 |
| R76R | TAATGTACTGCTCGATGCGSNNCTGCAGGCCCGCATCGTA | 92 |
| P94R | CGTCCGCGAGGGAGCCCGASNNGTTAGAGAGGCCCTGGAG | 93 |
| D100R | GCTCGCCGAGACCAGAGCCSNNCGCGAGGGAGCCCGAGGG | 94 |
| K114R | CCCAGTTGCCGGTGAAAGGSNNCAGGGTCAACTCAAACTT | 95 |
| F116R | GTCGACCCCAGTTGCCGGTSNNAGGCTTCAGGGTCAACTC | 96 |
| N119R | CCCGCTGCGGTCGACCCCASNNGCCGGTGAAAGGCTTCAG | 97 |
| R122R | CTGGGCCATCCCGCTGCGGSNNACCCCAGTTGCCGGTGAA | 98 |
| R125R | CTCGCAGAGCTGGGCCATCSNNCTGCGGTCGACCCCAGTT | 99 |
| N146R | TGGACACAGTCGACTGATASNNGTTGTTGATGAGCCACTT | 100 |
| Q148R | TGACGTTGGACACAGTCGASNNATAGTTGTTGTTGATGAG | 101 |
| Y169R | CAAAGCCGGTTTGGTTCCASNNCTGGGCAACATAGTTGAG | 102 |
| Q172R | CCCAGAGGTCAAAGCCGGTSNNGTTCCAGTACTGGGCAAC | 103 |
| F175R | TGACTTCTTCCCAGAGGTCSNNGCCGGTTTGGTTCCAGTA | 104 |
| W178R | AGCTCCCATTGACTTCTTCSNNGAGGTCAAAGCCGGTTTG | 105 |
| E180R | AGAATGAGCTCCCATTGACSNNTTCCCAGAGGTCAAAGCC | 106 |

TABLE 3-continued

Primers used to Generate TrGA SSM Libraries

| Primer | DNA sequence 5' to 3' | SEQ ID NO: |
|---|---|---|
| V181R | TAAAGAATGAGCTCCCATTSNNTTCTTCCCAGAGGTCAAA | 107 |
| Q208R | ATGAATAAGCGCTTCCCGASNNGCCAAGAGTGGCAGCAAG | 108 |
| S211R | GAGCAACAGATGAATAAGCSNNTCCCGACTGGCCAAGAGT | 109 |
| W228R | CGTATCCACCAGACGACACSNNGAATCGTTGGAGAAAGCA | 110 |
| N242R | CCTTGCCAGTCCTGCCCTCSNNGGTGTTGATGTTGGAGTC | 111 |
| E243R | CATCCTTGCCAGTCCTGCCSNNGTTGGTGTTGATGTTGGA | 112 |
| R245R | AGTTGACATCCTTGCCAGTSNNGCCCTCGTTGGTGTTGAT | 113 |
| I292R | TGCCCTTGTTCACGCCGTASNNGGAGCGGAAGGAGTCGAC | 114 |
| G294R | CAGGAATGCCCTTGTTCACSNNGTAGATGGAGCGGAAGGA | 115 |
| K297R | CAGCACCGGCAGGAATGCCSNNGTTCACGCCGTAGATGGA | 116 |
| R309R | AGTACACATCCTCTGCATASNNGCCAATGGCGACGGCAGC | 117 |
| Y310R | TGTAGTACACATCCTCTGCSNNCCGGCCAATGGCGACGGC | 118 |
| D313R | GGTTGCCGTTGTAGTACACSNNCTGCATACCGGCCAAT | 119 |
| V314R | AAGGGTTGCCGTTGTAGTASNNATCCTCTGCATACCGGCC | 120 |
| Y315R | ACCAAGGGTTGCCGTTGTASNNCACATCCTCTGCATACCG | 121 |
| Y316R | GATACCAAGGGTTGCCGTTSNNGTACACATCCTCTGCATA | 122 |
| N317R | CAAGATACCAAGGGTTGCCSNNGTAGTACACATCCTCTGC | 123 |
| W321R | CAGCAAATGTAGCAAGATASNNAGGGTTGCCGTTGTAGTA | 124 |
| K340R | CCGTGATGGAGCCCGTCTTSNNCCAGACGTAGATGGCATC | 125 |
| K341R | TCACCGTGATGGAGCCCGTSNNCTTCCAGACGTAGATGGC | 126 |
| T350R | CCTGGAAGAAGGCCAGGGASNNGGCGGTCACCGTGATGGA | 127 |
| Q356R | TCACGCCAGGAACAAGCTCSNNGAAGAAGGCCAGGGAGGT | 128 |
| T363R | TGCTGGAGTAGGTCCCGGCSNNCACGCCAGGAACAAGCTC | 129 |
| S368R | TAAAGGTCGAAGAGCTGCTSNNGTAGGTCCCGGCCGTCAC | 130 |
| S369R | TGGTAAAGGTCGAAGAGCTSNNGGAGTAGGTCCCGGCCGT | 131 |
| N376R | TCGAGACGGCGTTGATGATSNNGGTAAAGGTCGAAGAGCT | 132 |
| Y395R | GCGAACCGTCGGCGGGGACSNNCTTGGCAGCCTCGCTGAG | 133 |
| A398R | GCTCGGCCAGCGAACCGTCSNNGGGGACGTACTTGGCAGC | 134 |
| S401R | GGTCAAACTGCTCGGCCAGSNNACCGTCGGCGGGGACGTA | 135 |
| R408R | ACAGCGGAGTGCCGCTGTTSNNGTCAAACTGCTCGGCCAG | 136 |
| N409R | CAGACAGCGGAGTGCCGCTSNNGCGGTCAAACTGCTCGGC | 137 |
| T412R | GGTGAAGCGCAGACAGCGGSNNGCCGCTGTTGCGGTCAAA | 138 |
| H418R | AGGCGTACGACCACGTCAGSNNAAGCGCAGACAGCGGAGT | 139 |
| W421R | TCAAGAACGAGGCGTACGASNNCGTCAGGTGAAGCGCAGA | 140 |
| R433R | AGGGGGGCACGATGCCAGCSNNACGGGCCGTGGCTGTCAA | 141 |
| I436R | TGGCCCACGAGGGGGCACSNNGCCAGCCCGACGGGCCGT | 142 |
| S451R | CGGACGCGCCGGAGCACGTSNNGGGGATCGTGCTAGCGCT | 143 |

For each library, after overnight incubation at 37° C., colonies were pooled by resuspension of the clones in PSS. From the pooled *E. coli* transformants, total plasmid was isolated (Qiagen) using standard techniques. Briefly 10 of the plasmid solution was added to 1 µl of pRep3Y destination vector (FIG. 1A) solution and added to the LR Clonase™ II enzyme mix according to the protocol supplied by Invitrogen. A circular multimeric DNA was generated and transformed to *E. coli* Max EfficiencyDH5α as described by the supplier.

After overnight incubation at 37° C., 96 single colonies of each library were picked from 2×TY agar plates with 100 µg/ml ampicillin and grown for 24 hrs at 37° C. in a MTP containing 200 µL 2×TY medium with 100 µg/ml ampicillin. Cultures were used for sequence analyses (BaseClear B.V., Leiden, Netherlands).

The library numbers ranged from 1 to 65 with an addition referring to the codon of the TrGA sequence that is randomly mutated. After selection, each library included a maximum of 19 TrGA variants. These variants were individually transferred to *Schizosaccharomyces pombe* according to manufacturers instruction. (Zymo Research, Orange Calif. USA).

*S. pombe* transformations were plated on selective medium (EMM agar, Qbiogene, Irvine, USA Cat. No. 4110-232) and incubated at 28° C. for 4 days. Transformants were purified from the transformation plate by streaking the colonies on EMM agar.

Example 2

Description of the Growth Conditions and the Sample Pre-Treatment

*S. pombe* transformants were inoculated in 96 well microtiter plates (MTP) containing selective medium (2×EMM-C) [64.4 g/L EMM Broth (Qbiogene Cat. No: 4110-032), 0.62 g/L Complete Supplement Mixture (CSM-HIS-LEU-TRP, Qbiogene, Cat. No. 4530-122)] and incubated overnight at 28° C. From the overnight incubated microtiter plate, 2000 of grown *S. pombe* culture was inoculated in 20 ml of 2×EMM-C liquid medium in a 100 ml shake flask and incubated for 4 days at 26° C. at 280 rpm in a Multitron shaking incubator (Infors AG, Bottmingen, Switzerland). From the grown culture, 2 ml of *S. pombe* culture was sampled and centrifuged for 5 min at 14,000 rpm (Sigma). The supernatant was transferred into a 10 kD Vivaspin 500 HT filter set-up (VivaScience AG, Hannover, Germany) and centrifuged for 25 min at 1000 g. The retentate was diluted back to the original start volume with 50 mM NaAc pH 4.5 supplemented with 0.015% Tween-80. This solution was used in the different assays.

Example 3

Construction of a Combinatorial Library of 4 Variants of TrGA (A) Experiments were conducted for the construction of TrGA-variants carrying combinations of the following single site mutations: Q172F; Q208N; S211R and V314H. A review of the variants is shown below:
a) Q172F; Q208N
b) Q172F; S211R
c) Q172F; V314H
d) Q208N; S211R
e) Q208N V314H
f) S211R; V314H
g) Q172F; Q208N; S211R
h) Q172F; Q208N; V314H
i) Q172F; S211R; V314H
j) Q208N; S211R; V314H
k) Q172F; Q208N; S211R; V314H The Quikchange® multi site-directed mutagenesis (QCMS) kit (Stratagene) was used to construct the library. The 5' phosphorylated primers used to create the library are shown in Table 4. Optimal results in terms of incorporation of full length primers as well as significant reduction in primer-derived errors were obtained by the use of HPLC, PAGE or any other type of purified primers (Invitrogen).

TABLE 4

| Primer | Sequence | SEQ ID NO: |
|--------|----------|------------|
| I43R | GCATCTCCCAGCACACGAGACCCGGACTACTAT | 144 |
| I43Y | GCATCTCCCAGCACATACGACCCGGACTACTAT | 145 |
| R76L | GATGCGGGCCTGCAGCTGCGCATCGAGCAGTAC | 146 |
| N119T | CTGAAGCCTTTCACCGGCACCTGGGGTCGACCGCAGCGGG | 147 |
| N119Y | TGAAGCCTTTCACCGGCTACTGGGGTCGACCGCAGCGGG | 148 |
| N119D | CTGAAGCCTTTCACCGGCGACTGGGGTCGACCGCAGCGGG | 149 |
| N146 | AGTGGCTCATCAACAACGASTATCAGTCGACTGTGT | 150 |
| N146T | AGTGGCTCATCAACAACACCTATCAGTCGACTGTGT | 151 |
| N146W | GTGGCTCATCAACAATGGTATCAGTCGACTGTGT | 152 |
| N146L | AGTGGCTCATCAACAACCTGTATCAGTCGACTGTGT | 153 |
| N146S | AGTGGCTCATCAACAACTCCTATCAGTCGACTGTGT | 154 |
| Q172D/E | TTGCCCAGTACTGGAACGASACCGGCTTTGACCTCTGG | 155 |
| Q172V/L | TTGCCCAGTACTGGAACSTGACCGGCTTTGACCTCTGG | 156 |

TABLE 4-continued

| Primer | Sequence | SEQ ID NO: |
|---|---|---|
| Q172T | TTGCCCAGTACTGGAACACCACCGGCTTTGACCTCTGG | 157 |
| Q172R | TTGCCCAGTACTGGAACCGAACCGGCTTTGACCTCTGG | 158 |
| Q172C | TTGCCCAGTACTGGAACTGCACCGGCTTTGACCTCTGG | 159 |

The template plasmid pDONR-TrGA (FIG. 2) was used to construct the combinatorial library using the QCMS kit of Stratagene. The library was constructed as described by the supplier with modified primer concentrations used in the reactions. Specifically, 4 µl pDONR-TrGA (25-50 ng) was mixed with 11 µl of sterile distilled water; 1.5 µl of dNTP; 2.5 µl of 10×QCMS-buffer; 1 µl of enzyme blend and 1 µl of each mutant primer mix giving a total of 100 ng of primers in each reaction. The PCR conditions were 95° C. for 1 min, followed by 30 cycles of 95° for 1 min, 55° C. for 1 min, and 65° C. for 6 min, in an MJ Research thermocycler using thin-walled 0.2 ml PCR tubes. The reaction product was digested with 1 µl of Dpn1 from the QCMS kit by incubating at 37° C. overnight. A PCR purification kit (Qiagen) was used for sample purification and a second round of digestion was carried out with Dpn1 (Stratagene) for 1 hour at 37° C.

The reaction mixture was transformed to into *E. coli* Max efficiency DH5α (Invitrogen) and plated on selective agar (2×TY supplemented with 50 µg kanamycin/ml). After overnight incubation at 37° C., 96 single colonies were picked for sequence analysis (BaseClear B.V., Leiden, Netherlands). The combinatorial variants were cloned and expressed in a *T. reesei* host strain as described below and in WO 06/060062.

(B) A further six combinatorial libraries (Table 5) were synthetically made by Geneart (Regensburg, Germany) and were tested for thermal stability and in ethanol and sweetener application assays as described herein.

TABLE 5

| | combinatorial libraries |
|---|---|
| 1 | D24E, L/I43F, R/D44H, N/F175H/V181K, L/V314D, H, K/T363R |
| 2 | D24L, W, Y/Q208F/I292F, L, N, V/G294A, I, Q/K297A/Y310F, Q, R |
| 3 | V181F, K, L/E243A, N, M, R, y/I292F, L, N, V/K297A, D, H, M, N, Q/N317H/Y395Q, R |
| 4 | D24E, L, Y/V181F, K, L/Q208C/F/G294A, I, Q/T363R/N376Q/N409K, W |
| 5 | D24E, L, Y/V181F, K, L/I292F, L, N, V/G294A, I, Q/E243A, M, N, R, Y/N409K, W |
| 6 | I43R/E243A, M, N, R, Y/I292F, L, N, V/G294A/K297A, D, H, M, N, Q, S, R, W, Y |

Example 4

Variants with Improved Thermal Stability

The parent TrGA molecule under the conditions described had a residual activity between 15 and 44% (day-to-day variation). The performance index was calculated based on the TrGA thermostability of the same batch. The performance indices are the quotients PI=(Variant residual activity)/(TrGA residual activity). A performance index >1 indicates an improved stability. Variants which have a thermal stability performance index of more than 1.0 are shown in the following Table 6.

TABLE 6

Thermal stability screening

| Variant | PI Thermal Stability, 60° C., pH 4.5 | Variant | PI Thermal Stability, 60° C., pH 4.5 |
|---|---|---|---|
| D4P | 1.05 | S211M | 1.90 |
| I12E | 1.09 | E243A | 1.19 |
| I12Y | 1.40 | E243H | 1.04 |
| D24L | 1.09 | E243M | 1.53 |
| D24W | 1.13 | E243N | 1.35 |
| D24Y | 1.03 | E243P | 1.06 |
| I43R | 1.28 | E243R | 1.21 |
| D44N | 1.06 | E243S | 1.09 |
| D44Q | 1.10 | E243T | 1.48 |
| Q75N | 1.09 | E243Y | 1.43 |
| R76K | 1.03 | I292F | 1.17 |
| N146D | 1.20 | I292L | 1.10 |
| N146E | 1.24 | I292N | 1.31 |
| N146L | 1.10 | I292V | 1.02 |
| N146V | 1.28 | G294A | 1.30 |
| N146W | 1.17 | G294C | 1.41 |
| Q148D | 1.02 | G294D | 1.31 |
| F175I | 1.02 | G294E | 1.34 |
| F175Y | 1.06 | G294H | 1.17 |
| E180A | 1.41 | G294I | 2.15 |
| E180D | 1.02 | G294L | 2.01 |
| E180G | 1.13 | G294P | 1.13 |
| E180I | 1.41 | G294Q | 1.91 |
| E180L | 1.38 | G294R | 1.34 |
| E180M | 1.10 | G294V | 1.10 |
| E180N | 1.27 | K297A | 1.47 |
| E180Q | 1.72 | K297C | 1.10 |
| E180R | 1.59 | K297D | 1.50 |
| E180V | 1.08 | K297F | 1.24 |
| E180W | 1.30 | K297G | 1.25 |
| E180Y | 1.31 | K297H | 1.63 |
| V181I | 1.20 | K297L | 1.62 |
| V181K | 1.12 | K297M | 1.62 |
| V181L | 1.06 | K297N | 1.87 |
| V181Q | 1.09 | K297Q | 1.82 |
| V181R | 1.07 | K297R | 1.29 |
| Q208F | 1.06 | K297S | 1.22 |
| Q208T | 1.17 | K297T | 1.33 |
| Q208V | 1.15 | K297V | 1.10 |
| S211D | 1.10 | K297W | 1.85 |
| S211E | 1.02 | K297Y | 1.71 |
| S211I | 1.31 | R309S | 1.08 |
| Y310C | 1.06 | S369P | 1.16 |
| Y310F | 1.35 | S369R | 1.12 |
| Y310L | 1.11 | S369T | 1.25 |
| Y310Q | 1.40 | N376F | 1.12 |
| Y310R | 1.61 | N376G | 1.26 |
| Y315E | 1.24 | N376H | 1.21 |
| Y315H | 1.48 | N376K | 1.40 |
| Y315L | 1.35 | N376L | 1.34 |
| Y315N | 1.17 | N376P | 1.05 |
| Y315P | 1.19 | N376Q | 1.11 |
| Y315Q | 1.43 | N376S | 1.09 |
| Y315T | 1.34 | N376V | 1.19 |
| Y316D | 1.06 | N376W | 1.12 |
| N317H | 1.26 | N376Y | 1.05 |

TABLE 6-continued

Thermal stability screening

| Variant | PI Thermal Stability, 60° C., pH 4.5 | Variant | PI Thermal Stability, 60° C., pH 4.5 |
|---|---|---|---|
| N317Q | 1.09 | Y395A | 1.05 |
| K340H | 1.02 | Y395C | 1.02 |
| K340R | 1.09 | Y395F | 1.03 |
| K341I | 1.10 | Y395G | 1.13 |
| K341V | 1.07 | Y395H | 1.10 |
| T350G | 1.08 | Y395L | 1.50 |
| T350P | 1.08 | Y395N | 1.20 |
| T350S | 1.33 | Y395Q | 1.18 |
| Q356L | 1.20 | Y395R | 1.14 |
| T363N | 1.30 | Y395S | 1.13 |
| S368C | 1.12 | Y395T | 1.04 |
| S368E | 1.07 | A398C | 1.10 |
| S368F | 1.16 | A398D | 1.39 |
| S368H | 1.26 | A398F | 1.05 |
| S368I | 1.15 | A398G | 1.17 |
| S368L | 1.33 | A398H | 1.33 |
| S368N | 1.21 | A398I | 1.41 |
| S368P | 1.05 | A398K | 1.47 |
| S368Q | 1.10 | A398L | 1.44 |
| S368R | 1.14 | A398N | 1.23 |
| S368T | 1.15 | A398P | 1.38 |
| S368W | 1.16 | A398Q | 1.43 |
| S369A | 1.22 | A398R | 1.59 |
| S369D | 1.05 | A398S | 1.14 |
| S369F | 1.20 | A398T | 1.25 |
| S369G | 1.05 | A398V | 1.29 |
| S369K | 1.12 | A398W | 1.45 |
| S369L | 1.49 | A398Y | 1.38 |
| S369M | 1.36 | S401A | 1.12 |
| S369N | 1.25 | S401E | 1.08 |
| S401I | 1.05 | N409C | 1.18 |
| S401N | 1.12 | N409D | 1.21 |
| S401P | 1.15 | N409E | 1.27 |
| S401R | 1.25 | N409F | 1.32 |
| S401T | 1.26 | N409G | 1.14 |
| S401V | 1.18 | N409H | 1.29 |
| R408A | 1.14 | N409I | 1.56 |
| R408E | 1.41 | N409K | 1.44 |
| R408G | 1.15 | N409L | 1.57 |
| R408H | 1.12 | N409M | 1.17 |
| R408I | 1.19 | N409Q | 1.03 |
| R408K | 1.80 | N409R | 1.29 |
| R408L | 1.55 | N409V | 1.11 |
| R408N | 1.09 | N409W | 1.58 |
| R408Q | 1.23 | T412L | 1.10 |
| R408S | 1.17 | S451R | 1.01 |
| N409A | 1.25 | | |

Example 5

High Performing Variants from an Ethanol Screening Assay

Variants were tested in an ethanol screening assay using the assays described above. Table 7 shows the results of the screening assay for variants with a Performance Index (PI)>1.0 compared to the parent TrGA PI. The PI is a measure of specific activity (activity/mg enzyme). The PI of the specific activity is the quotient "Variant-specific activity/WT-specific activity." The PI of the specific activity is 1.0 and a variant with a PI>1.0 has a specific activity that is greater than the parent TrGA. The specific activity is the activity measured by the ethanol screening assay divided by the results obtained in the Bradford assay described above.

TABLE 7

Ethanol Screening

| Variant | P.I. 32° C., pH 4 | Variant | P.I. 32° C., pH 4 |
|---|---|---|---|
| D4A | 1.07 | Q75K | 1.77 |
| D4C | 1.08 | R76K | 1.06 |
| D4E | 1.23 | R76L | 1.11 |
| D4L | 1.34 | R76M | 1.13 |
| D4R | 1.18 | R76N | 1.02 |
| D4S | 1.17 | R76T | 1.04 |
| F5C | 1.35 | R76V | 1.05 |
| I12L | 1.19 | R76W | 1.02 |
| I12R | 1.13 | R76Y | 1.05 |
| D24E | 1.60 | D100A | 1.08 |
| D24L | 1.19 | D100I | 1.14 |
| D24W | 1.03 | D100L | 1.03 |
| D24Y | 1.14 | D100M | 1.12 |
| F29A | 1.05 | D100N | 1.06 |
| F29C | 1.12 | D100P | 1.09 |
| F29D | 1.20 | D100Q | 1.14 |
| F29E | 1.05 | D100T | 1.06 |
| F29I | 1.26 | D100W | 1.19 |
| F29L | 1.42 | D100Y | 1.05 |
| F29Q | 1.01 | N119E | 1.02 |
| F29S | 1.07 | N119F | 1.03 |
| F29V | 1.06 | N119Y | 1.28 |
| I43D | 1.14 | N146C | 1.11 |
| I43F | 1.33 | N146E | 1.02 |
| I43R | 1.21 | N146G | 1.11 |
| I43Y | 1.05 | N146H | 1.07 |
| D44E | 1.37 | N146K | 1.06 |
| D44F | 1.07 | Q148H | 1.10 |
| D44G | 1.03 | Q148N | 1.05 |
| D44H | 1.11 | Q148V | 1.18 |
| D44K | 1.09 | Q148W | 1.05 |
| D44N | 1.07 | Q148Y | 1.16 |
| D44S | 1.08 | Y169D | 1.18 |
| D44Y | 1.07 | Y169F | 1.10 |
| Y70E | 1.02 | Y169H | 1.05 |
| Y70G | 1.06 | Y169R | 1.02 |
| Y70K | 1.01 | Q172E | 1.08 |
| Y70M | 1.36 | Q172G | 1.05 |
| Y70P | 1.15 | Q172R | 1.22 |
| Y70R | 1.40 | Q172S | 1.03 |
| Y70S | 1.04 | F175C | 1.18 |
| Q75A | 1.10 | F175H | 1.26 |
| F175T | 1.28 | K297Y | 1.80 |
| F175W | 1.16 | R309L | 1.43 |
| F175Y | 1.05 | Y310F | 1.05 |
| V181F | 1.28 | Y310Q | 1.16 |
| V181K | 1.35 | Y310R | 1.24 |
| V181L | 1.37 | V314D | 1.10 |
| V181R | 1.01 | V314F | 1.04 |
| Q208A | 1.22 | V314H | 1.31 |
| Q208C | 1.17 | V314K | 1.08 |
| Q208F | 1.12 | V314L | 1.02 |
| Q208H | 1.02 | V314N | 1.05 |
| Q208I | 1.02 | V314R | 1.06 |
| Q208L | 1.32 | Y316R | 1.42 |
| S211A | 1.30 | Y316W | 1.05 |
| S211E | 1.30 | N317H | 1.14 |
| S211G | 1.05 | N317K | 1.02 |
| S211L | 1.04 | N317S | 1.03 |
| S211M | 1.05 | N317T | 1.23 |
| S211R | 1.34 | K340D | 1.33 |
| S211W | 1.07 | K340T | 1.16 |
| S211Y | 1.08 | K341D | 1.04 |
| E243A | 1.23 | K341F | 1.64 |
| E243L | 1.20 | K341G | 1.64 |
| E243M | 1.26 | K341L | 1.04 |
| E243N | 1.28 | K341N | 1.05 |
| E243R | 1.31 | K341S | 1.06 |
| E243Y | 1.25 | T350A | 1.56 |
| I292F | 1.23 | T350D | 1.04 |
| I292H | 1.04 | T350E | 1.59 |
| I292L | 1.21 | T350H | 1.03 |
| I292N | 1.27 | T350N | 1.06 |
| I292R | 1.02 | T350Q | 1.05 |
| I292V | 1.24 | T350R | 1.02 |

TABLE 7-continued

Ethanol Screening

| Variant | P.I. 32° C., pH 4 | Variant | P.I. 32° C., pH 4 |
|---|---|---|---|
| G294A | 1.91 | Q356D | 1.69 |
| G294I | 1.92 | Q356E | 1.07 |
| G294Q | 1.99 | Q356H | 1.03 |
| K297A | 1.82 | Q356K | 1.03 |
| K297D | 1.87 | T363A | 1.04 |
| K297H | 1.79 | T363C | 1.54 |
| K297M | 1.91 | T363G | 1.02 |
| K297N | 1.87 | T363H | 1.09 |
| K297Q | 1.85 | T363N | 1.02 |
| K297R | 1.71 | T363R | 1.61 |
| K297S | 1.72 | T363V | 1.05 |
| K297W | 1.70 | T363W | 1.08 |
| S368D | 1.11 | A398D | 1.05 |
| S368F | 1.08 | A398P | 1.03 |
| S368H | 1.04 | S401A | 1.04 |
| S368L | 1.07 | S401D | 1.01 |
| S368M | 1.03 | S401G | 1.04 |
| S368N | 1.02 | S401N | 1.02 |
| S368W | 1.24 | S401V | 1.06 |
| S369F | 1.68 | N409K | 1.30 |
| S369M | 1.04 | N409L | 1.04 |
| S369T | 1.05 | N409W | 1.31 |
| N376G | 1.05 | T412A | 1.04 |
| N376H | 1.10 | T412G | 1.06 |
| N376Q | 1.16 | T412K | 1.05 |
| N376S | 1.06 | R433Q | 1.16 |
| N376T | 1.12 | I436A | 1.32 |
| N376V | 1.64 | I436H | 1.02 |
| Y395A | 1.02 | I436T | 1.03 |
| Y395C | 1.05 | S451A | 1.03 |
| Y395G | 1.02 | S451M | 1.28 |
| Y395Q | 1.63 | S451T | 1.09 |
| Y395R | 1.20 | S451Y | 1.03 |
| Y395S | 1.09 | | |

Example 6

High Performing Variants from a Sweetener Screening Assay

Variants were tested in a sweetener screening assay as described hereinabove. Table 8 shows the results of the screening assay wherein variants with a Performance Index (PI)>1.00 compared to the parent TrGA PI are shown. The PI is a measure of specific activity (activity/mg enzyme). The PI of the specific activity is the quotient "Variant-specific activity/WT-specific activity." The PI of the specific activity is 1.0 and a variant with a PI>1.0 has a specific activity that is greater than the parent TrGA.

TABLE 8

Sweetener screening

| Variant | P.I. 60° C., pH 4.5 | Variant | P.I. 60° C., pH 4.5 |
|---|---|---|---|
| D4E | 1.09 | Q208T | 1.12 |
| D4L | 1.03 | S211H | 1.16 |
| D4S | 1.07 | S211M | 1.16 |
| D24E | 1.45 | S211R | 1.34 |
| D24L | 1.31 | S211W | 1.09 |
| D24Y | 1.01 | E243A | 1.06 |
| I43D | 1.05 | E243F | 1.01 |
| I43F | 1.31 | E243N | 1.05 |
| I43R | 1.28 | E243R | 1.14 |
| D44E | 1.09 | E243S | 1.09 |
| D44H | 1.12 | E243Y | 1.07 |
| D44N | 1.31 | R245A | 1.01 |
| Y70F | 1.26 | I292N | 1.04 |
| Y70L | 1.22 | I292V | 1.12 |
| Q75K | 1.12 | G294A | 1.06 |
| R76K | 1.11 | G294Q | 1.02 |
| R76M | 1.03 | K297A | 1.04 |
| R76P | 1.13 | K297D | 1.10 |
| R76T | 1.11 | K297Q | 1.07 |
| R76W | 1.07 | V314D | 1.22 |
| D100Y | 1.04 | V314H | 1.85 |
| N119E | 1.12 | V314K | 1.34 |
| N119Y | 1.01 | V314L | 1.13 |
| N146D | 1.05 | V314N | 1.08 |
| N146E | 1.11 | V314R | 1.20 |
| Q148D | 1.02 | V314Y | 1.05 |
| Q148W | 1.05 | Y316R | 1.20 |
| Q172H | 1.05 | N317H | 1.25 |
| Q172Y | 1.03 | N317K | 1.03 |
| F175H | 1.42 | K340D | 1.21 |
| F175Y | 1.11 | K340E | 1.05 |
| V181A | 1.10 | K341D | 1.08 |
| V181F | 1.01 | K341G | 1.22 |
| V181K | 1.43 | K341L | 1.08 |
| V181L | 1.42 | K341N | 1.08 |
| Q208C | 1.08 | K341S | 1.12 |
| Q208F | 1.20 | T350H | 1.03 |
| Q208H | 1.11 | T350L | 1.04 |
| Q208L | 1.03 | Q356D | 1.31 |
| Q208N | 1.03 | Q356E | 1.04 |
| Q208S | 1.06 | Q356K | 1.05 |
| T363C | 1.08 | N409T | 1.02 |
| T363G | 1.04 | N409W | 1.01 |
| T363N | 1.02 | T412G | 1.06 |
| T363R | 1.50 | T412S | 1.03 |
| S368G | 1.04 | I436D | 1.02 |
| S368M | 1.03 | I436Q | 1.06 |
| N376G | 1.02 | I436T | 1.16 |
| N376Q | 1.07 | S451D | 1.01 |
| Y395Q | 1.01 | S451E | 1.09 |
| A398H | 1.03 | S451F | 1.02 |
| A398S | 1.03 | S451H | 1.11 |
| S401A | 1.01 | S451T | 1.11 |
| N409K | 1.19 | | |

Example 7

Construction of Vectors and Transformation into *Trichoderma reesei* Host Cells

Figure 5A:
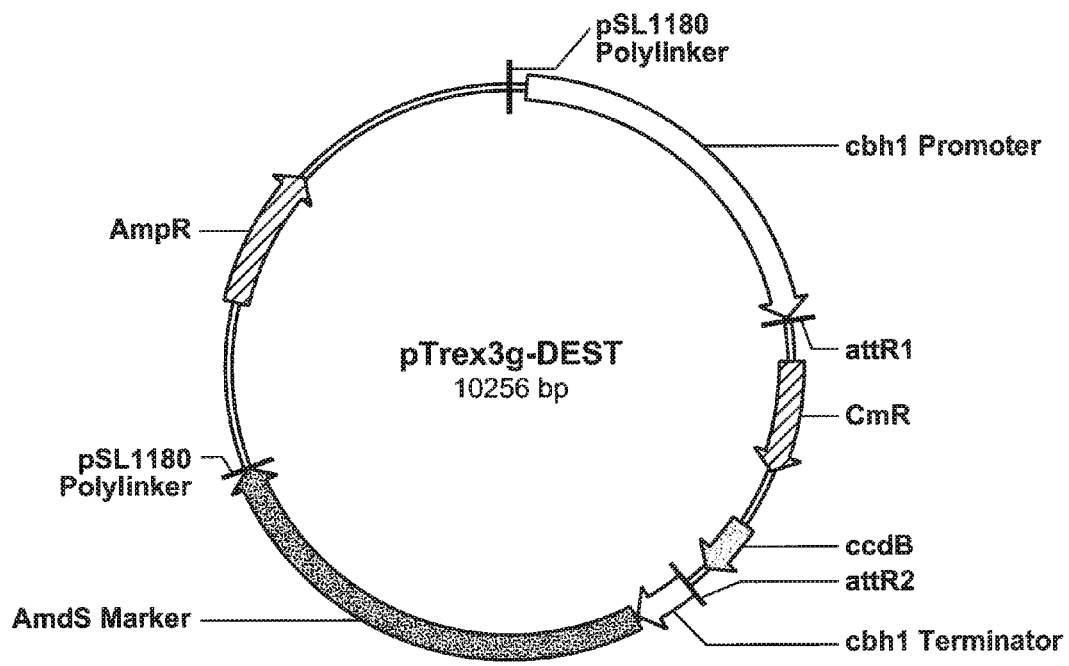
FIG. 5A illustrates the plasmid pTrex 3g-DEST and FIG. 5B illustrates the plasmid pTrex3g-TrGA which was used as an expression vector for expression and production of variant glucoamylases in a *Trichoderma reesei* host.
Figure 5B:
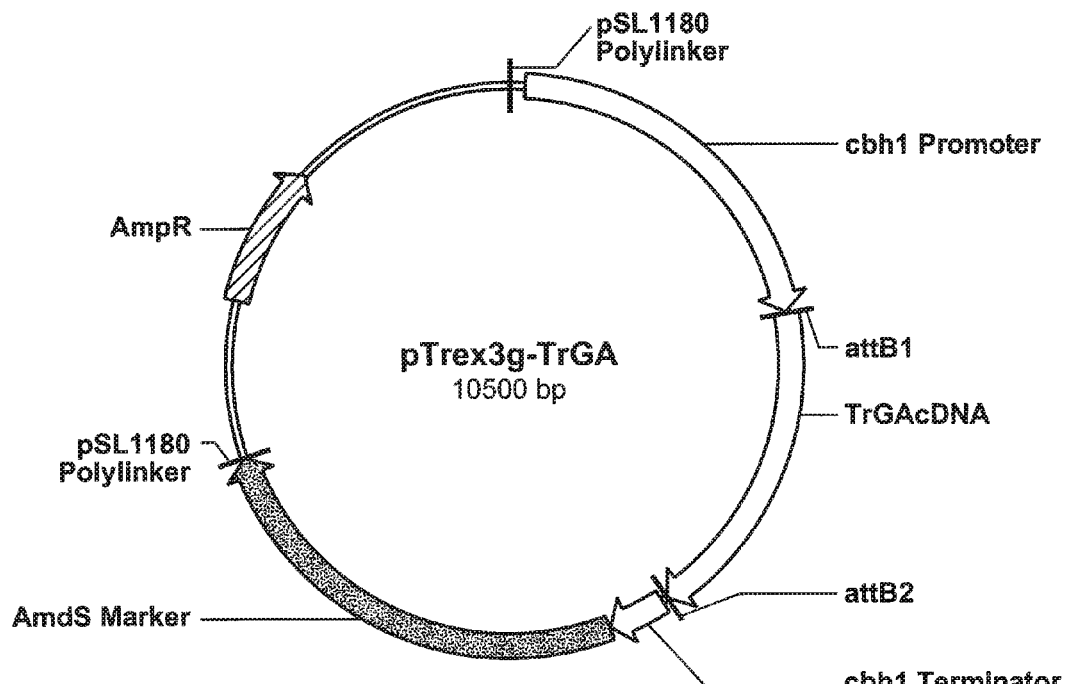

A. Construction of Expression Vectors Comprising a Polynucleotide Encoding a Variant GA The TrGA expression cassette comprising the DNA sequence SEQ ID NO:4 was cloned into pDONR™ 201, a Gateway® Entry vector (Invitrogen, Carlsbad, Calif.). The TrGA expression cassette was cloned into the Gateway compatible destination vector pTrex3g-DEST (FIG. 5), which is also described in WO 06/060062, by the Gateway® LR recombination reaction. The pTrex3g-TrGA expression vector (FIG. 5) enabled the expression of the TrGA protein (SEQ ID NO:2) in a *Trichoderma reesei* host. Vectors were constructed which included modified TrGA cDNA coding at least the following variants (1) V314H; (2) S211R; (3) Q208N and (4) Q172F.

B. Transformation.

An expression vector containing a variant GA was transformed into a *T. reesei* host strain derived from RL-P37 (IA52) and having various gene deletions (Δcbh1, Δcbh2, Δegl1, Δegl2) using particle bombardment by the PDS-1000/Helium System (BioRad Cat. No. 165-02257). The protocol is outlined below, and reference is also made to examples 6 and 11 of WO 05/001036.

A suspension of spores (approximately $5 \times 10^8$ spores/ml) from the strain of *T. reesei* was prepared. 100 µl-200 µl of spore suspension was spread onto the center of plates of Minimal Medium (MM) acetamide medium. (MM acetamide medium had the following composition: 0.6 g/L acetamide; 1.68 g/L CsCl; 20 g/L glucose; 20 g/L KH$_2$PO$_4$; 0.6 g/L CaCl$_2$.2H$_2$O; 1 ml/L 1000×trace elements solution; 20 g/L agar; and pH 5.5. 1 ml/L 400× trace element salt solution: citric acid 175 g/L, FeSO$_4$.7H$_2$O 200 g/L, ZnSO$_4$.7H$_2$O 16 g/L, CuSO$_4$.5H$_2$O 3.2 g/L, MnSO$_4$.H$_2$O 1.4 g/L, H$_3$BO$_3$ 0.8 g/L. The spore suspension was allowed to dry on the surface of the MM acetamide medium.

Transformation followed the manufacturers instruction. Briefly, 60 mg of M10 tungsten particles were placed in a microcentrifuge tube. 1 mL of ethanol was added and allowed to stand for 15 minutes. The particles were centrifuged at 15,000 rpm for 15 seconds. The ethanol was removed and the particles were washed three times with sterile dH$_2$O before 1 mL of 50% (v/v) sterile glycerol was added. 25 µl of tungsten particle suspension was placed into a microtrifuge tube. While continuously vortexing, the following were added: 0.5-5 µl (100-200 ng/µl) of plasmid DNA, 25 µl of 2.5M CaCl$_2$ and 10 µl of 0.1M spermidine. The particles were centrifuged for 3 seconds. The supernatant was removed and the particles were washed with 200 µl of 70% (v/v) ethanol and centrifuged for 3 seconds. The supernatant was removed and 24 µl 100% ethanol was added, mixed by pipetting, and the tube was placed in an ultrasonic bath, 8 µl aliquots of particles were removed and placed onto the center of macrocarrier disks that were held in a desiccator. Once the tungsten/DNA suspension had dried the microcarrier disk was placed in the bombardment chamber along with the plate of MM acetamide with spores and the bombardment process was performed according to the manufacturers instructions. After bombardment of the plated spores with the tungsten/DNA particles, the plates were incubated at 28° C. Transformed colonies were picked to fresh plates of MM acetamide after 4 days (Pentillä et al. (1987) Gene 61: 155-164).

C. Demonstration of GA activity from the expressed variant TrGA in transformed cells.

After 5 days growth on MM acetamide plates transformants displaying stable morphology were inoculated into 250 ml shake flasks containing 30 ml of Proflo medium. (Proflo medium contained: 30 g/L α-lactose; 6.5 g/L (NH$_4$)$_2$SO$_4$; 2 g/L KH$_2$PO$_4$; 0.3 g/L MgSO$_4$.7H$_2$O; 0.2 g/L CaCl$_2$.2H$_2$O; 1 ml/L 400×trace element salt solution: citric acid 175 g/L, FeSO$_4$.7H$_2$O 200 g/L, ZnSO$_4$.7H$_2$O 16 g/L, CuSO$_4$. 5H$_2$O 3.2 g/L, MnSO$_4$. H$_2$O 1.4 g/L, H$_3$BO$_3$ 0.8 g/L; 2 ml/L 10% Tween 80; 22.5 g/L ProFlo cottonseed flour (Traders protein, Memphis, Tenn.); 0.72 g/L CaCO$_3$. After two days growth at 28° C. and 140 rpm, 10% of the Proflo culture was transferred to a 250 ml shake flask containing 30 ml of Lactose Defined Media. The composition of the Lactose defined Media was as follows 5 g/L (NH$_4$)$_2$SO$_4$; 33 g/L 1,4-Piperazinebis(propanesulfonic acid) buffer; 9 g/L casamino acids; 4.5 g/L KH$_2$PO$_4$; 1.0 g/L MgSO$_4$.7H$_2$O; 5 ml/L Mazu DF60-P antifoam (Mazur Chemicals, IL); 1000× trace element solution; pH 5.5; 40 ml/L of 40% (w/v) lactose solution was added to the medium after sterilization. The Lactose Defined medium shake flasks were incubated at 28° C., 140 rpm for 4-5 days.

Samples of the culture supernatant were mixed with an appropriate volume of 2× sample loading buffer with reducing agent. Mycelium was removed by centrifugation and the supernatant was analyzed for total protein (BCA Protein Assay Kit, Pierce Cat. No. 23225).

GA activity was measured using the p-nitrophenyl-alpha-D-glucopyranoside (pNPG) assay with pNPG as a substrate (Sigma N-1377). In this assay the ability of glucoamylase to catalyze the hydrolysis of p-nitrophenyl-alpha-D-glucopyranoside (pNPG) to glucose and p-nitrophenol is measured. At an alkaline pH, the nitrophenol forms a yellow color that is proportional to glucoamylase activity and is monitored at 405 nm and compared against an enzyme standard measured as a GAU (Elder, M. T. and Montgomery R. S., Glucoamylase activity in industrial enzyme preparations using colorimetric enzymatic method, Journal of AOAC International, vol. 78(2), 1995). One GAU is defined as the amount of enzyme that will produce 1 gm of reducing sugar calculated as glucose per hour from a soluble starch substrate (4% ds) at pH 4.2 and 60° C.

The protein profile was determined by PAGE electrophoresis on NuPAGE® Novex 10% Bis-Tris Gel with MES SDS Running Buffer (Invitrogen, Carlsbad, Calif., USA).

Example 8

Small Scale Applications Testing of Selected Variants on Soluble Starch

*Trichoderma reesei* host strains expressing the single variants a) V314H, b) S211R, c) Q172F and d) Q208N were grown in fed-batch 14L fermentors at 34° C., pH 3.5 in nutrient media including glucose (Cerelose DE99), KH$_2$PO$_4$, MgSO$_4$.7H$_2$O, (NH$_4$)$_2$SO$_4$, CaCl$_2$.2H$_2$O, trace elements and Mazu anti-foam (DF6000K). Upon glucose depletion growth temperature and pH were shifted to 28° C. and 4.0, respectively. Cell material was removed by filtration and culture supernatants were collected and concentrated to contain greater than 90% glucoamylase as total protein.

Figure 6A:
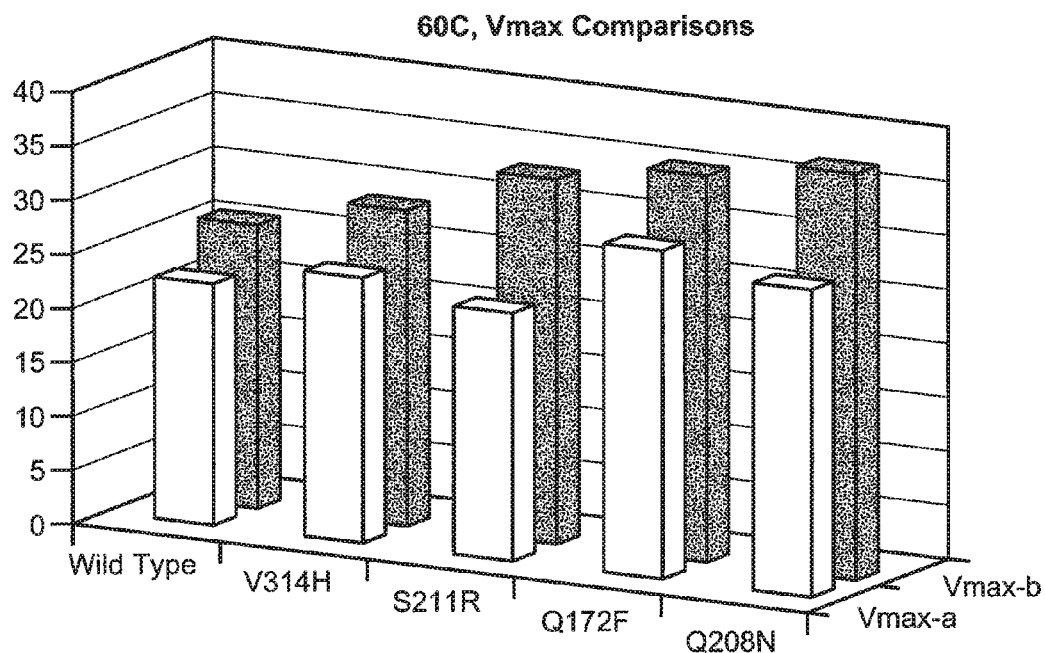
FIG. 6A and FIG. 6B illustrate the Vmax (μM glucose/sec) comparison between the parent (wild-type) TrGA and variants, V314, S211R, Q172F and Q208N at 60° C. and 32° C. as further discussed in example 8.
Figure 6B:
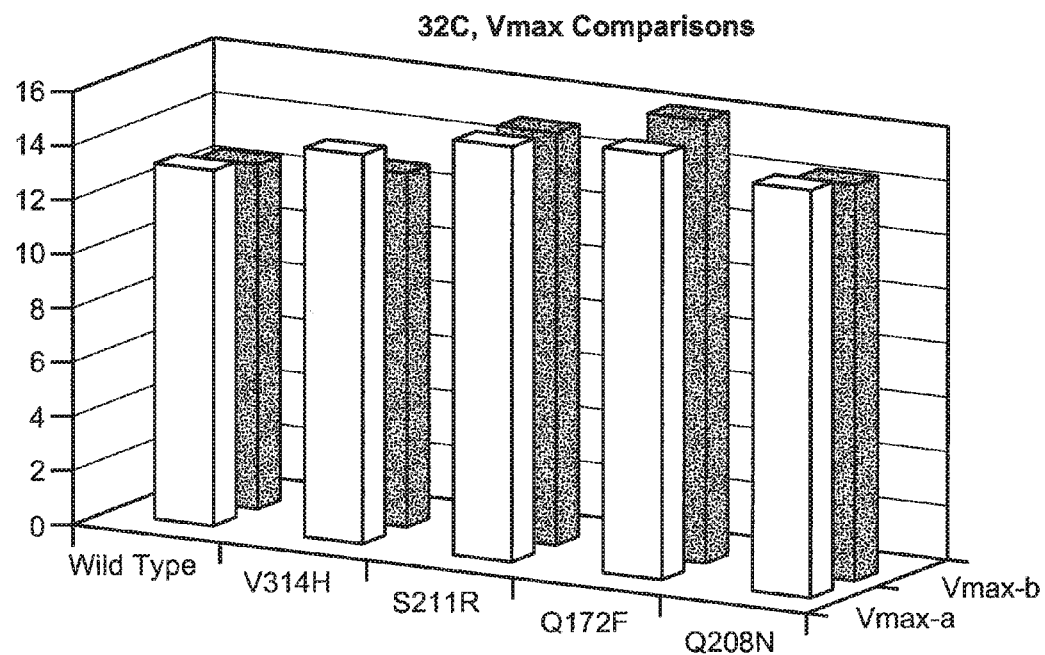

Various kinetic properties were determined for glucose production on soluble potato starch at pH 4.3 at 32° C. and at 60° C. and compared to the wild-type TrGA. Each of the four variants demonstrated increased Vmax (uM glucose/sec) values as compared to the wild type (TrGA) indicating elevated catalytic rates (kcat (sec$^{-1}$)). FIG. 6 illustrates the Vmax of two replicates for each temperature tested.

Example 9

Method to Determine the Performance on EtOH Production of Variants

Validation of the screening was performed on the variants that were identified as having a higher performance index as compared to the parent TrGA (see Table 7/8) using a novel small scale Ethanol application test. 24 variants derived from site evaluation and combinatorial (Table 9) libraries were selected and transformed directly into *T. reesei* for expression and testing on larger scale. The variants were tested for thermal unfolding using Differential Scanning Calorimetry (DSC analysis described hereinbelow) and performance using a novel secondary small scale ethanol application assay. The method consisted of two steps: 1) injection of variants onto an anion exchange column to accurately determine the protein concentration; and 2) titration of variants with three different TrGA concentrations (0.3-0.15-0.075 g/28 g ds) in order to calculate their performance on ethanol production relative to the wild type molecule.

TABLE 9 list of combinatorial variants

| variant | mutation |
|---|---|
| LR8 | Q172F/Q208N |
| LR6 | Q172F/Q208N/V314H |
| LR12 | Q172F/S211R |
| SW3-1 | D24E/I43R/D44N/F175H/V181L/V314H/T353R |
| SW3-2 | D24L/I43F/D44N/F175H/V181L/V314H/T353R |
| ET4-1 | D24L/Q208Q/I292V/G294A/K297A/Y310R |
| ET4-2 | D24W/Q208F/I292V/G294Q/K297A/Y310R |
| ET5-1 | V181L/E243A/I292N/K297N/N317N/Y395Q |
| ET5-2 | V181L/E243R/I292F/K297A/N317N/Y395Q |
| ET7-1 | D24Y/V181L/Q208C/G294A/T353R/N375N/N409W |
| ET7-2 | D24L/V181L/Q208C/G294A/T353R/N375Q/N409W |
| ET8-1 | D24E/V181K/E243Y/I292V/G294Q/N409K |
| ET8-2 | D24E/V181F/E243R/I292N/G294I/N409W |
| ET9-1 | I043R/E243R/I292F/G294A/K297A |
| ET9-2 | I043R/E243R/I292L/G294A/K297M |

Protein Purification and Determination

A crude enzyme preparation was purified using an AKTA explorer 100 FPLC system (Amersham Biosciences, Piscataway, N.J.). β-Cyclodextrin was (Sigma-Aldrich, Zwijndrecht, The Netherlands; 85.608-8) coupled to epoxy-activated Sepharose beads (GE Healthcare, Diegem, Belgium; 17-0480-01). The column was used to capture glucoamylases from the enzyme preparation. Enzyme was eluted from the beads using 25 mM Tris buffer pH 7.5 or 50 mM sodium acetate buffer pH 4.3 containing 10 mM α-cyclodextrin (Sigma, 28705). Purified samples were analyzed by SDS-PAGE. To accurately determine the protein concentration of the variants an FPLC based protein determination method was developed. The protein concentration of the purified marker TrGA molecule was first determined using a standard Bradford protocol (Bio-Rad cat#500-0205). Subsequently, purified samples were injected onto a ResourceQ_1 ml column (GE Healthcare) and enzyme was eluted with 25 mM Tris pH buffer containing 500 mM NaCl. Peak area was determined and the protein concentration was calculated relative to the peak area of the TrGA standard with known concentration.

Small Scale EtOH Application

Table 10 summarizes the production of ethanol and sugars (DP1, DP2, DP>3) by different combinatorial variants. A sample of corn mash liquefact obtained and diluted to 26% DS using thin stillage. The pH of the slurry was adjusted to pH 4.3 using 4N sulphuric acid. A 100 g aliquot of mash was placed into a 32° C. water bath and allowed to equilibrate. After 100 μl 400 ppm urea addition, 1 ml purified variant TrGA enzyme sample (150 μg/ml) or purified TrGA (300, 150, 75 μg/ml) was added to each corn mash sample. Finally, 333 μl of 30 minutes hydrated 15 g in 45 ml DI water solution of Red Star Red yeast (Lesaffre yeast Corp. Milwaukee, Wis.) was added to each sample. Samples were taken at 5, 21, 28, 48 and 52 hours and analyzed by HPLC using an Aminex HPX-87H column 9 (Bio-Rad).

Ethanol and Carbohydrate Determinations

A 2 ml eppendorf centrifuge tube was filled with fermentor beer and cooled on ice for 10 minutes. The sample was centrifuged for 3 minutes at 14.000×g and 500 μl of the supernatant was transferred to a test tube containing 50 μl of kill solution (1.1 N sulfuric acid) and allowed to stand for 5 minutes. 5.0 ml of water was added to the test tube and then filtered into a 0.22 μm filter plate (multiscreen, Millipore, Amsterdam, the Netherlands) and run on HPLC. Column Temperature: 60° C.; mobile phase: 0.01 N sulfuric acid; flow rate 0.6 ml/min; detector: RI; injection volume: 20 μl.

The column separates molecules based on charge and molecular weight; DP1 (monosaccharides); DP2 (disaccharides); DP3 (trisaccharides); DP>3 (oligosaccharides sugars having a degree of polymerization greater than 3); succinic acid; lactic acid; glycerol; methanol; ethanol.

DSC Analysis

The melting temperature of purified enzyme samples (0.2-0.4 mg/ml) was determined using Differential Scanning Calorimetry (DSC).

TABLE 10

Production of ethanol and saccharides

| | hours | DP > 3 (m/v)% | DP2 (m/v)% | DP1 (m/v)% | ethanol (v/v)% |
|---|---|---|---|---|---|
| TrGA (0.3 mg) | 5.5 | 3.46 | 2.70 | 0.91 | 1.02 |
| | 21.5 | 3.40 | 0.50 | 0.06 | 6.80 |
| | 28.5 | 1.68 | 1.46 | 0.07 | 8.13 |
| | 46 | 0.04 | 0.71 | 0.06 | 10.21 |
| | 52.5 | 0.04 | 0.45 | 0.03 | 10.96 |
| TrGA (0.150 mg) | 5.5 | 3.40 | 2.43 | 0.15 | 1.00 |
| | 21.5 | 3.78 | 0.21 | 0.03 | 4.23 |
| | 28.5 | 3.86 | 0.20 | 0.03 | 5.07 |
| | 46 | 2.73 | 0.52 | 0.06 | 7.86 |
| | 52.5 | 1.70 | 0.87 | 0.04 | 7.92 |
| TrGA (0.075 mg) | 5.5 | 3.43 | 2.16 | −0.01 | 0.94 |
| | 21.5 | 3.54 | 0.20 | 0.03 | 3.10 |
| | 28.5 | 3.43 | 0.18 | 0.03 | 3.14 |
| | 46 | 3.93 | 0.18 | 0.05 | 4.65 |
| | 52.5 | 4.01 | 0.18 | 0.03 | 4.79 |
| ET7-1 | 5.5 | 3.45 | 2.53 | 0.21 | 1.00 |
| | 21.5 | 3.94 | 0.22 | 0.04 | 4.77 |
| | 28.5 | 3.89 | 0.23 | 0.04 | 5.58 |
| | 46 | 1.58 | 1.22 | 0.06 | 8.64 |
| | 52.5 | 0.62 | 1.50 | 0.04 | 9.14 |
| LR8 | 5.5 | 3.43 | 2.50 | 0.17 | 1.00 |
| | 21.5 | 3.96 | 0.22 | 0.04 | 4.79 |
| | 28.5 | 3.86 | 0.21 | 0.04 | 6.21 |
| | 46 | 1.27 | 1.11 | 0.07 | 9.17 |
| | 52.5 | 0.45 | 1.24 | 0.04 | 8.73 |
| LR12 | 5.5 | 3.47 | 2.51 | 0.16 | 1.05 |
| | 21.5 | 3.86 | 0.22 | 0.04 | 4.44 |
| | 28.5 | 3.94 | 0.22 | 0.04 | 5.30 |
| | 46 | 2.09 | 1.08 | 0.07 | 8.56 |
| | 52.5 | 0.99 | 1.52 | 0.04 | 9.16 |
| LR6 | 5.5 | 3.37 | 2.44 | 0.18 | 0.96 |
| | 21.5 | 3.88 | 0.21 | 0.04 | 4.44 |
| | 28.5 | 3.90 | 0.20 | 0.04 | 5.10 |
| | 46 | 2.44 | 0.64 | 0.08 | 8.59 |
| | 52.5 | 1.27 | 1.01 | 0.04 | 8.97 |
| ET8-1 | 5.5 | 3.46 | 2.53 | 0.22 | 0.99 |
| | 21.5 | 3.99 | 0.21 | 0.04 | 4.86 |
| | 28.5 | 3.90 | 0.21 | 0.04 | 5.76 |
| | 46 | 1.29 | 1.11 | 0.08 | 8.94 |
| | 52.5 | 0.47 | 1.25 | 0.04 | 9.56 |
| ET7-2 | 5.5 | 3.57 | 2.46 | 0.17 | 1.02 |
| | 21.5 | 4.26 | 0.21 | 0.03 | 4.21 |
| | 28.5 | 4.37 | 0.20 | 0.04 | 5.14 |
| | 46 | 3.87 | 0.27 | 0.05 | 7.21 |
| | 52.5 | 3.27 | 0.33 | 0.03 | 8.07 |

Table 11 represents the final ethanol yields and the performance of the variants at 0.15 mg dosage. The performance was calculated by interpolation of the 0.3 mg and 0.15 mg values of the TrGA by the values of the variants.

TABLE 11

Ethanol Yields

| variant | EtOH %(v/v) | performance relative to TrGA |
|---|---|---|
| TrGA 0.3 mg | 10.21 | |
| TrGA 0.15 mg | 7.86 | 1.00 |

TABLE 11-continued

Ethanol Yields

| variant | EtOH %(v/v) | performance relative to TrGA |
|---|---|---|
| TrGA 0.075 mg | 4.65 | |
| ET7-1 | 8.64 | 1.33 |
| LR8 | 9.17 | 1.56 |
| LR12 | 8.56 | 1.30 |
| LR6 | 8.59 | 1.31 |
| ET8-1 | 8.94 | 1.46 |
| ET7-2 | 7.21 | 0.72 |

All combinatorial variants except ET7-2 performed better than TrGA wild type. LR8 performed the best with a 1.56 improved performance.

Table 12 gives an overview of all single site and combinational mutants tested using the small scale ethanol application assay. Variants that are shaded in Table 12 had a better performance than TrGA and also had a higher thermal unfolding temperature (dTm).

TABLE 12

Performance and thermal unfolding of variants relative to TrGA

| Variant | X TrGA | dTm |
|---|---|---|
| LR8 | 1.56 | 0.30 |
| ET8-1 | 1.46 | 1.60 |
| ET7-1 | 1.33 | 0.90 |
| LR6 | 1.31 | 0.73 |
| LR12 | 1.30 | −0.13 |
| ET5-2 | 1.29 | −0.31 |
| ET4-2 | 1.27 | 0.71 |
| Y213C | 1.27 | 0.06 |
| ET4-1 | 1.21 | −2.64 |
| SW3-1 | 1.21 | 0.29 |
| Q172F | 1.18 | −0.01 |
| V314H | 1.17 | −0.44 |
| G294I | 1.16 | −0.22 |
| S211R | 1.12 | −0.44 |
| Q208N | 1.08 | −0.22 |
| ET9-1 | 1.04 | −1.33 |
| K297A | 1.03 | −1.11 |
| SW3-2 | 1.00 | 0.88 |
| TrGA | 1.00 | 0.00 |
| G294Q | 0.99 | −0.86 |
| ET8/2 | 0.93 | −0.01 |
| P94N | 0.76 | −5.17 |
| ET5-1 | 0.76 | −3.28 |
| ET7-2 | 0.72 | −3.59 |
| S214L/C222F | 0.70 | −3.98 |

The results showed that Chromatography (FPLC) was a useful tool to accurately determine the protein concentration. The results also showed that titration of variants with three TrGA concentrations was a valuable method to determine the performance of variants on small scale. Seven variants performed better than TrGA wild type (see Table 12) and also had a higher thermal unfolding temperature and the variants that did not perform as well as TrGA also had a lower Tm.

Example 10: Specific Activity Determination of a Selected Set of Combinatorial and Single Site Variants and Substrate Specificity of LR8

The specific activity of a set of the combinatorial variants and several single site mutants that were used to construct combinatorial variants was analyzed (Table 13). LR8 (PI 1.56 determined with small scale application assay) was further studied with respect to substrate specificity. This was done by setting up an MTP assay to determine the glucose production rates of GA variants and to determine substrate specificity of the LR8 variant. The MTP assay was found to discriminate between variants and all variants except ET7-1 showed higher rates than the wildtype (wt) *Trichoderma reesei* glucoamylase. Further, several variants (LR8/ET8/Q172F) performed 20-30% better than TrGA. LR8 performed better on soluble corn starch and two different samples of corn mash liquefact compared to wildtype.

Substrates used in the following experiments were soluble corn starch stock solution prepared as follows: 8 g soluble corn starch (Sigma # S4180) was dissolved in 100 ml milliQ water and heated in a microwave for 1 minute. The dispersion was boiled for 5 minutes and after cooling the volume was adjusted to 100 ml. 4% soluble corn starch was prepared by diluting the stock solution 1:1 with 100 mM NaAc buffer pH 4. In one experiment, a corn liquefact substrate (NE) was prepared using a moisture analyzer to measure % ds, then substrate was diluted 7.5× with 50 mM NaAc to finally obtain 4% ds. The substrate was centrifuged for 5' at 2000×g and the supernatant was filtered with a 0.22 μm filter. In another experiment, a corn liquefact substrate (BSE) was prepared in the same way, except that the substrate was diluted 10×before centrifugation.

The enzyme was diluted using the Stock solution of 150 μg enzyme/ml (3 μg/180 μl reaction mixture). Solutions were further diluted with 50 mM NaAc pH 4.0 as follows: 300 ng (10×), 200 ng, 150 ng, 100 ng, 75 ng, 50 ng, 25 ng, 10 ng/180 μl reaction mixture The assay was performed as follows: 40 μl 50 mM NaAc pH 4.0, 120 μl 4% soluble corn starch, and 20 μl enzyme were added to each well. Samples were incubated for 2 hr at 32° C. 900 rpm and terminated on ice after addition of 90 μl 800 mM glycine-NaOH buffer pH 10 for 5 min. The plate was centrifuged for 5 min at 2000 rpm at 15° C. To a fresh plate, 85 μl milliQ water and 100 μl hexokinase cocktail (II test glucose (HK) kit, Instrumental Laboratory #182507-40) and 20 μl supernatant were added. For a glucose (0-1 mg/ml) calibration line 20 μl glucose stock was added instead. Plates were incubated for 10 min at room temperature in the dark followed by absorption measurement at 340 nm using the Spectramax.

TABLE 13 performance relative to wt

| | ng GA | | | | | | | |
|---|---|---|---|---|---|---|---|---|
| | 300 | 200 | 150 | 100 | 75 | 50 | 25 | 10 |
| graph1 | | | | | | | | |
| TrGA | 1.00 | 1.00 | 1.00 | 1.00 | 1.00 | 1.00 | 1.00 | 1.00 |
| ET7-1 | 0.94 | 0.98 | 0.91 | 0.92 | 0.63 | 0.38 | 3.50 | 0.53 |
| LR8 | 0.93 | 1.00 | 1.22 | 0.91 | 0.64 | 0.06 | −0.89 | −3.99 |
| LR12 | 0.94 | 0.99 | 1.17 | 0.83 | 0.66 | −0.15 | −0.99 | 0.62 |
| LR6 | 0.94 | 1.01 | 1.16 | 0.99 | 0.55 | 0.17 | −1.67 | −4.36 |
| ET8-1 | 0.87 | 0.95 | 1.29 | 1.02 | 0.62 | −0.05 | −1.64 | −3.42 |
| ET7-2 | 0.94 | 1.00 | 1.24 | 0.93 | 0.50 | 0.22 | −0.62 | −1.40 |
| graph2 | | | | | | | | |
| V314H | 0.95 | 0.97 | 1.24 | 0.91 | 0.78 | 0.54 | 0.74 | 1.89 |
| G294Q | 0.98 | 0.99 | 1.03 | 1.21 | 1.10 | 0.19 | −0.34 | −1.12 |
| S211R | 0.97 | 0.99 | 1.21 | 1.05 | 0.94 | 0.27 | −1.32 | 0.53 |
| Q208N | 0.97 | 1.01 | 1.13 | 0.95 | 0.90 | −0.05 | −1.01 | −2.81 |
| Q172F | 0.99 | 1.04 | 1.31 | 1.23 | 1.32 | 0.38 | −1.59 | −2.20 |
| G294I | 0.91 | 0.96 | 1.07 | 1.25 | 0.80 | 0.09 | −1.20 | −3.66 |
| P94N | 0.98 | 1.00 | 1.24 | 1.09 | 1.05 | 0.29 | 6.29 | −3.80 |
| TrGA | 1.00 | 1.00 | 1.00 | 1.00 | 1.00 | 1.00 | 1.00 | 1.00 |

Figure 7:
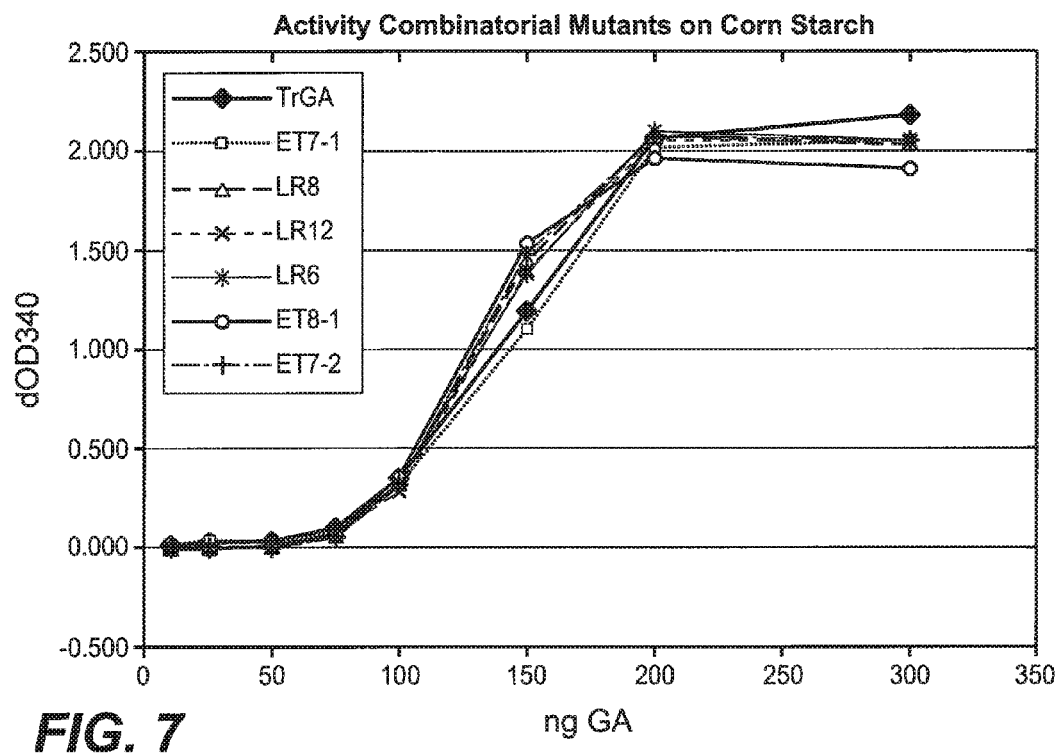
FIG. 7 illustrates the activity of combinatorial mutants on starch.
Figure 8:
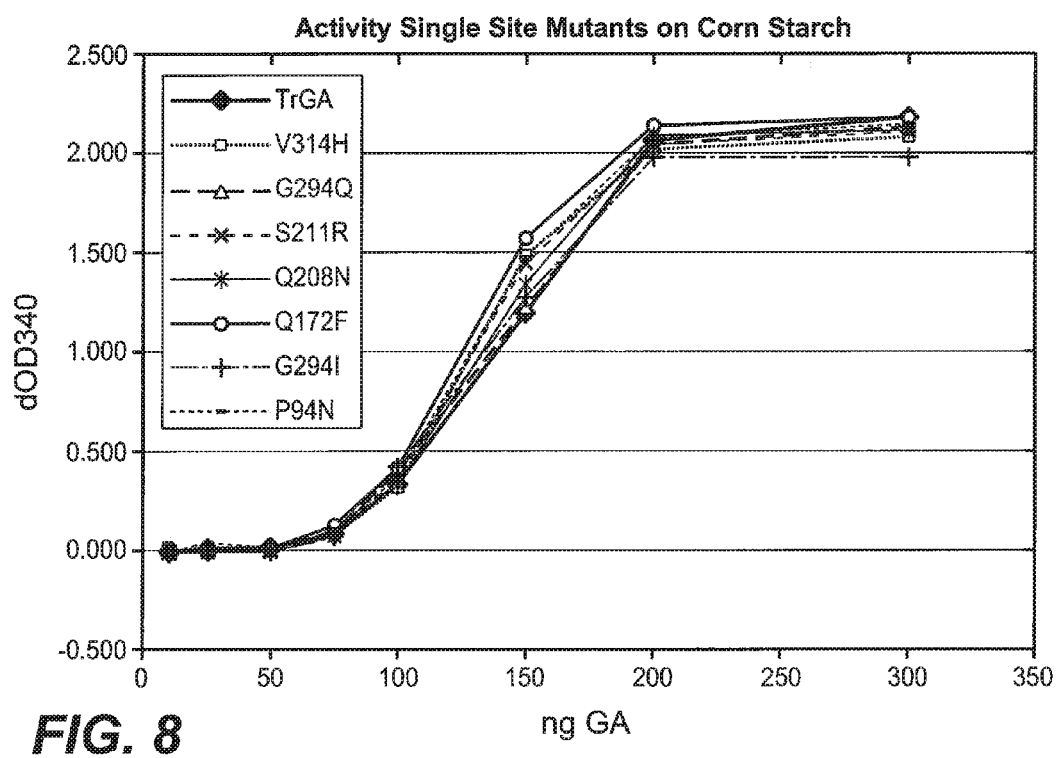
FIG. 8 illustrates the Activity of single site mutants on corn starch.

The results of the assay to determine the glucose production rates of by GA variants are shown in FIGS. 7 and 8. In these figures, the relative performance to TrGA was calculated per amount of enzyme added. Conclusions were drawn from the linear region of the graph at 150 ng of enzyme. The results in FIGS. 7, 8 and Table 13 showed that LR8, ET8, ET7-2, S211R, Q172F and P94N performed better than wildtype over the linear range.

Substrate Specificity of LR8—

Figure 9:
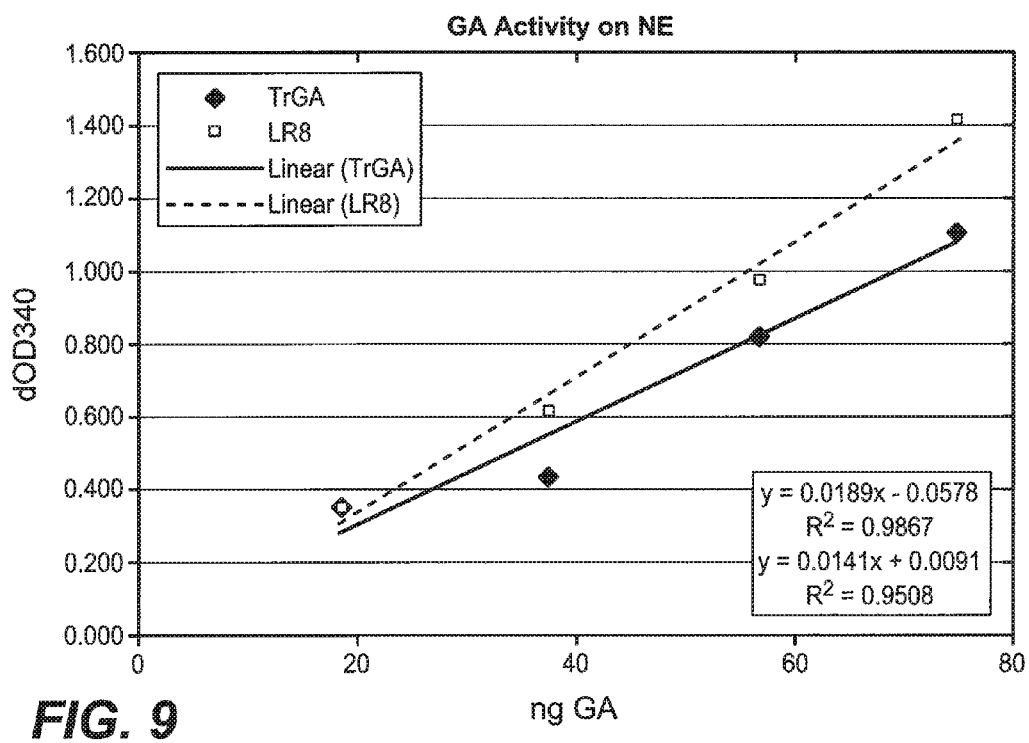
FIG. 9 illustrates the GA activity of TrGA and the TrGA variant LR8 on a sample of corn mash liquefact (NE) from Example 10.
Figure 10:
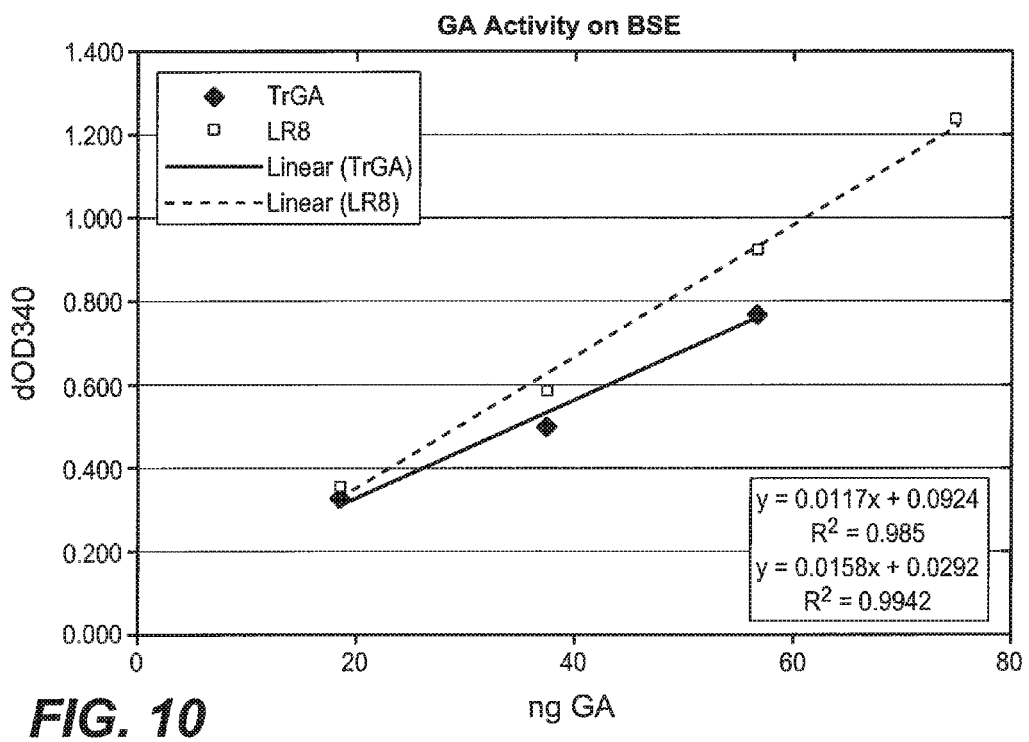
FIG. 10 illustrates the activity profile of TrGA and the TrGA variant LR8 on corn mash liquefact (BSE) from Example 10.
Figure 11:
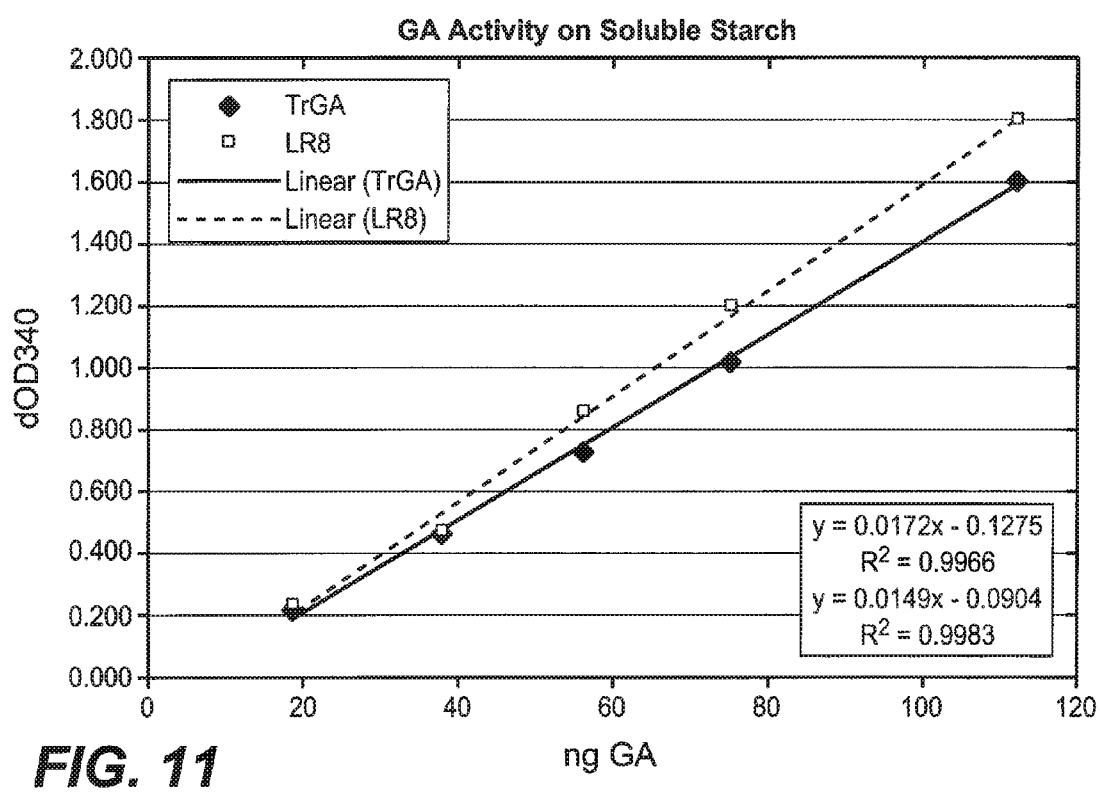
FIG. 11 illustrates the TrGA variant LR8 on soluble corn starch substrate.

The performance of LR8 and TrGA wildtype was tested on substrates (soluble corn starch, and the two corn mash substrates produced in Example 10) used in screening and application. When analyzed by HPLC, the substrates showed a difference in degree of polymerization (DP) pattern (see FIGS. 9-11). In NE and BSE DPI->=DP4 is present while soluble corn starch consist of at least four or more glucose molecules. On all substrates LR8 performed better than wildtype (see FIGS. 9, 10 and 11).

Example 11: Crystal Structure of TrGA

The complete three dimensional structure of *Trichoderma reesei* (*Hypocrea jecorina*) glucoamylase (TrGA) was determined at 1.9 Å resolution. Table 15 shows the coordinates for the *Trichoderma* glucoamylase crystal structure. TrGA was crystallized in an intact form containing 599 residues and all post-translational modifications that would normally occur in the natural host. The crystal structure was produced and analyzed as follows:

Protein expression and purification—The gene encoding *H. jecorina* GA was cloned and expressed according to the protocols described in the US patent application with publication No.: US 2006/0094080 A1, by Dunn-Coleman et al. and publication date May 4, 2006.

The TrGA protein material used for all crystallization experiments was initially purified in one step by anion exchange chromatography as follows: concentrated culture supernatants of expressed TrGA, consisting of 180 mg/ml total protein, were prepared by diluting sample 1:10 in a 25 mM Tris-HCl, pH 8.0 buffer. A HiPrep 16/10 Q Sepharose FF column (GE Helthcare) was employed for the anion exchange purification. The HiPrep column was equilibrated with 4 column volumes (CV) starting buffer (25 mM Tris-HCl, pH 8.0) followed by application of 10 ml of the diluted protein sample. An 8 CV linear gradient of 0 to 140 mM NaCl in the running buffer (25 mM Tris-HCl, pH 8.0) was applied to elute bound protein. Bound TrGA eluted from the HiPrep Q sepharose column at a salt concentration of approximately 80 mM NaCl. Fractions containing pure TrGA protein were pooled and concentrated to 50 mg/ml using a 25 ml Vivaspin centrifugal concentration tube (Viva Science) with a molecular weight cutoff (MWCO) of 10 kD. Purified and concentrated TrGA material was buffer exchanged using a DG-10 desalting column (Bio-Rad) equilibrated with 50 mM sodium acetate buffer, pH 4.3. Protein concentrations were determined by measuring the absorbance at 280 nm. The initially purified and concentrated TrGA protein stock was thereafter stored at −20° C.

Two additional purification steps, on additional anion exchange purification, and a size exclusion purification, were introduced to enhance the crystability of the TrGA protein material. These two additional purification steps were performed as follows: In the first anion exchange purification step a 10 ml MonoQ column (GE Helthcare) was employed. A Sample of 1 ml of the initially purified and frozen TrGA material (50 mg protein) was thawed and the buffer was changed to 20 mM Tris-HCl, pH 8.0, by repeated dilution of the sample to 6 ml in the new buffer, followed by a concentration of the sample again to 0.5 ml using a 6 ml 5 kD MWCO concentration tube. The TrGA sample was diluted after the last concentration step in distilled water until a conductivity of the protein sample was reached that corresponded to the conductivity of the starting buffer of the anion purification, i.e. 25 mM Tris-HCl, pH 8.0. The MonoQ column was first equilibrated with 4 column volumes (CV) starting buffer, followed by application of the diluted protein sample to the column. Bound protein was eluted from the MonoQ column by two different gradients. In the first a 4 CV linear pH gradient was applied where the pH of the starting buffer was decreased from 8.0 to 6.0. In the second gradient an 8 CV long salt gradient was applied in which the salt concentration was increased from 0 to 350 mM NaCl in the running buffer (25 mM Tris-HCl, pH 6.0). Bound TrGA was found to elute from the column during the second salt gradient at an approximate NaCl concentration of 150 mM. Fractions containing TrGA were pooled and concentrated to 2 ml using a 6 ml 5 kD MWCO Vivaspin concentration tube. The concentrated TrGA sample was thereafter applied to a Superdex 200 16/60 size exclusion column (GE Helthcare) equilibrated with 4 CV of 20 mM Tris-Cl, pH 8.0, and 50 mM NaCl, which also was used as running buffer. Fractions from the main elution peak after the size exclusion purification were pooled and concentrated to an approximate protein concentration of 7.5 mg/ml using a 6 ml 5 kD MWCO Vivaspin concentration tube.

Protein crystallization—The protein sample that was used to find the initial TrGA crystallization conditions was a sample of the TrGA material that was purified once by anion exchange purification and thereafter stored at −20° C. The TrGA protein sample was thawed and diluted with 50 mM sodium acetate buffer, pH 4.3, to approximately 12 mg/ml, prior to the initial crystallization experiments. The orthorhombic x-ray dataset, was used to solve the TrGA structure by molecular replacement (MR), and the high-resolution orthorhombic dataset, used for the final orthorhombic space group TrGA structure model. The orthorhombic TrGA crystals were found to grow in solution consisting of 25% PEG 3350, 0.20M ammonium acetate, 0.10M Bis-Tris pH 5.5 (reservoir solution), using the vapor-diffusion method with hanging drops (McPherson 1982), at 20° C. Crystallization drops were prepared by mixing equal amounts of protein solution (12 mg/ml) and reservoir solution to a final volume of 10 μl. The TrGA crystals were found to belong to the orthorhombic space group P212121 with approximate cell dimensions: a=52.2 Å, b=99.2 Å, c=121.2 Å, and have a calculated $V_m$ of 2.3 (Matthews 1968) with one molecules in the asymmetric unit.

X-ray data collection—The two orthorhombic TrGA datasets were collected from single crystals mounted in sealed capillary tubes, at room temperature. The initial lo-resolution orthorhombic TrGA x-ray dataset, used to solve the structure by molecular replacement methods (MR), was collected on a home x-ray source, an MSC/Rigaku (Molecular Structures Corp., The Woodlands, Tex.) Raxis IV++ image plate detector with focusing mirrors using Cu Kα radiation from a Rigaku RU200 rotating anode generator. This dataset was processed, scaled, and averaged using the d*trek software provided by MSC/Rigaku. The C centered monoclinic dataset was collected from a single frozen TrGA crystal at 100K, equilibrated in a cryo-protective agent comprised of 25% PEG 3350, 15% Glycerol 50 mM $CaCl_2$ and 0.1 M Bis-Tris pH 5.5 as cryoprotectant, mounted in rayon-fiber loops, and plunge frozen in liquid nitrogen prior to transportation to the synchrotron. The high-resolution orthorhombic (1.9 Å) data set and the C centric monoclinic dataset (1.8 Å) were both collected at a synchrotron source, beam line 911:5 at MAX LAB in Lund, Sweden. Both datasets that were collected at a synchrotron source were processed with MOSFLM, and scaled with program SCALA included in the CCP4 program package (Collaborative Computational Project Number 4 1994). All subsequent data processing was performed using the CCP4 program package (Collaborative Computational Project Number 4 1994), unless otherwise stated. A set of 5% of the reflections from each data set was set aside and used for monitoring the R-free (Brünger 1992).

Structure solution—The TrGA structure was initially solved by MR with the automatic replacement program MOLREP (Collaborative Computational Project Number 4 1994), included in the CCP4 program package, using the initial lo-resolution orthorhombic dataset, and using the coordinates of *Aspergillus. awamori* GA (AaGA) variant X100 (pdb entry 1GLM (Aleshin et al. 1992)) as search model. The *A. awamori* GA search model was edited to remove all glycosylation moieties attached to the protein molecule as N- and O-glycosylations, and all solvent molecules before carrying out the MR experiments. All reflections between 36.8 and 2.8 Å resolution, from the initial lo resolution TrGA dataset, was used for the MR solution. The MR program found a single rotation function solution, with a maxima of 11.1 σ above background, the next highest maxima was 3.8σ above the background. The translation function solution gave an R-factor of 48.7% and had a contrast factor of 17.4. The MR solution was refined for 10 cycles of restrained least squares refinement using the program Refmac 5.0 (Murshudov et al. 1997). This lowered the crystallographic R-factor to 31.1% while the R-free value dropped from 42.2% to 41.1%.

Model fitting and refinement—The refined MR solution model was used to calculate an initial density map from the lo-resolution orthorhombic TrGA dataset. Electron density for a disulfide bridge between residues 19 and 26 of TrGA, a disulfide bridge not present in the *A. awamori* variant X100 structure model, could readily be identified in this electron density map. This was taken as an indication that the electron density map was of sufficient quality to be used to build a structure model of TrGA from its amino acid sequence. The initial TrGA structure model, based on the lo-resolution dataset, was refined with alternating cycles of model building using Coot (Emsley and Cowtan 2004), and maximum likelihood refinement using Refmac 5.0.

The resolution of the initial TrGA structure model was extended to the resolution of the high-resolution orthorhombic dataset (1.9 Å) by refining the initial TrGA structure model against the high-resolution dataset for 10 cycles of restrained refinement using the program Refmac 5.0. Most water molecules in the structure models were located automatically by using the water picking protocols in the refinement programs, and then manually selected or discarded by inspection by eye. All structural comparisons were made with either Coot (Emsley and Cowtan 2004) or O (Jones et al. 1991), and figures were prepared with PyMOL (DeLano 2002).

From these results, it can be seen that the TrGA catalytic core segment followed the same $(\alpha/\alpha)_6$-barrel topology described by Aleshin et al. 1992 for the AaGA, consisting of a double barrel of alpha helices with the C-terminal of the outer helix leading into the N-terminus of an inner helix. It was possible to identify key differences in the electron density such as the disulfide bridge between residues 19 and 26 and an insertion (residues 257-260) relative to AaGA. The segment comprising 80-100 also underwent extensive model rebuilding. One major glycosylation site was identified at Asn 171, which had up to four glycoside moieties attached. A similar glycosylation site was identified in AaGA. Additionally, the catalytic core containing three cis-peptides between residues 22-23, 44-45 and 122-123 were conserved between TrGA and AaGA. Overall there was an rms variation of 0.535 Å between 409 out of 453 Cα atoms when comparing the coordinates of the catalytic cores of TrGA and AaGA.

Example 12: Homology Between TrGA and *Aspergillus awamori* GA

The crystal structure of the TrGA identified in Example 12, was superposed on the previously identified crystal structure of the *Aspergillus awamori* GA (AaGA). The AaGA crystal structure was obtained from the protein database (PDB) and the form of AaGa that was crystallized was the form containing only a catalytic domain. The structure of the *Trichoderma reesei* glucoamylase with all three regions intact was determined to 1.8 Angstrom resolution herein (see Table 15 and Example 12). Using the coordinates (see Table 15) the structure was aligned with the coordinates of the catalytic domain from *Aspergillus awamorii* strain X100 that was determined previously (Aleshin, A. E., Hoffman, C., Firsov, L. M., and Honzatko, R. B. 1994 Refined crystal structures of glucoamylase from *Aspergillus awamori* var. X100. *J Mol Biol* 238: 575-591 and the PDB). As seen in FIGS. 12 and 13 the structure of the catalytic domain overlapped very closely and allowed the identification of equivalent residues based on this structural superposition.

Based on this analysis, sites were identified that could be mutated in TrGA and result in increased stability and/or specific activity. These sites include 108, 124, 175 and 316 at the active site. Also identified were specific pairwise variants Y47W/Y315F and Y47F/Y315W. Other sites identified were 143, D44, P45, D46, R122, R125, V181, E242, Y310, D313, V314, N317, R408, and N409. Because of the high structural homology it is expected that beneficial variants found at sites in *Trichoderma Reesei* GA would have similar consequences in *Aspergillus awamori* and other homologous glucoamylases.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

TABLE 15

| CRYST1 | 52.185 | 99.232 | 121.240 | 90.00 | 90.00 | 90.00 |
|---|---|---|---|---|---|---|
| ORIGX1 | 1.000000 | 0.000000 | 0.000000 | 0.00000 | | |
| ORIGX2 | 0.000000 | 1.000000 | 0.000000 | 0.00000 | | |
| ORIGX3 | 0.000000 | 0.000000 | 1.000000 | 0.00000 | | |
| SCALE1 | 0.019163 | −0.000001 | −0.000001 | 0.00000 | | |

TABLE 15-continued

| | | | | | | | | | |
|---|---|---|---|---|---|---|---|---|---|
| SCALE2 | | 0.000000 | | | 0.010077 | 0.000000 | | 0.00000 | |
| SCALE3 | | 0.000000 | | | 0.000000 | 0.008248 | | 0.00000 | |
| ATOM | 1 | N | SER | A | 1 | −30.485 | 30.567 | −21.185 | 1.00 37.11 |
| ATOM | 2 | CA | SER | A | 1 | −30.568 | 29.350 | −20.326 | 1.00 37.00 |
| ATOM | 3 | CB | SER | A | 1 | −31.953 | 28.707 | −20.424 | 1.00 37.27 |
| ATOM | 4 | OG | SER | A | 1 | −32.137 | 28.089 | −21.695 | 1.00 40.11 |
| ATOM | 5 | C | SER | A | 1 | −29.519 | 28.345 | −20.772 | 1.00 35.91 |
| ATOM | 6 | O | SER | A | 1 | −29.043 | 28.415 | −21.911 | 1.00 35.46 |
| ATOM | 7 | N | VAL | A | 2 | −29.170 | 27.425 | −19.867 | 1.00 34.51 |
| ATOM | 8 | CA | VAL | A | 2 | −28.302 | 26.293 | −20.179 | 1.00 33.56 |
| ATOM | 9 | CB | VAL | A | 2 | −28.142 | 25.339 | −18.955 | 1.00 33.84 |
| ATOM | 10 | CG1 | VAL | A | 2 | −27.349 | 24.103 | −19.316 | 1.00 34.20 |
| ATOM | 11 | CG2 | VAL | A | 2 | −27.468 | 26.057 | −17.827 | 1.00 34.79 |
| ATOM | 12 | C | VAL | A | 2 | −28.846 | 25.506 | −21.363 | 1.00 32.48 |
| ATOM | 13 | O | VAL | A | 2 | −28.086 | 25.109 | −22.245 | 1.00 31.10 |
| ATOM | 14 | N | ASP | A | 3 | −30.160 | 25.286 | −21.381 | 1.00 31.43 |
| ATOM | 15 | CA | ASP | A | 3 | −30.791 | 24.530 | −22.457 | 1.00 31.38 |
| ATOM | 16 | CB | ASP | A | 3 | −32.283 | 24.323 | −22.190 | 1.00 32.17 |
| ATOM | 17 | CG | ASP | A | 3 | −32.522 | 23.492 | −20.943 | 1.00 35.28 |
| ATOM | 18 | OD1 | ASP | A | 3 | −32.413 | 22.251 | −21.028 | 1.00 36.80 |
| ATOM | 19 | OD2 | ASP | A | 3 | −32.786 | 24.092 | −19.870 | 1.00 40.63 |
| ATOM | 20 | C | ASP | A | 3 | −30.556 | 25.153 | −23.818 | 1.00 30.59 |
| ATOM | 21 | O | ASP | A | 3 | −30.282 | 24.446 | −24.778 | 1.00 30.19 |
| ATOM | 22 | N | ASP | A | 4 | −30.644 | 26.477 | −23.875 | 1.00 29.89 |
| ATOM | 23 | CA | ASP | A | 4 | −30.369 | 27.244 | −25.083 | 1.00 29.99 |
| ATOM | 24 | CB | ASP | A | 4 | −30.601 | 28.731 | −24.822 | 1.00 31.12 |
| ATOM | 25 | CG | ASP | A | 4 | −32.088 | 29.121 | −24.785 | 1.00 34.16 |
| ATOM | 26 | OD1 | ASP | A | 4 | −32.991 | 28.260 | −24.925 | 1.00 36.06 |
| ATOM | 27 | OD2 | ASP | A | 4 | −32.340 | 30.332 | −24.608 | 1.00 39.96 |
| ATOM | 28 | C | ASP | A | 4 | −28.925 | 27.049 | −25.579 | 1.00 28.65 |
| ATOM | 29 | O | ASP | A | 4 | −28.697 | 26.881 | −26.770 | 1.00 28.51 |
| ATOM | 30 | N | PHE | A | 5 | −27.961 | 27.096 | −24.660 | 1.00 26.74 |
| ATOM | 31 | CA | PHE | A | 5 | −26.553 | 26.860 | −24.994 | 1.00 25.21 |
| ATOM | 32 | CB | PHE | A | 5 | −25.666 | 27.110 | −23.764 | 1.00 25.59 |
| ATOM | 33 | CG | PHE | A | 5 | −24.244 | 26.646 | −23.931 | 1.00 26.03 |
| ATOM | 34 | CD1 | PHE | A | 5 | −23.395 | 27.259 | −24.854 | 1.00 27.29 |
| ATOM | 35 | CE1 | PHE | A | 5 | −22.063 | 26.823 | −25.009 | 1.00 27.33 |
| ATOM | 36 | CZ | PHE | A | 5 | −21.593 | 25.783 | −24.228 | 1.00 26.77 |
| ATOM | 37 | CE2 | PHE | A | 5 | −22.425 | 25.181 | −23.286 | 1.00 28.42 |
| ATOM | 38 | CD2 | PHE | A | 5 | −23.749 | 25.617 | −23.144 | 1.00 28.42 |
| ATOM | 39 | C | PHE | A | 5 | −26.352 | 25.438 | −25.539 | 1.00 24.23 |
| ATOM | 40 | O | PHE | A | 5 | −25.659 | 25.244 | −26.544 | 1.00 23.56 |
| ATOM | 41 | N | ILE | A | 6 | −26.974 | 24.458 | −24.892 | 1.00 22.71 |
| ATOM | 42 | CA | ILE | A | 6 | −26.835 | 23.065 | −25.312 | 1.00 22.36 |
| ATOM | 43 | CB | ILE | A | 6 | −27.491 | 22.106 | −24.299 | 1.00 21.86 |
| ATOM | 44 | CG1 | ILE | A | 6 | −26.744 | 22.181 | −22.956 | 1.00 22.27 |
| ATOM | 45 | CD1 | ILE | A | 6 | −27.384 | 21.347 | −21.834 | 1.00 22.36 |
| ATOM | 46 | CG2 | ILE | A | 6 | −27.571 | 20.669 | −24.848 | 1.00 21.69 |
| ATOM | 47 | C | ILE | A | 6 | −27.388 | 22.855 | −26.723 | 1.00 22.84 |
| ATOM | 48 | O | ILE | A | 6 | −26.753 | 22.216 | −27.573 | 1.00 21.76 |
| ATOM | 49 | N | SER | A | 7 | −28.556 | 23.420 | −26.996 | 1.00 23.10 |
| ATOM | 50 | CA | SER | A | 7 | −29.146 | 23.175 | −28.309 | 1.00 23.90 |
| ATOM | 51 | CB | SER | A | 7 | −30.627 | 23.570 | −28.320 | 1.00 25.04 |
| ATOM | 52 | OG | SER | A | 7 | −30.717 | 24.982 | −28.282 | 1.00 30.08 |
| ATOM | 53 | C | SER | A | 7 | −28.340 | 23.874 | −29.422 | 1.00 22.78 |
| ATOM | 54 | O | SER | A | 7 | −28.186 | 23.337 | −30.508 | 1.00 22.94 |
| ATOM | 55 | N | THR | A | 8 | −27.800 | 25.053 | −29.140 | 1.00 22.50 |
| ATOM | 56 | CA | THR | A | 8 | −26.984 | 25.780 | −30.115 | 1.00 23.05 |
| ATOM | 57 | CB | THR | A | 8 | −26.834 | 27.247 | −29.698 | 1.00 23.65 |
| ATOM | 58 | OG1 | THR | A | 8 | −28.138 | 27.839 | −29.700 | 1.00 27.60 |
| ATOM | 59 | CG2 | THR | A | 8 | −25.939 | 28.018 | −30.660 | 1.00 26.76 |
| ATOM | 60 | C | THR | A | 8 | −25.601 | 25.159 | −30.307 | 1.00 21.46 |
| ATOM | 61 | O | THR | A | 8 | −25.109 | 25.051 | −31.437 | 1.00 21.38 |
| ATOM | 62 | N | GLU | A | 9 | −24.978 | 24.768 | −29.200 | 1.00 19.11 |
| ATOM | 63 | CA | GLU | A | 9 | −23.596 | 24.269 | −29.243 | 1.00 18.01 |
| ATOM | 64 | CB | GLU | A | 9 | −22.959 | 24.334 | −27.847 | 1.00 17.76 |
| ATOM | 65 | CG | GLU | A | 9 | −21.449 | 23.945 | −27.794 | 1.00 17.71 |
| ATOM | 66 | CD | GLU | A | 9 | −20.536 | 24.892 | −28.609 | 1.00 20.86 |
| ATOM | 67 | OE1 | GLU | A | 9 | −20.949 | 26.010 | −28.971 | 1.00 19.89 |
| ATOM | 68 | OE2 | GLU | A | 9 | −19.389 | 24.500 | −28.909 | 1.00 19.22 |
| ATOM | 69 | C | GLU | A | 9 | −23.462 | 22.846 | −29.784 | 1.00 17.77 |
| ATOM | 70 | O | GLU | A | 9 | −22.423 | 22.505 | −30.368 | 1.00 18.05 |
| ATOM | 71 | N | THR | A | 10 | −24.485 | 22.020 | −29.593 | 1.00 15.87 |
| ATOM | 72 | CA | THR | A | 10 | −24.404 | 20.609 | −29.958 | 1.00 17.31 |
| ATOM | 73 | CB | THR | A | 10 | −25.677 | 19.823 | −29.525 | 1.00 17.46 |
| ATOM | 74 | OG1 | THR | A | 10 | −25.768 | 19.860 | −28.090 | 1.00 17.46 |
| ATOM | 75 | CG2 | THR | A | 10 | −25.616 | 18.374 | −30.037 | 1.00 18.42 |
| ATOM | 76 | C | THR | A | 10 | −24.026 | 20.346 | −31.430 | 1.00 17.40 |
| ATOM | 77 | O | THR | A | 10 | −23.073 | 19.615 | −31.682 | 1.00 17.22 |
| ATOM | 78 | N | PRO | A | 11 | −24.764 | 20.934 | −32.412 | 1.00 18.30 |

TABLE 15-continued

| | | | | | | | | | |
|---|---|---|---|---|---|---|---|---|---|
| ATOM | 79 | CA | PRO | A | 11 | −24.346 | 20.649 | −33.798 | 1.00 | 18.11 |
| ATOM | 80 | CB | PRO | A | 11 | −25.440 | 21.317 | −34.662 | 1.00 | 18.57 |
| ATOM | 81 | CG | PRO | A | 11 | −26.094 | 22.310 | −33.771 | 1.00 | 19.16 |
| ATOM | 82 | CD | PRO | A | 11 | −25.975 | 21.779 | −32.361 | 1.00 | 18.54 |
| ATOM | 83 | C | PRO | A | 11 | −22.963 | 21.231 | −34.142 | 1.00 | 17.81 |
| ATOM | 84 | O | PRO | A | 11 | −22.241 | 20.655 | −34.964 | 1.00 | 17.74 |
| ATOM | 85 | N | ILE | A | 12 | −22.601 | 22.353 | −33.520 | 1.00 | 16.85 |
| ATOM | 86 | CA | ILE | A | 12 | −21.279 | 22.936 | −33.731 | 1.00 | 16.66 |
| ATOM | 87 | CB | ILE | A | 12 | −21.161 | 24.319 | −33.112 | 1.00 | 17.25 |
| ATOM | 88 | CG1 | ILE | A | 12 | −22.194 | 25.267 | −33.751 | 1.00 | 19.25 |
| ATOM | 89 | CD1 | ILE | A | 12 | −22.289 | 26.635 | −33.101 | 1.00 | 21.45 |
| ATOM | 90 | CG2 | ILE | A | 12 | −19.714 | 24.855 | −33.270 | 1.00 | 18.75 |
| ATOM | 91 | C | ILE | A | 12 | −20.170 | 22.023 | −33.178 | 1.00 | 16.30 |
| ATOM | 92 | O | ILE | A | 12 | −19.155 | 21.798 | −33.848 | 1.00 | 14.64 |
| ATOM | 93 | N | ALA | A | 13 | −20.360 | 21.527 | −31.951 | 1.00 | 15.28 |
| ATOM | 94 | CA | ALA | A | 13 | −19.375 | 20.627 | −31.304 | 1.00 | 15.19 |
| ATOM | 95 | CB | ALA | A | 13 | −19.788 | 20.332 | −29.883 | 1.00 | 15.31 |
| ATOM | 96 | C | ALA | A | 13 | −19.204 | 19.326 | −32.092 | 1.00 | 15.37 |
| ATOM | 97 | O | ALA | A | 13 | −18.083 | 18.834 | −32.297 | 1.00 | 13.56 |
| ATOM | 98 | N | LEU | A | 14 | −20.320 | 18.743 | −32.531 | 1.00 | 15.13 |
| ATOM | 99 | CA | LEU | A | 14 | −20.225 | 17.503 | −33.285 | 1.00 | 16.06 |
| ATOM | 100 | CB | LEU | A | 14 | −21.630 | 16.921 | −33.510 | 1.00 | 17.33 |
| ATOM | 101 | CG | LEU | A | 14 | −21.689 | 15.563 | −34.212 | 1.00 | 20.02 |
| ATOM | 102 | CD1 | LEU | A | 14 | −20.946 | 14.460 | −33.471 | 1.00 | 23.09 |
| ATOM | 103 | CD2 | LEU | A | 14 | −23.150 | 15.225 | −34.390 | 1.00 | 21.86 |
| ATOM | 104 | C | LEU | A | 14 | −19.506 | 17.749 | −34.623 | 1.00 | 15.61 |
| ATOM | 105 | O | LEU | A | 14 | −18.651 | 16.947 | −35.039 | 1.00 | 14.82 |
| ATOM | 106 | N | ASN | A | 15 | −19.853 | 18.852 | −35.285 | 1.00 | 15.30 |
| ATOM | 107 | CA | ASN | A | 15 | −19.236 | 19.228 | −36.567 | 1.00 | 16.34 |
| ATOM | 108 | CB | ASN | A | 15 | −19.848 | 20.545 | −37.073 | 1.00 | 16.07 |
| ATOM | 109 | CG | ASN | A | 15 | −19.232 | 21.010 | −38.388 | 1.00 | 18.31 |
| ATOM | 110 | OD1 | ASN | A | 15 | −19.565 | 20.487 | −39.431 | 1.00 | 17.60 |
| ATOM | 111 | ND2 | ASN | A | 15 | −18.312 | 21.987 | −38.325 | 1.00 | 21.40 |
| ATOM | 112 | C | ASN | A | 15 | −17.736 | 19.450 | −36.405 | 1.00 | 15.35 |
| ATOM | 113 | O | ASN | A | 15 | −16.926 | 18.954 | −37.198 | 1.00 | 15.29 |
| ATOM | 114 | N | ASN | A | 16 | −17.385 | 20.180 | −35.355 | 1.00 | 14.82 |
| ATOM | 115 | CA | ASN | A | 16 | −15.992 | 20.555 | −35.144 | 1.00 | 15.27 |
| ATOM | 116 | CB | ASN | A | 16 | −15.872 | 21.693 | −34.148 | 1.00 | 15.41 |
| ATOM | 117 | CG | ASN | A | 16 | −16.276 | 23.023 | −34.737 | 1.00 | 16.53 |
| ATOM | 118 | OD1 | ASN | A | 16 | −16.517 | 23.136 | −35.954 | 1.00 | 18.08 |
| ATOM | 119 | ND2 | ASN | A | 16 | −16.326 | 24.050 | −33.896 | 1.00 | 16.35 |
| ATOM | 120 | C | ASN | A | 16 | −15.159 | 19.362 | −34.723 | 1.00 | 14.91 |
| ATOM | 121 | O | ASN | A | 16 | −13.975 | 19.261 | −35.099 | 1.00 | 15.34 |
| ATOM | 122 | N | LEU | A | 17 | −15.771 | 18.460 | −33.956 | 1.00 | 14.29 |
| ATOM | 123 | CA | LEU | A | 17 | −15.114 | 17.191 | −33.610 | 1.00 | 13.90 |
| ATOM | 124 | CB | LEU | A | 17 | −16.003 | 16.346 | −32.672 | 1.00 | 13.94 |
| ATOM | 125 | CG | LEU | A | 17 | −15.351 | 15.065 | −32.133 | 1.00 | 16.81 |
| ATOM | 126 | CD1 | LEU | A | 17 | −15.933 | 14.708 | −30.779 | 1.00 | 20.06 |
| ATOM | 127 | CD2 | LEU | A | 17 | −15.484 | 13.880 | −33.097 | 1.00 | 19.31 |
| ATOM | 128 | C | LEU | A | 17 | −14.763 | 16.409 | −34.880 | 1.00 | 14.06 |
| ATOM | 129 | O | LEU | A | 17 | −13.613 | 15.957 | −35.073 | 1.00 | 12.69 |
| ATOM | 130 | N | LEU | A | 18 | −15.774 | 16.215 | −35.730 | 1.00 | 13.19 |
| ATOM | 131 | CA | LEU | A | 18 | −15.589 | 15.441 | −36.957 | 1.00 | 14.25 |
| ATOM | 132 | CB | LEU | A | 18 | −16.952 | 15.027 | −37.545 | 1.00 | 13.56 |
| ATOM | 133 | CG | LEU | A | 18 | −17.717 | 14.013 | −36.684 | 1.00 | 16.49 |
| ATOM | 134 | CD1 | LEU | A | 18 | −19.171 | 13.874 | −37.165 | 1.00 | 16.33 |
| ATOM | 135 | CD2 | LEU | A | 18 | −17.020 | 12.647 | −36.655 | 1.00 | 18.51 |
| ATOM | 136 | C | LEU | A | 18 | −14.703 | 16.132 | −38.007 | 1.00 | 13.49 |
| ATOM | 137 | O | LEU | A | 18 | −14.083 | 15.435 | −38.820 | 1.00 | 14.69 |
| ATOM | 138 | N | CYS | A | 19 | −14.613 | 17.462 | −37.964 | 1.00 | 13.01 |
| ATOM | 139 | CA | CYS | A | 19 | −13.629 | 18.223 | −38.760 | 1.00 | 13.22 |
| ATOM | 140 | CB | CYS | A | 19 | −13.796 | 19.738 | −38.556 | 1.00 | 14.20 |
| ATOM | 141 | SG | CYS | A | 19 | −15.125 | 20.407 | −39.642 | 1.00 | 16.22 |
| ATOM | 142 | C | CYS | A | 19 | −12.182 | 17.808 | −38.450 | 1.00 | 13.86 |
| ATOM | 143 | O | CYS | A | 19 | −11.278 | 18.043 | −39.259 | 1.00 | 13.42 |
| ATOM | 144 | N | ASN | A | 20 | −11.968 | 17.219 | −37.272 | 1.00 | 13.21 |
| ATOM | 145 | CA | ASN | A | 20 | −10.594 | 16.850 | −36.830 | 1.00 | 13.62 |
| ATOM | 146 | CB | ASN | A | 20 | −10.394 | 17.184 | −35.324 | 1.00 | 13.52 |
| ATOM | 147 | CG | ASN | A | 20 | −10.242 | 18.687 | −35.055 | 1.00 | 16.17 |
| ATOM | 148 | OD1 | ASN | A | 20 | −10.035 | 19.119 | −33.897 | 1.00 | 17.34 |
| ATOM | 149 | ND2 | ASN | A | 20 | −10.343 | 19.486 | −36.090 | 1.00 | 11.87 |
| ATOM | 150 | C | ASN | A | 20 | −10.262 | 15.381 | −37.116 | 1.00 | 13.99 |
| ATOM | 151 | O | ASN | A | 20 | −9.238 | 14.857 | −36.646 | 1.00 | 14.28 |
| ATOM | 152 | N | VAL | A | 21 | −11.123 | 14.705 | −37.875 | 1.00 | 13.41 |
| ATOM | 153 | CA | VAL | A | 21 | −10.923 | 13.287 | −38.167 | 1.00 | 14.20 |
| ATOM | 154 | CB | VAL | A | 21 | −12.177 | 12.448 | −37.827 | 1.00 | 14.30 |
| ATOM | 155 | CG1 | VAL | A | 21 | −11.953 | 10.971 | −38.189 | 1.00 | 15.30 |
| ATOM | 156 | CG2 | VAL | A | 21 | −12.517 | 12.553 | −36.312 | 1.00 | 14.17 |
| ATOM | 157 | C | VAL | A | 21 | −10.551 | 13.136 | −39.644 | 1.00 | 14.35 |
| ATOM | 158 | O | VAL | A | 21 | −11.255 | 13.642 | −40.491 | 1.00 | 15.68 |

TABLE 15-continued

| | | | | | | | | | |
|---|---|---|---|---|---|---|---|---|---|
| ATOM | 159 | N | GLY | A | 22 | −9.461 | 12.449 | −39.953 | 1.00 | 15.67 |
| ATOM | 160 | CA | GLY | A | 22 | −9.061 | 12.300 | −41.377 | 1.00 | 15.70 |
| ATOM | 161 | C | GLY | A | 22 | −9.843 | 11.182 | −42.060 | 1.00 | 17.34 |
| ATOM | 162 | O | GLY | A | 22 | −10.453 | 10.358 | −41.397 | 1.00 | 17.15 |
| ATOM | 163 | N | PRO | A | 23 | −9.806 | 11.117 | −43.404 | 1.00 | 18.42 |
| ATOM | 164 | CA | PRO | A | 23 | −9.009 | 11.946 | −44.278 | 1.00 | 18.20 |
| ATOM | 165 | CB | PRO | A | 23 | −8.716 | 10.990 | −45.446 | 1.00 | 18.64 |
| ATOM | 166 | CG | PRO | A | 23 | −9.983 | 10.171 | −45.560 | 1.00 | 18.81 |
| ATOM | 167 | CD | PRO | A | 23 | −10.568 | 10.092 | −44.153 | 1.00 | 18.59 |
| ATOM | 168 | C | PRO | A | 23 | −9.761 | 13.182 | −44.753 | 1.00 | 19.05 |
| ATOM | 169 | O | PRO | A | 23 | −9.183 | 14.055 | −45.426 | 1.00 | 19.36 |
| ATOM | 170 | N | ASP | A | 24 | −11.034 | 13.288 | −44.385 | 1.00 | 18.76 |
| ATOM | 171 | CA | ASP | A | 24 | −11.878 | 14.305 | −44.996 | 1.00 | 19.39 |
| ATOM | 172 | CB | ASP | A | 24 | −13.015 | 13.636 | −45.781 | 1.00 | 20.87 |
| ATOM | 173 | CG | ASP | A | 24 | −13.920 | 12.784 | −44.913 | 1.00 | 24.34 |
| ATOM | 174 | OD1 | ASP | A | 24 | −13.502 | 12.291 | −43.839 | 1.00 | 27.70 |
| ATOM | 175 | OD2 | ASP | A | 24 | −15.079 | 12.580 | −45.330 | 1.00 | 28.83 |
| ATOM | 176 | C | ASP | A | 24 | −12.452 | 15.372 | −44.061 | 1.00 | 18.08 |
| ATOM | 177 | O | ASP | A | 24 | −13.208 | 16.245 | −44.509 | 1.00 | 17.78 |
| ATOM | 178 | N | GLY | A | 25 | −12.100 | 15.331 | −42.775 | 1.00 | 16.65 |
| ATOM | 179 | CA | GLY | A | 25 | −12.634 | 16.343 | −41.852 | 1.00 | 16.02 |
| ATOM | 180 | C | GLY | A | 25 | −12.152 | 17.718 | −42.292 | 1.00 | 15.70 |
| ATOM | 181 | O | GLY | A | 25 | −11.033 | 17.849 | −42.811 | 1.00 | 16.22 |
| ATOM | 182 | N | CYS | A | 26 | −12.979 | 18.752 | −42.086 | 1.00 | 15.10 |
| ATOM | 183 | CA | CYS | A | 26 | −12.698 | 20.078 | −42.637 | 1.00 | 15.46 |
| ATOM | 184 | CB | CYS | A | 26 | −13.899 | 21.037 | −42.475 | 1.00 | 15.47 |
| ATOM | 185 | SG | CYS | A | 26 | −14.147 | 21.739 | −40.786 | 1.00 | 16.91 |
| ATOM | 186 | C | CYS | A | 26 | −11.407 | 20.731 | −42.116 | 1.00 | 15.65 |
| ATOM | 187 | O | CYS | A | 26 | −10.896 | 21.643 | −42.763 | 1.00 | 15.80 |
| ATOM | 188 | N | ARG | A | 27 | −10.879 | 20.259 | −40.973 | 1.00 | 15.02 |
| ATOM | 189 | CA | ARG | A | 27 | −9.615 | 20.808 | −40.443 | 1.00 | 14.56 |
| ATOM | 190 | CB | ARG | A | 27 | −9.819 | 21.480 | −39.066 | 1.00 | 15.00 |
| ATOM | 191 | CG | ARG | A | 27 | −10.695 | 22.728 | −39.164 | 1.00 | 15.15 |
| ATOM | 192 | CD | ARG | A | 27 | −10.826 | 23.551 | −37.888 | 1.00 | 14.30 |
| ATOM | 193 | NE | ARG | A | 27 | −11.874 | 24.566 | −38.080 | 1.00 | 15.05 |
| ATOM | 194 | CZ | ARG | A | 27 | −13.160 | 24.420 | −37.761 | 1.00 | 17.96 |
| ATOM | 195 | NH1 | ARG | A | 27 | −13.623 | 23.293 | −37.211 | 1.00 | 17.37 |
| ATOM | 196 | NH2 | ARG | A | 27 | −14.009 | 25.415 | −38.025 | 1.00 | 19.55 |
| ATOM | 197 | C | ARG | A | 27 | −8.489 | 19.776 | −40.394 | 1.00 | 15.49 |
| ATOM | 198 | O | ARG | A | 27 | −7.389 | 20.079 | −39.888 | 1.00 | 15.40 |
| ATOM | 199 | N | ALA | A | 28 | −8.768 | 18.577 | −40.910 | 1.00 | 15.17 |
| ATOM | 200 | CA | ALA | A | 28 | −7.805 | 17.484 | −40.988 | 1.00 | 16.06 |
| ATOM | 201 | CB | ALA | A | 28 | −8.163 | 16.374 | −39.975 | 1.00 | 15.52 |
| ATOM | 202 | C | ALA | A | 28 | −7.744 | 16.913 | −42.394 | 1.00 | 16.96 |
| ATOM | 203 | O | ALA | A | 28 | −7.453 | 15.730 | −42.581 | 1.00 | 17.60 |
| ATOM | 204 | N | PHE | A | 29 | −8.028 | 17.756 | −43.380 | 1.00 | 17.45 |
| ATOM | 205 | CA | PHE | A | 29 | −8.188 | 17.272 | −44.744 | 1.00 | 18.68 |
| ATOM | 206 | CB | PHE | A | 29 | −8.728 | 18.376 | −45.636 | 1.00 | 19.45 |
| ATOM | 207 | CG | PHE | A | 29 | −9.299 | 17.864 | −46.919 | 1.00 | 20.86 |
| ATOM | 208 | CD1 | PHE | A | 29 | −8.515 | 17.827 | −48.071 | 1.00 | 23.76 |
| ATOM | 209 | CE1 | PHE | A | 29 | −9.042 | 17.343 | −49.267 | 1.00 | 25.46 |
| ATOM | 210 | CZ | PHE | A | 29 | −10.357 | 16.889 | −49.318 | 1.00 | 22.85 |
| ATOM | 211 | CE2 | PHE | A | 29 | −11.151 | 16.924 | −48.180 | 1.00 | 24.78 |
| ATOM | 212 | CD2 | PHE | A | 29 | −10.611 | 17.408 | −46.973 | 1.00 | 22.71 |
| ATOM | 213 | C | PHE | A | 29 | −6.853 | 16.783 | −45.296 | 1.00 | 19.10 |
| ATOM | 214 | O | PHE | A | 29 | −5.862 | 17.501 | −45.224 | 1.00 | 19.40 |
| ATOM | 215 | N | GLY | A | 30 | −6.830 | 15.558 | −45.816 | 1.00 | 18.73 |
| ATOM | 216 | CA | GLY | A | 30 | −5.603 | 15.008 | −46.398 | 1.00 | 19.00 |
| ATOM | 217 | C | GLY | A | 30 | −4.717 | 14.307 | −45.399 | 1.00 | 19.69 |
| ATOM | 218 | O | GLY | A | 30 | −3.657 | 13.809 | −45.768 | 1.00 | 19.61 |
| ATOM | 219 | N | THR | A | 31 | −5.133 | 14.255 | −44.123 | 1.00 | 18.86 |
| ATOM | 220 | CA | THR | A | 31 | −4.450 | 13.384 | −43.165 | 1.00 | 19.14 |
| ATOM | 221 | CB | THR | A | 31 | −4.846 | 13.689 | −41.689 | 1.00 | 18.79 |
| ATOM | 222 | OG1 | THR | A | 31 | −6.265 | 13.579 | −41.559 | 1.00 | 18.61 |
| ATOM | 223 | CG2 | THR | A | 31 | −4.410 | 15.106 | −41.262 | 1.00 | 16.47 |
| ATOM | 224 | C | THR | A | 31 | −4.812 | 11.925 | −43.498 | 1.00 | 19.11 |
| ATOM | 225 | O | THR | A | 31 | −5.713 | 11.661 | −44.313 | 1.00 | 19.69 |
| ATOM | 226 | N | SER | A | 32 | −4.107 | 10.982 | −42.881 | 1.00 | 19.74 |
| ATOM | 227 | CA | SER | A | 32 | −4.367 | 9.554 | −43.094 | 1.00 | 20.00 |
| ATOM | 228 | CB | SER | A | 32 | −3.411 | 8.722 | −42.248 | 1.00 | 20.73 |
| ATOM | 229 | OG | SER | A | 32 | −2.064 | 8.973 | −42.612 | 1.00 | 21.56 |
| ATOM | 230 | C | SER | A | 32 | −5.806 | 9.217 | −42.704 | 1.00 | 20.57 |
| ATOM | 231 | O | SER | A | 32 | −6.334 | 9.778 | −41.732 | 1.00 | 20.70 |
| ATOM | 232 | N | ALA | A | 33 | −6.443 | 8.319 | −43.452 | 1.00 | 19.94 |
| ATOM | 233 | CA | ALA | A | 33 | −7.768 | 7.823 | −43.068 | 1.00 | 19.61 |
| ATOM | 234 | CB | ALA | A | 33 | −8.232 | 6.729 | −44.035 | 1.00 | 19.31 |
| ATOM | 235 | C | ALA | A | 33 | −7.764 | 7.285 | −41.637 | 1.00 | 19.10 |
| ATOM | 236 | O | ALA | A | 33 | −6.906 | 6.482 | −41.264 | 1.00 | 19.49 |
| ATOM | 237 | N | GLY | A | 34 | −8.742 | 7.719 | −40.856 | 1.00 | 17.74 |
| ATOM | 238 | CA | GLY | A | 34 | −8.878 | 7.282 | −39.473 | 1.00 | 18.31 |

TABLE 15-continued

| | | | | | | | | | |
|---|---|---|---|---|---|---|---|---|---|
| ATOM | 239 | C | GLY | A | 34 | −7.988 | 8.020 | −38.473 | 1.00 | 18.48 |
| ATOM | 240 | O | GLY | A | 34 | −8.050 | 7.739 | −37.271 | 1.00 | 19.07 |
| ATOM | 241 | N | ALA | A | 35 | −7.173 | 8.959 | −38.937 | 1.00 | 17.05 |
| ATOM | 242 | CA | ALA | A | 35 | −6.329 | 9.723 | −38.000 | 1.00 | 17.17 |
| ATOM | 243 | CB | ALA | A | 35 | −5.167 | 10.376 | −38.730 | 1.00 | 17.10 |
| ATOM | 244 | C | ALA | A | 35 | −7.173 | 10.784 | −37.271 | 1.00 | 16.55 |
| ATOM | 245 | O | ALA | A | 35 | −8.174 | 11.271 | −37.808 | 1.00 | 17.35 |
| ATOM | 246 | N | VAL | A | 36 | −6.793 | 11.130 | −36.051 | 1.00 | 15.39 |
| ATOM | 247 | CA | VAL | A | 36 | −7.490 | 12.198 | −35.328 | 1.00 | 14.41 |
| ATOM | 248 | CB | VAL | A | 36 | −8.142 | 11.687 | −34.031 | 1.00 | 15.02 |
| ATOM | 249 | CG1 | VAL | A | 36 | −8.903 | 12.828 | −33.349 | 1.00 | 16.72 |
| ATOM | 250 | CG2 | VAL | A | 36 | −9.081 | 10.520 | −34.336 | 1.00 | 16.45 |
| ATOM | 251 | C | VAL | A | 36 | −6.407 | 13.201 | −34.944 | 1.00 | 14.36 |
| ATOM | 252 | O | VAL | A | 36 | −5.421 | 12.816 | −34.311 | 1.00 | 14.44 |
| ATOM | 253 | N | ILE | A | 37 | −6.566 | 14.454 | −35.331 | 1.00 | 13.68 |
| ATOM | 254 | CA | ILE | A | 37 | −5.614 | 15.470 | −34.893 | 1.00 | 13.67 |
| ATOM | 255 | CB | ILE | A | 37 | −5.528 | 16.687 | −35.849 | 1.00 | 13.66 |
| ATOM | 256 | CG1 | ILE | A | 37 | −6.847 | 17.486 | −35.901 | 1.00 | 14.31 |
| ATOM | 257 | CD1 | ILE | A | 37 | −6.773 | 18.712 | −36.864 | 1.00 | 14.21 |
| ATOM | 258 | CG2 | ILE | A | 37 | −5.158 | 16.214 | −37.260 | 1.00 | 14.62 |
| ATOM | 259 | C | ILE | A | 37 | −6.041 | 15.908 | −33.505 | 1.00 | 13.27 |
| ATOM | 260 | O | ILE | A | 37 | −7.235 | 16.011 | −33.224 | 1.00 | 12.99 |
| ATOM | 261 | N | ALA | A | 38 | −5.081 | 16.159 | −32.630 | 1.00 | 13.03 |
| ATOM | 262 | CA | ALA | A | 38 | −5.445 | 16.697 | −31.333 | 1.00 | 12.81 |
| ATOM | 263 | CB | ALA | A | 38 | −4.235 | 16.680 | −30.377 | 1.00 | 12.73 |
| ATOM | 264 | C | ALA | A | 38 | −6.046 | 18.122 | −31.497 | 1.00 | 12.45 |
| ATOM | 265 | O | ALA | A | 38 | −6.939 | 18.503 | −30.775 | 1.00 | 12.23 |
| ATOM | 266 | N | SER | A | 39 | −5.555 | 18.870 | −32.482 | 1.00 | 12.90 |
| ATOM | 267 | CA | SER | A | 39 | −5.973 | 20.246 | −32.769 | 1.00 | 12.85 |
| ATOM | 268 | CB | SER | A | 39 | −5.512 | 21.211 | −31.657 | 1.00 | 12.63 |
| ATOM | 269 | OG | SER | A | 39 | −5.312 | 22.563 | −32.108 | 1.00 | 12.57 |
| ATOM | 270 | C | SER | A | 39 | −5.281 | 20.593 | −34.090 | 1.00 | 13.33 |
| ATOM | 271 | O | SER | A | 39 | −4.215 | 20.043 | −34.376 | 1.00 | 13.48 |
| ATOM | 272 | N | PRO | A | 40 | −5.880 | 21.500 | −34.885 | 1.00 | 13.12 |
| ATOM | 273 | CA | PRO | A | 40 | −5.248 | 21.999 | −36.108 | 1.00 | 13.76 |
| ATOM | 274 | CB | PRO | A | 40 | −6.407 | 22.689 | −36.860 | 1.00 | 14.41 |
| ATOM | 275 | CG | PRO | A | 40 | −7.386 | 23.045 | −35.797 | 1.00 | 14.32 |
| ATOM | 276 | CD | PRO | A | 40 | −7.223 | 22.081 | −34.665 | 1.00 | 13.18 |
| ATOM | 277 | C | PRO | A | 40 | −4.126 | 23.010 | −35.860 | 1.00 | 14.27 |
| ATOM | 278 | O | PRO | A | 40 | −3.474 | 23.420 | −36.824 | 1.00 | 14.43 |
| ATOM | 279 | N | SER | A | 41 | −3.864 | 23.381 | −34.599 | 1.00 | 13.42 |
| ATOM | 280 | CA | SER | A | 41 | −2.799 | 24.336 | −34.318 | 1.00 | 14.56 |
| ATOM | 281 | CB | SER | A | 41 | −2.788 | 24.817 | −32.840 | 1.00 | 14.40 |
| ATOM | 282 | OG | SER | A | 41 | −3.962 | 25.574 | −32.534 | 1.00 | 16.91 |
| ATOM | 283 | C | SER | A | 41 | −1.446 | 23.713 | −34.676 | 1.00 | 14.51 |
| ATOM | 284 | O | SER | A | 41 | −1.123 | 22.626 | −34.218 | 1.00 | 13.96 |
| ATOM | 285 | N | THR | A | 42 | −0.650 | 24.433 | −35.470 | 1.00 | 15.63 |
| ATOM | 286 | CA | THR | A | 42 | 0.652 | 23.924 | −35.919 | 1.00 | 16.17 |
| ATOM | 287 | CB | THR | A | 42 | 0.750 | 23.997 | −37.458 | 1.00 | 17.02 |
| ATOM | 288 | OG1 | THR | A | 42 | 0.267 | 25.283 | −37.890 | 1.00 | 17.03 |
| ATOM | 289 | CG2 | THR | A | 42 | −0.110 | 22.906 | −38.078 | 1.00 | 16.03 |
| ATOM | 290 | C | THR | A | 42 | 1.814 | 24.732 | −35.322 | 1.00 | 17.44 |
| ATOM | 291 | O | THR | A | 42 | 2.967 | 24.297 | −35.382 | 1.00 | 17.10 |
| ATOM | 292 | N | ILE | A | 43 | 1.509 | 25.913 | −34.787 | 1.00 | 18.37 |
| ATOM | 293 | CA | ILE | A | 43 | 2.510 | 26.786 | −34.171 | 1.00 | 20.62 |
| ATOM | 294 | CB | ILE | A | 43 | 2.923 | 27.952 | −35.114 | 1.00 | 20.73 |
| ATOM | 295 | CG1 | ILE | A | 43 | 3.550 | 27.428 | −36.411 | 1.00 | 21.88 |
| ATOM | 296 | CD1 | ILE | A | 43 | 3.788 | 28.507 | −37.508 | 1.00 | 22.99 |
| ATOM | 297 | CG2 | ILE | A | 43 | 3.895 | 28.910 | −34.409 | 1.00 | 21.41 |
| ATOM | 298 | C | ILE | A | 43 | 1.908 | 27.395 | −32.935 | 1.00 | 21.00 |
| ATOM | 299 | O | ILE | A | 43 | 0.796 | 27.921 | −32.995 | 1.00 | 21.76 |
| ATOM | 300 | N | ASP | A | 44 | 2.683 | 27.470 | −31.874 | 1.00 | 21.61 |
| ATOM | 301 | CA | ASP | A | 44 | 2.237 | 27.975 | −30.572 | 1.00 | 23.04 |
| ATOM | 302 | CB | ASP | A | 44 | 2.408 | 29.506 | −30.492 | 1.00 | 24.75 |
| ATOM | 303 | CG | ASP | A | 44 | 2.170 | 30.064 | −29.098 | 1.00 | 31.28 |
| ATOM | 304 | OD1 | ASP | A | 44 | 2.362 | 29.340 | −28.094 | 1.00 | 37.92 |
| ATOM | 305 | OD2 | ASP | A | 44 | 1.766 | 31.260 | −28.997 | 1.00 | 40.00 |
| ATOM | 306 | C | ASP | A | 44 | 0.782 | 27.608 | −30.196 | 1.00 | 21.65 |
| ATOM | 307 | O | ASP | A | 44 | −0.046 | 28.502 | −29.981 | 1.00 | 22.69 |
| ATOM | 308 | N | PRO | A | 45 | 0.441 | 26.449 | −29.805 | 1.00 | 19.86 |
| ATOM | 309 | CA | PRO | A | 45 | 1.356 | 25.320 | −29.775 | 1.00 | 18.66 |
| ATOM | 310 | CB | PRO | A | 45 | 0.883 | 24.549 | −28.549 | 1.00 | 18.40 |
| ATOM | 311 | CG | PRO | A | 45 | −0.653 | 24.763 | −28.586 | 1.00 | 18.13 |
| ATOM | 312 | CD | PRO | A | 45 | −0.899 | 26.066 | −29.318 | 1.00 | 20.04 |
| ATOM | 313 | C | PRO | A | 45 | 1.253 | 24.454 | −31.026 | 1.00 | 17.74 |
| ATOM | 314 | O | PRO | A | 45 | 0.368 | 24.652 | −31.858 | 1.00 | 17.36 |
| ATOM | 315 | N | ASP | A | 46 | 2.178 | 23.512 | −31.160 | 1.00 | 15.95 |
| ATOM | 316 | CA | ASP | A | 46 | 2.124 | 22.573 | −32.275 | 1.00 | 14.75 |
| ATOM | 317 | CB | ASP | A | 46 | 3.551 | 22.255 | −32.738 | 1.00 | 14.59 |
| ATOM | 318 | CG | ASP | A | 46 | 3.601 | 21.161 | −33.818 | 1.00 | 16.17 |

TABLE 15-continued

| | | | | | | | | | |
|---|---|---|---|---|---|---|---|---|---|
| ATOM | 319 | OD1 | ASP | A | 46 | 2.543 | 20.787 | −34.389 | 1.00 | 15.61 |
| ATOM | 320 | OD2 | ASP | A | 46 | 4.712 | 20.641 | −34.054 | 1.00 | 20.18 |
| ATOM | 321 | C | ASP | A | 46 | 1.436 | 21.303 | −31.748 | 1.00 | 13.83 |
| ATOM | 322 | O | ASP | A | 46 | 2.081 | 20.489 | −31.089 | 1.00 | 13.59 |
| ATOM | 323 | N | TYR | A | 47 | 0.126 | 21.165 | −31.992 | 1.00 | 11.86 |
| ATOM | 324 | CA | TYR | A | 47 | −0.621 | 19.975 | −31.580 | 1.00 | 12.11 |
| ATOM | 325 | CB | TYR | A | 47 | −1.895 | 20.387 | −30.854 | 1.00 | 11.69 |
| ATOM | 326 | CG | TYR | A | 47 | −1.773 | 20.722 | −29.377 | 1.00 | 12.59 |
| ATOM | 327 | CD1 | TYR | A | 47 | −0.589 | 21.236 | −28.827 | 1.00 | 13.54 |
| ATOM | 328 | CE1 | TYR | A | 47 | −0.524 | 21.586 | −27.462 | 1.00 | 12.81 |
| ATOM | 329 | CZ | TYR | A | 47 | −1.652 | 21.407 | −26.673 | 1.00 | 13.40 |
| ATOM | 330 | OH | TYR | A | 47 | −1.620 | 21.755 | −25.354 | 1.00 | 13.08 |
| ATOM | 331 | CE2 | TYR | A | 47 | −2.825 | 20.887 | −27.208 | 1.00 | 12.02 |
| ATOM | 332 | CD2 | TYR | A | 47 | −2.876 | 20.540 | −28.532 | 1.00 | 12.76 |
| ATOM | 333 | C | TYR | A | 47 | −0.994 | 19.090 | −32.772 | 1.00 | 11.46 |
| ATOM | 334 | O | TYR | A | 47 | −1.885 | 18.239 | −32.692 | 1.00 | 11.66 |
| ATOM | 335 | N | TYR | A | 48 | −0.316 | 19.301 | −33.893 | 1.00 | 12.26 |
| ATOM | 336 | CA | TYR | A | 48 | −0.697 | 18.639 | −35.132 | 1.00 | 12.80 |
| ATOM | 337 | CB | TYR | A | 48 | −0.323 | 19.509 | −36.348 | 1.00 | 12.75 |
| ATOM | 338 | CG | TYR | A | 48 | −1.134 | 19.146 | −37.569 | 1.00 | 13.21 |
| ATOM | 339 | CD1 | TYR | A | 48 | −2.492 | 19.482 | −37.652 | 1.00 | 14.46 |
| ATOM | 340 | CE1 | TYR | A | 48 | −3.254 | 19.124 | −38.767 | 1.00 | 15.86 |
| ATOM | 341 | CZ | TYR | A | 48 | −2.643 | 18.453 | −39.823 | 1.00 | 14.62 |
| ATOM | 342 | OH | TYR | A | 48 | −3.390 | 18.106 | −40.936 | 1.00 | 16.20 |
| ATOM | 343 | CE2 | TYR | A | 48 | −1.295 | 18.086 | −39.756 | 1.00 | 15.86 |
| ATOM | 344 | CD2 | TYR | A | 48 | −0.543 | 18.456 | −38.638 | 1.00 | 13.44 |
| ATOM | 345 | C | TYR | A | 48 | −0.072 | 17.245 | −35.187 | 1.00 | 13.47 |
| ATOM | 346 | O | TYR | A | 48 | 0.877 | 16.986 | −35.940 | 1.00 | 13.95 |
| ATOM | 347 | N | TYR | A | 49 | −0.592 | 16.360 | −34.338 | 1.00 | 13.13 |
| ATOM | 348 | CA | TYR | A | 49 | −0.131 | 14.987 | −34.171 | 1.00 | 13.51 |
| ATOM | 349 | CB | TYR | A | 49 | 0.887 | 14.842 | −33.009 | 1.00 | 13.11 |
| ATOM | 350 | CG | TYR | A | 49 | 2.133 | 15.662 | −33.216 | 1.00 | 13.90 |
| ATOM | 351 | CD1 | TYR | A | 49 | 3.193 | 15.174 | −33.996 | 1.00 | 13.54 |
| ATOM | 352 | CE1 | TYR | A | 49 | 4.354 | 15.964 | −34.216 | 1.00 | 13.41 |
| ATOM | 353 | CZ | TYR | A | 49 | 4.419 | 17.225 | −33.665 | 1.00 | 14.69 |
| ATOM | 354 | OH | TYR | A | 49 | 5.511 | 18.016 | −33.883 | 1.00 | 17.21 |
| ATOM | 355 | CE2 | TYR | A | 49 | 3.365 | 17.737 | −32.906 | 1.00 | 13.49 |
| ATOM | 356 | CD2 | TYR | A | 49 | 2.227 | 16.952 | −32.698 | 1.00 | 13.78 |
| ATOM | 357 | C | TYR | A | 49 | −1.349 | 14.181 | −33.783 | 1.00 | 13.93 |
| ATOM | 358 | O | TYR | A | 49 | −2.390 | 14.759 | −33.406 | 1.00 | 13.00 |
| ATOM | 359 | N | MET | A | 50 | −1.203 | 12.857 | −33.839 | 1.00 | 13.66 |
| ATOM | 360 | CA | MET | A | 50 | −2.241 | 11.940 | −33.365 | 1.00 | 14.56 |
| ATOM | 361 | CB | MET | A | 50 | −2.447 | 10.822 | −34.381 | 1.00 | 15.21 |
| ATOM | 362 | CG | MET | A | 50 | −3.532 | 9.811 | −33.947 | 1.00 | 15.64 |
| ATOM | 363 | SD | MET | A | 50 | −3.996 | 8.804 | −35.361 | 1.00 | 19.52 |
| ATOM | 364 | CE | MET | A | 50 | −5.204 | 7.742 | −34.566 | 1.00 | 17.12 |
| ATOM | 365 | C | MET | A | 50 | −1.797 | 11.323 | −32.060 | 1.00 | 14.38 |
| ATOM | 366 | O | MET | A | 50 | −0.806 | 10.583 | −32.024 | 1.00 | 13.80 |
| ATOM | 367 | N | TRP | A | 51 | −2.528 | 11.608 | −30.984 | 1.00 | 13.47 |
| ATOM | 368 | CA | TRP | A | 51 | −2.265 | 10.965 | −29.720 | 1.00 | 13.13 |
| ATOM | 369 | CB | TRP | A | 51 | −2.598 | 11.930 | −28.585 | 1.00 | 12.85 |
| ATOM | 370 | CG | TRP | A | 51 | −1.478 | 12.809 | −28.116 | 1.00 | 13.64 |
| ATOM | 371 | CD1 | TRP | A | 51 | −0.671 | 12.604 | −27.011 | 1.00 | 13.49 |
| ATOM | 372 | NE1 | TRP | A | 51 | 0.211 | 13.657 | −26.864 | 1.00 | 12.36 |
| ATOM | 373 | CE2 | TRP | A | 51 | −0.023 | 14.573 | −27.858 | 1.00 | 11.83 |
| ATOM | 374 | CD2 | TRP | A | 51 | −1.076 | 14.065 | −28.674 | 1.00 | 13.12 |
| ATOM | 375 | CE3 | TRP | A | 51 | −1.506 | 14.825 | −29.772 | 1.00 | 11.07 |
| ATOM | 376 | CZ3 | TRP | A | 51 | −0.859 | 16.061 | −30.035 | 1.00 | 12.87 |
| ATOM | 377 | CH2 | TRP | A | 51 | 0.193 | 16.522 | −29.218 | 1.00 | 13.24 |
| ATOM | 378 | CZ2 | TRP | A | 51 | 0.618 | 15.806 | −28.127 | 1.00 | 12.61 |
| ATOM | 379 | C | TRP | A | 51 | −3.136 | 9.732 | −29.575 | 1.00 | 13.35 |
| ATOM | 380 | O | TRP | A | 51 | −4.322 | 9.769 | −29.907 | 1.00 | 12.89 |
| ATOM | 381 | N | THR | A | 52 | −2.576 | 8.652 | −29.024 | 1.00 | 13.20 |
| ATOM | 382 | CA | THR | A | 52 | −3.386 | 7.462 | −28.753 | 1.00 | 13.02 |
| ATOM | 383 | CB | THR | A | 52 | −2.520 | 6.300 | −28.235 | 1.00 | 13.66 |
| ATOM | 384 | OG1 | THR | A | 52 | −1.553 | 5.999 | −29.246 | 1.00 | 15.07 |
| ATOM | 385 | CG2 | THR | A | 52 | −3.341 | 5.026 | −27.952 | 1.00 | 12.21 |
| ATOM | 386 | C | THR | A | 52 | −4.533 | 7.807 | −27.800 | 1.00 | 12.48 |
| ATOM | 387 | O | THR | A | 52 | −5.670 | 7.402 | −28.034 | 1.00 | 12.78 |
| ATOM | 388 | N | ARG | A | 53 | −4.224 | 8.556 | −26.747 | 1.00 | 12.03 |
| ATOM | 389 | CA | ARG | A | 53 | −5.238 | 8.868 | −25.737 | 1.00 | 11.89 |
| ATOM | 390 | CB | ARG | A | 53 | −4.607 | 9.570 | −24.545 | 1.00 | 11.46 |
| ATOM | 391 | CG | ARG | A | 53 | −5.611 | 10.330 | −23.618 | 1.00 | 13.19 |
| ATOM | 392 | CD | ARG | A | 53 | −4.896 | 10.881 | −22.375 | 1.00 | 11.14 |
| ATOM | 393 | NE | ARG | A | 53 | −3.793 | 11.694 | −22.819 | 1.00 | 12.52 |
| ATOM | 394 | CZ | ARG | A | 53 | −2.509 | 11.330 | −22.769 | 1.00 | 13.67 |
| ATOM | 395 | NH1 | ARG | A | 53 | −2.148 | 10.182 | −22.180 | 1.00 | 13.97 |
| ATOM | 396 | NH2 | ARG | A | 53 | −1.590 | 12.151 | −23.270 | 1.00 | 13.05 |
| ATOM | 397 | C | ARG | A | 53 | −6.395 | 9.709 | −26.319 | 1.00 | 12.45 |
| ATOM | 398 | O | ARG | A | 53 | −7.558 | 9.289 | −26.244 | 1.00 | 11.74 |

TABLE 15-continued

| | | | | | | | | | |
|---|---|---|---|---|---|---|---|---|---|
| ATOM | 399 | N | ASP | A | 54 | −6.090 | 10.885 | −26.874 | 1.00 | 11.73 |
| ATOM | 400 | CA | ASP | A | 54 | −7.169 | 11.747 | −27.385 | 1.00 | 11.90 |
| ATOM | 401 | CB | ASP | A | 54 | −6.638 | 13.018 | −28.053 | 1.00 | 12.25 |
| ATOM | 402 | CG | ASP | A | 54 | −5.794 | 13.879 | −27.120 | 1.00 | 13.97 |
| ATOM | 403 | OD1 | ASP | A | 54 | −4.983 | 13.332 | −26.354 | 1.00 | 13.57 |
| ATOM | 404 | OD2 | ASP | A | 54 | −5.910 | 15.110 | −27.215 | 1.00 | 13.88 |
| ATOM | 405 | C | ASP | A | 54 | −8.002 | 11.005 | −28.420 | 1.00 | 12.00 |
| ATOM | 406 | O | ASP | A | 54 | −9.236 | 11.138 | −28.454 | 1.00 | 10.97 |
| ATOM | 407 | N | SER | A | 55 | −7.334 | 10.250 | −29.297 | 1.00 | 11.19 |
| ATOM | 408 | CA | SER | A | 55 | −8.034 | 9.544 | −30.388 | 1.00 | 12.36 |
| ATOM | 409 | CB | SER | A | 55 | −7.017 | 8.901 | −31.340 | 1.00 | 13.05 |
| ATOM | 410 | OG | SER | A | 55 | −6.171 | 9.930 | −31.882 | 1.00 | 14.23 |
| ATOM | 411 | C | SER | A | 55 | −8.996 | 8.489 | −29.838 | 1.00 | 12.57 |
| ATOM | 412 | O | SER | A | 55 | −10.130 | 8.348 | −30.327 | 1.00 | 12.76 |
| ATOM | 413 | N | ALA | A | 56 | −8.556 | 7.764 | −28.819 | 1.00 | 12.60 |
| ATOM | 414 | CA | ALA | A | 56 | −9.373 | 6.718 | −28.218 | 1.00 | 13.25 |
| ATOM | 415 | CB | ALA | A | 56 | −8.517 | 5.830 | −27.329 | 1.00 | 12.73 |
| ATOM | 416 | C | ALA | A | 56 | −10.551 | 7.301 | −27.415 | 1.00 | 13.85 |
| ATOM | 417 | O | ALA | A | 56 | −11.640 | 6.723 | −27.409 | 1.00 | 14.51 |
| ATOM | 418 | N | LEU | A | 57 | −10.328 | 8.420 | −26.723 | 1.00 | 14.23 |
| ATOM | 419 | CA | LEU | A | 57 | −11.417 | 9.059 | −25.954 | 1.00 | 13.95 |
| ATOM | 420 | CB | LEU | A | 57 | −10.891 | 10.186 | −25.060 | 1.00 | 14.45 |
| ATOM | 421 | CG | LEU | A | 57 | −10.088 | 9.751 | −23.834 | 1.00 | 14.89 |
| ATOM | 422 | CD1 | LEU | A | 57 | −9.507 | 11.013 | −23.161 | 1.00 | 16.19 |
| ATOM | 423 | CD2 | LEU | A | 57 | −10.919 | 8.911 | −22.867 | 1.00 | 16.02 |
| ATOM | 424 | C | LEU | A | 57 | −12.483 | 9.609 | −26.886 | 1.00 | 13.92 |
| ATOM | 425 | O | LEU | A | 57 | −13.685 | 9.488 | −26.627 | 1.00 | 13.70 |
| ATOM | 426 | N | VAL | A | 58 | −12.027 | 10.199 | −27.975 | 1.00 | 13.15 |
| ATOM | 427 | CA | VAL | A | 58 | −12.920 | 10.751 | −28.989 | 1.00 | 15.20 |
| ATOM | 428 | CB | VAL | A | 58 | −12.133 | 11.605 | −30.031 | 1.00 | 14.52 |
| ATOM | 429 | CG1 | VAL | A | 58 | −12.970 | 11.861 | −31.302 | 1.00 | 17.86 |
| ATOM | 430 | CG2 | VAL | A | 58 | −11.704 | 12.954 | −29.393 | 1.00 | 15.79 |
| ATOM | 431 | C | VAL | A | 58 | −13.704 | 9.624 | −29.655 | 1.00 | 15.20 |
| ATOM | 432 | O | VAL | A | 58 | −14.930 | 9.718 | −29.784 | 1.00 | 15.30 |
| ATOM | 433 | N | PHE | A | 59 | −13.026 | 8.553 | −30.058 | 1.00 | 15.02 |
| ATOM | 434 | CA | PHE | A | 59 | −13.766 | 7.477 | −30.713 | 1.00 | 15.23 |
| ATOM | 435 | CB | PHE | A | 59 | −12.882 | 6.601 | −31.582 | 1.00 | 15.78 |
| ATOM | 436 | CG | PHE | A | 59 | −12.859 | 7.058 | −33.003 | 1.00 | 15.10 |
| ATOM | 437 | CD1 | PHE | A | 59 | −11.872 | 7.927 | −33.444 | 1.00 | 16.45 |
| ATOM | 438 | CE1 | PHE | A | 59 | −11.861 | 8.401 | −34.768 | 1.00 | 19.37 |
| ATOM | 439 | CZ | PHE | A | 59 | −12.876 | 8.026 | −35.644 | 1.00 | 16.44 |
| ATOM | 440 | CE2 | PHE | A | 59 | −13.901 | 7.165 | −35.186 | 1.00 | 16.90 |
| ATOM | 441 | CD2 | PHE | A | 59 | −13.895 | 6.709 | −33.882 | 1.00 | 16.17 |
| ATOM | 442 | C | PHE | A | 59 | −14.674 | 6.681 | −29.785 | 1.00 | 15.69 |
| ATOM | 443 | O | PHE | A | 59 | −15.699 | 6.175 | −30.220 | 1.00 | 15.46 |
| ATOM | 444 | N | LYS | A | 60 | −14.321 | 6.586 | −28.510 | 1.00 | 15.65 |
| ATOM | 445 | CA | LYS | A | 60 | −15.257 | 5.994 | −27.552 | 1.00 | 16.61 |
| ATOM | 446 | CB | LYS | A | 60 | −14.661 | 5.954 | −26.144 | 1.00 | 16.44 |
| ATOM | 447 | CG | LYS | A | 60 | −15.626 | 5.363 | −25.059 | 1.00 | 17.65 |
| ATOM | 448 | CD | LYS | A | 60 | −16.174 | 3.992 | −25.433 | 1.00 | 18.35 |
| ATOM | 449 | CE | LYS | A | 60 | −16.738 | 3.234 | −24.199 | 1.00 | 19.79 |
| ATOM | 450 | NZ | LYS | A | 60 | −17.819 | 3.976 | −23.512 | 1.00 | 18.40 |
| ATOM | 451 | C | LYS | A | 60 | −16.577 | 6.779 | −27.579 | 1.00 | 16.72 |
| ATOM | 452 | O | LYS | A | 60 | −17.663 | 6.182 | −27.681 | 1.00 | 17.08 |
| ATOM | 453 | N | ASN | A | 61 | −16.487 | 8.101 | −27.508 | 1.00 | 16.77 |
| ATOM | 454 | CA | ASN | A | 61 | −17.680 | 8.948 | −27.628 | 1.00 | 18.06 |
| ATOM | 455 | CB | ASN | A | 61 | −17.278 | 10.424 | −27.573 | 1.00 | 19.41 |
| ATOM | 456 | CG | ASN | A | 61 | −18.465 | 11.375 | −27.643 | 1.00 | 22.93 |
| ATOM | 457 | OD1 | ASN | A | 61 | −19.585 | 11.057 | −27.231 | 1.00 | 30.05 |
| ATOM | 458 | ND2 | ASN | A | 61 | −18.206 | 12.568 | −28.130 | 1.00 | 29.54 |
| ATOM | 459 | C | ASN | A | 61 | −18.480 | 8.659 | −28.907 | 1.00 | 17.28 |
| ATOM | 460 | O | ASN | A | 61 | −19.697 | 8.475 | −28.852 | 1.00 | 18.11 |
| ATOM | 461 | N | LEU | A | 62 | −17.799 | 8.647 | −30.056 | 1.00 | 16.54 |
| ATOM | 462 | CA | LEU | A | 62 | −18.460 | 8.379 | −31.334 | 1.00 | 16.19 |
| ATOM | 463 | CB | LEU | A | 62 | −17.479 | 8.572 | −32.499 | 1.00 | 16.85 |
| ATOM | 464 | CG | LEU | A | 62 | −17.047 | 10.027 | −32.697 | 1.00 | 18.47 |
| ATOM | 465 | CD1 | LEU | A | 62 | −16.118 | 10.153 | −33.916 | 1.00 | 20.38 |
| ATOM | 466 | CD2 | LEU | A | 62 | −18.263 | 10.925 | −32.837 | 1.00 | 19.93 |
| ATOM | 467 | C | LEU | A | 62 | −19.089 | 6.991 | −31.371 | 1.00 | 16.01 |
| ATOM | 468 | O | LEU | A | 62 | −20.225 | 6.833 | −31.842 | 1.00 | 15.98 |
| ATOM | 469 | N | ILE | A | 63 | −18.387 | 5.998 | −30.831 | 1.00 | 15.67 |
| ATOM | 470 | CA | ILE | A | 63 | −18.910 | 4.628 | −30.810 | 1.00 | 15.86 |
| ATOM | 471 | CB | ILE | A | 63 | −17.803 | 3.610 | −30.372 | 1.00 | 15.88 |
| ATOM | 472 | CG1 | ILE | A | 63 | −16.756 | 3.466 | −31.478 | 1.00 | 14.98 |
| ATOM | 473 | CD1 | ILE | A | 63 | −15.375 | 2.976 | −30.966 | 1.00 | 15.62 |
| ATOM | 474 | CG2 | ILE | A | 63 | −18.398 | 2.251 | −30.016 | 1.00 | 15.96 |
| ATOM | 475 | C | ILE | A | 63 | −20.156 | 4.538 | −29.920 | 1.00 | 16.39 |
| ATOM | 476 | O | ILE | A | 63 | −21.137 | 3.854 | −30.272 | 1.00 | 16.90 |
| ATOM | 477 | N | ASP | A | 64 | −20.129 | 5.242 | −28.796 | 1.00 | 16.51 |
| ATOM | 478 | CA | ASP | A | 64 | −21.299 | 5.324 | −27.922 | 1.00 | 17.76 |

TABLE 15-continued

| | | | | | | | | | |
|---|---|---|---|---|---|---|---|---|---|
| ATOM | 479 | CB | ASP | A | 64 | −20.953 | 6.022 | −26.594 | 1.00 | 17.81 |
| ATOM | 480 | CG | ASP | A | 64 | −20.089 | 5.164 | −25.682 | 1.00 | 17.84 |
| ATOM | 481 | OD1 | ASP | A | 64 | −19.883 | 3.944 | −25.963 | 1.00 | 18.57 |
| ATOM | 482 | OD2 | ASP | A | 64 | −19.595 | 5.699 | −24.659 | 1.00 | 20.95 |
| ATOM | 483 | C | ASP | A | 64 | −22.492 | 5.982 | −28.617 | 1.00 | 18.64 |
| ATOM | 484 | O | ASP | A | 64 | −23.617 | 5.493 | −28.507 | 1.00 | 20.85 |
| ATOM | 485 | N | ARG | A | 65 | −22.262 | 7.070 | −29.348 | 1.00 | 19.57 |
| ATOM | 486 | CA | ARG | A | 65 | −23.341 | 7.750 | −30.097 | 1.00 | 20.59 |
| ATOM | 487 | CB | ARG | A | 65 | −22.823 | 9.046 | −30.733 | 1.00 | 20.62 |
| ATOM | 488 | CG | ARG | A | 65 | −22.465 | 10.083 | −29.693 | 1.00 | 25.00 |
| ATOM | 489 | CD | ARG | A | 65 | −22.010 | 11.385 | −30.324 | 1.00 | 28.44 |
| ATOM | 490 | NE | ARG | A | 65 | −23.106 | 12.071 | −30.990 | 1.00 | 31.14 |
| ATOM | 491 | CZ | ARG | A | 65 | −23.968 | 12.878 | −30.373 | 1.00 | 32.75 |
| ATOM | 492 | NH1 | ARG | A | 65 | −23.873 | 13.095 | −29.060 | 1.00 | 32.10 |
| ATOM | 493 | NH2 | ARG | A | 65 | −24.928 | 13.459 | −31.080 | 1.00 | 32.31 |
| ATOM | 494 | C | ARG | A | 65 | −23.907 | 6.841 | −31.184 | 1.00 | 20.83 |
| ATOM | 495 | O | ARG | A | 65 | −25.129 | 6.711 | −31.357 | 1.00 | 20.48 |
| ATOM | 496 | N | PHE | A | 66 | −22.998 | 6.213 | −31.910 | 1.00 | 20.52 |
| ATOM | 497 | CA | PHE | A | 66 | −23.340 | 5.271 | −32.966 | 1.00 | 21.42 |
| ATOM | 498 | CB | PHE | A | 66 | −22.046 | 4.778 | −33.604 | 1.00 | 21.97 |
| ATOM | 499 | CG | PHE | A | 66 | −22.224 | 3.603 | −34.520 | 1.00 | 21.97 |
| ATOM | 500 | CD1 | PHE | A | 66 | −22.601 | 3.791 | −35.844 | 1.00 | 23.23 |
| ATOM | 501 | CE1 | PHE | A | 66 | −22.768 | 2.690 | −36.699 | 1.00 | 22.87 |
| ATOM | 502 | CZ | PHE | A | 66 | −22.552 | 1.409 | −36.221 | 1.00 | 22.60 |
| ATOM | 503 | CE2 | PHE | A | 66 | −22.165 | 1.216 | −34.895 | 1.00 | 23.74 |
| ATOM | 504 | CD2 | PHE | A | 66 | −22.006 | 2.309 | −34.054 | 1.00 | 23.07 |
| ATOM | 505 | C | PHE | A | 66 | −24.152 | 4.084 | −32.415 | 1.00 | 21.98 |
| ATOM | 506 | O | PHE | A | 66 | −25.040 | 3.551 | −33.099 | 1.00 | 21.80 |
| ATOM | 507 | N | THR | A | 67 | −23.831 | 3.654 | −31.195 | 1.00 | 22.48 |
| ATOM | 508 | CA | THR | A | 67 | −24.546 | 2.537 | −30.576 | 1.00 | 23.79 |
| ATOM | 509 | CB | THR | A | 67 | −23.809 | 1.999 | −29.333 | 1.00 | 23.68 |
| ATOM | 510 | OG1 | THR | A | 67 | −22.551 | 1.439 | −29.745 | 1.00 | 23.93 |
| ATOM | 511 | CG2 | THR | A | 67 | −24.613 | 0.881 | −28.653 | 1.00 | 23.90 |
| ATOM | 512 | C | THR | A | 67 | −25.992 | 2.925 | −30.258 | 1.00 | 24.77 |
| ATOM | 513 | O | THR | A | 67 | −26.893 | 2.090 | −30.349 | 1.00 | 25.31 |
| ATOM | 514 | N | GLU | A | 68 | −26.207 | 4.189 | −29.916 | 1.00 | 25.62 |
| ATOM | 515 | CA | GLU | A | 68 | −27.540 | 4.688 | −29.616 | 1.00 | 27.41 |
| ATOM | 516 | CB | GLU | A | 68 | −27.466 | 6.038 | −28.894 | 1.00 | 28.13 |
| ATOM | 517 | CG | GLU | A | 68 | −26.997 | 5.951 | −27.446 | 1.00 | 32.86 |
| ATOM | 518 | CD | GLU | A | 68 | −28.095 | 5.487 | −26.468 | 1.00 | 38.33 |
| ATOM | 519 | OE1 | GLU | A | 68 | −29.241 | 5.982 | −26.542 | 1.00 | 40.42 |
| ATOM | 520 | OE2 | GLU | A | 68 | −27.799 | 4.633 | −25.607 | 1.00 | 42.48 |
| ATOM | 521 | C | GLU | A | 68 | −28.418 | 4.784 | −30.873 | 1.00 | 27.86 |
| ATOM | 522 | O | GLU | A | 68 | −29.602 | 4.429 | −30.845 | 1.00 | 28.00 |
| ATOM | 523 | N | THR | A | 69 | −27.833 | 5.260 | −31.968 | 1.00 | 27.32 |
| ATOM | 524 | CA | THR | A | 69 | −28.540 | 5.373 | −33.241 | 1.00 | 27.32 |
| ATOM | 525 | CB | THR | A | 69 | −29.113 | 6.792 | −33.451 | 1.00 | 27.49 |
| ATOM | 526 | OG1 | THR | A | 69 | −29.922 | 7.153 | −32.334 | 1.00 | 30.86 |
| ATOM | 527 | CG2 | THR | A | 69 | −29.945 | 6.843 | −34.719 | 1.00 | 29.06 |
| ATOM | 528 | C | THR | A | 69 | −27.563 | 5.133 | −34.359 | 1.00 | 26.07 |
| ATOM | 529 | O | THR | A | 69 | −26.619 | 5.905 | −34.523 | 1.00 | 25.25 |
| ATOM | 530 | N | TYR | A | 70 | −27.790 | 4.064 | −35.123 | 1.00 | 25.65 |
| ATOM | 531 | CA | TYR | A | 70 | −26.948 | 3.738 | −36.267 | 1.00 | 25.36 |
| ATOM | 532 | CB | TYR | A | 70 | −27.480 | 2.504 | −37.013 | 1.00 | 25.26 |
| ATOM | 533 | CG | TYR | A | 70 | −26.638 | 2.104 | −38.217 | 1.00 | 25.62 |
| ATOM | 534 | CD1 | TYR | A | 70 | −26.949 | 2.567 | −39.498 | 1.00 | 25.62 |
| ATOM | 535 | CE1 | TYR | A | 70 | −26.190 | 2.201 | −40.611 | 1.00 | 26.48 |
| ATOM | 536 | CZ | TYR | A | 70 | −25.099 | 1.360 | −40.437 | 1.00 | 25.36 |
| ATOM | 537 | OH | TYR | A | 70 | −24.354 | 0.995 | −41.520 | 1.00 | 24.80 |
| ATOM | 538 | CE2 | TYR | A | 70 | −24.770 | 0.883 | −39.175 | 1.00 | 25.59 |
| ATOM | 539 | CD2 | TYR | A | 70 | −25.538 | 1.259 | −38.071 | 1.00 | 25.36 |
| ATOM | 540 | C | TYR | A | 70 | −26.816 | 4.909 | −37.230 | 1.00 | 25.38 |
| ATOM | 541 | O | TYR | A | 70 | −27.802 | 5.573 | −37.583 | 1.00 | 24.87 |
| ATOM | 542 | N | ASP | A | 71 | −25.575 | 5.127 | −37.666 | 1.00 | 25.16 |
| ATOM | 543 | CA | ASP | A | 71 | −25.188 | 6.210 | −38.550 | 1.00 | 25.40 |
| ATOM | 544 | CB | ASP | A | 71 | −24.668 | 7.404 | −37.724 | 1.00 | 25.60 |
| ATOM | 545 | CG | ASP | A | 71 | −24.361 | 8.642 | −38.573 | 1.00 | 26.17 |
| ATOM | 546 | OD1 | ASP | A | 71 | −23.801 | 8.526 | −39.681 | 1.00 | 25.82 |
| ATOM | 547 | OD2 | ASP | A | 71 | −24.675 | 9.755 | −38.108 | 1.00 | 27.85 |
| ATOM | 548 | C | ASP | A | 71 | −24.061 | 5.619 | −39.386 | 1.00 | 25.64 |
| ATOM | 549 | O | ASP | A | 71 | −22.956 | 5.377 | −38.875 | 1.00 | 24.82 |
| ATOM | 550 | N | ALA | A | 72 | −24.347 | 5.379 | −40.665 | 1.00 | 24.95 |
| ATOM | 551 | CA | ALA | A | 72 | −23.380 | 4.764 | −41.586 | 1.00 | 24.24 |
| ATOM | 552 | CB | ALA | A | 72 | −24.047 | 4.434 | −42.921 | 1.00 | 24.35 |
| ATOM | 553 | C | ALA | A | 72 | −22.152 | 5.657 | −41.812 | 1.00 | 24.04 |
| ATOM | 554 | O | ALA | A | 72 | −21.054 | 5.159 | −42.086 | 1.00 | 23.21 |
| ATOM | 555 | N | GLY | A | 73 | −22.356 | 6.970 | −41.695 | 1.00 | 23.63 |
| ATOM | 556 | CA | GLY | A | 73 | −21.265 | 7.938 | −41.761 | 1.00 | 24.20 |
| ATOM | 557 | C | GLY | A | 73 | −20.285 | 7.809 | −40.596 | 1.00 | 23.85 |
| ATOM | 558 | O | GLY | A | 73 | −19.067 | 7.927 | −40.806 | 1.00 | 24.81 |

TABLE 15-continued

| | | | | | | | | | |
|---|---|---|---|---|---|---|---|---|---|
| ATOM | 559 | N | LEU | A | 74 | −20.798 | 7.588 | −39.376 | 1.00 | 22.78 |
| ATOM | 560 | CA | LEU | A | 74 | −19.927 | 7.347 | −38.232 | 1.00 | 22.21 |
| ATOM | 561 | CB | LEU | A | 74 | −20.662 | 7.449 | −36.879 | 1.00 | 22.58 |
| ATOM | 562 | CG | LEU | A | 74 | −21.132 | 8.846 | −36.434 | 1.00 | 24.06 |
| ATOM | 563 | CD1 | LEU | A | 74 | −21.732 | 8.793 | −35.019 | 1.00 | 22.31 |
| ATOM | 564 | CD2 | LEU | A | 74 | −20.002 | 9.869 | −36.503 | 1.00 | 26.04 |
| ATOM | 565 | C | LEU | A | 74 | −19.256 | 5.999 | −38.370 | 1.00 | 21.94 |
| ATOM | 566 | O | LEU | A | 74 | −18.060 | 5.872 | −38.098 | 1.00 | 20.62 |
| ATOM | 567 | N | GLN | A | 75 | −20.019 | 4.988 | −38.814 | 1.00 | 21.47 |
| ATOM | 568 | CA | GLN | A | 75 | −19.451 | 3.654 | −38.989 | 1.00 | 21.07 |
| ATOM | 569 | CB | GLN | A | 75 | −20.469 | 2.709 | −39.619 | 1.00 | 21.44 |
| ATOM | 570 | CG | GLN | A | 75 | −20.002 | 1.280 | −39.594 | 1.00 | 23.11 |
| ATOM | 571 | CD | GLN | A | 75 | −21.101 | 0.312 | −39.945 | 1.00 | 24.74 |
| ATOM | 572 | OE1 | GLN | A | 75 | −21.273 | −0.719 | −39.290 | 1.00 | 26.57 |
| ATOM | 573 | NE2 | GLN | A | 75 | −21.872 | 0.654 | −40.950 | 1.00 | 23.71 |
| ATOM | 574 | C | GLN | A | 75 | −18.219 | 3.704 | −39.889 | 1.00 | 21.05 |
| ATOM | 575 | O | GLN | A | 75 | −17.229 | 3.046 | −39.611 | 1.00 | 21.10 |
| ATOM | 576 | N | ARG | A | 76 | −18.294 | 4.466 | −40.975 | 1.00 | 20.73 |
| ATOM | 577 | CA | ARG | A | 76 | −17.184 | 4.551 | −41.910 | 1.00 | 21.56 |
| ATOM | 578 | CB | ARG | A | 76 | −17.544 | 5.460 | −43.101 | 1.00 | 22.06 |
| ATOM | 579 | CG | ARG | A | 76 | −16.452 | 5.627 | −44.168 | 1.00 | 24.00 |
| ATOM | 580 | CD | ARG | A | 76 | −15.586 | 6.895 | −43.934 | 1.00 | 27.60 |
| ATOM | 581 | NE | ARG | A | 76 | −16.275 | 8.150 | −44.280 | 1.00 | 30.93 |
| ATOM | 582 | CZ | ARG | A | 76 | −15.778 | 9.378 | −44.082 | 1.00 | 32.20 |
| ATOM | 583 | NH1 | ARG | A | 76 | −14.572 | 9.556 | −43.535 | 1.00 | 30.72 |
| ATOM | 584 | NH2 | ARG | A | 76 | −16.491 | 10.443 | −44.437 | 1.00 | 32.29 |
| ATOM | 585 | C | ARG | A | 76 | −15.942 | 5.063 | −41.162 | 1.00 | 20.85 |
| ATOM | 586 | O | ARG | A | 76 | −14.858 | 4.514 | −41.296 | 1.00 | 20.93 |
| ATOM | 587 | N | ARG | A | 77 | −16.116 | 6.119 | −40.378 | 1.00 | 20.17 |
| ATOM | 588 | CA | ARG | A | 77 | −14.990 | 6.723 | −39.631 | 1.00 | 19.61 |
| ATOM | 589 | CB | ARG | A | 77 | −15.419 | 8.058 | −39.009 | 1.00 | 19.11 |
| ATOM | 590 | CG | ARG | A | 77 | −15.719 | 9.106 | −40.075 | 1.00 | 20.18 |
| ATOM | 591 | CD | ARG | A | 77 | −16.379 | 10.299 | −39.459 | 1.00 | 22.42 |
| ATOM | 592 | NE | ARG | A | 77 | −16.489 | 11.411 | −40.396 | 1.00 | 24.06 |
| ATOM | 593 | CZ | ARG | A | 77 | −17.501 | 11.592 | −41.243 | 1.00 | 27.81 |
| ATOM | 594 | NH1 | ARG | A | 77 | −18.508 | 10.714 | −41.303 | 1.00 | 28.01 |
| ATOM | 595 | NH2 | ARG | A | 77 | −17.509 | 12.658 | −42.033 | 1.00 | 27.19 |
| ATOM | 596 | C | ARG | A | 77 | −14.425 | 5.789 | −38.570 | 1.00 | 18.77 |
| ATOM | 597 | O | ARG | A | 77 | −13.197 | 5.685 | −38.411 | 1.00 | 18.64 |
| ATOM | 598 | N | ILE | A | 78 | −15.320 | 5.117 | −37.852 | 1.00 | 17.79 |
| ATOM | 599 | CA | ILE | A | 78 | −14.931 | 4.125 | −36.857 | 1.00 | 18.13 |
| ATOM | 600 | CB | ILE | A | 78 | −16.165 | 3.514 | −36.151 | 1.00 | 17.88 |
| ATOM | 601 | CG1 | ILE | A | 78 | −16.862 | 4.564 | −35.282 | 1.00 | 18.78 |
| ATOM | 602 | CD1 | ILE | A | 78 | −18.274 | 4.154 | −34.879 | 1.00 | 19.16 |
| ATOM | 603 | CG2 | ILE | A | 78 | −15.772 | 2.279 | −35.308 | 1.00 | 18.15 |
| ATOM | 604 | C | ILE | A | 78 | −14.105 | 3.012 | −37.491 | 1.00 | 18.09 |
| ATOM | 605 | O | ILE | A | 78 | −13.088 | 2.612 | −36.949 | 1.00 | 17.42 |
| ATOM | 606 | N | GLU | A | 79 | −14.565 | 2.495 | −38.631 | 1.00 | 18.82 |
| ATOM | 607 | CA | GLU | A | 79 | −13.826 | 1.446 | −39.341 | 1.00 | 20.22 |
| ATOM | 608 | CB | GLU | A | 79 | −14.587 | 1.017 | −40.609 | 1.00 | 20.36 |
| ATOM | 609 | CG | GLU | A | 79 | −15.811 | 0.136 | −40.312 | 1.00 | 22.29 |
| ATOM | 610 | CD | GLU | A | 79 | −16.633 | −0.206 | −41.565 | 1.00 | 22.92 |
| ATOM | 611 | OE1 | GLU | A | 79 | −16.345 | 0.328 | −42.670 | 1.00 | 26.99 |
| ATOM | 612 | OE2 | GLU | A | 79 | −17.579 | −1.012 | −41.425 | 1.00 | 25.69 |
| ATOM | 613 | C | GLU | A | 79 | −12.418 | 1.918 | −39.704 | 1.00 | 18.80 |
| ATOM | 614 | O | GLU | A | 79 | −11.450 | 1.191 | −39.507 | 1.00 | 19.44 |
| ATOM | 615 | N | GLN | A | 80 | −12.301 | 3.147 | −40.211 | 1.00 | 18.84 |
| ATOM | 616 | CA | GLN | A | 80 | −10.998 | 3.661 | −40.636 | 1.00 | 17.90 |
| ATOM | 617 | CB | GLN | A | 80 | −11.149 | 4.921 | −41.482 | 1.00 | 18.92 |
| ATOM | 618 | CG | GLN | A | 80 | −11.794 | 4.593 | −42.844 | 1.00 | 21.99 |
| ATOM | 619 | CD | GLN | A | 80 | −12.040 | 5.799 | −43.707 | 1.00 | 27.48 |
| ATOM | 620 | OE1 | GLN | A | 80 | −12.265 | 6.898 | −43.223 | 1.00 | 30.45 |
| ATOM | 621 | NE2 | GLN | A | 80 | −12.037 | 5.586 | −45.013 | 1.00 | 32.63 |
| ATOM | 622 | C | GLN | A | 80 | −10.059 | 3.892 | −39.456 | 1.00 | 17.64 |
| ATOM | 623 | O | GLN | A | 80 | −8.862 | 3.612 | −39.535 | 1.00 | 17.21 |
| ATOM | 624 | N | TYR | A | 81 | −10.607 | 4.408 | −38.365 | 1.00 | 17.29 |
| ATOM | 625 | CA | TYR | A | 81 | −9.839 | 4.552 | −37.122 | 1.00 | 17.64 |
| ATOM | 626 | CB | TYR | A | 81 | −10.750 | 5.139 | −36.023 | 1.00 | 17.24 |
| ATOM | 627 | CG | TYR | A | 81 | −10.188 | 4.973 | −34.621 | 1.00 | 17.79 |
| ATOM | 628 | CD1 | TYR | A | 81 | −9.085 | 5.728 | −34.184 | 1.00 | 16.36 |
| ATOM | 629 | CE1 | TYR | A | 81 | −8.561 | 5.568 | −32.882 | 1.00 | 17.45 |
| ATOM | 630 | CZ | TYR | A | 81 | −9.146 | 4.646 | −32.009 | 1.00 | 16.35 |
| ATOM | 631 | OH | TYR | A | 81 | −8.654 | 4.457 | −30.724 | 1.00 | 17.06 |
| ATOM | 632 | CE2 | TYR | A | 81 | −10.238 | 3.890 | −32.423 | 1.00 | 17.51 |
| ATOM | 633 | CD2 | TYR | A | 81 | −10.754 | 4.055 | −33.729 | 1.00 | 17.00 |
| ATOM | 634 | C | TYR | A | 81 | −9.271 | 3.197 | −36.686 | 1.00 | 18.04 |
| ATOM | 635 | O | TYR | A | 81 | −8.098 | 3.083 | −36.321 | 1.00 | 17.85 |
| ATOM | 636 | N | ILE | A | 82 | −10.096 | 2.159 | −36.746 | 1.00 | 17.99 |
| ATOM | 637 | CA | ILE | A | 82 | −9.661 | 0.839 | −36.295 | 1.00 | 19.35 |
| ATOM | 638 | CB | ILE | A | 82 | −10.844 | −0.166 | −36.187 | 1.00 | 18.93 |

TABLE 15-continued

| | | | | | | | | | | |
|---|---|---|---|---|---|---|---|---|---|---|
| ATOM | 639 | CG1 | ILE | A | 82 | −11.753 | 0.233 | −35.017 | 1.00 | 19.40 |
| ATOM | 640 | CD1 | ILE | A | 82 | −13.093 | −0.565 | −34.896 | 1.00 | 20.46 |
| ATOM | 641 | CG2 | ILE | A | 82 | −10.301 | −1.587 | −35.984 | 1.00 | 20.61 |
| ATOM | 642 | C | ILE | A | 82 | −8.547 | 0.292 | −37.194 | 1.00 | 19.92 |
| ATOM | 643 | O | ILE | A | 82 | −7.543 | −0.239 | −36.708 | 1.00 | 20.26 |
| ATOM | 644 | N | THR | A | 83 | −8.713 | 0.432 | −38.503 | 1.00 | 20.05 |
| ATOM | 645 | CA | THR | A | 83 | −7.709 | −0.100 | −39.406 | 1.00 | 21.11 |
| ATOM | 646 | CB | THR | A | 83 | −8.241 | −0.297 | −40.845 | 1.00 | 21.63 |
| ATOM | 647 | OG1 | THR | A | 83 | −8.830 | 0.902 | −41.306 | 1.00 | 25.88 |
| ATOM | 648 | CG2 | THR | A | 83 | −9.330 | −1.347 | −40.851 | 1.00 | 21.56 |
| ATOM | 649 | C | THR | A | 83 | −6.410 | 0.690 | −39.337 | 1.00 | 20.59 |
| ATOM | 650 | O | THR | A | 83 | −5.338 | 0.105 | −39.511 | 1.00 | 20.72 |
| ATOM | 651 | N | ALA | A | 84 | −6.494 | 1.997 | −39.050 | 1.00 | 19.51 |
| ATOM | 652 | CA | ALA | A | 84 | −5.292 | 2.809 | −38.777 | 1.00 | 19.37 |
| ATOM | 653 | CB | ALA | A | 84 | −5.652 | 4.290 | −38.507 | 1.00 | 19.42 |
| ATOM | 654 | C | ALA | A | 84 | −4.436 | 2.231 | −37.643 | 1.00 | 19.32 |
| ATOM | 655 | O | ALA | A | 84 | −3.208 | 2.370 | −37.649 | 1.00 | 19.47 |
| ATOM | 656 | N | GLN | A | 85 | −5.063 | 1.535 | −36.695 | 1.00 | 19.34 |
| ATOM | 657 | CA | GLN | A | 85 | −4.325 | 0.998 | −35.544 | 1.00 | 18.78 |
| ATOM | 658 | CB | GLN | A | 85 | −5.266 | 0.609 | −34.396 | 1.00 | 19.29 |
| ATOM | 659 | CG | GLN | A | 85 | −6.260 | 1.735 | −34.007 | 1.00 | 17.98 |
| ATOM | 660 | CD | GLN | A | 85 | −5.593 | 3.098 | −33.830 | 1.00 | 17.20 |
| ATOM | 661 | OE1 | GLN | A | 85 | −6.021 | 4.095 | −34.418 | 1.00 | 20.82 |
| ATOM | 662 | NE2 | GLN | A | 85 | −4.540 | 3.143 | −33.034 | 1.00 | 13.47 |
| ATOM | 663 | C | GLN | A | 85 | −3.447 | −0.178 | −35.932 | 1.00 | 19.08 |
| ATOM | 664 | O | GLN | A | 85 | −2.478 | −0.473 | −35.251 | 1.00 | 17.94 |
| ATOM | 665 | N | VAL | A | 86 | −3.808 | −0.838 | −37.032 | 1.00 | 19.32 |
| ATOM | 666 | CA | VAL | A | 86 | −2.999 | −1.928 | −37.588 | 1.00 | 20.79 |
| ATOM | 667 | CB | VAL | A | 86 | −3.670 | −2.581 | −38.823 | 1.00 | 21.18 |
| ATOM | 668 | CG1 | VAL | A | 86 | −2.712 | −3.615 | −39.454 | 1.00 | 22.66 |
| ATOM | 669 | CG2 | VAL | A | 86 | −4.980 | −3.250 | −38.400 | 1.00 | 21.47 |
| ATOM | 670 | C | VAL | A | 86 | −1.617 | −1.381 | −37.940 | 1.00 | 20.63 |
| ATOM | 671 | O | VAL | A | 86 | −0.602 | −1.930 | −37.520 | 1.00 | 21.41 |
| ATOM | 672 | N | THR | A | 87 | −1.604 | −0.251 | −38.641 | 1.00 | 20.67 |
| ATOM | 673 | CA | THR | A | 87 | −0.361 | 0.419 | −39.015 | 1.00 | 21.10 |
| ATOM | 674 | CB | THR | A | 87 | −0.659 | 1.583 | −39.986 | 1.00 | 21.59 |
| ATOM | 675 | OG1 | THR | A | 87 | −1.176 | 1.033 | −41.202 | 1.00 | 23.63 |
| ATOM | 676 | CG2 | THR | A | 87 | 0.585 | 2.370 | −40.305 | 1.00 | 22.02 |
| ATOM | 677 | C | THR | A | 87 | 0.412 | 0.881 | −37.795 | 1.00 | 20.28 |
| ATOM | 678 | O | THR | A | 87 | 1.620 | 0.641 | −37.679 | 1.00 | 20.22 |
| ATOM | 679 | N | LEU | A | 88 | −0.280 | 1.543 | −36.874 | 1.00 | 19.11 |
| ATOM | 680 | CA | LEU | A | 88 | 0.367 | 2.097 | −35.697 | 1.00 | 18.71 |
| ATOM | 681 | CB | LEU | A | 88 | −0.585 | 3.015 | −34.903 | 1.00 | 18.08 |
| ATOM | 682 | CG | LEU | A | 88 | −1.016 | 4.294 | −35.596 | 1.00 | 18.50 |
| ATOM | 683 | CD1 | LEU | A | 88 | −2.038 | 5.058 | −34.706 | 1.00 | 19.12 |
| ATOM | 684 | CD2 | LEU | A | 88 | 0.206 | 5.193 | −35.937 | 1.00 | 19.81 |
| ATOM | 685 | C | LEU | A | 88 | 0.976 | 1.057 | −34.780 | 1.00 | 18.33 |
| ATOM | 686 | O | LEU | A | 88 | 2.101 | 1.244 | −34.336 | 1.00 | 18.76 |
| ATOM | 687 | N | GLN | A | 89 | 0.255 | −0.029 | −34.492 | 1.00 | 18.75 |
| ATOM | 688 | CA | GLN | A | 89 | 0.809 | −1.085 | −33.623 | 1.00 | 19.67 |
| ATOM | 689 | CB | GLN | A | 89 | −0.199 | −2.201 | −33.373 | 1.00 | 19.69 |
| ATOM | 690 | CG | GLN | A | 89 | −1.397 | −1.775 | −32.564 | 1.00 | 19.25 |
| ATOM | 691 | CD | GLN | A | 89 | −2.140 | −2.951 | −32.004 | 1.00 | 20.83 |
| ATOM | 692 | OE1 | GLN | A | 89 | −2.121 | −4.037 | −32.580 | 1.00 | 19.26 |
| ATOM | 693 | NE2 | GLN | A | 89 | −2.802 | −2.751 | −30.861 | 1.00 | 19.61 |
| ATOM | 694 | C | GLN | A | 89 | 2.097 | −1.683 | −34.203 | 1.00 | 20.68 |
| ATOM | 695 | O | GLN | A | 89 | 3.013 | −2.026 | −33.461 | 1.00 | 21.21 |
| ATOM | 696 | N | GLY | A | 90 | 2.164 | −1.778 | −35.524 | 1.00 | 21.75 |
| ATOM | 697 | CA | GLY | A | 90 | 3.330 | −2.374 | −36.173 | 1.00 | 23.35 |
| ATOM | 698 | C | GLY | A | 90 | 4.604 | −1.552 | −36.096 | 1.00 | 24.79 |
| ATOM | 699 | O | GLY | A | 90 | 5.699 | −2.104 | −36.299 | 1.00 | 25.52 |
| ATOM | 700 | N | ASN | A | 91 | 4.477 | −0.252 | −35.796 | 1.00 | 25.17 |
| ATOM | 701 | CA | ASN | A | 91 | 5.596 | 0.714 | −35.870 | 1.00 | 26.14 |
| ATOM | 702 | CB | ASN | A | 91 | 5.108 | 2.161 | −35.653 | 1.00 | 26.83 |
| ATOM | 703 | CG | ASN | A | 91 | 4.615 | 2.849 | −36.919 | 1.00 | 29.67 |
| ATOM | 704 | OD1 | ASN | A | 91 | 4.869 | 2.414 | −38.051 | 1.00 | 34.53 |
| ATOM | 705 | ND2 | ASN | A | 91 | 3.927 | 3.981 | −36.724 | 1.00 | 32.76 |
| ATOM | 706 | C | ASN | A | 91 | 6.656 | 0.489 | −34.820 | 1.00 | 25.67 |
| ATOM | 707 | O | ASN | A | 91 | 6.346 | 0.385 | −33.644 | 1.00 | 25.70 |
| ATOM | 708 | N | SER | A | 92 | 7.918 | 0.472 | −35.227 | 1.00 | 25.32 |
| ATOM | 709 | CA | SER | A | 92 | 8.990 | 0.668 | −34.257 | 1.00 | 25.27 |
| ATOM | 710 | CB | SER | A | 92 | 10.314 | 0.107 | −34.775 | 1.00 | 26.03 |
| ATOM | 711 | OG | SER | A | 92 | 10.212 | −1.305 | −34.803 | 1.00 | 30.67 |
| ATOM | 712 | C | SER | A | 92 | 9.103 | 2.171 | −34.003 | 1.00 | 23.80 |
| ATOM | 713 | O | SER | A | 92 | 9.055 | 2.979 | −34.942 | 1.00 | 24.56 |
| ATOM | 714 | N | ASN | A | 93 | 9.246 | 2.544 | −32.743 | 1.00 | 22.30 |
| ATOM | 715 | CA | ASN | A | 93 | 9.236 | 3.953 | −32.383 | 1.00 | 21.23 |
| ATOM | 716 | CB | ASN | A | 93 | 7.769 | 4.423 | −32.201 | 1.00 | 21.41 |
| ATOM | 717 | CG | ASN | A | 93 | 7.075 | 3.704 | −31.051 | 1.00 | 19.23 |
| ATOM | 718 | OD1 | ASN | A | 93 | 7.564 | 3.736 | −29.927 | 1.00 | 17.81 |

TABLE 15-continued

| | | | | | | | | | |
|---|---|---|---|---|---|---|---|---|---|
| ATOM | 719 | ND2 | ASN | A | 93 | 5.974 | 3.024 | −31.335 | 1.00 | 19.43 |
| ATOM | 720 | C | ASN | A | 93 | 10.103 | 4.149 | −31.150 | 1.00 | 20.39 |
| ATOM | 721 | O | ASN | A | 93 | 10.625 | 3.154 | −30.607 | 1.00 | 19.46 |
| ATOM | 722 | N | PRO | A | 94 | 10.337 | 5.410 | −30.732 | 1.00 | 19.95 |
| ATOM | 723 | CA | PRO | A | 94 | 11.228 | 5.604 | −29.574 | 1.00 | 19.89 |
| ATOM | 724 | CB | PRO | A | 94 | 11.235 | 7.131 | −29.385 | 1.00 | 19.51 |
| ATOM | 725 | CG | PRO | A | 94 | 10.988 | 7.653 | −30.753 | 1.00 | 19.96 |
| ATOM | 726 | CD | PRO | A | 94 | 9.952 | 6.717 | −31.325 | 1.00 | 19.99 |
| ATOM | 727 | C | PRO | A | 94 | 10.870 | 4.898 | −28.263 | 1.00 | 20.64 |
| ATOM | 728 | O | PRO | A | 94 | 11.756 | 4.727 | −27.430 | 1.00 | 20.54 |
| ATOM | 729 | N | SER | A | 95 | 9.610 | 4.485 | −28.073 | 1.00 | 20.36 |
| ATOM | 730 | CA | SER | A | 95 | 9.264 | 3.674 | −26.902 | 1.00 | 21.00 |
| ATOM | 731 | CB | SER | A | 95 | 7.770 | 3.736 | −26.587 | 1.00 | 20.05 |
| ATOM | 732 | OG | SER | A | 95 | 7.413 | 5.036 | −26.147 | 1.00 | 19.97 |
| ATOM | 733 | C | SER | A | 95 | 9.679 | 2.204 | −27.066 | 1.00 | 21.73 |
| ATOM | 734 | O | SER | A | 95 | 9.809 | 1.499 | −26.072 | 1.00 | 22.10 |
| ATOM | 735 | N | GLY | A | 96 | 9.853 | 1.748 | −28.306 | 1.00 | 21.90 |
| ATOM | 736 | CA | GLY | A | 96 | 10.229 | 0.350 | −28.562 | 1.00 | 23.56 |
| ATOM | 737 | C | GLY | A | 96 | 9.506 | −0.196 | −29.774 | 1.00 | 24.14 |
| ATOM | 738 | O | GLY | A | 96 | 9.121 | 0.557 | −30.664 | 1.00 | 24.24 |
| ATOM | 739 | N | SER | A | 97 | 9.315 | −1.510 | −29.828 | 1.00 | 25.24 |
| ATOM | 740 | CA | SER | A | 97 | 8.703 | −2.116 | −31.000 | 1.00 | 25.77 |
| ATOM | 741 | CB | SER | A | 97 | 9.751 | −2.874 | −31.834 | 1.00 | 27.15 |
| ATOM | 742 | OG | SER | A | 97 | 10.120 | −4.086 | −31.189 | 1.00 | 30.57 |
| ATOM | 743 | C | SER | A | 97 | 7.590 | −3.042 | −30.571 | 1.00 | 25.27 |
| ATOM | 744 | O | SER | A | 97 | 7.346 | −3.199 | −29.376 | 1.00 | 24.85 |
| ATOM | 745 | N | LEU | A | 98 | 6.930 | −3.655 | −31.543 | 1.00 | 24.82 |
| ATOM | 746 | CA | LEU | A | 98 | 5.826 | −4.559 | −31.252 | 1.00 | 25.88 |
| ATOM | 747 | CB | LEU | A | 98 | 4.982 | −4.813 | −32.504 | 1.00 | 25.31 |
| ATOM | 748 | CG | LEU | A | 98 | 3.714 | −5.673 | −32.420 | 1.00 | 25.89 |
| ATOM | 749 | CD1 | LEU | A | 98 | 2.745 | −5.169 | −31.337 | 1.00 | 25.58 |
| ATOM | 750 | CD2 | LEU | A | 98 | 3.006 | −5.724 | −33.778 | 1.00 | 26.27 |
| ATOM | 751 | C | LEU | A | 98 | 6.310 | −5.866 | −30.604 | 1.00 | 26.75 |
| ATOM | 752 | O | LEU | A | 98 | 5.607 | −6.438 | −29.762 | 1.00 | 27.41 |
| ATOM | 753 | N | ALA | A | 99 | 7.528 | −6.290 | −30.950 | 1.00 | 27.23 |
| ATOM | 754 | CA | ALA | A | 99 | 8.074 | −7.590 | −30.533 | 1.00 | 27.89 |
| ATOM | 755 | CB | ALA | A | 99 | 9.566 | −7.700 | −30.935 | 1.00 | 27.68 |
| ATOM | 756 | C | ALA | A | 99 | 7.893 | −7.911 | −29.053 | 1.00 | 27.86 |
| ATOM | 757 | O | ALA | A | 99 | 7.450 | −9.007 | −28.711 | 1.00 | 28.77 |
| ATOM | 758 | N | ASP | A | 100 | 8.241 | −6.966 | −28.181 | 1.00 | 27.75 |
| ATOM | 759 | CA | ASP | A | 100 | 8.030 | −7.137 | −26.741 | 1.00 | 27.20 |
| ATOM | 760 | CB | ASP | A | 100 | 9.328 | −6.937 | −25.966 | 1.00 | 27.10 |
| ATOM | 761 | CG | ASP | A | 100 | 9.845 | −5.525 | −26.038 | 1.00 | 30.19 |
| ATOM | 762 | OD1 | ASP | A | 100 | 10.891 | −5.281 | −25.419 | 1.00 | 32.28 |
| ATOM | 763 | OD2 | ASP | A | 100 | 9.225 | −4.654 | −26.694 | 1.00 | 30.36 |
| ATOM | 764 | C | ASP | A | 100 | 6.905 | −6.256 | −26.173 | 1.00 | 25.74 |
| ATOM | 765 | O | ASP | A | 100 | 6.761 | −6.108 | −24.956 | 1.00 | 26.33 |
| ATOM | 766 | N | GLY | A | 101 | 6.118 | −5.683 | −27.075 | 1.00 | 24.93 |
| ATOM | 767 | CA | GLY | A | 101 | 4.982 | −4.853 | −26.707 | 1.00 | 23.22 |
| ATOM | 768 | C | GLY | A | 101 | 5.326 | −3.418 | −26.342 | 1.00 | 22.68 |
| ATOM | 769 | O | GLY | A | 101 | 4.419 | −2.580 | −26.287 | 1.00 | 21.48 |
| ATOM | 770 | N | SER | A | 102 | 6.609 | −3.117 | −26.126 | 1.00 | 21.53 |
| ATOM | 771 | CA | SER | A | 102 | 6.996 | −1.815 | −25.563 | 1.00 | 21.49 |
| ATOM | 772 | CB | SER | A | 102 | 8.483 | −1.739 | −25.199 | 1.00 | 22.07 |
| ATOM | 773 | OG | SER | A | 102 | 9.283 | −1.958 | −26.345 | 1.00 | 21.77 |
| ATOM | 774 | C | SER | A | 102 | 6.604 | −0.643 | −26.449 | 1.00 | 20.66 |
| ATOM | 775 | O | SER | A | 102 | 6.279 | 0.403 | −25.925 | 1.00 | 20.67 |
| ATOM | 776 | N | GLY | A | 103 | 6.636 | −0.819 | −27.771 | 1.00 | 19.97 |
| ATOM | 777 | CA | GLY | A | 103 | 6.257 | 0.255 | −28.707 | 1.00 | 19.46 |
| ATOM | 778 | C | GLY | A | 103 | 4.824 | 0.777 | −28.539 | 1.00 | 18.94 |
| ATOM | 779 | O | GLY | A | 103 | 4.525 | 1.903 | −28.945 | 1.00 | 18.13 |
| ATOM | 780 | N | LEU | A | 104 | 3.939 | −0.043 | −27.956 | 1.00 | 18.13 |
| ATOM | 781 | CA | LEU | A | 104 | 2.517 | 0.326 | −27.818 | 1.00 | 16.92 |
| ATOM | 782 | CB | LEU | A | 104 | 1.672 | −0.924 | −27.447 | 1.00 | 17.28 |
| ATOM | 783 | CG | LEU | A | 104 | 1.715 | −2.104 | −28.430 | 1.00 | 16.76 |
| ATOM | 784 | CD1 | LEU | A | 104 | 1.072 | −3.356 | −27.836 | 1.00 | 21.62 |
| ATOM | 785 | CD2 | LEU | A | 104 | 1.069 | −1.751 | −29.761 | 1.00 | 19.06 |
| ATOM | 786 | C | LEU | A | 104 | 2.283 | 1.464 | −26.798 | 1.00 | 16.57 |
| ATOM | 787 | O | LEU | A | 104 | 1.202 | 2.092 | −26.807 | 1.00 | 16.79 |
| ATOM | 788 | N | GLY | A | 105 | 3.279 | 1.713 | −25.936 | 1.00 | 14.86 |
| ATOM | 789 | CA | GLY | A | 105 | 3.255 | 2.802 | −24.938 | 1.00 | 15.94 |
| ATOM | 790 | C | GLY | A | 105 | 3.558 | 4.199 | −25.482 | 1.00 | 15.05 |
| ATOM | 791 | O | GLY | A | 105 | 3.481 | 5.179 | −24.755 | 1.00 | 15.93 |
| ATOM | 792 | N | GLU | A | 106 | 3.869 | 4.292 | −26.780 | 1.00 | 14.63 |
| ATOM | 793 | CA | GLU | A | 106 | 4.236 | 5.548 | −27.416 | 1.00 | 14.49 |
| ATOM | 794 | CB | GLU | A | 106 | 4.728 | 5.250 | −28.847 | 1.00 | 13.83 |
| ATOM | 795 | CG | GLU | A | 106 | 5.215 | 6.470 | −29.678 | 1.00 | 16.14 |
| ATOM | 796 | CD | GLU | A | 106 | 6.479 | 7.155 | −29.139 | 1.00 | 18.44 |
| ATOM | 797 | OE1 | GLU | A | 106 | 6.978 | 6.817 | −28.044 | 1.00 | 21.44 |
| ATOM | 798 | OE2 | GLU | A | 106 | 6.972 | 8.083 | −29.817 | 1.00 | 21.04 |

TABLE 15-continued

| | | | | | | | | | |
|---|---|---|---|---|---|---|---|---|---|
| ATOM | 799 | C | GLU | A | 106 | 3.012 | 6.484 | −27.413 | 1.00 | 14.32 |
| ATOM | 800 | O | GLU | A | 106 | 1.928 | 6.074 | −27.828 | 1.00 | 15.51 |
| ATOM | 801 | N | PRO | A | 107 | 3.164 | 7.706 | −26.890 | 1.00 | 15.21 |
| ATOM | 802 | CA | PRO | A | 107 | 2.025 | 8.645 | −26.772 | 1.00 | 14.90 |
| ATOM | 803 | CB | PRO | A | 107 | 2.598 | 9.809 | −25.951 | 1.00 | 15.27 |
| ATOM | 804 | CG | PRO | A | 107 | 3.833 | 9.290 | −25.310 | 1.00 | 17.25 |
| ATOM | 805 | CD | PRO | A | 107 | 4.385 | 8.238 | −26.243 | 1.00 | 14.35 |
| ATOM | 806 | C | PRO | A | 107 | 1.468 | 9.219 | −28.066 | 1.00 | 14.48 |
| ATOM | 807 | O | PRO | A | 107 | 0.263 | 9.371 | −28.172 | 1.00 | 13.94 |
| ATOM | 808 | N | LYS | A | 108 | 2.320 | 9.567 | −29.027 | 1.00 | 14.24 |
| ATOM | 809 | CA | LYS | A | 108 | 1.837 | 10.309 | −30.204 | 1.00 | 14.51 |
| ATOM | 810 | CB | LYS | A | 108 | 1.853 | 11.828 | −29.960 | 1.00 | 14.26 |
| ATOM | 811 | CG | LYS | A | 108 | 3.225 | 12.524 | −30.029 | 1.00 | 13.88 |
| ATOM | 812 | CD | LYS | A | 108 | 3.102 | 14.033 | −29.775 | 1.00 | 15.15 |
| ATOM | 813 | CE | LYS | A | 108 | 4.299 | 14.820 | −30.283 | 1.00 | 17.08 |
| ATOM | 814 | NZ | LYS | A | 108 | 4.341 | 16.279 | −29.836 | 1.00 | 15.57 |
| ATOM | 815 | C | LYS | A | 108 | 2.608 | 9.953 | −31.454 | 1.00 | 14.69 |
| ATOM | 816 | O | LYS | A | 108 | 3.734 | 9.442 | −31.377 | 1.00 | 14.67 |
| ATOM | 817 | N | PHE | A | 109 | 1.976 | 10.203 | −32.594 | 1.00 | 14.54 |
| ATOM | 818 | CA | PHE | A | 109 | 2.530 | 9.860 | −33.902 | 1.00 | 15.20 |
| ATOM | 819 | CB | PHE | A | 109 | 1.839 | 8.594 | −34.451 | 1.00 | 15.67 |
| ATOM | 820 | CG | PHE | A | 109 | 1.973 | 7.407 | −33.553 | 1.00 | 16.81 |
| ATOM | 821 | CD1 | PHE | A | 109 | 1.081 | 7.219 | −32.490 | 1.00 | 17.93 |
| ATOM | 822 | CE1 | PHE | A | 109 | 1.205 | 6.117 | −31.649 | 1.00 | 21.93 |
| ATOM | 823 | CZ | PHE | A | 109 | 2.241 | 5.210 | −31.834 | 1.00 | 19.06 |
| ATOM | 824 | CE2 | PHE | A | 109 | 3.141 | 5.384 | −32.883 | 1.00 | 20.27 |
| ATOM | 825 | CD2 | PHE | A | 109 | 3.003 | 6.492 | −33.737 | 1.00 | 19.44 |
| ATOM | 826 | C | PHE | A | 109 | 2.301 | 10.992 | −34.881 | 1.00 | 15.19 |
| ATOM | 827 | O | PHE | A | 109 | 1.450 | 11.861 | −34.655 | 1.00 | 14.41 |
| ATOM | 828 | N | GLU | A | 110 | 3.039 | 10.971 | −35.993 | 1.00 | 15.14 |
| ATOM | 829 | CA | GLU | A | 110 | 2.756 | 11.905 | −37.077 | 1.00 | 15.24 |
| ATOM | 830 | CB | GLU | A | 110 | 3.905 | 11.933 | −38.103 | 1.00 | 15.00 |
| ATOM | 831 | CG | GLU | A | 110 | 5.302 | 12.204 | −37.493 | 1.00 | 16.29 |
| ATOM | 832 | CD | GLU | A | 110 | 5.554 | 13.673 | −37.174 | 1.00 | 17.52 |
| ATOM | 833 | OE1 | GLU | A | 110 | 4.708 | 14.544 | −37.504 | 1.00 | 17.65 |
| ATOM | 834 | OE2 | GLU | A | 110 | 6.619 | 13.963 | −36.587 | 1.00 | 18.74 |
| ATOM | 835 | C | GLU | A | 110 | 1.462 | 11.476 | −37.762 | 1.00 | 15.32 |
| ATOM | 836 | O | GLU | A | 110 | 1.093 | 10.278 | −37.753 | 1.00 | 15.26 |
| ATOM | 837 | N | LEU | A | 111 | 0.776 | 12.445 | −38.360 | 1.00 | 15.59 |
| ATOM | 838 | CA | LEU | A | 111 | −0.522 | 12.186 | −39.009 | 1.00 | 16.33 |
| ATOM | 839 | CB | LEU | A | 111 | −1.265 | 13.510 | −39.163 | 1.00 | 16.57 |
| ATOM | 840 | CG | LEU | A | 111 | −1.770 | 13.908 | −37.756 | 1.00 | 18.11 |
| ATOM | 841 | CD1 | LEU | A | 111 | −1.819 | 15.405 | −37.574 | 1.00 | 21.43 |
| ATOM | 842 | CD2 | LEU | A | 111 | −3.151 | 13.204 | −37.506 | 1.00 | 18.74 |
| ATOM | 843 | C | LEU | A | 111 | −0.409 | 11.436 | −40.350 | 1.00 | 17.37 |
| ATOM | 844 | O | LEU | A | 111 | −1.426 | 11.023 | −40.944 | 1.00 | 17.23 |
| ATOM | 845 | N | THR | A | 112 | 0.833 | 11.258 | −40.815 | 1.00 | 17.42 |
| ATOM | 846 | CA | THR | A | 112 | 1.144 | 10.301 | −41.887 | 1.00 | 17.92 |
| ATOM | 847 | CB | THR | A | 112 | 2.512 | 10.619 | −42.499 | 1.00 | 17.98 |
| ATOM | 848 | OG1 | THR | A | 112 | 3.476 | 10.702 | −41.445 | 1.00 | 18.32 |
| ATOM | 849 | CG2 | THR | A | 112 | 2.486 | 11.945 | −43.228 | 1.00 | 19.47 |
| ATOM | 850 | C | THR | A | 112 | 1.215 | 8.846 | −41.356 | 1.00 | 18.90 |
| ATOM | 851 | O | THR | A | 112 | 1.535 | 7.917 | −42.117 | 1.00 | 17.68 |
| ATOM | 852 | N | LEU | A | 113 | 0.944 | 8.664 | −40.055 | 1.00 | 18.48 |
| ATOM | 853 | CA | LEU | A | 113 | 1.041 | 7.379 | −39.348 | 1.00 | 19.78 |
| ATOM | 854 | CB | LEU | A | 113 | 0.061 | 6.319 | −39.904 | 1.00 | 19.45 |
| ATOM | 855 | CG | LEU | A | 113 | −1.411 | 6.699 | −40.074 | 1.00 | 21.71 |
| ATOM | 856 | CD1 | LEU | A | 113 | −2.194 | 5.470 | −40.477 | 1.00 | 23.46 |
| ATOM | 857 | CD2 | LEU | A | 113 | −2.005 | 7.323 | −38.800 | 1.00 | 21.59 |
| ATOM | 858 | C | LEU | A | 113 | 2.481 | 6.866 | −39.338 | 1.00 | 20.43 |
| ATOM | 859 | O | LEU | A | 113 | 2.737 | 5.704 | −39.653 | 1.00 | 20.96 |
| ATOM | 860 | N | LYS | A | 114 | 3.406 | 7.769 | −39.024 | 1.00 | 20.07 |
| ATOM | 861 | CA | LYS | A | 114 | 4.826 | 7.460 | −38.863 | 1.00 | 20.25 |
| ATOM | 862 | CB | LYS | A | 114 | 5.662 | 8.209 | −39.899 | 1.00 | 20.95 |
| ATOM | 863 | CG | LYS | A | 114 | 5.432 | 7.725 | −41.314 | 1.00 | 25.23 |
| ATOM | 864 | CD | LYS | A | 114 | 6.636 | 8.059 | −42.184 | 1.00 | 33.76 |
| ATOM | 865 | CE | LYS | A | 114 | 6.551 | 7.360 | −43.537 | 1.00 | 38.31 |
| ATOM | 866 | NZ | LYS | A | 114 | 5.285 | 7.711 | −44.251 | 1.00 | 41.29 |
| ATOM | 867 | C | LYS | A | 114 | 5.252 | 7.874 | −37.471 | 1.00 | 19.64 |
| ATOM | 868 | O | LYS | A | 114 | 4.576 | 8.708 | −36.845 | 1.00 | 19.39 |
| ATOM | 869 | N | PRO | A | 115 | 6.376 | 7.318 | −36.973 | 1.00 | 19.06 |
| ATOM | 870 | CA | PRO | A | 115 | 6.750 | 7.626 | −35.601 | 1.00 | 18.72 |
| ATOM | 871 | CB | PRO | A | 115 | 7.963 | 6.712 | −35.326 | 1.00 | 19.82 |
| ATOM | 872 | CG | PRO | A | 115 | 8.101 | 5.814 | −36.500 | 1.00 | 20.93 |
| ATOM | 873 | CD | PRO | A | 115 | 7.339 | 6.412 | −37.639 | 1.00 | 19.08 |
| ATOM | 874 | C | PRO | A | 115 | 7.156 | 9.093 | −35.434 | 1.00 | 18.70 |
| ATOM | 875 | O | PRO | A | 115 | 7.694 | 9.724 | −36.375 | 1.00 | 17.25 |
| ATOM | 876 | N | PHE | A | 116 | 6.844 | 9.628 | −34.256 | 1.00 | 18.55 |
| ATOM | 877 | CA | PHE | A | 116 | 7.342 | 10.918 | −33.805 | 1.00 | 18.27 |
| ATOM | 878 | CB | PHE | A | 116 | 6.359 | 11.566 | −32.809 | 1.00 | 18.41 |

TABLE 15-continued

| | | | | | | | | | |
|---|---|---|---|---|---|---|---|---|---|
| ATOM | 879 | CG | PHE | A | 116 | 6.908 | 12.804 | −32.151 | 1.00 | 17.33 |
| ATOM | 880 | CD1 | PHE | A | 116 | 6.942 | 14.014 | −32.847 | 1.00 | 16.98 |
| ATOM | 881 | CE1 | PHE | A | 116 | 7.457 | 15.173 | −32.254 | 1.00 | 16.22 |
| ATOM | 882 | CZ | PHE | A | 116 | 7.950 | 15.138 | −30.935 | 1.00 | 15.88 |
| ATOM | 883 | CE2 | PHE | A | 116 | 7.902 | 13.917 | −30.216 | 1.00 | 16.74 |
| ATOM | 884 | CD2 | PHE | A | 116 | 7.380 | 12.767 | −30.825 | 1.00 | 16.05 |
| ATOM | 885 | C | PHE | A | 116 | 8.701 | 10.695 | −33.141 | 1.00 | 19.14 |
| ATOM | 886 | O | PHE | A | 116 | 8.808 | 9.987 | −32.134 | 1.00 | 19.66 |
| ATOM | 887 | N | THR | A | 117 | 9.746 | 11.299 | −33.713 | 1.00 | 19.53 |
| ATOM | 888 | CA | THR | A | 117 | 11.116 | 11.020 | −33.315 | 1.00 | 20.15 |
| ATOM | 889 | CB | THR | A | 117 | 12.042 | 10.999 | −34.567 | 1.00 | 20.83 |
| ATOM | 890 | OG1 | THR | A | 117 | 11.988 | 12.277 | −35.222 | 1.00 | 22.59 |
| ATOM | 891 | CG2 | THR | A | 117 | 11.576 | 9.895 | −35.557 | 1.00 | 21.40 |
| ATOM | 892 | C | THR | A | 117 | 11.685 | 11.969 | −32.263 | 1.00 | 20.34 |
| ATOM | 893 | O | THR | A | 117 | 12.813 | 11.768 | −31.774 | 1.00 | 21.13 |
| ATOM | 894 | N | GLY | A | 118 | 10.943 | 13.017 | −31.914 | 1.00 | 19.25 |
| ATOM | 895 | CA | GLY | A | 118 | 11.451 | 14.018 | −30.974 | 1.00 | 19.41 |
| ATOM | 896 | C | GLY | A | 118 | 11.431 | 13.498 | −29.541 | 1.00 | 19.75 |
| ATOM | 897 | O | GLY | A | 118 | 10.913 | 12.397 | −29.281 | 1.00 | 19.99 |
| ATOM | 898 | N | ASN | A | 119 | 11.998 | 14.279 | −28.622 | 1.00 | 19.56 |
| ATOM | 899 | CA | ASN | A | 119 | 11.958 | 13.954 | −27.198 | 1.00 | 20.41 |
| ATOM | 900 | CB | ASN | A | 119 | 12.961 | 14.801 | −26.419 | 1.00 | 21.50 |
| ATOM | 901 | CG | ASN | A | 119 | 14.377 | 14.612 | −26.930 | 1.00 | 25.14 |
| ATOM | 902 | OD1 | ASN | A | 119 | 14.779 | 13.500 | −27.294 | 1.00 | 30.77 |
| ATOM | 903 | ND2 | ASN | A | 119 | 15.131 | 15.693 | −26.987 | 1.00 | 31.23 |
| ATOM | 904 | C | ASN | A | 119 | 10.550 | 14.194 | −26.696 | 1.00 | 20.06 |
| ATOM | 905 | O | ASN | A | 119 | 9.881 | 15.089 | −27.167 | 1.00 | 19.00 |
| ATOM | 906 | N | TRP | A | 120 | 10.084 | 13.348 | −25.787 | 1.00 | 19.74 |
| ATOM | 907 | CA | TRP | A | 120 | 8.707 | 13.466 | −25.316 | 1.00 | 19.03 |
| ATOM | 908 | CB | TRP | A | 120 | 7.717 | 12.917 | −26.359 | 1.00 | 18.71 |
| ATOM | 909 | CG | TRP | A | 120 | 6.351 | 13.522 | −26.162 | 1.00 | 19.76 |
| ATOM | 910 | CD1 | TRP | A | 120 | 5.239 | 12.901 | −25.673 | 1.00 | 19.81 |
| ATOM | 911 | NE1 | TRP | A | 120 | 4.186 | 13.799 | −25.593 | 1.00 | 19.49 |
| ATOM | 912 | CE2 | TRP | A | 120 | 4.612 | 15.021 | −26.042 | 1.00 | 19.44 |
| ATOM | 913 | CD2 | TRP | A | 120 | 5.975 | 14.886 | −26.410 | 1.00 | 19.35 |
| ATOM | 914 | CE3 | TRP | A | 120 | 6.657 | 16.014 | −26.895 | 1.00 | 18.94 |
| ATOM | 915 | CZ3 | TRP | A | 120 | 5.959 | 17.220 | −27.010 | 1.00 | 20.22 |
| ATOM | 916 | CH2 | TRP | A | 120 | 4.602 | 17.315 | −26.628 | 1.00 | 20.15 |
| ATOM | 917 | CZ2 | TRP | A | 120 | 3.918 | 16.233 | −26.160 | 1.00 | 18.83 |
| ATOM | 918 | C | TRP | A | 120 | 8.602 | 12.685 | −24.001 | 1.00 | 18.80 |
| ATOM | 919 | O | TRP | A | 120 | 9.454 | 11.833 | −23.722 | 1.00 | 18.83 |
| ATOM | 920 | N | GLY | A | 121 | 7.593 | 12.990 | −23.189 | 1.00 | 17.91 |
| ATOM | 921 | CA | GLY | A | 121 | 7.314 | 12.189 | −21.988 | 1.00 | 17.64 |
| ATOM | 922 | C | GLY | A | 121 | 6.721 | 10.834 | −22.362 | 1.00 | 18.93 |
| ATOM | 923 | O | GLY | A | 121 | 5.499 | 10.704 | −22.487 | 1.00 | 18.99 |
| ATOM | 924 | N | ARG | A | 122 | 7.589 | 9.828 | −22.536 | 1.00 | 17.95 |
| ATOM | 925 | CA | ARG | A | 122 | 7.195 | 8.483 | −22.958 | 1.00 | 17.86 |
| ATOM | 926 | CB | ARG | A | 122 | 7.686 | 8.193 | −24.394 | 1.00 | 17.37 |
| ATOM | 927 | CG | ARG | A | 122 | 9.181 | 8.529 | −24.626 | 1.00 | 19.53 |
| ATOM | 928 | CD | ARG | A | 122 | 9.689 | 7.987 | −25.969 | 1.00 | 17.88 |
| ATOM | 929 | NE | ARG | A | 122 | 9.012 | 8.549 | −27.159 | 1.00 | 18.08 |
| ATOM | 930 | CZ | ARG | A | 122 | 9.425 | 9.645 | −27.807 | 1.00 | 18.06 |
| ATOM | 931 | NH1 | ARG | A | 122 | 10.477 | 10.326 | −27.366 | 1.00 | 16.88 |
| ATOM | 932 | NH2 | ARG | A | 122 | 8.784 | 10.074 | −28.892 | 1.00 | 17.35 |
| ATOM | 933 | C | ARG | A | 122 | 7.799 | 7.450 | −21.976 | 1.00 | 17.48 |
| ATOM | 934 | O | ARG | A | 122 | 8.848 | 7.697 | −21.396 | 1.00 | 17.69 |
| ATOM | 935 | N | PRO | A | 123 | 7.142 | 6.298 | −21.781 | 1.00 | 17.14 |
| ATOM | 936 | CA | PRO | A | 123 | 5.886 | 5.916 | −22.382 | 1.00 | 16.01 |
| ATOM | 937 | CB | PRO | A | 123 | 5.908 | 4.385 | −22.266 | 1.00 | 16.51 |
| ATOM | 938 | CG | PRO | A | 123 | 6.585 | 4.144 | −20.969 | 1.00 | 16.30 |
| ATOM | 939 | CD | PRO | A | 123 | 7.658 | 5.238 | −20.873 | 1.00 | 16.95 |
| ATOM | 940 | C | PRO | A | 123 | 4.716 | 6.494 | −21.581 | 1.00 | 15.29 |
| ATOM | 941 | O | PRO | A | 123 | 4.926 | 7.057 | −20.521 | 1.00 | 15.07 |
| ATOM | 942 | N | GLN | A | 124 | 3.504 | 6.362 | −22.120 | 1.00 | 14.60 |
| ATOM | 943 | CA | GLN | A | 124 | 2.289 | 6.675 | −21.386 | 1.00 | 14.40 |
| ATOM | 944 | CB | GLN | A | 124 | 1.602 | 7.889 | −22.001 | 1.00 | 14.71 |
| ATOM | 945 | CG | GLN | A | 124 | 2.442 | 9.186 | −21.711 | 1.00 | 11.93 |
| ATOM | 946 | CD | GLN | A | 124 | 1.993 | 10.407 | −22.472 | 1.00 | 15.67 |
| ATOM | 947 | OE1 | GLN | A | 124 | 2.807 | 11.310 | −22.758 | 1.00 | 15.75 |
| ATOM | 948 | NE2 | GLN | A | 124 | 0.718 | 10.450 | −22.822 | 1.00 | 9.85 |
| ATOM | 949 | C | GLN | A | 124 | 1.441 | 5.421 | −21.511 | 1.00 | 14.28 |
| ATOM | 950 | O | GLN | A | 124 | 0.988 | 5.095 | −22.604 | 1.00 | 14.63 |
| ATOM | 951 | N | ARG | A | 125 | 1.241 | 4.731 | −20.390 | 1.00 | 13.50 |
| ATOM | 952 | CA | ARG | A | 125 | 0.700 | 3.382 | −20.398 | 1.00 | 13.96 |
| ATOM | 953 | CB | ARG | A | 125 | 1.331 | 2.567 | −19.256 | 1.00 | 14.28 |
| ATOM | 954 | CG | ARG | A | 125 | 2.864 | 2.703 | −19.249 | 1.00 | 15.16 |
| ATOM | 955 | CD | ARG | A | 125 | 3.503 | 1.577 | −18.439 | 1.00 | 18.07 |
| ATOM | 956 | NE | ARG | A | 125 | 4.924 | 1.827 | −18.132 | 1.00 | 17.46 |
| ATOM | 957 | CZ | ARG | A | 125 | 5.944 | 1.334 | −18.833 | 1.00 | 19.43 |
| ATOM | 958 | NH1 | ARG | A | 125 | 5.728 | 0.601 | −19.925 | 1.00 | 20.02 |

TABLE 15-continued

| | | | | | | | | | |
|---|---|---|---|---|---|---|---|---|---|
| ATOM | 959 | NH2 | ARG | A | 125 | 7.197 | 1.596 | −18.453 | 1.00 | 18.94 |
| ATOM | 960 | C | ARG | A | 125 | −0.829 | 3.335 | −20.359 | 1.00 | 14.48 |
| ATOM | 961 | O | ARG | A | 125 | −1.424 | 2.262 | −20.343 | 1.00 | 14.40 |
| ATOM | 962 | N | ASP | A | 126 | −1.462 | 4.509 | −20.374 | 1.00 | 14.03 |
| ATOM | 963 | CA | ASP | A | 126 | −2.919 | 4.568 | −20.542 | 1.00 | 13.39 |
| ATOM | 964 | CB | ASP | A | 126 | −3.488 | 5.922 | −20.067 | 1.00 | 13.17 |
| ATOM | 965 | CG | ASP | A | 126 | −2.926 | 7.092 | −20.845 | 1.00 | 14.17 |
| ATOM | 966 | OD1 | ASP | A | 126 | −1.713 | 7.108 | −21.143 | 1.00 | 12.29 |
| ATOM | 967 | OD2 | ASP | A | 126 | −3.705 | 8.003 | −21.187 | 1.00 | 16.69 |
| ATOM | 968 | C | ASP | A | 126 | −3.350 | 4.306 | −21.974 | 1.00 | 13.60 |
| ATOM | 969 | O | ASP | A | 126 | −4.452 | 3.806 | −22.189 | 1.00 | 13.56 |
| ATOM | 970 | N | GLY | A | 127 | −2.491 | 4.634 | −22.948 | 1.00 | 12.78 |
| ATOM | 971 | CA | GLY | A | 127 | −2.886 | 4.558 | −24.358 | 1.00 | 13.20 |
| ATOM | 972 | C | GLY | A | 127 | −3.473 | 3.213 | −24.794 | 1.00 | 12.77 |
| ATOM | 973 | O | GLY | A | 127 | −4.579 | 3.150 | −25.327 | 1.00 | 12.56 |
| ATOM | 974 | N | PRO | A | 128 | −2.720 | 2.120 | −24.613 | 1.00 | 13.94 |
| ATOM | 975 | CA | PRO | A | 128 | −3.262 | 0.810 | −24.978 | 1.00 | 12.97 |
| ATOM | 976 | CB | PRO | A | 128 | −2.135 | −0.162 | −24.552 | 1.00 | 14.15 |
| ATOM | 977 | CG | PRO | A | 128 | −0.907 | 0.656 | −24.721 | 1.00 | 14.39 |
| ATOM | 978 | CD | PRO | A | 128 | −1.323 | 2.010 | −24.150 | 1.00 | 13.67 |
| ATOM | 979 | C | PRO | A | 128 | −4.571 | 0.455 | −24.255 | 1.00 | 13.30 |
| ATOM | 980 | O | PRO | A | 128 | −5.433 | −0.161 | −24.869 | 1.00 | 13.72 |
| ATOM | 981 | N | ALA | A | 129 | −4.718 | 0.852 | −22.985 | 1.00 | 12.95 |
| ATOM | 982 | CA | ALA | A | 129 | −5.963 | 0.611 | −22.258 | 1.00 | 13.49 |
| ATOM | 983 | CB | ALA | A | 129 | −5.806 | 1.016 | −20.808 | 1.00 | 13.00 |
| ATOM | 984 | C | ALA | A | 129 | −7.162 | 1.329 | −22.923 | 1.00 | 13.43 |
| ATOM | 985 | O | ALA | A | 129 | −8.217 | 0.721 | −23.159 | 1.00 | 13.26 |
| ATOM | 986 | N | LEU | A | 130 | −6.998 | 2.619 | −23.221 | 1.00 | 12.51 |
| ATOM | 987 | CA | LEU | A | 130 | −8.068 | 3.409 | −23.813 | 1.00 | 12.69 |
| ATOM | 988 | CB | LEU | A | 130 | −7.678 | 4.903 | −23.806 | 1.00 | 12.56 |
| ATOM | 989 | CG | LEU | A | 130 | −7.458 | 5.555 | −22.426 | 1.00 | 14.76 |
| ATOM | 990 | CD1 | LEU | A | 130 | −6.959 | 6.991 | −22.643 | 1.00 | 15.23 |
| ATOM | 991 | CD2 | LEU | A | 130 | −8.776 | 5.544 | −21.651 | 1.00 | 15.30 |
| ATOM | 992 | C | LEU | A | 130 | −8.410 | 2.934 | −25.228 | 1.00 | 12.78 |
| ATOM | 993 | O | LEU | A | 130 | −9.571 | 2.863 | −25.607 | 1.00 | 12.83 |
| ATOM | 994 | N | ARG | A | 131 | −7.386 | 2.601 | −26.015 | 1.00 | 13.70 |
| ATOM | 995 | CA | ARG | A | 131 | −7.630 | 2.070 | −27.351 | 1.00 | 14.52 |
| ATOM | 996 | CB | ARG | A | 131 | −6.316 | 1.925 | −28.135 | 1.00 | 14.04 |
| ATOM | 997 | CG | ARG | A | 131 | −6.550 | 1.438 | −29.566 | 1.00 | 15.60 |
| ATOM | 998 | CD | ARG | A | 131 | −5.278 | 1.522 | −30.428 | 1.00 | 15.59 |
| ATOM | 999 | NE | ARG | A | 131 | −4.118 | 0.915 | −29.779 | 1.00 | 16.77 |
| ATOM | 1000 | CZ | ARG | A | 131 | −2.860 | 1.205 | −30.098 | 1.00 | 16.26 |
| ATOM | 1001 | NH1 | ARG | A | 131 | −2.610 | 2.104 | −31.054 | 1.00 | 16.37 |
| ATOM | 1002 | NH2 | ARG | A | 131 | −1.856 | 0.618 | −29.448 | 1.00 | 15.96 |
| ATOM | 1003 | C | ARG | A | 131 | −8.408 | 0.729 | −27.283 | 1.00 | 14.44 |
| ATOM | 1004 | O | ARG | A | 131 | −9.350 | 0.533 | −28.050 | 1.00 | 15.71 |
| ATOM | 1005 | N | ALA | A | 132 | −8.025 | −0.164 | −26.364 | 1.00 | 14.50 |
| ATOM | 1006 | CA | ALA | A | 132 | −8.738 | −1.456 | −26.195 | 1.00 | 15.06 |
| ATOM | 1007 | CB | ALA | A | 132 | −8.069 | −2.348 | −25.112 | 1.00 | 15.02 |
| ATOM | 1008 | C | ALA | A | 132 | −10.194 | −1.197 | −25.846 | 1.00 | 15.43 |
| ATOM | 1009 | O | ALA | A | 132 | −11.101 | −1.808 | −26.416 | 1.00 | 15.57 |
| ATOM | 1010 | N | ILE | A | 133 | −10.418 | −0.270 | −24.915 | 1.00 | 15.70 |
| ATOM | 1011 | CA | ILE | A | 133 | −11.777 | 0.049 | −24.491 | 1.00 | 14.44 |
| ATOM | 1012 | CB | ILE | A | 133 | −11.775 | 1.056 | −23.335 | 1.00 | 14.07 |
| ATOM | 1013 | CG1 | ILE | A | 133 | −11.268 | 0.387 | −22.046 | 1.00 | 15.40 |
| ATOM | 1014 | CD1 | ILE | A | 133 | −10.751 | 1.388 | −21.017 | 1.00 | 16.66 |
| ATOM | 1015 | CG2 | ILE | A | 133 | −13.176 | 1.702 | −23.101 | 1.00 | 13.98 |
| ATOM | 1016 | C | ILE | A | 133 | −12.633 | 0.517 | −25.679 | 1.00 | 14.36 |
| ATOM | 1017 | O | ILE | A | 133 | −13.781 | 0.102 | −25.807 | 1.00 | 14.69 |
| ATOM | 1018 | N | ALA | A | 134 | −12.079 | 1.362 | −26.545 | 1.00 | 13.69 |
| ATOM | 1019 | CA | ALA | A | 134 | −12.819 | 1.832 | −27.720 | 1.00 | 13.81 |
| ATOM | 1020 | CB | ALA | A | 134 | −12.019 | 2.949 | −28.452 | 1.00 | 13.99 |
| ATOM | 1021 | C | ALA | A | 134 | −13.140 | 0.662 | −28.657 | 1.00 | 14.62 |
| ATOM | 1022 | O | ALA | A | 134 | −14.279 | 0.473 | −29.087 | 1.00 | 14.90 |
| ATOM | 1023 | N | LEU | A | 135 | −12.133 | −0.155 | −28.947 | 1.00 | 14.66 |
| ATOM | 1024 | CA | LEU | A | 135 | −12.328 | −1.251 | −29.901 | 1.00 | 15.75 |
| ATOM | 1025 | CB | LEU | A | 135 | −10.984 | −1.875 | −30.311 | 1.00 | 15.75 |
| ATOM | 1026 | CG | LEU | A | 135 | −10.348 | −1.231 | −31.557 | 1.00 | 16.40 |
| ATOM | 1027 | CD1 | LEU | A | 135 | −10.257 | 0.308 | −31.471 | 1.00 | 18.56 |
| ATOM | 1028 | CD2 | LEU | A | 135 | −8.980 | −1.852 | −31.804 | 1.00 | 17.85 |
| ATOM | 1029 | C | LEU | A | 135 | −13.277 | −2.306 | −29.340 | 1.00 | 15.13 |
| ATOM | 1030 | O | LEU | A | 135 | −14.079 | −2.845 | −30.087 | 1.00 | 15.84 |
| ATOM | 1031 | N | ILE | A | 136 | −13.192 | −2.573 | −28.039 | 1.00 | 15.22 |
| ATOM | 1032 | CA | ILE | A | 136 | −14.153 | −3.473 | −27.377 | 1.00 | 15.71 |
| ATOM | 1033 | CB | ILE | A | 136 | −13.734 | −3.829 | −25.918 | 1.00 | 15.92 |
| ATOM | 1034 | CG1 | ILE | A | 136 | −12.408 | −4.598 | −25.904 | 1.00 | 15.39 |
| ATOM | 1035 | CD1 | ILE | A | 136 | −11.742 | −4.679 | −24.497 | 1.00 | 15.63 |
| ATOM | 1036 | CG2 | ILE | A | 136 | −14.842 | −4.611 | −25.204 | 1.00 | 16.20 |
| ATOM | 1037 | C | ILE | A | 136 | −15.565 | −2.902 | −27.457 | 1.00 | 17.10 |
| ATOM | 1038 | O | ILE | A | 136 | −16.531 | −3.631 | −27.728 | 1.00 | 17.48 |

TABLE 15-continued

| ATOM | 1039 | N   | GLY | A | 137 | -15.685 | -1.581  | -27.297 | 1.00 | 16.46 |
| ---- | ---- | --- | --- | - | --- | ------- | ------- | ------- | ---- | ----- |
| ATOM | 1040 | CA  | GLY | A | 137 | -16.979 | -0.902  | -27.484 | 1.00 | 16.59 |
| ATOM | 1041 | C   | GLY | A | 137 | -17.600 | -1.206  | -28.833 | 1.00 | 17.13 |
| ATOM | 1042 | O   | GLY | A | 137 | -18.778 | -1.605  | -28.920 | 1.00 | 16.92 |
| ATOM | 1043 | N   | TYR | A | 138 | -16.817 | -1.056  | -29.898 | 1.00 | 16.61 |
| ATOM | 1044 | CA  | TYR | A | 138 | -17.353 | -1.349  | -31.224 | 1.00 | 17.93 |
| ATOM | 1045 | CB  | TYR | A | 138 | -16.446 | -0.838  | -32.341 | 1.00 | 17.46 |
| ATOM | 1046 | CG  | TYR | A | 138 | -17.112 | -0.897  | -33.693 | 1.00 | 18.28 |
| ATOM | 1047 | CD1 | TYR | A | 138 | -18.350 | -0.268  | -33.914 | 1.00 | 18.85 |
| ATOM | 1048 | CE1 | TYR | A | 138 | -18.966 | -0.314  | -35.153 | 1.00 | 21.29 |
| ATOM | 1049 | CZ  | TYR | A | 138 | -18.358 | -1.001  | -36.207 | 1.00 | 20.99 |
| ATOM | 1050 | OH  | TYR | A | 138 | -18.994 | -1.055  | -37.433 | 1.00 | 20.06 |
| ATOM | 1051 | CE2 | TYR | A | 138 | -17.133 | -1.636  | -36.026 | 1.00 | 19.88 |
| ATOM | 1052 | CD2 | TYR | A | 138 | -16.512 | -1.583  | -34.766 | 1.00 | 18.25 |
| ATOM | 1053 | C   | TYR | A | 138 | -17.643 | -2.844  | -31.406 | 1.00 | 18.67 |
| ATOM | 1054 | O   | TYR | A | 138 | -18.654 | -3.207  | -32.037 | 1.00 | 20.06 |
| ATOM | 1055 | N   | SER | A | 139 | -16.766 | -3.686  | -30.864 | 1.00 | 19.48 |
| ATOM | 1056 | CA  | SER | A | 139 | -16.942 | -5.146  | -30.900 | 1.00 | 21.02 |
| ATOM | 1057 | CB  | SER | A | 139 | -15.808 | -5.829  | -30.129 | 1.00 | 21.09 |
| ATOM | 1058 | OG  | SER | A | 139 | -14.581 | -5.598  | -30.789 | 1.00 | 21.49 |
| ATOM | 1059 | C   | SER | A | 139 | -18.298 | -5.557  | -30.325 | 1.00 | 22.24 |
| ATOM | 1060 | O   | SER | A | 139 | -19.002 | -6.392  | -30.907 | 1.00 | 23.64 |
| ATOM | 1061 | N   | LYS | A | 140 | -18.669 | -4.976  | -29.188 | 1.00 | 22.77 |
| ATOM | 1062 | CA  | LYS | A | 140 | -19.987 | -5.225  | -28.595 | 1.00 | 24.29 |
| ATOM | 1063 | CB  | LYS | A | 140 | -20.218 | -4.343  | -27.370 | 1.00 | 24.29 |
| ATOM | 1064 | CG  | LYS | A | 140 | -19.384 | -4.695  | -26.170 | 1.00 | 26.62 |
| ATOM | 1065 | CD  | LYS | A | 140 | -19.696 | -3.693  | -25.060 | 1.00 | 28.24 |
| ATOM | 1066 | CE  | LYS | A | 140 | -18.589 | -3.635  | -24.056 | 1.00 | 28.19 |
| ATOM | 1067 | NZ  | LYS | A | 140 | -18.940 | -2.725  | -22.954 | 1.00 | 26.78 |
| ATOM | 1068 | C   | LYS | A | 140 | -21.126 | -5.001  | -29.584 | 1.00 | 24.17 |
| ATOM | 1069 | O   | LYS | A | 140 | -22.053 | -5.823  | -29.670 | 1.00 | 24.94 |
| ATOM | 1070 | N   | TRP | A | 141 | -21.062 | -3.898  | -30.321 | 1.00 | 23.60 |
| ATOM | 1071 | CA  | TRP | A | 141 | -22.054 | -3.613  | -31.338 | 1.00 | 24.29 |
| ATOM | 1072 | CB  | TRP | A | 141 | -21.847 | -2.226  | -31.953 | 1.00 | 24.36 |
| ATOM | 1073 | CG  | TRP | A | 141 | -22.973 | -1.833  | -32.874 | 1.00 | 24.25 |
| ATOM | 1074 | CD1 | TRP | A | 141 | -24.113 | -1.170  | -32.531 | 1.00 | 25.06 |
| ATOM | 1075 | NE1 | TRP | A | 141 | -24.921 | -1.016  | -33.638 | 1.00 | 25.22 |
| ATOM | 1076 | CE2 | TRP | A | 141 | -24.302 | -1.575  | -34.722 | 1.00 | 24.07 |
| ATOM | 1077 | CD2 | TRP | A | 141 | -23.078 | -2.115  | -34.276 | 1.00 | 24.80 |
| ATOM | 1078 | CE3 | TRP | A | 141 | -22.248 | -2.766  | -35.203 | 1.00 | 25.40 |
| ATOM | 1079 | CZ3 | TRP | A | 141 | -22.669 | -2.858  | -36.532 | 1.00 | 25.72 |
| ATOM | 1080 | CH2 | TRP | A | 141 | -23.891 | -2.304  | -36.940 | 1.00 | 24.95 |
| ATOM | 1081 | CZ2 | TRP | A | 141 | -24.721 | -1.666  | -36.051 | 1.00 | 25.14 |
| ATOM | 1082 | C   | TRP | A | 141 | -22.078 | -4.666  | -32.448 | 1.00 | 24.47 |
| ATOM | 1083 | O   | TRP | A | 141 | -23.155 | -5.152  | -32.831 | 1.00 | 24.52 |
| ATOM | 1084 | N   | LEU | A | 142 | -20.904 | -4.991  | -32.985 | 1.00 | 24.39 |
| ATOM | 1085 | CA  | LEU | A | 142 | -20.806 | -6.024  | -34.010 | 1.00 | 25.05 |
| ATOM | 1086 | CB  | LEU | A | 142 | -19.361 | -6.199  | -34.473 | 1.00 | 24.56 |
| ATOM | 1087 | CG  | LEU | A | 142 | -18.754 | -5.023  | -35.252 | 1.00 | 24.44 |
| ATOM | 1088 | CD1 | LEU | A | 142 | -17.274 | -5.304  | -35.441 | 1.00 | 23.72 |
| ATOM | 1089 | CD2 | LEU | A | 142 | -19.424 | -4.793  | -36.624 | 1.00 | 25.76 |
| ATOM | 1090 | C   | LEU | A | 142 | -21.406 | -7.364  | -33.556 | 1.00 | 25.97 |
| ATOM | 1091 | O   | LEU | A | 142 | -22.195 | -7.966  | -34.283 | 1.00 | 26.49 |
| ATOM | 1092 | N   | ILE | A | 143 | -21.045 | -7.814  | -32.359 | 1.00 | 27.04 |
| ATOM | 1093 | CA  | ILE | A | 143 | -21.596 | -9.040  | -31.792 | 1.00 | 28.46 |
| ATOM | 1094 | CB  | ILE | A | 143 | -20.959 | -9.362  | -30.425 | 1.00 | 28.30 |
| ATOM | 1095 | CG1 | ILE | A | 143 | -19.474 | -9.722  | -30.609 | 1.00 | 27.97 |
| ATOM | 1096 | CD1 | ILE | A | 143 | -18.707 | -9.814  | -29.301 | 1.00 | 29.85 |
| ATOM | 1097 | CG2 | ILE | A | 143 | -21.720 | -10.494 | -29.717 | 1.00 | 29.57 |
| ATOM | 1098 | C   | ILE | A | 143 | -23.124 | -8.992  | -31.682 | 1.00 | 29.52 |
| ATOM | 1099 | O   | ILE | A | 143 | -23.813 | -9.928  | -32.118 | 1.00 | 30.10 |
| ATOM | 1100 | N   | ASN | A | 144 | -23.655 | -7.916  | -31.111 | 1.00 | 30.37 |
| ATOM | 1101 | CA  | ASN | A | 144 | -25.109 | -7.768  | -30.988 | 1.00 | 32.18 |
| ATOM | 1102 | CB  | ASN | A | 144 | -25.479 | -6.522  | -30.186 | 1.00 | 32.73 |
| ATOM | 1103 | CG  | ASN | A | 144 | -26.960 | -6.489  | -29.792 | 1.00 | 36.88 |
| ATOM | 1104 | OD1 | ASN | A | 144 | -27.444 | -7.350  | -29.041 | 1.00 | 42.25 |
| ATOM | 1105 | ND2 | ASN | A | 144 | -27.685 | -5.488  | -30.291 | 1.00 | 40.10 |
| ATOM | 1106 | C   | ASN | A | 144 | -25.820 | -7.760  | -32.341 | 1.00 | 32.17 |
| ATOM | 1107 | O   | ASN | A | 144 | -27.012 | -8.029  | -32.411 | 1.00 | 32.73 |
| ATOM | 1108 | N   | ASN | A | 145 | -25.094 | -7.460  | -33.411 | 1.00 | 32.19 |
| ATOM | 1109 | CA  | ASN | A | 145 | -25.705 | -7.403  | -34.726 | 1.00 | 32.78 |
| ATOM | 1110 | CB  | ASN | A | 145 | -25.526 | -6.014  | -35.331 | 1.00 | 33.16 |
| ATOM | 1111 | CG  | ASN | A | 145 | -26.397 | -4.986  | -34.639 | 1.00 | 34.32 |
| ATOM | 1112 | OD1 | ASN | A | 145 | -27.576 | -4.841  | -34.969 | 1.00 | 37.42 |
| ATOM | 1113 | ND2 | ASN | A | 145 | -25.834 | -4.289  | -33.647 | 1.00 | 34.31 |
| ATOM | 1114 | C   | ASN | A | 145 | -25.285 | -8.533  | -35.671 | 1.00 | 33.13 |
| ATOM | 1115 | O   | ASN | A | 145 | -25.412 | -8.415  | -36.902 | 1.00 | 33.03 |
| ATOM | 1116 | N   | ASN | A | 146 | -24.789 | -9.618  | -35.065 | 1.00 | 33.43 |
| ATOM | 1117 | CA  | ASN | A | 146 | -24.475 | -10.885 | -35.736 | 1.00 | 34.14 |
| ATOM | 1118 | CB  | ASN | A | 146 | -25.710 | -11.459 | -36.461 | 1.00 | 34.85 |

TABLE 15-continued

| | | | | | | | | | |
|---|---|---|---|---|---|---|---|---|---|
| ATOM | 1119 | CG | ASN | A | 146 | −26.994 | −11.280 | −35.657 | 1.00 | 37.41 |
| ATOM | 1120 | OD1 | ASN | A | 146 | −27.033 | −11.543 | −34.450 | 1.00 | 41.43 |
| ATOM | 1121 | ND2 | ASN | A | 146 | −28.047 | −10.814 | −36.321 | 1.00 | 41.54 |
| ATOM | 1122 | C | ASN | A | 146 | −23.266 | −10.795 | −36.652 | 1.00 | 33.92 |
| ATOM | 1123 | O | ASN | A | 146 | −23.216 | −11.419 | −37.724 | 1.00 | 33.76 |
| ATOM | 1124 | N | TYR | A | 147 | −22.280 | −10.013 | −36.221 | 1.00 | 32.92 |
| ATOM | 1125 | CA | TYR | A | 147 | −21.049 | −9.870 | −36.974 | 1.00 | 32.90 |
| ATOM | 1126 | CB | TYR | A | 147 | −20.859 | −8.423 | −37.451 | 1.00 | 33.31 |
| ATOM | 1127 | CG | TYR | A | 147 | −21.966 | −7.893 | −38.339 | 1.00 | 33.29 |
| ATOM | 1128 | CD1 | TYR | A | 147 | −22.168 | −8.410 | −39.621 | 1.00 | 34.11 |
| ATOM | 1129 | CE1 | TYR | A | 147 | −23.177 | −7.924 | −40.438 | 1.00 | 34.19 |
| ATOM | 1130 | CZ | TYR | A | 147 | −23.986 | −6.888 | −39.983 | 1.00 | 34.10 |
| ATOM | 1131 | OH | TYR | A | 147 | −24.987 | −6.399 | −40.794 | 1.00 | 35.08 |
| ATOM | 1132 | CE2 | TYR | A | 147 | −23.798 | −6.345 | −38.722 | 1.00 | 32.48 |
| ATOM | 1133 | CD2 | TYR | A | 147 | −22.792 | −6.852 | −37.906 | 1.00 | 32.03 |
| ATOM | 1134 | C | TYR | A | 147 | −19.857 | −10.297 | −36.138 | 1.00 | 32.74 |
| ATOM | 1135 | O | TYR | A | 147 | −18.795 | −9.710 | −36.242 | 1.00 | 32.03 |
| ATOM | 1136 | N | GLN | A | 148 | −20.037 | −11.325 | −35.312 | 1.00 | 33.44 |
| ATOM | 1137 | CA | GLN | A | 148 | −18.977 | −11.807 | −34.427 | 1.00 | 34.39 |
| ATOM | 1138 | CB | GLN | A | 148 | −19.483 | −12.971 | −33.573 | 1.00 | 34.76 |
| ATOM | 1139 | CG | GLN | A | 148 | −18.523 | −13.445 | −32.481 | 1.00 | 35.56 |
| ATOM | 1140 | CD | GLN | A | 148 | −19.216 | −14.273 | −31.401 | 1.00 | 36.59 |
| ATOM | 1141 | OE1 | GLN | A | 148 | −20.296 | −13.913 | −30.916 | 1.00 | 41.20 |
| ATOM | 1142 | NE2 | GLN | A | 148 | −18.589 | −15.380 | −31.008 | 1.00 | 38.65 |
| ATOM | 1143 | C | GLN | A | 148 | −17.690 | −12.196 | −35.176 | 1.00 | 34.46 |
| ATOM | 1144 | O | GLN | A | 148 | −16.582 | −12.002 | −34.654 | 1.00 | 34.20 |
| ATOM | 1145 | N | PHE | A | 149 | −17.841 | −12.735 | −36.391 | 1.00 | 34.19 |
| ATOM | 1146 | CA | PHE | A | 149 | −16.696 | −13.131 | −37.217 | 1.00 | 34.10 |
| ATOM | 1147 | CB | PHE | A | 149 | −17.140 | −13.804 | −38.534 | 1.00 | 35.60 |
| ATOM | 1148 | CG | PHE | A | 149 | −18.346 | −13.168 | −39.193 | 1.00 | 38.70 |
| ATOM | 1149 | CD1 | PHE | A | 149 | −19.388 | −13.976 | −39.676 | 1.00 | 42.72 |
| ATOM | 1150 | CE1 | PHE | A | 149 | −20.518 | −13.417 | −40.295 | 1.00 | 43.69 |
| ATOM | 1151 | CZ | PHE | A | 149 | −20.615 | −12.019 | −40.437 | 1.00 | 43.12 |
| ATOM | 1152 | CE2 | PHE | A | 149 | −19.567 | −11.188 | −39.953 | 1.00 | 43.20 |
| ATOM | 1153 | CD2 | PHE | A | 149 | −18.451 | −11.772 | −39.341 | 1.00 | 42.33 |
| ATOM | 1154 | C | PHE | A | 149 | −15.746 | −11.960 | −37.517 | 1.00 | 32.49 |
| ATOM | 1155 | O | PHE | A | 149 | −14.528 | −12.132 | −37.548 | 1.00 | 32.23 |
| ATOM | 1156 | N | THR | A | 150 | −16.327 | −10.789 | −37.751 | 1.00 | 30.95 |
| ATOM | 1157 | CA | THR | A | 150 | −15.570 | −9.568 | −38.040 | 1.00 | 29.68 |
| ATOM | 1158 | CB | THR | A | 150 | −16.512 | −8.424 | −38.445 | 1.00 | 29.97 |
| ATOM | 1159 | OG1 | THR | A | 150 | −17.162 | −8.768 | −39.673 | 1.00 | 30.58 |
| ATOM | 1160 | CG2 | THR | A | 150 | −15.758 | −7.096 | −38.637 | 1.00 | 29.18 |
| ATOM | 1161 | C | THR | A | 150 | −14.727 | −9.203 | −36.822 | 1.00 | 28.54 |
| ATOM | 1162 | O | THR | A | 150 | −13.566 | −8.827 | −36.965 | 1.00 | 28.38 |
| ATOM | 1163 | N | VAL | A | 151 | −15.310 | −9.354 | −35.636 | 1.00 | 27.23 |
| ATOM | 1164 | CA | VAL | A | 151 | −14.597 | −9.146 | −34.374 | 1.00 | 26.78 |
| ATOM | 1165 | CB | VAL | A | 151 | −15.529 | −9.352 | −33.148 | 1.00 | 26.25 |
| ATOM | 1166 | CG1 | VAL | A | 151 | −14.752 | −9.213 | −31.832 | 1.00 | 26.50 |
| ATOM | 1167 | CG2 | VAL | A | 151 | −16.690 | −8.361 | −33.178 | 1.00 | 24.41 |
| ATOM | 1168 | C | VAL | A | 151 | −13.384 | −10.080 | −34.305 | 1.00 | 27.61 |
| ATOM | 1169 | O | VAL | A | 151 | −12.246 | −9.638 | −34.106 | 1.00 | 26.67 |
| ATOM | 1170 | N | SER | A | 152 | −13.625 | −11.375 | −34.505 | 1.00 | 28.53 |
| ATOM | 1171 | CA | SER | A | 152 | −12.551 | −12.369 | −34.470 | 1.00 | 30.01 |
| ATOM | 1172 | CB | SER | A | 152 | −13.102 | −13.759 | −34.773 | 1.00 | 30.18 |
| ATOM | 1173 | OG | SER | A | 152 | −13.612 | −14.300 | −33.586 | 1.00 | 32.28 |
| ATOM | 1174 | C | SER | A | 152 | −11.419 | −12.091 | −35.430 | 1.00 | 30.23 |
| ATOM | 1175 | O | SER | A | 152 | −10.250 | −12.250 | −35.090 | 1.00 | 30.95 |
| ATOM | 1176 | N | ASN | A | 153 | −11.762 | −11.705 | −36.641 | 1.00 | 31.46 |
| ATOM | 1177 | CA | ASN | A | 153 | −10.753 | −11.624 | −37.674 | 1.00 | 32.41 |
| ATOM | 1178 | CB | ASN | A | 153 | −11.333 | −12.118 | −38.997 | 1.00 | 33.62 |
| ATOM | 1179 | CG | ASN | A | 153 | −11.791 | −13.584 | −38.902 | 1.00 | 36.13 |
| ATOM | 1180 | OD1 | ASN | A | 153 | −12.931 | −13.918 | −39.231 | 1.00 | 40.99 |
| ATOM | 1181 | ND2 | ASN | A | 153 | −10.917 | −14.444 | −38.383 | 1.00 | 37.61 |
| ATOM | 1182 | C | ASN | A | 153 | −10.060 | −10.272 | −37.787 | 1.00 | 32.10 |
| ATOM | 1183 | O | ASN | A | 153 | −8.850 | −10.213 | −38.020 | 1.00 | 32.79 |
| ATOM | 1184 | N | VAL | A | 154 | −10.810 | −9.193 | −37.577 | 1.00 | 30.55 |
| ATOM | 1185 | CA | VAL | A | 154 | −10.251 | −7.854 | −37.750 | 1.00 | 28.93 |
| ATOM | 1186 | CB | VAL | A | 154 | −11.217 | −6.925 | −38.537 | 1.00 | 29.03 |
| ATOM | 1187 | CG1 | VAL | A | 154 | −10.565 | −5.577 | −38.827 | 1.00 | 29.23 |
| ATOM | 1188 | CG2 | VAL | A | 154 | −11.654 | −7.585 | −39.860 | 1.00 | 29.87 |
| ATOM | 1189 | C | VAL | A | 154 | −9.824 | −7.211 | −36.414 | 1.00 | 27.28 |
| ATOM | 1190 | O | VAL | A | 154 | −8.722 | −6.678 | −36.306 | 1.00 | 26.96 |
| ATOM | 1191 | N | ILE | A | 155 | −10.685 | −7.288 | −35.403 | 1.00 | 25.13 |
| ATOM | 1192 | CA | ILE | A | 155 | −10.525 | −6.459 | −34.197 | 1.00 | 23.05 |
| ATOM | 1193 | CB | ILE | A | 155 | −11.900 | −5.972 | −33.670 | 1.00 | 23.10 |
| ATOM | 1194 | CG1 | ILE | A | 155 | −12.596 | −5.128 | −34.741 | 1.00 | 22.49 |
| ATOM | 1195 | CD1 | ILE | A | 155 | −14.006 | −4.680 | −34.375 | 1.00 | 22.72 |
| ATOM | 1196 | CG2 | ILE | A | 155 | −11.731 | −5.144 | −32.399 | 1.00 | 23.05 |
| ATOM | 1197 | C | ILE | A | 155 | −9.710 | −7.136 | −33.092 | 1.00 | 22.44 |
| ATOM | 1198 | O | ILE | A | 155 | −8.789 | −6.537 | −32.533 | 1.00 | 21.14 |

TABLE 15-continued

| | | | | | | | | | |
|---|---|---|---|---|---|---|---|---|---|
| ATOM | 1199 | N | TRP | A | 156 | −10.006 | −8.409 | −32.822 | 1.00 | 21.48 |
| ATOM | 1200 | CA | TRP | A | 156 | −9.392 | −9.099 | −31.696 | 1.00 | 21.75 |
| ATOM | 1201 | CB | TRP | A | 156 | −9.958 | −10.520 | −31.511 | 1.00 | 22.50 |
| ATOM | 1202 | CG | TRP | A | 156 | −9.298 | −11.245 | −30.371 | 1.00 | 23.43 |
| ATOM | 1203 | CD1 | TRP | A | 156 | −8.420 | −12.298 | −30.461 | 1.00 | 24.92 |
| ATOM | 1204 | NE1 | TRP | A | 156 | −8.011 | −12.680 | −29.198 | 1.00 | 24.85 |
| ATOM | 1205 | CE2 | TRP | A | 156 | −8.600 | −11.863 | −28.269 | 1.00 | 26.38 |
| ATOM | 1206 | CD2 | TRP | A | 156 | −9.416 | −10.941 | −28.970 | 1.00 | 25.03 |
| ATOM | 1207 | CE3 | TRP | A | 156 | −10.139 | −9.983 | −28.236 | 1.00 | 25.01 |
| ATOM | 1208 | CZ3 | TRP | A | 156 | −10.024 | −9.982 | −26.844 | 1.00 | 24.30 |
| ATOM | 1209 | CH2 | TRP | A | 156 | −9.206 | −10.910 | −26.185 | 1.00 | 23.97 |
| ATOM | 1210 | CZ2 | TRP | A | 156 | −8.495 | −11.861 | −26.875 | 1.00 | 24.60 |
| ATOM | 1211 | C | TRP | A | 156 | −7.845 | −9.109 | −31.699 | 1.00 | 21.52 |
| ATOM | 1212 | O | TRP | A | 156 | −7.235 | −8.945 | −30.648 | 1.00 | 21.78 |
| ATOM | 1213 | N | PRO | A | 157 | −7.209 | −9.303 | −32.870 | 1.00 | 21.66 |
| ATOM | 1214 | CA | PRO | A | 157 | −5.726 | −9.258 | −32.878 | 1.00 | 21.40 |
| ATOM | 1215 | CB | PRO | A | 157 | −5.378 | −9.459 | −34.360 | 1.00 | 21.26 |
| ATOM | 1216 | CG | PRO | A | 157 | −6.583 | −10.172 | −34.955 | 1.00 | 22.82 |
| ATOM | 1217 | CD | PRO | A | 157 | −7.762 | −9.596 | −34.207 | 1.00 | 21.45 |
| ATOM | 1218 | C | PRO | A | 157 | −5.162 | −7.898 | −32.410 | 1.00 | 21.30 |
| ATOM | 1219 | O | PRO | A | 157 | −4.092 | −7.837 | −31.795 | 1.00 | 21.11 |
| ATOM | 1220 | N | ILE | A | 158 | −5.881 | −6.821 | −32.724 | 1.00 | 20.52 |
| ATOM | 1221 | CA | ILE | A | 158 | −5.457 | −5.467 | −32.318 | 1.00 | 19.93 |
| ATOM | 1222 | CB | ILE | A | 158 | −6.273 | −4.348 | −33.034 | 1.00 | 19.73 |
| ATOM | 1223 | CG1 | ILE | A | 158 | −6.261 | −4.527 | −34.559 | 1.00 | 21.25 |
| ATOM | 1224 | CD1 | ILE | A | 158 | −7.229 | −3.640 | −35.351 | 1.00 | 20.03 |
| ATOM | 1225 | CG2 | ILE | A | 158 | −5.686 | −2.971 | −32.670 | 1.00 | 20.16 |
| ATOM | 1226 | C | ILE | A | 158 | −5.632 | −5.366 | −30.816 | 1.00 | 19.58 |
| ATOM | 1227 | O | ILE | A | 158 | −4.701 | −5.023 | −30.081 | 1.00 | 19.04 |
| ATOM | 1228 | N | VAL | A | 159 | −6.840 | −5.704 | −30.359 | 1.00 | 19.39 |
| ATOM | 1229 | CA | VAL | A | 159 | −7.201 | −5.624 | −28.953 | 1.00 | 19.15 |
| ATOM | 1230 | CB | VAL | A | 159 | −8.687 | −6.026 | −28.744 | 1.00 | 19.06 |
| ATOM | 1231 | CG1 | VAL | A | 159 | −9.046 | −6.028 | −27.253 | 1.00 | 20.39 |
| ATOM | 1232 | CG2 | VAL | A | 159 | −9.604 | −5.090 | −29.511 | 1.00 | 20.08 |
| ATOM | 1233 | C | VAL | A | 159 | −6.280 | −6.501 | −28.105 | 1.00 | 19.39 |
| ATOM | 1234 | O | VAL | A | 159 | −5.794 | −6.089 | −27.036 | 1.00 | 18.63 |
| ATOM | 1235 | N | ARG | A | 160 | −6.022 | −7.721 | −28.585 | 1.00 | 18.93 |
| ATOM | 1236 | CA | ARG | A | 160 | −5.171 | −8.633 | −27.833 | 1.00 | 19.64 |
| ATOM | 1237 | CB | ARG | A | 160 | −5.078 | −10.005 | −28.513 | 1.00 | 19.17 |
| ATOM | 1238 | CG | ARG | A | 160 | −4.064 | −10.942 | −27.872 | 1.00 | 21.41 |
| ATOM | 1239 | CD | ARG | A | 160 | −3.978 | −12.278 | −28.637 | 1.00 | 23.47 |
| ATOM | 1240 | NE | ARG | A | 160 | −3.542 | −12.066 | −30.021 | 1.00 | 29.25 |
| ATOM | 1241 | CZ | ARG | A | 160 | −3.963 | −12.771 | −31.074 | 1.00 | 33.46 |
| ATOM | 1242 | NH1 | ARG | A | 160 | −4.839 | −13.764 | −30.929 | 1.00 | 36.48 |
| ATOM | 1243 | NH2 | ARG | A | 160 | −3.501 | −12.489 | −32.289 | 1.00 | 34.33 |
| ATOM | 1244 | C | ARG | A | 160 | −3.785 | −8.058 | −27.580 | 1.00 | 18.24 |
| ATOM | 1245 | O | ARG | A | 160 | −3.262 | −8.233 | −26.517 | 1.00 | 18.13 |
| ATOM | 1246 | N | ASN | A | 161 | −3.182 | −7.371 | −28.551 | 1.00 | 18.57 |
| ATOM | 1247 | CA | ASN | A | 161 | −1.875 | −6.717 | −28.289 | 1.00 | 18.40 |
| ATOM | 1248 | CB | ASN | A | 161 | −1.344 | −6.052 | −29.561 | 1.00 | 18.82 |
| ATOM | 1249 | CG | ASN | A | 161 | −0.772 | −7.055 | −30.549 | 1.00 | 20.68 |
| ATOM | 1250 | OD1 | ASN | A | 161 | −0.240 | −8.097 | −30.149 | 1.00 | 22.60 |
| ATOM | 1251 | ND2 | ASN | A | 161 | −0.883 | −6.751 | −31.837 | 1.00 | 19.81 |
| ATOM | 1252 | C | ASN | A | 161 | −1.946 | −5.656 | −27.182 | 1.00 | 18.36 |
| ATOM | 1253 | O | ASN | A | 161 | −1.078 | −5.581 | −26.313 | 1.00 | 17.42 |
| ATOM | 1254 | N | ASP | A | 162 | −2.982 | −4.816 | −27.233 | 1.00 | 17.86 |
| ATOM | 1255 | CA | ASP | A | 162 | −3.163 | −3.782 | −26.194 | 1.00 | 16.85 |
| ATOM | 1256 | CB | ASP | A | 162 | −4.293 | −2.821 | −26.586 | 1.00 | 16.71 |
| ATOM | 1257 | CG | ASP | A | 162 | −3.851 | −1.791 | −27.623 | 1.00 | 17.46 |
| ATOM | 1258 | OD1 | ASP | A | 162 | −2.648 | −1.440 | −27.681 | 1.00 | 16.98 |
| ATOM | 1259 | OD2 | ASP | A | 162 | −4.719 | −1.333 | −28.388 | 1.00 | 18.89 |
| ATOM | 1260 | C | ASP | A | 162 | −3.421 | −4.354 | −24.799 | 1.00 | 16.51 |
| ATOM | 1261 | O | ASP | A | 162 | −2.846 | −3.897 | −23.822 | 1.00 | 15.71 |
| ATOM | 1262 | N | LEU | A | 163 | −4.278 | −5.371 | −24.715 | 1.00 | 16.83 |
| ATOM | 1263 | CA | LEU | A | 163 | −4.532 | −6.071 | −23.459 | 1.00 | 16.55 |
| ATOM | 1264 | CB | LEU | A | 163 | −5.661 | −7.088 | −23.637 | 1.00 | 16.96 |
| ATOM | 1265 | CG | LEU | A | 163 | −7.030 | −6.506 | −23.975 | 1.00 | 19.29 |
| ATOM | 1266 | CD1 | LEU | A | 163 | −8.007 | −7.663 | −24.227 | 1.00 | 19.71 |
| ATOM | 1267 | CD2 | LEU | A | 163 | −7.484 | −5.631 | −22.818 | 1.00 | 21.19 |
| ATOM | 1268 | C | LEU | A | 163 | −3.279 | −6.750 | −22.883 | 1.00 | 16.19 |
| ATOM | 1269 | O | LEU | A | 163 | −3.035 | −6.690 | −21.688 | 1.00 | 15.47 |
| ATOM | 1270 | N | ASN | A | 164 | −2.495 | −7.401 | −23.748 | 1.00 | 16.85 |
| ATOM | 1271 | CA | ASN | A | 164 | −1.251 | −8.040 | −23.305 | 1.00 | 16.44 |
| ATOM | 1272 | CB | ASN | A | 164 | −0.602 | −8.836 | −24.450 | 1.00 | 17.06 |
| ATOM | 1273 | CG | ASN | A | 164 | −1.333 | −10.153 | −24.718 | 1.00 | 19.63 |
| ATOM | 1274 | OD1 | ASN | A | 164 | −2.274 | −10.513 | −23.982 | 1.00 | 20.97 |
| ATOM | 1275 | ND2 | ASN | A | 164 | −0.903 | −10.881 | −25.756 | 1.00 | 19.79 |
| ATOM | 1276 | C | ASN | A | 164 | −0.301 | −7.022 | −22.761 | 1.00 | 16.80 |
| ATOM | 1277 | O | ASN | A | 164 | 0.349 | −7.261 | −21.751 | 1.00 | 15.97 |
| ATOM | 1278 | N | TYR | A | 165 | −0.250 | −5.860 | −23.415 | 1.00 | 16.45 |

TABLE 15-continued

| | | | | | | | | | |
|---|---|---|---|---|---|---|---|---|---|
| ATOM | 1279 | CA | TYR | A | 165 | 0.573 | −4.744 | −22.930 | 1.00 | 16.15 |
| ATOM | 1280 | CB | TYR | A | 165 | 0.420 | −3.508 | −23.844 | 1.00 | 16.63 |
| ATOM | 1281 | CG | TYR | A | 165 | 1.286 | −2.356 | −23.391 | 1.00 | 16.41 |
| ATOM | 1282 | CD1 | TYR | A | 165 | 0.838 | −1.459 | −22.404 | 1.00 | 17.94 |
| ATOM | 1283 | CE1 | TYR | A | 165 | 1.651 | −0.402 | −21.958 | 1.00 | 17.84 |
| ATOM | 1284 | CZ | TYR | A | 165 | 2.916 | −0.223 | −22.517 | 1.00 | 18.36 |
| ATOM | 1285 | OH | TYR | A | 165 | 3.699 | 0.841 | −22.091 | 1.00 | 16.54 |
| ATOM | 1286 | CE2 | TYR | A | 165 | 3.383 | −1.105 | −23.502 | 1.00 | 16.73 |
| ATOM | 1287 | CD2 | TYR | A | 165 | 2.552 | −2.157 | −23.942 | 1.00 | 16.01 |
| ATOM | 1288 | C | TYR | A | 165 | 0.198 | −4.366 | −21.503 | 1.00 | 16.26 |
| ATOM | 1289 | O | TYR | A | 165 | 1.073 | −4.218 | −20.650 | 1.00 | 15.43 |
| ATOM | 1290 | N | VAL | A | 166 | −1.104 | −4.177 | −21.258 | 1.00 | 16.75 |
| ATOM | 1291 | CA | VAL | A | 166 | −1.600 | −3.786 | −19.933 | 1.00 | 17.39 |
| ATOM | 1292 | CB | VAL | A | 166 | −3.124 | −3.479 | −19.986 | 1.00 | 17.57 |
| ATOM | 1293 | CG1 | VAL | A | 166 | −3.712 | −3.197 | −18.582 | 1.00 | 19.25 |
| ATOM | 1294 | CG2 | VAL | A | 166 | −3.363 | −2.272 | −20.909 | 1.00 | 16.49 |
| ATOM | 1295 | C | VAL | A | 166 | −1.258 | −4.829 | −18.865 | 1.00 | 17.83 |
| ATOM | 1296 | O | VAL | A | 166 | −0.741 | −4.483 | −17.792 | 1.00 | 18.00 |
| ATOM | 1297 | N | ALA | A | 167 | −1.520 | −6.099 | −19.188 | 1.00 | 18.26 |
| ATOM | 1298 | CA | ALA | A | 167 | −1.233 | −7.218 | −18.285 | 1.00 | 18.92 |
| ATOM | 1299 | CB | ALA | A | 167 | −1.716 | −8.532 | −18.899 | 1.00 | 18.25 |
| ATOM | 1300 | C | ALA | A | 167 | 0.251 | −7.325 | −17.956 | 1.00 | 19.08 |
| ATOM | 1301 | O | ALA | A | 167 | 0.611 | −7.757 | −16.854 | 1.00 | 20.02 |
| ATOM | 1302 | N | GLN | A | 168 | 1.097 | −6.955 | −18.920 | 1.00 | 19.13 |
| ATOM | 1303 | CA | GLN | A | 168 | 2.558 | −7.022 | −18.749 | 1.00 | 19.21 |
| ATOM | 1304 | CB | GLN | A | 168 | 3.218 | −7.201 | −20.115 | 1.00 | 19.08 |
| ATOM | 1305 | CG | GLN | A | 168 | 4.739 | −7.373 | −20.053 | 1.00 | 20.55 |
| ATOM | 1306 | CD | GLN | A | 168 | 5.337 | −7.891 | −21.355 | 1.00 | 20.26 |
| ATOM | 1307 | OE1 | GLN | A | 168 | 4.634 | −8.378 | −22.238 | 1.00 | 22.69 |
| ATOM | 1308 | NE2 | GLN | A | 168 | 6.643 | −7.772 | −21.476 | 1.00 | 23.10 |
| ATOM | 1309 | C | GLN | A | 168 | 3.182 | −5.807 | −18.048 | 1.00 | 19.60 |
| ATOM | 1310 | O | GLN | A | 168 | 4.104 | −5.942 | −17.205 | 1.00 | 18.87 |
| ATOM | 1311 | N | TYR | A | 169 | 2.709 | −4.609 | −18.404 | 1.00 | 19.23 |
| ATOM | 1312 | CA | TYR | A | 169 | 3.399 | −3.377 | −18.011 | 1.00 | 19.45 |
| ATOM | 1313 | CB | TYR | A | 169 | 3.760 | −2.560 | −19.266 | 1.00 | 20.43 |
| ATOM | 1314 | CG | TYR | A | 169 | 4.773 | −3.203 | −20.203 | 1.00 | 21.30 |
| ATOM | 1315 | CD1 | TYR | A | 169 | 6.125 | −3.243 | −19.872 | 1.00 | 23.63 |
| ATOM | 1316 | CE1 | TYR | A | 169 | 7.065 | −3.822 | −20.723 | 1.00 | 24.59 |
| ATOM | 1317 | CZ | TYR | A | 169 | 6.651 | −4.359 | −21.926 | 1.00 | 23.11 |
| ATOM | 1318 | OH | TYR | A | 169 | 7.580 | −4.924 | −22.779 | 1.00 | 25.26 |
| ATOM | 1319 | CE2 | TYR | A | 169 | 5.309 | −4.330 | −22.288 | 1.00 | 22.49 |
| ATOM | 1320 | CD2 | TYR | A | 169 | 4.375 | −3.754 | −21.422 | 1.00 | 20.87 |
| ATOM | 1321 | C | TYR | A | 169 | 2.675 | −2.449 | −17.015 | 1.00 | 19.49 |
| ATOM | 1322 | O | TYR | A | 169 | 3.205 | −1.386 | −16.691 | 1.00 | 19.69 |
| ATOM | 1323 | N | TRP | A | 170 | 1.508 | −2.850 | −16.498 | 1.00 | 18.91 |
| ATOM | 1324 | CA | TRP | A | 170 | 0.735 | −1.981 | −15.588 | 1.00 | 19.29 |
| ATOM | 1325 | CB | TRP | A | 170 | −0.610 | −2.626 | −15.208 | 1.00 | 18.85 |
| ATOM | 1326 | CG | TRP | A | 170 | −0.489 | −3.743 | −14.215 | 1.00 | 21.04 |
| ATOM | 1327 | CD1 | TRP | A | 170 | −0.342 | −5.083 | −14.489 | 1.00 | 20.67 |
| ATOM | 1328 | NE1 | TRP | A | 170 | −0.259 | −5.793 | −13.317 | 1.00 | 22.09 |
| ATOM | 1329 | CE2 | TRP | A | 170 | −0.336 | −4.928 | −12.258 | 1.00 | 19.19 |
| ATOM | 1330 | CD2 | TRP | A | 170 | −0.481 | −3.621 | −12.789 | 1.00 | 20.35 |
| ATOM | 1331 | CE3 | TRP | A | 170 | −0.582 | −2.530 | −11.905 | 1.00 | 19.61 |
| ATOM | 1332 | CZ3 | TRP | A | 170 | −0.546 | −2.769 | −10.542 | 1.00 | 22.33 |
| ATOM | 1333 | CH2 | TRP | A | 170 | −0.404 | −4.090 | −10.038 | 1.00 | 21.08 |
| ATOM | 1334 | CZ2 | TRP | A | 170 | −0.297 | −5.179 | −10.884 | 1.00 | 20.76 |
| ATOM | 1335 | C | TRP | A | 170 | 1.526 | −1.592 | −14.336 | 1.00 | 19.20 |
| ATOM | 1336 | O | TRP | A | 170 | 1.395 | −0.475 | −13.808 | 1.00 | 19.24 |
| ATOM | 1337 | N | ASN | A | 171 | 2.371 | −2.504 | −13.858 | 1.00 | 19.13 |
| ATOM | 1338 | CA | ASN | A | 171 | 3.054 | −2.280 | −12.596 | 1.00 | 20.12 |
| ATOM | 1339 | CB | ASN | A | 171 | 3.178 | −3.603 | −11.820 | 1.00 | 20.59 |
| ATOM | 1340 | CG | ASN | A | 171 | 3.646 | −3.419 | −10.392 | 1.00 | 22.31 |
| ATOM | 1341 | OD1 | ASN | A | 171 | 4.531 | −4.155 | −9.938 | 1.00 | 23.68 |
| ATOM | 1342 | ND2 | ASN | A | 171 | 3.081 | −2.435 | −9.684 | 1.00 | 18.77 |
| ATOM | 1343 | C | ASN | A | 171 | 4.392 | −1.557 | −12.797 | 1.00 | 20.93 |
| ATOM | 1344 | O | ASN | A | 171 | 5.333 | −1.724 | −12.022 | 1.00 | 20.35 |
| ATOM | 1345 | N | GLN | A | 172 | 4.449 | −0.712 | −13.826 | 1.00 | 20.64 |
| ATOM | 1346 | CA | GLN | A | 172 | 5.644 | 0.061 | −14.156 | 1.00 | 22.31 |
| ATOM | 1347 | CB | GLN | A | 172 | 6.262 | −0.452 | −15.469 | 1.00 | 22.04 |
| ATOM | 1348 | CG | GLN | A | 172 | 6.784 | −1.895 | −15.312 | 1.00 | 25.79 |
| ATOM | 1349 | CD | GLN | A | 172 | 7.536 | −2.450 | −16.515 | 1.00 | 27.61 |
| ATOM | 1350 | OE1 | GLN | A | 172 | 8.276 | −1.735 | −17.214 | 1.00 | 35.65 |
| ATOM | 1351 | NE2 | GLN | A | 172 | 7.367 | −3.755 | −16.752 | 1.00 | 33.80 |
| ATOM | 1352 | C | GLN | A | 172 | 5.287 | 1.539 | −14.268 | 1.00 | 21.36 |
| ATOM | 1353 | O | GLN | A | 172 | 4.175 | 1.867 | −14.704 | 1.00 | 21.04 |
| ATOM | 1354 | N | THR | A | 173 | 6.209 | 2.417 | −13.871 | 1.00 | 19.73 |
| ATOM | 1355 | CA | THR | A | 173 | 5.948 | 3.871 | −13.928 | 1.00 | 20.07 |
| ATOM | 1356 | CB | THR | A | 173 | 7.001 | 4.703 | −13.168 | 1.00 | 19.48 |
| ATOM | 1357 | OG1 | THR | A | 173 | 8.300 | 4.427 | −13.707 | 1.00 | 21.56 |
| ATOM | 1358 | CG2 | THR | A | 173 | 6.988 | 4.375 | −11.690 | 1.00 | 20.86 |

TABLE 15-continued

| | | | | | | | | | |
|---|---|---|---|---|---|---|---|---|---|
| ATOM | 1359 | C | THR | A | 173 | 5.913 | 4.347 | −15.375 | 1.00 | 18.53 |
| ATOM | 1360 | O | THR | A | 173 | 6.395 | 3.665 | −16.292 | 1.00 | 18.48 |
| ATOM | 1361 | N | GLY | A | 174 | 5.345 | 5.528 | −15.582 | 1.00 | 18.38 |
| ATOM | 1362 | CA | GLY | A | 174 | 5.363 | 6.149 | −16.903 | 1.00 | 17.13 |
| ATOM | 1363 | C | GLY | A | 174 | 4.760 | 7.522 | −16.736 | 1.00 | 16.77 |
| ATOM | 1364 | O | GLY | A | 174 | 4.462 | 7.939 | −15.605 | 1.00 | 16.87 |
| ATOM | 1365 | N | PHE | A | 175 | 4.571 | 8.223 | −17.849 | 1.00 | 14.68 |
| ATOM | 1366 | CA | PHE | A | 175 | 4.004 | 9.577 | −17.776 | 1.00 | 14.68 |
| ATOM | 1367 | CB | PHE | A | 175 | 4.522 | 10.432 | −18.948 | 1.00 | 15.16 |
| ATOM | 1368 | CG | PHE | A | 175 | 5.943 | 10.847 | −18.756 | 1.00 | 15.28 |
| ATOM | 1369 | CD1 | PHE | A | 175 | 6.981 | 10.000 | −19.144 | 1.00 | 18.04 |
| ATOM | 1370 | CE1 | PHE | A | 175 | 8.313 | 10.359 | −18.915 | 1.00 | 19.53 |
| ATOM | 1371 | CZ | PHE | A | 175 | 8.609 | 11.582 | −18.278 | 1.00 | 19.12 |
| ATOM | 1372 | CE2 | PHE | A | 175 | 7.571 | 12.429 | −17.876 | 1.00 | 18.63 |
| ATOM | 1373 | CD2 | PHE | A | 175 | 6.247 | 12.054 | −18.113 | 1.00 | 17.67 |
| ATOM | 1374 | C | PHE | A | 175 | 2.483 | 9.584 | −17.655 | 1.00 | 14.11 |
| ATOM | 1375 | O | PHE | A | 175 | 1.799 | 8.683 | −18.175 | 1.00 | 14.32 |
| ATOM | 1376 | N | ASP | A | 176 | 1.972 | 10.591 | −16.938 | 1.00 | 14.79 |
| ATOM | 1377 | CA | ASP | A | 176 | 0.541 | 10.764 | −16.713 | 1.00 | 14.45 |
| ATOM | 1378 | CB | ASP | A | 176 | 0.297 | 11.661 | −15.506 | 1.00 | 13.51 |
| ATOM | 1379 | CG | ASP | A | 176 | 0.685 | 13.126 | −15.760 | 1.00 | 14.99 |
| ATOM | 1380 | OD1 | ASP | A | 176 | 1.774 | 13.399 | −16.329 | 1.00 | 14.32 |
| ATOM | 1381 | OD2 | ASP | A | 176 | −0.112 | 14.012 | −15.376 | 1.00 | 15.08 |
| ATOM | 1382 | C | ASP | A | 176 | −0.143 | 11.343 | −17.962 | 1.00 | 14.21 |
| ATOM | 1383 | O | ASP | A | 176 | 0.525 | 11.641 | −18.963 | 1.00 | 14.31 |
| ATOM | 1384 | N | LEU | A | 177 | −1.467 | 11.511 | −17.891 | 1.00 | 13.30 |
| ATOM | 1385 | CA | LEU | A | 177 | −2.235 | 11.981 | −19.048 | 1.00 | 13.44 |
| ATOM | 1386 | CB | LEU | A | 177 | −3.752 | 11.839 | −18.832 | 1.00 | 13.71 |
| ATOM | 1387 | CG | LEU | A | 177 | −4.483 | 12.896 | −18.012 | 1.00 | 14.11 |
| ATOM | 1388 | CD1 | LEU | A | 177 | −5.996 | 12.647 | −18.061 | 1.00 | 13.65 |
| ATOM | 1389 | CD2 | LEU | A | 177 | −4.007 | 12.922 | −16.553 | 1.00 | 14.74 |
| ATOM | 1390 | C | LEU | A | 177 | −1.884 | 13.424 | −19.452 | 1.00 | 13.51 |
| ATOM | 1391 | O | LEU | A | 177 | −2.131 | 13.813 | −20.600 | 1.00 | 13.74 |
| ATOM | 1392 | N | TRP | A | 178 | −1.319 | 14.206 | −18.521 | 1.00 | 12.53 |
| ATOM | 1393 | CA | TRP | A | 178 | −0.804 | 15.553 | −18.855 | 1.00 | 12.95 |
| ATOM | 1394 | CB | TRP | A | 178 | −0.890 | 16.507 | −17.660 | 1.00 | 12.67 |
| ATOM | 1395 | CG | TRP | A | 178 | −2.247 | 16.549 | −17.005 | 1.00 | 13.10 |
| ATOM | 1396 | CD1 | TRP | A | 178 | −2.504 | 16.508 | −15.662 | 1.00 | 13.10 |
| ATOM | 1397 | NE1 | TRP | A | 178 | −3.856 | 16.568 | −15.440 | 1.00 | 12.14 |
| ATOM | 1398 | CE2 | TRP | A | 178 | −4.501 | 16.646 | −16.646 | 1.00 | 13.00 |
| ATOM | 1399 | CD2 | TRP | A | 178 | −3.516 | 16.641 | −17.657 | 1.00 | 12.53 |
| ATOM | 1400 | CE3 | TRP | A | 178 | −3.919 | 16.715 | −19.002 | 1.00 | 12.38 |
| ATOM | 1401 | CZ3 | TRP | A | 178 | −5.309 | 16.813 | −19.290 | 1.00 | 13.91 |
| ATOM | 1402 | CH2 | TRP | A | 178 | −6.262 | 16.804 | −18.257 | 1.00 | 13.52 |
| ATOM | 1403 | CZ2 | TRP | A | 178 | −5.883 | 16.718 | −16.930 | 1.00 | 13.97 |
| ATOM | 1404 | C | TRP | A | 178 | 0.632 | 15.565 | −19.400 | 1.00 | 13.35 |
| ATOM | 1405 | O | TRP | A | 178 | 1.147 | 16.641 | −19.756 | 1.00 | 13.76 |
| ATOM | 1406 | N | GLU | A | 179 | 1.255 | 14.387 | −19.447 | 1.00 | 13.33 |
| ATOM | 1407 | CA | GLU | A | 179 | 2.532 | 14.151 | −20.117 | 1.00 | 13.32 |
| ATOM | 1408 | CB | GLU | A | 179 | 2.503 | 14.632 | −21.582 | 1.00 | 12.64 |
| ATOM | 1409 | CG | GLU | A | 179 | 1.165 | 14.344 | −22.280 | 1.00 | 13.03 |
| ATOM | 1410 | CD | GLU | A | 179 | 1.274 | 14.434 | −23.785 | 1.00 | 14.68 |
| ATOM | 1411 | OE1 | GLU | A | 179 | 0.895 | 15.478 | −24.340 | 1.00 | 15.98 |
| ATOM | 1412 | OE2 | GLU | A | 179 | 1.730 | 13.457 | −24.405 | 1.00 | 15.44 |
| ATOM | 1413 | C | GLU | A | 179 | 3.667 | 14.853 | −19.374 | 1.00 | 15.00 |
| ATOM | 1414 | O | GLU | A | 179 | 4.626 | 15.292 | −20.004 | 1.00 | 14.90 |
| ATOM | 1415 | N | GLU | A | 180 | 3.561 | 14.932 | −18.048 | 1.00 | 14.78 |
| ATOM | 1416 | CA | GLU | A | 180 | 4.476 | 15.745 | −17.246 | 1.00 | 16.76 |
| ATOM | 1417 | CB | GLU | A | 180 | 3.719 | 16.928 | −16.630 | 1.00 | 16.95 |
| ATOM | 1418 | CG | GLU | A | 180 | 3.282 | 17.972 | −17.654 | 1.00 | 18.69 |
| ATOM | 1419 | CD | GLU | A | 180 | 2.240 | 18.969 | −17.122 | 1.00 | 19.72 |
| ATOM | 1420 | OE1 | GLU | A | 180 | 1.587 | 18.715 | −16.077 | 1.00 | 19.00 |
| ATOM | 1421 | OE2 | GLU | A | 180 | 2.076 | 20.020 | −17.793 | 1.00 | 24.62 |
| ATOM | 1422 | C | GLU | A | 180 | 5.124 | 14.954 | −16.104 | 1.00 | 16.50 |
| ATOM | 1423 | O | GLU | A | 180 | 6.265 | 15.202 | −15.750 | 1.00 | 17.36 |
| ATOM | 1424 | N | VAL | A | 181 | 4.364 | 14.056 | −15.488 | 1.00 | 16.77 |
| ATOM | 1425 | CA | VAL | A | 181 | 4.775 | 13.426 | −14.218 | 1.00 | 16.87 |
| ATOM | 1426 | CB | VAL | A | 181 | 3.672 | 13.555 | −13.130 | 1.00 | 16.78 |
| ATOM | 1427 | CG1 | VAL | A | 181 | 4.030 | 12.732 | −11.893 | 1.00 | 18.56 |
| ATOM | 1428 | CG2 | VAL | A | 181 | 3.490 | 15.008 | −12.726 | 1.00 | 17.21 |
| ATOM | 1429 | C | VAL | A | 181 | 5.057 | 11.953 | −14.451 | 1.00 | 17.22 |
| ATOM | 1430 | O | VAL | A | 181 | 4.177 | 11.205 | −14.825 | 1.00 | 16.93 |
| ATOM | 1431 | N | ASN | A | 182 | 6.290 | 11.532 | −14.201 | 1.00 | 18.39 |
| ATOM | 1432 | CA | ASN | A | 182 | 6.674 | 10.123 | −14.394 | 1.00 | 18.57 |
| ATOM | 1433 | CB | ASN | A | 182 | 8.136 | 10.079 | −14.845 | 1.00 | 19.77 |
| ATOM | 1434 | CG | ASN | A | 182 | 8.665 | 8.669 | −15.056 | 1.00 | 23.96 |
| ATOM | 1435 | OD1 | ASN | A | 182 | 9.881 | 8.470 | −15.058 | 1.00 | 33.20 |
| ATOM | 1436 | ND2 | ASN | A | 182 | 7.794 | 7.706 | −15.258 | 1.00 | 23.63 |
| ATOM | 1437 | C | ASN | A | 182 | 6.440 | 9.375 | −13.073 | 1.00 | 18.31 |
| ATOM | 1438 | O | ASN | A | 182 | 7.132 | 9.621 | −12.087 | 1.00 | 18.80 |

TABLE 15-continued

| | | | | | | | | | |
|---|---|---|---|---|---|---|---|---|---|
| ATOM | 1439 | N | GLY | A | 183 | 5.436 | 8.508 | −13.034 | 1.00 | 16.83 |
| ATOM | 1440 | CA | GLY | A | 183 | 5.091 | 7.828 | −11.790 | 1.00 | 15.98 |
| ATOM | 1441 | C | GLY | A | 183 | 3.989 | 6.837 | −12.033 | 1.00 | 15.59 |
| ATOM | 1442 | O | GLY | A | 183 | 3.937 | 6.228 | −13.117 | 1.00 | 15.30 |
| ATOM | 1443 | N | SER | A | 184 | 3.119 | 6.670 | −11.035 | 1.00 | 14.95 |
| ATOM | 1444 | CA | SER | A | 184 | 1.927 | 5.823 | −11.151 | 1.00 | 15.45 |
| ATOM | 1445 | CB | SER | A | 184 | 1.844 | 4.792 | −10.017 | 1.00 | 15.76 |
| ATOM | 1446 | OG | SER | A | 184 | 2.998 | 3.935 | −10.027 | 1.00 | 17.33 |
| ATOM | 1447 | C | SER | A | 184 | 0.731 | 6.758 | −11.073 | 1.00 | 15.14 |
| ATOM | 1448 | O | SER | A | 184 | 0.646 | 7.546 | −10.148 | 1.00 | 15.83 |
| ATOM | 1449 | N | SER | A | 185 | −0.151 | 6.706 | −12.066 | 1.00 | 14.73 |
| ATOM | 1450 | CA | SER | A | 185 | −1.169 | 7.755 | −12.190 | 1.00 | 13.87 |
| ATOM | 1451 | CB | SER | A | 185 | −0.991 | 8.535 | −13.515 | 1.00 | 14.73 |
| ATOM | 1452 | OG | SER | A | 185 | −1.793 | 9.721 | −13.544 | 1.00 | 14.93 |
| ATOM | 1453 | C | SER | A | 185 | −2.551 | 7.140 | −12.127 | 1.00 | 13.49 |
| ATOM | 1454 | O | SER | A | 185 | −2.834 | 6.134 | −12.792 | 1.00 | 13.35 |
| ATOM | 1455 | N | PHE | A | 186 | −3.427 | 7.782 | −11.354 | 1.00 | 13.72 |
| ATOM | 1456 | CA | PHE | A | 186 | −4.764 | 7.275 | −11.092 | 1.00 | 13.43 |
| ATOM | 1457 | CB | PHE | A | 186 | −5.511 | 8.319 | −10.260 | 1.00 | 13.58 |
| ATOM | 1458 | CG | PHE | A | 186 | −6.807 | 7.839 | −9.662 | 1.00 | 13.52 |
| ATOM | 1459 | CD1 | PHE | A | 186 | −6.819 | 6.873 | −8.655 | 1.00 | 16.11 |
| ATOM | 1460 | CE1 | PHE | A | 186 | −8.004 | 6.489 | −8.036 | 1.00 | 17.80 |
| ATOM | 1461 | CZ | PHE | A | 186 | −9.214 | 7.062 | −8.442 | 1.00 | 16.18 |
| ATOM | 1462 | CE2 | PHE | A | 186 | −9.211 | 8.051 | −9.432 | 1.00 | 15.77 |
| ATOM | 1463 | CD2 | PHE | A | 186 | −8.003 | 8.435 | −10.030 | 1.00 | 14.62 |
| ATOM | 1464 | C | PHE | A | 186 | −5.552 | 6.946 | −12.372 | 1.00 | 13.57 |
| ATOM | 1465 | O | PHE | A | 186 | −6.053 | 5.839 | −12.524 | 1.00 | 13.36 |
| ATOM | 1466 | N | PHE | A | 187 | −5.693 | 7.927 | −13.267 | 1.00 | 12.53 |
| ATOM | 1467 | CA | PHE | A | 187 | −6.416 | 7.762 | −14.527 | 1.00 | 12.84 |
| ATOM | 1468 | CB | PHE | A | 187 | −6.284 | 9.056 | −15.356 | 1.00 | 11.69 |
| ATOM | 1469 | CG | PHE | A | 187 | −6.949 | 9.016 | −16.711 | 1.00 | 13.25 |
| ATOM | 1470 | CD1 | PHE | A | 187 | −8.284 | 9.338 | −16.855 | 1.00 | 12.86 |
| ATOM | 1471 | CE1 | PHE | A | 187 | −8.893 | 9.342 | −18.102 | 1.00 | 14.12 |
| ATOM | 1472 | CZ | PHE | A | 187 | −8.139 | 9.041 | −19.236 | 1.00 | 14.05 |
| ATOM | 1473 | CE2 | PHE | A | 187 | −6.806 | 8.721 | −19.111 | 1.00 | 14.30 |
| ATOM | 1474 | CD2 | PHE | A | 187 | −6.206 | 8.711 | −17.857 | 1.00 | 15.10 |
| ATOM | 1475 | C | PHE | A | 187 | −5.887 | 6.563 | −15.318 | 1.00 | 12.69 |
| ATOM | 1476 | O | PHE | A | 187 | −6.666 | 5.837 | −15.932 | 1.00 | 14.00 |
| ATOM | 1477 | N | THR | A | 188 | −4.571 | 6.357 | −15.294 | 1.00 | 12.97 |
| ATOM | 1478 | CA | THR | A | 188 | −3.938 | 5.302 | −16.084 | 1.00 | 13.65 |
| ATOM | 1479 | CB | THR | A | 188 | −2.411 | 5.541 | −16.104 | 1.00 | 13.69 |
| ATOM | 1480 | OG1 | THR | A | 188 | −2.158 | 6.789 | −16.753 | 1.00 | 15.37 |
| ATOM | 1481 | CG2 | THR | A | 188 | −1.648 | 4.432 | −16.833 | 1.00 | 13.24 |
| ATOM | 1482 | C | THR | A | 188 | −4.284 | 3.929 | −15.478 | 1.00 | 14.12 |
| ATOM | 1483 | O | THR | A | 188 | −4.766 | 3.039 | −16.173 | 1.00 | 14.40 |
| ATOM | 1484 | N | VAL | A | 189 | −4.066 | 3.798 | −14.173 | 1.00 | 13.34 |
| ATOM | 1485 | CA | VAL | A | 189 | −4.348 | 2.543 | −13.446 | 1.00 | 14.76 |
| ATOM | 1486 | CB | VAL | A | 189 | −3.893 | 2.612 | −11.958 | 1.00 | 14.90 |
| ATOM | 1487 | CG1 | VAL | A | 189 | −4.331 | 1.334 | −11.186 | 1.00 | 16.95 |
| ATOM | 1488 | CG2 | VAL | A | 189 | −2.374 | 2.799 | −11.865 | 1.00 | 15.31 |
| ATOM | 1489 | C | VAL | A | 189 | −5.836 | 2.167 | −13.560 | 1.00 | 14.48 |
| ATOM | 1490 | O | VAL | A | 189 | −6.159 | 1.024 | −13.853 | 1.00 | 14.65 |
| ATOM | 1491 | N | ALA | A | 190 | −6.732 | 3.146 | −13.372 | 1.00 | 13.77 |
| ATOM | 1492 | CA | ALA | A | 190 | −8.171 | 2.858 | −13.351 | 1.00 | 13.46 |
| ATOM | 1493 | CB | ALA | A | 190 | −8.996 | 4.128 | −12.922 | 1.00 | 12.74 |
| ATOM | 1494 | C | ALA | A | 190 | −8.614 | 2.388 | −14.706 | 1.00 | 13.27 |
| ATOM | 1495 | O | ALA | A | 190 | −9.432 | 1.479 | −14.815 | 1.00 | 13.24 |
| ATOM | 1496 | N | ASN | A | 191 | −8.093 | 3.017 | −15.760 | 1.00 | 12.50 |
| ATOM | 1497 | CA | ASN | A | 191 | −8.438 | 2.598 | −17.127 | 1.00 | 13.01 |
| ATOM | 1498 | CB | ASN | A | 191 | −8.122 | 3.707 | −18.137 | 1.00 | 12.65 |
| ATOM | 1499 | CG | ASN | A | 191 | −9.191 | 4.781 | −18.118 | 1.00 | 14.08 |
| ATOM | 1500 | OD1 | ASN | A | 191 | −10.319 | 4.541 | −18.554 | 1.00 | 16.39 |
| ATOM | 1501 | ND2 | ASN | A | 191 | −8.857 | 5.955 | −17.583 | 1.00 | 17.21 |
| ATOM | 1502 | C | ASN | A | 191 | −7.815 | 1.259 | −17.521 | 1.00 | 13.93 |
| ATOM | 1503 | O | ASN | A | 191 | −8.412 | 0.490 | −18.270 | 1.00 | 13.87 |
| ATOM | 1504 | N | GLN | A | 192 | −6.636 | 0.995 | −16.980 | 1.00 | 14.06 |
| ATOM | 1505 | CA | GLN | A | 192 | −5.988 | −0.311 | −17.139 | 1.00 | 14.96 |
| ATOM | 1506 | CB | GLN | A | 192 | −4.575 | −0.274 | −16.552 | 1.00 | 14.33 |
| ATOM | 1507 | CG | GLN | A | 192 | −3.555 | 0.435 | −17.500 | 1.00 | 13.64 |
| ATOM | 1508 | CD | GLN | A | 192 | −2.206 | 0.635 | −16.857 | 1.00 | 15.33 |
| ATOM | 1509 | OE1 | GLN | A | 192 | −2.074 | 0.568 | −15.646 | 1.00 | 15.48 |
| ATOM | 1510 | NE2 | GLN | A | 192 | −1.182 | 0.925 | −17.682 | 1.00 | 16.10 |
| ATOM | 1511 | C | GLN | A | 192 | −6.855 | −1.411 | −16.519 | 1.00 | 15.11 |
| ATOM | 1512 | O | GLN | A | 192 | −7.076 | −2.457 | −17.141 | 1.00 | 16.04 |
| ATOM | 1513 | N | HIS | A | 193 | −7.398 | −1.140 | −15.329 | 1.00 | 15.81 |
| ATOM | 1514 | CA | HIS | A | 193 | −8.314 | −2.069 | −14.668 | 1.00 | 16.01 |
| ATOM | 1515 | CB | HIS | A | 193 | −8.746 | −1.586 | −13.281 | 1.00 | 16.72 |
| ATOM | 1516 | CG | HIS | A | 193 | −9.806 | −2.454 | −12.669 | 1.00 | 17.39 |
| ATOM | 1517 | ND1 | HIS | A | 193 | −11.113 | −2.039 | −12.505 | 1.00 | 18.05 |
| ATOM | 1518 | CE1 | HIS | A | 193 | −11.821 | −3.028 | −11.983 | 1.00 | 18.70 |

TABLE 15-continued

| | | | | | | | | | |
|---|---|---|---|---|---|---|---|---|---|
| ATOM | 1519 | NE2 | HIS | A | 193 | −11.023 | −4.071 | −11.814 | 1.00 | 17.20 |
| ATOM | 1520 | CD2 | HIS | A | 193 | −9.758 | −3.739 | −12.242 | 1.00 | 18.04 |
| ATOM | 1521 | C | HIS | A | 193 | −9.536 | −2.343 | −15.521 | 1.00 | 15.85 |
| ATOM | 1522 | O | HIS | A | 193 | −9.898 | −3.501 | −15.732 | 1.00 | 15.70 |
| ATOM | 1523 | N | ARG | A | 194 | −10.185 | −1.285 | −15.995 | 1.00 | 15.27 |
| ATOM | 1524 | CA | ARG | A | 194 | −11.349 | −1.437 | −16.852 | 1.00 | 15.29 |
| ATOM | 1525 | CB | ARG | A | 194 | −11.922 | −0.073 | −17.234 | 1.00 | 14.30 |
| ATOM | 1526 | CG | ARG | A | 194 | −13.029 | −0.212 | −18.239 | 1.00 | 14.46 |
| ATOM | 1527 | CD | ARG | A | 194 | −13.614 | 1.102 | −18.723 | 1.00 | 15.43 |
| ATOM | 1528 | NE | ARG | A | 194 | −14.589 | 0.780 | −19.767 | 1.00 | 15.58 |
| ATOM | 1529 | CZ | ARG | A | 194 | −15.624 | 1.539 | −20.125 | 1.00 | 17.92 |
| ATOM | 1530 | NH1 | ARG | A | 194 | −15.815 | 2.744 | −19.576 | 1.00 | 14.60 |
| ATOM | 1531 | NH2 | ARG | A | 194 | −16.451 | 1.095 | −21.060 | 1.00 | 16.15 |
| ATOM | 1532 | C | ARG | A | 194 | −11.047 | −2.258 | −18.111 | 1.00 | 15.74 |
| ATOM | 1533 | O | ARG | A | 194 | −11.842 | −3.120 | −18.504 | 1.00 | 15.56 |
| ATOM | 1534 | N | ALA | A | 195 | −9.918 | −1.967 | −18.758 | 1.00 | 15.60 |
| ATOM | 1535 | CA | ALA | A | 195 | −9.562 | −2.638 | −20.004 | 1.00 | 15.90 |
| ATOM | 1536 | CB | ALA | A | 195 | −8.254 | −2.042 | −20.591 | 1.00 | 15.40 |
| ATOM | 1537 | C | ALA | A | 195 | −9.436 | −4.150 | −19.798 | 1.00 | 15.65 |
| ATOM | 1538 | O | ALA | A | 195 | −9.959 | −4.929 | −20.610 | 1.00 | 16.79 |
| ATOM | 1539 | N | LEU | A | 196 | −8.763 | −4.550 | −18.721 | 1.00 | 16.36 |
| ATOM | 1540 | CA | LEU | A | 196 | −8.552 | −5.976 | −18.423 | 1.00 | 17.02 |
| ATOM | 1541 | CB | LEU | A | 196 | −7.625 | −6.126 | −17.235 | 1.00 | 16.96 |
| ATOM | 1542 | CG | LEU | A | 196 | −6.167 | −5.744 | −17.532 | 1.00 | 16.96 |
| ATOM | 1543 | CD1 | LEU | A | 196 | −5.375 | −5.857 | −16.252 | 1.00 | 18.93 |
| ATOM | 1544 | CD2 | LEU | A | 196 | −5.590 | −6.636 | −18.630 | 1.00 | 20.38 |
| ATOM | 1545 | C | LEU | A | 196 | −9.877 | −6.685 | −18.167 | 1.00 | 17.92 |
| ATOM | 1546 | O | LEU | A | 196 | −10.102 | −7.795 | −18.643 | 1.00 | 18.98 |
| ATOM | 1547 | N | VAL | A | 197 | −10.779 | −6.014 | −17.454 | 1.00 | 18.51 |
| ATOM | 1548 | CA | VAL | A | 197 | −12.112 | −6.560 | −17.181 | 1.00 | 18.81 |
| ATOM | 1549 | CB | VAL | A | 197 | −12.875 | −5.702 | −16.130 | 1.00 | 18.26 |
| ATOM | 1550 | CG1 | VAL | A | 197 | −14.340 | −6.173 | −15.994 | 1.00 | 21.18 |
| ATOM | 1551 | CG2 | VAL | A | 197 | −12.149 | −5.784 | −14.778 | 1.00 | 19.79 |
| ATOM | 1552 | C | VAL | A | 197 | −12.924 | −6.779 | −18.462 | 1.00 | 19.05 |
| ATOM | 1553 | O | VAL | A | 197 | −13.456 | −7.884 | −18.693 | 1.00 | 18.62 |
| ATOM | 1554 | N | GLU | A | 198 | −13.010 | −5.752 | −19.308 | 1.00 | 18.43 |
| ATOM | 1555 | CA | GLU | A | 198 | −13.747 | −5.873 | −20.556 | 1.00 | 19.38 |
| ATOM | 1556 | CB | GLU | A | 198 | −13.849 | −4.517 | −21.241 | 1.00 | 19.38 |
| ATOM | 1557 | CG | GLU | A | 198 | −14.609 | −3.530 | −20.417 | 1.00 | 20.22 |
| ATOM | 1558 | CD | GLU | A | 198 | −15.334 | −2.537 | −21.298 | 1.00 | 22.66 |
| ATOM | 1559 | OE1 | GLU | A | 198 | −16.313 | −2.940 | −21.940 | 1.00 | 22.16 |
| ATOM | 1560 | OE2 | GLU | A | 198 | −14.924 | −1.369 | −21.342 | 1.00 | 22.92 |
| ATOM | 1561 | C | GLU | A | 198 | −13.094 | −6.861 | −21.509 | 1.00 | 19.78 |
| ATOM | 1562 | O | GLU | A | 198 | −13.780 | −7.506 | −22.303 | 1.00 | 20.29 |
| ATOM | 1563 | N | GLY | A | 199 | −11.770 | −6.944 | −21.435 | 1.00 | 19.78 |
| ATOM | 1564 | CA | GLY | A | 199 | −10.998 | −7.823 | −22.314 | 1.00 | 20.88 |
| ATOM | 1565 | C | GLY | A | 199 | −11.288 | −9.285 | −21.986 | 1.00 | 21.53 |
| ATOM | 1566 | O | GLY | A | 199 | −11.546 | −10.083 | −22.879 | 1.00 | 22.36 |
| ATOM | 1567 | N | ALA | A | 200 | −11.256 | −9.615 | −20.702 | 1.00 | 21.79 |
| ATOM | 1568 | CA | ALA | A | 200 | −11.605 | −10.956 | −20.234 | 1.00 | 22.44 |
| ATOM | 1569 | CB | ALA | A | 200 | −11.463 | −11.038 | −18.728 | 1.00 | 22.21 |
| ATOM | 1570 | C | ALA | A | 200 | −13.016 | −11.329 | −20.696 | 1.00 | 22.54 |
| ATOM | 1571 | O | ALA | A | 200 | −13.237 | −12.419 | −21.214 | 1.00 | 22.25 |
| ATOM | 1572 | N | THR | A | 201 | −13.965 | −10.403 | −20.573 | 1.00 | 22.56 |
| ATOM | 1573 | CA | THR | A | 201 | −15.345 | −10.671 | −20.989 | 1.00 | 22.77 |
| ATOM | 1574 | CB | THR | A | 201 | −16.302 | −9.527 | −20.551 | 1.00 | 22.83 |
| ATOM | 1575 | OG1 | THR | A | 201 | −16.219 | −9.387 | −19.134 | 1.00 | 24.92 |
| ATOM | 1576 | CG2 | THR | A | 201 | −17.756 | −9.819 | −20.929 | 1.00 | 23.76 |
| ATOM | 1577 | C | THR | A | 201 | −15.435 | −10.905 | −22.485 | 1.00 | 22.78 |
| ATOM | 1578 | O | THR | A | 201 | −16.099 | −11.851 | −22.925 | 1.00 | 22.95 |
| ATOM | 1579 | N | LEU | A | 202 | −14.760 | −10.069 | −23.275 | 1.00 | 21.78 |
| ATOM | 1580 | CA | LEU | A | 202 | −14.805 | −10.236 | −24.717 | 1.00 | 22.62 |
| ATOM | 1581 | CB | LEU | A | 202 | −14.149 | −9.055 | −25.434 | 1.00 | 22.14 |
| ATOM | 1582 | CG | LEU | A | 202 | −14.142 | −9.107 | −26.964 | 1.00 | 23.10 |
| ATOM | 1583 | CD1 | LEU | A | 202 | −15.544 | −9.198 | −27.564 | 1.00 | 24.20 |
| ATOM | 1584 | CD2 | LEU | A | 202 | −13.346 | −7.938 | −27.570 | 1.00 | 22.53 |
| ATOM | 1585 | C | LEU | A | 202 | −14.139 | −11.552 | −25.151 | 1.00 | 23.15 |
| ATOM | 1586 | O | LEU | A | 202 | −14.649 | −12.245 | −26.036 | 1.00 | 22.90 |
| ATOM | 1587 | N | ALA | A | 203 | −13.019 | −11.883 | −24.510 | 1.00 | 23.38 |
| ATOM | 1588 | CA | ALA | A | 203 | −12.300 | −13.129 | −24.787 | 1.00 | 24.07 |
| ATOM | 1589 | CB | ALA | A | 203 | −11.076 | −13.229 | −23.913 | 1.00 | 23.57 |
| ATOM | 1590 | C | ALA | A | 203 | −13.211 | −14.354 | −24.569 | 1.00 | 24.38 |
| ATOM | 1591 | O | ALA | A | 203 | −13.264 | −15.244 | −25.411 | 1.00 | 25.21 |
| ATOM | 1592 | N | ALA | A | 204 | −13.920 | −14.363 | −23.447 | 1.00 | 25.20 |
| ATOM | 1593 | CA | ALA | A | 204 | −14.849 | −15.442 | −23.093 | 1.00 | 26.63 |
| ATOM | 1594 | CB | ALA | A | 204 | −15.450 | −15.186 | −21.727 | 1.00 | 26.12 |
| ATOM | 1595 | C | ALA | A | 204 | −15.939 | −15.583 | −24.150 | 1.00 | 27.48 |
| ATOM | 1596 | O | ALA | A | 204 | −16.267 | −16.687 | −24.564 | 1.00 | 28.39 |
| ATOM | 1597 | N | THR | A | 205 | −16.494 | −14.461 | −24.593 | 1.00 | 27.71 |
| ATOM | 1598 | CA | THR | A | 205 | −17.497 | −14.470 | −25.652 | 1.00 | 28.39 |

TABLE 15-continued

| | | | | | | | | | |
|---|---|---|---|---|---|---|---|---|---|
| ATOM | 1599 | CB | THR | A | 205 | −18.088 | −13.051 | −25.855 | 1.00 | 28.42 |
| ATOM | 1600 | OG1 | THR | A | 205 | −18.669 | −12.631 | −24.622 | 1.00 | 29.32 |
| ATOM | 1601 | CG2 | THR | A | 205 | −19.150 | −13.051 | −26.932 | 1.00 | 27.32 |
| ATOM | 1602 | C | THR | A | 205 | −16.968 | −15.004 | −26.981 | 1.00 | 28.72 |
| ATOM | 1603 | O | THR | A | 205 | −17.697 | −15.690 | −27.719 | 1.00 | 29.06 |
| ATOM | 1604 | N | LEU | A | 206 | −15.712 | −14.698 | −27.288 | 1.00 | 28.58 |
| ATOM | 1605 | CA | LEU | A | 206 | −15.122 | −15.122 | −28.539 | 1.00 | 29.40 |
| ATOM | 1606 | CB | LEU | A | 206 | −14.034 | −14.144 | −29.001 | 1.00 | 29.40 |
| ATOM | 1607 | CG | LEU | A | 206 | −14.438 | −12.694 | −29.322 | 1.00 | 29.97 |
| ATOM | 1608 | CD1 | LEU | A | 206 | −13.212 | −11.899 | −29.755 | 1.00 | 30.30 |
| ATOM | 1609 | CD2 | LEU | A | 206 | −15.561 | −12.629 | −30.375 | 1.00 | 29.58 |
| ATOM | 1610 | C | LEU | A | 206 | −14.540 | −16.538 | −28.489 | 1.00 | 29.55 |
| ATOM | 1611 | O | LEU | A | 206 | −14.118 | −17.054 | −29.521 | 1.00 | 30.16 |
| ATOM | 1612 | N | GLY | A | 207 | −14.500 | −17.145 | −27.307 | 1.00 | 30.30 |
| ATOM | 1613 | CA | GLY | A | 207 | −13.786 | −18.419 | −27.122 | 1.00 | 30.91 |
| ATOM | 1614 | C | GLY | A | 207 | −12.294 | −18.274 | −27.375 | 1.00 | 31.55 |
| ATOM | 1615 | O | GLY | A | 207 | −11.654 | −19.173 | −27.935 | 1.00 | 31.31 |
| ATOM | 1616 | N | GLN | A | 208 | −11.746 | −17.115 | −26.989 | 1.00 | 31.08 |
| ATOM | 1617 | CA | GLN | A | 208 | −10.311 | −16.877 | −27.031 | 1.00 | 31.10 |
| ATOM | 1618 | CB | GLN | A | 208 | −9.999 | −15.540 | −27.703 | 1.00 | 31.08 |
| ATOM | 1619 | CG | GLN | A | 208 | −10.451 | −15.455 | −29.142 | 1.00 | 33.86 |
| ATOM | 1620 | CD | GLN | A | 208 | −9.469 | −16.059 | −30.126 | 1.00 | 38.19 |
| ATOM | 1621 | OE1 | GLN | A | 208 | −9.686 | −15.999 | −31.335 | 1.00 | 41.96 |
| ATOM | 1622 | NE2 | GLN | A | 208 | −8.386 | −16.633 | −29.626 | 1.00 | 38.96 |
| ATOM | 1623 | C | GLN | A | 208 | −9.765 | −16.909 | −25.611 | 1.00 | 30.45 |
| ATOM | 1624 | O | GLN | A | 208 | −10.516 | −17.048 | −24.658 | 1.00 | 30.63 |
| ATOM | 1625 | N | SER | A | 209 | −8.451 | −16.816 | −25.469 | 1.00 | 29.96 |
| ATOM | 1626 | CA | SER | A | 209 | −7.841 | −16.898 | −24.160 | 1.00 | 30.04 |
| ATOM | 1627 | CB | SER | A | 209 | −6.382 | −17.343 | −24.297 | 1.00 | 30.04 |
| ATOM | 1628 | OG | SER | A | 209 | −5.763 | −17.371 | −23.030 | 1.00 | 32.75 |
| ATOM | 1629 | C | SER | A | 209 | −7.948 | −15.564 | −23.409 | 1.00 | 29.53 |
| ATOM | 1630 | O | SER | A | 209 | −7.493 | −14.532 | −23.908 | 1.00 | 29.85 |
| ATOM | 1631 | N | GLY | A | 210 | −8.545 | −15.594 | −22.216 | 1.00 | 28.41 |
| ATOM | 1632 | CA | GLY | A | 210 | −8.745 | −14.388 | −21.401 | 1.00 | 27.16 |
| ATOM | 1633 | C | GLY | A | 210 | −8.344 | −14.480 | −19.938 | 1.00 | 26.83 |
| ATOM | 1634 | O | GLY | A | 210 | −8.425 | −13.498 | −19.203 | 1.00 | 26.61 |
| ATOM | 1635 | N | SER | A | 211 | −7.888 | −15.648 | −19.497 | 1.00 | 25.85 |
| ATOM | 1636 | CA | SER | A | 211 | −7.651 | −15.867 | −18.067 | 1.00 | 25.26 |
| ATOM | 1637 | CB | SER | A | 211 | −7.401 | −17.353 | −17.783 | 1.00 | 25.87 |
| ATOM | 1638 | OG | SER | A | 211 | −6.315 | −17.789 | −18.573 | 1.00 | 26.62 |
| ATOM | 1639 | C | SER | A | 211 | −6.509 | −15.026 | −17.498 | 1.00 | 24.55 |
| ATOM | 1640 | O | SER | A | 211 | −6.542 | −14.676 | −16.311 | 1.00 | 24.46 |
| ATOM | 1641 | N | ALA | A | 212 | −5.505 | −14.712 | −18.323 | 1.00 | 23.56 |
| ATOM | 1642 | CA | ALA | A | 212 | −4.423 | −13.816 | −17.906 | 1.00 | 23.42 |
| ATOM | 1643 | CB | ALA | A | 212 | −3.417 | −13.622 | −19.031 | 1.00 | 23.66 |
| ATOM | 1644 | C | ALA | A | 212 | −4.999 | −12.450 | −17.496 | 1.00 | 23.54 |
| ATOM | 1645 | O | ALA | A | 212 | −4.566 | −11.848 | −16.513 | 1.00 | 24.00 |
| ATOM | 1646 | N | TYR | A | 213 | −5.970 | −11.979 | −18.271 | 1.00 | 22.79 |
| ATOM | 1647 | CA | TYR | A | 213 | −6.594 | −10.676 | −18.017 | 1.00 | 22.18 |
| ATOM | 1648 | CB | TYR | A | 213 | −7.453 | −10.241 | −19.193 | 1.00 | 21.74 |
| ATOM | 1649 | CG | TYR | A | 213 | −6.761 | −10.345 | −20.515 | 1.00 | 20.05 |
| ATOM | 1650 | CD1 | TYR | A | 213 | −7.461 | −10.761 | −21.637 | 1.00 | 20.58 |
| ATOM | 1651 | CE1 | TYR | A | 213 | −6.854 | −10.854 | −22.868 | 1.00 | 21.95 |
| ATOM | 1652 | CZ | TYR | A | 213 | −5.503 | −10.545 | −22.988 | 1.00 | 20.62 |
| ATOM | 1653 | OH | TYR | A | 213 | −4.930 | −10.668 | −24.220 | 1.00 | 21.72 |
| ATOM | 1654 | CE2 | TYR | A | 213 | −4.758 | −10.149 | −21.888 | 1.00 | 19.76 |
| ATOM | 1655 | CD2 | TYR | A | 213 | −5.400 | −10.038 | −20.647 | 1.00 | 20.61 |
| ATOM | 1656 | C | TYR | A | 213 | −7.423 | −10.710 | −16.758 | 1.00 | 23.06 |
| ATOM | 1657 | O | TYR | A | 213 | −7.320 | −9.804 | −15.939 | 1.00 | 22.56 |
| ATOM | 1658 | N | SER | A | 214 | −8.226 | −11.767 | −16.578 | 1.00 | 23.15 |
| ATOM | 1659 | CA | SER | A | 214 | −9.064 | −11.832 | −15.392 | 1.00 | 23.90 |
| ATOM | 1660 | CB | SER | A | 214 | −10.244 | −12.798 | −15.580 | 1.00 | 24.54 |
| ATOM | 1661 | OG | SER | A | 214 | −9.776 | −14.085 | −15.939 | 1.00 | 27.95 |
| ATOM | 1662 | C | SER | A | 214 | −8.259 | −12.122 | −14.122 | 1.00 | 23.64 |
| ATOM | 1663 | O | SER | A | 214 | −8.676 | −11.762 | −13.026 | 1.00 | 23.43 |
| ATOM | 1664 | N | SER | A | 215 | −7.095 | −12.743 | −14.248 | 1.00 | 23.82 |
| ATOM | 1665 | CA | SER | A | 215 | −6.295 | −12.970 | −13.050 | 1.00 | 24.66 |
| ATOM | 1666 | CB | SER | A | 215 | −5.390 | −14.205 | −13.200 | 1.00 | 25.70 |
| ATOM | 1667 | OG | SER | A | 215 | −4.267 | −13.914 | −14.004 | 1.00 | 29.15 |
| ATOM | 1668 | C | SER | A | 215 | −5.491 | −11.739 | −12.610 | 1.00 | 23.98 |
| ATOM | 1669 | O | SER | A | 215 | −5.217 | −11.561 | −11.421 | 1.00 | 24.09 |
| ATOM | 1670 | N | VAL | A | 216 | −5.115 | −10.894 | −13.566 | 1.00 | 22.89 |
| ATOM | 1671 | CA | VAL | A | 216 | −4.347 | −9.679 | −13.272 | 1.00 | 22.50 |
| ATOM | 1672 | CB | VAL | A | 216 | −3.442 | −9.296 | −14.493 | 1.00 | 22.52 |
| ATOM | 1673 | CG1 | VAL | A | 216 | −2.855 | −7.888 | −14.369 | 1.00 | 24.11 |
| ATOM | 1674 | CG2 | VAL | A | 216 | −2.296 | −10.317 | −14.652 | 1.00 | 22.49 |
| ATOM | 1675 | C | VAL | A | 216 | −5.256 | −8.520 | −12.801 | 1.00 | 21.88 |
| ATOM | 1676 | O | VAL | A | 216 | −4.869 | −7.745 | −11.936 | 1.00 | 21.84 |
| ATOM | 1677 | N | ALA | A | 217 | −6.475 | −8.440 | −13.332 | 1.00 | 21.86 |
| ATOM | 1678 | CA | ALA | A | 217 | −7.374 | −7.303 | −13.050 | 1.00 | 21.59 |

TABLE 15-continued

| | | | | | | | | | |
|---|---|---|---|---|---|---|---|---|---|
| ATOM | 1679 | CB | ALA | A | 217 | −8.721 | −7.479 | −13.760 | 1.00 | 21.26 |
| ATOM | 1680 | C | ALA | A | 217 | −7.571 | −6.968 | −11.558 | 1.00 | 21.55 |
| ATOM | 1681 | O | ALA | A | 217 | −7.447 | −5.804 | −11.165 | 1.00 | 21.20 |
| ATOM | 1682 | N | PRO | A | 218 | −7.842 | −7.988 | −10.701 | 1.00 | 21.95 |
| ATOM | 1683 | CA | PRO | A | 218 | −8.030 | −7.700 | −9.282 | 1.00 | 21.59 |
| ATOM | 1684 | CB | PRO | A | 218 | −8.283 | −9.104 | −8.670 | 1.00 | 22.29 |
| ATOM | 1685 | CG | PRO | A | 218 | −8.789 | −9.905 | −9.789 | 1.00 | 22.61 |
| ATOM | 1686 | CD | PRO | A | 218 | −7.966 | −9.435 | −10.963 | 1.00 | 22.11 |
| ATOM | 1687 | C | PRO | A | 218 | −6.798 | −7.065 | −8.634 | 1.00 | 21.27 |
| ATOM | 1688 | O | PRO | A | 218 | −6.928 | −6.299 | −7.680 | 1.00 | 20.92 |
| ATOM | 1689 | N | GLN | A | 219 | −5.608 | −7.386 | −9.141 | 1.00 | 21.17 |
| ATOM | 1690 | CA | GLN | A | 219 | −4.378 | −6.786 | −8.609 | 1.00 | 21.51 |
| ATOM | 1691 | CB | GLN | A | 219 | −3.149 | −7.569 | −9.084 | 1.00 | 22.72 |
| ATOM | 1692 | CG | GLN | A | 219 | −3.113 | −8.985 | −8.516 | 1.00 | 24.90 |
| ATOM | 1693 | CD | GLN | A | 219 | −3.323 | −8.982 | −7.015 | 1.00 | 29.57 |
| ATOM | 1694 | OE1 | GLN | A | 219 | −2.715 | −8.188 | −6.288 | 1.00 | 31.58 |
| ATOM | 1695 | NE2 | GLN | A | 219 | −4.207 | −9.843 | −6.545 | 1.00 | 33.22 |
| ATOM | 1696 | C | GLN | A | 219 | −4.240 | −5.301 | −8.996 | 1.00 | 21.04 |
| ATOM | 1697 | O | GLN | A | 219 | −3.687 | −4.490 | −8.229 | 1.00 | 21.07 |
| ATOM | 1698 | N | VAL | A | 220 | −4.728 | −4.973 | −10.187 | 1.00 | 20.00 |
| ATOM | 1699 | CA | VAL | A | 220 | −4.746 | −3.577 | −10.630 | 1.00 | 19.34 |
| ATOM | 1700 | CB | VAL | A | 220 | −5.098 | −3.456 | −12.128 | 1.00 | 19.63 |
| ATOM | 1701 | CG1 | VAL | A | 220 | −4.991 | −2.000 | −12.581 | 1.00 | 19.15 |
| ATOM | 1702 | CG2 | VAL | A | 220 | −4.162 | −4.342 | −12.974 | 1.00 | 17.97 |
| ATOM | 1703 | C | VAL | A | 220 | −5.730 | −2.809 | −9.737 | 1.00 | 19.65 |
| ATOM | 1704 | O | VAL | A | 220 | −5.419 | −1.728 | −9.257 | 1.00 | 18.97 |
| ATOM | 1705 | N | LEU | A | 221 | −6.903 | −3.391 | −9.490 | 1.00 | 20.12 |
| ATOM | 1706 | CA | LEU | A | 221 | −7.895 | −2.776 | −8.620 | 1.00 | 20.83 |
| ATOM | 1707 | CB | LEU | A | 221 | −9.180 | −3.602 | −8.599 | 1.00 | 20.48 |
| ATOM | 1708 | CG | LEU | A | 221 | −10.336 | −2.991 | −7.790 | 1.00 | 22.48 |
| ATOM | 1709 | CD1 | LEU | A | 221 | −10.857 | −1.726 | −8.458 | 1.00 | 22.33 |
| ATOM | 1710 | CD2 | LEU | A | 221 | −11.430 | −4.011 | −7.637 | 1.00 | 22.51 |
| ATOM | 1711 | C | LEU | A | 221 | −7.360 | −2.591 | −7.192 | 1.00 | 21.44 |
| ATOM | 1712 | O | LEU | A | 221 | −7.617 | −1.578 | −6.539 | 1.00 | 20.45 |
| ATOM | 1713 | N | CYS | A | 222 | −6.600 | −3.572 | −6.718 | 1.00 | 22.60 |
| ATOM | 1714 | CA | CYS | A | 222 | −5.957 | −3.477 | −5.415 | 1.00 | 22.10 |
| ATOM | 1715 | CB | CYS | A | 222 | −5.159 | −4.749 | −5.125 | 1.00 | 23.41 |
| ATOM | 1716 | SG | CYS | A | 222 | −4.975 | −5.000 | −3.356 | 1.00 | 28.49 |
| ATOM | 1717 | C | CYS | A | 222 | −5.035 | −2.270 | −5.317 | 1.00 | 21.22 |
| ATOM | 1718 | O | CYS | A | 222 | −5.060 | −1.531 | −4.331 | 1.00 | 21.24 |
| ATOM | 1719 | N | PHE | A | 223 | −4.210 | −2.070 | −6.347 | 1.00 | 20.11 |
| ATOM | 1720 | CA | PHE | A | 223 | −3.287 | −0.955 | −6.368 | 1.00 | 19.03 |
| ATOM | 1721 | CB | PHE | A | 223 | −2.334 | −1.108 | −7.558 | 1.00 | 19.15 |
| ATOM | 1722 | CG | PHE | A | 223 | −1.297 | −0.011 | −7.669 | 1.00 | 19.23 |
| ATOM | 1723 | CD1 | PHE | A | 223 | −0.576 | 0.410 | −6.558 | 1.00 | 19.90 |
| ATOM | 1724 | CE1 | PHE | A | 223 | 0.380 | 1.417 | −6.661 | 1.00 | 20.91 |
| ATOM | 1725 | CZ | PHE | A | 223 | 0.645 | 2.017 | −7.902 | 1.00 | 21.07 |
| ATOM | 1726 | CE2 | PHE | A | 223 | −0.061 | 1.598 | −9.024 | 1.00 | 18.81 |
| ATOM | 1727 | CD2 | PHE | A | 223 | −1.022 | 0.581 | −8.909 | 1.00 | 18.23 |
| ATOM | 1728 | C | PHE | A | 223 | −4.032 | 0.397 | −6.423 | 1.00 | 18.38 |
| ATOM | 1729 | O | PHE | A | 223 | −3.597 | 1.376 | −5.818 | 1.00 | 18.27 |
| ATOM | 1730 | N | LEU | A | 224 | −5.148 | 0.428 | −7.142 | 1.00 | 18.45 |
| ATOM | 1731 | CA | LEU | A | 224 | −5.957 | 1.665 | −7.277 | 1.00 | 18.42 |
| ATOM | 1732 | CB | LEU | A | 224 | −7.208 | 1.403 | −8.127 | 1.00 | 17.70 |
| ATOM | 1733 | CG | LEU | A | 224 | −7.990 | 2.645 | −8.610 | 1.00 | 19.73 |
| ATOM | 1734 | CD1 | LEU | A | 224 | −7.133 | 3.427 | −9.584 | 1.00 | 20.37 |
| ATOM | 1735 | CD2 | LEU | A | 224 | −9.302 | 2.228 | −9.264 | 1.00 | 18.64 |
| ATOM | 1736 | C | LEU | A | 224 | −6.385 | 2.226 | −5.917 | 1.00 | 18.87 |
| ATOM | 1737 | O | LEU | A | 224 | −6.553 | 3.438 | −5.757 | 1.00 | 18.45 |
| ATOM | 1738 | N | GLN | A | 225 | −6.578 | 1.336 | −4.944 | 1.00 | 19.17 |
| ATOM | 1739 | CA | GLN | A | 225 | −6.984 | 1.743 | −3.585 | 1.00 | 20.00 |
| ATOM | 1740 | CB | GLN | A | 225 | −7.340 | 0.511 | −2.725 | 1.00 | 20.26 |
| ATOM | 1741 | CG | GLN | A | 225 | −8.295 | −0.463 | −3.409 | 1.00 | 21.22 |
| ATOM | 1742 | CD | GLN | A | 225 | −9.519 | 0.225 | −3.993 | 1.00 | 22.53 |
| ATOM | 1743 | OE1 | GLN | A | 225 | −10.280 | 0.870 | −3.262 | 1.00 | 23.09 |
| ATOM | 1744 | NE2 | GLN | A | 225 | −9.718 | 0.092 | −5.302 | 1.00 | 19.33 |
| ATOM | 1745 | C | GLN | A | 225 | −5.944 | 2.599 | −2.871 | 1.00 | 20.19 |
| ATOM | 1746 | O | GLN | A | 225 | −6.299 | 3.399 | −2.009 | 1.00 | 20.64 |
| ATOM | 1747 | N | ARG | A | 226 | −4.678 | 2.450 | −3.253 | 1.00 | 20.51 |
| ATOM | 1748 | CA | ARG | A | 226 | −3.564 | 3.144 | −2.608 | 1.00 | 21.40 |
| ATOM | 1749 | CB | ARG | A | 226 | −2.219 | 2.505 | −2.990 | 1.00 | 22.72 |
| ATOM | 1750 | CG | ARG | A | 226 | −2.081 | 1.010 | −2.683 | 1.00 | 26.14 |
| ATOM | 1751 | CD | ARG | A | 226 | −1.806 | 0.741 | −1.204 | 1.00 | 32.16 |
| ATOM | 1752 | NE | ARG | A | 226 | −3.035 | 0.843 | −0.432 | 1.00 | 37.77 |
| ATOM | 1753 | CZ | ARG | A | 226 | −3.997 | −0.079 | −0.413 | 1.00 | 41.09 |
| ATOM | 1754 | NH1 | ARG | A | 226 | −5.093 | 0.120 | 0.322 | 1.00 | 42.17 |
| ATOM | 1755 | NH2 | ARG | A | 226 | −3.874 | −1.196 | −1.127 | 1.00 | 42.78 |
| ATOM | 1756 | C | ARG | A | 226 | −3.499 | 4.645 | −2.915 | 1.00 | 21.23 |
| ATOM | 1757 | O | ARG | A | 226 | −2.723 | 5.358 | −2.288 | 1.00 | 20.95 |
| ATOM | 1758 | N | PHE | A | 227 | −4.298 | 5.123 | −3.869 | 1.00 | 20.28 |

TABLE 15-continued

| | | | | | | | | | |
|---|---|---|---|---|---|---|---|---|---|
| ATOM | 1759 | CA | PHE | A | 227 | −4.280 | 6.545 | −4.250 | 1.00 | 19.67 |
| ATOM | 1760 | CB | PHE | A | 227 | −4.777 | 6.704 | −5.693 | 1.00 | 19.40 |
| ATOM | 1761 | CG | PHE | A | 227 | −3.814 | 6.195 | −6.744 | 1.00 | 18.28 |
| ATOM | 1762 | CD1 | PHE | A | 227 | −3.733 | 4.831 | −7.040 | 1.00 | 18.14 |
| ATOM | 1763 | CE1 | PHE | A | 227 | −2.855 | 4.355 | −8.046 | 1.00 | 18.24 |
| ATOM | 1764 | CZ | PHE | A | 227 | −2.034 | 5.264 | −8.748 | 1.00 | 16.75 |
| ATOM | 1765 | CE2 | PHE | A | 227 | −2.113 | 6.641 | −8.456 | 1.00 | 18.79 |
| ATOM | 1766 | CD2 | PHE | A | 227 | −3.005 | 7.091 | −7.452 | 1.00 | 17.51 |
| ATOM | 1767 | C | PHE | A | 227 | −5.126 | 7.435 | −3.343 | 1.00 | 20.55 |
| ATOM | 1768 | O | PHE | A | 227 | −4.967 | 8.659 | −3.334 | 1.00 | 20.38 |
| ATOM | 1769 | N | TRP | A | 228 | −6.032 | 6.820 | −2.583 | 1.00 | 20.72 |
| ATOM | 1770 | CA | TRP | A | 228 | −6.924 | 7.545 | −1.671 | 1.00 | 20.71 |
| ATOM | 1771 | CB | TRP | A | 228 | −8.036 | 6.596 | −1.211 | 1.00 | 20.41 |
| ATOM | 1772 | CG | TRP | A | 228 | −9.030 | 7.228 | −0.283 | 1.00 | 20.59 |
| ATOM | 1773 | CD1 | TRP | A | 228 | −9.243 | 6.915 | 1.040 | 1.00 | 21.81 |
| ATOM | 1774 | NE1 | TRP | A | 228 | −10.255 | 7.722 | 1.557 | 1.00 | 22.69 |
| ATOM | 1775 | CE2 | TRP | A | 228 | −10.712 | 8.553 | 0.565 | 1.00 | 20.71 |
| ATOM | 1776 | CD2 | TRP | A | 228 | −9.958 | 8.280 | −0.607 | 1.00 | 18.88 |
| ATOM | 1777 | CE3 | TRP | A | 228 | −10.225 | 9.014 | −1.772 | 1.00 | 18.79 |
| ATOM | 1778 | CZ3 | TRP | A | 228 | −11.209 | 9.986 | −1.734 | 1.00 | 20.13 |
| ATOM | 1779 | CH2 | TRP | A | 228 | −11.937 | 10.242 | −0.552 | 1.00 | 21.18 |
| ATOM | 1780 | CZ2 | TRP | A | 228 | −11.710 | 9.537 | 0.601 | 1.00 | 21.65 |
| ATOM | 1781 | C | TRP | A | 228 | −6.193 | 8.120 | −0.463 | 1.00 | 21.38 |
| ATOM | 1782 | O | TRP | A | 228 | −5.479 | 7.394 | 0.236 | 1.00 | 21.50 |
| ATOM | 1783 | N | VAL | A | 229 | −6.379 | 9.416 | −0.209 | 1.00 | 21.95 |
| ATOM | 1784 | CA | VAL | A | 229 | −5.844 | 10.065 | 0.983 | 1.00 | 22.99 |
| ATOM | 1785 | CB | VAL | A | 229 | −5.205 | 11.436 | 0.654 | 1.00 | 22.81 |
| ATOM | 1786 | CG1 | VAL | A | 229 | −4.490 | 12.026 | 1.871 | 1.00 | 23.48 |
| ATOM | 1787 | CG2 | VAL | A | 229 | −4.226 | 11.292 | −0.493 | 1.00 | 23.28 |
| ATOM | 1788 | C | VAL | A | 229 | −6.984 | 10.206 | 2.000 | 1.00 | 24.08 |
| ATOM | 1789 | O | VAL | A | 229 | −7.803 | 11.119 | 1.899 | 1.00 | 23.70 |
| ATOM | 1790 | N | SER | A | 230 | −7.044 | 9.298 | 2.974 | 1.00 | 25.37 |
| ATOM | 1791 | CA | SER | A | 230 | −8.193 | 9.290 | 3.905 | 1.00 | 27.59 |
| ATOM | 1792 | CB | SER | A | 230 | −8.254 | 8.000 | 4.728 | 1.00 | 27.67 |
| ATOM | 1793 | OG | SER | A | 230 | −7.029 | 7.805 | 5.402 | 1.00 | 31.30 |
| ATOM | 1794 | C | SER | A | 230 | −8.241 | 10.513 | 4.820 | 1.00 | 27.93 |
| ATOM | 1795 | O | SER | A | 230 | −9.321 | 10.983 | 5.174 | 1.00 | 28.91 |
| ATOM | 1796 | N | SER | A | 231 | −7.088 | 11.059 | 5.165 | 1.00 | 28.76 |
| ATOM | 1797 | CA | SER | A | 231 | −7.059 | 12.237 | 6.030 | 1.00 | 29.72 |
| ATOM | 1798 | CB | SER | A | 231 | −5.671 | 12.461 | 6.639 | 1.00 | 30.39 |
| ATOM | 1799 | OG | SER | A | 231 | −4.703 | 12.713 | 5.635 | 1.00 | 34.43 |
| ATOM | 1800 | C | SER | A | 231 | −7.566 | 13.491 | 5.323 | 1.00 | 29.39 |
| ATOM | 1801 | O | SER | A | 231 | −8.154 | 14.364 | 5.966 | 1.00 | 30.97 |
| ATOM | 1802 | N | GLY | A | 232 | −7.373 | 13.579 | 4.005 | 1.00 | 27.59 |
| ATOM | 1803 | CA | GLY | A | 232 | −7.867 | 14.728 | 3.247 | 1.00 | 25.22 |
| ATOM | 1804 | C | GLY | A | 232 | −9.181 | 14.518 | 2.493 | 1.00 | 23.25 |
| ATOM | 1805 | O | GLY | A | 232 | −9.810 | 15.487 | 2.077 | 1.00 | 23.19 |
| ATOM | 1806 | N | GLY | A | 233 | −9.589 | 13.265 | 2.320 | 1.00 | 20.97 |
| ATOM | 1807 | CA | GLY | A | 233 | −10.809 | 12.937 | 1.578 | 1.00 | 19.35 |
| ATOM | 1808 | C | GLY | A | 233 | −10.673 | 13.226 | 0.094 | 1.00 | 18.83 |
| ATOM | 1809 | O | GLY | A | 233 | −11.636 | 13.655 | −0.561 | 1.00 | 19.20 |
| ATOM | 1810 | N | TYR | A | 234 | −9.487 | 12.977 | −0.463 | 1.00 | 17.56 |
| ATOM | 1811 | CA | TYR | A | 234 | −9.309 | 13.155 | −1.915 | 1.00 | 17.17 |
| ATOM | 1812 | CB | TYR | A | 234 | −8.851 | 14.584 | −2.232 | 1.00 | 18.33 |
| ATOM | 1813 | CG | TYR | A | 234 | −7.441 | 14.876 | −1.758 | 1.00 | 20.39 |
| ATOM | 1814 | CD1 | TYR | A | 234 | −7.203 | 15.340 | −0.454 | 1.00 | 20.72 |
| ATOM | 1815 | CE1 | TYR | A | 234 | −5.905 | 15.594 | −0.018 | 1.00 | 24.11 |
| ATOM | 1816 | CZ | TYR | A | 234 | −4.840 | 15.399 | −0.897 | 1.00 | 23.78 |
| ATOM | 1817 | OH | TYR | A | 234 | −3.556 | 15.663 | −0.483 | 1.00 | 26.50 |
| ATOM | 1818 | CE2 | TYR | A | 234 | −5.055 | 14.956 | −2.187 | 1.00 | 24.07 |
| ATOM | 1819 | CD2 | TYR | A | 234 | −6.353 | 14.699 | −2.611 | 1.00 | 20.58 |
| ATOM | 1820 | C | TYR | A | 234 | −8.318 | 12.141 | −2.482 | 1.00 | 16.60 |
| ATOM | 1821 | O | TYR | A | 234 | −7.615 | 11.465 | −1.735 | 1.00 | 16.29 |
| ATOM | 1822 | N | VAL | A | 235 | −8.260 | 12.059 | −3.805 | 1.00 | 15.36 |
| ATOM | 1823 | CA | VAL | A | 235 | −7.325 | 11.164 | −4.472 | 1.00 | 15.62 |
| ATOM | 1824 | CB | VAL | A | 235 | −7.948 | 10.638 | −5.798 | 1.00 | 15.96 |
| ATOM | 1825 | CG1 | VAL | A | 235 | −6.889 | 9.893 | −6.645 | 1.00 | 17.31 |
| ATOM | 1826 | CG2 | VAL | A | 235 | −9.134 | 9.723 | −5.506 | 1.00 | 15.87 |
| ATOM | 1827 | C | VAL | A | 235 | −6.011 | 11.904 | −4.742 | 1.00 | 15.54 |
| ATOM | 1828 | O | VAL | A | 235 | −6.006 | 12.998 | −5.320 | 1.00 | 15.39 |
| ATOM | 1829 | N | ASP | A | 236 | −4.886 | 11.316 | −4.325 | 1.00 | 15.24 |
| ATOM | 1830 | CA | ASP | A | 236 | −3.580 | 11.837 | −4.705 | 1.00 | 15.22 |
| ATOM | 1831 | CB | ASP | A | 236 | −2.533 | 11.431 | −3.652 | 1.00 | 16.45 |
| ATOM | 1832 | CG | ASP | A | 236 | −1.145 | 11.922 | −3.970 | 1.00 | 18.62 |
| ATOM | 1833 | OD1 | ASP | A | 236 | −0.937 | 12.617 | −4.992 | 1.00 | 17.17 |
| ATOM | 1834 | OD2 | ASP | A | 236 | −0.223 | 11.568 | −3.182 | 1.00 | 22.79 |
| ATOM | 1835 | C | ASP | A | 236 | −3.303 | 11.256 | −6.098 | 1.00 | 15.06 |
| ATOM | 1836 | O | ASP | A | 236 | −3.088 | 10.040 | −6.261 | 1.00 | 15.39 |
| ATOM | 1837 | N | SER | A | 237 | −3.384 | 12.104 | −7.125 | 1.00 | 14.24 |
| ATOM | 1838 | CA | SER | A | 237 | −3.518 | 11.587 | −8.503 | 1.00 | 14.09 |

TABLE 15-continued

| ATOM | 1839 | CB | SER | A | 237 | −4.000 | 12.697 | −9.446 | 1.00 | 13.76 |
|---|---|---|---|---|---|---|---|---|---|---|
| ATOM | 1840 | OG | SER | A | 237 | −5.312 | 13.094 | −9.070 | 1.00 | 14.52 |
| ATOM | 1841 | C | SER | A | 237 | −2.277 | 10.883 | −9.053 | 1.00 | 14.22 |
| ATOM | 1842 | O | SER | A | 237 | −2.376 | 10.067 | −9.965 | 1.00 | 13.80 |
| ATOM | 1843 | N | ASN | A | 238 | −1.099 | 11.219 | −8.521 | 1.00 | 14.70 |
| ATOM | 1844 | CA | ASN | A | 238 | 0.116 | 10.547 | −8.952 | 1.00 | 15.28 |
| ATOM | 1845 | CB | ASN | A | 238 | 0.968 | 11.439 | −9.856 | 1.00 | 14.84 |
| ATOM | 1846 | CG | ASN | A | 238 | 0.277 | 11.742 | −11.176 | 1.00 | 17.08 |
| ATOM | 1847 | OD1 | ASN | A | 238 | 0.244 | 10.901 | −12.072 | 1.00 | 16.61 |
| ATOM | 1848 | ND2 | ASN | A | 238 | −0.308 | 12.932 | −11.278 | 1.00 | 16.63 |
| ATOM | 1849 | C | ASN | A | 238 | 0.912 | 10.150 | −7.736 | 1.00 | 16.07 |
| ATOM | 1850 | O | ASN | A | 238 | 1.169 | 10.988 | −6.890 | 1.00 | 15.88 |
| ATOM | 1851 | N | ILE | A | 239 | 1.280 | 8.875 | −7.659 | 1.00 | 16.09 |
| ATOM | 1852 | CA | ILE | A | 239 | 2.125 | 8.410 | −6.567 | 1.00 | 18.07 |
| ATOM | 1853 | CB | ILE | A | 239 | 1.340 | 7.452 | −5.600 | 1.00 | 17.66 |
| ATOM | 1854 | CG1 | ILE | A | 239 | 0.893 | 6.180 | −6.336 | 1.00 | 18.85 |
| ATOM | 1855 | CD1 | ILE | A | 239 | 0.184 | 5.109 | −5.437 | 1.00 | 19.02 |
| ATOM | 1856 | CG2 | ILE | A | 239 | 0.116 | 8.194 | −4.974 | 1.00 | 16.96 |
| ATOM | 1857 | C | ILE | A | 239 | 3.381 | 7.760 | −7.169 | 1.00 | 19.32 |
| ATOM | 1858 | O | ILE | A | 239 | 3.571 | 7.797 | −8.392 | 1.00 | 19.19 |
| ATOM | 1859 | N | ASN | A | 240 | 4.242 | 7.170 | −6.329 | 1.00 | 20.56 |
| ATOM | 1860 | CA | ASN | A | 240 | 5.517 | 6.617 | −6.823 | 1.00 | 22.24 |
| ATOM | 1861 | CB | ASN | A | 240 | 5.275 | 5.385 | −7.717 | 1.00 | 21.93 |
| ATOM | 1862 | CG | ASN | A | 240 | 4.874 | 4.153 | −6.926 | 1.00 | 24.19 |
| ATOM | 1863 | OD1 | ASN | A | 240 | 5.269 | 3.995 | −5.772 | 1.00 | 25.98 |
| ATOM | 1864 | ND2 | ASN | A | 240 | 4.083 | 3.278 | −7.538 | 1.00 | 22.26 |
| ATOM | 1865 | C | ASN | A | 240 | 6.334 | 7.677 | −7.571 | 1.00 | 23.27 |
| ATOM | 1866 | O | ASN | A | 240 | 7.000 | 7.381 | −8.562 | 1.00 | 23.15 |
| ATOM | 1867 | N | THR | A | 241 | 6.261 | 8.919 | −7.096 | 1.00 | 25.02 |
| ATOM | 1868 | CA | THR | A | 241 | 6.939 | 10.038 | −7.729 | 1.00 | 28.12 |
| ATOM | 1869 | CB | THR | A | 241 | 6.044 | 10.720 | −8.817 | 1.00 | 28.09 |
| ATOM | 1870 | OG1 | THR | A | 241 | 6.741 | 11.836 | −9.369 | 1.00 | 28.75 |
| ATOM | 1871 | CG2 | THR | A | 241 | 4.727 | 11.208 | −8.231 | 1.00 | 28.30 |
| ATOM | 1872 | C | THR | A | 241 | 7.302 | 11.065 | −6.674 | 1.00 | 29.96 |
| ATOM | 1873 | O | THR | A | 241 | 6.749 | 11.037 | −5.589 | 1.00 | 30.58 |
| ATOM | 1874 | N | ASN | A | 242 | 8.209 | 11.984 | −6.991 | 1.00 | 33.17 |
| ATOM | 1875 | CA | ASN | A | 242 | 8.585 | 13.019 | −6.024 | 1.00 | 36.07 |
| ATOM | 1876 | CB | ASN | A | 242 | 10.059 | 12.880 | −5.616 | 1.00 | 37.13 |
| ATOM | 1877 | CG | ASN | A | 242 | 10.324 | 11.631 | −4.771 | 1.00 | 40.96 |
| ATOM | 1878 | OD1 | ASN | A | 242 | 9.509 | 11.235 | −3.921 | 1.00 | 45.33 |
| ATOM | 1879 | ND2 | ASN | A | 242 | 11.477 | 11.007 | −4.998 | 1.00 | 44.43 |
| ATOM | 1880 | C | ASN | A | 242 | 8.321 | 14.427 | −6.528 | 1.00 | 37.00 |
| ATOM | 1881 | O | ASN | A | 242 | 9.091 | 15.346 | −6.245 | 1.00 | 37.94 |
| ATOM | 1882 | N | GLU | A | 243 | 7.210 | 14.602 | −7.233 | 1.00 | 37.54 |
| ATOM | 1883 | CA | GLU | A | 243 | 6.895 | 15.869 | −7.907 | 1.00 | 38.05 |
| ATOM | 1884 | CB | GLU | A | 243 | 5.775 | 15.638 | −8.925 | 1.00 | 38.77 |
| ATOM | 1885 | CG | GLU | A | 243 | 5.650 | 16.732 | −9.977 | 1.00 | 42.65 |
| ATOM | 1886 | CD | GLU | A | 243 | 6.959 | 16.985 | −10.709 | 1.00 | 47.49 |
| ATOM | 1887 | OE1 | GLU | A | 243 | 7.424 | 16.084 | −11.453 | 1.00 | 49.14 |
| ATOM | 1888 | OE2 | GLU | A | 243 | 7.520 | 18.090 | −10.532 | 1.00 | 50.15 |
| ATOM | 1889 | C | GLU | A | 243 | 6.559 | 17.088 | −7.015 | 1.00 | 37.15 |
| ATOM | 1890 | O | GLU | A | 243 | 6.645 | 18.240 | −7.469 | 1.00 | 38.39 |
| ATOM | 1891 | N | GLY | A | 244 | 6.174 | 16.873 | −5.766 | 1.00 | 35.69 |
| ATOM | 1892 | CA | GLY | A | 244 | 5.858 | 18.019 | −4.911 | 1.00 | 33.51 |
| ATOM | 1893 | C | GLY | A | 244 | 4.609 | 18.775 | −5.369 | 1.00 | 31.80 |
| ATOM | 1894 | O | GLY | A | 244 | 4.634 | 19.999 | −5.535 | 1.00 | 33.32 |
| ATOM | 1895 | N | ARG | A | 245 | 3.529 | 18.036 | −5.612 | 1.00 | 27.92 |
| ATOM | 1896 | CA | ARG | A | 245 | 2.200 | 18.618 | −5.781 | 1.00 | 24.21 |
| ATOM | 1897 | CB | ARG | A | 245 | 1.638 | 18.224 | −7.130 | 1.00 | 24.30 |
| ATOM | 1898 | CG | ARG | A | 245 | 2.410 | 18.842 | −8.275 | 1.00 | 24.62 |
| ATOM | 1899 | CD | ARG | A | 245 | 1.625 | 18.681 | −9.532 | 1.00 | 22.11 |
| ATOM | 1900 | NE | ARG | A | 245 | 2.462 | 18.829 | −10.713 | 1.00 | 21.13 |
| ATOM | 1901 | CZ | ARG | A | 245 | 2.114 | 18.302 | −11.878 | 1.00 | 21.50 |
| ATOM | 1902 | NH1 | ARG | A | 245 | 0.982 | 17.621 | −11.945 | 1.00 | 18.57 |
| ATOM | 1903 | NH2 | ARG | A | 245 | 2.883 | 18.443 | −12.951 | 1.00 | 20.83 |
| ATOM | 1904 | C | ARG | A | 245 | 1.295 | 18.040 | −4.718 | 1.00 | 21.84 |
| ATOM | 1905 | O | ARG | A | 245 | 1.624 | 17.021 | −4.128 | 1.00 | 20.65 |
| ATOM | 1906 | N | THR | A | 246 | 0.140 | 18.652 | −4.483 | 1.00 | 19.15 |
| ATOM | 1907 | CA | THR | A | 246 | −0.824 | 18.058 | −3.540 | 1.00 | 17.46 |
| ATOM | 1908 | CB | THR | A | 246 | −1.989 | 18.997 | −3.238 | 1.00 | 17.87 |
| ATOM | 1909 | OG1 | THR | A | 246 | −2.752 | 19.155 | −4.440 | 1.00 | 15.85 |
| ATOM | 1910 | CG2 | THR | A | 246 | −1.495 | 20.370 | −2.730 | 1.00 | 17.50 |
| ATOM | 1911 | C | THR | A | 246 | −1.426 | 16.769 | −4.103 | 1.00 | 17.25 |
| ATOM | 1912 | O | THR | A | 246 | −1.884 | 15.914 | −3.351 | 1.00 | 17.57 |
| ATOM | 1913 | N | GLY | A | 247 | −1.482 | 16.646 | −5.430 | 1.00 | 15.60 |
| ATOM | 1914 | CA | GLY | A | 247 | −2.148 | 15.492 | −6.054 | 1.00 | 15.02 |
| ATOM | 1915 | C | GLY | A | 247 | −3.609 | 15.761 | −6.396 | 1.00 | 14.69 |
| ATOM | 1916 | O | GLY | A | 247 | −4.260 | 14.939 | −7.059 | 1.00 | 14.45 |
| ATOM | 1917 | N | LYS | A | 248 | −4.137 | 16.890 | −5.928 | 1.00 | 13.43 |
| ATOM | 1918 | CA | LYS | A | 248 | −5.508 | 17.286 | −6.259 | 1.00 | 13.00 |

TABLE 15-continued

| | | | | | | | | | |
|---|---|---|---|---|---|---|---|---|---|
| ATOM | 1919 | CB | LYS | A | 248 | −5.969 | 18.453 | −5.396 | 1.00 | 12.32 |
| ATOM | 1920 | CG | LYS | A | 248 | −5.965 | 18.179 | −3.881 | 1.00 | 13.12 |
| ATOM | 1921 | CD | LYS | A | 248 | −6.133 | 19.493 | −3.102 | 1.00 | 14.08 |
| ATOM | 1922 | CE | LYS | A | 248 | −5.985 | 19.253 | −1.584 | 1.00 | 17.84 |
| ATOM | 1923 | NZ | LYS | A | 248 | −6.335 | 20.492 | −0.835 | 1.00 | 16.74 |
| ATOM | 1924 | C | LYS | A | 248 | −5.490 | 17.713 | −7.736 | 1.00 | 12.73 |
| ATOM | 1925 | O | LYS | A | 248 | −4.866 | 18.707 | −8.104 | 1.00 | 12.75 |
| ATOM | 1926 | N | ASP | A | 249 | −6.185 | 16.964 | −8.580 | 1.00 | 11.92 |
| ATOM | 1927 | CA | ASP | A | 249 | −5.958 | 17.098 | −10.024 | 1.00 | 11.16 |
| ATOM | 1928 | CB | ASP | A | 249 | −4.761 | 16.199 | −10.385 | 1.00 | 10.83 |
| ATOM | 1929 | CG | ASP | A | 249 | −4.268 | 16.349 | −11.831 | 1.00 | 12.54 |
| ATOM | 1930 | OD1 | ASP | A | 249 | −5.078 | 16.422 | −12.785 | 1.00 | 11.42 |
| ATOM | 1931 | OD2 | ASP | A | 249 | −3.025 | 16.342 | −12.001 | 1.00 | 13.30 |
| ATOM | 1932 | C | ASP | A | 249 | −7.232 | 16.577 | −10.662 | 1.00 | 11.38 |
| ATOM | 1933 | O | ASP | A | 249 | −7.774 | 15.542 | −10.236 | 1.00 | 10.86 |
| ATOM | 1934 | N | VAL | A | 250 | −7.700 | 17.265 | −11.703 | 1.00 | 11.28 |
| ATOM | 1935 | CA | VAL | A | 250 | −8.885 | 16.793 | −12.438 | 1.00 | 11.59 |
| ATOM | 1936 | CB | VAL | A | 250 | −9.366 | 17.859 | −13.493 | 1.00 | 12.49 |
| ATOM | 1937 | CG1 | VAL | A | 250 | −8.480 | 17.815 | −14.728 | 1.00 | 13.03 |
| ATOM | 1938 | CG2 | VAL | A | 250 | −10.859 | 17.654 | −13.852 | 1.00 | 13.75 |
| ATOM | 1939 | C | VAL | A | 250 | −8.711 | 15.386 | −13.064 | 1.00 | 11.77 |
| ATOM | 1940 | O | VAL | A | 250 | −9.698 | 14.750 | −13.467 | 1.00 | 11.71 |
| ATOM | 1941 | N | ASN | A | 251 | −7.461 | 14.925 | −13.168 | 1.00 | 10.73 |
| ATOM | 1942 | CA | ASN | A | 251 | −7.131 | 13.491 | −13.378 | 1.00 | 11.20 |
| ATOM | 1943 | CB | ASN | A | 251 | −5.699 | 13.265 | −12.813 | 1.00 | 10.94 |
| ATOM | 1944 | CG | ASN | A | 251 | −5.221 | 11.810 | −12.892 | 1.00 | 11.58 |
| ATOM | 1945 | OD1 | ASN | A | 251 | −5.986 | 10.864 | −12.672 | 1.00 | 12.47 |
| ATOM | 1946 | ND2 | ASN | A | 251 | −3.898 | 11.639 | −13.164 | 1.00 | 14.40 |
| ATOM | 1947 | C | ASN | A | 251 | −8.151 | 12.560 | −12.706 | 1.00 | 10.99 |
| ATOM | 1948 | O | ASN | A | 251 | −8.755 | 11.706 | −13.355 | 1.00 | 11.49 |
| ATOM | 1949 | N | SER | A | 252 | −8.407 | 12.774 | −11.417 | 1.00 | 11.45 |
| ATOM | 1950 | CA | SER | A | 252 | −9.293 | 11.876 | −10.634 | 1.00 | 11.79 |
| ATOM | 1951 | CB | SER | A | 252 | −9.062 | 12.155 | −9.149 | 1.00 | 13.31 |
| ATOM | 1952 | OG | SER | A | 252 | −9.338 | 13.524 | −8.882 | 1.00 | 13.41 |
| ATOM | 1953 | C | SER | A | 252 | −10.784 | 12.002 | −10.996 | 1.00 | 11.39 |
| ATOM | 1954 | O | SER | A | 252 | −11.532 | 11.023 | −10.964 | 1.00 | 12.69 |
| ATOM | 1955 | N | VAL | A | 253 | −11.199 | 13.203 | −11.383 | 1.00 | 10.56 |
| ATOM | 1956 | CA | VAL | A | 253 | −12.582 | 13.459 | −11.821 | 1.00 | 10.70 |
| ATOM | 1957 | CB | VAL | A | 253 | −12.884 | 15.004 | −11.856 | 1.00 | 11.02 |
| ATOM | 1958 | CG1 | VAL | A | 253 | −14.335 | 15.262 | −12.345 | 1.00 | 11.24 |
| ATOM | 1959 | CG2 | VAL | A | 253 | −12.711 | 15.585 | −10.449 | 1.00 | 10.91 |
| ATOM | 1960 | C | VAL | A | 253 | −12.810 | 12.827 | −13.187 | 1.00 | 11.38 |
| ATOM | 1961 | O | VAL | A | 253 | −13.824 | 12.143 | −13.407 | 1.00 | 11.69 |
| ATOM | 1962 | N | LEU | A | 254 | −11.866 | 13.059 | −14.108 | 1.00 | 11.32 |
| ATOM | 1963 | CA | LEU | A | 254 | −11.891 | 12.393 | −15.417 | 1.00 | 12.12 |
| ATOM | 1964 | CB | LEU | A | 254 | −10.635 | 12.759 | −16.238 | 1.00 | 11.95 |
| ATOM | 1965 | CG | LEU | A | 254 | −10.634 | 14.202 | −16.763 | 1.00 | 12.23 |
| ATOM | 1966 | CD1 | LEU | A | 254 | −9.266 | 14.564 | −17.330 | 1.00 | 12.77 |
| ATOM | 1967 | CD2 | LEU | A | 254 | −11.714 | 14.371 | −17.845 | 1.00 | 15.26 |
| ATOM | 1968 | C | LEU | A | 254 | −11.963 | 10.872 | −15.271 | 1.00 | 12.22 |
| ATOM | 1969 | O | LEU | A | 254 | −12.675 | 10.201 | −16.024 | 1.00 | 12.01 |
| ATOM | 1970 | N | THR | A | 255 | −11.208 | 10.338 | −14.315 | 1.00 | 11.58 |
| ATOM | 1971 | CA | THR | A | 255 | −11.219 | 8.913 | −14.042 | 1.00 | 12.53 |
| ATOM | 1972 | CB | THR | A | 255 | −10.267 | 8.552 | −12.890 | 1.00 | 12.83 |
| ATOM | 1973 | OG1 | THR | A | 255 | −8.935 | 8.933 | −13.240 | 1.00 | 13.00 |
| ATOM | 1974 | CG2 | THR | A | 255 | −10.300 | 7.035 | −12.634 | 1.00 | 15.06 |
| ATOM | 1975 | C | THR | A | 255 | −12.632 | 8.448 | −13.705 | 1.00 | 13.12 |
| ATOM | 1976 | O | THR | A | 255 | −13.131 | 7.467 | −14.285 | 1.00 | 13.49 |
| ATOM | 1977 | N | SER | A | 256 | −13.289 | 9.158 | −12.790 | 1.00 | 13.46 |
| ATOM | 1978 | CA | SER | A | 256 | −14.641 | 8.781 | −12.343 | 1.00 | 12.85 |
| ATOM | 1979 | CB | SER | A | 256 | −15.152 | 9.760 | −11.282 | 1.00 | 13.40 |
| ATOM | 1980 | OG | SER | A | 256 | −16.332 | 9.252 | −10.674 | 1.00 | 16.69 |
| ATOM | 1981 | C | SER | A | 256 | −15.610 | 8.705 | −13.518 | 1.00 | 13.13 |
| ATOM | 1982 | O | SER | A | 256 | −16.360 | 7.711 | −13.654 | 1.00 | 13.10 |
| ATOM | 1983 | N | ILE | A | 257 | −15.594 | 9.728 | −14.377 | 1.00 | 12.32 |
| ATOM | 1984 | CA | ILE | A | 257 | −16.523 | 9.784 | −15.513 | 1.00 | 12.32 |
| ATOM | 1985 | CB | ILE | A | 257 | −16.747 | 11.215 | −16.072 | 1.00 | 11.55 |
| ATOM | 1986 | CG1 | ILE | A | 257 | −15.482 | 11.773 | −16.764 | 1.00 | 11.38 |
| ATOM | 1987 | CD1 | ILE | A | 257 | −15.699 | 13.143 | −17.441 | 1.00 | 13.23 |
| ATOM | 1988 | CG2 | ILE | A | 257 | −17.257 | 12.166 | −14.942 | 1.00 | 13.70 |
| ATOM | 1989 | C | ILE | A | 257 | −16.220 | 8.795 | −16.653 | 1.00 | 12.79 |
| ATOM | 1990 | O | ILE | A | 257 | −17.150 | 8.319 | −17.338 | 1.00 | 13.25 |
| ATOM | 1991 | N | HIS | A | 258 | −14.941 | 8.487 | −16.855 | 1.00 | 12.71 |
| ATOM | 1992 | CA | HIS | A | 258 | −14.565 | 7.566 | −17.931 | 1.00 | 13.41 |
| ATOM | 1993 | CB | HIS | A | 258 | −13.194 | 7.947 | −18.498 | 1.00 | 12.06 |
| ATOM | 1994 | CG | HIS | A | 258 | −13.268 | 9.175 | −19.341 | 1.00 | 13.92 |
| ATOM | 1995 | ND1 | HIS | A | 258 | −13.942 | 9.196 | −20.547 | 1.00 | 16.01 |
| ATOM | 1996 | CE1 | HIS | A | 258 | −13.891 | 10.421 | −21.047 | 1.00 | 18.57 |
| ATOM | 1997 | NE2 | HIS | A | 258 | −13.256 | 11.199 | −20.189 | 1.00 | 14.08 |
| ATOM | 1998 | CD2 | HIS | A | 258 | −12.861 | 10.449 | −19.108 | 1.00 | 13.51 |

TABLE 15-continued

| | | | | | | | | | |
|---|---|---|---|---|---|---|---|---|---|
| ATOM | 1999 | C | HIS | A | 258 | −14.649 | 6.091 | −17.565 | 1.00 | 14.12 |
| ATOM | 2000 | O | HIS | A | 258 | −14.645 | 5.239 | −18.454 | 1.00 | 14.90 |
| ATOM | 2001 | N | THR | A | 259 | −14.752 | 5.801 | −16.274 | 1.00 | 13.93 |
| ATOM | 2002 | CA | THR | A | 259 | −15.034 | 4.420 | −15.807 | 1.00 | 14.91 |
| ATOM | 2003 | CB | THR | A | 259 | −13.933 | 3.856 | −14.899 | 1.00 | 14.46 |
| ATOM | 2004 | OG1 | THR | A | 259 | −13.788 | 4.647 | −13.705 | 1.00 | 15.66 |
| ATOM | 2005 | CG2 | THR | A | 259 | −12.589 | 3.802 | −15.677 | 1.00 | 15.81 |
| ATOM | 2006 | C | THR | A | 259 | −16.433 | 4.248 | −15.173 | 1.00 | 14.21 |
| ATOM | 2007 | O | THR | A | 259 | −16.709 | 3.235 | −14.546 | 1.00 | 14.95 |
| ATOM | 2008 | N | PHE | A | 260 | −17.290 | 5.238 | −15.367 | 1.00 | 14.76 |
| ATOM | 2009 | CA | PHE | A | 260 | −18.691 | 5.194 | −14.926 | 1.00 | 15.13 |
| ATOM | 2010 | CB | PHE | A | 260 | −19.377 | 6.492 | −15.379 | 1.00 | 15.81 |
| ATOM | 2011 | CG | PHE | A | 260 | −20.886 | 6.508 | −15.228 | 1.00 | 15.47 |
| ATOM | 2012 | CD1 | PHE | A | 260 | −21.505 | 6.188 | −14.015 | 1.00 | 17.59 |
| ATOM | 2013 | CE1 | PHE | A | 260 | −22.903 | 6.259 | −13.898 | 1.00 | 19.11 |
| ATOM | 2014 | CZ | PHE | A | 260 | −23.682 | 6.653 | −14.991 | 1.00 | 17.18 |
| ATOM | 2015 | CE2 | PHE | A | 260 | −23.082 | 6.994 | −16.178 | 1.00 | 18.04 |
| ATOM | 2016 | CD2 | PHE | A | 260 | −21.679 | 6.917 | −16.296 | 1.00 | 17.22 |
| ATOM | 2017 | C | PHE | A | 260 | −19.436 | 3.977 | −15.475 | 1.00 | 15.55 |
| ATOM | 2018 | O | PHE | A | 260 | −19.426 | 3.725 | −16.684 | 1.00 | 15.81 |
| ATOM | 2019 | N | ASP | A | 261 | −20.093 | 3.235 | −14.586 | 1.00 | 15.51 |
| ATOM | 2020 | CA | ASP | A | 261 | −21.008 | 2.176 | −15.006 | 1.00 | 16.05 |
| ATOM | 2021 | CB | ASP | A | 261 | −20.303 | 0.813 | −15.015 | 1.00 | 16.46 |
| ATOM | 2022 | CG | ASP | A | 261 | −21.205 | −0.321 | −15.490 | 1.00 | 17.60 |
| ATOM | 2023 | OD1 | ASP | A | 261 | −22.440 | −0.122 | −15.579 | 1.00 | 18.97 |
| ATOM | 2024 | OD2 | ASP | A | 261 | −20.656 | −1.404 | −15.810 | 1.00 | 18.29 |
| ATOM | 2025 | C | ASP | A | 261 | −22.117 | 2.185 | −13.972 | 1.00 | 16.30 |
| ATOM | 2026 | O | ASP | A | 261 | −21.882 | 1.809 | −12.840 | 1.00 | 15.53 |
| ATOM | 2027 | N | PRO | A | 262 | −23.320 | 2.610 | −14.374 | 1.00 | 18.21 |
| ATOM | 2028 | CA | PRO | A | 262 | −24.438 | 2.716 | −13.412 | 1.00 | 20.39 |
| ATOM | 2029 | CB | PRO | A | 262 | −25.589 | 3.308 | −14.247 | 1.00 | 20.43 |
| ATOM | 2030 | CG | PRO | A | 262 | −25.235 | 3.044 | −15.669 | 1.00 | 20.06 |
| ATOM | 2031 | CD | PRO | A | 262 | −23.709 | 2.994 | −15.734 | 1.00 | 17.40 |
| ATOM | 2032 | C | PRO | A | 262 | −24.815 | 1.382 | −12.753 | 1.00 | 22.31 |
| ATOM | 2033 | O | PRO | A | 262 | −25.356 | 1.374 | −11.622 | 1.00 | 22.24 |
| ATOM | 2034 | N | ASN | A | 263 | −24.508 | 0.267 | −13.421 | 1.00 | 22.99 |
| ATOM | 2035 | CA | ASN | A | 263 | −24.750 | −1.048 | −12.838 | 1.00 | 25.42 |
| ATOM | 2036 | CB | ASN | A | 263 | −24.574 | −2.149 | −13.890 | 1.00 | 26.62 |
| ATOM | 2037 | CG | ASN | A | 263 | −25.680 | −2.128 | −14.948 | 1.00 | 30.74 |
| ATOM | 2038 | OD1 | ASN | A | 263 | −26.688 | −1.419 | −14.814 | 1.00 | 35.92 |
| ATOM | 2039 | ND2 | ASN | A | 263 | −25.490 | −2.906 | −16.007 | 1.00 | 35.87 |
| ATOM | 2040 | C | ASN | A | 263 | −23.894 | −1.316 | −11.598 | 1.00 | 25.45 |
| ATOM | 2041 | O | ASN | A | 263 | −24.210 | −2.190 | −10.795 | 1.00 | 26.56 |
| ATOM | 2042 | N | LEU | A | 264 | −22.835 | −0.529 | −11.413 | 1.00 | 24.54 |
| ATOM | 2043 | CA | LEU | A | 264 | −22.022 | −0.616 | −10.213 | 1.00 | 24.27 |
| ATOM | 2044 | CB | LEU | A | 264 | −20.549 | −0.287 | −10.520 | 1.00 | 24.43 |
| ATOM | 2045 | CG | LEU | A | 264 | −19.752 | −1.346 | −11.288 | 1.00 | 25.38 |
| ATOM | 2046 | CD1 | LEU | A | 264 | −18.375 | −0.809 | −11.659 | 1.00 | 26.05 |
| ATOM | 2047 | CD2 | LEU | A | 264 | −19.619 | −2.672 | −10.523 | 1.00 | 26.24 |
| ATOM | 2048 | C | LEU | A | 264 | −22.542 | 0.273 | −9.066 | 1.00 | 23.47 |
| ATOM | 2049 | O | LEU | A | 264 | −21.956 | 0.292 | −7.988 | 1.00 | 23.97 |
| ATOM | 2050 | N | GLY | A | 265 | −23.631 | 1.000 | −9.292 | 1.00 | 23.32 |
| ATOM | 2051 | CA | GLY | A | 265 | −24.218 | 1.840 | −8.237 | 1.00 | 22.74 |
| ATOM | 2052 | C | GLY | A | 265 | −23.204 | 2.843 | −7.729 | 1.00 | 21.84 |
| ATOM | 2053 | O | GLY | A | 265 | −22.416 | 3.373 | −8.510 | 1.00 | 22.83 |
| ATOM | 2054 | N | CYS | A | 266 | −23.175 | 3.086 | −6.424 | 1.00 | 21.37 |
| ATOM | 2055 | CA | CYS | A | 266 | −22.233 | 4.073 | −5.883 | 1.00 | 21.00 |
| ATOM | 2056 | CB | CYS | A | 266 | −22.947 | 5.049 | −4.936 | 1.00 | 20.86 |
| ATOM | 2057 | SG | CYS | A | 266 | −24.347 | 5.912 | −5.711 | 1.00 | 20.96 |
| ATOM | 2058 | C | CYS | A | 266 | −20.992 | 3.427 | −5.275 | 1.00 | 20.98 |
| ATOM | 2059 | O | CYS | A | 266 | −20.513 | 3.814 | −4.203 | 1.00 | 21.01 |
| ATOM | 2060 | N | ASP | A | 267 | −20.462 | 2.443 | −6.002 | 1.00 | 20.39 |
| ATOM | 2061 | CA | ASP | A | 267 | −19.303 | 1.686 | −5.577 | 1.00 | 20.67 |
| ATOM | 2062 | CB | ASP | A | 267 | −18.961 | 0.621 | −6.618 | 1.00 | 20.84 |
| ATOM | 2063 | CG | ASP | A | 267 | −17.666 | −0.101 | −6.288 | 1.00 | 24.28 |
| ATOM | 2064 | OD1 | ASP | A | 267 | −16.852 | −0.322 | −7.200 | 1.00 | 25.84 |
| ATOM | 2065 | OD2 | ASP | A | 267 | −17.455 | −0.407 | −5.098 | 1.00 | 27.46 |
| ATOM | 2066 | C | ASP | A | 267 | −18.072 | 2.567 | −5.391 | 1.00 | 19.78 |
| ATOM | 2067 | O | ASP | A | 267 | −17.593 | 3.161 | −6.353 | 1.00 | 18.61 |
| ATOM | 2068 | N | ALA | A | 268 | −17.544 | 2.621 | −4.174 | 1.00 | 18.35 |
| ATOM | 2069 | CA | ALA | A | 268 | −16.315 | 3.395 | −3.944 | 1.00 | 19.35 |
| ATOM | 2070 | CB | ALA | A | 268 | −16.207 | 3.868 | −2.472 | 1.00 | 19.46 |
| ATOM | 2071 | C | ALA | A | 268 | −15.017 | 2.701 | −4.415 | 1.00 | 19.46 |
| ATOM | 2072 | O | ALA | A | 268 | −14.009 | 3.371 | −4.665 | 1.00 | 19.42 |
| ATOM | 2073 | N | GLY | A | 269 | −15.029 | 1.370 | −4.534 | 1.00 | 19.01 |
| ATOM | 2074 | CA | GLY | A | 269 | −13.826 | 0.644 | −4.936 | 1.00 | 19.17 |
| ATOM | 2075 | C | GLY | A | 269 | −13.370 | 1.032 | −6.343 | 1.00 | 18.75 |
| ATOM | 2076 | O | GLY | A | 269 | −12.175 | 1.134 | −6.624 | 1.00 | 19.54 |
| ATOM | 2077 | N | THR | A | 270 | −14.330 | 1.257 | −7.230 | 1.00 | 17.92 |
| ATOM | 2078 | CA | THR | A | 270 | −14.016 | 1.662 | −8.594 | 1.00 | 18.35 |

TABLE 15-continued

| | | | | | | | | | |
|---|---|---|---|---|---|---|---|---|---|
| ATOM | 2079 | CB | THR | A | 270 | −14.852 | 0.882 | −9.616 | 1.00 | 18.43 |
| ATOM | 2080 | OG1 | THR | A | 270 | −16.246 | 1.085 | −9.350 | 1.00 | 18.51 |
| ATOM | 2081 | CG2 | THR | A | 270 | −14.529 | −0.626 | −9.555 | 1.00 | 19.75 |
| ATOM | 2082 | C | THR | A | 270 | −14.261 | 3.172 | −8.771 | 1.00 | 18.25 |
| ATOM | 2083 | O | THR | A | 270 | −14.326 | 3.674 | −9.904 | 1.00 | 17.88 |
| ATOM | 2084 | N | PHE | A | 271 | −14.434 | 3.880 | −7.650 | 1.00 | 17.17 |
| ATOM | 2085 | CA | PHE | A | 271 | −14.531 | 5.359 | −7.656 | 1.00 | 17.38 |
| ATOM | 2086 | CB | PHE | A | 271 | −13.183 | 5.965 | −8.121 | 1.00 | 17.67 |
| ATOM | 2087 | CG | PHE | A | 271 | −12.946 | 7.376 | −7.673 | 1.00 | 21.97 |
| ATOM | 2088 | CD1 | PHE | A | 271 | −12.656 | 7.653 | −6.337 | 1.00 | 24.90 |
| ATOM | 2089 | CE1 | PHE | A | 271 | −12.447 | 8.981 | −5.923 | 1.00 | 24.46 |
| ATOM | 2090 | CZ | PHE | A | 271 | −12.474 | 10.043 | −6.863 | 1.00 | 23.20 |
| ATOM | 2091 | CE2 | PHE | A | 271 | −12.733 | 9.783 | −8.196 | 1.00 | 21.92 |
| ATOM | 2092 | CD2 | PHE | A | 271 | −12.956 | 8.436 | −8.599 | 1.00 | 24.30 |
| ATOM | 2093 | C | PHE | A | 271 | −15.677 | 5.856 | −8.551 | 1.00 | 16.63 |
| ATOM | 2094 | O | PHE | A | 271 | −15.479 | 6.764 | −9.358 | 1.00 | 15.93 |
| ATOM | 2095 | N | GLN | A | 272 | −16.861 | 5.249 | −8.439 | 1.00 | 15.21 |
| ATOM | 2096 | CA | GLN | A | 272 | −18.011 | 5.673 | −9.251 | 1.00 | 14.97 |
| ATOM | 2097 | CB | GLN | A | 272 | −19.227 | 4.755 | −9.013 | 1.00 | 14.93 |
| ATOM | 2098 | CG | GLN | A | 272 | −19.021 | 3.355 | −9.615 | 1.00 | 16.30 |
| ATOM | 2099 | CD | GLN | A | 272 | −18.755 | 3.413 | −11.102 | 1.00 | 15.81 |
| ATOM | 2100 | OE1 | GLN | A | 272 | −19.575 | 3.909 | −11.883 | 1.00 | 16.97 |
| ATOM | 2101 | NE2 | GLN | A | 272 | −17.617 | 2.861 | −11.512 | 1.00 | 18.50 |
| ATOM | 2102 | C | GLN | A | 272 | −18.402 | 7.118 | −8.929 | 1.00 | 14.73 |
| ATOM | 2103 | O | GLN | A | 272 | −18.194 | 7.555 | −7.800 | 1.00 | 15.60 |
| ATOM | 2104 | N | PRO | A | 273 | −18.955 | 7.859 | −9.914 | 1.00 | 14.45 |
| ATOM | 2105 | CA | PRO | A | 273 | −19.342 | 9.255 | −9.682 | 1.00 | 14.57 |
| ATOM | 2106 | CB | PRO | A | 273 | −20.157 | 9.597 | −10.927 | 1.00 | 14.64 |
| ATOM | 2107 | CG | PRO | A | 273 | −19.443 | 8.767 | −12.031 | 1.00 | 14.70 |
| ATOM | 2108 | CD | PRO | A | 273 | −19.156 | 7.458 | −11.326 | 1.00 | 14.10 |
| ATOM | 2109 | C | PRO | A | 273 | −20.162 | 9.542 | −8.407 | 1.00 | 15.22 |
| ATOM | 2110 | O | PRO | A | 273 | −19.910 | 10.562 | −7.752 | 1.00 | 15.03 |
| ATOM | 2111 | N | CYS | A | 274 | −21.130 | 8.682 | −8.075 | 1.00 | 15.76 |
| ATOM | 2112 | CA | CYS | A | 274 | −21.926 | 8.913 | −6.853 | 1.00 | 16.22 |
| ATOM | 2113 | CB | CYS | A | 274 | −23.389 | 8.489 | −7.039 | 1.00 | 16.57 |
| ATOM | 2114 | SG | CYS | A | 274 | −23.611 | 6.769 | −7.423 | 1.00 | 17.39 |
| ATOM | 2115 | C | CYS | A | 274 | −21.331 | 8.281 | −5.605 | 1.00 | 16.64 |
| ATOM | 2116 | O | CYS | A | 274 | −21.958 | 8.329 | −4.529 | 1.00 | 16.55 |
| ATOM | 2117 | N | SER | A | 275 | −20.137 | 7.681 | −5.715 | 1.00 | 15.61 |
| ATOM | 2118 | CA | SER | A | 275 | −19.476 | 7.117 | −4.528 | 1.00 | 15.81 |
| ATOM | 2119 | CB | SER | A | 275 | −18.244 | 6.253 | −4.877 | 1.00 | 15.06 |
| ATOM | 2120 | OG | SER | A | 275 | −17.144 | 7.041 | −5.315 | 1.00 | 14.92 |
| ATOM | 2121 | C | SER | A | 275 | −19.097 | 8.232 | −3.545 | 1.00 | 16.06 |
| ATOM | 2122 | O | SER | A | 275 | −18.818 | 9.366 | −3.949 | 1.00 | 14.39 |
| ATOM | 2123 | N | ASP | A | 276 | −19.103 | 7.919 | −2.248 | 1.00 | 16.42 |
| ATOM | 2124 | CA | ASP | A | 276 | −18.731 | 8.935 | −1.271 | 1.00 | 16.52 |
| ATOM | 2125 | CB | ASP | A | 276 | −19.020 | 8.511 | 0.189 | 1.00 | 16.27 |
| ATOM | 2126 | CG | ASP | A | 276 | −18.244 | 7.281 | 0.656 | 1.00 | 19.14 |
| ATOM | 2127 | OD1 | ASP | A | 276 | −18.371 | 7.001 | 1.873 | 1.00 | 19.62 |
| ATOM | 2128 | OD2 | ASP | A | 276 | −17.544 | 6.593 | −0.120 | 1.00 | 17.10 |
| ATOM | 2129 | C | ASP | A | 276 | −17.312 | 9.469 | −1.492 | 1.00 | 16.17 |
| ATOM | 2130 | O | ASP | A | 276 | −17.084 | 10.683 | −1.415 | 1.00 | 15.20 |
| ATOM | 2131 | N | LYS | A | 277 | −16.381 | 8.577 | −1.823 | 1.00 | 15.43 |
| ATOM | 2132 | CA | LYS | A | 277 | −14.994 | 8.982 | −2.115 | 1.00 | 15.34 |
| ATOM | 2133 | CB | LYS | A | 277 | −14.089 | 7.763 | −2.326 | 1.00 | 15.23 |
| ATOM | 2134 | CG | LYS | A | 277 | −13.924 | 6.905 | −1.059 | 1.00 | 17.01 |
| ATOM | 2135 | CD | LYS | A | 277 | −12.752 | 5.929 | −1.204 | 1.00 | 21.20 |
| ATOM | 2136 | CE | LYS | A | 277 | −12.662 | 5.017 | 0.015 | 1.00 | 22.94 |
| ATOM | 2137 | NZ | LYS | A | 277 | −11.533 | 4.067 | −0.165 | 1.00 | 29.19 |
| ATOM | 2138 | C | LYS | A | 277 | −14.900 | 9.915 | −3.324 | 1.00 | 14.30 |
| ATOM | 2139 | O | LYS | A | 277 | −14.152 | 10.887 | −3.288 | 1.00 | 14.70 |
| ATOM | 2140 | N | ALA | A | 278 | −15.644 | 9.620 | −4.393 | 1.00 | 14.45 |
| ATOM | 2141 | CA | ALA | A | 278 | −15.588 | 10.464 | −5.605 | 1.00 | 13.61 |
| ATOM | 2142 | CB | ALA | A | 278 | −16.250 | 9.775 | −6.783 | 1.00 | 13.30 |
| ATOM | 2143 | C | ALA | A | 278 | −16.210 | 11.827 | −5.357 | 1.00 | 13.50 |
| ATOM | 2144 | O | ALA | A | 278 | −15.730 | 12.840 | −5.864 | 1.00 | 13.02 |
| ATOM | 2145 | N | LEU | A | 279 | −17.283 | 11.855 | −4.565 | 1.00 | 13.22 |
| ATOM | 2146 | CA | LEU | A | 279 | −17.936 | 13.132 | −4.239 | 1.00 | 12.92 |
| ATOM | 2147 | CB | LEU | A | 279 | −19.323 | 12.893 | −3.625 | 1.00 | 13.21 |
| ATOM | 2148 | CG | LEU | A | 279 | −20.384 | 12.358 | −4.601 | 1.00 | 13.94 |
| ATOM | 2149 | CD1 | LEU | A | 279 | −21.707 | 11.969 | −3.887 | 1.00 | 17.68 |
| ATOM | 2150 | CD2 | LEU | A | 279 | −20.653 | 13.319 | −5.781 | 1.00 | 17.52 |
| ATOM | 2151 | C | LEU | A | 279 | −17.065 | 13.995 | −3.348 | 1.00 | 12.84 |
| ATOM | 2152 | O | LEU | A | 279 | −16.941 | 15.203 | −3.577 | 1.00 | 13.54 |
| ATOM | 2153 | N | SER | A | 280 | −16.463 | 13.390 | −2.315 | 1.00 | 12.45 |
| ATOM | 2154 | CA | SER | A | 280 | −15.502 | 14.106 | −1.459 | 1.00 | 13.53 |
| ATOM | 2155 | CB | SER | A | 280 | −14.951 | 13.168 | −0.364 | 1.00 | 13.65 |
| ATOM | 2156 | OG | SER | A | 280 | −14.008 | 13.863 | 0.468 | 1.00 | 15.07 |
| ATOM | 2157 | C | SER | A | 280 | −14.332 | 14.672 | −2.285 | 1.00 | 14.09 |
| ATOM | 2158 | O | SER | A | 280 | −13.925 | 15.856 | −2.130 | 1.00 | 13.43 |

TABLE 15-continued

| | | | | | | | | | |
|---|---|---|---|---|---|---|---|---|---|
| ATOM | 2159 | N | ASN | A | 281 | −13.795 | 13.830 | −3.166 | 1.00 | 13.27 |
| ATOM | 2160 | CA | ASN | A | 281 | −12.690 | 14.257 | −4.027 | 1.00 | 13.19 |
| ATOM | 2161 | CB | ASN | A | 281 | −12.239 | 13.078 | −4.888 | 1.00 | 12.05 |
| ATOM | 2162 | CG | ASN | A | 281 | −11.116 | 13.455 | −5.849 | 1.00 | 13.13 |
| ATOM | 2163 | OD1 | ASN | A | 281 | −9.989 | 13.637 | −5.446 | 1.00 | 13.26 |
| ATOM | 2164 | ND2 | ASN | A | 281 | −11.442 | 13.573 | −7.124 | 1.00 | 11.63 |
| ATOM | 2165 | C | ASN | A | 281 | −13.096 | 15.432 | −4.933 | 1.00 | 12.33 |
| ATOM | 2166 | O | ASN | A | 281 | −12.330 | 16.380 | −5.109 | 1.00 | 13.49 |
| ATOM | 2167 | N | LEU | A | 282 | −14.287 | 15.355 | −5.506 | 1.00 | 12.05 |
| ATOM | 2168 | CA | LEU | A | 282 | −14.760 | 16.422 | −6.376 | 1.00 | 13.21 |
| ATOM | 2169 | CB | LEU | A | 282 | −16.147 | 16.109 | −6.949 | 1.00 | 12.17 |
| ATOM | 2170 | CG | LEU | A | 282 | −16.791 | 17.216 | −7.820 | 1.00 | 14.57 |
| ATOM | 2171 | CD1 | LEU | A | 282 | −16.011 | 17.378 | −9.126 | 1.00 | 16.58 |
| ATOM | 2172 | CD2 | LEU | A | 282 | −18.241 | 16.863 | −8.170 | 1.00 | 15.68 |
| ATOM | 2173 | C | LEU | A | 282 | −14.739 | 17.754 | −5.638 | 1.00 | 12.69 |
| ATOM | 2174 | O | LEU | A | 282 | −14.201 | 18.735 | −6.153 | 1.00 | 13.45 |
| ATOM | 2175 | N | LYS | A | 283 | −15.283 | 17.791 | −4.415 | 1.00 | 12.75 |
| ATOM | 2176 | CA | LYS | A | 283 | −15.306 | 19.026 | −3.656 | 1.00 | 12.89 |
| ATOM | 2177 | CB | LYS | A | 283 | −16.079 | 18.860 | −2.334 | 1.00 | 12.90 |
| ATOM | 2178 | CG | LYS | A | 283 | −15.912 | 20.089 | −1.432 | 1.00 | 13.94 |
| ATOM | 2179 | CD | LYS | A | 283 | −16.909 | 20.076 | −0.252 | 1.00 | 14.67 |
| ATOM | 2180 | CE | LYS | A | 283 | −16.530 | 21.136 | 0.797 | 1.00 | 13.67 |
| ATOM | 2181 | NZ | LYS | A | 283 | −16.315 | 22.489 | 0.212 | 1.00 | 19.03 |
| ATOM | 2182 | C | LYS | A | 283 | −13.889 | 19.537 | −3.385 | 1.00 | 12.43 |
| ATOM | 2183 | O | LYS | A | 283 | −13.612 | 20.710 | −3.556 | 1.00 | 12.14 |
| ATOM | 2184 | N | VAL | A | 284 | −12.988 | 18.652 | −2.966 | 1.00 | 12.02 |
| ATOM | 2185 | CA | VAL | A | 284 | −11.624 | 19.055 | −2.633 | 1.00 | 12.77 |
| ATOM | 2186 | CB | VAL | A | 284 | −10.845 | 17.875 | −2.014 | 1.00 | 13.17 |
| ATOM | 2187 | CG1 | VAL | A | 284 | −9.320 | 18.169 | −1.936 | 1.00 | 13.21 |
| ATOM | 2188 | CG2 | VAL | A | 284 | −11.391 | 17.557 | −0.630 | 1.00 | 15.81 |
| ATOM | 2189 | C | VAL | A | 284 | −10.927 | 19.599 | −3.881 | 1.00 | 12.74 |
| ATOM | 2190 | O | VAL | A | 284 | −10.228 | 20.636 | −3.827 | 1.00 | 12.21 |
| ATOM | 2191 | N | VAL | A | 285 | −11.153 | 18.927 | −5.012 | 1.00 | 11.54 |
| ATOM | 2192 | CA | VAL | A | 285 | −10.560 | 19.389 | −6.287 | 1.00 | 12.35 |
| ATOM | 2193 | CB | VAL | A | 285 | −10.694 | 18.330 | −7.425 | 1.00 | 12.36 |
| ATOM | 2194 | CG1 | VAL | A | 285 | −10.316 | 18.944 | −8.813 | 1.00 | 12.25 |
| ATOM | 2195 | CG2 | VAL | A | 285 | −9.795 | 17.104 | −7.140 | 1.00 | 13.25 |
| ATOM | 2196 | C | VAL | A | 285 | −11.130 | 20.770 | −6.712 | 1.00 | 12.08 |
| ATOM | 2197 | O | VAL | A | 285 | −10.367 | 21.696 | −6.989 | 1.00 | 12.60 |
| ATOM | 2198 | N | VAL | A | 286 | −12.452 | 20.913 | −6.728 | 1.00 | 11.87 |
| ATOM | 2199 | CA | VAL | A | 286 | −13.089 | 22.196 | −7.074 | 1.00 | 12.87 |
| ATOM | 2200 | CB | VAL | A | 286 | −14.631 | 22.080 | −7.038 | 1.00 | 13.01 |
| ATOM | 2201 | CG1 | VAL | A | 286 | −15.300 | 23.468 | −7.140 | 1.00 | 14.31 |
| ATOM | 2202 | CG2 | VAL | A | 286 | −15.103 | 21.157 | −8.200 | 1.00 | 14.42 |
| ATOM | 2203 | C | VAL | A | 286 | −12.586 | 23.324 | −6.164 | 1.00 | 12.84 |
| ATOM | 2204 | O | VAL | A | 286 | −12.206 | 24.402 | −6.635 | 1.00 | 13.75 |
| ATOM | 2205 | N | ASP | A | 287 | −12.552 | 23.064 | −4.853 | 1.00 | 12.85 |
| ATOM | 2206 | CA | ASP | A | 287 | −12.116 | 24.059 | −3.870 | 1.00 | 13.90 |
| ATOM | 2207 | CB | ASP | A | 287 | −12.199 | 23.506 | −2.440 | 1.00 | 13.12 |
| ATOM | 2208 | CG | ASP | A | 287 | −13.637 | 23.441 | −1.924 | 1.00 | 16.00 |
| ATOM | 2209 | OD1 | ASP | A | 287 | −14.541 | 24.002 | −2.583 | 1.00 | 16.20 |
| ATOM | 2210 | OD2 | ASP | A | 287 | −13.857 | 22.835 | −0.858 | 1.00 | 16.76 |
| ATOM | 2211 | C | ASP | A | 287 | −10.727 | 24.564 | −4.136 | 1.00 | 14.28 |
| ATOM | 2212 | O | ASP | A | 287 | −10.425 | 25.722 | −3.841 | 1.00 | 15.53 |
| ATOM | 2213 | N | SER | A | 288 | −9.862 | 23.709 | −4.677 | 1.00 | 14.50 |
| ATOM | 2214 | CA | SER | A | 288 | −8.478 | 24.093 | −4.949 | 1.00 | 14.58 |
| ATOM | 2215 | CB | SER | A | 288 | −7.625 | 22.843 | −5.229 | 1.00 | 14.15 |
| ATOM | 2216 | OG | SER | A | 288 | −7.758 | 22.417 | −6.565 | 1.00 | 13.73 |
| ATOM | 2217 | C | SER | A | 288 | −8.326 | 25.186 | −6.038 | 1.00 | 14.61 |
| ATOM | 2218 | O | SER | A | 288 | −7.274 | 25.847 | −6.143 | 1.00 | 14.59 |
| ATOM | 2219 | N | PHE | A | 289 | −9.392 | 25.416 | −6.809 | 1.00 | 13.99 |
| ATOM | 2220 | CA | PHE | A | 289 | −9.419 | 26.447 | −7.831 | 1.00 | 14.09 |
| ATOM | 2221 | CB | PHE | A | 289 | −9.994 | 25.882 | −9.135 | 1.00 | 13.52 |
| ATOM | 2222 | CG | PHE | A | 289 | −9.169 | 24.807 | −9.704 | 1.00 | 11.38 |
| ATOM | 2223 | CD1 | PHE | A | 289 | −7.976 | 25.114 | −10.367 | 1.00 | 12.17 |
| ATOM | 2224 | CE1 | PHE | A | 289 | −7.184 | 24.095 | −10.905 | 1.00 | 13.93 |
| ATOM | 2225 | CZ | PHE | A | 289 | −7.572 | 22.783 | −10.771 | 1.00 | 13.96 |
| ATOM | 2226 | CE2 | PHE | A | 289 | −8.756 | 22.452 | −10.097 | 1.00 | 11.77 |
| ATOM | 2227 | CD2 | PHE | A | 289 | −9.555 | 23.472 | −9.571 | 1.00 | 11.08 |
| ATOM | 2228 | C | PHE | A | 289 | −10.219 | 27.698 | −7.491 | 1.00 | 14.73 |
| ATOM | 2229 | O | PHE | A | 289 | −10.092 | 28.713 | −8.189 | 1.00 | 14.71 |
| ATOM | 2230 | N | ARG | A | 290 | −11.054 | 27.621 | −6.464 | 1.00 | 15.09 |
| ATOM | 2231 | CA | ARG | A | 290 | −11.953 | 28.740 | −6.140 | 1.00 | 16.64 |
| ATOM | 2232 | CB | ARG | A | 290 | −12.842 | 28.401 | −4.936 | 1.00 | 15.99 |
| ATOM | 2233 | CG | ARG | A | 290 | −13.913 | 27.375 | −5.230 | 1.00 | 15.65 |
| ATOM | 2234 | CD | ARG | A | 290 | −14.821 | 27.163 | −4.012 | 1.00 | 16.79 |
| ATOM | 2235 | NE | ARG | A | 290 | −15.843 | 26.172 | −4.330 | 1.00 | 15.04 |
| ATOM | 2236 | CZ | ARG | A | 290 | −16.986 | 26.470 | −4.933 | 1.00 | 17.22 |
| ATOM | 2237 | NH1 | ARG | A | 290 | −17.248 | 27.734 | −5.243 | 1.00 | 15.41 |
| ATOM | 2238 | NH2 | ARG | A | 290 | −17.855 | 25.511 | −5.239 | 1.00 | 15.94 |

TABLE 15-continued

| | | | | | | | | | |
|---|---|---|---|---|---|---|---|---|---|
| ATOM | 2239 | C | ARG | A | 290 | −11.240 | 30.046 | −5.864 | 1.00 | 18.04 |
| ATOM | 2240 | O | ARG | A | 290 | −11.690 | 31.125 | −6.279 | 1.00 | 19.61 |
| ATOM | 2241 | N | SER | A | 291 | −10.150 | 29.984 | −5.128 | 1.00 | 19.44 |
| ATOM | 2242 | CA | SER | A | 291 | −9.571 | 31.246 | −4.667 | 1.00 | 21.57 |
| ATOM | 2243 | CB | SER | A | 291 | −9.146 | 31.101 | −3.212 | 1.00 | 22.18 |
| ATOM | 2244 | OG | SER | A | 291 | −7.998 | 30.284 | −3.144 | 1.00 | 28.35 |
| ATOM | 2245 | C | SER | A | 291 | −8.423 | 31.762 | −5.534 | 1.00 | 20.65 |
| ATOM | 2246 | O | SER | A | 291 | −7.865 | 32.851 | −5.272 | 1.00 | 22.43 |
| ATOM | 2247 | N | ILE | A | 292 | −8.066 | 31.019 | −6.576 | 1.00 | 19.16 |
| ATOM | 2248 | CA | ILE | A | 292 | −6.855 | 31.367 | −7.330 | 1.00 | 17.65 |
| ATOM | 2249 | CB | ILE | A | 292 | −5.805 | 30.185 | −7.408 | 1.00 | 18.07 |
| ATOM | 2250 | CG1 | ILE | A | 292 | −6.379 | 28.972 | −8.194 | 1.00 | 17.67 |
| ATOM | 2251 | CD1 | ILE | A | 292 | −5.315 | 27.924 | −8.649 | 1.00 | 17.27 |
| ATOM | 2252 | CG2 | ILE | A | 292 | −5.341 | 29.795 | −5.994 | 1.00 | 18.29 |
| ATOM | 2253 | C | ILE | A | 292 | −7.065 | 31.973 | −8.708 | 1.00 | 17.20 |
| ATOM | 2254 | O | ILE | A | 292 | −6.136 | 32.563 | −9.251 | 1.00 | 16.35 |
| ATOM | 2255 | N | TYR | A | 293 | −8.252 | 31.797 | −9.290 | 1.00 | 15.85 |
| ATOM | 2256 | CA | TYR | A | 293 | −8.509 | 32.304 | −10.648 | 1.00 | 15.83 |
| ATOM | 2257 | CB | TYR | A | 293 | −9.301 | 31.270 | −11.474 | 1.00 | 15.43 |
| ATOM | 2258 | CG | TYR | A | 293 | −8.571 | 30.014 | −11.886 | 1.00 | 15.10 |
| ATOM | 2259 | CD1 | TYR | A | 293 | −7.183 | 29.960 | −11.965 | 1.00 | 14.38 |
| ATOM | 2260 | CE1 | TYR | A | 293 | −6.540 | 28.795 | −12.395 | 1.00 | 14.38 |
| ATOM | 2261 | CZ | TYR | A | 293 | −7.306 | 27.685 | −12.743 | 1.00 | 14.90 |
| ATOM | 2262 | OH | TYR | A | 293 | −6.700 | 26.522 | −13.158 | 1.00 | 15.55 |
| ATOM | 2263 | CE2 | TYR | A | 293 | −8.670 | 27.722 | −12.671 | 1.00 | 15.47 |
| ATOM | 2264 | CD2 | TYR | A | 293 | −9.298 | 28.875 | −12.255 | 1.00 | 13.91 |
| ATOM | 2265 | C | TYR | A | 293 | −9.351 | 33.581 | −10.591 | 1.00 | 15.69 |
| ATOM | 2266 | O | TYR | A | 293 | −10.404 | 33.594 | −9.942 | 1.00 | 15.47 |
| ATOM | 2267 | N | GLY | A | 294 | −8.892 | 34.629 | −11.276 | 1.00 | 14.83 |
| ATOM | 2268 | CA | GLY | A | 294 | −9.641 | 35.899 | −11.353 | 1.00 | 15.57 |
| ATOM | 2269 | C | GLY | A | 294 | −11.078 | 35.702 | −11.858 | 1.00 | 15.93 |
| ATOM | 2270 | O | GLY | A | 294 | −12.010 | 36.359 | −11.376 | 1.00 | 15.66 |
| ATOM | 2271 | N | VAL | A | 295 | −11.288 | 34.773 | −12.799 | 1.00 | 15.60 |
| ATOM | 2272 | CA | VAL | A | 295 | −12.651 | 34.520 | −13.270 | 1.00 | 16.24 |
| ATOM | 2273 | CB | VAL | A | 295 | −12.753 | 33.561 | −14.501 | 1.00 | 16.31 |
| ATOM | 2274 | CG1 | VAL | A | 295 | −12.170 | 34.195 | −15.740 | 1.00 | 16.26 |
| ATOM | 2275 | CG2 | VAL | A | 295 | −12.128 | 32.184 | −14.199 | 1.00 | 16.19 |
| ATOM | 2276 | C | VAL | A | 295 | −13.596 | 34.013 | −12.172 | 1.00 | 16.97 |
| ATOM | 2277 | O | VAL | A | 295 | −14.813 | 34.108 | −12.320 | 1.00 | 18.03 |
| ATOM | 2278 | N | ASN | A | 296 | −13.047 | 33.463 | −11.092 | 1.00 | 16.93 |
| ATOM | 2279 | CA | ASN | A | 296 | −13.878 | 32.920 | −10.020 | 1.00 | 17.69 |
| ATOM | 2280 | CB | ASN | A | 296 | −13.250 | 31.633 | −9.472 | 1.00 | 17.57 |
| ATOM | 2281 | CG | ASN | A | 296 | −13.296 | 30.493 | −10.482 | 1.00 | 16.44 |
| ATOM | 2282 | OD1 | ASN | A | 296 | −14.158 | 30.481 | −11.356 | 1.00 | 17.29 |
| ATOM | 2283 | ND2 | ASN | A | 296 | −12.401 | 29.513 | −10.336 | 1.00 | 15.99 |
| ATOM | 2284 | C | ASN | A | 296 | −14.187 | 33.915 | −8.896 | 1.00 | 19.30 |
| ATOM | 2285 | O | ASN | A | 296 | −14.945 | 33.601 | −7.979 | 1.00 | 19.07 |
| ATOM | 2286 | N | LYS | A | 297 | −13.617 | 35.116 | −9.007 | 1.00 | 20.37 |
| ATOM | 2287 | CA | LYS | A | 297 | −13.811 | 36.203 | −8.038 | 1.00 | 22.43 |
| ATOM | 2288 | CB | LYS | A | 297 | −13.209 | 37.502 | −8.584 | 1.00 | 22.90 |
| ATOM | 2289 | CG | LYS | A | 297 | −11.741 | 37.680 | −8.316 | 1.00 | 30.03 |
| ATOM | 2290 | CD | LYS | A | 297 | −11.401 | 39.189 | −8.309 | 1.00 | 35.34 |
| ATOM | 2291 | CE | LYS | A | 297 | −12.247 | 39.913 | −7.255 | 1.00 | 39.86 |
| ATOM | 2292 | NZ | LYS | A | 297 | −11.995 | 41.386 | −7.178 | 1.00 | 42.72 |
| ATOM | 2293 | C | LYS | A | 297 | −15.275 | 36.453 | −7.782 | 1.00 | 21.89 |
| ATOM | 2294 | O | LYS | A | 297 | −16.061 | 36.585 | −8.712 | 1.00 | 21.96 |
| ATOM | 2295 | N | GLY | A | 298 | −15.659 | 36.537 | −6.517 | 1.00 | 22.72 |
| ATOM | 2296 | CA | GLY | A | 298 | −17.050 | 36.869 | −6.219 | 1.00 | 22.99 |
| ATOM | 2297 | C | GLY | A | 298 | −18.043 | 35.720 | −6.278 | 1.00 | 23.54 |
| ATOM | 2298 | O | GLY | A | 298 | −19.180 | 35.885 | −5.855 | 1.00 | 25.04 |
| ATOM | 2299 | N | ILE | A | 299 | −17.647 | 34.546 | −6.784 | 1.00 | 22.16 |
| ATOM | 2300 | CA | ILE | A | 299 | −18.574 | 33.393 | −6.763 | 1.00 | 21.47 |
| ATOM | 2301 | CB | ILE | A | 299 | −18.251 | 32.350 | −7.884 | 1.00 | 21.22 |
| ATOM | 2302 | CG1 | ILE | A | 299 | −18.356 | 32.985 | −9.274 | 1.00 | 19.64 |
| ATOM | 2303 | CD1 | ILE | A | 299 | −17.740 | 32.095 | −10.415 | 1.00 | 19.76 |
| ATOM | 2304 | CG2 | ILE | A | 299 | −19.163 | 31.091 | −7.762 | 1.00 | 20.54 |
| ATOM | 2305 | C | ILE | A | 299 | −18.562 | 32.740 | −5.375 | 1.00 | 22.34 |
| ATOM | 2306 | O | ILE | A | 299 | −17.486 | 32.395 | −4.861 | 1.00 | 22.29 |
| ATOM | 2307 | N | PRO | A | 300 | −19.743 | 32.580 | −4.751 | 1.00 | 23.04 |
| ATOM | 2308 | CA | PRO | A | 300 | −19.791 | 32.018 | −3.392 | 1.00 | 23.60 |
| ATOM | 2309 | CB | PRO | A | 300 | −21.217 | 32.364 | −2.922 | 1.00 | 24.19 |
| ATOM | 2310 | CG | PRO | A | 300 | −22.015 | 32.437 | −4.178 | 1.00 | 23.80 |
| ATOM | 2311 | CD | PRO | A | 300 | −21.085 | 32.934 | −5.253 | 1.00 | 23.06 |
| ATOM | 2312 | C | PRO | A | 300 | −19.584 | 30.500 | −3.322 | 1.00 | 23.50 |
| ATOM | 2313 | O | PRO | A | 300 | −19.664 | 29.810 | −4.347 | 1.00 | 22.46 |
| ATOM | 2314 | N | ALA | A | 301 | −19.325 | 29.985 | −2.116 | 1.00 | 22.68 |
| ATOM | 2315 | CA | ALA | A | 301 | −19.380 | 28.549 | −1.905 | 1.00 | 22.89 |
| ATOM | 2316 | CB | ALA | A | 301 | −18.988 | 28.185 | −0.465 | 1.00 | 23.54 |
| ATOM | 2317 | C | ALA | A | 301 | −20.788 | 28.074 | −2.236 | 1.00 | 21.91 |
| ATOM | 2318 | O | ALA | A | 301 | −21.759 | 28.834 | −2.108 | 1.00 | 23.09 |

TABLE 15-continued

| | | | | | | | | | |
|---|---|---|---|---|---|---|---|---|---|
| ATOM | 2319 | N | GLY | A | 302 | −20.898 | 26.838 | −2.698 | 1.00 | 20.96 |
| ATOM | 2320 | CA | GLY | A | 302 | −22.173 | 26.272 | −3.115 | 1.00 | 19.69 |
| ATOM | 2321 | C | GLY | A | 302 | −22.565 | 26.637 | −4.537 | 1.00 | 19.78 |
| ATOM | 2322 | O | GLY | A | 302 | −23.661 | 26.283 | −4.991 | 1.00 | 19.32 |
| ATOM | 2323 | N | ALA | A | 303 | −21.686 | 27.355 | −5.235 | 1.00 | 17.97 |
| ATOM | 2324 | CA | ALA | A | 303 | −21.948 | 27.708 | −6.635 | 1.00 | 17.13 |
| ATOM | 2325 | CB | ALA | A | 303 | −22.168 | 29.212 | −6.812 | 1.00 | 16.73 |
| ATOM | 2326 | C | ALA | A | 303 | −20.784 | 27.245 | −7.481 | 1.00 | 16.19 |
| ATOM | 2327 | O | ALA | A | 303 | −19.647 | 27.171 | −7.004 | 1.00 | 16.23 |
| ATOM | 2328 | N | ALA | A | 304 | −21.067 | 26.956 | −8.746 | 1.00 | 15.66 |
| ATOM | 2329 | CA | ALA | A | 304 | −20.069 | 26.378 | −9.640 | 1.00 | 15.10 |
| ATOM | 2330 | CB | ALA | A | 304 | −20.750 | 25.795 | −10.860 | 1.00 | 15.80 |
| ATOM | 2331 | C | ALA | A | 304 | −19.002 | 27.394 | −10.044 | 1.00 | 14.74 |
| ATOM | 2332 | O | ALA | A | 304 | −19.270 | 28.587 | −10.121 | 1.00 | 14.27 |
| ATOM | 2333 | N | VAL | A | 305 | −17.783 | 26.914 | −10.300 | 1.00 | 14.18 |
| ATOM | 2334 | CA | VAL | A | 305 | −16.680 | 27.783 | −10.698 | 1.00 | 13.54 |
| ATOM | 2335 | CB | VAL | A | 305 | −15.656 | 27.971 | −9.543 | 1.00 | 13.42 |
| ATOM | 2336 | CG1 | VAL | A | 305 | −16.224 | 28.881 | −8.418 | 1.00 | 14.25 |
| ATOM | 2337 | CG2 | VAL | A | 305 | −15.218 | 26.597 | −8.966 | 1.00 | 14.99 |
| ATOM | 2338 | C | VAL | A | 305 | −15.952 | 27.141 | −11.873 | 1.00 | 13.34 |
| ATOM | 2339 | O | VAL | A | 305 | −16.121 | 25.944 | −12.126 | 1.00 | 12.46 |
| ATOM | 2340 | N | ALA | A | 306 | −15.130 | 27.921 | −12.562 | 1.00 | 13.38 |
| ATOM | 2341 | CA | ALA | A | 306 | −14.233 | 27.376 | −13.573 | 1.00 | 14.37 |
| ATOM | 2342 | CB | ALA | A | 306 | −13.709 | 28.504 | −14.470 | 1.00 | 15.32 |
| ATOM | 2343 | C | ALA | A | 306 | −13.082 | 26.626 | −12.938 | 1.00 | 14.68 |
| ATOM | 2344 | O | ALA | A | 306 | −12.457 | 27.116 | −11.974 | 1.00 | 15.21 |
| ATOM | 2345 | N | ILE | A | 307 | −12.781 | 25.452 | −13.484 | 1.00 | 13.50 |
| ATOM | 2346 | CA | ILE | A | 307 | −11.667 | 24.668 | −12.975 | 1.00 | 13.67 |
| ATOM | 2347 | CB | ILE | A | 307 | −12.134 | 23.438 | −12.163 | 1.00 | 14.45 |
| ATOM | 2348 | CG1 | ILE | A | 307 | −12.756 | 22.386 | −13.072 | 1.00 | 15.37 |
| ATOM | 2349 | CD1 | ILE | A | 307 | −12.921 | 21.033 | −12.368 | 1.00 | 19.15 |
| ATOM | 2350 | CG2 | ILE | A | 307 | −13.119 | 23.848 | −11.005 | 1.00 | 15.52 |
| ATOM | 2351 | C | ILE | A | 307 | −10.646 | 24.290 | −14.059 | 1.00 | 12.52 |
| ATOM | 2352 | O | ILE | A | 307 | −10.974 | 24.232 | −15.264 | 1.00 | 12.22 |
| ATOM | 2353 | N | GLY | A | 308 | −9.405 | 24.095 | −13.604 | 1.00 | 11.71 |
| ATOM | 2354 | CA | GLY | A | 308 | −8.276 | 23.737 | −14.452 | 1.00 | 11.64 |
| ATOM | 2355 | C | GLY | A | 308 | −7.853 | 22.306 | −14.199 | 1.00 | 11.62 |
| ATOM | 2356 | O | GLY | A | 308 | −8.667 | 21.444 | −13.806 | 1.00 | 12.05 |
| ATOM | 2357 | N | ARG | A | 309 | −6.583 | 22.026 | −14.454 | 1.00 | 11.39 |
| ATOM | 2358 | CA | ARG | A | 309 | −6.091 | 20.661 | −14.337 | 1.00 | 11.23 |
| ATOM | 2359 | CB | ARG | A | 309 | −4.896 | 20.467 | −15.275 | 1.00 | 11.37 |
| ATOM | 2360 | CG | ARG | A | 309 | −5.220 | 20.697 | −16.791 | 1.00 | 11.29 |
| ATOM | 2361 | CD | ARG | A | 309 | −4.066 | 20.130 | −17.625 | 1.00 | 12.62 |
| ATOM | 2362 | NE | ARG | A | 309 | −2.845 | 20.919 | −17.425 | 1.00 | 12.15 |
| ATOM | 2363 | CZ | ARG | A | 309 | −1.701 | 20.665 | −18.047 | 1.00 | 15.00 |
| ATOM | 2364 | NH1 | ARG | A | 309 | −1.630 | 19.633 | −18.910 | 1.00 | 12.05 |
| ATOM | 2365 | NH2 | ARG | A | 309 | −0.624 | 21.395 | −17.778 | 1.00 | 13.85 |
| ATOM | 2366 | C | ARG | A | 309 | −5.654 | 20.425 | −12.888 | 1.00 | 11.83 |
| ATOM | 2367 | O | ARG | A | 309 | −6.093 | 19.481 | −12.221 | 1.00 | 11.38 |
| ATOM | 2368 | N | TYR | A | 310 | −4.806 | 21.322 | −12.399 | 1.00 | 11.88 |
| ATOM | 2369 | CA | TYR | A | 310 | −4.293 | 21.215 | −11.022 | 1.00 | 11.17 |
| ATOM | 2370 | CB | TYR | A | 310 | −3.225 | 20.082 | −10.878 | 1.00 | 12.49 |
| ATOM | 2371 | CG | TYR | A | 310 | −2.065 | 20.201 | −11.844 | 1.00 | 13.10 |
| ATOM | 2372 | CD1 | TYR | A | 310 | −2.128 | 19.622 | −13.138 | 1.00 | 12.57 |
| ATOM | 2373 | CE1 | TYR | A | 310 | −1.069 | 19.772 | −14.039 | 1.00 | 15.63 |
| ATOM | 2374 | CZ | TYR | A | 310 | 0.065 | 20.475 | −13.649 | 1.00 | 14.31 |
| ATOM | 2375 | OH | TYR | A | 310 | 1.119 | 20.611 | −14.529 | 1.00 | 14.42 |
| ATOM | 2376 | CE2 | TYR | A | 310 | 0.159 | 21.030 | −12.379 | 1.00 | 12.68 |
| ATOM | 2377 | CD2 | TYR | A | 310 | −0.909 | 20.906 | −11.485 | 1.00 | 14.04 |
| ATOM | 2378 | C | TYR | A | 310 | −3.779 | 22.596 | −10.644 | 1.00 | 12.74 |
| ATOM | 2379 | O | TYR | A | 310 | −3.333 | 23.356 | −11.505 | 1.00 | 12.44 |
| ATOM | 2380 | N | ALA | A | 311 | −3.872 | 22.945 | −9.362 | 1.00 | 11.99 |
| ATOM | 2381 | CA | ALA | A | 311 | −3.618 | 24.337 | −8.975 | 1.00 | 13.33 |
| ATOM | 2382 | CB | ALA | A | 311 | −4.084 | 24.589 | −7.508 | 1.00 | 12.88 |
| ATOM | 2383 | C | ALA | A | 311 | −2.157 | 24.768 | −9.197 | 1.00 | 13.50 |
| ATOM | 2384 | O | ALA | A | 311 | −1.906 | 25.951 | −9.468 | 1.00 | 14.52 |
| ATOM | 2385 | N | GLU | A | 312 | −1.216 | 23.823 | −9.140 | 1.00 | 13.52 |
| ATOM | 2386 | CA | GLU | A | 312 | 0.219 | 24.134 | −9.332 | 1.00 | 14.23 |
| ATOM | 2387 | CB | GLU | A | 312 | 1.111 | 23.020 | −8.790 | 1.00 | 15.44 |
| ATOM | 2388 | CG | GLU | A | 312 | 0.933 | 22.802 | −7.303 | 1.00 | 16.54 |
| ATOM | 2389 | CD | GLU | A | 312 | −0.130 | 21.762 | −6.950 | 1.00 | 18.91 |
| ATOM | 2390 | OE1 | GLU | A | 312 | −0.941 | 21.338 | −7.808 | 1.00 | 16.89 |
| ATOM | 2391 | OE2 | GLU | A | 312 | −0.150 | 21.345 | −5.778 | 1.00 | 18.72 |
| ATOM | 2392 | C | GLU | A | 312 | 0.591 | 24.380 | −10.796 | 1.00 | 14.80 |
| ATOM | 2393 | O | GLU | A | 312 | 1.741 | 24.736 | −11.100 | 1.00 | 14.98 |
| ATOM | 2394 | N | ASP | A | 313 | −0.374 | 24.197 | −11.697 | 1.00 | 13.37 |
| ATOM | 2395 | CA | ASP | A | 313 | −0.112 | 24.258 | −13.155 | 1.00 | 13.71 |
| ATOM | 2396 | CB | ASP | A | 313 | −1.457 | 24.079 | −13.888 | 1.00 | 12.88 |
| ATOM | 2397 | CG | ASP | A | 313 | −1.320 | 23.671 | −15.343 | 1.00 | 14.44 |
| ATOM | 2398 | OD1 | ASP | A | 313 | −0.197 | 23.597 | −15.900 | 1.00 | 13.19 |

TABLE 15-continued

| ATOM | 2399 | OD2 | ASP | A | 313 | −2.400 | 23.406 | −15.923 | 1.00 | 13.61 |
| ATOM | 2400 | C | ASP | A | 313 | 0.512 | 25.589 | −13.587 | 1.00 | 14.00 |
| ATOM | 2401 | O | ASP | A | 313 | 0.007 | 26.662 | −13.219 | 1.00 | 14.35 |
| ATOM | 2402 | N | VAL | A | 314 | 1.577 | 25.530 | −14.399 | 1.00 | 13.84 |
| ATOM | 2403 | CA | VAL | A | 314 | 2.145 | 26.747 | −14.988 | 1.00 | 15.19 |
| ATOM | 2404 | CB | VAL | A | 314 | 3.602 | 27.016 | −14.520 | 1.00 | 16.70 |
| ATOM | 2405 | CG1 | VAL | A | 314 | 3.638 | 27.295 | −13.009 | 1.00 | 17.94 |
| ATOM | 2406 | CG2 | VAL | A | 314 | 4.551 | 25.857 | −14.915 | 1.00 | 16.69 |
| ATOM | 2407 | C | VAL | A | 314 | 2.123 | 26.729 | −16.528 | 1.00 | 15.30 |
| ATOM | 2408 | O | VAL | A | 314 | 2.712 | 27.598 | −17.165 | 1.00 | 15.13 |
| ATOM | 2409 | N | TYR | A | 315 | 1.441 | 25.743 | −17.111 | 1.00 | 14.51 |
| ATOM | 2410 | CA | TYR | A | 315 | 1.351 | 25.634 | −18.580 | 1.00 | 15.65 |
| ATOM | 2411 | CB | TYR | A | 315 | 0.768 | 24.264 | −18.957 | 1.00 | 15.82 |
| ATOM | 2412 | CG | TYR | A | 315 | 0.694 | 23.988 | −20.457 | 1.00 | 16.29 |
| ATOM | 2413 | CD1 | TYR | A | 315 | 1.824 | 24.124 | −21.265 | 1.00 | 17.01 |
| ATOM | 2414 | CE1 | TYR | A | 315 | 1.778 | 23.859 | −22.634 | 1.00 | 18.92 |
| ATOM | 2415 | CZ | TYR | A | 315 | 0.588 | 23.421 | −23.208 | 1.00 | 16.14 |
| ATOM | 2416 | OH | TYR | A | 315 | 0.557 | 23.164 | −24.577 | 1.00 | 16.95 |
| ATOM | 2417 | CE2 | TYR | A | 315 | −0.552 | 23.261 | −22.423 | 1.00 | 15.41 |
| ATOM | 2418 | CD2 | TYR | A | 315 | −0.492 | 23.539 | −21.044 | 1.00 | 14.48 |
| ATOM | 2419 | C | TYR | A | 315 | 0.489 | 26.777 | −19.107 | 1.00 | 15.56 |
| ATOM | 2420 | O | TYR | A | 315 | −0.688 | 26.888 | −18.748 | 1.00 | 16.36 |
| ATOM | 2421 | N | TYR | A | 316 | 1.072 | 27.645 | −19.944 | 1.00 | 16.61 |
| ATOM | 2422 | CA | TYR | A | 316 | 0.404 | 28.890 | −20.380 | 1.00 | 17.53 |
| ATOM | 2423 | CB | TYR | A | 316 | −0.778 | 28.603 | −21.337 | 1.00 | 18.31 |
| ATOM | 2424 | CG | TYR | A | 316 | −0.329 | 28.321 | −22.742 | 1.00 | 19.74 |
| ATOM | 2425 | CD1 | TYR | A | 316 | −0.071 | 27.026 | −23.169 | 1.00 | 18.95 |
| ATOM | 2426 | CE1 | TYR | A | 316 | 0.353 | 26.757 | −24.466 | 1.00 | 18.69 |
| ATOM | 2427 | CZ | TYR | A | 316 | 0.551 | 27.812 | −25.342 | 1.00 | 21.77 |
| ATOM | 2428 | OH | TYR | A | 316 | 1.002 | 27.557 | −26.617 | 1.00 | 23.75 |
| ATOM | 2429 | CE2 | TYR | A | 316 | 0.329 | 29.125 | −24.932 | 1.00 | 22.39 |
| ATOM | 2430 | CD2 | TYR | A | 316 | −0.111 | 29.369 | −23.639 | 1.00 | 21.90 |
| ATOM | 2431 | C | TYR | A | 316 | −0.037 | 29.730 | −19.173 | 1.00 | 17.87 |
| ATOM | 2432 | O | TYR | A | 316 | −0.968 | 30.517 | −19.266 | 1.00 | 17.06 |
| ATOM | 2433 | N | ASN | A | 317 | 0.689 | 29.555 | −18.066 | 1.00 | 18.34 |
| ATOM | 2434 | CA | ASN | A | 317 | 0.483 | 30.231 | −16.766 | 1.00 | 19.27 |
| ATOM | 2435 | CB | ASN | A | 317 | 0.106 | 31.699 | −16.921 | 1.00 | 20.01 |
| ATOM | 2436 | CG | ASN | A | 317 | 1.171 | 32.489 | −17.624 | 1.00 | 24.51 |
| ATOM | 2437 | OD1 | ASN | A | 317 | 2.363 | 32.384 | −17.305 | 1.00 | 29.46 |
| ATOM | 2438 | ND2 | ASN | A | 317 | 0.756 | 33.269 | −18.603 | 1.00 | 29.08 |
| ATOM | 2439 | C | ASN | A | 317 | −0.506 | 29.551 | −15.842 | 1.00 | 18.28 |
| ATOM | 2440 | O | ASN | A | 317 | −0.706 | 30.001 | −14.719 | 1.00 | 19.05 |
| ATOM | 2441 | N | GLY | A | 318 | −1.114 | 28.459 | −16.300 | 1.00 | 17.74 |
| ATOM | 2442 | CA | GLY | A | 318 | −2.086 | 27.721 | −15.475 | 1.00 | 15.34 |
| ATOM | 2443 | C | GLY | A | 318 | −3.458 | 28.356 | −15.550 | 1.00 | 15.47 |
| ATOM | 2444 | O | GLY | A | 318 | −3.700 | 29.390 | −14.932 | 1.00 | 15.75 |
| ATOM | 2445 | N | ASN | A | 319 | −4.369 | 27.733 | −16.306 | 1.00 | 13.16 |
| ATOM | 2446 | CA | ASN | A | 319 | −5.672 | 28.305 | −16.557 | 1.00 | 12.74 |
| ATOM | 2447 | CB | ASN | A | 319 | −5.693 | 28.883 | −17.980 | 1.00 | 12.31 |
| ATOM | 2448 | CG | ASN | A | 319 | −4.676 | 29.979 | −18.187 | 1.00 | 13.01 |
| ATOM | 2449 | OD1 | ASN | A | 319 | −4.832 | 31.117 | −17.699 | 1.00 | 14.18 |
| ATOM | 2450 | ND2 | ASN | A | 319 | −3.640 | 29.665 | −18.942 | 1.00 | 11.49 |
| ATOM | 2451 | C | ASN | A | 319 | −6.799 | 27.271 | −16.442 | 1.00 | 12.27 |
| ATOM | 2452 | O | ASN | A | 319 | −6.545 | 26.071 | −16.456 | 1.00 | 12.28 |
| ATOM | 2453 | N | PRO | A | 320 | −8.054 | 27.732 | −16.334 | 1.00 | 12.96 |
| ATOM | 2454 | CA | PRO | A | 320 | −9.113 | 26.759 | −16.472 | 1.00 | 12.58 |
| ATOM | 2455 | CB | PRO | A | 320 | −10.395 | 27.579 | −16.324 | 1.00 | 13.28 |
| ATOM | 2456 | CG | PRO | A | 320 | −10.007 | 29.011 | −16.183 | 1.00 | 14.34 |
| ATOM | 2457 | CD | PRO | A | 320 | −8.537 | 29.090 | −15.991 | 1.00 | 12.66 |
| ATOM | 2458 | C | PRO | A | 320 | −9.101 | 26.090 | −17.851 | 1.00 | 12.18 |
| ATOM | 2459 | O | PRO | A | 320 | −8.643 | 26.698 | −18.820 | 1.00 | 11.99 |
| ATOM | 2460 | N | TRP | A | 321 | −9.589 | 24.852 | −17.912 | 1.00 | 11.79 |
| ATOM | 2461 | CA | TRP | A | 321 | −9.739 | 24.116 | −19.154 | 1.00 | 11.97 |
| ATOM | 2462 | CB | TRP | A | 321 | −8.988 | 22.775 | −19.063 | 1.00 | 11.15 |
| ATOM | 2463 | CG | TRP | A | 321 | −7.469 | 22.900 | −19.200 | 1.00 | 12.16 |
| ATOM | 2464 | CD1 | TRP | A | 321 | −6.658 | 23.837 | −18.627 | 1.00 | 13.28 |
| ATOM | 2465 | NE1 | TRP | A | 321 | −5.347 | 23.636 | −19.016 | 1.00 | 13.24 |
| ATOM | 2466 | CE2 | TRP | A | 321 | −5.290 | 22.538 | −19.831 | 1.00 | 13.51 |
| ATOM | 2467 | CD2 | TRP | A | 321 | −6.617 | 22.054 | −19.978 | 1.00 | 12.68 |
| ATOM | 2468 | CE3 | TRP | A | 321 | −6.846 | 20.938 | −20.787 | 1.00 | 14.41 |
| ATOM | 2469 | CZ3 | TRP | A | 321 | −5.741 | 20.323 | −21.428 | 1.00 | 13.49 |
| ATOM | 2470 | CH2 | TRP | A | 321 | −4.436 | 20.819 | −21.250 | 1.00 | 13.43 |
| ATOM | 2471 | CZ2 | TRP | A | 321 | −4.193 | 21.948 | −20.479 | 1.00 | 14.69 |
| ATOM | 2472 | C | TRP | A | 321 | −11.202 | 23.797 | −19.342 | 1.00 | 11.99 |
| ATOM | 2473 | O | TRP | A | 321 | −11.875 | 23.448 | −18.388 | 1.00 | 11.51 |
| ATOM | 2474 | N | TYR | A | 322 | −11.696 | 23.896 | −20.579 | 1.00 | 11.47 |
| ATOM | 2475 | CA | TYR | A | 322 | −13.088 | 23.511 | −20.841 | 1.00 | 11.31 |
| ATOM | 2476 | CB | TYR | A | 322 | −13.433 | 23.691 | −22.322 | 1.00 | 12.14 |
| ATOM | 2477 | CG | TYR | A | 322 | −13.352 | 25.130 | −22.793 | 1.00 | 12.81 |
| ATOM | 2478 | CD1 | TYR | A | 322 | −12.260 | 25.574 | −23.509 | 1.00 | 11.43 |

TABLE 15-continued

| ATOM | 2479 | CE1 | TYR | A | 322 | −12.173 | 26.914 | −23.965 | 1.00 | 12.91 |
| --- | --- | --- | --- | --- | --- | --- | --- | --- | --- | --- |
| ATOM | 2480 | CZ | TYR | A | 322 | −13.216 | 27.802 | −23.697 | 1.00 | 14.27 |
| ATOM | 2481 | OH | TYR | A | 322 | −13.127 | 29.104 | −24.146 | 1.00 | 15.10 |
| ATOM | 2482 | CE2 | TYR | A | 322 | −14.324 | 27.373 | −22.982 | 1.00 | 13.40 |
| ATOM | 2483 | CD2 | TYR | A | 322 | −14.378 | 26.031 | −22.522 | 1.00 | 11.58 |
| ATOM | 2484 | C | TYR | A | 322 | −13.367 | 22.082 | −20.433 | 1.00 | 11.31 |
| ATOM | 2485 | O | TYR | A | 322 | −14.380 | 21.795 | −19.771 | 1.00 | 11.08 |
| ATOM | 2486 | N | LEU | A | 323 | −12.480 | 21.169 | −20.814 | 1.00 | 10.96 |
| ATOM | 2487 | CA | LEU | A | 323 | −12.770 | 19.750 | −20.561 | 1.00 | 11.04 |
| ATOM | 2488 | CB | LEU | A | 323 | −11.787 | 18.844 | −21.315 | 1.00 | 11.26 |
| ATOM | 2489 | CG | LEU | A | 323 | −10.314 | 18.876 | −20.903 | 1.00 | 10.53 |
| ATOM | 2490 | CD1 | LEU | A | 323 | −10.074 | 17.902 | −19.745 | 1.00 | 14.57 |
| ATOM | 2491 | CD2 | LEU | A | 323 | −9.474 | 18.437 | −22.112 | 1.00 | 13.19 |
| ATOM | 2492 | C | LEU | A | 323 | −12.778 | 19.449 | −19.048 | 1.00 | 11.68 |
| ATOM | 2493 | O | LEU | A | 323 | −13.444 | 18.510 | −18.602 | 1.00 | 12.06 |
| ATOM | 2494 | N | ALA | A | 324 | −12.036 | 20.239 | −18.268 | 1.00 | 9.86 |
| ATOM | 2495 | CA | ALA | A | 324 | −11.969 | 20.017 | −16.812 | 1.00 | 10.09 |
| ATOM | 2496 | CB | ALA | A | 324 | −10.746 | 20.767 | −16.234 | 1.00 | 9.76 |
| ATOM | 2497 | C | ALA | A | 324 | −13.272 | 20.518 | −16.178 | 1.00 | 10.17 |
| ATOM | 2498 | O | ALA | A | 324 | −13.866 | 19.840 | −15.325 | 1.00 | 10.29 |
| ATOM | 2499 | N | THR | A | 325 | −13.758 | 21.662 | −16.665 | 1.00 | 9.84 |
| ATOM | 2500 | CA | THR | A | 325 | −15.000 | 22.267 | −16.172 | 1.00 | 11.14 |
| ATOM | 2501 | CB | THR | A | 325 | −15.102 | 23.765 | −16.623 | 1.00 | 12.15 |
| ATOM | 2502 | OG1 | THR | A | 325 | −14.002 | 24.498 | −16.063 | 1.00 | 13.16 |
| ATOM | 2503 | CG2 | THR | A | 325 | −16.402 | 24.411 | −16.152 | 1.00 | 11.83 |
| ATOM | 2504 | C | THR | A | 325 | −16.218 | 21.413 | −16.570 | 1.00 | 11.50 |
| ATOM | 2505 | O | THR | A | 325 | −17.086 | 21.126 | −15.727 | 1.00 | 10.79 |
| ATOM | 2506 | N | PHE | A | 326 | −16.234 | 20.925 | −17.816 | 1.00 | 10.79 |
| ATOM | 2507 | CA | PHE | A | 326 | −17.272 | 19.959 | −18.240 | 1.00 | 12.12 |
| ATOM | 2508 | CB | PHE | A | 326 | −17.194 | 19.652 | −19.746 | 1.00 | 12.14 |
| ATOM | 2509 | CG | PHE | A | 326 | −17.518 | 20.851 | −20.640 | 1.00 | 13.71 |
| ATOM | 2510 | CD1 | PHE | A | 326 | −16.777 | 21.077 | −21.804 | 1.00 | 15.21 |
| ATOM | 2511 | CE1 | PHE | A | 326 | −17.043 | 22.188 | −22.635 | 1.00 | 14.99 |
| ATOM | 2512 | CZ | PHE | A | 326 | −18.072 | 23.066 | −22.311 | 1.00 | 16.33 |
| ATOM | 2513 | CE2 | PHE | A | 326 | −18.851 | 22.832 | −21.160 | 1.00 | 20.12 |
| ATOM | 2514 | CD2 | PHE | A | 326 | −18.561 | 21.717 | −20.331 | 1.00 | 16.63 |
| ATOM | 2515 | C | PHE | A | 326 | −17.216 | 18.643 | −17.464 | 1.00 | 11.56 |
| ATOM | 2516 | O | PHE | A | 326 | −18.263 | 18.069 | −17.180 | 1.00 | 11.74 |
| ATOM | 2517 | N | ALA | A | 327 | −16.014 | 18.174 | −17.103 | 1.00 | 11.35 |
| ATOM | 2518 | CA | ALA | A | 327 | −15.889 | 16.909 | −16.346 | 1.00 | 11.41 |
| ATOM | 2519 | CB | ALA | A | 327 | −14.397 | 16.538 | −16.158 | 1.00 | 11.95 |
| ATOM | 2520 | C | ALA | A | 327 | −16.612 | 16.964 | −14.965 | 1.00 | 12.04 |
| ATOM | 2521 | O | ALA | A | 327 | −17.260 | 15.985 | −14.561 | 1.00 | 12.69 |
| ATOM | 2522 | N | ALA | A | 328 | −16.505 | 18.097 | −14.266 | 1.00 | 12.13 |
| ATOM | 2523 | CA | ALA | A | 328 | −17.207 | 18.293 | −12.985 | 1.00 | 12.24 |
| ATOM | 2524 | CB | ALA | A | 328 | −16.871 | 19.662 | −12.369 | 1.00 | 12.48 |
| ATOM | 2525 | C | ALA | A | 328 | −18.707 | 18.157 | −13.177 | 1.00 | 12.90 |
| ATOM | 2526 | O | ALA | A | 328 | −19.378 | 17.454 | −12.411 | 1.00 | 13.60 |
| ATOM | 2527 | N | ALA | A | 329 | −19.239 | 18.814 | −14.202 | 1.00 | 12.55 |
| ATOM | 2528 | CA | ALA | A | 329 | −20.669 | 18.682 | −14.504 | 1.00 | 12.31 |
| ATOM | 2529 | CB | ALA | A | 329 | −21.027 | 19.551 | −15.692 | 1.00 | 12.87 |
| ATOM | 2530 | C | ALA | A | 329 | −21.035 | 17.226 | −14.788 | 1.00 | 12.71 |
| ATOM | 2531 | O | ALA | A | 329 | −22.016 | 16.700 | −14.266 | 1.00 | 12.32 |
| ATOM | 2532 | N | GLU | A | 330 | −20.231 | 16.572 | −15.629 | 1.00 | 12.54 |
| ATOM | 2533 | CA | GLU | A | 330 | −20.500 | 15.187 | −16.003 | 1.00 | 12.84 |
| ATOM | 2534 | CB | GLU | A | 330 | −19.519 | 14.718 | −17.100 | 1.00 | 12.55 |
| ATOM | 2535 | CG | GLU | A | 330 | −19.850 | 13.303 | −17.626 | 1.00 | 13.80 |
| ATOM | 2536 | CD | GLU | A | 330 | −19.108 | 12.953 | −18.917 | 1.00 | 13.54 |
| ATOM | 2537 | OE1 | GLU | A | 330 | −18.650 | 13.889 | −19.604 | 1.00 | 12.29 |
| ATOM | 2538 | OE2 | GLU | A | 330 | −18.998 | 11.739 | −19.209 | 1.00 | 14.52 |
| ATOM | 2539 | C | GLU | A | 330 | −20.523 | 14.231 | −14.809 | 1.00 | 12.94 |
| ATOM | 2540 | O | GLU | A | 330 | −21.400 | 13.346 | −14.726 | 1.00 | 12.90 |
| ATOM | 2541 | N | GLN | A | 331 | −19.598 | 14.402 | −13.866 | 1.00 | 12.03 |
| ATOM | 2542 | CA | GLN | A | 331 | −19.589 | 13.502 | −12.726 | 1.00 | 12.38 |
| ATOM | 2543 | CB | GLN | A | 331 | −18.415 | 13.795 | −11.797 | 1.00 | 12.24 |
| ATOM | 2544 | CG | GLN | A | 331 | −18.357 | 12.759 | −10.670 | 1.00 | 13.61 |
| ATOM | 2545 | CD | GLN | A | 331 | −17.327 | 13.072 | −9.608 | 1.00 | 15.82 |
| ATOM | 2546 | OE1 | GLN | A | 331 | −16.263 | 13.617 | −9.895 | 1.00 | 15.39 |
| ATOM | 2547 | NE2 | GLN | A | 331 | −17.628 | 12.702 | −8.372 | 1.00 | 13.76 |
| ATOM | 2548 | C | GLN | A | 331 | −20.912 | 13.643 | −11.969 | 1.00 | 12.33 |
| ATOM | 2549 | O | GLN | A | 331 | −21.512 | 12.659 | −11.556 | 1.00 | 12.45 |
| ATOM | 2550 | N | LEU | A | 332 | −21.377 | 14.873 | −11.844 | 1.00 | 12.57 |
| ATOM | 2551 | CA | LEU | A | 332 | −22.628 | 15.138 | −11.134 | 1.00 | 13.59 |
| ATOM | 2552 | CB | LEU | A | 332 | −22.747 | 16.631 | −10.868 | 1.00 | 13.17 |
| ATOM | 2553 | CG | LEU | A | 332 | −21.681 | 17.142 | −9.867 | 1.00 | 16.56 |
| ATOM | 2554 | CD1 | LEU | A | 332 | −21.718 | 18.678 | −9.801 | 1.00 | 18.10 |
| ATOM | 2555 | CD2 | LEU | A | 332 | −21.851 | 16.476 | −8.492 | 1.00 | 19.47 |
| ATOM | 2556 | C | LEU | A | 332 | −23.861 | 14.600 | −11.864 | 1.00 | 13.57 |
| ATOM | 2557 | O | LEU | A | 332 | −24.770 | 14.053 | −11.239 | 1.00 | 13.24 |
| ATOM | 2558 | N | TYR | A | 333 | −23.909 | 14.766 | −13.179 | 1.00 | 13.90 |

TABLE 15-continued

| ATOM | 2559 | CA | TYR | A | 333 | −24.988 | 14.131 | −13.972 | 1.00 | 14.37 |
|---|---|---|---|---|---|---|---|---|---|---|
| ATOM | 2560 | CB | TYR | A | 333 | −24.901 | 14.523 | −15.468 | 1.00 | 14.48 |
| ATOM | 2561 | CG | TYR | A | 333 | −25.056 | 16.001 | −15.721 | 1.00 | 13.91 |
| ATOM | 2562 | CD1 | TYR | A | 333 | −26.086 | 16.738 | −15.118 | 1.00 | 14.64 |
| ATOM | 2563 | CE1 | TYR | A | 333 | −26.208 | 18.117 | −15.350 | 1.00 | 15.65 |
| ATOM | 2564 | CZ | TYR | A | 333 | −25.315 | 18.758 | −16.196 | 1.00 | 16.47 |
| ATOM | 2565 | OH | TYR | A | 333 | −25.431 | 20.101 | −16.442 | 1.00 | 17.22 |
| ATOM | 2566 | CE2 | TYR | A | 333 | −24.310 | 18.050 | −16.836 | 1.00 | 16.59 |
| ATOM | 2567 | CD2 | TYR | A | 333 | −24.192 | 16.669 | −16.601 | 1.00 | 11.27 |
| ATOM | 2568 | C | TYR | A | 333 | −25.022 | 12.613 | −13.843 | 1.00 | 15.03 |
| ATOM | 2569 | O | TYR | A | 333 | −26.108 | 12.012 | −13.824 | 1.00 | 14.78 |
| ATOM | 2570 | N | ASP | A | 334 | −23.836 | 11.998 | −13.807 | 1.00 | 14.06 |
| ATOM | 2571 | CA | ASP | A | 334 | −23.714 | 10.555 | −13.602 | 1.00 | 14.83 |
| ATOM | 2572 | CB | ASP | A | 334 | −22.239 | 10.114 | −13.714 | 1.00 | 13.83 |
| ATOM | 2573 | CG | ASP | A | 334 | −21.708 | 10.149 | −15.136 | 1.00 | 15.84 |
| ATOM | 2574 | OD1 | ASP | A | 334 | −22.495 | 10.373 | −16.081 | 1.00 | 13.95 |
| ATOM | 2575 | OD2 | ASP | A | 334 | −20.470 | 9.943 | −15.313 | 1.00 | 15.50 |
| ATOM | 2576 | C | ASP | A | 334 | −24.254 | 10.163 | −12.224 | 1.00 | 15.21 |
| ATOM | 2577 | O | ASP | A | 334 | −24.941 | 9.132 | −12.080 | 1.00 | 15.93 |
| ATOM | 2578 | N | ALA | A | 335 | −23.933 | 10.969 | −11.213 | 1.00 | 15.09 |
| ATOM | 2579 | CA | ALA | A | 335 | −24.454 | 10.735 | −9.855 | 1.00 | 16.00 |
| ATOM | 2580 | CB | ALA | A | 335 | −23.809 | 11.719 | −8.864 | 1.00 | 15.13 |
| ATOM | 2581 | C | ALA | A | 335 | −25.980 | 10.823 | −9.803 | 1.00 | 16.10 |
| ATOM | 2582 | O | ALA | A | 335 | −26.643 | 9.916 | −9.245 | 1.00 | 16.77 |
| ATOM | 2583 | N | ILE | A | 336 | −26.530 | 11.879 | −10.398 | 1.00 | 16.35 |
| ATOM | 2584 | CA | ILE | A | 336 | −27.987 | 12.087 | −10.470 | 1.00 | 18.39 |
| ATOM | 2585 | CB | ILE | A | 336 | −28.332 | 13.422 | −11.162 | 1.00 | 18.85 |
| ATOM | 2586 | CG1 | ILE | A | 336 | −27.891 | 14.596 | −10.279 | 1.00 | 19.14 |
| ATOM | 2587 | CD1 | ILE | A | 336 | −27.879 | 15.904 | −10.986 | 1.00 | 22.50 |
| ATOM | 2588 | CG2 | ILE | A | 336 | −29.839 | 13.539 | −11.506 | 1.00 | 20.14 |
| ATOM | 2589 | C | ILE | A | 336 | −28.681 | 10.902 | −11.156 | 1.00 | 18.83 |
| ATOM | 2590 | O | ILE | A | 336 | −29.707 | 10.404 | −10.675 | 1.00 | 18.06 |
| ATOM | 2591 | N | TYR | A | 337 | −28.102 | 10.443 | −12.267 | 1.00 | 18.50 |
| ATOM | 2592 | CA | TYR | A | 337 | −28.642 | 9.287 | −12.970 | 1.00 | 18.99 |
| ATOM | 2593 | CB | TYR | A | 337 | −27.753 | 8.908 | −14.169 | 1.00 | 19.80 |
| ATOM | 2594 | CG | TYR | A | 337 | −28.328 | 7.737 | −14.954 | 1.00 | 20.76 |
| ATOM | 2595 | CD1 | TYR | A | 337 | −27.988 | 6.429 | −14.620 | 1.00 | 20.95 |
| ATOM | 2596 | CE1 | TYR | A | 337 | −28.511 | 5.345 | −15.322 | 1.00 | 22.94 |
| ATOM | 2597 | CZ | TYR | A | 337 | −29.382 | 5.559 | −16.356 | 1.00 | 22.19 |
| ATOM | 2598 | OH | TYR | A | 337 | −29.877 | 4.447 | −17.018 | 1.00 | 24.87 |
| ATOM | 2599 | CE2 | TYR | A | 337 | −29.752 | 6.845 | −16.721 | 1.00 | 22.31 |
| ATOM | 2600 | CD2 | TYR | A | 337 | −29.220 | 7.942 | −16.009 | 1.00 | 21.58 |
| ATOM | 2601 | C | TYR | A | 337 | −28.839 | 8.083 | −12.057 | 1.00 | 18.60 |
| ATOM | 2602 | O | TYR | A | 337 | −29.918 | 7.476 | −12.041 | 1.00 | 18.61 |
| ATOM | 2603 | N | VAL | A | 338 | −27.802 | 7.737 | −11.297 | 1.00 | 18.67 |
| ATOM | 2604 | CA | VAL | A | 338 | −27.837 | 6.573 | −10.406 | 1.00 | 18.90 |
| ATOM | 2605 | CB | VAL | A | 338 | −26.424 | 6.195 | −9.919 | 1.00 | 18.99 |
| ATOM | 2606 | CG1 | VAL | A | 338 | −26.462 | 5.121 | −8.820 | 1.00 | 19.71 |
| ATOM | 2607 | CG2 | VAL | A | 338 | −25.600 | 5.698 | −11.111 | 1.00 | 18.75 |
| ATOM | 2608 | C | VAL | A | 338 | −28.810 | 6.788 | −9.234 | 1.00 | 19.41 |
| ATOM | 2609 | O | VAL | A | 338 | −29.565 | 5.871 | −8.869 | 1.00 | 19.45 |
| ATOM | 2610 | N | TRP | A | 339 | −28.797 | 7.987 | −8.654 | 1.00 | 19.81 |
| ATOM | 2611 | CA | TRP | A | 339 | −29.743 | 8.290 | −7.559 | 1.00 | 20.46 |
| ATOM | 2612 | CB | TRP | A | 339 | −29.514 | 9.705 | −7.029 | 1.00 | 20.35 |
| ATOM | 2613 | CG | TRP | A | 339 | −28.222 | 9.830 | −6.329 | 1.00 | 18.64 |
| ATOM | 2614 | CD1 | TRP | A | 339 | −27.540 | 8.846 | −5.676 | 1.00 | 16.51 |
| ATOM | 2615 | NE1 | TRP | A | 339 | −26.391 | 9.359 | −5.126 | 1.00 | 17.81 |
| ATOM | 2616 | CE2 | TRP | A | 339 | −26.312 | 10.693 | −5.423 | 1.00 | 17.12 |
| ATOM | 2617 | CD2 | TRP | A | 339 | −27.452 | 11.025 | −6.183 | 1.00 | 17.64 |
| ATOM | 2618 | CE3 | TRP | A | 339 | −27.624 | 12.343 | −6.614 | 1.00 | 17.59 |
| ATOM | 2619 | CZ3 | TRP | A | 339 | −26.637 | 13.283 | −6.284 | 1.00 | 19.24 |
| ATOM | 2620 | CH2 | TRP | A | 339 | −25.510 | 12.912 | −5.520 | 1.00 | 18.24 |
| ATOM | 2621 | CZ2 | TRP | A | 339 | −25.320 | 11.626 | −5.103 | 1.00 | 18.45 |
| ATOM | 2622 | C | TRP | A | 339 | −31.201 | 8.108 | −7.997 | 1.00 | 21.83 |
| ATOM | 2623 | O | TRP | A | 339 | −31.981 | 7.478 | −7.274 | 1.00 | 22.01 |
| ATOM | 2624 | N | LYS | A | 340 | −31.549 | 8.646 | −9.168 | 1.00 | 22.85 |
| ATOM | 2625 | CA | LYS | A | 340 | −32.904 | 8.541 | −9.721 | 1.00 | 25.61 |
| ATOM | 2626 | CB | LYS | A | 340 | −33.066 | 9.411 | −10.967 | 1.00 | 25.52 |
| ATOM | 2627 | CG | LYS | A | 340 | −33.174 | 10.905 | −10.689 | 1.00 | 28.19 |
| ATOM | 2628 | CD | LYS | A | 340 | −33.227 | 11.692 | −11.991 | 1.00 | 34.04 |
| ATOM | 2629 | CE | LYS | A | 340 | −33.966 | 13.011 | −11.805 | 1.00 | 38.04 |
| ATOM | 2630 | NZ | LYS | A | 340 | −33.868 | 13.876 | −13.017 | 1.00 | 41.83 |
| ATOM | 2631 | C | LYS | A | 340 | −33.276 | 7.108 | −10.062 | 1.00 | 27.14 |
| ATOM | 2632 | O | LYS | A | 340 | −34.413 | 6.686 | −9.830 | 1.00 | 27.56 |
| ATOM | 2633 | N | LYS | A | 341 | −32.317 | 6.358 | −10.604 | 1.00 | 28.13 |
| ATOM | 2634 | CA | LYS | A | 341 | −32.552 | 4.975 | −11.018 | 1.00 | 30.18 |
| ATOM | 2635 | CB | LYS | A | 341 | −31.358 | 4.428 | −11.800 | 1.00 | 29.83 |
| ATOM | 2636 | CG | LYS | A | 341 | −31.688 | 3.173 | −12.624 | 1.00 | 33.04 |
| ATOM | 2637 | CD | LYS | A | 341 | −30.472 | 2.624 | −13.395 | 1.00 | 33.62 |
| ATOM | 2638 | CE | LYS | A | 341 | −29.652 | 1.592 | −12.588 | 1.00 | 38.22 |

TABLE 15-continued

| | | | | | | | | | |
|---|---|---|---|---|---|---|---|---|---|
| ATOM | 2639 | NZ | LYS | A | 341 | −28.691 | 2.188 | −11.573 | 1.00 | 40.88 |
| ATOM | 2640 | C | LYS | A | 341 | −32.816 | 4.081 | −9.817 | 1.00 | 30.19 |
| ATOM | 2641 | O | LYS | A | 341 | −33.744 | 3.260 | −9.837 | 1.00 | 30.15 |
| ATOM | 2642 | N | THR | A | 342 | −31.999 | 4.246 | −8.777 | 1.00 | 29.52 |
| ATOM | 2643 | CA | THR | A | 342 | −32.074 | 3.400 | −7.595 | 1.00 | 29.75 |
| ATOM | 2644 | CB | THR | A | 342 | −30.687 | 3.221 | −6.916 | 1.00 | 29.68 |
| ATOM | 2645 | OG1 | THR | A | 342 | −30.254 | 4.458 | −6.333 | 1.00 | 32.01 |
| ATOM | 2646 | CG2 | THR | A | 342 | −29.628 | 2.735 | −7.929 | 1.00 | 31.40 |
| ATOM | 2647 | C | THR | A | 342 | −33.129 | 3.901 | −6.596 | 1.00 | 29.01 |
| ATOM | 2648 | O | THR | A | 342 | −33.572 | 3.148 | −5.734 | 1.00 | 29.92 |
| ATOM | 2649 | N | GLY | A | 343 | −33.534 | 5.158 | −6.732 | 1.00 | 28.20 |
| ATOM | 2650 | CA | GLY | A | 343 | −34.537 | 5.782 | −5.862 | 1.00 | 28.30 |
| ATOM | 2651 | C | GLY | A | 343 | −34.068 | 6.045 | −4.438 | 1.00 | 27.91 |
| ATOM | 2652 | O | GLY | A | 343 | −34.887 | 6.133 | −3.519 | 1.00 | 28.16 |
| ATOM | 2653 | N | SER | A | 344 | −32.760 | 6.226 | −4.260 | 1.00 | 27.22 |
| ATOM | 2654 | CA | SER | A | 344 | −32.142 | 6.306 | −2.939 | 1.00 | 26.60 |
| ATOM | 2655 | CB | SER | A | 344 | −31.870 | 4.880 | −2.462 | 1.00 | 27.28 |
| ATOM | 2656 | OG | SER | A | 344 | −31.354 | 4.855 | −1.161 | 1.00 | 29.50 |
| ATOM | 2657 | C | SER | A | 344 | −30.823 | 7.107 | −2.979 | 1.00 | 26.02 |
| ATOM | 2658 | O | SER | A | 344 | −30.068 | 6.992 | −3.944 | 1.00 | 25.80 |
| ATOM | 2659 | N | ILE | A | 345 | −30.557 | 7.900 | −1.936 | 1.00 | 24.20 |
| ATOM | 2660 | CA | ILE | A | 345 | −29.295 | 8.641 | −1.770 | 1.00 | 23.04 |
| ATOM | 2661 | CB | ILE | A | 345 | −29.477 | 10.171 | −1.954 | 1.00 | 23.03 |
| ATOM | 2662 | CG1 | ILE | A | 345 | −30.021 | 10.474 | −3.340 | 1.00 | 22.44 |
| ATOM | 2663 | CD1 | ILE | A | 345 | −30.399 | 11.918 | −3.599 | 1.00 | 23.24 |
| ATOM | 2664 | CG2 | ILE | A | 345 | −28.138 | 10.918 | −1.670 | 1.00 | 22.00 |
| ATOM | 2665 | C | ILE | A | 345 | −28.726 | 8.415 | −0.378 | 1.00 | 23.13 |
| ATOM | 2666 | O | ILE | A | 345 | −29.392 | 8.684 | 0.623 | 1.00 | 23.57 |
| ATOM | 2667 | N | THR | A | 346 | −27.490 | 7.943 | −0.307 | 1.00 | 22.23 |
| ATOM | 2668 | CA | THR | A | 346 | −26.820 | 7.765 | 0.963 | 1.00 | 23.25 |
| ATOM | 2669 | CB | THR | A | 346 | −26.246 | 6.338 | 1.101 | 1.00 | 23.78 |
| ATOM | 2670 | OG1 | THR | A | 346 | −27.327 | 5.396 | 1.020 | 1.00 | 27.42 |
| ATOM | 2671 | CG2 | THR | A | 346 | −25.507 | 6.129 | 2.443 | 1.00 | 24.74 |
| ATOM | 2672 | C | THR | A | 346 | −25.753 | 8.849 | 1.138 | 1.00 | 23.03 |
| ATOM | 2673 | O | THR | A | 346 | −24.916 | 9.067 | 0.260 | 1.00 | 23.47 |
| ATOM | 2674 | N | VAL | A | 347 | −25.848 | 9.561 | 2.255 | 1.00 | 21.33 |
| ATOM | 2675 | CA | VAL | A | 347 | −24.845 | 10.537 | 2.674 | 1.00 | 20.11 |
| ATOM | 2676 | CB | VAL | A | 347 | −25.522 | 11.844 | 3.212 | 1.00 | 19.06 |
| ATOM | 2677 | CG1 | VAL | A | 347 | −24.489 | 12.834 | 3.700 | 1.00 | 19.66 |
| ATOM | 2678 | CG2 | VAL | A | 347 | −26.418 | 12.465 | 2.137 | 1.00 | 20.32 |
| ATOM | 2679 | C | VAL | A | 347 | −24.066 | 9.865 | 3.785 | 1.00 | 20.14 |
| ATOM | 2680 | O | VAL | A | 347 | −24.667 | 9.340 | 4.728 | 1.00 | 19.79 |
| ATOM | 2681 | N | THR | A | 348 | −22.734 | 9.878 | 3.671 | 1.00 | 19.85 |
| ATOM | 2682 | CA | THR | A | 348 | −21.851 | 9.274 | 4.660 | 1.00 | 19.92 |
| ATOM | 2683 | CB | THR | A | 348 | −20.965 | 8.185 | 4.018 | 1.00 | 19.82 |
| ATOM | 2684 | OG1 | THR | A | 348 | −19.921 | 8.815 | 3.277 | 1.00 | 20.35 |
| ATOM | 2685 | CG2 | THR | A | 348 | −21.785 | 7.278 | 3.092 | 1.00 | 21.67 |
| ATOM | 2686 | C | THR | A | 348 | −20.964 | 10.354 | 5.256 | 1.00 | 19.60 |
| ATOM | 2687 | O | THR | A | 348 | −20.961 | 11.484 | 4.760 | 1.00 | 19.51 |
| ATOM | 2688 | N | ALA | A | 349 | −20.191 | 10.006 | 6.292 | 1.00 | 19.18 |
| ATOM | 2689 | CA | ALA | A | 349 | −19.243 | 10.932 | 6.885 | 1.00 | 20.02 |
| ATOM | 2690 | CB | ALA | A | 349 | −18.494 | 10.275 | 8.044 | 1.00 | 20.61 |
| ATOM | 2691 | C | ALA | A | 349 | −18.240 | 11.466 | 5.842 | 1.00 | 19.79 |
| ATOM | 2692 | O | ALA | A | 349 | −17.756 | 12.601 | 5.947 | 1.00 | 20.15 |
| ATOM | 2693 | N | THR | A | 350 | −17.906 | 10.619 | 4.873 | 1.00 | 18.87 |
| ATOM | 2694 | CA | THR | A | 350 | −16.911 | 10.971 | 3.850 | 1.00 | 18.30 |
| ATOM | 2695 | CB | THR | A | 350 | −16.435 | 9.717 | 3.093 | 1.00 | 18.67 |
| ATOM | 2696 | OG1 | THR | A | 350 | −15.780 | 8.850 | 4.027 | 1.00 | 19.82 |
| ATOM | 2697 | CG2 | THR | A | 350 | −15.426 | 10.097 | 1.974 | 1.00 | 17.73 |
| ATOM | 2698 | C | THR | A | 350 | −17.463 | 12.003 | 2.871 | 1.00 | 17.30 |
| ATOM | 2699 | O | THR | A | 350 | −16.747 | 12.930 | 2.487 | 1.00 | 17.99 |
| ATOM | 2700 | N | SER | A | 351 | −18.716 | 11.847 | 2.467 | 1.00 | 16.16 |
| ATOM | 2701 | CA | SER | A | 351 | −19.316 | 12.803 | 1.517 | 1.00 | 15.78 |
| ATOM | 2702 | CB | SER | A | 351 | −20.214 | 12.076 | 0.512 | 1.00 | 15.85 |
| ATOM | 2703 | OG | SER | A | 351 | −21.280 | 11.412 | 1.156 | 1.00 | 17.14 |
| ATOM | 2704 | C | SER | A | 351 | −20.087 | 13.941 | 2.193 | 1.00 | 15.63 |
| ATOM | 2705 | O | SER | A | 351 | −20.736 | 14.743 | 1.524 | 1.00 | 13.62 |
| ATOM | 2706 | N | LEU | A | 352 | −20.048 | 14.006 | 3.527 | 1.00 | 15.09 |
| ATOM | 2707 | CA | LEU | A | 352 | −20.901 | 14.985 | 4.212 | 1.00 | 16.29 |
| ATOM | 2708 | CB | LEU | A | 352 | −20.759 | 14.851 | 5.736 | 1.00 | 16.64 |
| ATOM | 2709 | CG | LEU | A | 352 | −21.713 | 15.734 | 6.570 | 1.00 | 17.22 |
| ATOM | 2710 | CD1 | LEU | A | 352 | −23.138 | 15.281 | 6.418 | 1.00 | 19.06 |
| ATOM | 2711 | CD2 | LEU | A | 352 | −21.263 | 15.636 | 8.032 | 1.00 | 20.02 |
| ATOM | 2712 | C | LEU | A | 352 | −20.592 | 16.427 | 3.787 | 1.00 | 16.09 |
| ATOM | 2713 | O | LEU | A | 352 | −21.499 | 17.219 | 3.601 | 1.00 | 16.35 |
| ATOM | 2714 | N | ALA | A | 353 | −19.311 | 16.763 | 3.643 | 1.00 | 16.19 |
| ATOM | 2715 | CA | ALA | A | 353 | −18.933 | 18.148 | 3.354 | 1.00 | 15.74 |
| ATOM | 2716 | CB | ALA | A | 353 | −17.460 | 18.314 | 3.424 | 1.00 | 16.30 |
| ATOM | 2717 | C | ALA | A | 353 | −19.459 | 18.544 | 1.972 | 1.00 | 16.11 |
| ATOM | 2718 | O | ALA | A | 353 | −19.957 | 19.668 | 1.781 | 1.00 | 15.44 |

TABLE 15-continued

| ATOM | 2719 | N   | PHE | A | 354 | −19.367 | 17.607 | 1.021  | 1.00 | 16.10 |
| ATOM | 2720 | CA  | PHE | A | 354 | −19.885 | 17.849 | −0.325 | 1.00 | 15.25 |
| ATOM | 2721 | CB  | PHE | A | 354 | −19.718 | 16.618 | −1.220 | 1.00 | 16.59 |
| ATOM | 2722 | CG  | PHE | A | 354 | −20.497 | 16.707 | −2.500 | 1.00 | 15.45 |
| ATOM | 2723 | CD1 | PHE | A | 354 | −19.959 | 17.375 | −3.603 | 1.00 | 16.95 |
| ATOM | 2724 | CE1 | PHE | A | 354 | −20.664 | 17.489 | −4.793 | 1.00 | 17.06 |
| ATOM | 2725 | CZ  | PHE | A | 354 | −21.956 | 16.953 | −4.888 | 1.00 | 16.75 |
| ATOM | 2726 | CE2 | PHE | A | 354 | −22.517 | 16.276 | −3.791 | 1.00 | 16.91 |
| ATOM | 2727 | CD2 | PHE | A | 354 | −21.778 | 16.160 | −2.594 | 1.00 | 17.48 |
| ATOM | 2728 | C   | PHE | A | 354 | −21.374 | 18.188 | −0.226 | 1.00 | 15.56 |
| ATOM | 2729 | O   | PHE | A | 354 | −21.815 | 19.183 | −0.797 | 1.00 | 15.08 |
| ATOM | 2730 | N   | PHE | A | 355 | −22.140 | 17.347 | 0.474  | 1.00 | 14.54 |
| ATOM | 2731 | CA  | PHE | A | 355 | −23.588 | 17.544 | 0.517  | 1.00 | 15.29 |
| ATOM | 2732 | CB  | PHE | A | 355 | −24.295 | 16.319 | 1.078  | 1.00 | 15.61 |
| ATOM | 2733 | CG  | PHE | A | 355 | −24.386 | 15.176 | 0.112  | 1.00 | 15.51 |
| ATOM | 2734 | CD1 | PHE | A | 355 | −25.306 | 15.205 | −0.945 | 1.00 | 14.91 |
| ATOM | 2735 | CE1 | PHE | A | 355 | −25.404 | 14.131 | −1.832 | 1.00 | 16.52 |
| ATOM | 2736 | CZ  | PHE | A | 355 | −24.567 | 13.033 | −1.676 | 1.00 | 16.12 |
| ATOM | 2737 | CE2 | PHE | A | 355 | −23.648 | 12.994 | −0.628 | 1.00 | 15.62 |
| ATOM | 2738 | CD2 | PHE | A | 355 | −23.562 | 14.071 | 0.255  | 1.00 | 13.62 |
| ATOM | 2739 | C   | PHE | A | 355 | −23.988 | 18.789 | 1.303  | 1.00 | 15.19 |
| ATOM | 2740 | O   | PHE | A | 355 | −24.920 | 19.477 | 0.902  | 1.00 | 15.69 |
| ATOM | 2741 | N   | GLN | A | 356 | −23.283 | 19.084 | 2.398  | 1.00 | 15.78 |
| ATOM | 2742 | CA  | GLN | A | 356 | −23.679 | 20.216 | 3.257  | 1.00 | 16.16 |
| ATOM | 2743 | CB  | GLN | A | 356 | −22.987 | 20.165 | 4.627  | 1.00 | 16.84 |
| ATOM | 2744 | CG  | GLN | A | 356 | −23.564 | 19.115 | 5.579  | 1.00 | 17.13 |
| ATOM | 2745 | CD  | GLN | A | 356 | −22.907 | 19.170 | 6.973  | 1.00 | 18.06 |
| ATOM | 2746 | OE1 | GLN | A | 356 | −21.808 | 19.707 | 7.138  | 1.00 | 20.29 |
| ATOM | 2747 | NE2 | GLN | A | 356 | −23.569 | 18.589 | 7.965  | 1.00 | 20.95 |
| ATOM | 2748 | C   | GLN | A | 356 | −23.444 | 21.546 | 2.584  | 1.00 | 16.08 |
| ATOM | 2749 | O   | GLN | A | 356 | −24.142 | 22.507 | 2.868  | 1.00 | 15.59 |
| ATOM | 2750 | N   | GLU | A | 357 | −22.482 | 21.599 | 1.661  | 1.00 | 16.07 |
| ATOM | 2751 | CA  | GLU | A | 357 | −22.261 | 22.808 | 0.884  | 1.00 | 16.41 |
| ATOM | 2752 | CB  | GLU | A | 357 | −20.994 | 22.683 | 0.005  | 1.00 | 16.33 |
| ATOM | 2753 | CG  | GLU | A | 357 | −20.671 | 23.942 | −0.770 | 1.00 | 15.64 |
| ATOM | 2754 | CD  | GLU | A | 357 | −19.326 | 23.894 | −1.516 | 1.00 | 17.67 |
| ATOM | 2755 | OE1 | GLU | A | 357 | −18.931 | 24.947 | −2.066 | 1.00 | 19.03 |
| ATOM | 2756 | OE2 | GLU | A | 357 | −18.685 | 22.822 | −1.575 | 1.00 | 14.75 |
| ATOM | 2757 | C   | GLU | A | 357 | −23.492 | 23.105 | 0.019  | 1.00 | 15.84 |
| ATOM | 2758 | O   | GLU | A | 357 | −23.786 | 24.237 | −0.224 | 1.00 | 18.07 |
| ATOM | 2759 | N   | LEU | A | 358 | −24.213 | 22.084 | −0.420 | 1.00 | 14.72 |
| ATOM | 2760 | CA  | LEU | A | 358 | −25.364 | 22.251 | −1.310 | 1.00 | 15.75 |
| ATOM | 2761 | CB  | LEU | A | 358 | −25.368 | 21.147 | −2.369 | 1.00 | 16.49 |
| ATOM | 2762 | CG  | LEU | A | 358 | −24.057 | 21.100 | −3.168 | 1.00 | 16.81 |
| ATOM | 2763 | CD1 | LEU | A | 358 | −24.087 | 19.977 | −4.182 | 1.00 | 19.73 |
| ATOM | 2764 | CD2 | LEU | A | 358 | −23.775 | 22.465 | −3.846 | 1.00 | 19.34 |
| ATOM | 2765 | C   | LEU | A | 358 | −26.708 | 22.251 | −0.582 | 1.00 | 15.36 |
| ATOM | 2766 | O   | LEU | A | 358 | −27.656 | 22.911 | −1.028 | 1.00 | 14.78 |
| ATOM | 2767 | N   | VAL | A | 359 | −26.786 | 21.511 | 0.520  | 1.00 | 15.34 |
| ATOM | 2768 | CA  | VAL | A | 359 | −28.001 | 21.404 | 1.321  | 1.00 | 15.00 |
| ATOM | 2769 | CB  | VAL | A | 359 | −28.691 | 20.006 | 1.154  | 1.00 | 15.90 |
| ATOM | 2770 | CG1 | VAL | A | 359 | −29.999 | 19.917 | 1.962  | 1.00 | 15.16 |
| ATOM | 2771 | CG2 | VAL | A | 359 | −28.967 | 19.685 | −0.348 | 1.00 | 16.26 |
| ATOM | 2772 | C   | VAL | A | 359 | −27.531 | 21.624 | 2.775  | 1.00 | 14.72 |
| ATOM | 2773 | O   | VAL | A | 359 | −27.192 | 20.653 | 3.500  | 1.00 | 14.22 |
| ATOM | 2774 | N   | PRO | A | 360 | −27.467 | 22.893 | 3.193  | 1.00 | 14.98 |
| ATOM | 2775 | CA  | PRO | A | 360 | −26.937 | 23.179 | 4.539  | 1.00 | 15.45 |
| ATOM | 2776 | CB  | PRO | A | 360 | −27.150 | 24.700 | 4.700  | 1.00 | 15.45 |
| ATOM | 2777 | CG  | PRO | A | 360 | −27.188 | 25.219 | 3.274  | 1.00 | 16.15 |
| ATOM | 2778 | CD  | PRO | A | 360 | −27.854 | 24.127 | 2.471  | 1.00 | 14.54 |
| ATOM | 2779 | C   | PRO | A | 360 | −27.692 | 22.385 | 5.611  | 1.00 | 15.31 |
| ATOM | 2780 | O   | PRO | A | 360 | −28.918 | 22.262 | 5.555  | 1.00 | 15.07 |
| ATOM | 2781 | N   | GLY | A | 361 | −26.936 | 21.842 | 6.560  | 1.00 | 15.94 |
| ATOM | 2782 | CA  | GLY | A | 361 | −27.512 | 21.143 | 7.709  | 1.00 | 16.53 |
| ATOM | 2783 | C   | GLY | A | 361 | −27.870 | 19.680 | 7.488  | 1.00 | 17.03 |
| ATOM | 2784 | O   | GLY | A | 361 | −28.268 | 18.997 | 8.429  | 1.00 | 17.68 |
| ATOM | 2785 | N   | VAL | A | 362 | −27.762 | 19.176 | 6.261  | 1.00 | 16.13 |
| ATOM | 2786 | CA  | VAL | A | 362 | −28.163 | 17.769 | 6.037  | 1.00 | 16.72 |
| ATOM | 2787 | CB  | VAL | A | 362 | −28.217 | 17.416 | 4.525  | 1.00 | 16.47 |
| ATOM | 2788 | CG1 | VAL | A | 362 | −26.808 | 17.311 | 3.947  | 1.00 | 16.75 |
| ATOM | 2789 | CG2 | VAL | A | 362 | −29.054 | 16.142 | 4.280  | 1.00 | 17.21 |
| ATOM | 2790 | C   | VAL | A | 362 | −27.208 | 16.849 | 6.811  | 1.00 | 17.24 |
| ATOM | 2791 | O   | VAL | A | 362 | −26.044 | 17.187 | 7.006  | 1.00 | 17.07 |
| ATOM | 2792 | N   | THR | A | 363 | −27.695 | 15.703 | 7.274  | 1.00 | 18.15 |
| ATOM | 2793 | CA  | THR | A | 363 | −26.821 | 14.789 | 8.025  | 1.00 | 19.86 |
| ATOM | 2794 | CB  | THR | A | 363 | −27.388 | 14.459 | 9.405  | 1.00 | 20.59 |
| ATOM | 2795 | OG1 | THR | A | 363 | −28.634 | 13.776 | 9.217  | 1.00 | 22.85 |
| ATOM | 2796 | CG2 | THR | A | 363 | −27.610 | 15.742 | 10.182 | 1.00 | 22.71 |
| ATOM | 2797 | C   | THR | A | 363 | −26.660 | 13.476 | 7.310  | 1.00 | 19.18 |
| ATOM | 2798 | O   | THR | A | 363 | −27.398 | 13.184 | 6.371  | 1.00 | 18.87 |

TABLE 15-continued

| | | | | | | | | | |
|---|---|---|---|---|---|---|---|---|---|
| ATOM | 2799 | N | ALA | A | 364 | −25.697 | 12.679 | 7.769 | 1.00 | 19.67 |
| ATOM | 2800 | CA | ALA | A | 364 | −25.495 | 11.342 | 7.222 | 1.00 | 20.19 |
| ATOM | 2801 | CB | ALA | A | 364 | −24.361 | 10.637 | 7.930 | 1.00 | 20.38 |
| ATOM | 2802 | C | ALA | A | 364 | −26.783 | 10.541 | 7.343 | 1.00 | 21.17 |
| ATOM | 2803 | O | ALA | A | 364 | −27.551 | 10.720 | 8.293 | 1.00 | 21.92 |
| ATOM | 2804 | N | GLY | A | 365 | −27.041 | 9.687 | 6.360 | 1.00 | 21.67 |
| ATOM | 2805 | CA | GLY | A | 365 | −28.207 | 8.823 | 6.371 | 1.00 | 22.35 |
| ATOM | 2806 | C | GLY | A | 365 | −28.584 | 8.415 | 4.968 | 1.00 | 23.66 |
| ATOM | 2807 | O | GLY | A | 365 | −27.924 | 8.804 | 3.991 | 1.00 | 23.66 |
| ATOM | 2808 | N | THR | A | 366 | −29.639 | 7.615 | 4.862 | 1.00 | 23.70 |
| ATOM | 2809 | CA | THR | A | 366 | −30.148 | 7.183 | 3.582 | 1.00 | 24.56 |
| ATOM | 2810 | CB | THR | A | 366 | −30.188 | 5.644 | 3.491 | 1.00 | 25.67 |
| ATOM | 2811 | OG1 | THR | A | 366 | −28.849 | 5.143 | 3.649 | 1.00 | 27.09 |
| ATOM | 2812 | CG2 | THR | A | 366 | −30.715 | 5.216 | 2.159 | 1.00 | 25.47 |
| ATOM | 2813 | C | THR | A | 366 | −31.520 | 7.769 | 3.344 | 1.00 | 25.15 |
| ATOM | 2814 | O | THR | A | 366 | −32.427 | 7.612 | 4.177 | 1.00 | 25.01 |
| ATOM | 2815 | N | TYR | A | 367 | −31.668 | 8.447 | 2.210 | 1.00 | 24.20 |
| ATOM | 2816 | CA | TYR | A | 367 | −32.900 | 9.146 | 1.883 | 1.00 | 24.30 |
| ATOM | 2817 | CB | TYR | A | 367 | −32.616 | 10.648 | 1.701 | 1.00 | 23.51 |
| ATOM | 2818 | CG | TYR | A | 367 | −31.924 | 11.238 | 2.907 | 1.00 | 22.68 |
| ATOM | 2819 | CD1 | TYR | A | 367 | −32.639 | 11.506 | 4.078 | 1.00 | 21.99 |
| ATOM | 2820 | CE1 | TYR | A | 367 | −32.012 | 12.019 | 5.199 | 1.00 | 20.27 |
| ATOM | 2821 | CZ | TYR | A | 367 | −30.650 | 12.263 | 5.176 | 1.00 | 22.67 |
| ATOM | 2822 | OH | TYR | A | 367 | −30.036 | 12.789 | 6.287 | 1.00 | 21.24 |
| ATOM | 2823 | CE2 | TYR | A | 367 | −29.897 | 11.994 | 4.023 | 1.00 | 20.71 |
| ATOM | 2824 | CD2 | TYR | A | 367 | −30.541 | 11.479 | 2.904 | 1.00 | 20.37 |
| ATOM | 2825 | C | TYR | A | 367 | −33.531 | 8.542 | 0.641 | 1.00 | 25.39 |
| ATOM | 2826 | O | TYR | A | 367 | −32.900 | 8.456 | −0.415 | 1.00 | 24.86 |
| ATOM | 2827 | N | SER | A | 368 | −34.782 | 8.109 | 0.758 | 1.00 | 25.82 |
| ATOM | 2828 | CA | SER | A | 368 | −35.416 | 7.454 | −0.374 | 1.00 | 27.29 |
| ATOM | 2829 | CB | SER | A | 368 | −36.339 | 6.332 | 0.107 | 1.00 | 27.90 |
| ATOM | 2830 | OG | SER | A | 368 | −37.519 | 6.895 | 0.634 | 1.00 | 30.69 |
| ATOM | 2831 | C | SER | A | 368 | −36.171 | 8.466 | −1.218 | 1.00 | 27.68 |
| ATOM | 2832 | O | SER | A | 368 | −36.361 | 9.612 | −0.805 | 1.00 | 26.96 |
| ATOM | 2833 | N | SER | A | 369 | −36.629 | 8.025 | −2.388 | 1.00 | 28.98 |
| ATOM | 2834 | CA | SER | A | 369 | −37.260 | 8.908 | −3.367 | 1.00 | 30.52 |
| ATOM | 2835 | CB | SER | A | 369 | −37.520 | 8.167 | −4.681 | 1.00 | 30.90 |
| ATOM | 2836 | OG | SER | A | 369 | −38.269 | 6.983 | −4.452 | 1.00 | 32.57 |
| ATOM | 2837 | C | SER | A | 369 | −38.536 | 9.583 | −2.871 | 1.00 | 31.50 |
| ATOM | 2838 | O | SER | A | 369 | −38.954 | 10.572 | −3.442 | 1.00 | 32.33 |
| ATOM | 2839 | N | SER | A | 370 | −39.150 | 9.067 | −1.809 | 1.00 | 32.18 |
| ATOM | 2840 | CA | SER | A | 370 | −40.365 | 9.712 | −1.279 | 1.00 | 32.96 |
| ATOM | 2841 | CB | SER | A | 370 | −41.313 | 8.692 | −0.624 | 1.00 | 33.18 |
| ATOM | 2842 | OG | SER | A | 370 | −40.610 | 7.847 | 0.273 | 1.00 | 34.18 |
| ATOM | 2843 | C | SER | A | 370 | −40.049 | 10.864 | −0.323 | 1.00 | 32.37 |
| ATOM | 2844 | O | SER | A | 370 | −40.901 | 11.729 | −0.078 | 1.00 | 33.26 |
| ATOM | 2845 | N | SER | A | 371 | −38.825 | 10.893 | 0.197 | 1.00 | 31.13 |
| ATOM | 2846 | CA | SER | A | 371 | −38.443 | 11.911 | 1.174 | 1.00 | 30.04 |
| ATOM | 2847 | CB | SER | A | 371 | −37.180 | 11.487 | 1.912 | 1.00 | 29.83 |
| ATOM | 2848 | OG | SER | A | 371 | −36.046 | 11.714 | 1.100 | 1.00 | 30.43 |
| ATOM | 2849 | C | SER | A | 371 | −38.247 | 13.295 | 0.553 | 1.00 | 29.13 |
| ATOM | 2850 | O | SER | A | 371 | −37.795 | 13.424 | −0.589 | 1.00 | 28.84 |
| ATOM | 2851 | N | SER | A | 372 | −38.571 | 14.340 | 1.312 | 1.00 | 27.84 |
| ATOM | 2852 | CA | SER | A | 372 | −38.300 | 15.689 | 0.845 | 1.00 | 27.18 |
| ATOM | 2853 | CB | SER | A | 372 | −38.896 | 16.737 | 1.789 | 1.00 | 27.36 |
| ATOM | 2854 | OG | SER | A | 372 | −38.331 | 16.609 | 3.080 | 1.00 | 28.50 |
| ATOM | 2855 | C | SER | A | 372 | −36.783 | 15.902 | 0.680 | 1.00 | 25.79 |
| ATOM | 2856 | O | SER | A | 372 | −36.358 | 16.690 | −0.173 | 1.00 | 26.29 |
| ATOM | 2857 | N | THR | A | 373 | −35.979 | 15.193 | 1.479 | 1.00 | 24.06 |
| ATOM | 2858 | CA | THR | A | 373 | −34.517 | 15.337 | 1.448 | 1.00 | 22.51 |
| ATOM | 2859 | CB | THR | A | 373 | −33.833 | 14.501 | 2.545 | 1.00 | 22.26 |
| ATOM | 2860 | OG1 | THR | A | 373 | −34.543 | 14.636 | 3.788 | 1.00 | 23.04 |
| ATOM | 2861 | CG2 | THR | A | 373 | −32.370 | 14.926 | 2.734 | 1.00 | 21.06 |
| ATOM | 2862 | C | THR | A | 373 | −33.984 | 14.906 | 0.076 | 1.00 | 21.61 |
| ATOM | 2863 | O | THR | A | 373 | −33.134 | 15.578 | −0.513 | 1.00 | 19.74 |
| ATOM | 2864 | N | PHE | A | 374 | −34.493 | 13.777 | −0.413 | 1.00 | 21.13 |
| ATOM | 2865 | CA | PHE | A | 374 | −34.137 | 13.280 | −1.749 | 1.00 | 22.10 |
| ATOM | 2866 | CB | PHE | A | 374 | −34.950 | 12.023 | −2.051 | 1.00 | 22.12 |
| ATOM | 2867 | CG | PHE | A | 374 | −34.624 | 11.380 | −3.366 | 1.00 | 22.90 |
| ATOM | 2868 | CD1 | PHE | A | 374 | −33.677 | 10.368 | −3.432 | 1.00 | 23.83 |
| ATOM | 2869 | CE1 | PHE | A | 374 | −33.381 | 9.749 | −4.649 | 1.00 | 22.56 |
| ATOM | 2870 | CZ | PHE | A | 374 | −34.041 | 10.162 | −5.802 | 1.00 | 23.24 |
| ATOM | 2871 | CE2 | PHE | A | 374 | −34.985 | 11.161 | −5.752 | 1.00 | 23.36 |
| ATOM | 2872 | CD2 | PHE | A | 374 | −35.280 | 11.769 | −4.523 | 1.00 | 23.73 |
| ATOM | 2873 | C | PHE | A | 374 | −34.343 | 14.349 | −2.818 | 1.00 | 22.24 |
| ATOM | 2874 | O | PHE | A | 374 | −33.413 | 14.681 | −3.548 | 1.00 | 22.63 |
| ATOM | 2875 | N | THR | A | 375 | −35.549 | 14.923 | −2.880 | 1.00 | 22.72 |
| ATOM | 2876 | CA | THR | A | 375 | −35.890 | 15.963 | −3.852 | 1.00 | 23.34 |
| ATOM | 2877 | CB | THR | A | 375 | −37.364 | 16.398 | −3.683 | 1.00 | 23.63 |
| ATOM | 2878 | OG1 | THR | A | 375 | −38.193 | 15.244 | −3.809 | 1.00 | 27.83 |

TABLE 15-continued

| | | | | | | | | |
|---|---|---|---|---|---|---|---|---|
| ATOM | 2879 | CG2 | THR | A | 375 | −37.768 | 17.413 −4.749 | 1.00 | 27.05 |
| ATOM | 2880 | C | THR | A | 375 | −35.003 | 17.203 −3.746 | 1.00 | 22.66 |
| ATOM | 2881 | O | THR | A | 375 | −34.603 | 17.766 −4.756 | 1.00 | 21.43 |
| ATOM | 2882 | N | ASN | A | 376 | −34.744 | 17.632 −2.508 | 1.00 | 20.80 |
| ATOM | 2883 | CA | ASN | A | 376 | −33.880 | 18.766 −2.207 | 1.00 | 21.33 |
| ATOM | 2884 | CB | ASN | A | 376 | −33.856 | 18.975 −0.688 | 1.00 | 21.98 |
| ATOM | 2885 | CG | ASN | A | 376 | −33.343 | 20.354 −0.278 | 1.00 | 27.01 |
| ATOM | 2886 | OD1 | ASN | A | 376 | −32.582 | 21.011 −1.004 | 1.00 | 31.72 |
| ATOM | 2887 | ND2 | ASN | A | 376 | −33.748 | 20.793 0.913 | 1.00 | 30.14 |
| ATOM | 2888 | C | ASN | A | 376 | −32.465 | 18.527 −2.733 | 1.00 | 19.80 |
| ATOM | 2889 | O | ASN | A | 376 | −31.898 | 19.389 −3.415 | 1.00 | 19.75 |
| ATOM | 2890 | N | ILE | A | 377 | −31.915 | 17.354 −2.431 | 1.00 | 19.00 |
| ATOM | 2891 | CA | ILE | A | 377 | −30.586 | 16.983 −2.916 | 1.00 | 18.66 |
| ATOM | 2892 | CB | ILE | A | 377 | −30.081 | 15.651 −2.319 | 1.00 | 18.56 |
| ATOM | 2893 | CG1 | ILE | A | 377 | −29.834 | 15.813 −0.800 | 1.00 | 18.42 |
| ATOM | 2894 | CD1 | ILE | A | 377 | −29.634 | 14.481 −0.028 | 1.00 | 19.35 |
| ATOM | 2895 | CG2 | ILE | A | 377 | −28.787 | 15.233 −3.025 | 1.00 | 18.07 |
| ATOM | 2896 | C | ILE | A | 377 | −30.546 | 16.964 −4.451 | 1.00 | 18.87 |
| ATOM | 2897 | O | ILE | A | 377 | −29.655 | 17.575 −5.058 | 1.00 | 18.47 |
| ATOM | 2898 | N | ILE | A | 378 | −31.513 | 16.293 −5.068 | 1.00 | 18.45 |
| ATOM | 2899 | CA | ILE | A | 378 | −31.556 | 16.216 −6.539 | 1.00 | 19.78 |
| ATOM | 2900 | CB | ILE | A | 378 | −32.738 | 15.359 −7.085 | 1.00 | 20.45 |
| ATOM | 2901 | CG1 | ILE | A | 378 | −32.593 | 13.891 −6.650 | 1.00 | 22.32 |
| ATOM | 2902 | CD1 | ILE | A | 378 | −31.414 | 13.145 −7.270 | 1.00 | 24.68 |
| ATOM | 2903 | CG2 | ILE | A | 378 | −32.829 | 15.472 −8.646 | 1.00 | 21.27 |
| ATOM | 2904 | C | ILE | A | 378 | −31.561 | 17.588 −1.111 | 1.00 | 19.82 |
| ATOM | 2905 | O | ILE | A | 378 | −30.760 | 17.849 −8.101 | 1.00 | 19.62 |
| ATOM | 2906 | N | ASN | A | 379 | −32.441 | 18.470 −6.689 | 1.00 | 18.68 |
| ATOM | 2907 | CA | ASN | A | 379 | −32.531 | 19.820 −7.224 | 1.00 | 19.13 |
| ATOM | 2908 | CB | ASN | A | 379 | −33.738 | 20.578 −6.658 | 1.00 | 20.08 |
| ATOM | 2909 | CG | ASN | A | 379 | −35.066 | 19.956 −7.087 | 1.00 | 25.11 |
| ATOM | 2910 | OD1 | ASN | A | 379 | −35.121 | 19.173 −8.044 | 1.00 | 29.37 |
| ATOM | 2911 | ND2 | ASN | A | 379 | −36.144 | 20.289 −6.369 | 1.00 | 29.08 |
| ATOM | 2912 | C | ASN | A | 379 | −31.241 | 20.604 −7.040 | 1.00 | 17.96 |
| ATOM | 2913 | O | ASN | A | 379 | −30.774 | 21.273 −7.981 | 1.00 | 17.85 |
| ATOM | 2914 | N | ALA | A | 380 | −30.662 | 20.497 −5.841 | 1.00 | 15.93 |
| ATOM | 2915 | CA | ALA | A | 380 | −29.458 | 21.241 −5.509 | 1.00 | 16.08 |
| ATOM | 2916 | CB | ALA | A | 380 | −29.120 | 21.061 −4.033 | 1.00 | 16.14 |
| ATOM | 2917 | C | ALA | A | 380 | −28.299 | 20.783 −6.389 | 1.00 | 15.64 |
| ATOM | 2918 | O | ALA | A | 380 | −27.566 | 21.607 −6.938 | 1.00 | 16.56 |
| ATOM | 2919 | N | VAL | A | 381 | −28.153 | 19.471 −6.519 | 1.00 | 15.22 |
| ATOM | 2920 | CA | VAL | A | 381 | −27.039 | 18.912 −7.302 | 1.00 | 15.77 |
| ATOM | 2921 | CB | VAL | A | 381 | −26.823 | 17.403 −6.999 | 1.00 | 15.61 |
| ATOM | 2922 | CG1 | VAL | A | 381 | −25.747 | 16.777 −7.940 | 1.00 | 14.83 |
| ATOM | 2923 | CG2 | VAL | A | 381 | −26.386 | 17.234 −5.551 | 1.00 | 14.84 |
| ATOM | 2924 | C | VAL | A | 381 | −27.243 | 19.211 −8.794 | 1.00 | 16.08 |
| ATOM | 2925 | O | VAL | A | 381 | −26.281 | 19.508 −9.505 | 1.00 | 16.62 |
| ATOM | 2926 | N | SER | A | 382 | −28.482 | 19.112 −9.278 | 1.00 | 16.66 |
| ATOM | 2927 | CA | SER | A | 382 | −28.772 | 19.453-10.690 | 1.00 | 18.67 |
| ATOM | 2928 | CB | SER | A | 382 | −30.246 | 19.212-11.043 | 1.00 | 18.26 |
| ATOM | 2929 | OG | SER | A | 382 | −30.538 | 17.855-10.893 | 1.00 | 24.56 |
| ATOM | 2930 | C | SER | A | 382 | −28.434 | 20.894-11.005 | 1.00 | 18.10 |
| ATOM | 2931 | O | SER | A | 382 | −27.815 | 21.183-12.027 | 1.00 | 18.05 |
| ATOM | 2932 | N | THR | A | 383 | −28.853 | 21.810-10.132 | 1.00 | 17.66 |
| ATOM | 2933 | CA | THR | A | 383 | −28.521 | 23.216-10.298 | 1.00 | 17.72 |
| ATOM | 2934 | CB | THR | A | 383 | −29.199 | 24.063 −9.180 | 1.00 | 18.48 |
| ATOM | 2935 | OG1 | THR | A | 383 | −30.606 | 23.985 −9.373 | 1.00 | 19.72 |
| ATOM | 2936 | CG2 | THR | A | 383 | −28.771 | 25.550 −9.227 | 1.00 | 19.59 |
| ATOM | 2937 | C | THR | A | 383 | −27.017 | 23.470-10.314 | 1.00 | 17.09 |
| ATOM | 2938 | O | THR | A | 383 | −26.524 | 24.286-11.109 | 1.00 | 17.00 |
| ATOM | 2939 | N | TYR | A | 384 | −26.299 | 22.774 −9.435 | 1.00 | 15.62 |
| ATOM | 2940 | CA | TYR | A | 384 | −24.858 | 22.925 −9.312 | 1.00 | 15.37 |
| ATOM | 2941 | CB | TYR | A | 384 | −24.397 | 22.164 −8.068 | 1.00 | 15.00 |
| ATOM | 2942 | CG | TYR | A | 384 | −22.958 | 22.345 −7.630 | 1.00 | 15.08 |
| ATOM | 2943 | CD1 | TYR | A | 384 | −22.361 | 23.601 −7.578 | 1.00 | 15.83 |
| ATOM | 2944 | CE1 | TYR | A | 384 | −21.049 | 23.752 −7.131 | 1.00 | 16.33 |
| ATOM | 2945 | CZ | TYR | A | 384 | −20.321 | 22.623 −6.737 | 1.00 | 16.13 |
| ATOM | 2946 | OH | TYR | A | 384 | −19.018 | 22.738 −6.302 | 1.00 | 16.22 |
| ATOM | 2947 | CE2 | TYR | A | 384 | −20.890 | 21.386 −6.778 | 1.00 | 13.72 |
| ATOM | 2948 | CD2 | TYR | A | 384 | −22.203 | 21.242 −7.232 | 1.00 | 14.72 |
| ATOM | 2949 | C | TYR | A | 384 | −24.186 | 22.396-10.590 | 1.00 | 15.13 |
| ATOM | 2950 | O | TYR | A | 384 | −23.319 | 23.065-11.173 | 1.00 | 14.43 |
| ATOM | 2951 | N | ALA | A | 385 | −24.605 | 21.213-11.033 | 1.00 | 15.02 |
| ATOM | 2952 | CA | ALA | A | 385 | −24.045 | 20.639-12.263 | 1.00 | 15.60 |
| ATOM | 2953 | CB | ALA | A | 385 | −24.634 | 19.295-12.503 | 1.00 | 15.85 |
| ATOM | 2954 | C | ALA | A | 385 | −24.249 | 21.564-13.477 | 1.00 | 16.15 |
| ATOM | 2955 | O | ALA | A | 385 | −23.292 | 21.857-14.211 | 1.00 | 15.49 |
| ATOM | 2956 | N | ASP | A | 386 | −25.483 | 22.055-13.660 | 1.00 | 15.57 |
| ATOM | 2957 | CA | ASP | A | 386 | −25.782 | 23.058-14.694 | 1.00 | 16.09 |
| ATOM | 2958 | CB | ASP | A | 386 | −27.279 | 23.433-14.687 | 1.00 | 15.88 |

TABLE 15-continued

| | | | | | | | | | |
|---|---|---|---|---|---|---|---|---|---|
| ATOM | 2959 | CG | ASP | A | 386 | −28.158 | 22.379 | −15.349 | 1.00 | 18.85 |
| ATOM | 2960 | OD1 | ASP | A | 386 | −27.672 | 21.307 | −15.766 | 1.00 | 18.94 |
| ATOM | 2961 | OD2 | ASP | A | 386 | −29.365 | 22.624 | −15.461 | 1.00 | 23.88 |
| ATOM | 2962 | C | ASP | A | 386 | −24.938 | 24.322 | −14.526 | 1.00 | 15.81 |
| ATOM | 2963 | O | ASP | A | 386 | −24.594 | 24.998 | −15.501 | 1.00 | 16.29 |
| ATOM | 2964 | N | GLY | A | 387 | −24.591 | 24.640 | −13.290 | 1.00 | 15.76 |
| ATOM | 2965 | CA | GLY | A | 387 | −23.735 | 25.787 | −13.038 | 1.00 | 14.35 |
| ATOM | 2966 | C | GLY | A | 387 | −22.354 | 25.654 | −13.663 | 1.00 | 14.35 |
| ATOM | 2967 | O | GLY | A | 387 | −21.791 | 26.644 | −14.129 | 1.00 | 13.79 |
| ATOM | 2968 | N | PHE | A | 388 | −21.771 | 24.453 | −13.624 | 1.00 | 14.30 |
| ATOM | 2969 | CA | PHE | A | 388 | −20.479 | 24.217 | −14.312 | 1.00 | 14.69 |
| ATOM | 2970 | CB | PHE | A | 388 | −19.912 | 22.824 | −13.987 | 1.00 | 14.42 |
| ATOM | 2971 | CG | PHE | A | 388 | −19.359 | 22.730 | −12.584 | 1.00 | 13.79 |
| ATOM | 2972 | CD1 | PHE | A | 388 | −18.139 | 23.335 | −12.269 | 1.00 | 14.50 |
| ATOM | 2973 | CE1 | PHE | A | 388 | −17.621 | 23.261 | −10.947 | 1.00 | 16.38 |
| ATOM | 2974 | CZ | PHE | A | 388 | −18.377 | 22.627 | −9.951 | 1.00 | 14.77 |
| ATOM | 2975 | CE2 | PHE | A | 388 | −19.604 | 22.045 | −10.265 | 1.00 | 16.35 |
| ATOM | 2976 | CD2 | PHE | A | 388 | −20.088 | 22.100 | −11.578 | 1.00 | 14.00 |
| ATOM | 2977 | C | PHE | A | 388 | −20.601 | 24.428 | −15.821 | 1.00 | 15.31 |
| ATOM | 2978 | O | PHE | A | 388 | −19.740 | 25.078 | −16.440 | 1.00 | 15.55 |
| ATOM | 2979 | N | LEU | A | 389 | −21.669 | 23.913 | −16.415 | 1.00 | 16.52 |
| ATOM | 2980 | CA | LEU | A | 389 | −21.889 | 24.159 | −17.856 | 1.00 | 17.84 |
| ATOM | 2981 | CB | LEU | A | 389 | −23.137 | 23.431 | −18.382 | 1.00 | 17.83 |
| ATOM | 2982 | CG | LEU | A | 389 | −23.172 | 21.911 | −18.427 | 1.00 | 22.75 |
| ATOM | 2983 | CD1 | LEU | A | 389 | −24.247 | 21.418 | −19.401 | 1.00 | 22.55 |
| ATOM | 2984 | CD2 | LEU | A | 389 | −21.805 | 21.333 | −18.806 | 1.00 | 24.63 |
| ATOM | 2985 | C | LEU | A | 389 | −22.013 | 25.634 | −18.136 | 1.00 | 18.32 |
| ATOM | 2986 | O | LEU | A | 389 | −21.409 | 26.138 | −19.091 | 1.00 | 19.50 |
| ATOM | 2987 | N | SER | A | 390 | −22.775 | 26.341 | −17.295 | 1.00 | 18.55 |
| ATOM | 2988 | CA | SER | A | 390 | −23.021 | 27.767 | −17.469 | 1.00 | 19.33 |
| ATOM | 2989 | CB | SER | A | 390 | −24.090 | 28.246 | −16.491 | 1.00 | 19.89 |
| ATOM | 2990 | OG | SER | A | 390 | −25.325 | 27.693 | −16.891 | 1.00 | 24.07 |
| ATOM | 2991 | C | SER | A | 390 | −21.763 | 28.603 | −17.323 | 1.00 | 19.51 |
| ATOM | 2992 | O | SER | A | 390 | −21.575 | 29.585 | −18.055 | 1.00 | 19.69 |
| ATOM | 2993 | N | GLU | A | 391 | −20.893 | 28.200 | −16.399 | 1.00 | 18.87 |
| ATOM | 2994 | CA | GLU | A | 391 | −19.633 | 28.879 | −16.220 | 1.00 | 19.59 |
| ATOM | 2995 | CB | GLU | A | 391 | −18.901 | 28.393 | −14.952 | 1.00 | 20.02 |
| ATOM | 2996 | CG | GLU | A | 391 | −19.528 | 28.924 | −13.668 | 1.00 | 23.54 |
| ATOM | 2997 | CD | GLU | A | 391 | −19.590 | 30.448 | −13.634 | 1.00 | 26.61 |
| ATOM | 2998 | OE1 | GLU | A | 391 | −18.609 | 31.102 | −14.023 | 1.00 | 28.42 |
| ATOM | 2999 | OE2 | GLU | A | 391 | −20.637 | 30.994 | −13.227 | 1.00 | 29.52 |
| ATOM | 3000 | C | GLU | A | 391 | −18.738 | 28.729 | −17.457 | 1.00 | 19.12 |
| ATOM | 3001 | O | GLU | A | 391 | −18.123 | 29.709 | −17.906 | 1.00 | 19.40 |
| ATOM | 3002 | N | ALA | A | 392 | −18.654 | 27.516 | −17.991 | 1.00 | 18.81 |
| ATOM | 3003 | CA | ALA | A | 392 | −17.861 | 27.304 | −19.201 | 1.00 | 19.72 |
| ATOM | 3004 | CB | ALA | A | 392 | −17.758 | 25.815 | −19.526 | 1.00 | 19.45 |
| ATOM | 3005 | C | ALA | A | 392 | −18.478 | 28.098 | −20.363 | 1.00 | 19.59 |
| ATOM | 3006 | O | ALA | A | 392 | −17.764 | 28.724 | −21.157 | 1.00 | 18.65 |
| ATOM | 3007 | N | ALA | A | 393 | −19.808 | 28.117 | −20.425 | 1.00 | 20.40 |
| ATOM | 3008 | CA | ALA | A | 393 | −20.526 | 28.820 | −21.507 | 1.00 | 21.27 |
| ATOM | 3009 | CB | ALA | A | 393 | −22.035 | 28.524 | −21.421 | 1.00 | 21.83 |
| ATOM | 3010 | C | ALA | A | 393 | −20.266 | 30.334 | −21.574 | 1.00 | 21.79 |
| ATOM | 3011 | O | ALA | A | 393 | −20.283 | 30.920 | −22.664 | 1.00 | 21.96 |
| ATOM | 3012 | N | LYS | A | 394 | −19.976 | 30.971 | −20.435 | 1.00 | 21.37 |
| ATOM | 3013 | CA | LYS | A | 394 | −19.626 | 32.383 | −20.447 | 1.00 | 22.02 |
| ATOM | 3014 | CB | LYS | A | 394 | −19.289 | 32.916 | −19.043 | 1.00 | 23.11 |
| ATOM | 3015 | CG | LYS | A | 394 | −20.411 | 32.980 | −18.044 | 1.00 | 25.98 |
| ATOM | 3016 | CD | LYS | A | 394 | −19.782 | 33.341 | −16.700 | 1.00 | 28.89 |
| ATOM | 3017 | CE | LYS | A | 394 | −20.793 | 33.314 | −15.576 | 1.00 | 34.05 |
| ATOM | 3018 | NZ | LYS | A | 394 | −20.097 | 33.674 | −14.290 | 1.00 | 33.96 |
| ATOM | 3019 | C | LYS | A | 394 | −18.403 | 32.626 | −21.310 | 1.00 | 21.55 |
| ATOM | 3020 | O | LYS | A | 394 | −18.188 | 33.742 | −21.771 | 1.00 | 22.41 |
| ATOM | 3021 | N | TYR | A | 395 | −17.570 | 31.604 | −21.488 | 1.00 | 19.98 |
| ATOM | 3022 | CA | TYR | A | 395 | −16.287 | 31.824 | −22.132 | 1.00 | 19.46 |
| ATOM | 3023 | CB | TYR | A | 395 | −15.137 | 31.464 | −21.185 | 1.00 | 20.82 |
| ATOM | 3024 | CG | TYR | A | 395 | −15.291 | 32.165 | −19.872 | 1.00 | 22.04 |
| ATOM | 3025 | CD1 | TYR | A | 395 | −15.644 | 31.450 | −18.716 | 1.00 | 23.21 |
| ATOM | 3026 | CE1 | TYR | A | 395 | −15.806 | 32.097 | −17.508 | 1.00 | 23.70 |
| ATOM | 3027 | CZ | TYR | A | 395 | −15.661 | 33.473 | −17.460 | 1.00 | 23.93 |
| ATOM | 3028 | OH | TYR | A | 395 | −15.828 | 34.143 | −16.272 | 1.00 | 26.14 |
| ATOM | 3029 | CE2 | TYR | A | 395 | −15.327 | 34.202 | −18.593 | 1.00 | 24.38 |
| ATOM | 3030 | CD2 | TYR | A | 395 | −15.157 | 33.548 | −19.791 | 1.00 | 22.37 |
| ATOM | 3031 | C | TYR | A | 395 | −16.157 | 31.119 | −23.451 | 1.00 | 19.22 |
| ATOM | 3032 | O | TYR | A | 395 | −15.045 | 30.940 | −23.941 | 1.00 | 18.70 |
| ATOM | 3033 | N | VAL | A | 396 | −17.299 | 30.718 | −24.018 | 1.00 | 18.16 |
| ATOM | 3034 | CA | VAL | A | 396 | −17.331 | 30.135 | −25.352 | 1.00 | 19.03 |
| ATOM | 3035 | CB | VAL | A | 396 | −18.396 | 29.025 | −25.458 | 1.00 | 18.18 |
| ATOM | 3036 | CG1 | VAL | A | 396 | −18.469 | 28.465 | −26.898 | 1.00 | 18.63 |
| ATOM | 3037 | CG2 | VAL | A | 396 | −18.094 | 27.915 | −24.452 | 1.00 | 18.97 |
| ATOM | 3038 | C | VAL | A | 396 | −17.654 | 31.288 | −26.308 | 1.00 | 19.65 |

TABLE 15-continued

| | | | | | | | | | |
|---|---|---|---|---|---|---|---|---|---|
| ATOM | 3039 | O | VAL | A | 396 | −18.644 | 31.986 | −26.098 | 1.00 | 19.66 |
| ATOM | 3040 | N | PRO | A | 397 | −16.810 | 31.507 | −27.328 | 1.00 | 20.41 |
| ATOM | 3041 | CA | PRO | A | 397 | −17.016 | 32.626 | −28.256 | 1.00 | 20.82 |
| ATOM | 3042 | CB | PRO | A | 397 | −15.794 | 32.561 | −29.175 | 1.00 | 21.47 |
| ATOM | 3043 | CG | PRO | A | 397 | −14.819 | 31.725 | −28.475 | 1.00 | 21.69 |
| ATOM | 3044 | CD | PRO | A | 397 | −15.598 | 30.741 | −27.661 | 1.00 | 19.70 |
| ATOM | 3045 | C | PRO | A | 397 | −18.280 | 32.434 | −29.073 | 1.00 | 21.11 |
| ATOM | 3046 | O | PRO | A | 397 | −18.844 | 31.339 | −29.088 | 1.00 | 19.88 |
| ATOM | 3047 | N | ALA | A | 398 | −18.713 | 33.492 | −29.765 | 1.00 | 21.26 |
| ATOM | 3048 | CA | ALA | A | 398 | −19.951 | 33.424 | −30.559 | 1.00 | 21.44 |
| ATOM | 3049 | CB | ALA | A | 398 | −20.227 | 34.766 | −31.230 | 1.00 | 22.38 |
| ATOM | 3050 | C | ALA | A | 398 | −19.971 | 32.297 | −31.587 | 1.00 | 21.30 |
| ATOM | 3051 | O | ALA | A | 398 | −21.038 | 31.769 | −31.901 | 1.00 | 22.15 |
| ATOM | 3052 | N | ASP | A | 399 | −18.804 | 31.896 | −32.102 | 1.00 | 20.30 |
| ATOM | 3053 | CA | ASP | A | 399 | −18.780 | 30.858 | −33.133 | 1.00 | 19.40 |
| ATOM | 3054 | CB | ASP | A | 399 | −17.587 | 31.032 | −34.071 | 1.00 | 19.42 |
| ATOM | 3055 | CG | ASP | A | 399 | −16.233 | 30.835 | −33.381 | 1.00 | 21.84 |
| ATOM | 3056 | OD1 | ASP | A | 399 | −16.146 | 30.569 | −32.159 | 1.00 | 20.91 |
| ATOM | 3057 | OD2 | ASP | A | 399 | −15.229 | 30.950 | −34.104 | 1.00 | 24.62 |
| ATOM | 3058 | C | ASP | A | 399 | −18.834 | 29.435 | −32.579 | 1.00 | 18.14 |
| ATOM | 3059 | O | ASP | A | 399 | −18.802 | 28.465 | −33.350 | 1.00 | 16.78 |
| ATOM | 3060 | N | GLY | A | 400 | −18.891 | 29.322 | −31.245 | 1.00 | 16.82 |
| ATOM | 3061 | CA | GLY | A | 400 | −18.996 | 28.015 | −30.607 | 1.00 | 15.41 |
| ATOM | 3062 | C | GLY | A | 400 | −17.693 | 27.229 | −30.556 | 1.00 | 15.07 |
| ATOM | 3063 | O | GLY | A | 400 | −17.704 | 26.041 | −30.203 | 1.00 | 15.23 |
| ATOM | 3064 | N | SER | A | 401 | −16.572 | 27.861 | −30.882 | 1.00 | 14.21 |
| ATOM | 3065 | CA | SER | A | 401 | −15.312 | 27.119 | −30.893 | 1.00 | 14.76 |
| ATOM | 3066 | CB | SER | A | 401 | −14.241 | 27.840 | −31.718 | 1.00 | 14.71 |
| ATOM | 3067 | OG | SER | A | 401 | −14.059 | 29.160 | −31.257 | 1.00 | 16.86 |
| ATOM | 3068 | C | SER | A | 401 | −14.815 | 26.866 | −29.448 | 1.00 | 14.38 |
| ATOM | 3069 | O | SER | A | 401 | −14.992 | 21.111 | −28.562 | 1.00 | 14.58 |
| ATOM | 3070 | N | LEU | A | 402 | −14.169 | 25.720 | −29.249 | 1.00 | 13.54 |
| ATOM | 3071 | CA | LEU | A | 402 | −13.603 | 25.364 | −27.968 | 1.00 | 13.21 |
| ATOM | 3072 | CB | LEU | A | 402 | −14.271 | 24.080 | −27.450 | 1.00 | 13.42 |
| ATOM | 3073 | CG | LEU | A | 402 | −15.776 | 24.192 | −27.162 | 1.00 | 14.06 |
| ATOM | 3074 | CD1 | LEU | A | 402 | −16.289 | 22.834 | −26.668 | 1.00 | 13.87 |
| ATOM | 3075 | CD2 | LEU | A | 402 | −15.997 | 25.264 | −26.109 | 1.00 | 17.00 |
| ATOM | 3076 | C | LEU | A | 402 | −12.111 | 25.143 | −28.109 | 1.00 | 12.99 |
| ATOM | 3077 | O | LEU | A | 402 | −11.695 | 24.166 | −28.707 | 1.00 | 13.19 |
| ATOM | 3078 | N | ALA | A | 403 | −11.320 | 26.070 | −27.578 | 1.00 | 13.02 |
| ATOM | 3079 | CA | ALA | A | 403 | −9.884 | 25.870 | −27.454 | 1.00 | 12.06 |
| ATOM | 3080 | CB | ALA | A | 403 | −9.194 | 27.226 | −27.220 | 1.00 | 11.77 |
| ATOM | 3081 | C | ALA | A | 403 | −9.591 | 24.907 | −26.300 | 1.00 | 12.81 |
| ATOM | 3082 | O | ALA | A | 403 | −10.508 | 24.315 | −25.714 | 1.00 | 12.36 |
| ATOM | 3083 | N | GLU | A | 404 | −8.308 | 24.772 | −25.959 | 1.00 | 11.39 |
| ATOM | 3084 | CA | GLU | A | 404 | −7.918 | 23.922 | −24.855 | 1.00 | 11.47 |
| ATOM | 3085 | CB | GLU | A | 404 | −6.412 | 23.689 | −24.931 | 1.00 | 11.02 |
| ATOM | 3086 | CG | GLU | A | 404 | −5.865 | 22.723 | −23.873 | 1.00 | 11.30 |
| ATOM | 3087 | CD | GLU | A | 404 | −4.363 | 22.669 | −23.954 | 1.00 | 12.25 |
| ATOM | 3088 | OE1 | GLU | A | 404 | −3.729 | 23.692 | −23.622 | 1.00 | 12.06 |
| ATOM | 3089 | OE2 | GLU | A | 404 | −3.818 | 21.624 | −24.390 | 1.00 | 12.60 |
| ATOM | 3090 | C | GLU | A | 404 | −8.246 | 24.635 | −23.538 | 1.00 | 11.77 |
| ATOM | 3091 | O | GLU | A | 404 | −8.755 | 24.006 | −22.590 | 1.00 | 11.08 |
| ATOM | 3092 | N | GLN | A | 405 | −7.890 | 25.924 | −23.453 | 1.00 | 12.07 |
| ATOM | 3093 | CA | GLN | A | 405 | −7.952 | 26.655 | −22.196 | 1.00 | 13.33 |
| ATOM | 3094 | CB | GLN | A | 405 | −6.539 | 26.986 | −21.678 | 1.00 | 13.24 |
| ATOM | 3095 | CG | GLN | A | 405 | −5.625 | 25.821 | −21.553 | 1.00 | 15.96 |
| ATOM | 3096 | CD | GLN | A | 405 | −4.229 | 26.213 | −21.051 | 1.00 | 14.97 |
| ATOM | 3097 | OE1 | GLN | A | 405 | −4.068 | 27.130 | −20.236 | 1.00 | 15.09 |
| ATOM | 3098 | NE2 | GLN | A | 405 | −3.236 | 25.475 | −21.496 | 1.00 | 15.87 |
| ATOM | 3099 | C | GLN | A | 405 | −8.687 | 27.985 | −22.356 | 1.00 | 13.51 |
| ATOM | 3100 | O | GLN | A | 405 | −8.870 | 28.475 | −23.489 | 1.00 | 13.74 |
| ATOM | 3101 | N | PHE | A | 406 | −9.041 | 28.587 | −21.226 | 1.00 | 12.60 |
| ATOM | 3102 | CA | PHE | A | 406 | −9.516 | 29.990 | −21.207 | 1.00 | 13.82 |
| ATOM | 3103 | CB | PHE | A | 406 | −11.058 | 30.104 | −21.232 | 1.00 | 13.56 |
| ATOM | 3104 | CG | PHE | A | 406 | −11.800 | 29.385 | −20.123 | 1.00 | 15.20 |
| ATOM | 3105 | CD1 | PHE | A | 406 | −12.155 | 28.026 | −20.242 | 1.00 | 16.33 |
| ATOM | 3106 | CE1 | PHE | A | 406 | −12.879 | 27.370 | −19.239 | 1.00 | 16.80 |
| ATOM | 3107 | CZ | PHE | A | 406 | −13.340 | 28.094 | −18.114 | 1.00 | 16.74 |
| ATOM | 3108 | CE2 | PHE | A | 406 | −13.020 | 29.453 | −17.993 | 1.00 | 15.37 |
| ATOM | 3109 | CD2 | PHE | A | 406 | −12.260 | 30.101 | −19.000 | 1.00 | 17.56 |
| ATOM | 3110 | C | PHE | A | 406 | −8.836 | 30.737 | −20.078 | 1.00 | 13.80 |
| ATOM | 3111 | O | PHE | A | 406 | −8.587 | 30.151 | −19.018 | 1.00 | 14.02 |
| ATOM | 3112 | N | ASP | A | 407 | −8.481 | 31.997 | −20.321 | 1.00 | 14.98 |
| ATOM | 3113 | CA | ASP | A | 407 | −7.547 | 32.726 | −19.438 | 1.00 | 15.04 |
| ATOM | 3114 | CB | ASP | A | 407 | −7.237 | 34.115 | −20.032 | 1.00 | 15.99 |
| ATOM | 3115 | CG | ASP | A | 407 | −6.159 | 34.829 | −19.293 | 1.00 | 18.17 |
| ATOM | 3116 | OD1 | ASP | A | 407 | −6.474 | 35.508 | −18.293 | 1.00 | 20.41 |
| ATOM | 3117 | OD2 | ASP | A | 407 | −4.993 | 34.683 | −19.685 | 1.00 | 20.75 |
| ATOM | 3118 | C | ASP | A | 407 | −8.100 | 32.829 | −18.005 | 1.00 | 14.54 |

TABLE 15-continued

| | | | | | | | | | |
|---|---|---|---|---|---|---|---|---|---|
| ATOM | 3119 | O | ASP | A | 407 | −9.257 | 33.185 | −17.800 | 1.00 | 15.12 |
| ATOM | 3120 | N | ARG | A | 408 | −7.248 | 32.548 | −17.018 | 1.00 | 14.63 |
| ATOM | 3121 | CA | ARG | A | 408 | −7.644 | 32.530 | −15.609 | 1.00 | 15.33 |
| ATOM | 3122 | CB | ARG | A | 408 | −6.453 | 32.095 | −14.753 | 1.00 | 15.32 |
| ATOM | 3123 | CG | ARG | A | 408 | −5.236 | 33.062 | −14.828 | 1.00 | 14.48 |
| ATOM | 3124 | CD | ARG | A | 408 | −4.009 | 32.479 | −14.122 | 1.00 | 16.22 |
| ATOM | 3125 | NE | ARG | A | 408 | −4.237 | 32.248 | −12.695 | 1.00 | 15.55 |
| ATOM | 3126 | CZ | ARG | A | 408 | −3.613 | 31.323 | −11.961 | 1.00 | 18.66 |
| ATOM | 3127 | NH1 | ARG | A | 408 | −3.878 | 31.231 | −10.658 | 1.00 | 17.51 |
| ATOM | 3128 | NH2 | ARG | A | 408 | −2.717 | 30.499 | −12.511 | 1.00 | 17.12 |
| ATOM | 3129 | C | ARG | A | 408 | −8.167 | 33.886 | −15.108 | 1.00 | 16.66 |
| ATOM | 3130 | O | ARG | A | 408 | −8.898 | 33.943 | −14.110 | 1.00 | 16.82 |
| ATOM | 3131 | N | ASN | A | 409 | −7.781 | 34.964 | −15.790 | 1.00 | 18.00 |
| ATOM | 3132 | CA | ASN | A | 409 | −8.252 | 36.316 | −15.421 | 1.00 | 20.06 |
| ATOM | 3133 | CB | ASN | A | 409 | −7.069 | 37.275 | −15.355 | 1.00 | 20.32 |
| ATOM | 3134 | CG | ASN | A | 409 | −6.119 | 36.937 | −14.224 | 1.00 | 21.65 |
| ATOM | 3135 | OD1 | ASN | A | 409 | −6.549 | 36.678 | −13.111 | 1.00 | 24.42 |
| ATOM | 3136 | ND2 | ASN | A | 409 | −4.830 | 36.914 | −14.516 | 1.00 | 23.96 |
| ATOM | 3137 | C | ASN | A | 409 | −9.320 | 36.903 | −16.336 | 1.00 | 21.43 |
| ATOM | 3138 | O | ASN | A | 409 | −10.272 | 37.524 | −15.857 | 1.00 | 22.03 |
| ATOM | 3139 | N | SER | A | 410 | −9.152 | 36.724 | −17.646 | 1.00 | 22.25 |
| ATOM | 3140 | CA | SER | A | 410 | −10.007 | 37.410 | −18.624 | 1.00 | 22.76 |
| ATOM | 3141 | CB | SER | A | 410 | −9.146 | 38.159 | −19.636 | 1.00 | 23.45 |
| ATOM | 3142 | OG | SER | A | 410 | −8.470 | 37.260 | −20.495 | 1.00 | 23.38 |
| ATOM | 3143 | C | SER | A | 410 | −10.971 | 36.472 | −19.343 | 1.00 | 22.82 |
| ATOM | 3144 | O | SER | A | 410 | −11.898 | 36.925 | −20.010 | 1.00 | 23.59 |
| ATOM | 3145 | N | GLY | A | 411 | −10.758 | 35.161 | −19.238 | 1.00 | 21.64 |
| ATOM | 3146 | CA | GLY | A | 411 | −11.668 | 34.221 | −19.877 | 1.00 | 20.39 |
| ATOM | 3147 | C | GLY | A | 411 | −11.476 | 34.087 | −21.379 | 1.00 | 19.99 |
| ATOM | 3148 | O | GLY | A | 411 | −12.223 | 33.368 | −22.029 | 1.00 | 20.85 |
| ATOM | 3149 | N | THR | A | 412 | −10.478 | 34.750 | −21.941 | 1.00 | 19.04 |
| ATOM | 3150 | CA | THR | A | 412 | −10.268 | 34.658 | −23.383 | 1.00 | 20.25 |
| ATOM | 3151 | CB | THR | A | 412 | −9.447 | 35.853 | −23.922 | 1.00 | 21.81 |
| ATOM | 3152 | OG1 | THR | A | 412 | −8.187 | 35.900 | −23.257 | 1.00 | 26.24 |
| ATOM | 3153 | CG2 | THR | A | 412 | −10.160 | 37.163 | −23.631 | 1.00 | 23.82 |
| ATOM | 3154 | C | THR | A | 412 | −9.615 | 33.294 | −23.732 | 1.00 | 19.17 |
| ATOM | 3155 | O | THR | A | 412 | −8.786 | 32.796 | −22.970 | 1.00 | 17.70 |
| ATOM | 3156 | N | PRO | A | 413 | −9.996 | 32.688 | −24.874 | 1.00 | 18.84 |
| ATOM | 3157 | CA | PRO | A | 413 | −9.466 | 31.348 | −25.234 | 1.00 | 18.32 |
| ATOM | 3158 | CB | PRO | A | 413 | −10.220 | 31.002 | −26.525 | 1.00 | 18.75 |
| ATOM | 3159 | CG | PRO | A | 413 | −11.513 | 31.928 | −26.451 | 1.00 | 19.42 |
| ATOM | 3160 | CD | PRO | A | 413 | −10.943 | 33.195 | −25.891 | 1.00 | 19.40 |
| ATOM | 3161 | C | PRO | A | 413 | −7.959 | 31.399 | −25.464 | 1.00 | 18.87 |
| ATOM | 3162 | O | PRO | A | 413 | −7.436 | 32.406 | −25.955 | 1.00 | 18.20 |
| ATOM | 3163 | N | LEU | A | 414 | −7.253 | 30.353 | −25.051 | 1.00 | 18.44 |
| ATOM | 3164 | CA | LEU | A | 414 | −5.822 | 30.275 | −25.305 | 1.00 | 18.90 |
| ATOM | 3165 | CB | LEU | A | 414 | −4.992 | 30.974 | −24.208 | 1.00 | 21.66 |
| ATOM | 3166 | CG | LEU | A | 414 | −5.019 | 30.574 | −22.754 | 1.00 | 24.35 |
| ATOM | 3167 | CD1 | LEU | A | 414 | −4.134 | 31.484 | −21.892 | 1.00 | 27.42 |
| ATOM | 3168 | CD2 | LEU | A | 414 | −6.406 | 30.669 | −22.224 | 1.00 | 30.77 |
| ATOM | 3169 | C | LEU | A | 414 | −5.362 | 28.854 | −25.518 | 1.00 | 17.24 |
| ATOM | 3170 | O | LEU | A | 414 | −6.138 | 27.913 | −25.406 | 1.00 | 15.97 |
| ATOM | 3171 | N | SER | A | 415 | −4.091 | 28.733 | −25.865 | 1.00 | 15.34 |
| ATOM | 3172 | CA | SER | A | 415 | −3.473 | 27.481 | −26.257 | 1.00 | 15.28 |
| ATOM | 3173 | CB | SER | A | 415 | −3.434 | 26.468 | −25.101 | 1.00 | 14.94 |
| ATOM | 3174 | OG | SER | A | 415 | −2.632 | 25.355 | −25.445 | 1.00 | 14.00 |
| ATOM | 3175 | C | SER | A | 415 | −4.141 | 26.932 | −27.528 | 1.00 | 15.13 |
| ATOM | 3176 | O | SER | A | 415 | −4.665 | 27.718 | −28.334 | 1.00 | 14.92 |
| ATOM | 3177 | N | ALA | A | 416 | −4.097 | 25.618 | −27.714 | 1.00 | 14.27 |
| ATOM | 3178 | CA | ALA | A | 416 | −4.540 | 24.977 | −28.976 | 1.00 | 14.25 |
| ATOM | 3179 | CB | ALA | A | 416 | −4.380 | 23.486 | −28.889 | 1.00 | 13.68 |
| ATOM | 3180 | C | ALA | A | 416 | −5.981 | 25.314 | −29.315 | 1.00 | 14.33 |
| ATOM | 3181 | O | ALA | A | 416 | −6.854 | 25.216 | −28.459 | 1.00 | 14.09 |
| ATOM | 3182 | N | LEU | A | 417 | −6.223 | 25.680 | −30.567 | 1.00 | 13.34 |
| ATOM | 3183 | CA | LEU | A | 417 | −7.584 | 25.985 | −31.006 | 1.00 | 14.22 |
| ATOM | 3184 | CB | LEU | A | 417 | −7.536 | 26.931 | −32.194 | 1.00 | 16.32 |
| ATOM | 3185 | CG | LEU | A | 417 | −6.841 | 28.283 | −31.942 | 1.00 | 18.75 |
| ATOM | 3186 | CD1 | LEU | A | 417 | −7.005 | 29.127 | −33.163 | 1.00 | 23.81 |
| ATOM | 3187 | CD2 | LEU | A | 417 | −7.419 | 28.991 | −30.712 | 1.00 | 21.76 |
| ATOM | 3188 | C | LEU | A | 417 | −8.279 | 24.687 | −31.413 | 1.00 | 13.18 |
| ATOM | 3189 | O | LEU | A | 417 | −7.610 | 23.712 | −31.775 | 1.00 | 13.19 |
| ATOM | 3190 | N | HIS | A | 418 | −9.609 | 24.658 | −31.311 | 1.00 | 12.26 |
| ATOM | 3191 | CA | HIS | A | 418 | −10.399 | 23.496 | −31.764 | 1.00 | 11.77 |
| ATOM | 3192 | CB | HIS | A | 418 | −10.487 | 23.454 | −33.303 | 1.00 | 13.41 |
| ATOM | 3193 | CG | HIS | A | 418 | −11.294 | 24.566 | −33.898 | 1.00 | 14.68 |
| ATOM | 3194 | ND1 | HIS | A | 418 | −12.646 | 24.717 | −33.660 | 1.00 | 16.00 |
| ATOM | 3195 | CE1 | HIS | A | 418 | −13.095 | 25.762 | −34.341 | 1.00 | 17.83 |
| ATOM | 3196 | NE2 | HIS | A | 418 | −12.085 | 26.290 | −35.015 | 1.00 | 17.38 |
| ATOM | 3197 | CD2 | HIS | A | 418 | −10.948 | 25.557 | −34.763 | 1.00 | 17.65 |
| ATOM | 3198 | C | HIS | A | 418 | −9.826 | 22.187 | −31.206 | 1.00 | 12.24 |

TABLE 15-continued

| | | | | | | | | | |
|---|---|---|---|---|---|---|---|---|---|
| ATOM | 3199 | O | HIS | A | 418 | −9.540 | 21.250 | −31.947 | 1.00 | 12.10 |
| ATOM | 3200 | N | LEU | A | 419 | −9.656 | 22.116 | −29.880 | 1.00 | 10.99 |
| ATOM | 3201 | CA | LEU | A | 419 | −9.152 | 20.881 | −29.301 | 1.00 | 10.46 |
| ATOM | 3202 | CB | LEU | A | 419 | −8.742 | 21.069 | −27.826 | 1.00 | 10.91 |
| ATOM | 3203 | CG | LEU | A | 419 | −7.983 | 19.883 | −27.220 | 1.00 | 10.16 |
| ATOM | 3204 | CD1 | LEU | A | 419 | −6.524 | 19.944 | −27.669 | 1.00 | 11.45 |
| ATOM | 3205 | CD2 | LEU | A | 419 | −8.080 | 19.960 | −25.657 | 1.00 | 10.73 |
| ATOM | 3206 | C | LEU | A | 419 | −10.215 | 19.812 | −29.398 | 1.00 | 10.49 |
| ATOM | 3207 | O | LEU | A | 419 | −11.312 | 19.973 | −28.863 | 1.00 | 10.67 |
| ATOM | 3208 | N | THR | A | 420 | −9.860 | 18.686 | −30.021 | 1.00 | 10.22 |
| ATOM | 3209 | CA | THR | A | 420 | −10.833 | 17.629 | −30.296 | 1.00 | 10.90 |
| ATOM | 3210 | CB | THR | A | 420 | −10.201 | 16.460 | −31.096 | 1.00 | 11.55 |
| ATOM | 3211 | OG1 | THR | A | 420 | −9.357 | 16.999 | −32.115 | 1.00 | 12.00 |
| ATOM | 3212 | CG2 | THR | A | 420 | −11.310 | 15.625 | −31.786 | 1.00 | 12.52 |
| ATOM | 3213 | C | THR | A | 420 | −11.426 | 17.135 | −28.995 | 1.00 | 11.43 |
| ATOM | 3214 | O | THR | A | 420 | −12.648 | 16.903 | −28.891 | 1.00 | 11.83 |
| ATOM | 3215 | N | TRP | A | 421 | −10.569 | 16.987 | −27.980 | 1.00 | 9.79 |
| ATOM | 3216 | CA | TRP | A | 421 | −11.052 | 16.511 | −26.688 | 1.00 | 11.67 |
| ATOM | 3217 | CB | TRP | A | 421 | −9.839 | 16.184 | −25.803 | 1.00 | 12.06 |
| ATOM | 3218 | CG | TRP | A | 421 | −10.075 | 15.476 | −24.508 | 1.00 | 11.94 |
| ATOM | 3219 | CD1 | TRP | A | 421 | −11.274 | 15.202 | −23.881 | 1.00 | 14.46 |
| ATOM | 3220 | NE1 | TRP | A | 421 | −11.044 | 14.590 | −22.663 | 1.00 | 14.38 |
| ATOM | 3221 | CE2 | TRP | A | 421 | −9.691 | 14.497 | −22.468 | 1.00 | 13.52 |
| ATOM | 3222 | CD2 | TRP | A | 421 | −9.053 | 15.039 | −23.616 | 1.00 | 13.01 |
| ATOM | 3223 | CE3 | TRP | A | 421 | −7.652 | 15.045 | −23.680 | 1.00 | 15.38 |
| ATOM | 3224 | CZ3 | TRP | A | 421 | −6.932 | 14.503 | −22.605 | 1.00 | 16.10 |
| ATOM | 3225 | CH2 | TRP | A | 421 | −7.603 | 13.973 | −21.475 | 1.00 | 14.87 |
| ATOM | 3226 | CZ2 | TRP | A | 421 | −8.973 | 13.945 | −21.398 | 1.00 | 14.27 |
| ATOM | 3227 | C | TRP | A | 421 | −12.035 | 17.514 | −26.032 | 1.00 | 10.89 |
| ATOM | 3228 | O | TRP | A | 421 | −12.966 | 17.092 | −25.357 | 1.00 | 10.96 |
| ATOM | 3229 | N | SER | A | 422 | −11.844 | 18.822 | −26.211 | 1.00 | 10.49 |
| ATOM | 3230 | CA | SER | A | 422 | −12.833 | 19.794 | −25.696 | 1.00 | 11.13 |
| ATOM | 3231 | CB | SER | A | 422 | −12.459 | 21.243 | −26.049 | 1.00 | 10.97 |
| ATOM | 3232 | OG | SER | A | 422 | −11.302 | 21.682 | −25.338 | 1.00 | 13.73 |
| ATOM | 3233 | C | SER | A | 422 | −14.229 | 19.496 | −26.257 | 1.00 | 11.40 |
| ATOM | 3234 | O | SER | A | 422 | −15.204 | 19.468 | −25.530 | 1.00 | 12.11 |
| ATOM | 3235 | N | TYR | A | 423 | −14.320 | 19.281 | −27.563 | 1.00 | 11.29 |
| ATOM | 3236 | CA | TYR | A | 423 | −15.617 | 18.990 | −28.170 | 1.00 | 11.29 |
| ATOM | 3237 | CB | TYR | A | 423 | −15.502 | 19.020 | −29.717 | 1.00 | 11.85 |
| ATOM | 3238 | CG | TYR | A | 423 | −15.132 | 20.389 | −30.274 | 1.00 | 12.18 |
| ATOM | 3239 | CD1 | TYR | A | 423 | −16.002 | 21.485 | −30.145 | 1.00 | 10.35 |
| ATOM | 3240 | CE1 | TYR | A | 423 | −15.668 | 22.741 | −30.643 | 1.00 | 11.83 |
| ATOM | 3241 | CZ | TYR | A | 423 | −14.468 | 22.912 | −31.316 | 1.00 | 12.29 |
| ATOM | 3242 | OH | TYR | A | 423 | −14.157 | 24.145 | −31.783 | 1.00 | 13.08 |
| ATOM | 3243 | CE2 | TYR | A | 423 | −13.588 | 21.845 | −31.496 | 1.00 | 13.57 |
| ATOM | 3244 | CD2 | TYR | A | 423 | −13.942 | 20.572 | −30.991 | 1.00 | 12.74 |
| ATOM | 3245 | C | TYR | A | 423 | −16.217 | 17.673 | −27.658 | 1.00 | 12.12 |
| ATOM | 3246 | O | TYR | A | 423 | −17.430 | 17.622 | −27.323 | 1.00 | 12.13 |
| ATOM | 3247 | N | ALA | A | 424 | −15.385 | 16.623 | −27.539 | 1.00 | 10.99 |
| ATOM | 3248 | CA | ALA | A | 424 | −15.853 | 15.337 | −26.986 | 1.00 | 11.26 |
| ATOM | 3249 | CB | ALA | A | 424 | −14.717 | 14.294 | −26.952 | 1.00 | 11.73 |
| ATOM | 3250 | C | ALA | A | 424 | −16.411 | 15.535 | −25.588 | 1.00 | 10.93 |
| ATOM | 3251 | O | ALA | A | 424 | −17.465 | 14.974 | −25.246 | 1.00 | 11.68 |
| ATOM | 3252 | N | SER | A | 425 | −15.696 | 16.308 | −24.770 | 1.00 | 9.74 |
| ATOM | 3253 | CA | SER | A | 425 | −16.077 | 16.519 | −23.379 | 1.00 | 10.92 |
| ATOM | 3254 | CB | SER | A | 425 | −14.948 | 17.228 | −22.602 | 1.00 | 11.59 |
| ATOM | 3255 | OG | SER | A | 425 | −14.817 | 18.604 | −22.957 | 1.00 | 13.86 |
| ATOM | 3256 | C | SER | A | 425 | −17.402 | 17.291 | −23.219 | 1.00 | 11.65 |
| ATOM | 3257 | O | SER | A | 425 | −18.132 | 17.043 | −22.276 | 1.00 | 11.86 |
| ATOM | 3258 | N | PHE | A | 426 | −17.683 | 18.220 | −24.133 | 1.00 | 12.13 |
| ATOM | 3259 | CA | PHE | A | 426 | −18.983 | 18.891 | −24.154 | 1.00 | 12.95 |
| ATOM | 3260 | CB | PHE | A | 426 | −19.018 | 20.053 | −25.173 | 1.00 | 13.14 |
| ATOM | 3261 | CG | PHE | A | 426 | −20.410 | 20.575 | −25.391 | 1.00 | 15.93 |
| ATOM | 3262 | CD1 | PHE | A | 426 | −20.951 | 21.522 | −24.516 | 1.00 | 17.76 |
| ATOM | 3263 | CE1 | PHE | A | 426 | −22.279 | 21.980 | −24.688 | 1.00 | 17.49 |
| ATOM | 3264 | CZ | PHE | A | 426 | −23.064 | 21.455 | −25.716 | 1.00 | 17.22 |
| ATOM | 3265 | CE2 | PHE | A | 426 | −22.561 | 20.496 | −26.558 | 1.00 | 17.04 |
| ATOM | 3266 | CD2 | PHE | A | 426 | −21.225 | 20.045 | −26.396 | 1.00 | 17.29 |
| ATOM | 3267 | C | PHE | A | 426 | −20.079 | 17.878 | −24.502 | 1.00 | 13.31 |
| ATOM | 3268 | O | PHE | A | 426 | −21.120 | 17.827 | −23.850 | 1.00 | 13.38 |
| ATOM | 3269 | N | LEU | A | 427 | −19.834 | 17.077 | −25.539 | 1.00 | 13.23 |
| ATOM | 3270 | CA | LEU | A | 427 | −20.811 | 16.090 | −25.996 | 1.00 | 14.41 |
| ATOM | 3271 | CB | LEU | A | 427 | −20.339 | 15.410 | −27.291 | 1.00 | 14.32 |
| ATOM | 3272 | CG | LEU | A | 427 | −20.363 | 16.336 | −28.506 | 1.00 | 15.96 |
| ATOM | 3273 | CD1 | LEU | A | 427 | −19.661 | 15.639 | −29.689 | 1.00 | 18.66 |
| ATOM | 3274 | CD2 | LEU | A | 427 | −21.773 | 16.800 | −28.876 | 1.00 | 16.20 |
| ATOM | 3275 | C | LEU | A | 427 | −21.137 | 15.045 | −24.959 | 1.00 | 14.86 |
| ATOM | 3276 | O | LEU | A | 427 | −22.307 | 14.667 | −24.833 | 1.00 | 16.01 |
| ATOM | 3277 | N | THR | A | 428 | −20.130 | 14.551 | −24.235 | 1.00 | 13.81 |
| ATOM | 3278 | CA | THR | A | 428 | −20.397 | 13.544 | −23.196 | 1.00 | 13.67 |

TABLE 15-continued

| | | | | | | | | | |
|---|---|---|---|---|---|---|---|---|---|
| ATOM | 3279 | CB | THR | A | 428 | −19.134 | 12.732 | −22.745 | 1.00 | 12.87 |
| ATOM | 3280 | OG1 | THR | A | 428 | −18.127 | 13.597 | −22.185 | 1.00 | 12.33 |
| ATOM | 3281 | CG2 | THR | A | 428 | −18.533 | 11.902 | −23.923 | 1.00 | 13.77 |
| ATOM | 3282 | C | THR | A | 428 | −21.146 | 14.133 | −21.980 | 1.00 | 13.66 |
| ATOM | 3283 | O | THR | A | 428 | −22.102 | 13.517 | −21.478 | 1.00 | 15.09 |
| ATOM | 3284 | N | ALA | A | 429 | −20.738 | 15.312 | −21.524 | 1.00 | 13.72 |
| ATOM | 3285 | CA | ALA | A | 429 | −21.367 | 15.942 | −20.355 | 1.00 | 14.65 |
| ATOM | 3286 | CB | ALA | A | 429 | −20.704 | 17.295 | −20.036 | 1.00 | 14.11 |
| ATOM | 3287 | C | ALA | A | 429 | −22.852 | 16.158 | −20.643 | 1.00 | 15.47 |
| ATOM | 3288 | O | ALA | A | 429 | −23.704 | 15.908 | −19.783 | 1.00 | 15.97 |
| ATOM | 3289 | N | THR | A | 430 | −23.151 | 16.622 | −21.854 | 1.00 | 15.48 |
| ATOM | 3290 | CA | THR | A | 430 | −24.554 | 16.940 | −22.208 | 1.00 | 15.64 |
| ATOM | 3291 | CB | THR | A | 430 | −24.675 | 17.968 | −23.353 | 1.00 | 16.50 |
| ATOM | 3292 | OG1 | THR | A | 430 | −23.980 | 17.494 | −24.514 | 1.00 | 16.24 |
| ATOM | 3293 | CG2 | THR | A | 430 | −24.101 | 19.317 | −22.916 | 1.00 | 16.43 |
| ATOM | 3294 | C | THR | A | 430 | −25.401 | 15.690 | −22.463 | 1.00 | 15.41 |
| ATOM | 3295 | O | THR | A | 430 | −26.611 | 15.674 | −22.158 | 1.00 | 15.67 |
| ATOM | 3296 | N | ALA | A | 431 | −24.772 | 14.632 | −22.968 | 1.00 | 15.22 |
| ATOM | 3297 | CA | ALA | A | 431 | −25.437 | 13.311 | −23.049 | 1.00 | 16.26 |
| ATOM | 3298 | CB | ALA | A | 431 | −24.560 | 12.300 | −23.762 | 1.00 | 16.39 |
| ATOM | 3299 | C | ALA | A | 431 | −25.842 | 12.797 | −21.673 | 1.00 | 16.53 |
| ATOM | 3300 | O | ALA | A | 431 | −26.985 | 12.319 | −21.485 | 1.00 | 16.61 |
| ATOM | 3301 | N | ARG | A | 432 | −24.937 | 12.895 | −20.689 | 1.00 | 15.66 |
| ATOM | 3302 | CA | ARG | A | 432 | −25.256 | 12.410 | −19.342 | 1.00 | 15.64 |
| ATOM | 3303 | CB | ARG | A | 432 | −24.022 | 12.413 | −18.432 | 1.00 | 15.83 |
| ATOM | 3304 | CG | ARG | A | 432 | −22.862 | 11.574 | −18.994 | 1.00 | 14.85 |
| ATOM | 3305 | CD | ARG | A | 432 | −23.174 | 10.051 | −19.154 | 1.00 | 17.10 |
| ATOM | 3306 | NE | ARG | A | 432 | −21.958 | 9.472 | −19.708 | 1.00 | 18.67 |
| ATOM | 3307 | CZ | ARG | A | 432 | −21.766 | 9.225 | −21.003 | 1.00 | 20.81 |
| ATOM | 3308 | NH1 | ARG | A | 432 | −22.769 | 9.372 | −21.868 | 1.00 | 17.45 |
| ATOM | 3309 | NH2 | ARG | A | 432 | −20.576 | 8.781 | −21.427 | 1.00 | 19.90 |
| ATOM | 3310 | C | ARG | A | 432 | −26.375 | 13.235 | −18.719 | 1.00 | 16.42 |
| ATOM | 3311 | O | ARG | A | 432 | −27.256 | 12.685 | −18.030 | 1.00 | 17.47 |
| ATOM | 3312 | N | ARG | A | 433 | −26.371 | 14.535 | −18.996 | 1.00 | 16.54 |
| ATOM | 3313 | CA | ARG | A | 433 | −27.425 | 15.418 | −18.493 | 1.00 | 17.60 |
| ATOM | 3314 | CB | ARG | A | 433 | −27.204 | 16.852 | −18.960 | 1.00 | 16.74 |
| ATOM | 3315 | CG | ARG | A | 433 | −28.287 | 17.833 | −18.461 | 1.00 | 18.39 |
| ATOM | 3316 | CD | ARG | A | 433 | −27.931 | 19.239 | −18.866 | 1.00 | 20.79 |
| ATOM | 3317 | NE | ARG | A | 433 | −28.739 | 20.260 | −18.166 | 1.00 | 23.05 |
| ATOM | 3318 | CZ | ARG | A | 433 | −29.859 | 20.799 | −18.654 | 1.00 | 26.97 |
| ATOM | 3319 | NH1 | ARG | A | 433 | −30.333 | 20.404 | −19.837 | 1.00 | 24.94 |
| ATOM | 3320 | NH2 | ARG | A | 433 | −30.506 | 21.738 | −17.954 | 1.00 | 25.73 |
| ATOM | 3321 | C | ARG | A | 433 | −28.793 | 14.943 | −18.956 | 1.00 | 17.90 |
| ATOM | 3322 | O | ARG | A | 433 | −29.761 | 14.984 | −18.184 | 1.00 | 18.50 |
| ATOM | 3323 | N | ALA | A | 434 | −28.861 | 14.502 | −20.210 | 1.00 | 18.06 |
| ATOM | 3324 | CA | ALA | A | 434 | −30.103 | 13.993 | −20.806 | 1.00 | 19.10 |
| ATOM | 3325 | CB | ALA | A | 434 | −30.067 | 14.202 | −22.318 | 1.00 | 19.95 |
| ATOM | 3326 | C | ALA | A | 434 | −30.399 | 12.532 | −20.475 | 1.00 | 20.48 |
| ATOM | 3327 | O | ALA | A | 434 | −31.371 | 11.975 | −20.980 | 1.00 | 21.63 |
| ATOM | 3328 | N | GLY | A | 435 | −29.594 | 11.904 | −19.620 | 1.00 | 19.94 |
| ATOM | 3329 | CA | GLY | A | 435 | −29.865 | 10.531 | −19.182 | 1.00 | 21.09 |
| ATOM | 3330 | C | GLY | A | 435 | −29.415 | 9.475 | −20.188 | 1.00 | 21.57 |
| ATOM | 3331 | O | GLY | A | 435 | −29.847 | 8.304 | −20.130 | 1.00 | 21.64 |
| ATOM | 3332 | N | ILE | A | 436 | −28.529 | 9.873 | −21.100 | 1.00 | 20.44 |
| ATOM | 3333 | CA | ILE | A | 436 | −27.951 | 8.937 | −22.060 | 1.00 | 20.81 |
| ATOM | 3334 | CB | ILE | A | 436 | −27.753 | 9.601 | −23.447 | 1.00 | 20.75 |
| ATOM | 3335 | CG1 | ILE | A | 436 | −29.132 | 9.977 | −24.027 | 1.00 | 23.03 |
| ATOM | 3336 | CD1 | ILE | A | 436 | −29.103 | 11.031 | −25.128 | 1.00 | 26.34 |
| ATOM | 3337 | CG2 | ILE | A | 436 | −27.031 | 8.643 | −24.395 | 1.00 | 21.35 |
| ATOM | 3338 | C | ILE | A | 436 | −26.634 | 8.412 | −21.485 | 1.00 | 20.99 |
| ATOM | 3339 | O | ILE | A | 436 | −25.666 | 9.171 | −21.339 | 1.00 | 20.46 |
| ATOM | 3340 | N | VAL | A | 437 | −26.616 | 7.120 | −21.162 | 1.00 | 20.70 |
| ATOM | 3341 | CA | VAL | A | 437 | −25.465 | 6.479 | −20.517 | 1.00 | 21.39 |
| ATOM | 3342 | CB | VAL | A | 437 | −25.848 | 5.826 | −19.160 | 1.00 | 21.74 |
| ATOM | 3343 | CG1 | VAL | A | 437 | −26.340 | 6.911 | −18.205 | 1.00 | 22.12 |
| ATOM | 3344 | CG2 | VAL | A | 437 | −26.909 | 4.703 | −19.334 | 1.00 | 21.83 |
| ATOM | 3345 | C | VAL | A | 437 | −24.802 | 5.459 | −21.444 | 1.00 | 21.79 |
| ATOM | 3346 | O | VAL | A | 437 | −25.459 | 4.901 | −22.312 | 1.00 | 22.18 |
| ATOM | 3347 | N | PRO | A | 438 | −23.497 | 5.208 | −21.255 | 1.00 | 22.28 |
| ATOM | 3348 | CA | PRO | A | 438 | −22.837 | 4.291 | −22.181 | 1.00 | 22.83 |
| ATOM | 3349 | CB | PRO | A | 438 | −21.365 | 4.642 | −22.009 | 1.00 | 22.45 |
| ATOM | 3350 | CG | PRO | A | 438 | −21.248 | 5.054 | −20.578 | 1.00 | 23.88 |
| ATOM | 3351 | CD | PRO | A | 438 | −22.575 | 5.707 | −20.214 | 1.00 | 22.50 |
| ATOM | 3352 | C | PRO | A | 438 | −23.093 | 2.840 | −21.753 | 1.00 | 22.80 |
| ATOM | 3353 | O | PRO | A | 438 | −23.580 | 2.604 | −20.626 | 1.00 | 23.06 |
| ATOM | 3354 | N | PRO | A | 439 | −22.796 | 1.878 | −22.639 | 1.00 | 22.65 |
| ATOM | 3355 | CA | PRO | A | 439 | −22.911 | 0.452 | −22.283 | 1.00 | 22.08 |
| ATOM | 3356 | CB | PRO | A | 439 | −22.300 | −0.269 | −23.499 | 1.00 | 21.30 |
| ATOM | 3357 | CG | PRO | A | 439 | −22.526 | 0.664 | −24.618 | 1.00 | 22.81 |
| ATOM | 3358 | CD | PRO | A | 439 | −22.391 | 2.062 | −24.050 | 1.00 | 22.29 |

TABLE 15-continued

| | | | | | | | | | |
|---|---|---|---|---|---|---|---|---|---|
| ATOM | 3359 | C | PRO | A | 439 | −22.122 | 0.129 | −21.037 | 1.00 | 21.88 |
| ATOM | 3360 | O | PRO | A | 439 | −21.075 | 0.750 | −20.776 | 1.00 | 20.95 |
| ATOM | 3361 | N | SER | A | 440 | −22.628 | −0.818 | −20.253 | 1.00 | 22.34 |
| ATOM | 3362 | CA | SER | A | 440 | −21.932 | −1.273 | −19.060 | 1.00 | 23.42 |
| ATOM | 3363 | CB | SER | A | 440 | −22.818 | −2.195 | −18.224 | 1.00 | 24.01 |
| ATOM | 3364 | OG | SER | A | 440 | −23.805 | −1.412 | −17.566 | 1.00 | 26.78 |
| ATOM | 3365 | C | SER | A | 440 | −20.654 | −1.992 | −19.430 | 1.00 | 23.78 |
| ATOM | 3366 | O | SER | A | 440 | −20.540 | −2.554 | −20.522 | 1.00 | 23.97 |
| ATOM | 3367 | N | TRP | A | 441 | −19.681 | −1.929 | −18.536 | 1.00 | 24.15 |
| ATOM | 3368 | CA | TRP | A | 441 | −18.431 | −2.646 | −18.718 | 1.00 | 24.63 |
| ATOM | 3369 | CB | TRP | A | 441 | −17.255 | −1.679 | −18.819 | 1.00 | 22.62 |
| ATOM | 3370 | CG | TRP | A | 441 | −16.963 | −0.837 | −17.583 | 1.00 | 19.24 |
| ATOM | 3371 | CD1 | TRP | A | 441 | −17.409 | 0.432 | −17.339 | 1.00 | 16.95 |
| ATOM | 3372 | NE1 | TRP | A | 441 | −16.909 | 0.878 | −16.138 | 1.00 | 17.89 |
| ATOM | 3373 | CE2 | TRP | A | 441 | −16.111 | −0.098 | −15.595 | 1.00 | 17.88 |
| ATOM | 3374 | CD2 | TRP | A | 441 | −16.130 | −1.194 | −16.476 | 1.00 | 18.22 |
| ATOM | 3375 | CE3 | TRP | A | 441 | −15.377 | −2.338 | −16.149 | 1.00 | 19.64 |
| ATOM | 3376 | CZ3 | TRP | A | 441 | −14.658 | −2.355 | −14.961 | 1.00 | 18.61 |
| ATOM | 3377 | CH2 | TRP | A | 441 | −14.670 | −1.246 | −14.094 | 1.00 | 20.62 |
| ATOM | 3378 | CZ2 | TRP | A | 441 | −15.400 | −0.114 | −14.391 | 1.00 | 19.39 |
| ATOM | 3379 | C | TRP | A | 441 | −18.179 | −3.661 | −17.625 | 1.00 | 26.71 |
| ATOM | 3380 | O | TRP | A | 441 | −17.410 | −4.592 | −17.813 | 1.00 | 25.60 |
| ATOM | 3381 | N | ALA | A | 442 | −18.798 | −3.471 | −16.468 | 1.00 | 29.78 |
| ATOM | 3382 | CA | ALA | A | 442 | −18.442 | −4.292 | −15.330 | 1.00 | 33.94 |
| ATOM | 3383 | CB | ALA | A | 442 | −18.347 | −3.447 | −14.082 | 1.00 | 33.18 |
| ATOM | 3384 | C | ALA | A | 442 | −19.447 | −5.412 | −15.136 | 1.00 | 37.28 |
| ATOM | 3385 | O | ALA | A | 442 | −20.383 | −5.561 | −15.915 | 1.00 | 38.51 |
| ATOM | 3386 | N | ASN | A | 443 | −19.201 | −6.222 | −14.116 | 1.00 | 41.45 |
| ATOM | 3387 | CA | ASN | A | 443 | −20.226 | −7.030 | −13.467 | 1.00 | 45.10 |
| ATOM | 3388 | CB | ASN | A | 443 | −20.135 | −8.490 | −13.914 | 1.00 | 45.75 |
| ATOM | 3389 | CG | ASN | A | 443 | −18.815 | −9.129 | −13.531 | 1.00 | 48.14 |
| ATOM | 3390 | OD1 | ASN | A | 443 | −18.620 | −9.524 | −12.380 | 1.00 | 50.51 |
| ATOM | 3391 | ND2 | ASN | A | 443 | −17.888 | −9.212 | −14.492 | 1.00 | 50.01 |
| ATOM | 3392 | C | ASN | A | 443 | −19.946 | −6.892 | −11.972 | 1.00 | 46.93 |
| ATOM | 3393 | O | ASN | A | 443 | −18.878 | −6.396 | −11.580 | 1.00 | 47.13 |
| ATOM | 3394 | N | SER | A | 444 | −20.873 | −7.343 | −11.135 | 1.00 | 49.21 |
| ATOM | 3395 | CA | SER | A | 444 | −20.719 | −7.201 | −9.684 | 1.00 | 51.08 |
| ATOM | 3396 | CB | SER | A | 444 | −21.713 | −8.096 | −8.936 | 1.00 | 51.21 |
| ATOM | 3397 | OG | SER | A | 444 | −21.738 | −7.735 | −7.563 | 1.00 | 52.90 |
| ATOM | 3398 | C | SER | A | 444 | −19.291 | −7.452 | −9.165 | 1.00 | 51.89 |
| ATOM | 3399 | O | SER | A | 444 | −18.743 | −6.610 | −8.433 | 1.00 | 52.46 |
| ATOM | 3400 | N | SER | A | 445 | −18.700 | −8.588 | −9.558 | 1.00 | 52.45 |
| ATOM | 3401 | CA | SER | A | 445 | −17.400 | −9.030 | −9.029 | 1.00 | 52.98 |
| ATOM | 3402 | CB | SER | A | 445 | −17.138 | −10.497 | −9.385 | 1.00 | 53.12 |
| ATOM | 3403 | OG | SER | A | 445 | −16.901 | −10.650 | −10.775 | 1.00 | 54.45 |
| ATOM | 3404 | C | SER | A | 445 | −16.202 | −8.159 | −9.449 | 1.00 | 52.99 |
| ATOM | 3405 | O | SER | A | 445 | −15.184 | −8.112 | −8.738 | 1.00 | 53.28 |
| ATOM | 3406 | N | ALA | A | 446 | −16.328 | −7.472 | −10.588 | 1.00 | 52.67 |
| ATOM | 3407 | CA | ALA | A | 446 | −15.301 | −6.536 | −11.063 | 1.00 | 52.20 |
| ATOM | 3408 | CB | ALA | A | 446 | −15.695 | −5.960 | −12.425 | 1.00 | 52.45 |
| ATOM | 3409 | C | ALA | A | 446 | −14.996 | −5.406 | −10.059 | 1.00 | 51.92 |
| ATOM | 3410 | O | ALA | A | 446 | −14.144 | −4.553 | −10.322 | 1.00 | 51.77 |
| ATOM | 3411 | N | SER | A | 447 | −15.696 | −5.413 | −8.919 | 1.00 | 51.23 |
| ATOM | 3412 | CA | SER | A | 447 | −15.471 | −4.453 | −7.827 | 1.00 | 50.73 |
| ATOM | 3413 | CB | SER | A | 447 | −16.769 | −3.706 | −7.495 | 1.00 | 50.70 |
| ATOM | 3414 | OG | SER | A | 447 | −17.765 | −4.605 | −7.021 | 1.00 | 50.91 |
| ATOM | 3415 | C | SER | A | 447 | −14.886 | −5.072 | −6.537 | 1.00 | 50.31 |
| ATOM | 3416 | O | SER | A | 447 | −14.604 | −4.345 | −5.580 | 1.00 | 50.16 |
| ATOM | 3417 | N | THR | A | 448 | −14.704 | −6.394 | −6.508 | 1.00 | 49.55 |
| ATOM | 3418 | CA | THR | A | 448 | −14.165 | −7.070 | −5.314 | 1.00 | 49.05 |
| ATOM | 3419 | CB | THR | A | 448 | −14.579 | −8.561 | −5.233 | 1.00 | 49.15 |
| ATOM | 3420 | OG1 | THR | A | 448 | −14.076 | −9.255 | −6.378 | 1.00 | 49.97 |
| ATOM | 3421 | CG2 | THR | A | 448 | −16.096 | −8.705 | −5.180 | 1.00 | 49.11 |
| ATOM | 3422 | C | THR | A | 448 | −12.641 | −6.958 | −5.215 | 1.00 | 48.34 |
| ATOM | 3423 | O | THR | A | 448 | −11.911 | −7.325 | −6.135 | 1.00 | 47.84 |
| ATOM | 3424 | N | ILE | A | 449 | −12.174 | −6.444 | −4.084 | 1.00 | 47.93 |
| ATOM | 3425 | CA | ILE | A | 449 | −10.760 | −6.150 | −3.891 | 1.00 | 47.42 |
| ATOM | 3426 | CB | ILE | A | 449 | −10.577 | −4.798 | −3.142 | 1.00 | 47.53 |
| ATOM | 3427 | CG1 | ILE | A | 449 | −11.346 | −3.680 | −3.863 | 1.00 | 46.60 |
| ATOM | 3428 | CD1 | ILE | A | 449 | −11.727 | −2.523 | −2.981 | 1.00 | 45.49 |
| ATOM | 3429 | CG2 | ILE | A | 449 | −9.097 | −4.438 | −2.999 | 1.00 | 46.84 |
| ATOM | 3430 | C | ILE | A | 449 | −10.104 | −7.299 | −3.124 | 1.00 | 47.45 |
| ATOM | 3431 | O | ILE | A | 449 | −10.606 | −7.688 | −2.067 | 1.00 | 47.66 |
| ATOM | 3432 | N | PRO | A | 450 | −8.993 | −7.857 | −3.663 | 1.00 | 47.28 |
| ATOM | 3433 | CA | PRO | A | 450 | −8.202 | −8.926 | −3.036 | 1.00 | 47.25 |
| ATOM | 3434 | CB | PRO | A | 450 | −6.982 | −9.040 | −3.946 | 1.00 | 47.03 |
| ATOM | 3435 | CG | PRO | A | 450 | −7.430 | −8.535 | −5.237 | 1.00 | 47.02 |
| ATOM | 3436 | CD | PRO | A | 450 | −8.431 | −7.470 | −4.969 | 1.00 | 47.07 |
| ATOM | 3437 | C | PRO | A | 450 | −7.731 | −8.562 | −1.639 | 1.00 | 47.48 |
| ATOM | 3438 | O | PRO | A | 450 | −7.608 | −7.377 | −1.322 | 1.00 | 47.43 |

TABLE 15-continued

| | | | | | | | | | |
|---|---|---|---|---|---|---|---|---|---|
| ATOM | 3439 | N | SER | A | 451 | −7.452 | −9.587 | −0.832 | 1.00 | 47.94 |
| ATOM | 3440 | CA | SER | A | 451 | −7.020 | −9.436 | 0.568 | 1.00 | 48.19 |
| ATOM | 3441 | CB | SER | A | 451 | −7.017 | −10.801 | 1.277 | 1.00 | 48.52 |
| ATOM | 3442 | OG | SER | A | 451 | −8.297 | −11.414 | 1.235 | 1.00 | 49.64 |
| ATOM | 3443 | C | SER | A | 451 | −5.641 | −8.799 | 0.701 | 1.00 | 47.83 |
| ATOM | 3444 | O | SER | A | 451 | −5.415 | −7.963 | 1.575 | 1.00 | 48.39 |
| ATOM | 3445 | N | THR | A | 452 | −4.715 | −9.212 | −0.158 | 1.00 | 47.14 |
| ATOM | 3446 | CA | THR | A | 452 | −3.379 | −8.613 | −0.211 | 1.00 | 46.42 |
| ATOM | 3447 | CB | THR | A | 452 | −2.323 | −9.540 | 0.434 | 1.00 | 46.66 |
| ATOM | 3448 | OG1 | THR | A | 452 | −2.518 | −10.887 | −0.032 | 1.00 | 48.38 |
| ATOM | 3449 | CG2 | THR | A | 452 | −2.446 | −9.514 | 1.962 | 1.00 | 47.77 |
| ATOM | 3450 | C | THR | A | 452 | −3.011 | −8.323 | −1.673 | 1.00 | 44.81 |
| ATOM | 3451 | O | THR | A | 452 | −3.348 | −9.107 | −2.558 | 1.00 | 44.97 |
| ATOM | 3452 | N | CYS | A | 453 | −2.363 | −7.187 | −1.931 | 1.00 | 43.37 |
| ATOM | 3453 | CA | CYS | A | 453 | −1.971 | −6.854 | −3.306 | 1.00 | 41.40 |
| ATOM | 3454 | CB | CYS | A | 453 | −1.918 | −5.339 | −3.574 | 1.00 | 41.01 |
| ATOM | 3455 | SG | CYS | A | 453 | −3.187 | −4.199 | −2.908 | 1.00 | 40.58 |
| ATOM | 3456 | C | CYS | A | 453 | −0.591 | −7.408 | −3.602 | 1.00 | 40.33 |
| ATOM | 3457 | O | CYS | A | 453 | 0.293 | −7.370 | −2.753 | 1.00 | 39.88 |
| ATOM | 3458 | N | SER | A | 454 | −0.405 | −7.911 | −4.812 | 1.00 | 39.25 |
| ATOM | 3459 | CA | SER | A | 454 | 0.937 | −8.142 | −5.336 | 1.00 | 38.68 |
| ATOM | 3460 | CB | SER | A | 454 | 1.222 | −9.638 | −5.484 | 1.00 | 38.56 |
| ATOM | 3461 | OG | SER | A | 454 | 0.276 | −10.251 | −6.349 | 1.00 | 40.44 |
| ATOM | 3462 | C | SER | A | 454 | 1.047 | −7.450 | −6.690 | 1.00 | 37.78 |
| ATOM | 3463 | O | SER | A | 454 | 0.030 | −7.187 | −7.347 | 1.00 | 36.71 |
| ATOM | 3464 | N | GLY | A | 455 | 2.275 | −7.175 | −7.111 | 1.00 | 37.06 |
| ATOM | 3465 | CA | GLY | A | 455 | 2.514 | −6.613 | −8.431 | 1.00 | 36.79 |
| ATOM | 3466 | C | GLY | A | 455 | 2.493 | −7.658 | −9.539 | 1.00 | 36.18 |
| ATOM | 3467 | O | GLY | A | 455 | 3.410 | −7.708 | −10.367 | 1.00 | 36.73 |
| ATOM | 3468 | N | ALA | A | 456 | 1.445 | −8.480 | −9.562 | 1.00 | 35.26 |
| ATOM | 3469 | CA | ALA | A | 456 | 1.321 | −9.584 | −10.512 | 1.00 | 34.46 |
| ATOM | 3470 | CB | ALA | A | 456 | 0.125 | −10.454 | −10.158 | 1.00 | 34.50 |
| ATOM | 3471 | C | ALA | A | 456 | 1.195 | −9.111 | −11.963 | 1.00 | 34.16 |
| ATOM | 3472 | O | ALA | A | 456 | 0.283 | −8.353 | −12.301 | 1.00 | 33.56 |
| ATOM | 3473 | N | SER | A | 457 | 2.097 | −9.588 | −12.817 | 1.00 | 33.11 |
| ATOM | 3474 | CA | SER | A | 457 | 2.013 | −9.302 | −14.241 | 1.00 | 32.60 |
| ATOM | 3475 | CB | SER | A | 457 | 3.022 | −8.219 | −14.635 | 1.00 | 32.50 |
| ATOM | 3476 | OG | SER | A | 457 | 4.352 | −8.691 | −14.519 | 1.00 | 33.28 |
| ATOM | 3477 | C | SER | A | 457 | 2.228 | −10.575 | −15.044 | 1.00 | 32.31 |
| ATOM | 3478 | O | SER | A | 457 | 2.641 | −11.605 | −14.494 | 1.00 | 32.32 |
| ATOM | 3479 | N | VAL | A | 458 | 1.908 | −10.511 | −16.330 | 1.00 | 31.12 |
| ATOM | 3480 | CA | VAL | A | 458 | 2.063 | −11.629 | −17.246 | 1.00 | 31.09 |
| ATOM | 3481 | CB | VAL | A | 458 | 0.682 | −12.199 | −17.659 | 1.00 | 31.00 |
| ATOM | 3482 | CG1 | VAL | A | 458 | 0.806 | −13.173 | −18.830 | 1.00 | 30.72 |
| ATOM | 3483 | CG2 | VAL | A | 458 | −0.014 | −12.847 | −16.459 | 1.00 | 31.08 |
| ATOM | 3484 | C | VAL | A | 458 | 2.817 | −11.144 | −18.480 | 1.00 | 30.88 |
| ATOM | 3485 | O | VAL | A | 458 | 2.401 | −10.177 | −19.126 | 1.00 | 29.70 |
| ATOM | 3486 | N | VAL | A | 459 | 3.924 | −11.811 | −18.805 | 1.00 | 30.81 |
| ATOM | 3487 | CA | VAL | A | 459 | 4.643 | −11.525 | −20.051 | 1.00 | 30.95 |
| ATOM | 3488 | CB | VAL | A | 459 | 6.046 | −12.172 | −20.071 | 1.00 | 31.34 |
| ATOM | 3489 | CG1 | VAL | A | 459 | 6.664 | −12.102 | −21.492 | 1.00 | 30.45 |
| ATOM | 3490 | CG2 | VAL | A | 459 | 6.947 | −11.522 | −19.030 | 1.00 | 32.03 |
| ATOM | 3491 | C | VAL | A | 459 | 3.805 | −12.032 | −21.227 | 1.00 | 31.37 |
| ATOM | 3492 | O | VAL | A | 459 | 3.443 | −13.214 | −21.288 | 1.00 | 31.84 |
| ATOM | 3493 | N | GLY | A | 460 | 3.480 | −11.137 | −22.154 | 1.00 | 30.71 |
| ATOM | 3494 | CA | GLY | A | 460 | 2.596 | −11.495 | −23.258 | 1.00 | 30.77 |
| ATOM | 3495 | C | GLY | A | 460 | 3.349 | −11.799 | −24.536 | 1.00 | 30.66 |
| ATOM | 3496 | O | GLY | A | 460 | 4.585 | −11.773 | −24.582 | 1.00 | 30.90 |
| ATOM | 3497 | N | SER | A | 461 | 2.606 | −12.094 | −25.584 | 1.00 | 30.44 |
| ATOM | 3498 | CA | SER | A | 461 | 3.219 | −12.227 | −26.877 | 1.00 | 31.06 |
| ATOM | 3499 | CB | SER | A | 461 | 3.301 | −13.695 | −27.308 | 1.00 | 31.44 |
| ATOM | 3500 | OG | SER | A | 461 | 2.018 | −14.278 | −27.419 | 1.00 | 34.77 |
| ATOM | 3501 | C | SER | A | 461 | 2.463 | −11.357 | −27.864 | 1.00 | 30.21 |
| ATOM | 3502 | O | SER | A | 461 | 1.246 | −11.156 | −27.736 | 1.00 | 30.87 |
| ATOM | 3503 | N | TYR | A | 462 | 3.192 | −10.822 | −28.836 | 1.00 | 28.84 |
| ATOM | 3504 | CA | TYR | A | 462 | 2.651 | −9.797 | −29.712 | 1.00 | 28.13 |
| ATOM | 3505 | CB | TYR | A | 462 | 3.365 | −8.471 | −29.426 | 1.00 | 26.74 |
| ATOM | 3506 | CG | TYR | A | 462 | 3.264 | −8.098 | −27.976 | 1.00 | 25.28 |
| ATOM | 3507 | CD1 | TYR | A | 462 | 2.184 | −7.335 | −27.508 | 1.00 | 23.75 |
| ATOM | 3508 | CE1 | TYR | A | 462 | 2.066 | −7.022 | −26.162 | 1.00 | 23.41 |
| ATOM | 3509 | CZ | TYR | A | 462 | 3.030 | −7.458 | −25.268 | 1.00 | 23.32 |
| ATOM | 3510 | OH | TYR | A | 462 | 2.907 | −7.155 | −23.941 | 1.00 | 23.50 |
| ATOM | 3511 | CE2 | TYR | A | 462 | 4.113 | −8.226 | −25.698 | 1.00 | 22.57 |
| ATOM | 3512 | CD2 | TYR | A | 462 | 4.223 | −8.537 | −27.050 | 1.00 | 24.71 |
| ATOM | 3513 | C | TYR | A | 462 | 2.844 | −10.191 | −31.152 | 1.00 | 28.83 |
| ATOM | 3514 | O | TYR | A | 462 | 3.898 | −10.697 | −31.529 | 1.00 | 29.33 |
| ATOM | 3515 | N | SER | A | 463 | 1.828 | −9.973 | −31.961 | 1.00 | 29.66 |
| ATOM | 3516 | CA | SER | A | 463 | 1.970 | −10.202 | −33.388 | 1.00 | 30.77 |
| ATOM | 3517 | CB | SER | A | 463 | 1.424 | −11.574 | −33.784 | 1.00 | 30.99 |
| ATOM | 3518 | OG | SER | A | 463 | 0.168 | −11.815 | −33.192 | 1.00 | 33.22 |

TABLE 15-continued

| | | | | | | | | |
|---|---|---|---|---|---|---|---|---|
| ATOM | 3519 | C | SER | A | 463 | 1.311 | −9.082 | −34.170 | 1.00 | 31.28 |
| ATOM | 3520 | O | SER | A | 463 | 0.329 | −8.481 | −33.723 | 1.00 | 30.40 |
| ATOM | 3521 | N | ARG | A | 464 | 1.886 | −8.789 | −35.330 | 1.00 | 31.94 |
| ATOM | 3522 | CA | ARG | A | 464 | 1.377 | −7.775 | −36.225 | 1.00 | 32.97 |
| ATOM | 3523 | CB | ARG | A | 464 | 2.362 | −7.620 | −37.385 | 1.00 | 33.68 |
| ATOM | 3524 | CG | ARG | A | 464 | 2.353 | −6.274 | −38.061 | 1.00 | 36.94 |
| ATOM | 3525 | CD | ARG | A | 464 | 3.502 | −6.206 | −39.088 | 1.00 | 42.45 |
| ATOM | 3526 | NE | ARG | A | 464 | 4.794 | −6.065 | −38.415 | 1.00 | 45.53 |
| ATOM | 3527 | CZ | ARG | A | 464 | 5.416 | −4.903 | −38.227 | 1.00 | 47.50 |
| ATOM | 3528 | NH1 | ARG | A | 464 | 4.882 | −3.775 | −38.688 | 1.00 | 49.50 |
| ATOM | 3529 | NH2 | ARG | A | 464 | 6.580 | −4.863 | −37.592 | 1.00 | 48.59 |
| ATOM | 3530 | C | ARG | A | 464 | −0.017 | −8.171 | −36.741 | 1.00 | 33.03 |
| ATOM | 3531 | O | ARG | A | 464 | −0.166 | −9.228 | −37.358 | 1.00 | 33.00 |
| ATOM | 3532 | N | PRO | A | 465 | −1.053 | −7.333 | −36.479 | 1.00 | 32.72 |
| ATOM | 3533 | CA | PRO | A | 465 | −2.344 | −7.593 | −37.131 | 1.00 | 32.69 |
| ATOM | 3534 | CB | PRO | A | 465 | −3.274 | −6.504 | −36.558 | 1.00 | 32.50 |
| ATOM | 3535 | CG | PRO | A | 465 | −2.581 | −5.981 | −35.345 | 1.00 | 32.47 |
| ATOM | 3536 | CD | PRO | A | 465 | −1.102 | −6.134 | −35.618 | 1.00 | 32.83 |
| ATOM | 3537 | C | PRO | A | 465 | −2.189 | −7.421 | −38.642 | 1.00 | 33.30 |
| ATOM | 3538 | O | PRO | A | 465 | −1.332 | −6.661 | −39.097 | 1.00 | 33.20 |
| ATOM | 3539 | N | THR | A | 466 | −2.990 | −8.136 | −39.412 | 1.00 | 34.26 |
| ATOM | 3540 | CA | THR | A | 466 | −2.810 | −8.131 | −40.855 | 1.00 | 35.62 |
| ATOM | 3541 | CB | THR | A | 466 | −2.264 | −9.486 | −41.370 | 1.00 | 35.33 |
| ATOM | 3542 | OG1 | THR | A | 466 | −3.225 | −10.512 | −41.136 | 1.00 | 36.81 |
| ATOM | 3543 | CG2 | THR | A | 466 | −0.965 | −9.848 | −40.656 | 1.00 | 35.91 |
| ATOM | 3544 | C | THR | A | 466 | −4.076 | −7.711 | −41.600 | 1.00 | 36.15 |
| ATOM | 3545 | O | THR | A | 466 | −3.983 | −7.077 | −42.648 | 1.00 | 36.93 |
| ATOM | 3546 | N | ALA | A | 467 | −5.242 | −8.051 | −41.048 | 1.00 | 36.82 |
| ATOM | 3547 | CA | ALA | A | 467 | −6.540 | −7.648 | −41.609 | 1.00 | 37.30 |
| ATOM | 3548 | CB | ALA | A | 467 | −7.663 | −8.403 | −40.930 | 1.00 | 37.04 |
| ATOM | 3549 | C | ALA | A | 467 | −6.767 | −6.136 | −41.509 | 1.00 | 38.13 |
| ATOM | 3550 | O | ALA | A | 467 | −6.715 | −5.556 | −40.417 | 1.00 | 37.96 |
| ATOM | 3551 | N | THR | A | 468 | −7.011 | −5.502 | −42.653 | 1.00 | 38.66 |
| ATOM | 3552 | CA | THR | A | 468 | −7.146 | −4.050 | −42.702 | 1.00 | 39.18 |
| ATOM | 3553 | CB | THR | A | 468 | −5.970 | −3.406 | −43.428 | 1.00 | 39.43 |
| ATOM | 3554 | OG1 | THR | A | 468 | −5.955 | −3.879 | −44.778 | 1.00 | 40.06 |
| ATOM | 3555 | CG2 | THR | A | 468 | −4.637 | −3.717 | −42.734 | 1.00 | 39.67 |
| ATOM | 3556 | C | THR | A | 468 | −8.405 | −3.591 | −43.427 | 1.00 | 39.33 |
| ATOM | 3557 | O | THR | A | 468 | −8.468 | −2.451 | −43.890 | 1.00 | 39.79 |
| ATOM | 3558 | N | SER | A | 469 | −9.403 | −4.457 | −43.529 | 1.00 | 39.12 |
| ATOM | 3559 | CA | SER | A | 469 | −10.651 | −4.065 | −44.176 | 1.00 | 39.41 |
| ATOM | 3560 | CB | SER | A | 469 | −10.624 | −4.369 | −45.684 | 1.00 | 39.77 |
| ATOM | 3561 | OG | SER | A | 469 | −10.476 | −5.763 | −45.916 | 1.00 | 41.02 |
| ATOM | 3562 | C | SER | A | 469 | −11.850 | −4.732 | −43.537 | 1.00 | 38.54 |
| ATOM | 3563 | O | SER | A | 469 | −11.771 | −5.856 | −43.046 | 1.00 | 38.85 |
| ATOM | 3564 | N | PHE | A | 470 | −12.962 | −4.014 | −43.558 | 1.00 | 38.00 |
| ATOM | 3565 | CA | PHE | A | 470 | −14.216 | −4.507 | −43.031 | 1.00 | 37.29 |
| ATOM | 3566 | CB | PHE | A | 470 | −14.880 | −3.406 | −42.220 | 1.00 | 36.87 |
| ATOM | 3567 | CG | PHE | A | 470 | −14.277 | −3.212 | −40.865 | 1.00 | 35.43 |
| ATOM | 3568 | CD1 | PHE | A | 470 | −13.146 | −2.428 | −40.696 | 1.00 | 35.15 |
| ATOM | 3569 | CE1 | PHE | A | 470 | −12.589 | −2.252 | −39.437 | 1.00 | 33.73 |
| ATOM | 3570 | CZ | PHE | A | 470 | −13.159 | −2.852 | −38.332 | 1.00 | 35.04 |
| ATOM | 3571 | CE2 | PHE | A | 470 | −14.292 | −3.638 | −38.479 | 1.00 | 36.26 |
| ATOM | 3572 | CD2 | PHE | A | 470 | −14.844 | −3.816 | −39.751 | 1.00 | 35.71 |
| ATOM | 3573 | C | PHE | A | 470 | −15.128 | −4.923 | −44.181 | 1.00 | 37.34 |
| ATOM | 3574 | O | PHE | A | 470 | −15.059 | −4.337 | −45.258 | 1.00 | 37.21 |
| ATOM | 3575 | N | PRO | A | 471 | −15.987 | −5.931 | −43.959 | 1.00 | 37.46 |
| ATOM | 3576 | CA | PRO | A | 471 | −16.983 | −6.243 | −44.985 | 1.00 | 38.04 |
| ATOM | 3577 | CB | PRO | A | 471 | −17.790 | −7.383 | −44.361 | 1.00 | 37.60 |
| ATOM | 3578 | CG | PRO | A | 471 | −16.877 | −7.986 | −43.337 | 1.00 | 38.09 |
| ATOM | 3579 | CD | PRO | A | 471 | −16.093 | −6.828 | −42.795 | 1.00 | 37.31 |
| ATOM | 3580 | C | PRO | A | 471 | −17.879 | −5.033 | −45.231 | 1.00 | 38.96 |
| ATOM | 3581 | O | PRO | A | 471 | −18.108 | −4.245 | −44.306 | 1.00 | 38.78 |
| ATOM | 3582 | N | PRO | A | 472 | −18.378 | −4.869 | −46.471 | 1.00 | 39.78 |
| ATOM | 3583 | CA | PRO | A | 472 | −19.238 | −3.723 | −46.771 | 1.00 | 39.87 |
| ATOM | 3584 | CB | PRO | A | 472 | −19.378 | −3.780 | −48.293 | 1.00 | 40.09 |
| ATOM | 3585 | CG | PRO | A | 472 | −19.171 | −5.225 | −48.635 | 1.00 | 40.28 |
| ATOM | 3586 | CD | PRO | A | 472 | −18.171 | −5.740 | −47.649 | 1.00 | 40.02 |
| ATOM | 3587 | C | PRO | A | 472 | −20.604 | −3.864 | −46.114 | 1.00 | 39.75 |
| ATOM | 3588 | O | PRO | A | 472 | −21.017 | −4.980 | −45.798 | 1.00 | 40.10 |
| ATOM | 3589 | N | SER | A | 473 | −21.268 | −2.734 | −45.881 | 1.00 | 39.71 |
| ATOM | 3590 | CA | SER | A | 473 | −22.675 | −2.696 | −45.467 | 1.00 | 39.61 |
| ATOM | 3591 | CB | SER | A | 473 | −23.571 | −3.070 | −46.651 | 1.00 | 40.16 |
| ATOM | 3592 | OG | SER | A | 473 | −23.468 | −2.074 | −47.658 | 1.00 | 42.55 |
| ATOM | 3593 | C | SER | A | 473 | −23.043 | −3.509 | −44.221 | 1.00 | 38.94 |
| ATOM | 3594 | O | SER | A | 473 | −24.041 | −4.258 | −44.210 | 1.00 | 39.07 |
| ATOM | 3595 | N | GLN | A | 474 | −22.257 | −3.340 | −43.159 | 1.00 | 37.75 |
| ATOM | 3596 | CA | GLN | A | 474 | −22.558 | −3.993 | −41.888 | 1.00 | 36.60 |
| ATOM | 3597 | CB | GLN | A | 474 | −21.291 | −4.205 | −41.057 | 1.00 | 36.41 |
| ATOM | 3598 | CG | GLN | A | 474 | −20.331 | −5.169 | −41.732 | 1.00 | 36.24 |

TABLE 15-continued

| | | | | | | | | | |
|---|---|---|---|---|---|---|---|---|---|
| ATOM | 3599 | CD | GLN | A | 474 | −19.295 | −5.757 | −40.795 | 1.00 | 36.45 |
| ATOM | 3600 | OE1 | GLN | A | 474 | −18.478 | −5.040 | −40.211 | 1.00 | 35.30 |
| ATOM | 3601 | NE2 | GLN | A | 474 | −19.304 | −7.077 | −40.671 | 1.00 | 36.85 |
| ATOM | 3602 | C | GLN | A | 474 | −23.620 | −3.191 | −41.149 | 1.00 | 36.40 |
| ATOM | 3603 | O | GLN | A | 474 | −23.329 | −2.444 | −40.208 | 1.00 | 35.99 |
| ATOM | 3604 | N | THR | A | 475 | −24.859 | −3.350 | −41.616 | 1.00 | 35.59 |
| ATOM | 3605 | CA | THR | A | 475 | −26.012 | −2.595 | −41.148 | 1.00 | 35.20 |
| ATOM | 3606 | CB | THR | A | 475 | −27.051 | −2.478 | −42.287 | 1.00 | 35.73 |
| ATOM | 3607 | OG1 | THR | A | 475 | −27.120 | −3.737 | −42.959 | 1.00 | 36.85 |
| ATOM | 3608 | CG2 | THR | A | 475 | −26.642 | −1.418 | −43.310 | 1.00 | 34.51 |
| ATOM | 3609 | C | THR | A | 475 | −26.635 | −3.256 | −39.910 | 1.00 | 35.16 |
| ATOM | 3610 | O | THR | A | 475 | −26.363 | −4.420 | −39.622 | 1.00 | 34.47 |
| ATOM | 3611 | N | PRO | A | 476 | −27.453 | −2.510 | −39.148 | 1.00 | 35.36 |
| ATOM | 3612 | CA | PRO | A | 476 | −27.990 | −3.111 | −37.923 | 1.00 | 36.40 |
| ATOM | 3613 | CB | PRO | A | 476 | −28.567 | −1.910 | −37.167 | 1.00 | 36.04 |
| ATOM | 3614 | CG | PRO | A | 476 | −28.890 | −0.912 | −38.230 | 1.00 | 35.98 |
| ATOM | 3615 | CD | PRO | A | 476 | −27.907 | −1.119 | −39.339 | 1.00 | 35.70 |
| ATOM | 3616 | C | PRO | A | 476 | −29.085 | −4.171 | −38.158 | 1.00 | 37.45 |
| ATOM | 3617 | O | PRO | A | 476 | −29.654 | −4.244 | −39.254 | 1.00 | 36.95 |
| ATOM | 3618 | N | LYS | A | 477 | −29.342 | −4.984 | −37.133 | 1.00 | 39.01 |
| ATOM | 3619 | CA | LYS | A | 477 | −30.472 | −5.911 | −37.111 | 1.00 | 41.20 |
| ATOM | 3620 | CB | LYS | A | 477 | −30.541 | −6.641 | −35.774 | 1.00 | 41.46 |
| ATOM | 3621 | CG | LYS | A | 477 | −29.665 | −7.850 | −35.604 | 1.00 | 41.87 |
| ATOM | 3622 | CD | LYS | A | 477 | −29.939 | −8.517 | −34.237 | 1.00 | 42.36 |
| ATOM | 3623 | CE | LYS | A | 477 | −29.996 | −7.497 | −33.076 | 1.00 | 44.55 |
| ATOM | 3624 | NZ | LYS | A | 477 | −29.705 | −8.110 | −31.718 | 1.00 | 44.56 |
| ATOM | 3625 | C | LYS | A | 477 | −31.766 | −5.118 | −37.230 | 1.00 | 42.27 |
| ATOM | 3626 | O | LYS | A | 477 | −31.818 | −3.960 | −36.798 | 1.00 | 42.18 |
| ATOM | 3627 | N | PRO | A | 478 | −32.831 | −5.743 | −37.780 | 1.00 | 43.46 |
| ATOM | 3628 | CA | PRO | A | 478 | −34.150 | −5.106 | −37.669 | 1.00 | 44.02 |
| ATOM | 3629 | CB | PRO | A | 478 | −35.106 | −6.144 | −38.267 | 1.00 | 43.89 |
| ATOM | 3630 | CG | PRO | A | 478 | −34.255 | −7.033 | −39.105 | 1.00 | 44.08 |
| ATOM | 3631 | CD | PRO | A | 478 | −32.885 | −7.034 | −38.493 | 1.00 | 43.41 |
| ATOM | 3632 | C | PRO | A | 478 | −34.480 | −4.892 | −36.194 | 1.00 | 44.52 |
| ATOM | 3633 | O | PRO | A | 478 | −34.197 | −5.769 | −35.364 | 1.00 | 44.73 |
| ATOM | 3634 | N | GLY | A | 479 | −35.043 | −3.728 | −35.874 | 1.00 | 45.20 |
| ATOM | 3635 | CA | GLY | A | 479 | −35.421 | −3.395 | −34.494 | 1.00 | 45.90 |
| ATOM | 3636 | C | GLY | A | 479 | −34.386 | −2.601 | −33.711 | 1.00 | 46.37 |
| ATOM | 3637 | O | GLY | A | 479 | −34.576 | −2.331 | −32.520 | 1.00 | 46.98 |
| ATOM | 3638 | N | VAL | A | 480 | −33.282 | −2.244 | −34.367 | 1.00 | 46.28 |
| ATOM | 3639 | CA | VAL | A | 480 | −32.261 | −1.383 | −33.760 | 1.00 | 46.15 |
| ATOM | 3640 | CB | VAL | A | 480 | −30.820 | −1.863 | −34.121 | 1.00 | 46.20 |
| ATOM | 3641 | CG1 | VAL | A | 480 | −29.755 | −0.899 | −33.584 | 1.00 | 45.85 |
| ATOM | 3642 | CG2 | VAL | A | 480 | −30.569 | −3.281 | −33.603 | 1.00 | 46.25 |
| ATOM | 3643 | C | VAL | A | 480 | −32.498 | 0.046 | −34.260 | 1.00 | 45.93 |
| ATOM | 3644 | O | VAL | A | 480 | −32.673 | 0.240 | −35.465 | 1.00 | 46.15 |
| ATOM | 3645 | N | PRO | A | 481 | −32.534 | 1.049 | −33.344 | 1.00 | 45.70 |
| ATOM | 3646 | CA | PRO | A | 481 | −32.648 | 2.443 | −33.804 | 1.00 | 45.36 |
| ATOM | 3647 | CB | PRO | A | 481 | −32.388 | 3.266 | −32.542 | 1.00 | 45.39 |
| ATOM | 3648 | CG | PRO | A | 481 | −32.778 | 2.375 | −31.427 | 1.00 | 45.52 |
| ATOM | 3649 | CD | PRO | A | 481 | −32.481 | 0.962 | −31.873 | 1.00 | 45.83 |
| ATOM | 3650 | C | PRO | A | 481 | −31.609 | 2.762 | −34.877 | 1.00 | 45.08 |
| ATOM | 3651 | O | PRO | A | 481 | −30.405 | 2.555 | −34.681 | 1.00 | 44.45 |
| ATOM | 3652 | N | SER | A | 482 | −32.100 | 3.241 | −36.011 | 1.00 | 44.83 |
| ATOM | 3653 | CA | SER | A | 482 | −31.281 | 3.485 | −37.180 | 1.00 | 44.52 |
| ATOM | 3654 | CB | SER | A | 482 | −31.502 | 2.375 | −38.211 | 1.00 | 44.74 |
| ATOM | 3655 | OG | SER | A | 482 | −30.769 | 2.622 | −39.399 | 1.00 | 45.89 |
| ATOM | 3656 | C | SER | A | 482 | −31.661 | 4.836 | −37.765 | 1.00 | 43.84 |
| ATOM | 3657 | O | SER | A | 482 | −32.836 | 5.219 | −37.741 | 1.00 | 44.07 |
| ATOM | 3658 | N | GLY | A | 483 | −30.667 | 5.550 | −38.282 | 1.00 | 42.68 |
| ATOM | 3659 | CA | GLY | A | 483 | −30.872 | 6.872 | −38.853 | 1.00 | 41.64 |
| ATOM | 3660 | C | GLY | A | 483 | −30.085 | 7.095 | −40.130 | 1.00 | 41.05 |
| ATOM | 3661 | O | GLY | A | 483 | −29.430 | 6.179 | −40.647 | 1.00 | 41.09 |
| ATOM | 3662 | N | THR | A | 484 | −30.155 | 8.317 | −40.647 | 1.00 | 40.22 |
| ATOM | 3663 | CA | THR | A | 484 | −29.461 | 8.677 | −41.888 | 1.00 | 39.91 |
| ATOM | 3664 | CB | THR | A | 484 | −30.148 | 9.876 | −42.619 | 1.00 | 40.21 |
| ATOM | 3665 | OG1 | THR | A | 484 | −30.115 | 11.040 | −41.780 | 1.00 | 41.48 |
| ATOM | 3666 | CG2 | THR | A | 484 | −31.604 | 9.541 | −43.000 | 1.00 | 40.86 |
| ATOM | 3667 | C | THR | A | 484 | −27.995 | 9.033 | −41.603 | 1.00 | 38.43 |
| ATOM | 3668 | O | THR | A | 484 | −27.669 | 9.421 | −40.483 | 1.00 | 38.52 |
| ATOM | 3669 | N | PRO | A | 485 | −27.109 | 8.893 | −42.612 | 1.00 | 37.36 |
| ATOM | 3670 | CA | PRO | A | 485 | −25.695 | 9.226 | −42.413 | 1.00 | 36.29 |
| ATOM | 3671 | CB | PRO | A | 485 | −25.077 | 8.974 | −43.795 | 1.00 | 36.75 |
| ATOM | 3672 | CG | PRO | A | 485 | −25.997 | 7.985 | −44.442 | 1.00 | 37.04 |
| ATOM | 3673 | CD | PRO | A | 485 | −27.359 | 8.393 | −43.976 | 1.00 | 37.30 |
| ATOM | 3674 | C | PRO | A | 485 | −25.460 | 10.684 | −41.988 | 1.00 | 35.20 |
| ATOM | 3675 | O | PRO | A | 485 | −26.201 | 11.599 | −42.396 | 1.00 | 34.39 |
| ATOM | 3676 | N | TYR | A | 486 | −24.428 | 10.887 | −41.174 | 1.00 | 33.60 |
| ATOM | 3677 | CA | TYR | A | 486 | −24.025 | 12.233 | −40.782 | 1.00 | 32.74 |
| ATOM | 3678 | CB | TYR | A | 486 | −22.821 | 12.180 | −39.826 | 1.00 | 32.31 |

TABLE 15-continued

| | | | | | | | | | |
|---|---|---|---|---|---|---|---|---|---|
| ATOM | 3679 | CG | TYR | A | 486 | −22.348 | 13.564 | −39.452 | 1.00 | 32.79 |
| ATOM | 3680 | CD1 | TYR | A | 486 | −21.243 | 14.146 | −40.083 | 1.00 | 31.74 |
| ATOM | 3681 | CE1 | TYR | A | 486 | −20.827 | 15.430 | −39.742 | 1.00 | 30.85 |
| ATOM | 3682 | CZ | TYR | A | 486 | −21.527 | 16.141 | −38.778 | 1.00 | 31.99 |
| ATOM | 3683 | OH | TYR | A | 486 | −21.143 | 17.423 | −38.427 | 1.00 | 32.20 |
| ATOM | 3684 | CE2 | TYR | A | 486 | −22.629 | 15.588 | −38.160 | 1.00 | 31.88 |
| ATOM | 3685 | CD2 | TYR | A | 486 | −23.036 | 14.311 | −38.500 | 1.00 | 32.49 |
| ATOM | 3686 | C | TYR | A | 486 | −23.652 | 13.082 | −41.999 | 1.00 | 31.99 |
| ATOM | 3687 | O | TYR | A | 486 | −22.949 | 12.602 | −42.900 | 1.00 | 31.62 |
| ATOM | 3688 | N | THR | A | 487 | −24.106 | 14.336 | −42.004 | 1.00 | 31.14 |
| ATOM | 3689 | CA | THR | A | 487 | −23.676 | 15.336 | −42.986 | 1.00 | 31.43 |
| ATOM | 3690 | CB | THR | A | 487 | −24.879 | 15.785 | −43.869 | 1.00 | 31.94 |
| ATOM | 3691 | OG1 | THR | A | 487 | −25.321 | 14.665 | −44.644 | 1.00 | 35.19 |
| ATOM | 3692 | CG2 | THR | A | 487 | −24.489 | 16.904 | −44.810 | 1.00 | 32.95 |
| ATOM | 3693 | C | THR | A | 487 | −23.110 | 16.561 | −42.261 | 1.00 | 29.79 |
| ATOM | 3694 | O | THR | A | 487 | −23.761 | 17.078 | −41.363 | 1.00 | 29.20 |
| ATOM | 3695 | N | PRO | A | 488 | −21.901 | 17.027 | −42.644 | 1.00 | 29.20 |
| ATOM | 3696 | CA | PRO | A | 488 | −21.309 | 18.228 | −42.005 | 1.00 | 28.77 |
| ATOM | 3697 | CB | PRO | A | 488 | −19.988 | 18.435 | −42.763 | 1.00 | 28.75 |
| ATOM | 3698 | CG | PRO | A | 488 | −19.684 | 17.126 | −43.408 | 1.00 | 29.52 |
| ATOM | 3699 | CD | PRO | A | 488 | −21.010 | 16.448 | −43.667 | 1.00 | 29.41 |
| ATOM | 3700 | C | PRO | A | 488 | −22.175 | 19.463 | −42.194 | 1.00 | 28.44 |
| ATOM | 3701 | O | PRO | A | 488 | −23.003 | 19.499 | −43.116 | 1.00 | 28.51 |
| ATOM | 3702 | N | LEU | A | 489 | −21.971 | 20.469 | −41.345 | 1.00 | 27.28 |
| ATOM | 3703 | CA | LEU | A | 489 | −22.606 | 21.775 | −41.522 | 1.00 | 26.52 |
| ATOM | 3704 | CB | LEU | A | 489 | −22.269 | 22.708 | −40.365 | 1.00 | 27.19 |
| ATOM | 3705 | CG | LEU | A | 489 | −22.805 | 22.303 | −38.987 | 1.00 | 27.53 |
| ATOM | 3706 | CD1 | LEU | A | 489 | −22.233 | 23.242 | −37.929 | 1.00 | 26.81 |
| ATOM | 3707 | CD2 | LEU | A | 489 | −24.332 | 22.323 | −38.970 | 1.00 | 28.98 |
| ATOM | 3708 | C | LEU | A | 489 | −22.137 | 22.402 | −42.833 | 1.00 | 26.65 |
| ATOM | 3709 | O | LEU | A | 489 | −20.983 | 22.210 | −43.245 | 1.00 | 25.40 |
| ATOM | 3710 | N | PRO | A | 490 | −23.030 | 23.153 | −43.503 | 1.00 | 26.84 |
| ATOM | 3711 | CA | PRO | A | 490 | −22.636 | 23.745 | −44.786 | 1.00 | 26.44 |
| ATOM | 3712 | CB | PRO | A | 490 | −23.983 | 24.107 | −45.432 | 1.00 | 27.00 |
| ATOM | 3713 | CG | PRO | A | 490 | −24.900 | 24.341 | −44.289 | 1.00 | 27.68 |
| ATOM | 3714 | CD | PRO | A | 490 | −24.425 | 23.475 | −43.137 | 1.00 | 26.91 |
| ATOM | 3715 | C | PRO | A | 490 | −21.737 | 24.982 | −44.668 | 1.00 | 26.22 |
| ATOM | 3716 | O | PRO | A | 490 | −21.826 | 25.729 | −43.698 | 1.00 | 25.74 |
| ATOM | 3717 | N | CYS | A | 491 | −20.858 | 25.182 | −45.650 | 1.00 | 26.06 |
| ATOM | 3718 | CA | CYS | A | 491 | −20.079 | 26.412 | −45.754 | 1.00 | 26.88 |
| ATOM | 3719 | CB | CYS | A | 491 | −18.630 | 26.194 | −45.302 | 1.00 | 27.00 |
| ATOM | 3720 | SG | CYS | A | 491 | −18.450 | 25.196 | −43.819 | 1.00 | 27.23 |
| ATOM | 3721 | C | CYS | A | 491 | −20.032 | 26.822 | −47.217 | 1.00 | 27.27 |
| ATOM | 3722 | O | CYS | A | 491 | −20.369 | 26.026 | −48.083 | 1.00 | 27.34 |
| ATOM | 3723 | N | ALA | A | 492 | −19.577 | 28.045 | −47.484 | 1.00 | 28.05 |
| ATOM | 3724 | CA | ALA | A | 492 | −19.205 | 28.449 | −48.845 | 1.00 | 29.40 |
| ATOM | 3725 | CB | ALA | A | 492 | −18.837 | 29.928 | −48.866 | 1.00 | 29.49 |
| ATOM | 3726 | C | ALA | A | 492 | −18.023 | 27.599 | −49.320 | 1.00 | 30.37 |
| ATOM | 3727 | O | ALA | A | 492 | −17.310 | 26.998 | −48.497 | 1.00 | 30.36 |
| ATOM | 3728 | N | THR | A | 493 | −17.828 | 27.508 | −50.633 | 1.00 | 31.27 |
| ATOM | 3729 | CA | THR | A | 493 | −16.612 | 26.883 | −51.163 | 1.00 | 32.43 |
| ATOM | 3730 | CB | THR | A | 493 | −16.845 | 26.234 | −52.533 | 1.00 | 33.22 |
| ATOM | 3731 | OG1 | THR | A | 493 | −17.944 | 25.324 | −52.431 | 1.00 | 38.55 |
| ATOM | 3732 | CG2 | THR | A | 493 | −15.590 | 25.464 | −52.996 | 1.00 | 33.71 |
| ATOM | 3733 | C | THR | A | 493 | −15.596 | 28.006 | −51.254 | 1.00 | 31.35 |
| ATOM | 3734 | O | THR | A | 493 | −15.916 | 29.068 | −51.795 | 1.00 | 31.58 |
| ATOM | 3735 | N | PRO | A | 494 | −14.390 | 27.815 | −50.682 | 1.00 | 30.44 |
| ATOM | 3736 | CA | PRO | A | 494 | −13.464 | 28.947 | −50.696 | 1.00 | 30.01 |
| ATOM | 3737 | CB | PRO | A | 494 | −12.414 | 28.555 | −49.645 | 1.00 | 30.26 |
| ATOM | 3738 | CG | PRO | A | 494 | −12.416 | 27.077 | −49.658 | 1.00 | 30.56 |
| ATOM | 3739 | CD | PRO | A | 494 | −13.815 | 26.635 | −49.997 | 1.00 | 30.85 |
| ATOM | 3740 | C | PRO | A | 494 | −12.809 | 29.089 | −52.060 | 1.00 | 28.81 |
| ATOM | 3741 | O | PRO | A | 494 | −12.801 | 28.137 | −52.834 | 1.00 | 28.82 |
| ATOM | 3742 | N | THR | A | 495 | −12.260 | 30.258 | −52.352 | 1.00 | 28.43 |
| ATOM | 3743 | CA | THR | A | 495 | −11.551 | 30.419 | −53.623 | 1.00 | 28.44 |
| ATOM | 3744 | CB | THR | A | 495 | −11.885 | 31.748 | −54.319 | 1.00 | 28.68 |
| ATOM | 3745 | OG1 | THR | A | 495 | −11.449 | 32.839 | −53.500 | 1.00 | 30.39 |
| ATOM | 3746 | CG2 | THR | A | 495 | −13.383 | 31.858 | −54.564 | 1.00 | 29.85 |
| ATOM | 3747 | C | THR | A | 495 | −10.057 | 30.335 | −53.404 | 1.00 | 27.94 |
| ATOM | 3748 | O | THR | A | 495 | −9.289 | 30.159 | −54.352 | 1.00 | 27.63 |
| ATOM | 3749 | N | SER | A | 496 | −9.671 | 30.463 | −52.139 | 1.00 | 27.51 |
| ATOM | 3750 | CA | SER | A | 496 | −8.279 | 30.492 | −51.722 | 1.00 | 27.18 |
| ATOM | 3751 | CB | SER | A | 496 | −7.928 | 31.916 | −51.329 | 1.00 | 27.72 |
| ATOM | 3752 | OG | SER | A | 496 | −6.531 | 32.076 | −51.240 | 1.00 | 32.60 |
| ATOM | 3753 | C | SER | A | 496 | −8.134 | 29.583 | −50.501 | 1.00 | 25.85 |
| ATOM | 3754 | O | SER | A | 496 | −9.024 | 29.548 | −49.634 | 1.00 | 25.10 |
| ATOM | 3755 | N | VAL | A | 497 | −7.039 | 28.824 | −50.430 | 1.00 | 24.43 |
| ATOM | 3756 | CA | VAL | A | 497 | −6.801 | 28.032 | −49.209 | 1.00 | 22.17 |
| ATOM | 3757 | CB | VAL | A | 497 | −7.281 | 26.511 | −49.290 | 1.00 | 23.00 |
| ATOM | 3758 | CG1 | VAL | A | 497 | −6.224 | 25.445 | −48.881 | 1.00 | 22.48 |

TABLE 15-continued

| | | | | | | | | | |
|---|---|---|---|---|---|---|---|---|---|
| ATOM | 3759 | CG2 | VAL | A | 497 | −8.049 | 26.161 | −50.578 | 1.00 | 22.62 |
| ATOM | 3760 | C | VAL | A | 497 | −5.388 | 28.251 | −48.672 | 1.00 | 21.13 |
| ATOM | 3761 | O | VAL | A | 497 | −4.419 | 28.359 | −49.439 | 1.00 | 20.38 |
| ATOM | 3762 | N | ALA | A | 498 | −5.302 | 28.395 | −47.355 | 1.00 | 19.70 |
| ATOM | 3763 | CA | ALA | A | 498 | −4.020 | 28.576 | −46.702 | 1.00 | 18.92 |
| ATOM | 3764 | CB | ALA | A | 498 | −4.226 | 29.126 | −45.290 | 1.00 | 19.31 |
| ATOM | 3765 | C | ALA | A | 498 | −3.396 | 27.185 | −46.655 | 1.00 | 18.67 |
| ATOM | 3766 | O | ALA | A | 498 | −3.966 | 26.266 | −46.047 | 1.00 | 19.29 |
| ATOM | 3767 | N | VAL | A | 499 | −2.252 | 27.021 | −47.319 | 1.00 | 17.23 |
| ATOM | 3768 | CA | VAL | A | 499 | −1.551 | 25.735 | −47.361 | 1.00 | 16.09 |
| ATOM | 3769 | CB | VAL | A | 499 | −1.165 | 25.347 | −48.814 | 1.00 | 16.97 |
| ATOM | 3770 | CG1 | VAL | A | 499 | −0.403 | 23.984 | −48.863 | 1.00 | 16.08 |
| ATOM | 3771 | CG2 | VAL | A | 499 | −2.413 | 25.291 | −49.696 | 1.00 | 17.03 |
| ATOM | 3772 | C | VAL | A | 499 | −0.306 | 25.841 | −46.491 | 1.00 | 15.95 |
| ATOM | 3773 | O | VAL | A | 499 | 0.604 | 26.607 | −46.791 | 1.00 | 16.15 |
| ATOM | 3774 | N | THR | A | 500 | −0.279 | 25.085 | −45.404 | 1.00 | 15.16 |
| ATOM | 3775 | CA | THR | A | 500 | 0.863 | 25.116 | −44.505 | 1.00 | 14.85 |
| ATOM | 3776 | CB | THR | A | 500 | 0.415 | 24.916 | −43.035 | 1.00 | 14.76 |
| ATOM | 3777 | OG1 | THR | A | 500 | −0.403 | 26.022 | −42.635 | 1.00 | 16.00 |
| ATOM | 3778 | CG2 | THR | A | 500 | 1.639 | 24.856 | −42.136 | 1.00 | 15.39 |
| ATOM | 3779 | C | THR | A | 500 | 1.796 | 23.993 | −44.932 | 1.00 | 14.99 |
| ATOM | 3780 | O | THR | A | 500 | 1.480 | 22.804 | −44.792 | 1.00 | 14.81 |
| ATOM | 3781 | N | PHE | A | 501 | 2.941 | 24.370 | −45.481 | 1.00 | 14.71 |
| ATOM | 3782 | CA | PHE | A | 501 | 3.981 | 23.411 | −45.793 | 1.00 | 15.64 |
| ATOM | 3783 | CB | PHE | A | 501 | 4.943 | 23.964 | −46.832 | 1.00 | 15.86 |
| ATOM | 3784 | CG | PHE | A | 501 | 4.289 | 24.172 | −48.168 | 1.00 | 18.38 |
| ATOM | 3785 | CD1 | PHE | A | 501 | 3.676 | 25.388 | −48.469 | 1.00 | 19.85 |
| ATOM | 3786 | CE1 | PHE | A | 501 | 3.052 | 25.581 | −49.709 | 1.00 | 21.58 |
| ATOM | 3787 | CZ | PHE | A | 501 | 3.015 | 24.547 | −50.642 | 1.00 | 19.80 |
| ATOM | 3788 | CE2 | PHE | A | 501 | 3.607 | 23.324 | −50.356 | 1.00 | 21.69 |
| ATOM | 3789 | CD2 | PHE | A | 501 | 4.231 | 23.134 | −49.095 | 1.00 | 21.96 |
| ATOM | 3790 | C | PHE | A | 501 | 4.711 | 23.009 | −44.536 | 1.00 | 15.81 |
| ATOM | 3791 | O | PHE | A | 501 | 5.207 | 23.852 | −43.804 | 1.00 | 16.78 |
| ATOM | 3792 | N | HIS | A | 502 | 4.789 | 21.698 | −44.317 | 1.00 | 14.85 |
| ATOM | 3793 | CA | HIS | A | 502 | 5.239 | 21.175 | −43.027 | 1.00 | 14.17 |
| ATOM | 3794 | CB | HIS | A | 502 | 3.987 | 20.565 | −42.356 | 1.00 | 14.85 |
| ATOM | 3795 | CG | HIS | A | 502 | 4.221 | 19.875 | −41.054 | 1.00 | 13.69 |
| ATOM | 3796 | ND1 | HIS | A | 502 | 4.819 | 18.637 | −40.966 | 1.00 | 12.55 |
| ATOM | 3797 | CE1 | HIS | A | 502 | 4.816 | 18.241 | −39.702 | 1.00 | 15.76 |
| ATOM | 3798 | NE2 | HIS | A | 502 | 4.191 | 19.155 | −38.980 | 1.00 | 14.42 |
| ATOM | 3799 | CD2 | HIS | A | 502 | 3.797 | 20.183 | −39.804 | 1.00 | 14.92 |
| ATOM | 3800 | C | HIS | A | 502 | 6.317 | 20.161 | −43.412 | 1.00 | 14.16 |
| ATOM | 3801 | O | HIS | A | 502 | 6.013 | 19.043 | −43.824 | 1.00 | 13.85 |
| ATOM | 3802 | N | GLU | A | 503 | 7.577 | 20.590 | −43.352 | 1.00 | 13.63 |
| ATOM | 3803 | CA | GLU | A | 503 | 8.678 | 19.821 | −43.968 | 1.00 | 14.46 |
| ATOM | 3804 | CB | GLU | A | 503 | 9.434 | 20.712 | −44.996 | 1.00 | 14.22 |
| ATOM | 3805 | CG | GLU | A | 503 | 10.782 | 20.121 | −45.524 | 1.00 | 16.31 |
| ATOM | 3806 | CD | GLU | A | 503 | 10.620 | 18.973 | −46.539 | 1.00 | 21.32 |
| ATOM | 3807 | OE1 | GLU | A | 503 | 11.523 | 18.819 | −47.393 | 1.00 | 21.21 |
| ATOM | 3808 | OE2 | GLU | A | 503 | 9.609 | 18.230 | −46.510 | 1.00 | 20.10 |
| ATOM | 3809 | C | GLU | A | 503 | 9.657 | 19.322 | −42.917 | 1.00 | 14.22 |
| ATOM | 3810 | O | GLU | A | 503 | 10.175 | 20.121 | −42.131 | 1.00 | 15.31 |
| ATOM | 3811 | N | LEU | A | 504 | 9.960 | 18.027 | −42.927 | 1.00 | 14.92 |
| ATOM | 3812 | CA | LEU | A | 504 | 11.026 | 17.518 | −42.052 | 1.00 | 15.49 |
| ATOM | 3813 | CB | LEU | A | 504 | 10.658 | 16.147 | −41.489 | 1.00 | 16.33 |
| ATOM | 3814 | CG | LEU | A | 504 | 9.479 | 16.178 | −40.498 | 1.00 | 17.19 |
| ATOM | 3815 | CD1 | LEU | A | 504 | 8.922 | 14.753 | −40.320 | 1.00 | 19.08 |
| ATOM | 3816 | CD2 | LEU | A | 504 | 9.953 | 16.723 | −39.198 | 1.00 | 17.28 |
| ATOM | 3817 | C | LEU | A | 504 | 12.318 | 17.428 | −42.846 | 1.00 | 16.59 |
| ATOM | 3818 | O | LEU | A | 504 | 12.403 | 16.656 | −43.785 | 1.00 | 16.72 |
| ATOM | 3819 | N | VAL | A | 505 | 13.317 | 18.201 | −42.444 | 1.00 | 17.20 |
| ATOM | 3820 | CA | VAL | A | 505 | 14.592 | 18.235 | −43.154 | 1.00 | 19.16 |
| ATOM | 3821 | CB | VAL | A | 505 | 14.548 | 19.141 | −44.418 | 1.00 | 18.88 |
| ATOM | 3822 | CG1 | VAL | A | 505 | 14.028 | 20.539 | −44.090 | 1.00 | 19.28 |
| ATOM | 3823 | CG2 | VAL | A | 505 | 15.948 | 19.219 | −45.095 | 1.00 | 21.65 |
| ATOM | 3824 | C | VAL | A | 505 | 15.674 | 18.705 | −42.188 | 1.00 | 20.00 |
| ATOM | 3825 | O | VAL | A | 505 | 15.595 | 19.785 | −41.595 | 1.00 | 19.92 |
| ATOM | 3826 | N | SER | A | 506 | 16.685 | 17.868 | −42.011 | 1.00 | 21.73 |
| ATOM | 3827 | CA | SER | A | 506 | 17.761 | 18.216 | −41.104 | 1.00 | 23.33 |
| ATOM | 3828 | CB | SER | A | 506 | 18.570 | 16.974 | −40.771 | 1.00 | 23.74 |
| ATOM | 3829 | OG | SER | A | 506 | 19.583 | 17.320 | −39.847 | 1.00 | 28.30 |
| ATOM | 3830 | C | SER | A | 506 | 18.646 | 19.284 | −41.759 | 1.00 | 23.03 |
| ATOM | 3831 | O | SER | A | 506 | 19.070 | 19.139 | −42.908 | 1.00 | 23.20 |
| ATOM | 3832 | N | THR | A | 507 | 18.888 | 20.371 | −41.049 | 1.00 | 24.01 |
| ATOM | 3833 | CA | THR | A | 507 | 19.685 | 21.464 | −41.600 | 1.00 | 25.15 |
| ATOM | 3834 | CB | THR | A | 507 | 18.845 | 22.725 | −41.833 | 1.00 | 25.01 |
| ATOM | 3835 | OG1 | THR | A | 507 | 18.104 | 23.015 | −40.650 | 1.00 | 24.43 |
| ATOM | 3836 | CG2 | THR | A | 507 | 17.891 | 22.536 | −43.000 | 1.00 | 24.71 |
| ATOM | 3837 | C | THR | A | 507 | 20.795 | 21.812 | −40.623 | 1.00 | 27.09 |
| ATOM | 3838 | O | THR | A | 507 | 20.729 | 21.448 | −39.451 | 1.00 | 26.15 |

TABLE 15-continued

| | | | | | | | | | |
|---|---|---|---|---|---|---|---|---|---|
| ATOM | 3839 | N | GLN | A | 508 | 21.798 | 22.536 | −41.113 | 1.00 | 29.34 |
| ATOM | 3840 | CA | GLN | A | 508 | 22.912 | 22.986 | −40.272 | 1.00 | 32.54 |
| ATOM | 3841 | CB | GLN | A | 508 | 24.239 | 22.542 | −40.897 | 1.00 | 32.54 |
| ATOM | 3842 | CG | GLN | A | 508 | 24.369 | 21.010 | −40.972 | 1.00 | 34.32 |
| ATOM | 3843 | CD | GLN | A | 508 | 25.400 | 20.515 | −41.991 | 1.00 | 36.23 |
| ATOM | 3844 | OE1 | GLN | A | 508 | 26.283 | 19.700 | −41.660 | 1.00 | 41.79 |
| ATOM | 3845 | NE2 | GLN | A | 508 | 25.279 | 20.977 | −43.242 | 1.00 | 40.42 |
| ATOM | 3846 | C | GLN | A | 508 | 22.827 | 24.502 | −40.100 | 1.00 | 33.06 |
| ATOM | 3847 | O | GLN | A | 508 | 22.136 | 25.178 | −40.873 | 1.00 | 32.49 |
| ATOM | 3848 | N | PHE | A | 509 | 23.494 | 25.037 | −39.075 | 1.00 | 33.80 |
| ATOM | 3849 | CA | PHE | A | 509 | 23.432 | 26.476 | −38.782 | 1.00 | 35.03 |
| ATOM | 3850 | CB | PHE | A | 509 | 24.413 | 26.837 | −37.651 | 1.00 | 36.75 |
| ATOM | 3851 | CG | PHE | A | 509 | 24.481 | 28.315 | −37.340 | 1.00 | 39.07 |
| ATOM | 3852 | CD1 | PHE | A | 509 | 23.592 | 28.893 | −36.428 | 1.00 | 41.58 |
| ATOM | 3853 | CE1 | PHE | A | 509 | 23.642 | 30.265 | −36.140 | 1.00 | 42.61 |
| ATOM | 3854 | CZ | PHE | A | 509 | 24.603 | 31.073 | −36.766 | 1.00 | 41.78 |
| ATOM | 3855 | CE2 | PHE | A | 509 | 25.507 | 30.503 | −37.678 | 1.00 | 42.48 |
| ATOM | 3856 | CD2 | PHE | A | 509 | 25.441 | 29.127 | −37.955 | 1.00 | 41.46 |
| ATOM | 3857 | C | PHE | A | 509 | 23.712 | 27.311 | −40.040 | 1.00 | 34.58 |
| ATOM | 3858 | O | PHE | A | 509 | 24.614 | 26.990 | −40.815 | 1.00 | 34.58 |
| ATOM | 3859 | N | GLY | A | 510 | 22.912 | 28.355 | −40.256 | 1.00 | 33.85 |
| ATOM | 3860 | CA | GLY | A | 510 | 23.101 | 29.241 | −41.407 | 1.00 | 33.22 |
| ATOM | 3861 | C | GLY | A | 510 | 22.352 | 28.826 | −42.671 | 1.00 | 32.36 |
| ATOM | 3862 | O | GLY | A | 510 | 22.369 | 29.545 | −43.679 | 1.00 | 32.97 |
| ATOM | 3863 | N | GLN | A | 511 | 21.705 | 27.663 | −42.628 | 1.00 | 30.50 |
| ATOM | 3864 | CA | GLN | A | 511 | 20.885 | 27.217 | −43.745 | 1.00 | 29.02 |
| ATOM | 3865 | CB | GLN | A | 511 | 21.026 | 25.712 | −43.931 | 1.00 | 28.92 |
| ATOM | 3866 | CG | GLN | A | 511 | 22.436 | 25.276 | −44.349 | 1.00 | 29.91 |
| ATOM | 3867 | CD | GLN | A | 511 | 22.571 | 23.776 | −44.439 | 1.00 | 31.36 |
| ATOM | 3868 | OE1 | GLN | A | 511 | 21.760 | 23.036 | −43.879 | 1.00 | 31.69 |
| ATOM | 3869 | NE2 | GLN | A | 511 | 23.590 | 23.309 | −45.160 | 1.00 | 30.72 |
| ATOM | 3870 | C | GLN | A | 511 | 19.418 | 27.619 | −43.543 | 1.00 | 27.82 |
| ATOM | 3871 | O | GLN | A | 511 | 18.928 | 27.695 | −42.399 | 1.00 | 27.36 |
| ATOM | 3872 | N | THR | A | 512 | 18.727 | 27.895 | −44.650 | 1.00 | 25.92 |
| ATOM | 3873 | CA | THR | A | 512 | 17.305 | 28.271 | −44.613 | 1.00 | 24.51 |
| ATOM | 3874 | CB | THR | A | 512 | 17.126 | 29.763 | −44.994 | 1.00 | 24.95 |
| ATOM | 3875 | OG1 | THR | A | 512 | 17.769 | 30.580 | −44.004 | 1.00 | 27.43 |
| ATOM | 3876 | CG2 | THR | A | 512 | 15.653 | 30.151 | −45.069 | 1.00 | 25.94 |
| ATOM | 3877 | C | THR | A | 512 | 16.536 | 27.384 | −45.600 | 1.00 | 23.09 |
| ATOM | 3878 | O | THR | A | 512 | 16.994 | 27.152 | −46.717 | 1.00 | 22.75 |
| ATOM | 3879 | N | VAL | A | 513 | 15.376 | 26.877 | −45.200 | 1.00 | 20.62 |
| ATOM | 3880 | CA | VAL | A | 513 | 14.593 | 26.074 | −46.136 | 1.00 | 19.05 |
| ATOM | 3881 | CB | VAL | A | 513 | 13.946 | 24.855 | −45.428 | 1.00 | 19.18 |
| ATOM | 3882 | CG1 | VAL | A | 513 | 13.041 | 24.064 | −46.397 | 1.00 | 18.87 |
| ATOM | 3883 | CG2 | VAL | A | 513 | 15.042 | 23.938 | −44.895 | 1.00 | 20.56 |
| ATOM | 3884 | C | VAL | A | 513 | 13.536 | 26.979 | −46.748 | 1.00 | 17.98 |
| ATOM | 3885 | O | VAL | A | 513 | 12.910 | 27.768 | −46.029 | 1.00 | 16.65 |
| ATOM | 3886 | N | LYS | A | 514 | 13.346 | 26.857 | −48.063 | 1.00 | 17.91 |
| ATOM | 3887 | CA | LYS | A | 514 | 12.279 | 27.583 | −48.757 | 1.00 | 18.14 |
| ATOM | 3888 | CB | LYS | A | 514 | 12.845 | 28.712 | −49.638 | 1.00 | 17.66 |
| ATOM | 3889 | CG | LYS | A | 514 | 13.867 | 29.576 | −48.945 | 1.00 | 19.26 |
| ATOM | 3890 | CD | LYS | A | 514 | 14.197 | 30.839 | −49.765 | 1.00 | 21.27 |
| ATOM | 3891 | CE | LYS | A | 514 | 15.224 | 31.675 | −49.001 | 1.00 | 26.06 |
| ATOM | 3892 | NZ | LYS | A | 514 | 15.461 | 33.022 | −49.626 | 1.00 | 28.70 |
| ATOM | 3893 | C | LYS | A | 514 | 11.494 | 26.621 | −49.625 | 1.00 | 18.22 |
| ATOM | 3894 | O | LYS | A | 514 | 11.949 | 25.502 | −49.912 | 1.00 | 18.39 |
| ATOM | 3895 | N | VAL | A | 515 | 10.304 | 27.037 | −50.045 | 1.00 | 18.20 |
| ATOM | 3896 | CA | VAL | A | 515 | 9.546 | 26.212 | −50.980 | 1.00 | 19.00 |
| ATOM | 3897 | CB | VAL | A | 515 | 8.198 | 25.731 | −50.404 | 1.00 | 20.00 |
| ATOM | 3898 | CG1 | VAL | A | 515 | 7.403 | 26.904 | −49.879 | 1.00 | 21.01 |
| ATOM | 3899 | CG2 | VAL | A | 515 | 7.417 | 24.903 | −51.447 | 1.00 | 20.10 |
| ATOM | 3900 | C | VAL | A | 515 | 9.421 | 26.973 | −52.302 | 1.00 | 18.89 |
| ATOM | 3901 | O | VAL | A | 515 | 9.079 | 28.159 | −52.317 | 1.00 | 18.67 |
| ATOM | 3902 | N | ALA | A | 516 | 9.781 | 26.295 | −53.390 | 1.00 | 19.87 |
| ATOM | 3903 | CA | ALA | A | 516 | 9.796 | 26.898 | −54.732 | 1.00 | 20.38 |
| ATOM | 3904 | CB | ALA | A | 516 | 11.177 | 26.768 | −55.356 | 1.00 | 20.58 |
| ATOM | 3905 | C | ALA | A | 516 | 8.789 | 26.110 | −55.525 | 1.00 | 20.65 |
| ATOM | 3906 | O | ALA | A | 516 | 8.638 | 24.910 | −55.303 | 1.00 | 20.40 |
| ATOM | 3907 | N | GLY | A | 517 | 8.075 | 26.765 | −56.430 | 1.00 | 20.80 |
| ATOM | 3908 | CA | GLY | A | 517 | 7.092 | 26.039 | −57.214 | 1.00 | 22.32 |
| ATOM | 3909 | C | GLY | A | 517 | 6.536 | 26.853 | −58.352 | 1.00 | 22.86 |
| ATOM | 3910 | O | GLY | A | 517 | 6.902 | 28.024 | −58.527 | 1.00 | 22.58 |
| ATOM | 3911 | N | ASN | A | 518 | 5.642 | 26.233 | −59.116 | 1.00 | 24.66 |
| ATOM | 3912 | CA | ASN | A | 518 | 5.201 | 26.817 | −60.390 | 1.00 | 26.74 |
| ATOM | 3913 | CB | ASN | A | 518 | 4.670 | 25.754 | −61.354 | 1.00 | 26.97 |
| ATOM | 3914 | CG | ASN | A | 518 | 3.386 | 25.117 | −60.872 | 1.00 | 31.69 |
| ATOM | 3915 | OD1 | ASN | A | 518 | 3.004 | 25.226 | −59.677 | 1.00 | 28.89 |
| ATOM | 3916 | ND2 | ASN | A | 518 | 2.707 | 24.419 | −61.786 | 1.00 | 31.65 |
| ATOM | 3917 | C | ASN | A | 518 | 4.199 | 27.937 | −60.232 | 1.00 | 27.20 |
| ATOM | 3918 | O | ASN | A | 518 | 4.154 | 28.822 | −61.079 | 1.00 | 28.68 |

TABLE 15-continued

| | | | | | | | | | |
|---|---|---|---|---|---|---|---|---|---|
| ATOM | 3919 | N | ALA | A | 519 | 3.399 | 27.907 | −59.163 | 1.00 | 27.04 |
| ATOM | 3920 | CA | ALA | A | 519 | 2.424 | 28.978 | −58.898 | 1.00 | 26.47 |
| ATOM | 3921 | CB | ALA | A | 519 | 1.473 | 28.598 | −57.747 | 1.00 | 27.02 |
| ATOM | 3922 | C | ALA | A | 519 | 3.090 | 30.322 | −58.629 | 1.00 | 26.35 |
| ATOM | 3923 | O | ALA | A | 519 | 4.226 | 30.394 | −58.135 | 1.00 | 25.27 |
| ATOM | 3924 | N | ALA | A | 520 | 2.369 | 31.394 | −58.954 | 1.00 | 26.25 |
| ATOM | 3925 | CA | ALA | A | 520 | 2.887 | 32.741 | −58.784 | 1.00 | 26.77 |
| ATOM | 3926 | CB | ALA | A | 520 | 1.872 | 33.775 | −59.298 | 1.00 | 27.50 |
| ATOM | 3927 | C | ALA | A | 520 | 3.250 | 33.004 | −57.317 | 1.00 | 26.68 |
| ATOM | 3928 | O | ALA | A | 520 | 4.301 | 33.560 | −57.030 | 1.00 | 26.01 |
| ATOM | 3929 | N | ALA | A | 521 | 2.395 | 32.548 | −56.399 | 1.00 | 26.75 |
| ATOM | 3930 | CA | ALA | A | 521 | 2.628 | 32.712 | −54.963 | 1.00 | 26.82 |
| ATOM | 3931 | CB | ALA | A | 521 | 1.395 | 32.251 | −54.167 | 1.00 | 26.85 |
| ATOM | 3932 | C | ALA | A | 521 | 3.876 | 31.950 | −54.504 | 1.00 | 26.51 |
| ATOM | 3933 | O | ALA | A | 521 | 4.485 | 32.305 | −53.494 | 1.00 | 26.63 |
| ATOM | 3934 | N | LEU | A | 522 | 4.261 | 30.919 | −55.259 | 1.00 | 26.79 |
| ATOM | 3935 | CA | LEU | A | 522 | 5.452 | 30.113 | −54.932 | 1.00 | 26.50 |
| ATOM | 3936 | CB | LEU | A | 522 | 5.185 | 28.626 | −55.155 | 1.00 | 26.64 |
| ATOM | 3937 | CG | LEU | A | 522 | 4.224 | 27.946 | −54.169 | 1.00 | 26.58 |
| ATOM | 3938 | CD1 | LEU | A | 522 | 4.049 | 26.489 | −54.533 | 1.00 | 27.59 |
| ATOM | 3939 | CD2 | LEU | A | 522 | 4.718 | 28.092 | −52.730 | 1.00 | 28.08 |
| ATOM | 3940 | C | LEU | A | 522 | 6.696 | 30.559 | −55.709 | 1.00 | 26.54 |
| ATOM | 3941 | O | LEU | A | 522 | 7.779 | 29.987 | −55.547 | 1.00 | 25.56 |
| ATOM | 3942 | N | GLY | A | 523 | 6.518 | 31.575 | −56.552 | 1.00 | 26.25 |
| ATOM | 3943 | CA | GLY | A | 523 | 7.637 | 32.267 | −57.199 | 1.00 | 26.16 |
| ATOM | 3944 | C | GLY | A | 523 | 7.996 | 31.809 | −58.607 | 1.00 | 26.84 |
| ATOM | 3945 | O | GLY | A | 523 | 9.029 | 32.227 | −59.152 | 1.00 | 25.81 |
| ATOM | 3946 | N | ASN | A | 524 | 7.162 | 30.946 | −59.193 | 1.00 | 27.13 |
| ATOM | 3947 | CA | ASN | A | 524 | 7.413 | 30.419 | −60.539 | 1.00 | 27.74 |
| ATOM | 3948 | CB | ASN | A | 524 | 7.046 | 31.484 | −61.591 | 1.00 | 28.43 |
| ATOM | 3949 | CG | ASN | A | 524 | 7.123 | 30.960 | −63.015 | 1.00 | 30.79 |
| ATOM | 3950 | OD1 | ASN | A | 524 | 6.856 | 29.780 | −63.285 | 1.00 | 30.80 |
| ATOM | 3951 | ND2 | ASN | A | 524 | 7.515 | 31.838 | −63.936 | 1.00 | 33.61 |
| ATOM | 3952 | C | ASN | A | 524 | 8.845 | 29.857 | −60.710 | 1.00 | 28.44 |
| ATOM | 3953 | O | ASN | A | 524 | 9.531 | 30.104 | −61.720 | 1.00 | 27.82 |
| ATOM | 3954 | N | TRP | A | 525 | 9.280 | 29.111 | −59.693 | 1.00 | 27.99 |
| ATOM | 3955 | CA | TRP | A | 525 | 10.573 | 28.398 | −59.659 | 1.00 | 28.92 |
| ATOM | 3956 | CB | TRP | A | 525 | 10.787 | 27.507 | −60.896 | 1.00 | 28.31 |
| ATOM | 3957 | CG | TRP | A | 525 | 9.803 | 26.394 | −61.060 | 1.00 | 27.68 |
| ATOM | 3958 | CD1 | TRP | A | 525 | 8.902 | 26.247 | −62.078 | 1.00 | 27.96 |
| ATOM | 3959 | NE1 | TRP | A | 525 | 8.166 | 25.106 | −61.907 | 1.00 | 27.55 |
| ATOM | 3960 | CE2 | TRP | A | 525 | 8.589 | 24.471 | −60.762 | 1.00 | 30.58 |
| ATOM | 3961 | CD2 | TRP | A | 525 | 9.609 | 25.277 | −60.184 | 1.00 | 27.84 |
| ATOM | 3962 | CE3 | TRP | A | 525 | 10.230 | 24.842 | −59.001 | 1.00 | 26.50 |
| ATOM | 3963 | CZ3 | TRP | A | 525 | 9.787 | 23.655 | −58.411 | 1.00 | 27.55 |
| ATOM | 3964 | CH2 | TRP | A | 525 | 8.752 | 22.889 | −58.998 | 1.00 | 27.90 |
| ATOM | 3965 | CZ2 | TRP | A | 525 | 8.144 | 23.279 | −60.168 | 1.00 | 26.22 |
| ATOM | 3966 | C | TRP | A | 525 | 11.790 | 29.301 | −59.452 | 1.00 | 29.66 |
| ATOM | 3967 | O | TRP | A | 525 | 12.921 | 28.804 | −59.346 | 1.00 | 30.61 |
| ATOM | 3968 | N | SER | A | 526 | 11.570 | 30.613 | −59.380 | 1.00 | 30.33 |
| ATOM | 3969 | CA | SER | A | 526 | 12.645 | 31.536 | −59.004 | 1.00 | 31.13 |
| ATOM | 3970 | CB | SER | A | 526 | 12.213 | 32.993 | −59.187 | 1.00 | 31.02 |
| ATOM | 3971 | OG | SER | A | 526 | 13.166 | 33.838 | −58.562 | 1.00 | 33.69 |
| ATOM | 3972 | C | SER | A | 526 | 13.086 | 31.312 | −57.560 | 1.00 | 31.29 |
| ATOM | 3973 | O | SER | A | 526 | 12.271 | 31.381 | −56.627 | 1.00 | 31.21 |
| ATOM | 3974 | N | THR | A | 527 | 14.373 | 31.049 | −57.367 | 1.00 | 31.34 |
| ATOM | 3975 | CA | THR | A | 527 | 14.880 | 30.794 | −56.021 | 1.00 | 31.64 |
| ATOM | 3976 | CB | THR | A | 527 | 16.259 | 30.098 | −56.024 | 1.00 | 31.79 |
| ATOM | 3977 | OG1 | THR | A | 527 | 17.217 | 30.931 | −56.682 | 1.00 | 31.43 |
| ATOM | 3978 | CG2 | THR | A | 527 | 16.169 | 28.739 | −56.724 | 1.00 | 32.27 |
| ATOM | 3979 | C | THR | A | 527 | 14.911 | 32.045 | −55.152 | 1.00 | 31.99 |
| ATOM | 3980 | O | THR | A | 527 | 14.847 | 31.959 | −53.922 | 1.00 | 32.36 |
| ATOM | 3981 | N | SER | A | 528 | 14.986 | 33.209 | −55.787 | 1.00 | 31.79 |
| ATOM | 3982 | CA | SER | A | 528 | 14.928 | 34.463 | −55.054 | 1.00 | 32.02 |
| ATOM | 3983 | CB | SER | A | 528 | 15.517 | 35.615 | −55.885 | 1.00 | 32.70 |
| ATOM | 3984 | OG | SER | A | 528 | 14.712 | 35.882 | −57.031 | 1.00 | 34.94 |
| ATOM | 3985 | C | SER | A | 528 | 13.497 | 34.784 | −54.579 | 1.00 | 31.23 |
| ATOM | 3986 | O | SER | A | 528 | 13.330 | 35.435 | −53.550 | 1.00 | 32.02 |
| ATOM | 3987 | N | ALA | A | 529 | 12.479 | 34.314 | −55.306 | 1.00 | 29.33 |
| ATOM | 3988 | CA | ALA | A | 529 | 11.093 | 34.506 | −54.893 | 1.00 | 27.60 |
| ATOM | 3989 | CB | ALA | A | 529 | 10.211 | 34.864 | −56.086 | 1.00 | 27.34 |
| ATOM | 3990 | C | ALA | A | 529 | 10.482 | 33.328 | −54.112 | 1.00 | 26.40 |
| ATOM | 3991 | O | ALA | A | 529 | 9.311 | 33.382 | −53.754 | 1.00 | 26.54 |
| ATOM | 3992 | N | ALA | A | 530 | 11.268 | 32.286 | −53.842 | 1.00 | 25.12 |
| ATOM | 3993 | CA | ALA | A | 530 | 10.777 | 31.114 | −53.096 | 1.00 | 24.19 |
| ATOM | 3994 | CB | ALA | A | 530 | 11.855 | 30.063 | −52.991 | 1.00 | 23.88 |
| ATOM | 3995 | C | ALA | A | 530 | 10.336 | 31.555 | −51.706 | 1.00 | 23.55 |
| ATOM | 3996 | O | ALA | A | 530 | 10.848 | 32.540 | −51.182 | 1.00 | 23.61 |
| ATOM | 3997 | N | VAL | A | 531 | 9.396 | 30.833 | −51.110 | 1.00 | 22.18 |
| ATOM | 3998 | CA | VAL | A | 531 | 8.851 | 31.248 | −49.821 | 1.00 | 22.62 |

TABLE 15-continued

| ATOM | 3999 | CB | VAL | A | 531 | 7.380 | 30.821 | −49.677 | 1.00 | 22.81 |
|------|------|-----|-----|---|-----|--------|--------|---------|------|-------|
| ATOM | 4000 | CG1 | VAL | A | 531 | 6.815 | 31.335 | −48.346 | 1.00 | 25.06 |
| ATOM | 4001 | CG2 | VAL | A | 531 | 6.551 | 31.353 | −50.886 | 1.00 | 25.38 |
| ATOM | 4002 | C | VAL | A | 531 | 9.659 | 30.646 | −48.674 | 1.00 | 21.29 |
| ATOM | 4003 | O | VAL | A | 531 | 9.768 | 29.425 | −48.564 | 1.00 | 20.72 |
| ATOM | 4004 | N | ALA | A | 532 | 10.215 | 31.493 | −47.819 | 1.00 | 20.86 |
| ATOM | 4005 | CA | ALA | A | 532 | 11.008 | 30.999 | −46.698 | 1.00 | 20.26 |
| ATOM | 4006 | CB | ALA | A | 532 | 11.850 | 32.128 | −46.084 | 1.00 | 21.02 |
| ATOM | 4007 | C | ALA | A | 532 | 10.093 | 30.356 | −45.646 | 1.00 | 20.51 |
| ATOM | 4008 | O | ALA | A | 532 | 9.019 | 30.884 | −45.337 | 1.00 | 20.05 |
| ATOM | 4009 | N | LEU | A | 533 | 10.514 | 29.200 | −45.129 | 1.00 | 19.00 |
| ATOM | 4010 | CA | LEU | A | 533 | 9.855 | 28.565 | −43.999 | 1.00 | 18.65 |
| ATOM | 4011 | CB | LEU | A | 533 | 9.901 | 27.029 | −44.148 | 1.00 | 18.14 |
| ATOM | 4012 | CG | LEU | A | 533 | 9.395 | 26.450 | −45.483 | 1.00 | 19.25 |
| ATOM | 4013 | CD1 | LEU | A | 533 | 9.385 | 24.923 | −45.427 | 1.00 | 21.28 |
| ATOM | 4014 | CD2 | LEU | A | 533 | 8.030 | 26.980 | −45.894 | 1.00 | 18.58 |
| ATOM | 4015 | C | LEU | A | 533 | 10.541 | 29.014 | −42.702 | 1.00 | 18.95 |
| ATOM | 4016 | O | LEU | A | 533 | 11.622 | 29.648 | −42.744 | 1.00 | 18.94 |
| ATOM | 4017 | N | ASP | A | 534 | 9.905 | 28.715 | −41.570 | 1.00 | 18.56 |
| ATOM | 4018 | CA | ASP | A | 534 | 10.381 | 29.096 | −40.238 | 1.00 | 18.36 |
| ATOM | 4019 | CB | ASP | A | 534 | 9.220 | 29.634 | −39.374 | 1.00 | 19.76 |
| ATOM | 4020 | CG | ASP | A | 534 | 8.757 | 30.992 | −39.798 | 1.00 | 23.55 |
| ATOM | 4021 | OD1 | ASP | A | 534 | 7.548 | 31.264 | −39.659 | 1.00 | 26.14 |
| ATOM | 4022 | OD2 | ASP | A | 534 | 9.600 | 31.774 | −40.283 | 1.00 | 27.39 |
| ATOM | 4023 | C | ASP | A | 534 | 10.877 | 27.867 | −39.504 | 1.00 | 17.68 |
| ATOM | 4024 | O | ASP | A | 534 | 10.310 | 26.780 | −39.667 | 1.00 | 16.10 |
| ATOM | 4025 | N | ALA | A | 535 | 11.883 | 28.057 | −38.654 | 1.00 | 17.05 |
| ATOM | 4026 | CA | ALA | A | 535 | 12.405 | 26.950 | −37.835 | 1.00 | 17.76 |
| ATOM | 4027 | CB | ALA | A | 535 | 13.926 | 26.952 | −37.832 | 1.00 | 17.96 |
| ATOM | 4028 | C | ALA | A | 535 | 11.872 | 27.027 | −36.403 | 1.00 | 17.82 |
| ATOM | 4029 | O | ALA | A | 535 | 12.482 | 26.490 | −35.474 | 1.00 | 18.36 |
| ATOM | 4030 | N | VAL | A | 536 | 10.745 | 27.706 | −36.225 | 1.00 | 17.68 |
| ATOM | 4031 | CA | VAL | A | 536 | 10.138 | 27.861 | −34.898 | 1.00 | 18.65 |
| ATOM | 4032 | CB | VAL | A | 536 | 8.824 | 28.719 | −34.975 | 1.00 | 18.66 |
| ATOM | 4033 | CG1 | VAL | A | 536 | 7.805 | 28.123 | −35.971 | 1.00 | 19.98 |
| ATOM | 4034 | CG2 | VAL | A | 536 | 8.208 | 28.962 | −33.570 | 1.00 | 20.19 |
| ATOM | 4035 | C | VAL | A | 536 | 9.938 | 26.514 | −34.155 | 1.00 | 18.51 |
| ATOM | 4036 | O | VAL | A | 536 | 10.124 | 26.437 | −32.923 | 1.00 | 19.61 |
| ATOM | 4037 | N | ASN | A | 537 | 9.570 | 25.468 | −34.883 | 1.00 | 18.59 |
| ATOM | 4038 | CA | ASN | A | 537 | 9.344 | 24.154 | −34.261 | 1.00 | 19.07 |
| ATOM | 4039 | CB | ASN | A | 537 | 8.074 | 23.498 | −34.816 | 1.00 | 19.28 |
| ATOM | 4040 | CG | ASN | A | 537 | 6.800 | 24.252 | −34.448 | 1.00 | 21.02 |
| ATOM | 4041 | OD1 | ASN | A | 537 | 6.742 | 24.940 | −33.435 | 1.00 | 24.12 |
| ATOM | 4042 | ND2 | ASN | A | 537 | 5.762 | 24.089 | −35.265 | 1.00 | 20.99 |
| ATOM | 4043 | C | ASN | A | 537 | 10.518 | 23.182 | −34.445 | 1.00 | 19.15 |
| ATOM | 4044 | O | ASN | A | 537 | 10.394 | 21.971 | −34.196 | 1.00 | 18.60 |
| ATOM | 4045 | N | TYR | A | 538 | 11.653 | 23.699 | −34.897 | 1.00 | 19.05 |
| ATOM | 4046 | CA | TYR | A | 538 | 12.767 | 22.830 | −35.234 | 1.00 | 20.32 |
| ATOM | 4047 | CB | TYR | A | 538 | 13.816 | 23.618 | −36.026 | 1.00 | 20.37 |
| ATOM | 4048 | CG | TYR | A | 538 | 14.916 | 22.747 | −36.588 | 1.00 | 20.37 |
| ATOM | 4049 | CD1 | TYR | A | 538 | 14.822 | 22.238 | −37.886 | 1.00 | 20.39 |
| ATOM | 4050 | CE1 | TYR | A | 538 | 15.853 | 21.436 | −38.437 | 1.00 | 20.49 |
| ATOM | 4051 | CZ | TYR | A | 538 | 16.961 | 21.137 | −37.670 | 1.00 | 20.65 |
| ATOM | 4052 | OH | TYR | A | 538 | 17.946 | 20.341 | −38.218 | 1.00 | 21.53 |
| ATOM | 4053 | CE2 | TYR | A | 538 | 17.066 | 21.602 | −36.361 | 1.00 | 22.05 |
| ATOM | 4054 | CD2 | TYR | A | 538 | 16.043 | 22.418 | −35.825 | 1.00 | 21.95 |
| ATOM | 4055 | C | TYR | A | 538 | 13.436 | 22.209 | −33.981 | 1.00 | 21.29 |
| ATOM | 4056 | O | TYR | A | 538 | 13.733 | 22.919 | −33.036 | 1.00 | 21.89 |
| ATOM | 4057 | N | ALA | A | 539 | 13.695 | 20.902 | −34.014 | 1.00 | 22.15 |
| ATOM | 4058 | CA | ALA | A | 539 | 14.646 | 20.258 | −33.083 | 1.00 | 23.67 |
| ATOM | 4059 | CB | ALA | A | 539 | 13.909 | 19.536 | −31.976 | 1.00 | 23.94 |
| ATOM | 4060 | C | ALA | A | 539 | 15.545 | 19.289 | −33.849 | 1.00 | 24.35 |
| ATOM | 4061 | O | ALA | A | 539 | 15.117 | 18.698 | −34.833 | 1.00 | 23.63 |
| ATOM | 4062 | N | ASP | A | 540 | 16.793 | 19.118 | −33.405 | 1.00 | 25.69 |
| ATOM | 4063 | CA | ASP | A | 540 | 17.722 | 18.196 | −34.099 | 1.00 | 27.42 |
| ATOM | 4064 | CB | ASP | A | 540 | 19.044 | 18.051 | −33.339 | 1.00 | 28.62 |
| ATOM | 4065 | CG | ASP | A | 540 | 19.724 | 19.368 | −33.140 | 1.00 | 33.80 |
| ATOM | 4066 | OD1 | ASP | A | 540 | 19.875 | 20.115 | −34.147 | 1.00 | 36.83 |
| ATOM | 4067 | OD2 | ASP | A | 540 | 20.080 | 19.663 | −31.970 | 1.00 | 40.32 |
| ATOM | 4068 | C | ASP | A | 540 | 17.150 | 16.818 | −34.400 | 1.00 | 26.63 |
| ATOM | 4069 | O | ASP | A | 540 | 17.386 | 16.277 | −35.485 | 1.00 | 27.28 |
| ATOM | 4070 | N | ASN | A | 541 | 16.403 | 16.247 | −33.458 | 1.00 | 25.08 |
| ATOM | 4071 | CA | ASN | A | 541 | 15.827 | 14.922 | −33.687 | 1.00 | 24.03 |
| ATOM | 4072 | CB | ASN | A | 541 | 15.988 | 14.032 | −32.441 | 1.00 | 25.14 |
| ATOM | 4073 | CG | ASN | A | 541 | 15.337 | 14.623 | −31.191 | 1.00 | 27.81 |
| ATOM | 4074 | OD1 | ASN | A | 541 | 15.366 | 14.001 | −30.118 | 1.00 | 31.57 |
| ATOM | 4075 | ND2 | ASN | A | 541 | 14.771 | 15.824 | −31.306 | 1.00 | 28.81 |
| ATOM | 4076 | C | ASN | A | 541 | 14.349 | 14.991 | −34.118 | 1.00 | 22.46 |
| ATOM | 4077 | O | ASN | A | 541 | 13.660 | 13.979 | −34.172 | 1.00 | 22.35 |
| ATOM | 4078 | N | HIS | A | 542 | 13.871 | 16.197 | −34.403 | 1.00 | 19.85 |

TABLE 15-continued

| | | | | | | | | | |
|---|---|---|---|---|---|---|---|---|---|
| ATOM | 4079 | CA | HIS | A | 542 | 12.580 | 16.354 | −35.083 | 1.00 | 18.22 |
| ATOM | 4080 | CB | HIS | A | 542 | 11.426 | 16.392 | −34.062 | 1.00 | 16.89 |
| ATOM | 4081 | CG | HIS | A | 542 | 10.071 | 16.341 | −34.699 | 1.00 | 17.32 |
| ATOM | 4082 | ND1 | HIS | A | 542 | 9.211 | 17.417 | −34.711 | 1.00 | 16.28 |
| ATOM | 4083 | CE1 | HIS | A | 542 | 8.111 | 17.088 | −35.371 | 1.00 | 14.64 |
| ATOM | 4084 | NE2 | HIS | A | 542 | 8.217 | 15.834 | −35.765 | 1.00 | 15.41 |
| ATOM | 4085 | CD2 | HIS | A | 542 | 9.435 | 15.340 | −35.358 | 1.00 | 15.14 |
| ATOM | 4086 | C | HIS | A | 542 | 12.662 | 17.650 | −35.902 | 1.00 | 17.48 |
| ATOM | 4087 | O | HIS | A | 542 | 12.198 | 18.698 | −35.446 | 1.00 | 17.79 |
| ATOM | 4088 | N | PRO | A | 543 | 13.324 | 17.584 | −37.083 | 1.00 | 17.00 |
| ATOM | 4089 | CA | PRO | A | 543 | 13.797 | 18.752 | −37.832 | 1.00 | 17.09 |
| ATOM | 4090 | CB | PRO | A | 543 | 14.948 | 18.164 | −38.677 | 1.00 | 16.57 |
| ATOM | 4091 | CG | PRO | A | 543 | 14.472 | 16.759 | −38.994 | 1.00 | 18.22 |
| ATOM | 4092 | CD | PRO | A | 543 | 13.676 | 16.321 | −37.764 | 1.00 | 17.39 |
| ATOM | 4093 | C | PRO | A | 543 | 12.718 | 19.435 | −38.691 | 1.00 | 16.46 |
| ATOM | 4094 | O | PRO | A | 543 | 12.811 | 19.497 | −39.922 | 1.00 | 17.09 |
| ATOM | 4095 | N | LEU | A | 544 | 11.726 | 19.987 | −38.009 | 1.00 | 15.36 |
| ATOM | 4096 | CA | LEU | A | 544 | 10.534 | 20.535 | −38.636 | 1.00 | 15.10 |
| ATOM | 4097 | CB | LEU | A | 544 | 9.341 | 20.376 | −37.672 | 1.00 | 15.29 |
| ATOM | 4098 | CG | LEU | A | 544 | 7.968 | 20.927 | −38.134 | 1.00 | 16.53 |
| ATOM | 4099 | CD1 | LEU | A | 544 | 7.524 | 20.364 | −39.494 | 1.00 | 15.92 |
| ATOM | 4100 | CD2 | LEU | A | 544 | 6.900 | 20.700 | −37.062 | 1.00 | 14.59 |
| ATOM | 4101 | C | LEU | A | 544 | 10.694 | 22.018 | −39.025 | 1.00 | 15.09 |
| ATOM | 4102 | O | LEU | A | 544 | 11.037 | 22.851 | −38.197 | 1.00 | 15.34 |
| ATOM | 4103 | N | TRP | A | 545 | 10.456 | 22.298 | −40.303 | 1.00 | 15.03 |
| ATOM | 4104 | CA | TRP | A | 545 | 10.327 | 23.637 | −40.843 | 1.00 | 15.36 |
| ATOM | 4105 | CB | TRP | A | 545 | 11.288 | 23.790 | −42.023 | 1.00 | 15.40 |
| ATOM | 4106 | CG | TRP | A | 545 | 12.758 | 23.921 | −41.663 | 1.00 | 15.62 |
| ATOM | 4107 | CD1 | TRP | A | 545 | 13.653 | 22.903 | −41.384 | 1.00 | 16.85 |
| ATOM | 4108 | NE1 | TRP | A | 545 | 14.906 | 23.437 | −41.129 | 1.00 | 18.69 |
| ATOM | 4109 | CE2 | TRP | A | 545 | 14.837 | 24.803 | −41.246 | 1.00 | 17.78 |
| ATOM | 4110 | CD2 | TRP | A | 545 | 13.498 | 25.140 | −41.584 | 1.00 | 17.01 |
| ATOM | 4111 | CE3 | TRP | A | 545 | 13.163 | 26.488 | −41.777 | 1.00 | 17.17 |
| ATOM | 4112 | CZ3 | TRP | A | 545 | 14.165 | 27.456 | −41.637 | 1.00 | 18.29 |
| ATOM | 4113 | CH2 | TRP | A | 545 | 15.483 | 27.085 | −41.295 | 1.00 | 17.22 |
| ATOM | 4114 | CZ2 | TRP | A | 545 | 15.835 | 25.767 | −41.111 | 1.00 | 19.09 |
| ATOM | 4115 | C | TRP | A | 545 | 8.907 | 23.832 | −41.359 | 1.00 | 15.14 |
| ATOM | 4116 | O | TRP | A | 545 | 8.327 | 22.933 | −41.986 | 1.00 | 14.45 |
| ATOM | 4117 | N | ILE | A | 546 | 8.362 | 25.025 | −41.149 | 1.00 | 15.19 |
| ATOM | 4118 | CA | ILE | A | 546 | 6.938 | 25.244 | −41.428 | 1.00 | 16.51 |
| ATOM | 4119 | CB | ILE | A | 546 | 6.107 | 24.988 | −40.130 | 1.00 | 17.39 |
| ATOM | 4120 | CG1 | ILE | A | 546 | 4.615 | 24.852 | −40.420 | 1.00 | 20.44 |
| ATOM | 4121 | CD1 | ILE | A | 546 | 3.882 | 23.992 | −39.392 | 1.00 | 23.59 |
| ATOM | 4122 | CG2 | ILE | A | 546 | 6.391 | 26.064 | −39.050 | 1.00 | 17.70 |
| ATOM | 4123 | C | ILE | A | 546 | 6.674 | 26.635 | −42.006 | 1.00 | 16.75 |
| ATOM | 4124 | O | ILE | A | 546 | 7.352 | 27.593 | −41.647 | 1.00 | 15.81 |
| ATOM | 4125 | N | ALA | A | 547 | 5.716 | 26.743 | −42.925 | 1.00 | 16.88 |
| ATOM | 4126 | CA | ALA | A | 547 | 5.197 | 28.057 | −43.279 | 1.00 | 17.94 |
| ATOM | 4127 | CB | ALA | A | 547 | 6.222 | 28.893 | −43.931 | 1.00 | 21.49 |
| ATOM | 4128 | C | ALA | A | 547 | 4.009 | 27.919 | −44.167 | 1.00 | 18.29 |
| ATOM | 4129 | O | ALA | A | 547 | 3.727 | 26.828 | −44.655 | 1.00 | 18.52 |
| ATOM | 4130 | N | THR | A | 548 | 3.316 | 29.031 | −44.362 | 1.00 | 17.99 |
| ATOM | 4131 | CA | THR | A | 548 | 1.970 | 29.017 | −44.919 | 1.00 | 18.72 |
| ATOM | 4132 | CB | THR | A | 548 | 0.929 | 29.419 | −43.855 | 1.00 | 18.65 |
| ATOM | 4133 | OG1 | THR | A | 548 | 1.000 | 28.500 | −42.751 | 1.00 | 19.46 |
| ATOM | 4134 | CG2 | THR | A | 548 | −0.491 | 29.379 | −44.438 | 1.00 | 18.79 |
| ATOM | 4135 | C | THR | A | 548 | 1.865 | 29.960 | −46.104 | 1.00 | 19.60 |
| ATOM | 4136 | O | THR | A | 548 | 2.347 | 31.090 | −46.040 | 1.00 | 19.83 |
| ATOM | 4137 | N | VAL | A | 549 | 1.227 | 29.485 | −47.164 | 1.00 | 20.41 |
| ATOM | 4138 | CA | VAL | A | 549 | 1.048 | 30.280 | −48.389 | 1.00 | 22.36 |
| ATOM | 4139 | CB | VAL | A | 549 | 1.944 | 29.722 | −49.537 | 1.00 | 22.77 |
| ATOM | 4140 | CG1 | VAL | A | 549 | 1.717 | 30.491 | −50.845 | 1.00 | 25.80 |
| ATOM | 4141 | CG2 | VAL | A | 549 | 3.429 | 29.781 | −49.148 | 1.00 | 24.78 |
| ATOM | 4142 | C | VAL | A | 549 | −0.399 | 30.119 | −48.800 | 1.00 | 22.21 |
| ATOM | 4143 | O | VAL | A | 549 | −0.943 | 29.018 | −48.719 | 1.00 | 21.56 |
| ATOM | 4144 | N | ASN | A | 550 | −1.028 | 31.211 | −49.240 | 1.00 | 22.80 |
| ATOM | 4145 | CA | ASN | A | 550 | −2.356 | 31.107 | −49.831 | 1.00 | 23.95 |
| ATOM | 4146 | CB | ASN | A | 550 | −3.114 | 32.411 | −49.649 | 1.00 | 24.39 |
| ATOM | 4147 | CG | ASN | A | 550 | −3.367 | 32.706 | −48.201 | 1.00 | 27.42 |
| ATOM | 4148 | OD1 | ASN | A | 550 | −3.811 | 31.838 | −47.462 | 1.00 | 28.69 |
| ATOM | 4149 | ND2 | ASN | A | 550 | −3.041 | 33.911 | −47.771 | 1.00 | 31.89 |
| ATOM | 4150 | C | ASN | A | 550 | −2.278 | 30.733 | −51.294 | 1.00 | 23.98 |
| ATOM | 4151 | O | ASN | A | 550 | −1.598 | 31.400 | −52.065 | 1.00 | 24.73 |
| ATOM | 4152 | N | LEU | A | 551 | −2.973 | 29.667 | −51.662 | 1.00 | 24.24 |
| ATOM | 4153 | CA | LEU | A | 551 | −3.016 | 29.180 | −53.020 | 1.00 | 24.78 |
| ATOM | 4154 | CB | LEU | A | 551 | −2.348 | 27.797 | −53.135 | 1.00 | 25.00 |
| ATOM | 4155 | CG | LEU | A | 551 | −0.858 | 27.721 | −52.787 | 1.00 | 25.19 |
| ATOM | 4156 | CD1 | LEU | A | 551 | −0.356 | 26.284 | −52.803 | 1.00 | 27.45 |
| ATOM | 4157 | CD2 | LEU | A | 551 | −0.018 | 28.613 | −53.718 | 1.00 | 26.73 |
| ATOM | 4158 | C | LEU | A | 551 | −4.471 | 29.104 | −53.488 | 1.00 | 25.46 |

TABLE 15-continued

| | | | | | | | | | |
|---|---|---|---|---|---|---|---|---|---|
| ATOM | 4159 | O | LEU | A | 551 | −5.393 | 29.018 | −52.675 | 1.00 | 24.27 |
| ATOM | 4160 | N | GLU | A | 552 | −4.661 | 29.148 | −54.804 | 1.00 | 26.15 |
| ATOM | 4161 | CA | GLU | A | 552 | −6.004 | 29.165 | −55.366 | 1.00 | 28.20 |
| ATOM | 4162 | CB | GLU | A | 552 | −5.955 | 29.639 | −56.823 | 1.00 | 28.30 |
| ATOM | 4163 | CG | GLU | A | 552 | −7.326 | 29.739 | −57.494 | 1.00 | 32.28 |
| ATOM | 4164 | CD | GLU | A | 552 | −7.250 | 30.281 | −58.926 | 1.00 | 33.44 |
| ATOM | 4165 | OE1 | GLU | A | 552 | −8.110 | 31.126 | −59.274 | 1.00 | 41.80 |
| ATOM | 4166 | OE2 | GLU | A | 552 | −6.340 | 29.873 | −59.695 | 1.00 | 39.14 |
| ATOM | 4167 | C | GLU | A | 552 | −6.610 | 27.768 | −55.253 | 1.00 | 26.97 |
| ATOM | 4168 | O | GLU | A | 552 | −5.979 | 26.783 | −55.622 | 1.00 | 26.49 |
| ATOM | 4169 | N | ALA | A | 553 | −7.822 | 27.684 | −54.723 | 1.00 | 27.21 |
| ATOM | 4170 | CA | ALA | A | 553 | −8.502 | 26.399 | −54.603 | 1.00 | 27.89 |
| ATOM | 4171 | CB | ALA | A | 553 | −9.876 | 26.574 | −53.953 | 1.00 | 28.37 |
| ATOM | 4172 | C | ALA | A | 553 | −8.637 | 25.773 | −55.979 | 1.00 | 28.57 |
| ATOM | 4173 | O | ALA | A | 553 | −8.900 | 26.477 | −56.952 | 1.00 | 28.83 |
| ATOM | 4174 | N | GLY | A | 554 | −8.438 | 24.465 | −56.064 | 1.00 | 28.44 |
| ATOM | 4175 | CA | GLY | A | 554 | −8.556 | 23.753 | −57.330 | 1.00 | 29.66 |
| ATOM | 4176 | C | GLY | A | 554 | −7.274 | 23.693 | −58.145 | 1.00 | 30.04 |
| ATOM | 4177 | O | GLY | A | 554 | −7.122 | 22.814 | −59.000 | 1.00 | 30.33 |
| ATOM | 4178 | N | ASP | A | 555 | −6.347 | 24.606 | −57.869 | 1.00 | 30.23 |
| ATOM | 4179 | CA | ASP | A | 555 | −5.098 | 24.716 | −58.630 | 1.00 | 30.61 |
| ATOM | 4180 | CB | ASP | A | 555 | −4.313 | 25.939 | −58.161 | 1.00 | 30.85 |
| ATOM | 4181 | CG | ASP | A | 555 | −3.382 | 26.503 | −59.236 | 1.00 | 34.49 |
| ATOM | 4182 | OD1 | ASP | A | 555 | −3.441 | 26.053 | −60.407 | 1.00 | 37.19 |
| ATOM | 4183 | OD2 | ASP | A | 555 | −2.572 | 27.408 | −58.901 | 1.00 | 36.59 |
| ATOM | 4184 | C | ASP | A | 555 | −4.238 | 23.467 | −58.486 | 1.00 | 30.14 |
| ATOM | 4185 | O | ASP | A | 555 | −4.156 | 22.882 | −57.419 | 1.00 | 30.07 |
| ATOM | 4186 | N | VAL | A | 556 | −3.602 | 23.046 | −59.572 | 1.00 | 29.55 |
| ATOM | 4187 | CA | VAL | A | 556 | −2.628 | 21.963 | −59.492 | 1.00 | 28.74 |
| ATOM | 4188 | CB | VAL | A | 556 | −2.732 | 20.987 | −60.680 | 1.00 | 29.35 |
| ATOM | 4189 | CG1 | VAL | A | 556 | −1.666 | 19.877 | −60.569 | 1.00 | 28.99 |
| ATOM | 4190 | CG2 | VAL | A | 556 | −4.125 | 20.365 | −60.720 | 1.00 | 30.44 |
| ATOM | 4191 | C | VAL | A | 556 | −1.261 | 22.623 | −59.448 | 1.00 | 28.04 |
| ATOM | 4192 | O | VAL | A | 556 | −0.869 | 23.336 | −60.384 | 1.00 | 27.25 |
| ATOM | 4193 | N | VAL | A | 557 | −0.544 | 22.389 | −58.352 | 1.00 | 26.81 |
| ATOM | 4194 | CA | VAL | A | 557 | 0.739 | 23.040 | −58.100 | 1.00 | 26.14 |
| ATOM | 4195 | CB | VAL | A | 557 | 0.690 | 23.859 | −56.759 | 1.00 | 26.71 |
| ATOM | 4196 | CG1 | VAL | A | 557 | 2.073 | 24.140 | −56.219 | 1.00 | 27.82 |
| ATOM | 4197 | CG2 | VAL | A | 557 | −0.088 | 25.175 | −56.952 | 1.00 | 27.34 |
| ATOM | 4198 | C | VAL | A | 557 | 1.856 | 21.999 | −58.092 | 1.00 | 25.64 |
| ATOM | 4199 | O | VAL | A | 557 | 1.646 | 20.845 | −57.693 | 1.00 | 25.24 |
| ATOM | 4200 | N | GLU | A | 558 | 3.035 | 22.409 | −58.553 | 1.00 | 24.16 |
| ATOM | 4201 | CA | GLU | A | 558 | 4.223 | 21.579 | −58.516 | 1.00 | 24.38 |
| ATOM | 4202 | CB | GLU | A | 558 | 4.737 | 21.296 | −59.933 | 1.00 | 24.86 |
| ATOM | 4203 | CG | GLU | A | 558 | 4.064 | 20.108 | −60.606 | 1.00 | 26.34 |
| ATOM | 4204 | CD | GLU | A | 558 | 4.670 | 19.790 | −61.962 | 1.00 | 27.68 |
| ATOM | 4205 | OE1 | GLU | A | 558 | 5.917 | 19.684 | −62.065 | 1.00 | 30.56 |
| ATOM | 4206 | OE2 | GLU | A | 558 | 3.883 | 19.638 | −62.915 | 1.00 | 32.45 |
| ATOM | 4207 | C | GLU | A | 558 | 5.262 | 22.337 | −57.730 | 1.00 | 22.54 |
| ATOM | 4208 | O | GLU | A | 558 | 5.389 | 23.550 | −57.883 | 1.00 | 22.93 |
| ATOM | 4209 | N | TYR | A | 559 | 5.992 | 21.640 | −56.867 | 1.00 | 21.45 |
| ATOM | 4210 | CA | TYR | A | 559 | 6.927 | 22.346 | −55.995 | 1.00 | 19.96 |
| ATOM | 4211 | CB | TYR | A | 559 | 6.188 | 22.972 | −54.784 | 1.00 | 19.42 |
| ATOM | 4212 | CG | TYR | A | 559 | 5.624 | 21.952 | −53.796 | 1.00 | 18.65 |
| ATOM | 4213 | CD1 | TYR | A | 559 | 6.383 | 21.524 | −52.703 | 1.00 | 18.64 |
| ATOM | 4214 | CE1 | TYR | A | 559 | 5.887 | 20.595 | −51.794 | 1.00 | 19.09 |
| ATOM | 4215 | CZ | TYR | A | 559 | 4.614 | 20.090 | −51.955 | 1.00 | 18.58 |
| ATOM | 4216 | OH | TYR | A | 559 | 4.135 | 19.160 | −51.056 | 1.00 | 20.55 |
| ATOM | 4217 | CE2 | TYR | A | 559 | 3.819 | 20.493 | −53.024 | 1.00 | 18.22 |
| ATOM | 4218 | CD2 | TYR | A | 559 | 4.335 | 21.438 | −53.946 | 1.00 | 18.82 |
| ATOM | 4219 | C | TYR | A | 559 | 8.066 | 21.445 | −55.541 | 1.00 | 20.13 |
| ATOM | 4220 | O | TYR | A | 559 | 8.008 | 20.215 | −55.679 | 1.00 | 20.26 |
| ATOM | 4221 | N | LYS | A | 560 | 9.098 | 22.079 | −54.995 | 1.00 | 19.51 |
| ATOM | 4222 | CA | LYS | A | 560 | 10.208 | 21.379 | −54.349 | 1.00 | 19.72 |
| ATOM | 4223 | CB | LYS | A | 560 | 11.410 | 21.175 | −55.282 | 1.00 | 19.66 |
| ATOM | 4224 | CG | LYS | A | 560 | 11.390 | 19.870 | −56.058 | 1.00 | 22.20 |
| ATOM | 4225 | CD | LYS | A | 560 | 12.767 | 19.633 | −56.714 | 1.00 | 24.46 |
| ATOM | 4226 | CE | LYS | A | 560 | 12.781 | 18.341 | −57.531 | 1.00 | 26.96 |
| ATOM | 4227 | NZ | LYS | A | 560 | 14.189 | 18.050 | −57.980 | 1.00 | 26.97 |
| ATOM | 4228 | C | LYS | A | 560 | 10.680 | 22.257 | −53.234 | 1.00 | 18.68 |
| ATOM | 4229 | O | LYS | A | 560 | 10.583 | 23.484 | −53.318 | 1.00 | 19.68 |
| ATOM | 4230 | N | TYR | A | 561 | 11.240 | 21.640 | −52.206 | 1.00 | 17.87 |
| ATOM | 4231 | CA | TYR | A | 561 | 11.927 | 22.420 | −51.187 | 1.00 | 17.82 |
| ATOM | 4232 | CB | TYR | A | 561 | 11.921 | 21.690 | −49.840 | 1.00 | 17.42 |
| ATOM | 4233 | CG | TYR | A | 561 | 10.518 | 21.449 | −49.346 | 1.00 | 16.12 |
| ATOM | 4234 | CD1 | TYR | A | 561 | 9.831 | 20.276 | −49.661 | 1.00 | 15.94 |
| ATOM | 4235 | CE1 | TYR | A | 561 | 8.511 | 20.062 | −49.199 | 1.00 | 15.79 |
| ATOM | 4236 | CZ | TYR | A | 561 | 7.897 | 21.050 | −48.456 | 1.00 | 15.89 |
| ATOM | 4237 | OH | TYR | A | 561 | 6.614 | 20.889 | −47.981 | 1.00 | 17.17 |
| ATOM | 4238 | CE2 | TYR | A | 561 | 8.557 | 22.224 | −48.164 | 1.00 | 16.19 |

TABLE 15-continued

| | | | | | | | | | |
|---|---|---|---|---|---|---|---|---|---|
| ATOM | 4239 | CD2 | TYR | A | 561 | 9.856 | 22.430 | −48.625 | 1.00 | 17.57 |
| ATOM | 4240 | C | TYR | A | 561 | 13.360 | 22.650 | −51.607 | 1.00 | 18.63 |
| ATOM | 4241 | O | TYR | A | 561 | 13.963 | 21.786 | −52.265 | 1.00 | 18.40 |
| ATOM | 4242 | N | ILE | A | 562 | 13.904 | 23.792 | −51.201 | 1.00 | 18.56 |
| ATOM | 4243 | CA | ILE | A | 562 | 15.322 | 24.085 | −51.434 | 1.00 | 20.18 |
| ATOM | 4244 | CB | ILE | A | 562 | 15.524 | 25.247 | −52.419 | 1.00 | 19.65 |
| ATOM | 4245 | CG1 | ILE | A | 562 | 14.837 | 26.520 | −51.896 | 1.00 | 21.64 |
| ATOM | 4246 | CD1 | ILE | A | 562 | 15.074 | 27.789 | −52.741 | 1.00 | 21.24 |
| ATOM | 4247 | CG2 | ILE | A | 562 | 15.017 | 24.829 | −53.797 | 1.00 | 20.44 |
| ATOM | 4248 | C | ILE | A | 562 | 15.971 | 24.446 | −50.128 | 1.00 | 20.56 |
| ATOM | 4249 | O | ILE | A | 562 | 15.316 | 24.956 | −49.229 | 1.00 | 19.84 |
| ATOM | 4250 | N | ASN | A | 563 | 17.254 | 24.134 | −50.029 | 1.00 | 21.41 |
| ATOM | 4251 | CA | ASN | A | 563 | 18.076 | 24.467 | −48.886 | 1.00 | 22.99 |
| ATOM | 4252 | CB | ASN | A | 563 | 18.833 | 23.209 | −48.435 | 1.00 | 22.69 |
| ATOM | 4253 | CG | ASN | A | 563 | 19.629 | 23.433 | −47.156 | 1.00 | 25.48 |
| ATOM | 4254 | OD1 | ASN | A | 563 | 20.203 | 24.492 | −46.965 | 1.00 | 28.81 |
| ATOM | 4255 | ND2 | ASN | A | 563 | 19.669 | 22.436 | −46.285 | 1.00 | 25.82 |
| ATOM | 4256 | C | ASN | A | 563 | 19.039 | 25.561 | −49.372 | 1.00 | 24.66 |
| ATOM | 4257 | O | ASN | A | 563 | 19.794 | 25.326 | −50.323 | 1.00 | 24.16 |
| ATOM | 4258 | N | VAL | A | 564 | 18.977 | 26.749 | −48.780 | 1.00 | 26.20 |
| ATOM | 4259 | CA | VAL | A | 564 | 19.877 | 27.837 | −49.206 | 1.00 | 28.74 |
| ATOM | 4260 | CB | VAL | A | 564 | 19.156 | 29.091 | −49.832 | 1.00 | 28.91 |
| ATOM | 4261 | CG1 | VAL | A | 564 | 19.461 | 30.408 | −49.087 | 1.00 | 31.10 |
| ATOM | 4262 | CG2 | VAL | A | 564 | 17.655 | 28.836 | −50.079 | 1.00 | 28.92 |
| ATOM | 4263 | C | VAL | A | 564 | 20.886 | 28.181 | −48.122 | 1.00 | 29.56 |
| ATOM | 4264 | O | VAL | A | 564 | 20.538 | 28.320 | −46.954 | 1.00 | 29.10 |
| ATOM | 4265 | N | GLY | A | 565 | 22.150 | 28.266 | −48.527 | 1.00 | 32.02 |
| ATOM | 4266 | CA | GLY | A | 565 | 23.252 | 28.423 | −47.577 | 1.00 | 34.92 |
| ATOM | 4267 | C | GLY | A | 565 | 23.539 | 29.876 | −47.248 | 1.00 | 37.47 |
| ATOM | 4268 | O | GLY | A | 565 | 22.969 | 30.788 | −47.871 | 1.00 | 37.66 |
| ATOM | 4269 | N | GLN | A | 566 | 24.419 | 30.098 | −46.267 | 1.00 | 39.85 |
| ATOM | 4270 | CA | GLN | A | 566 | 24.897 | 31.456 | −45.926 | 1.00 | 42.75 |
| ATOM | 4271 | CB | GLN | A | 566 | 26.054 | 31.398 | −44.918 | 1.00 | 42.83 |
| ATOM | 4272 | CG | GLN | A | 566 | 25.727 | 30.761 | −43.565 | 1.00 | 44.99 |
| ATOM | 4273 | CD | GLN | A | 566 | 26.940 | 30.689 | −42.626 | 1.00 | 44.88 |
| ATOM | 4274 | OE1 | GLN | A | 566 | 27.972 | 30.089 | −42.958 | 1.00 | 47.67 |
| ATOM | 4275 | NE2 | GLN | A | 566 | 26.810 | 31.293 | −41.441 | 1.00 | 47.62 |
| ATOM | 4276 | C | GLN | A | 566 | 25.373 | 32.195 | −47.181 | 1.00 | 43.30 |
| ATOM | 4277 | O | GLN | A | 566 | 25.052 | 33.365 | −47.389 | 1.00 | 44.01 |
| ATOM | 4278 | N | ASP | A | 567 | 26.118 | 31.479 | −48.023 | 1.00 | 44.30 |
| ATOM | 4279 | CA | ASP | A | 567 | 26.739 | 32.029 | −49.236 | 1.00 | 44.62 |
| ATOM | 4280 | CB | ASP | A | 567 | 27.916 | 31.139 | −49.650 | 1.00 | 45.13 |
| ATOM | 4281 | CG | ASP | A | 567 | 27.492 | 29.702 | −49.966 | 1.00 | 47.62 |
| ATOM | 4282 | OD1 | ASP | A | 567 | 26.421 | 29.255 | −49.485 | 1.00 | 48.73 |
| ATOM | 4283 | OD2 | ASP | A | 567 | 28.245 | 29.010 | −50.693 | 1.00 | 50.47 |
| ATOM | 4284 | C | ASP | A | 567 | 25.776 | 32.197 | −50.421 | 1.00 | 44.04 |
| ATOM | 4285 | O | ASP | A | 567 | 26.196 | 32.575 | −51.522 | 1.00 | 44.36 |
| ATOM | 4286 | N | GLY | A | 568 | 24.497 | 31.899 | −50.205 | 1.00 | 42.85 |
| ATOM | 4287 | CA | GLY | A | 568 | 23.488 | 32.045 | −51.247 | 1.00 | 41.38 |
| ATOM | 4288 | C | GLY | A | 568 | 23.359 | 30.851 | −52.177 | 1.00 | 40.41 |
| ATOM | 4289 | O | GLY | A | 568 | 22.496 | 30.854 | −53.054 | 1.00 | 40.62 |
| ATOM | 4290 | N | SER | A | 569 | 24.195 | 29.827 | −51.990 | 1.00 | 39.02 |
| ATOM | 4291 | CA | SER | A | 569 | 24.137 | 28.623 | −52.827 | 1.00 | 37.72 |
| ATOM | 4292 | CB | SER | A | 569 | 25.365 | 27.746 | −52.600 | 1.00 | 38.07 |
| ATOM | 4293 | OG | SER | A | 569 | 25.454 | 27.359 | −51.238 | 1.00 | 39.18 |
| ATOM | 4294 | C | SER | A | 569 | 22.868 | 27.819 | −52.540 | 1.00 | 36.72 |
| ATOM | 4295 | O | SER | A | 569 | 22.474 | 27.672 | −51.382 | 1.00 | 36.47 |
| ATOM | 4296 | N | VAL | A | 570 | 22.222 | 27.313 | −53.583 | 1.00 | 35.25 |
| ATOM | 4297 | CA | VAL | A | 570 | 20.988 | 26.558 | −53.365 | 1.00 | 34.26 |
| ATOM | 4298 | CB | VAL | A | 570 | 19.709 | 27.243 | −53.987 | 1.00 | 34.42 |
| ATOM | 4299 | CG1 | VAL | A | 570 | 18.992 | 26.358 | −55.020 | 1.00 | 35.11 |
| ATOM | 4300 | CG2 | VAL | A | 570 | 20.010 | 28.651 | −54.506 | 1.00 | 35.12 |
| ATOM | 4301 | C | VAL | A | 570 | 21.113 | 25.080 | −53.718 | 1.00 | 33.29 |
| ATOM | 4302 | O | VAL | A | 570 | 21.735 | 24.694 | −54.714 | 1.00 | 32.88 |
| ATOM | 4303 | N | THR | A | 571 | 20.515 | 24.261 | −52.864 | 1.00 | 31.66 |
| ATOM | 4304 | CA | THR | A | 571 | 20.480 | 22.825 | −53.021 | 1.00 | 30.87 |
| ATOM | 4305 | CB | THR | A | 571 | 21.016 | 22.146 | −51.752 | 1.00 | 30.96 |
| ATOM | 4306 | OG1 | THR | A | 571 | 22.311 | 22.686 | −51.442 | 1.00 | 33.18 |
| ATOM | 4307 | CG2 | THR | A | 571 | 21.117 | 20.637 | −51.935 | 1.00 | 30.95 |
| ATOM | 4308 | C | THR | A | 571 | 19.018 | 22.473 | −53.210 | 1.00 | 29.72 |
| ATOM | 4309 | O | THR | A | 571 | 18.186 | 22.832 | −52.373 | 1.00 | 28.84 |
| ATOM | 4310 | N | TRP | A | 572 | 18.697 | 21.846 | −54.337 | 1.00 | 29.01 |
| ATOM | 4311 | CA | TRP | A | 572 | 17.331 | 21.388 | −54.589 | 1.00 | 28.49 |
| ATOM | 4312 | CB | TRP | A | 572 | 17.004 | 21.367 | −56.086 | 1.00 | 28.99 |
| ATOM | 4313 | CG | TRP | A | 572 | 16.950 | 22.690 | −56.739 | 1.00 | 29.65 |
| ATOM | 4314 | CD1 | TRP | A | 572 | 18.014 | 23.419 | −57.217 | 1.00 | 30.67 |
| ATOM | 4315 | NE1 | TRP | A | 572 | 17.564 | 24.603 | −57.769 | 1.00 | 31.84 |
| ATOM | 4316 | CE2 | TRP | A | 572 | 16.196 | 24.655 | −57.668 | 1.00 | 30.45 |
| ATOM | 4317 | CD2 | TRP | A | 572 | 15.770 | 23.464 | −57.028 | 1.00 | 30.30 |
| ATOM | 4318 | CE3 | TRP | A | 572 | 14.398 | 23.274 | −56.791 | 1.00 | 29.43 |

TABLE 15-continued

| | | | | | | | | | |
|---|---|---|---|---|---|---|---|---|---|
| ATOM | 4319 | CZ3 | TRP | A | 572 | 13.502 | 24.266 | −57.205 | 1.00 | 30.24 |
| ATOM | 4320 | CH2 | TRP | A | 572 | 13.959 | 25.437 | −57.846 | 1.00 | 30.31 |
| ATOM | 4321 | CZ2 | TRP | A | 572 | 15.298 | 25.649 | −58.083 | 1.00 | 29.71 |
| ATOM | 4322 | C | TRP | A | 572 | 17.205 | 19.991 | −54.031 | 1.00 | 28.21 |
| ATOM | 4323 | O | TRP | A | 572 | 18.168 | 19.212 | −54.060 | 1.00 | 27.50 |
| ATOM | 4324 | N | GLU | A | 573 | 16.033 | 19.647 | −53.499 | 1.00 | 27.69 |
| ATOM | 4325 | CA | GLU | A | 573 | 15.819 | 18.251 | −53.123 | 1.00 | 27.17 |
| ATOM | 4326 | CB | GLU | A | 573 | 14.586 | 18.074 | −52.222 | 1.00 | 27.18 |
| ATOM | 4327 | CG | GLU | A | 573 | 13.287 | 18.406 | −52.901 | 1.00 | 26.04 |
| ATOM | 4328 | CD | GLU | A | 573 | 12.059 | 18.111 | −52.028 | 1.00 | 26.20 |
| ATOM | 4329 | OE1 | GLU | A | 573 | 12.112 | 17.224 | −51.141 | 1.00 | 25.84 |
| ATOM | 4330 | OE2 | GLU | A | 573 | 11.032 | 18.764 | −52.264 | 1.00 | 22.24 |
| ATOM | 4331 | C | GLU | A | 573 | 15.725 | 17.419 | −54.405 | 1.00 | 27.91 |
| ATOM | 4332 | O | GLU | A | 573 | 15.498 | 17.957 | −55.497 | 1.00 | 26.94 |
| ATOM | 4333 | N | SER | A | 574 | 15.907 | 16.108 | −54.267 | 1.00 | 28.48 |
| ATOM | 4334 | CA | SER | A | 574 | 15.880 | 15.201 | −55.410 | 1.00 | 29.59 |
| ATOM | 4335 | CB | SER | A | 574 | 16.296 | 13.805 | −54.975 | 1.00 | 29.73 |
| ATOM | 4336 | OG | SER | A | 574 | 17.609 | 13.875 | −54.449 | 1.00 | 32.74 |
| ATOM | 4337 | C | SER | A | 574 | 14.526 | 15.134 | −56.095 | 1.00 | 29.70 |
| ATOM | 4338 | O | SER | A | 574 | 13.500 | 15.482 | −55.513 | 1.00 | 29.12 |
| ATOM | 4339 | N | ASP | A | 575 | 14.544 | 14.669 | −57.339 | 1.00 | 29.54 |
| ATOM | 4340 | CA | ASP | A | 575 | 13.337 | 14.435 | −58.109 | 1.00 | 29.98 |
| ATOM | 4341 | CB | ASP | A | 575 | 13.705 | 14.000 | −59.534 | 1.00 | 30.69 |
| ATOM | 4342 | CG | ASP | A | 575 | 14.324 | 15.125 | −60.331 | 1.00 | 33.96 |
| ATOM | 4343 | OD1 | ASP | A | 575 | 14.056 | 16.299 | −59.997 | 1.00 | 36.25 |
| ATOM | 4344 | OD2 | ASP | A | 575 | 15.083 | 14.846 | −61.290 | 1.00 | 37.94 |
| ATOM | 4345 | C | ASP | A | 575 | 12.519 | 13.358 | −57.428 | 1.00 | 28.93 |
| ATOM | 4346 | O | ASP | A | 575 | 13.050 | 12.633 | −56.600 | 1.00 | 28.34 |
| ATOM | 4347 | N | PRO | A | 576 | 11.217 | 13.267 | −57.760 | 1.00 | 28.58 |
| ATOM | 4348 | CA | PRO | A | 576 | 10.469 | 14.173 | −58.650 | 1.00 | 27.92 |
| ATOM | 4349 | CB | PRO | A | 576 | 9.319 | 13.294 | −59.131 | 1.00 | 28.52 |
| ATOM | 4350 | CG | PRO | A | 576 | 9.053 | 12.378 | −57.954 | 1.00 | 28.29 |
| ATOM | 4351 | CD | PRO | A | 576 | 10.377 | 12.159 | −57.267 | 1.00 | 28.76 |
| ATOM | 4352 | C | PRO | A | 576 | 9.894 | 15.397 | −57.938 | 1.00 | 27.25 |
| ATOM | 4353 | O | PRO | A | 576 | 9.887 | 15.452 | −56.703 | 1.00 | 28.13 |
| ATOM | 4354 | N | ASN | A | 577 | 9.394 | 16.360 | −58.707 | 1.00 | 25.62 |
| ATOM | 4355 | CA | ASN | A | 577 | 8.612 | 17.449 | −58.129 | 1.00 | 24.83 |
| ATOM | 4356 | CB | ASN | A | 577 | 8.013 | 18.336 | −59.224 | 1.00 | 24.90 |
| ATOM | 4357 | CG | ASN | A | 577 | 9.055 | 19.184 | −59.913 | 1.00 | 25.61 |
| ATOM | 4358 | OD1 | ASN | A | 577 | 10.176 | 19.321 | −59.423 | 1.00 | 25.83 |
| ATOM | 4359 | ND2 | ASN | A | 577 | 8.693 | 19.756 | −61.060 | 1.00 | 25.07 |
| ATOM | 4360 | C | ASN | A | 577 | 7.466 | 16.868 | −57.322 | 1.00 | 24.22 |
| ATOM | 4361 | O | ASN | A | 577 | 6.949 | 15.798 | −57.672 | 1.00 | 23.69 |
| ATOM | 4362 | N | HIS | A | 578 | 7.057 | 17.562 | −56.259 | 1.00 | 23.20 |
| ATOM | 4363 | CA | HIS | A | 578 | 5.830 | 17.179 | −55.570 | 1.00 | 22.96 |
| ATOM | 4364 | CB | HIS | A | 578 | 5.734 | 17.844 | −54.200 | 1.00 | 22.09 |
| ATOM | 4365 | CG | HIS | A | 578 | 6.874 | 17.538 | −53.285 | 1.00 | 21.80 |
| ATOM | 4366 | ND1 | HIS | A | 578 | 6.809 | 16.558 | −52.318 | 1.00 | 21.62 |
| ATOM | 4367 | CE1 | HIS | A | 578 | 7.948 | 16.530 | −51.645 | 1.00 | 21.36 |
| ATOM | 4368 | NE2 | HIS | A | 578 | 8.743 | 17.465 | −52.133 | 1.00 | 20.16 |
| ATOM | 4369 | CD2 | HIS | A | 578 | 8.096 | 18.109 | −53.160 | 1.00 | 19.78 |
| ATOM | 4370 | C | HIS | A | 578 | 4.697 | 17.707 | −56.429 | 1.00 | 23.58 |
| ATOM | 4371 | O | HIS | A | 578 | 4.814 | 18.794 | −56.976 | 1.00 | 23.64 |
| ATOM | 4372 | N | THR | A | 579 | 3.603 | 16.955 | −56.534 | 1.00 | 23.98 |
| ATOM | 4373 | CA | THR | A | 579 | 2.426 | 17.448 | −57.254 | 1.00 | 25.34 |
| ATOM | 4374 | CB | THR | A | 579 | 2.092 | 16.568 | −58.477 | 1.00 | 26.08 |
| ATOM | 4375 | OG1 | THR | A | 579 | 3.162 | 16.672 | −59.429 | 1.00 | 29.14 |
| ATOM | 4376 | CG2 | THR | A | 579 | 0.749 | 16.979 | −59.126 | 1.00 | 26.14 |
| ATOM | 4377 | C | THR | A | 579 | 1.259 | 17.480 | −56.291 | 1.00 | 25.05 |
| ATOM | 4378 | O | THR | A | 579 | 0.977 | 16.487 | −55.629 | 1.00 | 25.73 |
| ATOM | 4379 | N | TYR | A | 580 | 0.591 | 18.619 | −56.213 | 1.00 | 25.23 |
| ATOM | 4380 | CA | TYR | A | 580 | −0.450 | 18.802 | −55.211 | 1.00 | 25.68 |
| ATOM | 4381 | CB | TYR | A | 580 | 0.098 | 19.556 | −53.976 | 1.00 | 25.88 |
| ATOM | 4382 | CG | TYR | A | 580 | −0.931 | 19.763 | −52.866 | 1.00 | 26.21 |
| ATOM | 4383 | CD1 | TYR | A | 580 | −1.284 | 21.048 | −52.429 | 1.00 | 26.22 |
| ATOM | 4384 | CE1 | TYR | A | 580 | −2.256 | 21.233 | −51.399 | 1.00 | 27.53 |
| ATOM | 4385 | CZ | TYR | A | 580 | −2.860 | 20.111 | −50.841 | 1.00 | 27.08 |
| ATOM | 4386 | OH | TYR | A | 580 | −3.806 | 20.207 | −49.844 | 1.00 | 27.88 |
| ATOM | 4387 | CE2 | TYR | A | 580 | −2.510 | 18.841 | −51.264 | 1.00 | 26.97 |
| ATOM | 4388 | CD2 | TYR | A | 580 | −1.562 | 18.671 | −52.276 | 1.00 | 26.29 |
| ATOM | 4389 | C | TYR | A | 580 | −1.634 | 19.523 | −55.828 | 1.00 | 25.65 |
| ATOM | 4390 | O | TYR | A | 580 | −1.490 | 20.596 | −56.403 | 1.00 | 25.29 |
| ATOM | 4391 | N | THR | A | 581 | −2.813 | 18.915 | −55.732 | 1.00 | 25.95 |
| ATOM | 4392 | CA | THR | A | 581 | −4.015 | 19.629 | −56.117 | 1.00 | 25.78 |
| ATOM | 4393 | CB | THR | A | 581 | −5.016 | 18.700 | −56.806 | 1.00 | 26.75 |
| ATOM | 4394 | OG1 | THR | A | 581 | −4.332 | 18.000 | −57.855 | 1.00 | 26.57 |
| ATOM | 4395 | CG2 | THR | A | 581 | −6.189 | 19.498 | −57.397 | 1.00 | 27.62 |
| ATOM | 4396 | C | THR | A | 581 | −4.627 | 20.285 | −54.874 | 1.00 | 25.36 |
| ATOM | 4397 | O | THR | A | 581 | −5.024 | 19.595 | −53.935 | 1.00 | 25.22 |
| ATOM | 4398 | N | VAL | A | 582 | −4.685 | 21.615 | −54.880 | 1.00 | 24.54 |

TABLE 15-continued

| | | | | | | | | | |
|---|---|---|---|---|---|---|---|---|---|
| ATOM | 4399 | CA  | VAL | A | 582 | −5.255  | 22.382 | −53.777 | 1.00 | 24.15 |
| ATOM | 4400 | CB  | VAL | A | 582 | −5.006  | 23.915 | −53.953 | 1.00 | 24.21 |
| ATOM | 4401 | CG1 | VAL | A | 582 | −5.472  | 24.700 | −52.744 | 1.00 | 23.87 |
| ATOM | 4402 | CG2 | VAL | A | 582 | −3.514  | 24.218 | −54.219 | 1.00 | 25.33 |
| ATOM | 4403 | C   | VAL | A | 582 | −6.759  | 22.063 | −53.706 | 1.00 | 24.32 |
| ATOM | 4404 | O   | VAL | A | 582 | −7.478  | 22.204 | −54.700 | 1.00 | 23.26 |
| ATOM | 4405 | N   | PRO | A | 583 | −7.236  | 21.587 | −52.546 | 1.00 | 24.10 |
| ATOM | 4406 | CA  | PRO | A | 583 | −8.665  | 21.230 | −52.476 | 1.00 | 24.34 |
| ATOM | 4407 | CB  | PRO | A | 583 | −8.865  | 20.763 | −51.022 | 1.00 | 24.33 |
| ATOM | 4408 | CG  | PRO | A | 583 | −7.516  | 20.538 | −50.468 | 1.00 | 25.16 |
| ATOM | 4409 | CD  | PRO | A | 583 | −6.508  | 21.310 | −51.294 | 1.00 | 24.72 |
| ATOM | 4410 | C   | PRO | A | 583 | −9.597  | 22.404 | −52.768 | 1.00 | 24.50 |
| ATOM | 4411 | O   | PRO | A | 583 | −9.262  | 23.558 | −52.487 | 1.00 | 23.93 |
| ATOM | 4412 | N   | ALA | A | 584 | −10.756 | 22.104 | −53.350 | 1.00 | 24.61 |
| ATOM | 4413 | CA  | ALA | A | 584 | −11.817 | 23.084 | −53.477 | 1.00 | 24.77 |
| ATOM | 4414 | CB  | ALA | A | 584 | −12.065 | 23.439 | −54.943 | 1.00 | 25.29 |
| ATOM | 4415 | C   | ALA | A | 584 | −13.036 | 22.434 | −52.847 | 1.00 | 24.94 |
| ATOM | 4416 | O   | ALA | A | 584 | −13.922 | 21.932 | −53.537 | 1.00 | 25.03 |
| ATOM | 4417 | N   | VAL | A | 585 | −13.052 | 22.406 | −51.517 | 1.00 | 24.24 |
| ATOM | 4418 | CA  | VAL | A | 585 | −14.075 | 21.673 | −50.776 | 1.00 | 23.75 |
| ATOM | 4419 | CB  | VAL | A | 585 | −13.465 | 20.452 | −50.029 | 1.00 | 24.50 |
| ATOM | 4420 | CG1 | VAL | A | 585 | −14.515 | 19.770 | −49.151 | 1.00 | 24.48 |
| ATOM | 4421 | CG2 | VAL | A | 585 | −12.863 | 19.447 | −51.026 | 1.00 | 25.32 |
| ATOM | 4422 | C   | VAL | A | 585 | −14.707 | 22.639 | −49.781 | 1.00 | 23.20 |
| ATOM | 4423 | O   | VAL | A | 585 | −13.999 | 23.347 | −49.065 | 1.00 | 22.13 |
| ATOM | 4424 | N   | ALA | A | 586 | −16.044 | 22.679 | −49.739 | 1.00 | 22.43 |
| ATOM | 4425 | CA  | ALA | A | 586 | −16.749 | 23.546 | −48.804 | 1.00 | 21.79 |
| ATOM | 4426 | CB  | ALA | A | 586 | −18.240 | 23.212 | −48.820 | 1.00 | 22.19 |
| ATOM | 4427 | C   | ALA | A | 586 | −16.160 | 23.324 | −47.389 | 1.00 | 21.57 |
| ATOM | 4428 | O   | ALA | A | 586 | −15.954 | 22.180 | −46.990 | 1.00 | 20.89 |
| ATOM | 4429 | N   | CYS | A | 587 | −15.872 | 24.414 | −46.679 | 1.00 | 21.59 |
| ATOM | 4430 | CA  | CYS | A | 587 | −15.388 | 24.379 | −45.268 | 1.00 | 21.68 |
| ATOM | 4431 | CB  | CYS | A | 587 | −16.131 | 23.323 | −44.441 | 1.00 | 22.08 |
| ATOM | 4432 | SG  | CYS | A | 587 | −17.952 | 23.374 | −44.507 | 1.00 | 23.60 |
| ATOM | 4433 | C   | CYS | A | 587 | −13.886 | 24.129 | −45.094 | 1.00 | 21.27 |
| ATOM | 4434 | O   | CYS | A | 587 | −13.386 | 24.225 | −43.980 | 1.00 | 21.08 |
| ATOM | 4435 | N   | VAL | A | 588 | −13.178 | 23.780 | −46.170 | 1.00 | 20.53 |
| ATOM | 4436 | CA  | VAL | A | 588 | −11.742 | 23.499 | −46.085 | 1.00 | 20.52 |
| ATOM | 4437 | CB  | VAL | A | 588 | −11.351 | 22.268 | −46.958 | 1.00 | 20.47 |
| ATOM | 4438 | CG1 | VAL | A | 588 | −9.846  | 21.959 | −46.844 | 1.00 | 20.87 |
| ATOM | 4439 | CG2 | VAL | A | 588 | −12.163 | 21.042 | −46.549 | 1.00 | 20.51 |
| ATOM | 4440 | C   | VAL | A | 588 | −10.949 | 24.731 | −46.504 | 1.00 | 20.59 |
| ATOM | 4441 | O   | VAL | A | 588 | −10.699 | 24.950 | −47.705 | 1.00 | 21.88 |
| ATOM | 4442 | N   | THR | A | 589 | −10.533 | 25.522 | −45.528 | 1.00 | 19.56 |
| ATOM | 4443 | CA  | THR | A | 589 | −9.903  | 26.807 | −45.795 | 1.00 | 19.48 |
| ATOM | 4444 | CB  | THR | A | 589 | −10.595 | 27.914 | −44.988 | 1.00 | 20.13 |
| ATOM | 4445 | OG1 | THR | A | 589 | −10.527 | 27.565 | −43.592 | 1.00 | 21.49 |
| ATOM | 4446 | CG2 | THR | A | 589 | −12.085 | 28.018 | −45.410 | 1.00 | 20.03 |
| ATOM | 4447 | C   | THR | A | 589 | −8.424  | 26.819 | −45.427 | 1.00 | 19.42 |
| ATOM | 4448 | O   | THR | A | 589 | −7.694  | 27.767 | −45.743 | 1.00 | 18.66 |
| ATOM | 4449 | N   | GLN | A | 590 | −7.995  | 25.772 | −44.734 | 1.00 | 19.62 |
| ATOM | 4450 | CA  | GLN | A | 590 | −6.606  | 25.629 | −44.317 | 1.00 | 20.20 |
| ATOM | 4451 | CB  | GLN | A | 590 | −6.359  | 26.261 | −42.939 | 1.00 | 21.06 |
| ATOM | 4452 | CG  | GLN | A | 590 | −4.950  | 25.956 | −42.410 | 1.00 | 27.00 |
| ATOM | 4453 | CD  | GLN | A | 590 | −4.184  | 27.189 | −41.989 | 1.00 | 33.74 |
| ATOM | 4454 | OE1 | GLN | A | 590 | −4.771  | 28.196 | −41.611 | 1.00 | 37.22 |
| ATOM | 4455 | NE2 | GLN | A | 590 | −2.855  | 27.118 | −42.066 | 1.00 | 36.77 |
| ATOM | 4456 | C   | GLN | A | 590 | −6.247  | 24.159 | −44.295 | 1.00 | 19.00 |
| ATOM | 4457 | O   | GLN | A | 590 | −7.004  | 23.335 | −43.771 | 1.00 | 18.70 |
| ATOM | 4458 | N   | VAL | A | 591 | −5.113  | 23.811 | −44.904 | 1.00 | 17.70 |
| ATOM | 4459 | CA  | VAL | A | 591 | −4.682  | 22.404 | −44.940 | 1.00 | 17.15 |
| ATOM | 4460 | CB  | VAL | A | 591 | −4.843  | 21.750 | −46.330 | 1.00 | 17.82 |
| ATOM | 4461 | CG1 | VAL | A | 591 | −6.316  | 21.701 | −46.744 | 1.00 | 18.11 |
| ATOM | 4462 | CG2 | VAL | A | 591 | −3.970  | 22.470 | −47.390 | 1.00 | 17.60 |
| ATOM | 4463 | C   | VAL | A | 591 | −3.213  | 22.360 | −44.551 | 1.00 | 17.42 |
| ATOM | 4464 | O   | VAL | A | 591 | −2.531  | 23.377 | −44.638 | 1.00 | 17.32 |
| ATOM | 4465 | N   | VAL | A | 592 | −2.731  | 21.206 | −44.090 | 1.00 | 17.26 |
| ATOM | 4466 | CA  | VAL | A | 592 | −1.291  | 21.092 | −43.887 | 1.00 | 17.03 |
| ATOM | 4467 | CB  | VAL | A | 592 | −0.762  | 21.198 | −42.365 | 1.00 | 18.70 |
| ATOM | 4468 | CG1 | VAL | A | 592 | 0.335   | 20.217 | −41.930 | 1.00 | 18.75 |
| ATOM | 4469 | CG2 | VAL | A | 592 | −1.810  | 21.731 | −41.315 | 1.00 | 15.36 |
| ATOM | 4470 | C   | VAL | A | 592 | −0.736  | 19.951 | −44.730 | 1.00 | 16.99 |
| ATOM | 4471 | O   | VAL | A | 592 | −1.318  | 18.862 | −44.828 | 1.00 | 16.23 |
| ATOM | 4472 | N   | LYS | A | 593 | 0.357   | 20.253 | −45.403 | 1.00 | 15.38 |
| ATOM | 4473 | CA  | LYS | A | 593 | 0.953   | 19.302 | −46.293 | 1.00 | 16.27 |
| ATOM | 4474 | CB  | LYS | A | 593 | 1.301   | 20.010 | −47.616 | 1.00 | 16.69 |
| ATOM | 4475 | CG  | LYS | A | 593 | 1.835   | 19.096 | −48.694 | 1.00 | 20.55 |
| ATOM | 4476 | CD  | LYS | A | 593 | 0.791   | 18.101 | −49.203 | 1.00 | 24.73 |
| ATOM | 4477 | CE  | LYS | A | 593 | 1.330   | 17.311 | −50.409 | 1.00 | 27.26 |
| ATOM | 4478 | NZ  | LYS | A | 593 | 2.395   | 16.299 | −50.074 | 1.00 | 28.37 |

TABLE 15-continued

| | | | | | | | | | |
|---|---|---|---|---|---|---|---|---|---|
| ATOM | 4479 | C | LYS | A | 593 | 2.209 | 18.783 | −45.588 | 1.00 | 16.01 |
| ATOM | 4480 | O | LYS | A | 593 | 3.175 | 19.525 | −45.427 | 1.00 | 15.12 |
| ATOM | 4481 | N | GLU | A | 594 | 2.195 | 17.519 | −45.175 | 1.00 | 15.82 |
| ATOM | 4482 | CA | GLU | A | 594 | 3.308 | 16.969 | −44.407 | 1.00 | 16.23 |
| ATOM | 4483 | CB | GLU | A | 594 | 2.798 | 16.017 | −43.317 | 1.00 | 16.26 |
| ATOM | 4484 | CG | GLU | A | 594 | 1.866 | 16.732 | −42.299 | 1.00 | 16.62 |
| ATOM | 4485 | CD | GLU | A | 594 | 1.727 | 15.949 | −40.991 | 1.00 | 18.94 |
| ATOM | 4486 | OE1 | GLU | A | 594 | 1.267 | 14.778 | −41.024 | 1.00 | 21.31 |
| ATOM | 4487 | OE2 | GLU | A | 594 | 2.107 | 16.507 | −39.940 | 1.00 | 16.43 |
| ATOM | 4488 | C | GLU | A | 594 | 4.286 | 16.245 | −45.323 | 1.00 | 17.34 |
| ATOM | 4489 | O | GLU | A | 594 | 3.973 | 15.177 | −45.852 | 1.00 | 17.78 |
| ATOM | 4490 | N | ASP | A | 595 | 5.463 | 16.833 | −45.487 | 1.00 | 17.05 |
| ATOM | 4491 | CA | ASP | A | 595 | 6.481 | 16.326 | −46.405 | 1.00 | 17.21 |
| ATOM | 4492 | CB | ASP | A | 595 | 6.823 | 17.379 | −47.475 | 1.00 | 16.63 |
| ATOM | 4493 | CG | ASP | A | 595 | 5.678 | 17.619 | −48.455 | 1.00 | 17.91 |
| ATOM | 4494 | OD1 | ASP | A | 595 | 5.023 | 16.631 | −48.857 | 1.00 | 20.73 |
| ATOM | 4495 | OD2 | ASP | A | 595 | 5.434 | 18.795 | −48.844 | 1.00 | 18.08 |
| ATOM | 4496 | C | ASP | A | 595 | 7.734 | 15.955 | −45.631 | 1.00 | 17.47 |
| ATOM | 4497 | O | ASP | A | 595 | 7.915 | 16.375 | −44.492 | 1.00 | 16.44 |
| ATOM | 4498 | N | THR | A | 596 | 8.598 | 15.162 | −46.277 | 1.00 | 18.11 |
| ATOM | 4499 | CA | THR | A | 596 | 9.917 | 14.835 | −45.747 | 1.00 | 18.85 |
| ATOM | 4500 | CB | THR | A | 596 | 9.991 | 13.390 | −45.188 | 1.00 | 19.58 |
| ATOM | 4501 | OG1 | THR | A | 596 | 9.057 | 13.248 | −44.116 | 1.00 | 20.97 |
| ATOM | 4502 | CG2 | THR | A | 596 | 11.385 | 13.124 | −44.598 | 1.00 | 20.94 |
| ATOM | 4503 | C | THR | A | 596 | 10.895 | 14.978 | −46.914 | 1.00 | 19.34 |
| ATOM | 4504 | O | THR | A | 596 | 10.588 | 14.531 | −48.024 | 1.00 | 19.05 |
| ATOM | 4505 | N | TRP | A | 597 | 12.050 | 15.581 | −46.631 | 1.00 | 20.24 |
| ATOM | 4506 | CA | TRP | A | 597 | 13.074 | 15.921 | −47.633 | 1.00 | 21.94 |
| ATOM | 4507 | CB | TRP | A | 597 | 14.325 | 16.453 | −46.940 | 1.00 | 22.34 |
| ATOM | 4508 | CG | TRP | A | 597 | 15.445 | 16.854 | −47.882 | 1.00 | 23.75 |
| ATOM | 4509 | CD1 | TRP | A | 597 | 16.509 | 16.079 | −48.275 | 1.00 | 25.08 |
| ATOM | 4510 | NE1 | TRP | A | 597 | 17.327 | 16.801 | −49.138 | 1.00 | 24.85 |
| ATOM | 4511 | CE2 | TRP | A | 597 | 16.802 | 18.059 | −49.300 | 1.00 | 25.25 |
| ATOM | 4512 | CD2 | TRP | A | 597 | 15.611 | 18.128 | −48.527 | 1.00 | 24.09 |
| ATOM | 4513 | CE3 | TRP | A | 597 | 14.875 | 19.325 | −48.519 | 1.00 | 24.91 |
| ATOM | 4514 | CZ3 | TRP | A | 597 | 15.334 | 20.401 | −49.262 | 1.00 | 23.38 |
| ATOM | 4515 | CH2 | TRP | A | 597 | 16.520 | 20.299 | −50.028 | 1.00 | 25.14 |
| ATOM | 4516 | CZ2 | TRP | A | 597 | 17.265 | 19.137 | −50.053 | 1.00 | 22.49 |
| ATOM | 4517 | C | TRP | A | 597 | 13.424 | 14.708 | −48.473 | 1.00 | 23.42 |
| ATOM | 4518 | O | TRP | A | 597 | 13.675 | 13.635 | −47.939 | 1.00 | 22.37 |
| ATOM | 4519 | N | GLN | A | 598 | 13.409 | 14.904 | −49.788 | 1.00 | 25.26 |
| ATOM | 4520 | CA | GLN | A | 598 | 13.698 | 13.850 | −50.755 | 1.00 | 27.05 |
| ATOM | 4521 | CB | GLN | A | 598 | 12.936 | 14.124 | −52.052 | 1.00 | 26.51 |
| ATOM | 4522 | CG | GLN | A | 598 | 11.418 | 13.948 | −51.895 | 1.00 | 26.10 |
| ATOM | 4523 | CD | GLN | A | 598 | 10.642 | 14.209 | −53.156 | 1.00 | 26.76 |
| ATOM | 4524 | OE1 | GLN | A | 598 | 11.194 | 14.620 | −54.175 | 1.00 | 27.68 |
| ATOM | 4525 | NE2 | GLN | A | 598 | 9.340 | 13.990 | −53.095 | 1.00 | 25.96 |
| ATOM | 4526 | C | GLN | A | 598 | 15.204 | 13.787 | −50.977 | 1.00 | 29.21 |
| ATOM | 4527 | O | GLN | A | 598 | 15.794 | 14.694 | −51.574 | 1.00 | 28.61 |
| ATOM | 4528 | N | SER | A | 599 | 15.818 | 12.722 | −50.453 | 1.00 | 32.41 |
| ATOM | 4529 | CA | SER | A | 599 | 17.273 | 12.530 | −50.498 | 1.00 | 35.70 |
| ATOM | 4530 | CB | SER | A | 599 | 17.747 | 11.698 | −49.302 | 1.00 | 35.61 |
| ATOM | 4531 | OG | SER | A | 599 | 17.374 | 12.296 | −48.072 | 1.00 | 39.62 |
| ATOM | 4532 | C | SER | A | 599 | 17.703 | 11.831 | −51.785 | 1.00 | 36.66 |
| ATOM | 4533 | O | SER | A | 599 | 16.916 | 11.145 | −52.433 | 1.00 | 37.44 |
| ATOM | 4534 | OXT | SER | A | 599 | 18.863 | 11.922 | −52.194 | 1.00 | 38.18 |
| ATOM | 4535 | C1 | MAN | A | 601 | −3.602 | −3.018 | −46.412 | 1.00 | 102.64 |
| ATOM | 4536 | C2 | MAN | A | 601 | −4.584 | −2.109 | −47.156 | 1.00 | 102.73 |
| ATOM | 4537 | O2 | MAN | A | 601 | −3.951 | −1.548 | −48.288 | 1.00 | 102.91 |
| ATOM | 4538 | C3 | MAN | A | 601 | −5.867 | −2.845 | −47.570 | 1.00 | 102.38 |
| ATOM | 4539 | O3 | MAN | A | 601 | −6.544 | −2.112 | −48.566 | 1.00 | 102.32 |
| ATOM | 4540 | C4 | MAN | A | 601 | −5.640 | −4.269 | −48.082 | 1.00 | 102.18 |
| ATOM | 4541 | O4 | MAN | A | 601 | −6.860 | −4.967 | −47.984 | 1.00 | 101.76 |
| ATOM | 4542 | C5 | MAN | A | 601 | −4.561 | −5.018 | −47.298 | 1.00 | 102.40 |
| ATOM | 4543 | C6 | MAN | A | 601 | −4.172 | −6.307 | −48.010 | 1.00 | 102.48 |
| ATOM | 4544 | O6 | MAN | A | 601 | −3.156 | −6.957 | −47.280 | 1.00 | 102.80 |
| ATOM | 4545 | O5 | MAN | A | 601 | −3.400 | −4.222 | −47.131 | 1.00 | 102.71 |
| ATOM | 4546 | C1 | MAN | A | 602 | −29.428 | −4.974 | −42.477 | 1.00 | 77.32 |
| ATOM | 4547 | C2 | MAN | A | 602 | −28.973 | −6.434 | −42.405 | 1.00 | 77.44 |
| ATOM | 4548 | O2 | MAN | A | 602 | −30.120 | −7.253 | −42.347 | 1.00 | 77.72 |
| ATOM | 4549 | C3 | MAN | A | 602 | −28.044 | −6.835 | −43.565 | 1.00 | 77.20 |
| ATOM | 4550 | O3 | MAN | A | 602 | −27.940 | −8.239 | −43.664 | 1.00 | 76.96 |
| ATOM | 4551 | C4 | MAN | A | 602 | −28.487 | −6.260 | −44.909 | 1.00 | 77.22 |
| ATOM | 4552 | O4 | MAN | A | 602 | −27.471 | −6.474 | −45.862 | 1.00 | 76.90 |
| ATOM | 4553 | C5 | MAN | A | 602 | −28.766 | −4.766 | −44.768 | 1.00 | 77.47 |
| ATOM | 4554 | C6 | MAN | A | 602 | −29.185 | −4.115 | −46.081 | 1.00 | 77.84 |
| ATOM | 4555 | O6 | MAN | A | 602 | −28.163 | −3.228 | −46.483 | 1.00 | 78.24 |
| ATOM | 4556 | O5 | MAN | A | 602 | −29.768 | −4.562 | −43.790 | 1.00 | 77.46 |
| ATOM | 4557 | C1 | MAN | A | 603 | −18.689 | 25.235 | −53.677 | 1.00 | 47.04 |
| ATOM | 4558 | C2 | MAN | A | 603 | −20.074 | 24.872 | −53.114 | 1.00 | 51.09 |

TABLE 15-continued

| | | | | | | | | | |
|---|---|---|---|---|---|---|---|---|---|
| ATOM | 4559 | O2 | MAN | A | 603 | −21.044 | 25.065 | −54.120 | 1.00 | 52.42 |
| ATOM | 4560 | C3 | MAN | A | 603 | −20.141 | 23.420 | −52.620 | 1.00 | 51.78 |
| ATOM | 4561 | O3 | MAN | A | 603 | −21.465 | 23.079 | −52.262 | 1.00 | 53.36 |
| ATOM | 4562 | C4 | MAN | A | 603 | −19.602 | 22.466 | −53.686 | 1.00 | 51.72 |
| ATOM | 4563 | O4 | MAN | A | 603 | −19.615 | 21.142 | −53.209 | 1.00 | 51.94 |
| ATOM | 4564 | C5 | MAN | A | 603 | −18.179 | 22.911 | −54.021 | 1.00 | 51.66 |
| ATOM | 4565 | C6 | MAN | A | 603 | −17.421 | 21.906 | −54.892 | 1.00 | 53.80 |
| ATOM | 4566 | O6 | MAN | A | 603 | −17.915 | 21.885 | −56.214 | 1.00 | 55.49 |
| ATOM | 4567 | O5 | MAN | A | 603 | −18.217 | 24.223 | −54.581 | 1.00 | 49.62 |
| ATOM | 4568 | C1 | MAN | A | 605 | −4.678 | 15.117 | −57.896 | 1.00 | 58.79 |
| ATOM | 4569 | C2 | MAN | A | 605 | −3.360 | 15.555 | −58.538 | 1.00 | 58.65 |
| ATOM | 4570 | O2 | MAN | A | 605 | −2.564 | 14.412 | −58.722 | 1.00 | 59.38 |
| ATOM | 4571 | C3 | MAN | A | 605 | −3.570 | 16.269 | −59.878 | 1.00 | 58.70 |
| ATOM | 4572 | O3 | MAN | A | 605 | −2.523 | 15.985 | −60.778 | 1.00 | 59.27 |
| ATOM | 4573 | C4 | MAN | A | 605 | −4.915 | 15.892 | −60.491 | 1.00 | 58.73 |
| ATOM | 4574 | O4 | MAN | A | 605 | −5.084 | 16.538 | −61.730 | 1.00 | 59.62 |
| ATOM | 4575 | C5 | MAN | A | 605 | −6.054 | 16.284 | −59.547 | 1.00 | 58.90 |
| ATOM | 4576 | C6 | MAN | A | 605 | −7.370 | 15.612 | −59.932 | 1.00 | 58.75 |
| ATOM | 4577 | O6 | MAN | A | 605 | −7.255 | 14.219 | −59.738 | 1.00 | 59.42 |
| ATOM | 4578 | O5 | MAN | A | 605 | −5.730 | 16.034 | −58.173 | 1.00 | 58.30 |
| ATOM | 4579 | C1 | MAN | A | 606 | −10.273 | 28.688 | −42.727 | 1.00 | 25.90 |
| ATOM | 4580 | C2 | MAN | A | 606 | −9.839 | 27.944 | −41.452 | 1.00 | 28.64 |
| ATOM | 4581 | O2 | MAN | A | 606 | −9.245 | 28.909 | −40.620 | 1.00 | 28.84 |
| ATOM | 4582 | C3 | MAN | A | 606 | −10.999 | 27.249 | −40.710 | 1.00 | 29.65 |
| ATOM | 4583 | O3 | MAN | A | 606 | −10.568 | 26.763 | −39.441 | 1.00 | 28.85 |
| ATOM | 4584 | C4 | MAN | A | 606 | −12.203 | 28.177 | −40.551 | 1.00 | 30.36 |
| ATOM | 4585 | O4 | MAN | A | 606 | −13.330 | 27.463 | −40.084 | 1.00 | 30.29 |
| ATOM | 4586 | C5 | MAN | A | 606 | −12.553 | 28.769 | −41.914 | 1.00 | 30.72 |
| ATOM | 4587 | C6 | MAN | A | 606 | −13.730 | 29.731 | −41.778 | 1.00 | 33.97 |
| ATOM | 4588 | O6 | MAN | A | 606 | −13.624 | 30.732 | −42.762 | 1.00 | 36.82 |
| ATOM | 4589 | O5 | MAN | A | 606 | −11.434 | 29.464 | −42.435 | 1.00 | 28.12 |
| ATOM | 4590 | C1 | MAN | A | 607 | −31.396 | 1.963 | −40.521 | 1.00 | 50.29 |
| ATOM | 4591 | C2 | MAN | A | 607 | −30.220 | 1.790 | −41.485 | 1.00 | 52.65 |
| ATOM | 4592 | O2 | MAN | A | 607 | −30.541 | 0.785 | −42.419 | 1.00 | 54.93 |
| ATOM | 4593 | C3 | MAN | A | 607 | −29.845 | 3.092 | −42.208 | 1.00 | 52.48 |
| ATOM | 4594 | O3 | MAN | A | 607 | −28.932 | 2.836 | −43.251 | 1.00 | 53.01 |
| ATOM | 4595 | C4 | MAN | A | 607 | −31.068 | 3.818 | −42.766 | 1.00 | 52.78 |
| ATOM | 4596 | O4 | MAN | A | 607 | −30.672 | 5.070 | −43.297 | 1.00 | 52.92 |
| ATOM | 4597 | C5 | MAN | A | 607 | −32.103 | 3.985 | −41.652 | 1.00 | 52.23 |
| ATOM | 4598 | C6 | MAN | A | 607 | −33.331 | 4.749 | −42.153 | 1.00 | 52.96 |
| ATOM | 4599 | O6 | MAN | A | 607 | −34.520 | 4.076 | −41.791 | 1.00 | 52.95 |
| ATOM | 4600 | O5 | MAN | A | 607 | −32.451 | 2.702 | −41.127 | 1.00 | 51.79 |
| ATOM | 4601 | C1 | MAN | A | 608 | 3.870 | 15.416 | −59.489 | 1.00 | 37.21 |
| ATOM | 4602 | C2 | MAN | A | 608 | 5.134 | 15.938 | −60.168 | 1.00 | 40.45 |
| ATOM | 4603 | O2 | MAN | A | 608 | 6.091 | 14.903 | −60.120 | 1.00 | 38.47 |
| ATOM | 4604 | C3 | MAN | A | 608 | 4.872 | 16.381 | −61.608 | 1.00 | 42.66 |
| ATOM | 4605 | O3 | MAN | A | 608 | 6.071 | 16.726 | −62.263 | 1.00 | 44.20 |
| ATOM | 4606 | C4 | MAN | A | 608 | 4.122 | 15.321 | −62.401 | 1.00 | 44.80 |
| ATOM | 4607 | O4 | MAN | A | 608 | 3.708 | 15.907 | −63.612 | 1.00 | 47.73 |
| ATOM | 4608 | C5 | MAN | A | 608 | 2.893 | 14.887 | −61.597 | 1.00 | 44.80 |
| ATOM | 4609 | C6 | MAN | A | 608 | 2.042 | 13.861 | −62.342 | 1.00 | 47.55 |
| ATOM | 4610 | O6 | MAN | A | 608 | 1.085 | 14.582 | −63.104 | 1.00 | 49.87 |
| ATOM | 4611 | O5 | MAN | A | 608 | 3.262 | 14.423 | −60.302 | 1.00 | 42.18 |
| ATOM | 4612 | C1 | NAG | A | 611 | 3.450 | −2.354 | −8.282 | 1.00 | 23.44 |
| ATOM | 4613 | C2 | NAG | A | 611 | 3.474 | −0.875 | −7.878 | 1.00 | 24.51 |
| ATOM | 4614 | N2 | NAG | A | 611 | 4.425 | −0.077 | −8.630 | 1.00 | 21.95 |
| ATOM | 4615 | C7 | NAG | A | 611 | 4.123 | 0.454 | −9.818 | 1.00 | 22.94 |
| ATOM | 4616 | O7 | NAG | A | 611 | 3.030 | 0.322 | −10.367 | 1.00 | 20.93 |
| ATOM | 4617 | C8 | NAG | A | 611 | 5.216 | 1.232 | −10.481 | 1.00 | 21.54 |
| ATOM | 4618 | C3 | NAG | A | 611 | 3.741 | −0.713 | −6.380 | 1.00 | 25.60 |
| ATOM | 4619 | O3 | NAG | A | 611 | 3.676 | 0.655 | −6.047 | 1.00 | 24.91 |
| ATOM | 4620 | C4 | NAG | A | 611 | 2.741 | −1.528 | −5.554 | 1.00 | 25.70 |
| ATOM | 4621 | O4 | NAG | A | 611 | 3.196 | −1.598 | −4.227 | 1.00 | 28.27 |
| ATOM | 4622 | C5 | NAG | A | 611 | 2.648 | −2.952 | −6.086 | 1.00 | 26.18 |
| ATOM | 4623 | C6 | NAG | A | 611 | 1.524 | −3.738 | −5.397 | 1.00 | 26.64 |
| ATOM | 4624 | O6 | NAG | A | 611 | 0.278 | −3.081 | −5.497 | 1.00 | 25.38 |
| ATOM | 4625 | O5 | NAG | A | 611 | 2.437 | −2.975 | −7.488 | 1.00 | 24.34 |
| ATOM | 4626 | C1 | NAG | A | 612 | 2.499 | −0.713 | −3.326 | 1.00 | 32.04 |
| ATOM | 4627 | C2 | NAG | A | 612 | 2.710 | −1.192 | −1.879 | 1.00 | 35.81 |
| ATOM | 4628 | N2 | NAG | A | 612 | 2.254 | −2.556 | −1.666 | 1.00 | 37.89 |
| ATOM | 4629 | C7 | NAG | A | 612 | 3.072 | −3.605 | −1.753 | 1.00 | 39.19 |
| ATOM | 4630 | O7 | NAG | A | 612 | 4.277 | −3.517 | −2.031 | 1.00 | 40.58 |
| ATOM | 4631 | C8 | NAG | A | 612 | 2.439 | −4.947 | −1.507 | 1.00 | 38.98 |
| ATOM | 4632 | C3 | NAG | A | 612 | 2.012 | −0.256 | −0.899 | 1.00 | 37.96 |
| ATOM | 4633 | O3 | NAG | A | 612 | 2.352 | −0.666 | 0.403 | 1.00 | 41.23 |
| ATOM | 4634 | C4 | NAG | A | 612 | 2.491 | 1.176 | −1.129 | 1.00 | 37.63 |
| ATOM | 4635 | O4 | NAG | A | 612 | 1.789 | 2.053 | −0.278 | 1.00 | 40.85 |
| ATOM | 4636 | C5 | NAG | A | 612 | 2.294 | 1.565 | −2.604 | 1.00 | 35.10 |
| ATOM | 4637 | C6 | NAG | A | 612 | 2.785 | 2.982 | −2.903 | 1.00 | 31.93 |
| ATOM | 4638 | O6 | NAG | A | 612 | 4.188 | 2.994 | −3.008 | 0.58 | 32.70 |

TABLE 15-continued

| | | | | | | | | | |
|---|---|---|---|---|---|---|---|---|---|
| ATOM | 4639 | O5 | NAG | A | 612 | 2.974 | 0.625 | −3.425 | 1.00 | 31.95 |
| ATOM | 4640 | O8 | BTB | A | 620 | −1.213 | 18.638 | −21.639 | 1.00 | 23.78 |
| ATOM | 4641 | C8 | BTB | A | 620 | −1.255 | 19.440 | −22.838 | 1.00 | 17.50 |
| ATOM | 4642 | C7 | BTB | A | 620 | −2.257 | 18.851 | −23.831 | 1.00 | 15.39 |
| ATOM | 4643 | N | BTB | A | 620 | −1.808 | 17.505 | −24.294 | 1.00 | 13.88 |
| ATOM | 4644 | C5 | BTB | A | 620 | −1.274 | 17.600 | −25.684 | 1.00 | 12.99 |
| ATOM | 4645 | C6 | BTB | A | 620 | 0.017 | 18.399 | −25.786 | 1.00 | 14.67 |
| ATOM | 4646 | O6 | BTB | A | 620 | 0.949 | 18.004 | −24.768 | 1.00 | 16.93 |
| ATOM | 4647 | C2 | BTB | A | 620 | −2.926 | 16.495 | −24.191 | 1.00 | 13.33 |
| ATOM | 4648 | C4 | BTB | A | 620 | −4.238 | 16.972 | −24.835 | 1.00 | 13.45 |
| ATOM | 4649 | O4 | BTB | A | 620 | −4.167 | 17.018 | −26.265 | 1.00 | 14.77 |
| ATOM | 4650 | C3 | BTB | A | 620 | −3.213 | 16.295 | −22.703 | 1.00 | 13.18 |
| ATOM | 4651 | O3 | BTB | A | 620 | −1.984 | 15.920 | −22.059 | 1.00 | 12.74 |
| ATOM | 4652 | C1 | BTB | A | 620 | −2.501 | 15.161 | −24.845 | 1.00 | 13.57 |
| ATOM | 4653 | O1 | BTB | A | 620 | −3.463 | 14.138 | −24.525 | 1.00 | 13.07 |
| ATOM | 4654 | O | WAT | W | 1 | −7.741 | 16.530 | −28.587 | 1.00 | 12.90 |
| ATOM | 4655 | O | WAT | W | 2 | −1.955 | 18.721 | −7.814 | 1.00 | 11.77 |
| ATOM | 4656 | O | WAT | W | 3 | −17.101 | 16.033 | −19.836 | 1.00 | 15.26 |
| ATOM | 4657 | O | WAT | W | 4 | −1.389 | 7.464 | −24.070 | 1.00 | 15.86 |
| ATOM | 4658 | O | WAT | W | 5 | −8.070 | 20.758 | −43.462 | 1.00 | 19.56 |
| ATOM | 4659 | O | WAT | W | 6 | −12.959 | 28.534 | −26.860 | 1.00 | 16.12 |
| ATOM | 4660 | O | WAT | W | 7 | −0.502 | 31.488 | −57.004 | 1.00 | 33.06 |
| ATOM | 4661 | O | WAT | W | 8 | 2.095 | 5.710 | −17.808 | 1.00 | 18.68 |
| ATOM | 4662 | O | WAT | W | 9 | −7.601 | 14.567 | −6.827 | 1.00 | 14.97 |
| ATOM | 4663 | O | WAT | W | 10 | 24.863 | 23.325 | −37.431 | 1.00 | 32.31 |
| ATOM | 4664 | O | WAT | W | 11 | −22.569 | 7.289 | −10.357 | 1.00 | 17.52 |
| ATOM | 4665 | O | WAT | W | 12 | −18.987 | 1.758 | −22.078 | 1.00 | 23.03 |
| ATOM | 4666 | O | WAT | W | 13 | −3.226 | 16.264 | −54.338 | 1.00 | 32.98 |
| ATOM | 4667 | O | WAT | W | 14 | 6.141 | 16.546 | −42.196 | 1.00 | 16.00 |
| ATOM | 4668 | O | WAT | W | 15 | −10.356 | 21.827 | −22.675 | 1.00 | 13.52 |
| ATOM | 4669 | O | WAT | W | 16 | −3.130 | 25.355 | −17.925 | 1.00 | 14.01 |
| ATOM | 4670 | O | WAT | W | 17 | −11.823 | 29.479 | −29.411 | 1.00 | 17.50 |
| ATOM | 4671 | O | WAT | W | 18 | −14.383 | 15.964 | −19.553 | 1.00 | 13.02 |
| ATOM | 4672 | O | WAT | W | 19 | −1.180 | 16.935 | −10.101 | 1.00 | 18.86 |
| ATOM | 4673 | O | WAT | W | 20 | −31.133 | 23.501 | 4.462 | 1.00 | 16.66 |
| ATOM | 4674 | O | WAT | W | 21 | −4.819 | 24.193 | −15.023 | 1.00 | 14.31 |
| ATOM | 4675 | O | WAT | W | 22 | 1.709 | 22.276 | −4.126 | 1.00 | 21.96 |
| ATOM | 4676 | O | WAT | W | 23 | −5.339 | 21.386 | −7.463 | 1.00 | 15.78 |
| ATOM | 4677 | O | WAT | W | 24 | −17.232 | 15.476 | 1.374 | 1.00 | 17.64 |
| ATOM | 4678 | O | WAT | W | 25 | −11.449 | 4.860 | −24.929 | 1.00 | 17.45 |
| ATOM | 4679 | O | WAT | W | 26 | −17.555 | 17.679 | −39.815 | 1.00 | 23.23 |
| ATOM | 4680 | O | WAT | W | 27 | 10.075 | 17.015 | −49.295 | 1.00 | 24.05 |
| ATOM | 4681 | O | WAT | W | 28 | −16.018 | −0.740 | −24.205 | 1.00 | 18.07 |
| ATOM | 4682 | O | WAT | W | 29 | 9.446 | 24.991 | −37.612 | 1.00 | 19.20 |
| ATOM | 4683 | O | WAT | W | 30 | −4.165 | 26.137 | −12.642 | 1.00 | 18.33 |
| ATOM | 4684 | O | WAT | W | 31 | 2.771 | 22.947 | −14.916 | 1.00 | 25.80 |
| ATOM | 4685 | O | WAT | W | 32 | −12.297 | 21.394 | −35.680 | 1.00 | 14.89 |
| ATOM | 4686 | O | WAT | W | 33 | −24.061 | 13.570 | 10.081 | 1.00 | 24.96 |
| ATOM | 4687 | O | WAT | W | 34 | 10.032 | 29.725 | −56.684 | 1.00 | 26.97 |
| ATOM | 4688 | O | WAT | W | 35 | 0.231 | 4.133 | −28.595 | 1.00 | 17.67 |
| ATOM | 4689 | O | WAT | W | 36 | 0.335 | 2.173 | −30.650 | 1.00 | 18.32 |
| ATOM | 4690 | O | WAT | W | 37 | −10.199 | 24.315 | −42.717 | 1.00 | 22.38 |
| ATOM | 4691 | O | WAT | W | 38 | −14.151 | 12.872 | −8.204 | 1.00 | 16.16 |
| ATOM | 4692 | O | WAT | W | 39 | −2.710 | 9.564 | −16.092 | 1.00 | 14.10 |
| ATOM | 4693 | O | WAT | W | 40 | 5.954 | 7.990 | −32.401 | 1.00 | 16.59 |
| ATOM | 4694 | O | WAT | W | 41 | 0.294 | 5.561 | −25.249 | 1.00 | 17.87 |
| ATOM | 4695 | O | WAT | W | 42 | 2.102 | 15.148 | −37.718 | 1.00 | 14.64 |
| ATOM | 4696 | O | WAT | W | 43 | −19.351 | 1.384 | −26.295 | 1.00 | 20.27 |
| ATOM | 4697 | O | WAT | W | 44 | −19.623 | 9.533 | −17.751 | 1.00 | 14.67 |
| ATOM | 4698 | O | WAT | W | 45 | 3.117 | 18.767 | −36.336 | 1.00 | 12.66 |
| ATOM | 4699 | O | WAT | W | 46 | −15.016 | 16.950 | 0.662 | 1.00 | 20.14 |
| ATOM | 4700 | O | WAT | W | 47 | −22.261 | 4.600 | −10.993 | 1.00 | 16.38 |
| ATOM | 4701 | O | WAT | W | 48 | −12.926 | 5.474 | −22.680 | 1.00 | 19.85 |
| ATOM | 4702 | O | WAT | W | 49 | 5.564 | 17.071 | −37.018 | 1.00 | 16.82 |
| ATOM | 4703 | O | WAT | W | 50 | −19.848 | 20.552 | −2.718 | 1.00 | 19.38 |
| ATOM | 4704 | O | WAT | W | 51 | −15.859 | 17.744 | −41.901 | 1.00 | 19.69 |
| ATOM | 4705 | O | WAT | W | 52 | −16.430 | 25.522 | −1.123 | 1.00 | 19.97 |
| ATOM | 4706 | O | WAT | W | 53 | −15.978 | 5.366 | −12.193 | 1.00 | 26.02 |
| ATOM | 4707 | O | WAT | W | 54 | −1.637 | 9.365 | −26.035 | 1.00 | 14.42 |
| ATOM | 4708 | O | WAT | W | 55 | −10.759 | 27.212 | −30.898 | 1.00 | 17.28 |
| ATOM | 4709 | O | WAT | W | 56 | −11.509 | 0.756 | −13.101 | 1.00 | 20.70 |
| ATOM | 4710 | O | WAT | W | 57 | −16.950 | 15.108 | 4.727 | 1.00 | 23.86 |
| ATOM | 4711 | O | WAT | W | 58 | −25.368 | 26.009 | −7.106 | 1.00 | 25.08 |
| ATOM | 4712 | O | WAT | W | 59 | −16.870 | 22.937 | −3.651 | 1.00 | 17.56 |
| ATOM | 4713 | O | WAT | W | 60 | −14.388 | 13.258 | −40.897 | 1.00 | 27.90 |
| ATOM | 4714 | O | WAT | W | 61 | −1.509 | −4.779 | −6.723 | 1.00 | 31.01 |
| ATOM | 4715 | O | WAT | W | 62 | −1.973 | 27.723 | −11.521 | 1.00 | 21.99 |
| ATOM | 4716 | O | WAT | W | 63 | −1.159 | −10.623 | −29.592 | 1.00 | 36.68 |
| ATOM | 4717 | O | WAT | W | 64 | −1.943 | 16.930 | −42.957 | 1.00 | 21.57 |
| ATOM | 4718 | O | WAT | W | 65 | −1.507 | 25.238 | −40.032 | 1.00 | 31.36 |

TABLE 15-continued

| | | | | | | | | | |
|---|---|---|---|---|---|---|---|---|---|
| ATOM | 4719 | O | WAT | W | 66 | −4.023 | 5.499 | −31.787 | 1.00 | 20.03 |
| ATOM | 4720 | O | WAT | W | 67 | −13.383 | 13.873 | −21.065 | 1.00 | 12.01 |
| ATOM | 4721 | O | WAT | W | 68 | −15.098 | 10.726 | −24.467 | 1.00 | 24.34 |
| ATOM | 4722 | O | WAT | W | 69 | −2.122 | 13.975 | −13.435 | 1.00 | 12.51 |
| ATOM | 4723 | O | WAT | W | 70 | −4.807 | 19.360 | −43.270 | 1.00 | 20.93 |
| ATOM | 4724 | O | WAT | W | 71 | −26.028 | 26.143 | −33.768 | 1.00 | 28.78 |
| ATOM | 4725 | O | WAT | W | 72 | −19.347 | 21.638 | 3.482 | 1.00 | 19.92 |
| ATOM | 4726 | O | WAT | W | 73 | −27.299 | 24.219 | −6.045 | 1.00 | 20.97 |
| ATOM | 4727 | O | WAT | W | 74 | −21.114 | −0.343 | −28.050 | 1.00 | 22.38 |
| ATOM | 4728 | O | WAT | W | 75 | −5.818 | 34.483 | −11.645 | 1.00 | 20.61 |
| ATOM | 4729 | O | WAT | W | 76 | 6.048 | 1.098 | −23.393 | 1.00 | 16.77 |
| ATOM | 4730 | O | WAT | W | 77 | −3.946 | 23.711 | −39.552 | 1.00 | 25.07 |
| ATOM | 4731 | O | WAT | W | 78 | −18.572 | 21.631 | −41.884 | 1.00 | 25.98 |
| ATOM | 4732 | O | WAT | W | 79 | 5.239 | 26.273 | −31.646 | 1.00 | 27.95 |
| ATOM | 4733 | O | WAT | W | 80 | 0.054 | 15.597 | −45.905 | 1.00 | 28.45 |
| ATOM | 4734 | O | WAT | W | 81 | −3.130 | 21.534 | −5.652 | 1.00 | 20.95 |
| ATOM | 4735 | O | WAT | W | 82 | −12.534 | 4.331 | −20.095 | 1.00 | 17.49 |
| ATOM | 4736 | O | WAT | W | 83 | 0.785 | 16.541 | −14.558 | 1.00 | 14.65 |
| ATOM | 4737 | O | WAT | W | 84 | −5.197 | 12.827 | −31.553 | 1.00 | 14.10 |
| ATOM | 4738 | O | WAT | W | 85 | −16.738 | 26.994 | −34.463 | 1.00 | 23.74 |
| ATOM | 4739 | O | WAT | W | 86 | 3.596 | 22.076 | −36.828 | 1.00 | 22.68 |
| ATOM | 4740 | O | WAT | W | 87 | 5.170 | 14.460 | −40.572 | 1.00 | 26.56 |
| ATOM | 4741 | O | WAT | W | 88 | −12.322 | 21.050 | 0.328 | 1.00 | 30.36 |
| ATOM | 4742 | O | WAT | W | 89 | 7.426 | 14.327 | −48.857 | 1.00 | 26.44 |
| ATOM | 4743 | O | WAT | W | 90 | −13.702 | 19.025 | 1.863 | 1.00 | 28.28 |
| ATOM | 4744 | O | WAT | W | 91 | 8.794 | 2.010 | −23.444 | 1.00 | 34.69 |
| ATOM | 4745 | O | WAT | W | 92 | −6.185 | 5.529 | −30.210 | 1.00 | 17.03 |
| ATOM | 4746 | O | WAT | W | 93 | −18.081 | 20.709 | −4.839 | 1.00 | 17.61 |
| ATOM | 4747 | O | WAT | W | 94 | −15.469 | 13.082 | −22.717 | 1.00 | 15.55 |
| ATOM | 4748 | O | WAT | W | 95 | 13.101 | 16.811 | −29.771 | 1.00 | 29.16 |
| ATOM | 4749 | O | WAT | W | 96 | −25.944 | 7.031 | −2.628 | 1.00 | 27.42 |
| ATOM | 4750 | O | WAT | W | 97 | −4.552 | 34.207 | −7.388 | 1.00 | 22.19 |
| ATOM | 4751 | O | WAT | W | 98 | −2.231 | −9.858 | −32.291 | 1.00 | 26.28 |
| ATOM | 4752 | O | WAT | W | 99 | 5.314 | 10.271 | −28.762 | 1.00 | 29.39 |
| ATOM | 4753 | O | WAT | W | 100 | −15.379 | 27.478 | −46.620 | 1.00 | 37.77 |
| ATOM | 4754 | O | WAT | W | 101 | 26.815 | 24.874 | −36.295 | 1.00 | 31.11 |
| ATOM | 4755 | O | WAT | W | 102 | −18.489 | −0.112 | −24.256 | 1.00 | 23.63 |
| ATOM | 4756 | O | WAT | W | 103 | −23.763 | 26.890 | −9.454 | 1.00 | 20.50 |
| ATOM | 4757 | O | WAT | W | 104 | −10.933 | 23.904 | −50.315 | 1.00 | 25.63 |
| ATOM | 4758 | O | WAT | W | 105 | 5.864 | 12.071 | −41.668 | 1.00 | 29.27 |
| ATOM | 4759 | O | WAT | W | 106 | 2.526 | 9.409 | −13.116 | 1.00 | 20.75 |
| ATOM | 4760 | O | WAT | W | 107 | −11.557 | −6.653 | −10.981 | 1.00 | 30.68 |
| ATOM | 4761 | O | WAT | W | 108 | −14.882 | 7.238 | −22.254 | 1.00 | 24.81 |
| ATOM | 4762 | O | WAT | W | 109 | −5.331 | −13.390 | −25.293 | 1.00 | 35.63 |
| ATOM | 4763 | O | WAT | W | 110 | −8.068 | 24.248 | −40.534 | 1.00 | 39.14 |
| ATOM | 4764 | O | WAT | W | 111 | −0.779 | 14.419 | −43.060 | 1.00 | 24.01 |
| ATOM | 4765 | O | WAT | W | 112 | −22.279 | 12.054 | −26.750 | 1.00 | 32.13 |
| ATOM | 4766 | O | WAT | W | 113 | −26.829 | 1.352 | −33.787 | 1.00 | 26.97 |
| ATOM | 4767 | O | WAT | W | 114 | −14.120 | 14.116 | 3.214 | 1.00 | 36.89 |
| ATOM | 4768 | O | WAT | W | 115 | 0.582 | −9.914 | −21.103 | 1.00 | 23.30 |
| ATOM | 4769 | O | WAT | W | 116 | −24.305 | 22.723 | 6.995 | 1.00 | 21.67 |
| ATOM | 4770 | O | WAT | W | 117 | −28.275 | 12.468 | −15.419 | 1.00 | 21.87 |
| ATOM | 4771 | O | WAT | W | 118 | 3.699 | 27.669 | −20.781 | 1.00 | 34.08 |
| ATOM | 4772 | O | WAT | W | 119 | −30.428 | 26.452 | 3.757 | 1.00 | 24.51 |
| ATOM | 4773 | O | WAT | W | 120 | 19.168 | 26.858 | −59.022 | 1.00 | 33.45 |
| ATOM | 4774 | O | WAT | W | 121 | −8.803 | 21.729 | −1.693 | 1.00 | 18.30 |
| ATOM | 4775 | O | WAT | W | 122 | 2.863 | 1.621 | −31.755 | 1.00 | 19.96 |
| ATOM | 4776 | O | WAT | W | 123 | −2.357 | 28.930 | −56.725 | 1.00 | 35.51 |
| ATOM | 4777 | O | WAT | W | 124 | −16.780 | 5.504 | −21.523 | 1.00 | 31.34 |
| ATOM | 4778 | O | WAT | W | 125 | 6.216 | 18.141 | −30.592 | 1.00 | 20.87 |
| ATOM | 4779 | O | WAT | W | 126 | 11.789 | 32.722 | −38.773 | 1.00 | 40.41 |
| ATOM | 4780 | O | WAT | W | 127 | −5.001 | 7.195 | −45.656 | 1.00 | 35.03 |
| ATOM | 4781 | O | WAT | W | 128 | −18.743 | 1.608 | −1.861 | 1.00 | 32.49 |
| ATOM | 4782 | O | WAT | W | 129 | −25.089 | −1.945 | −20.935 | 1.00 | 35.17 |
| ATOM | 4783 | O | WAT | W | 130 | −7.097 | −2.177 | −28.928 | 1.00 | 30.93 |
| ATOM | 4784 | O | WAT | W | 131 | −12.591 | 2.907 | −11.929 | 1.00 | 18.60 |
| ATOM | 4785 | O | WAT | W | 132 | −17.913 | −2.374 | −39.429 | 1.00 | 29.36 |
| ATOM | 4786 | O | WAT | W | 133 | −6.507 | −7.038 | −37.710 | 1.00 | 37.27 |
| ATOM | 4787 | O | WAT | W | 134 | −0.628 | 7.596 | −18.660 | 1.00 | 20.01 |
| ATOM | 4788 | O | WAT | W | 135 | −11.683 | 28.527 | −37.016 | 1.00 | 36.45 |
| ATOM | 4789 | O | WAT | W | 136 | −3.169 | 33.267 | −18.049 | 1.00 | 24.89 |
| ATOM | 4790 | O | WAT | W | 137 | −16.742 | 8.938 | −23.161 | 1.00 | 26.79 |
| ATOM | 4791 | O | WAT | W | 138 | −28.456 | 17.726 | −22.449 | 1.00 | 32.61 |
| ATOM | 4792 | O | WAT | W | 139 | 25.559 | 27.237 | −45.392 | 1.00 | 43.21 |
| ATOM | 4793 | O | WAT | W | 140 | −26.925 | 5.789 | −41.722 | 1.00 | 26.97 |
| ATOM | 4794 | O | WAT | W | 141 | −16.907 | 20.013 | −43.283 | 1.00 | 29.68 |
| ATOM | 4795 | O | WAT | W | 142 | −20.029 | 5.119 | −1.799 | 1.00 | 24.76 |
| ATOM | 4796 | O | WAT | W | 143 | 8.706 | 1.050 | −13.115 | 1.00 | 32.81 |
| ATOM | 4797 | O | WAT | W | 144 | −4.353 | 22.506 | −1.252 | 1.00 | 24.86 |
| ATOM | 4798 | O | WAT | W | 145 | −29.660 | 14.750 | −15.295 | 1.00 | 32.62 |

TABLE 15-continued

| | | | | | | | | | |
|---|---|---|---|---|---|---|---|---|---|
| ATOM | 4799 | O | WAT | W | 146 | 2.173 | 2.240 | −12.124 | 1.00 | 26.38 |
| ATOM | 4800 | O | WAT | W | 147 | 4.174 | −4.659 | −14.794 | 1.00 | 25.20 |
| ATOM | 4801 | O | WAT | W | 148 | −10.913 | 29.083 | −33.130 | 1.00 | 27.78 |
| ATOM | 4802 | O | WAT | W | 149 | −21.448 | 30.157 | −10.670 | 1.00 | 25.07 |
| ATOM | 4803 | O | WAT | W | 150 | −23.296 | 18.641 | −36.646 | 1.00 | 27.11 |
| ATOM | 4804 | O | WAT | W | 151 | −19.426 | 8.262 | −24.240 | 1.00 | 25.11 |
| ATOM | 4805 | O | WAT | W | 152 | 4.729 | −0.512 | −31.679 | 1.00 | 23.50 |
| ATOM | 4806 | O | WAT | W | 153 | 9.247 | 19.703 | −33.306 | 1.00 | 23.44 |
| ATOM | 4807 | O | WAT | W | 154 | 6.024 | 15.401 | −22.768 | 1.00 | 27.11 |
| ATOM | 4808 | O | WAT | W | 155 | −16.077 | 30.180 | −4.530 | 1.00 | 23.52 |
| ATOM | 4809 | O | WAT | W | 156 | −0.038 | 14.751 | −8.812 | 1.00 | 25.64 |
| ATOM | 4810 | O | WAT | W | 157 | 2.962 | 18.631 | −29.190 | 1.00 | 18.13 |
| ATOM | 4811 | O | WAT | W | 158 | 8.793 | 12.371 | −36.745 | 1.00 | 23.77 |
| ATOM | 4812 | O | WAT | W | 159 | −22.406 | 9.468 | −0.415 | 1.00 | 21.66 |
| ATOM | 4813 | O | WAT | W | 160 | −10.961 | 33.685 | −7.076 | 1.00 | 25.30 |
| ATOM | 4814 | O | WAT | W | 161 | −8.504 | 27.891 | −3.964 | 1.00 | 33.88 |
| ATOM | 4815 | O | WAT | W | 162 | 6.836 | 20.663 | −32.439 | 1.00 | 24.97 |
| ATOM | 4816 | O | WAT | W | 163 | 4.292 | 23.232 | −29.206 | 1.00 | 32.74 |
| ATOM | 4817 | O | WAT | W | 164 | 2.350 | 3.656 | −15.645 | 1.00 | 23.29 |
| ATOM | 4818 | O | WAT | W | 165 | −17.377 | 10.190 | −20.605 | 1.00 | 25.21 |
| ATOM | 4819 | O | WAT | W | 166 | −23.426 | 24.714 | 4.551 | 1.00 | 26.12 |
| ATOM | 4820 | O | WAT | W | 167 | 0.338 | 1.730 | −14.995 | 1.00 | 31.29 |
| ATOM | 4821 | O | WAT | W | 168 | −3.303 | 17.836 | −46.350 | 1.00 | 28.34 |
| ATOM | 4822 | O | WAT | W | 169 | 1.465 | 6.514 | −14.840 | 1.00 | 22.81 |
| ATOM | 4823 | O | WAT | W | 170 | 2.409 | 11.466 | −4.481 | 1.00 | 29.82 |
| ATOM | 4824 | O | WAT | W | 171 | 0.998 | 19.313 | −20.348 | 1.00 | 31.57 |
| ATOM | 4825 | O | WAT | W | 172 | 7.556 | −3.076 | −34.213 | 1.00 | 31.62 |
| ATOM | 4826 | O | WAT | W | 173 | −25.163 | 1.132 | −18.852 | 1.00 | 33.45 |
| ATOM | 4827 | O | WAT | W | 174 | −25.606 | 17.471 | −26.509 | 1.00 | 27.89 |
| ATOM | 4828 | O | WAT | W | 175 | 5.952 | 32.621 | −65.955 | 1.00 | 42.20 |
| ATOM | 4829 | O | WAT | W | 176 | −27.397 | 26.421 | −12.489 | 1.00 | 29.06 |
| ATOM | 4830 | O | WAT | W | 177 | −17.506 | 35.918 | −29.284 | 1.00 | 36.40 |
| ATOM | 4831 | O | WAT | W | 178 | −18.298 | 7.055 | −19.628 | 1.00 | 30.04 |
| ATOM | 4832 | O | WAT | W | 179 | −24.383 | 14.811 | −26.605 | 1.00 | 29.51 |
| ATOM | 4833 | O | WAT | W | 180 | −1.204 | 27.462 | −35.328 | 1.00 | 29.93 |
| ATOM | 4834 | O | WAT | W | 181 | −14.112 | 33.822 | −23.916 | 1.00 | 34.66 |
| ATOM | 4835 | O | WAT | W | 182 | 2.887 | 26.714 | −9.619 | 1.00 | 34.18 |
| ATOM | 4836 | O | WAT | W | 183 | −16.062 | 4.698 | 1.046 | 1.00 | 32.44 |
| ATOM | 4837 | O | WAT | W | 184 | −13.340 | 36.111 | −4.359 | 1.00 | 39.14 |
| ATOM | 4838 | O | WAT | W | 185 | 9.661 | 34.457 | −47.977 | 1.00 | 37.66 |
| ATOM | 4839 | O | WAT | W | 186 | −8.465 | 24.284 | −1.237 | 1.00 | 33.71 |
| ATOM | 4840 | O | WAT | W | 187 | 16.971 | 15.520 | −43.951 | 1.00 | 42.49 |
| ATOM | 4841 | O | WAT | W | 188 | −12.038 | −14.614 | −20.299 | 1.00 | 34.37 |
| ATOM | 4842 | O | WAT | W | 189 | −5.887 | 22.387 | −40.784 | 1.00 | 33.70 |
| ATOM | 4843 | O | WAT | W | 190 | −3.962 | −18.100 | −17.720 | 1.00 | 31.33 |
| ATOM | 4844 | O | WAT | W | 191 | −30.888 | 11.643 | −15.288 | 1.00 | 36.84 |
| ATOM | 4845 | O | WAT | W | 192 | 11.576 | 13.142 | −37.752 | 1.00 | 32.89 |
| ATOM | 4846 | O | WAT | W | 193 | −7.856 | 3.348 | −41.927 | 1.00 | 34.02 |
| ATOM | 4847 | O | WAT | W | 194 | −20.849 | 7.518 | 7.652 | 1.00 | 32.37 |
| ATOM | 4848 | O | WAT | W | 195 | 16.954 | 13.938 | −58.514 | 1.00 | 42.65 |
| ATOM | 4849 | O | WAT | W | 196 | −31.884 | 7.593 | −13.893 | 1.00 | 37.54 |
| ATOM | 4850 | O | WAT | W | 197 | 4.560 | −14.190 | −17.137 | 1.00 | 36.09 |
| ATOM | 4851 | O | WAT | W | 198 | 1.116 | 27.617 | −39.051 | 1.00 | 37.08 |
| ATOM | 4852 | O | WAT | W | 199 | −1.019 | −12.134 | −21.800 | 1.00 | 36.12 |
| ATOM | 4853 | O | WAT | W | 200 | 8.350 | 0.111 | −21.198 | 1.00 | 36.56 |
| ATOM | 4854 | O | WAT | W | 201 | −2.691 | 31.235 | −26.910 | 1.00 | 32.08 |
| ATOM | 4855 | O | WAT | W | 202 | 13.222 | 30.530 | −38.626 | 1.00 | 36.46 |
| ATOM | 4856 | O | WAT | W | 203 | −11.218 | 19.535 | −54.549 | 1.00 | 35.12 |
| ATOM | 4857 | O | WAT | W | 204 | −5.623 | 10.865 | −46.910 | 1.00 | 35.48 |
| ATOM | 4858 | O | WAT | W | 205 | −18.073 | 1.743 | −43.946 | 1.00 | 40.62 |
| ATOM | 4859 | O | WAT | W | 206 | −32.195 | 23.231 | 2.102 | 1.00 | 34.73 |
| ATOM | 4860 | O | WAT | W | 207 | −24.204 | 8.994 | −2.941 | 1.00 | 30.29 |
| ATOM | 4861 | O | WAT | W | 208 | −4.771 | 18.292 | −48.610 | 1.00 | 31.87 |
| ATOM | 4862 | O | WAT | W | 209 | −17.156 | 23.843 | −40.674 | 1.00 | 35.73 |
| ATOM | 4863 | O | WAT | W | 210 | 8.319 | 13.422 | −13.297 | 1.00 | 37.43 |
| ATOM | 4864 | O | WAT | W | 211 | −25.962 | 8.559 | −33.791 | 1.00 | 33.46 |
| ATOM | 4865 | O | WAT | W | 212 | −36.129 | 8.276 | 3.147 | 1.00 | 40.24 |
| ATOM | 4866 | O | WAT | W | 213 | 20.833 | 21.074 | −56.185 | 1.00 | 39.11 |
| ATOM | 4867 | O | WAT | W | 214 | −17.726 | 14.087 | 8.330 | 1.00 | 39.10 |
| ATOM | 4868 | O | WAT | W | 215 | 8.944 | 8.011 | −10.493 | 1.00 | 41.24 |
| ATOM | 4869 | O | WAT | W | 216 | −16.566 | 35.858 | −11.282 | 1.00 | 38.90 |
| ATOM | 4870 | O | WAT | W | 217 | −20.560 | 11.198 | −43.128 | 1.00 | 34.83 |
| ATOM | 4871 | O | WAT | W | 218 | 3.261 | −0.833 | −39.177 | 1.00 | 32.67 |
| ATOM | 4872 | O | WAT | W | 219 | −22.370 | −13.152 | −34.412 | 1.00 | 59.42 |
| ATOM | 4873 | O | WAT | W | 220 | −24.775 | 6.925 | 5.968 | 1.00 | 34.28 |
| ATOM | 4874 | O | WAT | W | 221 | −20.357 | 21.098 | −45.702 | 1.00 | 36.83 |
| ATOM | 4875 | O | WAT | W | 222 | 2.502 | 28.932 | −40.686 | 1.00 | 36.85 |
| ATOM | 4876 | O | WAT | W | 223 | −17.630 | −5.533 | −21.334 | 1.00 | 35.08 |
| ATOM | 4877 | O | WAT | W | 224 | −19.358 | −1.912 | −43.190 | 1.00 | 35.83 |
| ATOM | 4878 | O | WAT | W | 225 | −14.632 | 25.995 | −42.094 | 1.00 | 41.12 |

TABLE 15-continued

| | | | | | | | | | |
|---|---|---|---|---|---|---|---|---|---|
| ATOM | 4879 | O | WAT | W | 226 | −28.967 | 5.606 | −22.103 | 1.00 | 45.63 |
| ATOM | 4880 | O | WAT | W | 227 | −4.326 | 9.934 | 5.097 | 1.00 | 44.46 |
| ATOM | 4881 | O | WAT | W | 228 | 3.983 | 22.711 | −17.336 | 1.00 | 46.21 |
| ATOM | 4882 | O | WAT | W | 229 | −17.238 | 16.931 | 6.949 | 1.00 | 42.44 |
| ATOM | 4883 | O | WAT | W | 230 | −25.871 | 18.809 | 10.364 | 1.00 | 36.15 |
| ATOM | 4884 | O | WAT | W | 231 | −23.524 | 31.294 | −19.082 | 1.00 | 35.99 |
| ATOM | 4885 | O | WAT | W | 232 | −5.261 | −9.321 | −38.277 | 1.00 | 43.42 |
| ATOM | 4886 | O | WAT | W | 233 | −22.757 | 28.188 | −29.173 | 1.00 | 39.56 |
| ATOM | 4887 | O | WAT | W | 234 | −25.699 | 26.238 | −0.299 | 1.00 | 40.26 |
| ATOM | 4888 | O | WAT | W | 235 | −21.884 | −4.007 | −22.294 | 1.00 | 38.01 |
| ATOM | 4889 | O | WAT | W | 236 | −6.696 | −17.346 | −27.753 | 1.00 | 39.83 |
| ATOM | 4890 | O | WAT | W | 237 | −18.052 | 5.515 | 3.888 | 1.00 | 37.82 |
| ATOM | 4891 | O | WAT | W | 238 | −6.073 | 35.708 | −9.057 | 1.00 | 36.25 |
| ATOM | 4892 | O | WAT | W | 239 | −8.876 | 2.984 | −44.368 | 1.00 | 45.85 |
| ATOM | 4893 | O | WAT | W | 240 | 9.232 | 31.613 | −65.496 | 1.00 | 45.82 |
| ATOM | 4894 | O | WAT | W | 241 | −28.246 | 26.806 | −0.118 | 1.00 | 36.45 |
| ATOM | 4895 | O | WAT | W | 242 | −27.793 | 14.675 | −45.312 | 1.00 | 52.10 |
| ATOM | 4896 | O | WAT | W | 243 | 7.463 | 14.079 | −55.045 | 1.00 | 36.97 |
| ATOM | 4897 | O | WAT | W | 244 | −28.572 | 4.769 | −1.130 | 1.00 | 36.20 |
| ATOM | 4898 | O | WAT | W | 245 | 8.221 | 12.936 | −50.870 | 1.00 | 38.81 |
| ATOM | 4899 | O | WAT | W | 246 | −23.302 | −2.082 | −27.191 | 1.00 | 32.98 |
| ATOM | 4900 | O | WAT | W | 247 | −13.035 | 8.248 | −46.620 | 1.00 | 51.73 |
| ATOM | 4901 | O | WAT | W | 248 | −11.869 | 31.852 | −50.157 | 1.00 | 56.13 |
| ATOM | 4902 | O | WAT | W | 249 | 0.898 | 13.920 | −6.521 | 1.00 | 27.38 |
| ATOM | 4903 | O | WAT | W | 250 | 20.427 | 30.852 | −45.446 | 1.00 | 35.54 |
| ATOM | 4904 | O | WAT | W | 251 | −1.397 | 12.400 | −44.617 | 1.00 | 39.33 |
| ATOM | 4905 | O | WAT | W | 252 | −27.354 | 24.696 | −3.162 | 1.00 | 35.38 |
| ATOM | 4906 | O | WAT | W | 253 | 17.587 | 20.557 | −31.069 | 1.00 | 41.51 |
| ATOM | 4907 | O | WAT | W | 254 | −7.936 | 35.055 | −7.354 | 1.00 | 39.02 |
| ATOM | 4908 | O | WAT | W | 255 | −22.469 | 7.215 | −2.044 | 1.00 | 38.25 |
| ATOM | 4909 | O | WAT | W | 256 | 2.038 | 15.474 | −52.963 | 1.00 | 50.04 |
| ATOM | 4910 | O | WAT | W | 257 | 10.889 | 10.184 | −21.700 | 1.00 | 44.84 |
| ATOM | 4911 | O | WAT | W | 258 | −11.714 | 10.583 | 4.136 | 1.00 | 42.70 |
| ATOM | 4912 | O | WAT | W | 259 | −14.719 | 6.574 | 2.959 | 1.00 | 43.18 |
| ATOM | 4913 | O | WAT | W | 260 | −16.694 | 25.390 | −37.688 | 1.00 | 36.77 |
| ATOM | 4914 | O | WAT | W | 261 | −9.212 | 13.388 | −48.363 | 1.00 | 38.05 |
| ATOM | 4915 | O | WAT | W | 264 | −0.611 | −1.965 | −3.253 | 1.00 | 37.95 |
| ATOM | 4916 | O | WAT | W | 265 | −16.380 | 30.998 | −14.262 | 1.00 | 32.44 |
| ATOM | 4917 | O | WAT | W | 266 | 9.420 | 16.012 | −61.368 | 1.00 | 35.22 |
| ATOM | 4918 | O | WAT | W | 267 | −4.976 | −15.180 | −21.223 | 1.00 | 45.50 |
| ATOM | 4919 | O | WAT | W | 268 | −16.631 | 33.287 | −14.201 | 1.00 | 34.50 |
| ATOM | 4920 | O | WAT | W | 269 | −16.883 | 34.052 | −32.249 | 1.00 | 36.88 |
| ATOM | 4921 | O | WAT | W | 270 | −8.293 | −16.006 | −14.535 | 1.00 | 34.80 |
| ATOM | 4922 | O | WAT | W | 273 | 0.240 | 4.589 | −13.868 | 1.00 | 32.34 |
| ATOM | 4923 | O | WAT | W | 275 | 3.657 | 14.447 | −55.516 | 1.00 | 43.54 |
| ATOM | 4924 | O | WAT | W | 276 | −17.602 | 20.784 | −51.471 | 1.00 | 38.88 |
| ATOM | 4925 | O | WAT | W | 277 | −10.479 | 31.683 | −30.513 | 1.00 | 40.35 |
| ATOM | 4926 | O | WAT | W | 278 | −10.974 | 4.308 | −5.745 | 1.00 | 40.30 |
| ATOM | 4927 | O | WAT | W | 280 | −4.336 | 36.908 | −17.666 | 1.00 | 34.01 |
| ATOM | 4928 | O | WAT | W | 281 | 6.720 | 33.970 | −53.572 | 1.00 | 38.81 |
| ATOM | 4929 | O | WAT | W | 282 | −30.457 | 23.527 | −0.621 | 1.00 | 34.61 |
| ATOM | 4930 | O | WAT | W | 283 | 16.969 | 17.394 | −30.816 | 1.00 | 55.74 |
| ATOM | 4931 | O | WAT | W | 284 | −24.391 | 5.834 | −24.909 | 1.00 | 37.92 |
| ATOM | 4932 | O | WAT | W | 285 | 4.567 | 9.814 | −4.438 | 1.00 | 44.83 |
| ATOM | 4933 | O | WAT | W | 286 | −24.370 | −7.328 | −27.875 | 1.00 | 56.18 |
| ATOM | 4934 | O | WAT | W | 287 | −21.605 | 11.887 | 9.715 | 1.00 | 43.15 |
| ATOM | 4935 | O | WAT | W | 288 | 8.603 | 0.412 | −37.887 | 1.00 | 40.47 |
| ATOM | 4936 | O | WAT | W | 290 | −20.056 | 21.495 | 6.073 | 1.00 | 41.68 |
| ATOM | 4937 | O | WAT | W | 291 | −3.221 | 28.158 | −33.448 | 1.00 | 44.24 |
| ATOM | 4938 | O | WAT | W | 292 | 9.171 | 9.103 | −38.735 | 1.00 | 34.30 |
| ATOM | 4939 | O | WAT | W | 293 | 2.894 | 22.763 | −25.829 | 1.00 | 38.57 |
| ATOM | 4940 | O | WAT | W | 294 | −29.901 | 19.604 | −14.929 | 1.00 | 37.66 |
| ATOM | 4941 | O | WAT | W | 296 | −4.579 | 30.229 | −29.110 | 1.00 | 40.57 |
| ATOM | 4942 | O | WAT | W | 297 | −23.821 | 11.441 | −33.187 | 1.00 | 42.81 |
| ATOM | 4943 | O | WAT | W | 298 | −26.753 | −3.087 | −31.243 | 1.00 | 39.08 |
| ATOM | 4944 | O | WAT | W | 300 | −10.820 | 35.024 | −53.050 | 1.00 | 55.39 |
| ATOM | 4945 | O | WAT | W | 302 | −1.992 | 7.169 | −31.692 | 1.00 | 39.12 |
| ATOM | 4946 | O | WAT | W | 303 | −15.282 | −19.000 | −23.770 | 1.00 | 34.62 |
| ATOM | 4947 | O | WAT | W | 304 | 12.106 | 10.568 | −25.112 | 1.00 | 39.04 |
| ATOM | 4948 | O | WAT | W | 305 | 2.585 | 2.766 | 1.880 | 1.00 | 53.88 |
| ATOM | 4949 | O | WAT | W | 306 | 3.680 | 21.122 | −19.818 | 1.00 | 46.35 |
| ATOM | 4950 | O | WAT | W | 307 | 22.759 | 24.721 | −48.099 | 1.00 | 40.35 |
| ATOM | 4951 | O | WAT | W | 309 | −17.062 | −6.726 | −19.202 | 1.00 | 41.54 |
| ATOM | 4952 | O | WAT | W | 311 | 12.594 | 1.109 | −31.461 | 1.00 | 47.85 |
| ATOM | 4953 | O | WAT | W | 312 | 23.347 | 25.060 | −50.638 | 1.00 | 49.64 |
| ATOM | 4954 | O | WAT | W | 314 | −18.291 | 4.422 | −19.151 | 1.00 | 39.17 |
| ATOM | 4955 | O | WAT | W | 315 | −11.815 | −7.807 | −8.676 | 1.00 | 37.74 |
| ATOM | 4956 | O | WAT | W | 316 | −25.147 | 1.885 | −4.649 | 1.00 | 44.72 |
| ATOM | 4957 | O | WAT | W | 317 | −36.473 | 13.592 | 5.315 | 1.00 | 44.38 |
| ATOM | 4958 | O | WAT | W | 318 | −17.587 | 20.023 | −46.231 | 1.00 | 48.30 |

TABLE 15-continued

| ATOM | 4959 | O | WAT | W | 319 | −16.081 | 29.024 | −54.668 | 1.00 | 39.40 |
|---|---|---|---|---|---|---|---|---|---|---|
| ATOM | 4960 | O | WAT | W | 320 | −14.210 | 32.143 | −5.494 | 1.00 | 42.73 |
| ATOM | 4961 | O | WAT | W | 321 | −15.274 | 28.830 | −38.916 | 1.00 | 46.47 |
| ATOM | 4962 | O | WAT | W | 322 | −32.792 | 22.221 | −3.433 | 1.00 | 41.52 |
| ATOM | 4963 | O | WAT | W | 323 | −32.475 | 16.905 | −12.401 | 1.00 | 46.29 |
| ATOM | 4964 | O | WAT | W | 325 | 15.341 | 22.212 | −60.490 | 1.00 | 34.67 |
| ATOM | 4965 | O | WAT | W | 326 | −12.668 | 8.518 | −41.723 | 1.00 | 36.26 |
| ATOM | 4966 | O | WAT | W | 327 | 4.709 | 20.490 | −10.568 | 1.00 | 38.04 |
| ATOM | 4967 | O | WAT | W | 328 | 13.937 | 10.625 | −29.312 | 1.00 | 38.32 |
| ATOM | 4968 | O | WAT | W | 329 | −21.964 | 9.615 | −24.896 | 1.00 | 40.43 |
| ATOM | 4969 | O | WAT | W | 330 | 19.325 | 25.925 | −40.199 | 1.00 | 51.36 |
| ATOM | 4970 | O | WAT | W | 331 | −19.010 | 8.073 | −45.255 | 1.00 | 46.06 |
| ATOM | 4971 | O | WAT | W | 332 | −25.024 | −2.892 | −29.306 | 1.00 | 41.74 |
| ATOM | 4972 | O | WAT | W | 333 | −16.593 | −7.067 | −23.297 | 1.00 | 38.54 |
| ATOM | 4973 | O | WAT | W | 334 | −17.517 | 24.078 | 2.157 | 1.00 | 45.82 |
| ATOM | 4974 | O | WAT | W | 335 | −19.123 | 31.941 | 0.010 | 1.00 | 38.91 |
| ATOM | 4975 | O | WAT | W | 337 | 10.677 | 21.901 | −62.740 | 1.00 | 44.31 |
| ATOM | 4976 | O | WAT | W | 338 | 4.510 | 15.230 | −51.810 | 1.00 | 42.12 |
| ATOM | 4977 | O | WAT | W | 339 | 13.979 | 14.161 | −43.380 | 1.00 | 46.42 |
| ATOM | 4978 | O | WAT | W | 341 | 5.979 | −11.625 | −28.739 | 1.00 | 43.09 |
| ATOM | 4979 | O | WAT | W | 342 | −19.453 | 13.347 | 10.394 | 1.00 | 42.44 |
| ATOM | 4980 | O | WAT | W | 343 | 7.085 | 23.050 | −30.796 | 1.00 | 34.94 |
| ATOM | 4981 | O | WAT | W | 345 | 6.471 | 24.087 | −63.943 | 1.00 | 45.16 |
| ATOM | 4982 | O | WAT | W | 347 | 3.734 | 22.842 | −12.031 | 1.00 | 43.85 |
| ATOM | 4983 | O | WAT | W | 348 | −17.739 | 7.564 | 5.723 | 1.00 | 43.77 |
| ATOM | 4984 | O | WAT | W | 351 | −22.014 | 31.372 | −24.708 | 1.00 | 42.69 |
| ATOM | 4985 | O | WAT | W | 352 | 25.016 | 25.103 | −46.967 | 1.00 | 40.51 |
| ATOM | 4986 | O | WAT | W | 353 | 7.969 | 32.464 | −67.637 | 1.00 | 57.78 |
| ATOM | 4987 | O | WAT | W | 354 | −27.444 | 5.101 | 5.861 | 1.00 | 48.31 |
| ATOM | 4988 | O | WAT | W | 356 | 8.012 | 11.087 | −40.867 | 1.00 | 47.51 |
| ATOM | 4989 | O | WAT | W | 357 | 4.974 | 29.116 | −17.433 | 1.00 | 43.72 |
| ATOM | 4990 | O | WAT | W | 358 | −0.457 | 9.488 | −45.288 | 1.00 | 45.63 |
| ATOM | 4991 | O | WAT | W | 360 | −3.090 | 36.536 | −12.138 | 1.00 | 46.29 |
| ATOM | 4992 | O | WAT | W | 361 | 20.072 | 19.772 | −36.896 | 1.00 | 38.73 |
| ATOM | 4993 | O | WAT | W | 363 | −26.217 | 15.345 | −28.735 | 1.00 | 49.07 |
| ATOM | 4994 | O | WAT | W | 365 | −25.308 | 0.100 | −48.602 | 1.00 | 60.01 |
| ATOM | 4995 | O | WAT | W | 367 | 19.369 | 29.586 | −58.438 | 1.00 | 48.19 |
| ATOM | 4996 | O | WAT | W | 369 | 12.808 | 11.144 | −54.427 | 1.00 | 48.48 |
| ATOM | 4997 | O | WAT | W | 370 | 9.410 | 2.674 | −16.115 | 1.00 | 44.59 |
| ATOM | 4998 | O | WAT | W | 372 | −10.249 | 38.564 | −13.215 | 1.00 | 48.60 |
| ATOM | 4999 | O | WAT | W | 373 | −24.151 | 16.211 | 10.617 | 1.00 | 42.16 |
| ATOM | 5000 | O | WAT | W | 375 | −6.459 | 31.697 | −48.106 | 1.00 | 46.03 |
| ATOM | 5001 | O | WAT | W | 376 | −11.605 | 27.116 | −1.562 | 1.00 | 44.58 |
| ATOM | 5002 | O | WAT | W | 377 | −4.703 | 24.150 | −62.673 | 1.00 | 48.70 |
| ATOM | 5003 | O | WAT | W | 379 | 6.889 | 0.036 | −7.530 | 1.00 | 45.35 |
| ATOM | 5004 | O | WAT | W | 381 | −13.601 | 32.742 | −32.002 | 1.00 | 51.37 |
| ATOM | 5005 | O | WAT | W | 383 | −28.077 | 5.243 | −4.688 | 1.00 | 37.46 |
| END | | | | | | | | | | |

What is claimed is:

1. An isolated glucoamylase variant comprising an amino acid sequence having at least 90% sequence identity to SEQ ID NO: 2, wherein said variant includes a substitution at position Y315 compared to the amino acid sequence of SEQ ID NO: 2.

2. The isolated glucoamylase variant of claim 1, wherein said variant includes the substitution Y315F compared to the amino acid sequence of SEQ ID NO: 2.

3. The isolated glucoamylase variant of claim 1, wherein the variant further comprises a substitution in a position selected from: D4L/E/R/S/C/A/Q/W, F5C/M/N/R/S/T/V/W, D24E/L/Y/T, F29L/I/D/C/S/V/W, I43R/F/D/Y/S, D44E/H/K/S/N/Y/F/R, Y47W, Y49N, Q70R/K/M/P/G/L/F, Q75R/K/A, R76L/M/K/T/P, P94L, D100W/I/Q/M/P/A/N, N119P/T/Y/D/E, N146S/G/C/H/E/D/T/W/L/M, Q148V/Y/H/A/C/D/G/M/R/S/T, Y169D/F, Q172C/A/D/R/E/F/H/V/L/M/N/S/T/V, E180A/C/G/H/I/L/N/P/Q/R/S/T/V/Y, V181E/C/D/G/H/I/P/T/Y/S/K/F/A, S211C/R/E/A/Y/W/M/H/L/I/R/Q/T, E243S/R/N/M/Y/A/L, R245A/E/M/I/P/V, I292D/H/P/R/T/N/V/F/L, G294D/E/T/Q/I/A, K297F/L/P/T/M/D/N/Q/A/Y/H/S/R/W, R309A/C/G/H/I/N/P/Q/S/T/W/Y/L, Y310E/G/L/P/S/W/R/Q, D313Q, V314A/R/N/D/C/E/Q/G/H/I/K/L/M/F/P/S/T/W/Y, Y316Q/R, N317T/H, K340D/T, K341F/D/P/V/G/S, T350S/E/A/N, Q356H/D/E, T363L/R/C/H/W, S368W/D/F/L, S369F, N376Q/T/H/S/V, Y395Q/R/S, A398S/I/T, S401C/V, R408S, N409W/T/K, T412A/h/K/G, R433H/Q, I436A/T and S451M/T/H compared to the amino acid sequence of SEQ ID NO: 2.

4. The isolated glucoamylase variant of claim 1, wherein said variant exhibits increased thermostability as compared to the glucoamylase of SEQ ID NO: 2.

5. The isolated glucoamylase variant of claim 1, wherein said variant exhibits increased specific activity compared to the glucoamylase of SEQ ID NO: 2.

* * * * *

SEQUENCE LISTING

<160> NUMBER OF SEQ ID NOS: 160

<210> SEQ ID NO 1
<211> LENGTH: 632
<212> TYPE: PRT
<213> ORGANISM: Trichoderma reesei

<400> SEQUENCE: 1

Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

```
Tyr Tyr Met Trp Thr Arg Asp Ser Ala Leu Val Phe Lys Asn Leu Ile
            85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
            115                 120                 125

Gly Ser Leu Ala Asp Gly Ser Gly Leu Gly Glu Pro Lys Phe Glu Leu
            130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
            165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
            195                 200                 205

Asp Leu Trp Glu Glu Val Asn Gly Ser Ser Phe Phe Thr Val Ala Asn
            210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
            245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
            275                 280                 285

Ser Ile His Thr Phe Asp Pro Asn Leu Gly Cys Asp Ala Gly Thr Phe
            290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
            325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
            355                 360                 365

Ile Tyr Val Trp Lys Lys Thr Gly Ser Ile Thr Val Thr Ala Thr Ser
            370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
            405                 410                 415

Tyr Ala Asp Gly Phe Leu Ser Glu Ala Ala Lys Tyr Val Pro Ala Asp
            420                 425                 430

Gly Ser Leu Ala Glu Gln Phe Asp Arg Asn Ser Gly Thr Pro Leu Ser
            435                 440                 445

Ala Leu His Leu Thr Trp Ser Tyr Ala Ser Phe Leu Thr Ala Thr Ala
            450                 455                 460

Arg Arg Ala Gly Ile Val Pro Pro Ser Trp Ala Asn Ser Ser Ala Ser
465                 470                 475                 480

Thr Ile Pro Ser Thr Cys Ser Gly Ala Ser Val Val Gly Ser Tyr Ser
            485                 490                 495
```

```
Arg Pro Thr Ala Thr Ser Phe Pro Pro Ser Gln Thr Pro Lys Pro Gly
                500                 505                 510

Val Pro Ser Gly Thr Pro Tyr Thr Pro Leu Pro Cys Ala Thr Pro Thr
        515                 520                 525

Ser Val Ala Val Thr Phe His Glu Leu Val Ser Thr Gln Phe Gly Gln
        530                 535                 540

Thr Val Lys Val Ala Gly Asn Ala Ala Leu Gly Asn Trp Ser Thr
545                 550                 555                 560

Ser Ala Ala Val Ala Leu Asp Ala Val Asn Tyr Ala Asp Asn His Pro
                565                 570                 575

Leu Trp Ile Gly Thr Val Asn Leu Glu Ala Gly Asp Val Val Glu Tyr
        580                 585                 590

Lys Tyr Ile Asn Val Gly Gln Asp Gly Ser Val Thr Trp Glu Ser Asp
                595                 600                 605

Pro Asn His Thr Tyr Thr Val Pro Ala Val Ala Cys Val Thr Gln Val
        610                 615                 620

Val Lys Glu Asp Thr Trp Gln Ser
625                 630

<210> SEQ ID NO 2
<211> LENGTH: 599
<212> TYPE: PRT
<213> ORGANISM: Trichoderma reesei

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
            35                  40                  45

Tyr Met Trp Thr Arg Asp Ser Ala Leu Val Phe Lys Asn Leu Ile Asp
        50                  55                  60

Arg Phe Thr Glu Thr Tyr Asp Ala Gly Leu Gln Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240
```

Thr Asn Glu Gly Arg Thr Gly Lys Asp Val Asn Ser Val Leu Thr Ser
            245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
            275                 280                 285

Phe Arg Ser Ile Tyr Gly Val Asn Lys Gly Ile Pro Ala Gly Ala Ala
            290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Glu Gln Leu Tyr Asp Ala Ile
            325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
            355                 360                 365

Ser Ser Ser Ser Thr Phe Thr Asn Ile Ile Asn Ala Val Ser Thr Tyr
            370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
            405                 410                 415

Leu His Leu Thr Trp Ser Tyr Ala Ser Phe Leu Thr Ala Thr Ala Arg
            420                 425                 430

Arg Ala Gly Ile Val Pro Pro Ser Trp Ala Asn Ser Ser Ala Ser Thr
            435                 440                 445

Ile Pro Ser Thr Cys Ser Gly Ala Ser Val Val Gly Ser Tyr Ser Arg
            450                 455                 460

Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
            485                 490                 495

Val Ala Val Thr Phe His Glu Leu Val Ser Thr Gln Phe Gly Gln Thr
            500                 505                 510

Val Lys Val Ala Gly Asn Ala Ala Ala Leu Gly Asn Trp Ser Thr Ser
            515                 520                 525

Ala Ala Val Ala Leu Asp Ala Val Asn Tyr Ala Asp Asn His Pro Leu
            530                 535                 540

Trp Ile Gly Thr Val Asn Leu Glu Ala Gly Asp Val Val Glu Tyr Lys
545                 550                 555                 560

Tyr Ile Asn Val Gly Gln Asp Gly Ser Val Thr Trp Glu Ser Asp Pro
            565                 570                 575

Asn His Thr Tyr Thr Val Pro Ala Val Ala Cys Val Thr Gln Val Val
            580                 585                 590

Lys Glu Asp Thr Trp Gln Ser
            595

<210> SEQ ID NO 3
<211> LENGTH: 453
<212> TYPE: PRT
<213> ORGANISM: Trichoderma reesei

<400> SEQUENCE: 3

Ser Val Asp Asp Phe Ile Ser Thr Glu Thr Pro Ile Ala Leu Asn Asn

-continued

```
1               5                   10                  15
Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
    50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
    210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
        275                 280                 285

Phe Arg Ser Ile Tyr Gly Val Asn Lys Gly Ile Pro Ala Gly Ala Ala
    290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
        355                 360                 365

Ser Ser Ser Ser Thr Phe Thr Asn Ile Ile Asn Ala Val Ser Thr Tyr
    370                 375                 380

Ala Asp Gly Phe Leu Ser Glu Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Leu His Leu Thr Trp Ser Tyr Ala Ser Phe Leu Thr Ala Thr Ala Arg
            420                 425                 430
```

Arg Ala Gly Ile Val Pro Pro Ser Trp Ala Asn Ser Ser Ala Ser Thr
        435                 440                 445

Ile Pro Ser Thr Cys
    450

<210> SEQ ID NO 4
<211> LENGTH: 1899
<212> TYPE: DNA
<213> ORGANISM: Trichoderma reesei

<400> SEQUENCE: 4

| | | | | |
|---|---|---|---|---|
| atgcacgtcc | tgtcgactgc | ggtgctgctc | ggctccgttg | ccgttcaaaa | ggtcctggga | 60 |
| agaccaggat | caagcggtct | gtccgacgtc | accaagaggt | ctgttgacga | cttcatcagc | 120 |
| accgagacgc | ctattgcact | gaacaatctt | ctttgcaatg | ttggtcctga | tggatgccgt | 180 |
| gcattcggca | catcagctgg | tgcggtgatt | gcatctccca | gcacaattga | cccggactac | 240 |
| tattacatgt | ggacgcgaga | tagcgctctt | gtcttcaaga | acctcatcga | ccgcttcacc | 300 |
| gaaacgtacg | atgcgggcct | gcagcgccgc | atcgagcagt | acattactgc | ccaggtcact | 360 |
| ctccagggcc | tctctaaccc | ctcgggctcc | ctcgcggacg | gctctggtct | cggcgagccc | 420 |
| aagtttgagt | tgaccctgaa | gcctttcacc | ggcaactggg | gtcgaccgca | gcgggatggc | 480 |
| ccagctctgc | gagccattgc | cttgattgga | tactcaaagt | ggctcatcaa | caacaactat | 540 |
| cagtcgactg | tgtccaacgt | catctggcct | attgtgcgca | acgacctcaa | ctatgttgcc | 600 |
| cagtactgga | accaaaccgg | ctttgacctc | tgggaagaag | tcaatgggag | ctcattcttt | 660 |
| actgttgcca | accagcaccg | agcacttgtc | gagggcgcca | ctcttgctgc | cactcttggc | 720 |
| cagtcgggaa | gcgcttattc | atctgttgct | ccccaggttt | tgtgctttct | ccaacgattc | 780 |
| tgggtgtcgt | ctggtggata | cgtcgactcc | aacatcaaca | ccaacgaggg | caggactggc | 840 |
| aaggatgtca | actccgtcct | gacttccatc | acaccttcg | atcccaacct | tggctgtgac | 900 |
| gcaggcacct | tccagccatg | cagtgacaaa | gcgctctcca | acctcaaggt | tgttgtcgac | 960 |
| tccttccgct | ccatctacgg | cgtgaacaag | ggcattcctg | ccggtgctgc | cgtcgccatt | 1020 |
| ggccggtatg | cagaggatgt | gtactacaac | ggcaaccctt | ggtatcttgc | tcatttgct | 1080 |
| gctgccgagc | agctgtacga | tgccatctac | gtctggaaga | agacgggctc | catcacggtg | 1140 |
| accgccacct | ccctggcctt | cttccaggag | cttgttcctg | gcgtgacggc | cgggacctac | 1200 |
| tccagcagct | cttcgacctt | taccaacatc | atcaacgccg | tctcgacata | cgccgatggc | 1260 |
| ttcctcagcg | aggctgccaa | gtacgtcccc | gccgacggtt | cgctggccga | gcagtttgac | 1320 |
| cgcaacagcg | gcactccgct | gtctgcgctt | cacctgacgt | ggtcgtacgc | ctcgttcttg | 1380 |
| acagccacgg | cccgtcgggc | tggcatcgtg | cccccctcgt | gggccaacag | cagcgctagc | 1440 |
| acgatcccct | cgacgtgctc | cggcgcgtcc | gtggtcggat | cctactcgcg | tcccaccgcc | 1500 |
| acgtcattcc | ctccgtcgca | gacgccaag | cctggcgtgc | cttccggtac | tccctacacg | 1560 |
| cccctgccct | gcgcgacccc | aacctccgtg | gccgtcacct | tccacgagct | cgtgtcgaca | 1620 |
| cagtttggcc | agacggtcaa | ggtggcgggc | aacgccgcgg | ccctgggcaa | ctggagcacg | 1680 |
| agcgccgccg | tggctctgga | cgccgtcaac | tatgccgata | ccacccccct | gtggattggg | 1740 |
| acggtcaacc | tcgaggctgg | agacgtcgtg | gagtacaagt | acatcaatgt | gggccaagat | 1800 |
| ggctccgtga | cctgggagag | tgatcccaac | cacacttaca | cggttcctgc | ggtggcttgt | 1860 |
| gtgacgcagg | ttgtcaagga | ggacacctgg | cagtcgtaa | | | 1899 |

<210> SEQ ID NO 5
<211> LENGTH: 448
<212> TYPE: PRT
<213> ORGANISM: Aspergillus awamori

<400> SEQUENCE: 5

```
Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
            20                  25                  30

Asp Ser Gly Ile Val Val Ala Ser Pro Ser Thr Asp Asn Pro Asp Tyr
        35                  40                  45

Phe Tyr Thr Trp Thr Arg Asp Ser Gly Leu Val Ile Lys Thr Leu Val
    50                  55                  60

Asp Leu Phe Arg Asn Gly Asp Thr Asp Leu Leu Ser Thr Ile Glu Asn
65                  70                  75                  80

Tyr Ile Ser Ser Gln Ala Ile Val Gln Gly Ile Ser Asn Pro Ser Gly
                85                  90                  95

Asp Leu Ser Ser Gly Gly Leu Gly Glu Pro Lys Phe Asn Val Asp Glu
            100                 105                 110

Thr Ala Tyr Thr Gly Ser Trp Gly Arg Pro Gln Arg Asp Gly Pro Ala
        115                 120                 125

Leu Arg Ala Thr Ala Met Ile Gly Phe Arg Gln Trp Leu Leu Asp Asn
130                 135                 140

Gly Tyr Thr Ser Ala Ala Thr Glu Ile Val Trp Pro Leu Val Arg Asn
145                 150                 155                 160

Asp Leu Ser Tyr Val Ala Gln Tyr Trp Asn Gln Thr Gly Tyr Asp Leu
                165                 170                 175

Trp Glu Glu Val Asn Gly Ser Ser Phe Phe Thr Ile Ala Val Gln His
            180                 185                 190

Arg Ala Leu Val Glu Gly Ser Ala Phe Ala Thr Ala Val Gly Ser Ser
        195                 200                 205

Cys Ser Trp Cys Asp Ser Gln Ala Pro Gln Ile Leu Cys Tyr Leu Gln
210                 215                 220

Ser Phe Trp Thr Gly Glu Tyr Ile Leu Ala Asn Phe Asp Ser Ser Arg
225                 230                 235                 240

Ser Gly Lys Asp Thr Asn Thr Leu Leu Gly Ser Ile His Thr Phe Asp
                245                 250                 255

Pro Glu Ala Gly Cys Asp Asp Ser Thr Phe Gln Pro Cys Ser Pro Arg
            260                 265                 270

Ala Leu Ala Asn His Lys Glu Val Val Asp Ser Phe Arg Ser Ile Tyr
        275                 280                 285

Thr Leu Asn Asp Gly Leu Ser Asp Ser Glu Ala Val Ala Val Gly Arg
290                 295                 300

Tyr Pro Lys Asp Ser Tyr Tyr Asn Gly Asn Pro Trp Phe Leu Cys Thr
305                 310                 315                 320

Leu Ala Ala Ala Glu Gln Leu Tyr Asp Ala Leu Tyr Gln Trp Asp Lys
                325                 330                 335

Gln Gly Ser Leu Glu Ile Thr Asp Val Ser Leu Asp Phe Phe Gln Ala
            340                 345                 350

Leu Tyr Ser Asp Ala Ala Thr Gly Thr Tyr Ser Ser Ser Ser Ser Thr
        355                 360                 365

Tyr Ser Ser Ile Val Asp Ala Val Lys Thr Phe Ala Asp Gly Phe Val
370                 375                 380
```

```
Ser Ile Val Glu Thr His Ala Ala Ser Asn Gly Ser Leu Ser Glu Gln
385                 390                 395                 400

Tyr Asp Lys Ser Asp Gly Asp Glu Leu Ser Ala Arg Asp Leu Thr Trp
            405                 410                 415

Ser Tyr Ala Ala Leu Leu Thr Ala Asn Asn Arg Arg Asn Ser Val Met
            420                 425                 430

Pro Pro Ser Trp Gly Glu Thr Ser Ala Ser Ser Val Pro Gly Thr Cys
            435                 440                 445

<210> SEQ ID NO 6
<211> LENGTH: 449
<212> TYPE: PRT
<213> ORGANISM: Aspergillus niger

<400> SEQUENCE: 6

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
                20                  25                  30

Asp Ser Gly Ile Val Val Ala Ser Pro Ser Thr Asp Asn Pro Asp Tyr
            35                  40                  45

Phe Tyr Thr Trp Thr Arg Asp Ser Gly Leu Val Leu Lys Thr Leu Val
50                  55                  60

Asp Leu Phe Arg Asn Gly Asp Thr Ser Leu Leu Ser Thr Ile Glu Asn
65                  70                  75                  80

Tyr Ile Ser Ala Gln Ala Ile Val Gln Gly Ile Ser Asn Pro Ser Gly
                85                  90                  95

Asp Leu Ser Ser Gly Ala Gly Leu Gly Glu Pro Lys Phe Asn Val Asp
            100                 105                 110

Glu Thr Ala Tyr Thr Gly Ser Trp Gly Arg Pro Gln Arg Asp Gly Pro
            115                 120                 125

Ala Leu Arg Ala Thr Ala Met Ile Gly Phe Gly Gln Trp Leu Leu Asp
            130                 135                 140

Asn Gly Tyr Thr Ser Thr Ala Thr Asp Ile Val Trp Pro Leu Val Arg
145                 150                 155                 160

Asn Asp Leu Ser Tyr Val Ala Gln Tyr Trp Asn Gln Thr Gly Tyr Asp
                165                 170                 175

Leu Trp Glu Glu Val Asn Gly Ser Ser Phe Phe Thr Ile Ala Val Gln
            180                 185                 190

His Arg Ala Leu Val Glu Gly Ser Ala Phe Ala Thr Ala Val Gly Ser
            195                 200                 205

Ser Cys Ser Trp Cys Asp Ser Gln Ala Pro Glu Ile Leu Cys Tyr Leu
            210                 215                 220

Gln Ser Phe Trp Thr Gly Ser Phe Ile Leu Ala Asn Phe Asp Ser Ser
225                 230                 235                 240

Arg Ser Gly Lys Asp Ala Asn Thr Leu Leu Gly Ser Ile His Thr Phe
                245                 250                 255

Asp Pro Glu Ala Ala Cys Asp Asp Ser Thr Phe Gln Pro Cys Ser Pro
            260                 265                 270

Arg Ala Leu Ala Asn His Lys Glu Val Val Asp Ser Phe Arg Ser Ile
            275                 280                 285

Tyr Thr Leu Asn Asp Gly Leu Ser Asp Ser Glu Ala Val Ala Val Gly
            290                 295                 300

Arg Tyr Pro Glu Asp Thr Tyr Tyr Asn Gly Asn Pro Trp Phe Leu Cys
```

```
                305                 310                 315                 320
        Thr Leu Ala Ala Ala Glu Gln Leu Tyr Asp Ala Leu Tyr Gln Trp Asp
                        325                 330                 335

Lys Gln Gly Ser Leu Glu Val Thr Asp Val Ser Leu Asp Phe Phe Lys
                        340                 345                 350

Ala Leu Tyr Ser Asp Ala Ala Thr Gly Thr Tyr Ser Ser Ser Ser Ser
                        355                 360                 365

Thr Tyr Ser Ser Ile Val Asp Ala Val Lys Thr Phe Ala Asp Gly Phe
                        370                 375                 380

Val Ser Ile Val Glu Thr His Ala Ala Ser Asn Gly Ser Met Ser Glu
        385                 390                 395                 400

Gln Tyr Asp Lys Ser Asp Gly Glu Gln Leu Ser Ala Arg Asp Leu Thr
                        405                 410                 415

Trp Ser Tyr Ala Ala Leu Leu Thr Ala Asn Asn Arg Arg Asn Ser Val
                        420                 425                 430

Val Pro Ala Ser Trp Gly Glu Thr Ser Ala Ser Ser Val Pro Gly Thr
                        435                 440                 445

Cys

<210> SEQ ID NO 7
<211> LENGTH: 450
<212> TYPE: PRT
<213> ORGANISM: Aspergillus orzyae

<400> SEQUENCE: 7

Gln Ser Asp Leu Asn Ala Phe Ile Glu Ala Gln Thr Pro Ile Ala Lys
        1               5                   10                  15

Gln Gly Tyr Leu Asn Asn Ile Gly Ala Asp Gly Lys Leu Val Glu Gly
                        20                  25                  30

Ala Ala Ala Gly Ile Val Tyr Ala Ser Pro Ser Lys Ser Asn Pro Asp
                        35                  40                  45

Tyr Phe Tyr Thr Trp Thr Arg Asp Ala Gly Leu Thr Met Glu Glu Tyr
                        50                  55                  60

Ile Glu Gln Phe Ile Gly Gly Asp Ala Thr Leu Glu Ser Thr Ile Gln
        65                  70                  75                  80

Asn Tyr Val Asp Ser Gln Ala Asn Glu Gln Ala Val Ser Asn Pro Ser
                        85                  90                  95

Gly Gly Leu Ser Asp Gly Ser Gly Leu Ala Glu Pro Lys Phe Tyr Tyr
                        100                 105                 110

Asn Ile Ser Gln Phe Thr Asp Ser Trp Gly Arg Pro Gln Arg Asp Gly
                        115                 120                 125

Pro Ala Leu Arg Ala Ser Ala Leu Ile Ala Tyr Gly Asn Ser Leu Ile
                        130                 135                 140

Ser Ser Asp Lys Gln Ser Val Val Lys Ala Asn Ile Trp Pro Ile Tyr
        145                 150                 155                 160

Gln Asn Asp Leu Ser Tyr Val Gly Gln Tyr Trp Asn Gln Thr Gly Phe
                        165                 170                 175

Asp Leu Trp Glu Glu Val Gln Gly Ser Ser Phe Phe Thr Val Ala Val
                        180                 185                 190

Gln His Lys Ala Leu Val Glu Gly Asp Ala Phe Ala Lys Ala Leu Gly
                        195                 200                 205

Glu Glu Cys Gln Ala Cys Ser Val Ala Pro Gln Ile Leu Cys His Leu
                        210                 215                 220

Gln Asp Phe Trp Asn Gly Ser Ala Val Leu Ser Asn Leu Pro Thr Asn
```

```
                225                 230                 235                 240
        Gly Arg Ser Gly Leu Asp Thr Asn Ser Leu Leu Gly Ser Ile His Thr
                        245                 250                 255

Phe Asp Pro Ala Ala Ala Cys Asp Asp Thr Thr Phe Gln Pro Cys Ser
                        260                 265                 270

Ser Arg Ala Leu Ser Asn His Lys Leu Val Val Asp Ser Phe Arg Ser
                        275                 280                 285

Val Tyr Gly Ile Asn Asn Gly Arg Gly Ala Gly Lys Ala Ala Ala Val
                        290                 295                 300

Gly Pro Tyr Ala Glu Asp Thr Tyr Gln Gly Gly Asn Pro Trp Tyr Leu
        305                 310                 315                 320

Thr Thr Leu Val Ala Ala Glu Leu Leu Tyr Asp Ala Leu Tyr Gln Trp
                        325                 330                 335

Asp Lys Gln Gly Gln Val Asn Val Thr Glu Thr Ser Leu Pro Phe Phe
                        340                 345                 350

Lys Asp Leu Ser Ser Asn Val Thr Thr Gly Ser Tyr Ala Lys Ser Ser
                        355                 360                 365

Ser Ala Tyr Glu Ser Leu Thr Ser Ala Val Lys Thr Tyr Ala Asp Gly
                        370                 375                 380

Phe Ile Ser Val Val Gln Glu Tyr Thr Pro Asp Gly Gly Ala Leu Ala
        385                 390                 395                 400

Glu Gln Tyr Ser Arg Asp Gln Gly Thr Pro Val Ser Ala Ser Asp Leu
                        405                 410                 415

Thr Trp Ser Tyr Ala Ala Phe Leu Ser Ala Val Gly Arg Arg Asn Gly
                        420                 425                 430

Thr Val Pro Ala Ser Trp Gly Ser Ser Thr Ala Asn Ala Val Pro Ser
                        435                 440                 445

Gln Cys
            450

<210> SEQ ID NO 8
<211> LENGTH: 441
<212> TYPE: PRT
<213> ORGANISM: Humicola grisea

<400> SEQUENCE: 8

Ala Ala Val Asp Thr Phe Ile Asn Thr Glu Lys Pro Ile Ala Trp Asn
        1               5                   10                  15

Lys Leu Leu Ala Asn Ile Gly Pro Asn Gly Lys Ala Ala Pro Gly Ala
                        20                  25                  30

Ala Ala Gly Val Val Ile Ala Ser Pro Ser Arg Thr Asp Pro Pro Tyr
                        35                  40                  45

Phe Phe Thr Trp Thr Pro Asp Ala Ala Leu Val Leu Thr Gly Ile Ile
                        50                  55                  60

Glu Ser Leu Gly His Asn Tyr Asn Thr Thr Leu Gln Gln Val Ser Asn
        65                  70                  75                  80

Pro Ser Gly Thr Phe Ala Asp Gly Ser Gly Leu Gly Glu Ala Lys Phe
                        85                  90                  95

Asn Val Asp Leu Thr Ala Phe Thr Gly Glu Trp Gly Arg Pro Gln Arg
                        100                 105                 110

Asp Gly Pro Pro Leu Arg Ala Ile Ala Leu Ile Gln Tyr Ala Lys Trp
                        115                 120                 125

Leu Ile Ala Asn Gly Tyr Lys Ser Thr Ala Lys Ser Val Val Trp Pro
                        130                 135                 140
```

-continued

```
Val Val Lys Asn Asp Leu Ala Tyr Thr Ala Gln Tyr Trp Asn Glu Thr
145                 150                 155                 160

Gly Phe Asp Leu Trp Glu Glu Val Pro Gly Ser Ser Phe Phe Thr Ile
                165                 170                 175

Ala Ser Ser His Arg Ala Leu Thr Glu Gly Ala Tyr Leu Ala Ala Gln
            180                 185                 190

Leu Asp Thr Glu Cys Pro Pro Cys Thr Thr Val Ala Pro Gln Val Leu
        195                 200                 205

Cys Phe Gln Gln Ala Phe Trp Asn Ser Lys Gly Asn Tyr Val Val Ser
    210                 215                 220

Thr Ser Thr Ala Gly Glu Tyr Arg Ser Gly Lys Asp Ala Asn Ser Ile
225                 230                 235                 240

Leu Ala Ser Ile His Asn Phe Asp Pro Glu Ala Gly Cys Asp Asn Leu
                245                 250                 255

Thr Phe Gln Pro Cys Ser Glu Arg Ala Leu Ala Asn His Lys Ala Tyr
            260                 265                 270

Val Asp Ser Phe Arg Asn Leu Tyr Ala Ile Asn Lys Gly Ile Ala Gln
        275                 280                 285

Gly Lys Ala Val Ala Val Gly Arg Tyr Ser Glu Asp Val Tyr Tyr Asn
    290                 295                 300

Gly Asn Pro Trp Tyr Leu Ala Asn Phe Ala Ala Glu Gln Leu Tyr
305                 310                 315                 320

Asp Ala Ile Tyr Val Trp Asn Lys Gln Gly Ser Ile Thr Val Thr Ser
                325                 330                 335

Val Ser Leu Pro Phe Phe Arg Asp Leu Val Ser Ser Val Ser Thr Gly
            340                 345                 350

Thr Tyr Ser Lys Ser Ser Ser Thr Phe Thr Asn Ile Val Asn Ala Val
        355                 360                 365

Lys Ala Tyr Ala Asp Gly Phe Ile Glu Val Ala Lys Tyr Thr Pro
    370                 375                 380

Ser Asn Gly Ala Leu Ala Glu Gln Tyr Asp Arg Asn Thr Gly Lys Pro
385                 390                 395                 400

Asp Ser Ala Ala Asp Leu Thr Trp Ser Tyr Ser Ala Phe Leu Ser Ala
                405                 410                 415

Ile Asp Arg Arg Ala Gly Leu Val Pro Pro Ser Trp Arg Ala Ser Val
            420                 425                 430

Ala Lys Ser Gln Leu Pro Ser Thr Cys
    435                 440
```

```
<210> SEQ ID NO 9
<211> LENGTH: 452
<212> TYPE: PRT
<213> ORGANISM: Hypocrea vinosa

<400> SEQUENCE: 9

Ser Val Asp Asp Phe Ile Asn Thr Gln Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Thr Asp Pro Asp Tyr Tyr
            35                  40                  45

Tyr Met Trp Thr Arg Asp Ser Ala Leu Val Phe Lys Asn Ile Val Asp
        50                  55                  60

Arg Phe Thr Gln Gln Tyr Asp Ala Gly Leu Gln Arg Arg Ile Glu Gln
65                  70                  75                  80
```

Tyr Ile Ser Ala Gln Val Thr Leu Gln Gly Ile Ser Asn Pro Ser Gly
                85                  90                  95

Ser Leu Ser Asp Gly Ser Gly Leu Gly Glu Pro Lys Phe Glu Leu Thr
            100                 105                 110

Leu Ser Gln Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
    130                 135                 140

Asn Asn Tyr Gln Ser Thr Val Ser Asn Ile Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Thr Tyr Ser Ser Val Ala Pro Gln Ile Leu Cys Phe Leu
    210                 215                 220

Gln Arg Phe Trp Val Ser Gly Gly Tyr Ile Asp Ser Asn Ile Asn Thr
225                 230                 235                 240

Asn Glu Gly Arg Thr Gly Lys Asp Ala Asn Ser Leu Leu Ala Ser Ile
                245                 250                 255

His Thr Phe Asp Pro Ser Leu Gly Cys Asp Ala Ser Thr Phe Gln Pro
            260                 265                 270

Cys Ser Asp Lys Ala Leu Ser Asn Leu Lys Val Val Asp Ser Phe
        275                 280                 285

Arg Ser Ile Tyr Gly Val Asn Lys Gly Ile Pro Ala Gly Ser Ala Val
    290                 295                 300

Ala Ile Gly Arg Tyr Pro Glu Asp Val Tyr Phe Asn Gly Asn Pro Trp
305                 310                 315                 320

Tyr Leu Ala Thr Phe Ala Ala Ala Glu Gln Leu Tyr Asp Ser Val Tyr
                325                 330                 335

Val Trp Lys Lys Thr Gly Ser Ile Thr Val Thr Ser Ser Ser Ala
            340                 345                 350

Phe Phe Gln Glu Leu Val Pro Gly Val Ala Gly Thr Tyr Ser Ser
        355                 360                 365

Ser Gln Ser Thr Phe Thr Ser Ile Ile Asn Ala Ile Ser Thr Tyr Ala
    370                 375                 380

Asp Gly Phe Leu Ser Glu Ala Ala Lys Tyr Val Pro Ala Asp Gly Ser
385                 390                 395                 400

Leu Ala Glu Gln Phe Asp Arg Asn Thr Gly Thr Pro Leu Ser Ala Val
                405                 410                 415

His Leu Thr Trp Ser Tyr Ala Ser Phe Leu Thr Ala Ala Arg Arg
            420                 425                 430

Ala Gly Val Val Pro Pro Ser Trp Ala Ser Ser Gly Ala Asn Thr Val
    435                 440                 445

Pro Ser Ser Cys
    450

<210> SEQ ID NO 10
<211> LENGTH: 25
<212> TYPE: DNA
<213> ORGANISM: Artificial
<220> FEATURE:

<223> OTHER INFORMATION: synthetic primer

<400> SEQUENCE: 10
tcgcgttaac gctagcatgg atctc                                    25

<210> SEQ ID NO 11
<211> LENGTH: 31
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (10)..(11)
<223> OTHER INFORMATION: n is a, c, g, or t

<400> SEQUENCE: 11
tctgttgacn nsttcatcag caccgagacg c                             31

<210> SEQ ID NO 12
<211> LENGTH: 34
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (13)..(14)
<223> OTHER INFORMATION: n is a, c, g, or t

<400> SEQUENCE: 12
tctgttgacg acnnsatcag caccgagacg ccta                          34

<210> SEQ ID NO 13
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 13
atcagcaccg agacgcctnn sgcactgaac aatcttcttt                    40

<210> SEQ ID NO 14
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 14
ctttgcaatg ttggtcctnn sggatgccgt gcattcggca                    40

<210> SEQ ID NO 15
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature

```
<222> LOCATION: (19)..(20)
<223> OTHER INFORMATION: n is a, c, g, or t

<400> SEQUENCE: 15
cctgatggat gccgtgcann sggcacatca gctggtgcgg                              40

<210> SEQ ID NO 16
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 16
attgcatctc ccagcacann sgacccggac tactattaca                              40

<210> SEQ ID NO 17
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 17
gcatctccca gcacaattnn sccggactac tattacatgt                              40

<210> SEQ ID NO 18
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 18
tctcccagca caattgacnn sgactactat tacatgtgga                              40

<210> SEQ ID NO 19
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 19
cccagcacaa ttgacccgnn stactattac atgtggacgc                              40

<210> SEQ ID NO 20
<211> LENGTH: 40
<212> TYPE: DNA
<213> ORGANISM: Artificial
<220> FEATURE:
<223> OTHER INFORMATION: synthetic primer
<220> FEATURE:
```

<221> NAME/KEY: misc_feature
<222> LOCATION: (19)..(20)
<223> OTHER INFORMATION: n is a, c, g, or t

<400> SEQUENCE: 20
agcacaattg acccggacnn stattacatg tggacgcgag                              40

<210> SEQ ID NO 21
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 21
attgacccgg actactatnn satgtggacg cgagatagcg                              40

<210> SEQ ID NO 22
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 22
ccggactact attacatgnn sacgcgagat agcgctcttg                              40

<210> SEQ ID NO 23
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 23
gaccgcttca ccgaaacgnn sgatgcgggc ctgcagcgcc                              40

<210> SEQ ID NO 24
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 24
acgtacgatg cgggcctgnn scgccgcatc gagcagtaca                              40

<210> SEQ ID NO 25
<211> LENGTH: 40
<212> TYPE: DNA
<213> ORGANISM: Artificial
<220> FEATURE:
<223> OTHER INFORMATION: synthetic primer

```
<220> FEATURE:
<221> NAME/KEY: misc_feature
<222> LOCATION: (19)..(20)
<223> OTHER INFORMATION: n is a, c, g, or t

<400> SEQUENCE: 25
tacgatgcgg gcctgcagnn scgcatcgag cagtacatta                              40

<210> SEQ ID NO 26
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 26
ctccagggcc tctctaacnn stcgggctcc ctcgcggacg                              40

<210> SEQ ID NO 27
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 27
ccctcgggct ccctcgcgnn sggctctggt ctcggcgagc                              40

<210> SEQ ID NO 28
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 28
aagtttgagt tgaccctgnn scctttcacc ggcaactggg                              40

<210> SEQ ID NO 29
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 29
gagttgaccc tgaagcctnn saccggcaac tggggtcgac                              40

<210> SEQ ID NO 30
<211> LENGTH: 40
<212> TYPE: DNA
<213> ORGANISM: Artificial
<220> FEATURE:
```

```
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 30
ctgaagcctt tcaccggcnn stggggtcga ccgcagcggg                40

<210> SEQ ID NO 31
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 31
ttcaccggca actggggtnn sccgcagcgg gatggcccag                40

<210> SEQ ID NO 32
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 32
aactggggtc gaccgcagnn sgatggccca gctctgcgag                40

<210> SEQ ID NO 33
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 33
aagtggctca tcaacaacnn statcagtcg actgtgtcca                40

<210> SEQ ID NO 34
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 34
ctcatcaaca acaactatnn stcgactgtg tccaacgtca                40

<210> SEQ ID NO 35
<211> LENGTH: 40
<212> TYPE: DNA
<213> ORGANISM: Artificial
```

<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 35
ctcaactatg ttgcccagnn stggaaccaa accggctttg                              40

<210> SEQ ID NO 36
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 36
gttgcccagt actggaacnn saccggcttt gacctctggg                              40

<210> SEQ ID NO 37
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 37
tactggaacc aaaccggcnn sgacctctgg gaagaagtca                              40

<210> SEQ ID NO 38
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 38
caaaccggct ttgacctcnn sgaagaagtc aatgggagct                              40

<210> SEQ ID NO 39
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 39
ggctttgacc tctgggaann sgtcaatggg agctcattct                              40

<210> SEQ ID NO 40
<211> LENGTH: 40
<212> TYPE: DNA

```
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 40
tttgacctct gggaagaann saatgggagc tcattcttta                  40

<210> SEQ ID NO 41
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 41
cttgctgcca ctcttggcnn stcgggaagc gcttattcat                  40

<210> SEQ ID NO 42
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 42
actcttggcc agtcgggann sgcttattca tctgttgctc                  40

<210> SEQ ID NO 43
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 43
tgctttctcc aacgattcnn sgtgtcgtct ggtggatacg                  40

<210> SEQ ID NO 44
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 44
gactccaaca tcaacaccnn sgagggcagg actggcaagg                  40

<210> SEQ ID NO 45
<211> LENGTH: 40
```

-continued

```
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 45
tccaacatca acaccaacnn sggcaggact ggcaaggatg                    40

<210> SEQ ID NO 46
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 46
atcaacacca acgagggcnn sactggcaag gatgtcaact                    40

<210> SEQ ID NO 47
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 47
gtcgactcct tccgctccnn stacggcgtg aacaagggca                    40

<210> SEQ ID NO 48
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 48
tccttccgct ccatctacnn sgtgaacaag ggcattcctg                    40

<210> SEQ ID NO 49
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 49
tccatctacg gcgtgaacnn sggcattcct gccggtgctg                    40

<210> SEQ ID NO 50
```

```
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 50
gctgccgtcg ccattggcnn statgcagag gatgtgtact                    40

<210> SEQ ID NO 51
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 51
gccgtcgcca ttggccggnn sgcagaggat gtgtactaca                    40

<210> SEQ ID NO 52
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 52
attggccggt atgcagagnn sgtgtactac aacggcaacc                    40

<210> SEQ ID NO 53
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 53
ggccggtatg cagaggatnn stactacaac ggcaaccctt                    40

<210> SEQ ID NO 54
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 54
cggtatgcag aggatgtgnn stacaacggc aacccttggt                    40
```

```
<210> SEQ ID NO 55
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 55
tatgcagagg atgtgtacnn saacggcaac ccttggtatc            40

<210> SEQ ID NO 56
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 56
gcagaggatg tgtactacnn sggcaaccct tggtatcttg            40

<210> SEQ ID NO 57
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 57
tactacaacg gcaaccctnn statcttgct acatttgctg            40

<210> SEQ ID NO 58
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 58
gatgccatct acgtctggnn saagacgggc tccatcacgg            40

<210> SEQ ID NO 59
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 59
gccatctacg tctggaagnn sacgggctcc atcacggtga            40
```

```
<210> SEQ ID NO 60
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 60
tccatcacgg tgaccgccnn stccctggcc ttcttccagg              40

<210> SEQ ID NO 61
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 61
acctccctgg ccttcttcnn sgagcttgtt cctggcgtga              40

<210> SEQ ID NO 62
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 62
gagcttgttc ctggcgtgnn sgccgggacc tactccagca              40

<210> SEQ ID NO 63
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 63
gtgacggccg ggacctacnn sagcagctct tcgaccttta              40

<210> SEQ ID NO 64
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 64
acggccggga cctactccnn sagctcttcg acctttacca              40
```

<210> SEQ ID NO 65
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 65
agctcttcga cctttaccnn satcatcaac gccgtctcga     40

<210> SEQ ID NO 66
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 66
ctcagcgagg ctgccaagnn sgtccccgcc gacggttcgc     40

<210> SEQ ID NO 67
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 67
gctgccaagt acgtccccnn sgacggttcg ctggccgagc     40

<210> SEQ ID NO 68
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 68
tacgtccccg ccgacggtnn sctggccgag cagtttgacc     40

<210> SEQ ID NO 69
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 69
ctggccgagc agtttgacnn saacagcggc actccgctgt        40

<210> SEQ ID NO 70
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 70
gccgagcagt tgaccgcnn sagcggcact ccgctgtctg        40

<210> SEQ ID NO 71
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 71
tttgaccgca acagcggcnn sccgctgtct gcgcttcacc        40

<210> SEQ ID NO 72
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 72
actccgctgt ctgcgcttnn sctgacgtgg tcgtacgcct        40

<210> SEQ ID NO 73
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 73
tctgcgcttc acctgacgnn stcgtacgcc tcgttcttga        40

<210> SEQ ID NO 74
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 74
ttgacagcca cggcccgtnn sgctggcatc gtgccccct                               40

<210> SEQ ID NO 75
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 75
acggcccgtc gggctggcnn sgtgcccccc tcgtgggcca                              40

<210> SEQ ID NO 76
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 76
agcgctagca cgatccccnn sacgtgctcc ggcgcgtccg                              40

<210> SEQ ID NO 77
<211> LENGTH: 24
<212> TYPE: DNA
<213> ORGANISM: Artificial
<220> FEATURE:
<223> OTHER INFORMATION: synthetic primer

<400> SEQUENCE: 77
gtaacatcag agattttgag acac                                              24

<210> SEQ ID NO 78
<211> LENGTH: 31
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 78
gcgtctcggt gctgatgaas nngtcaacag a                                      31

<210> SEQ ID NO 79
<211> LENGTH: 34
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 79
taggcgtctc ggtgctgats nngtcgtcaa caga                                   34

```
<210> SEQ ID NO 80
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 80
aaagaagatt gttcagtgcs nnaggcgtct cggtgctgat                              40

<210> SEQ ID NO 81
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 81
tgccgaatgc acggcatccs nnaggaccaa cattgcaaag                              40

<210> SEQ ID NO 82
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 82
ccgcaccagc tgatgtgccs nntgcacggc atccatcagg                              40

<210> SEQ ID NO 83
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 83
tgtaatagta gtccgggtcs nntgtgctgg gagatgcaat                              40

<210> SEQ ID NO 84
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 84
acatgtaata gtagtccggs nnaattgtgc tgggagatgc                              40
```

```
<210> SEQ ID NO 85
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 85
tccacatgta atagtagtcs nngtcaattg tgctgggaga                            40

<210> SEQ ID NO 86
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 86
gcgtccacat gtaatagtas nncgggtcaa ttgtgctggg                            40

<210> SEQ ID NO 87
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 87
ctcgcgtcca catgtaatas nngtccgggt caattgtgct                            40

<210> SEQ ID NO 88
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 88
cgctatctcg cgtccacats nnatagtagt ccgggtcaat                            40

<210> SEQ ID NO 89
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 89
```
caagagcgct atctcgcgts nncatgtaat agtagtccgg    40

<210> SEQ ID NO 90
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 90
ggcgctgcag gcccgcatcs nncgtttcgg tgaagcggtc    40

<210> SEQ ID NO 91
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 91
tgtactgctc gatgcggcgs nncaggcccg catcgtacgt    40

<210> SEQ ID NO 92
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 92
taatgtactg ctcgatgcgs nnctgcaggc ccgcatcgta    40

<210> SEQ ID NO 93
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 93
cgtccgcgag ggagcccgas nngttagaga ggccctggag    40

<210> SEQ ID NO 94
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 94
gctcgccgag accagagccs nncgcgaggg agcccgaggg        40

<210> SEQ ID NO 95
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 95
cccagttgcc ggtgaaaggs nncagggtca actcaaactt        40

<210> SEQ ID NO 96
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 96
gtcgacccca gttgccggts nnaggcttca gggtcaactc        40

<210> SEQ ID NO 97
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 97
cccgctgcgg tcgacccccas nngccggtga aaggcttcag        40

<210> SEQ ID NO 98
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 98
ctgggccatc ccgctgcggs nnaccccagt tgccggtgaa        40

<210> SEQ ID NO 99
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

```
<400> SEQUENCE: 99
ctcgcagagc tgggccatcs nnctgcggtc gaccccagtt                             40

<210> SEQ ID NO 100
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 100
tggacacagt cgactgatas nngttgttga tgagccactt                             40

<210> SEQ ID NO 101
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 101
tgacgttgga cacagtcgas nnatagttgt tgttgatgag                             40

<210> SEQ ID NO 102
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 102
caaagccggt ttggttccas nnctgggcaa catagttgag                             40

<210> SEQ ID NO 103
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 103
cccagaggtc aaagccggts nngttccagt actgggcaac                             40

<210> SEQ ID NO 104
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t
```

<400> SEQUENCE: 104
tgacttcttc ccagaggtcs nngccggttt ggttccagta                          40

<210> SEQ ID NO 105
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 105
agctcccatt gacttcttcs nngaggtcaa agccggtttg                          40

<210> SEQ ID NO 106
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 106
agaatgagct cccattgacs nnttcccaga ggtcaaagcc                          40

<210> SEQ ID NO 107
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 107
taaagaatga gctcccatts nnttcttccc agaggtcaaa                          40

<210> SEQ ID NO 108
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 108
atgaataagc gcttcccgas nngccaagag tggcagcaag                          40

<210> SEQ ID NO 109
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)

<223> OTHER INFORMATION: n is a, c, g, or t

<400> SEQUENCE: 109
gagcaacaga tgaataagcs nntcccgact ggccaagagt                40

<210> SEQ ID NO 110
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 110
cgtatccacc agacgacacs nngaatcgtt ggagaaagca                40

<210> SEQ ID NO 111
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 111
ccttgccagt cctgccctcs nnggtgttga tgttggagtc                40

<210> SEQ ID NO 112
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 112
catccttgcc agtcctgccs nngttggtgt tgatgttgga                40

<210> SEQ ID NO 113
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 113
agttgacatc cttgccagts nngccctcgt tggtgttgat                40

<210> SEQ ID NO 114
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 114
tgcccttgtt cacgccgtas nnggagcgga aggagtcgac                    40

<210> SEQ ID NO 115
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 115
caggaatgcc cttgttcacs nngtagatgg agcggaagga                    40

<210> SEQ ID NO 116
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 116
cagcaccggc aggaatgccs nngttcacgc cgtagatgga                    40

<210> SEQ ID NO 117
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 117
agtacacatc ctctgcatas nngccaatgg cgacggcagc                    40

<210> SEQ ID NO 118
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 118
tgtagtacac atcctctgcs nnccggccaa tggcgacggc                    40

<210> SEQ ID NO 119
<211> LENGTH: 40
<212> TYPE: DNA
<213> ORGANISM: Artificial
<220> FEATURE:
<223> OTHER INFORMATION: synthetic primer

```
<220> FEATURE:
<221> NAME/KEY: misc_feature
<222> LOCATION: (21)..(22)
<223> OTHER INFORMATION: n is a, c, g, or t

<400> SEQUENCE: 119
ggttgccgtt gtagtacacs nnctctgcat accggccaat                    40

<210> SEQ ID NO 120
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 120
aagggttgcc gttgtagtas nnatcctctg cataccggcc                    40

<210> SEQ ID NO 121
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 121
accaagggtt gccgttgtas nncacatcct ctgcataccg                    40

<210> SEQ ID NO 122
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 122
gataccaagg gttgccgtts nngtacacat cctctgcata                    40

<210> SEQ ID NO 123
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 123
caagatacca agggttgccs nngtagtaca catcctctgc                    40

<210> SEQ ID NO 124
<211> LENGTH: 40
<212> TYPE: DNA
<213> ORGANISM: Artificial
```

```
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 124
cagcaaatgt agcaagatas nnagggttgc cgttgtagta                              40

<210> SEQ ID NO 125
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 125
ccgtgatgga gcccgtctts nnccagacgt agatggcatc                              40

<210> SEQ ID NO 126
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 126
tcaccgtgat ggagcccgts nncttccaga cgtagatggc                              40

<210> SEQ ID NO 127
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 127
cctggaagaa ggccagggas nnggcggtca ccgtgatgga                              40

<210> SEQ ID NO 128
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 128
tcacgccagg aacaagctcs nngaagaagg ccagggaggt                              40
```

```
<210> SEQ ID NO 129
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 129
tgctggagta ggtcccggcs nncacgccag gaacaagctc                              40

<210> SEQ ID NO 130
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 130
taaaggtcga agagctgcts nngtaggtcc cggccgtcac                              40

<210> SEQ ID NO 131
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 131
tggtaaaggt cgaagagcts nnggagtagg tcccggccgt                              40

<210> SEQ ID NO 132
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 132
tcgagacggc gttgatgats nnggtaaagg tcgaagagct                              40

<210> SEQ ID NO 133
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 133
gcgaaccgtc ggcggggacs nncttggcag cctcgctgag                              40
```

```
<210> SEQ ID NO 134
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 134
gctcggccag cgaaccgtcs nnggggacgt acttggcagc                              40

<210> SEQ ID NO 135
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 135
ggtcaaactg ctcggccags nnaccgtcgg cggggacgta                              40

<210> SEQ ID NO 136
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 136
acagcggagt gccgctgtts nngtcaaact gctcggccag                              40

<210> SEQ ID NO 137
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 137
cagacagcgg agtgccgcts nngcggtcaa actgctcggc                              40

<210> SEQ ID NO 138
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 138
ggtgaagcgc agacagcggs nngccgctgt tgcggtcaaa                              40
```

<210> SEQ ID NO 139
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 139
aggcgtacga ccacgtcags nnaagcgcag acagcggagt        40

<210> SEQ ID NO 140
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 140
tcaagaacga ggcgtacgas nncgtcaggt gaagcgcaga        40

<210> SEQ ID NO 141
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 141
aggggggcac gatgccagcs nnacgggccg tggctgtcaa        40

<210> SEQ ID NO 142
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 142
tggcccacga gggggcacs nngccagccc gacgggccgt        40

<210> SEQ ID NO 143
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 143
cggacgcgcc ggagcacgts nnggggatcg tgctagcgct        40

<210> SEQ ID NO 144
<211> LENGTH: 33
<212> TYPE: DNA
<213> ORGANISM: Artificial
<220> FEATURE:
<223> OTHER INFORMATION: synthetic primer

<400> SEQUENCE: 144
gcatctccca gcacacgaga cccggactac tat                33

<210> SEQ ID NO 145
<211> LENGTH: 33
<212> TYPE: DNA
<213> ORGANISM: Artificial
<220> FEATURE:
<223> OTHER INFORMATION: synthetic primer

<400> SEQUENCE: 145
gcatctccca gcacatacga cccggactac tat                33

<210> SEQ ID NO 146
<211> LENGTH: 33
<212> TYPE: DNA
<213> ORGANISM: Artificial
<220> FEATURE:
<223> OTHER INFORMATION: synthetic primer

<400> SEQUENCE: 146
gatgcgggcc tgcagctgcg catcgagcag tac                33

<210> SEQ ID NO 147
<211> LENGTH: 40
<212> TYPE: DNA
<213> ORGANISM: Artificial
<220> FEATURE:
<223> OTHER INFORMATION: synthetic primer

<400> SEQUENCE: 147
ctgaagcctt tcaccggcac ctggggtcga ccgcagcggg          40

<210> SEQ ID NO 148
<211> LENGTH: 39
<212> TYPE: DNA
<213> ORGANISM: Artificial
<220> FEATURE:
<223> OTHER INFORMATION: synthetic primer

<400> SEQUENCE: 148
tgaagccttt caccggctac tggggtcgac cgcagcggg           39

<210> SEQ ID NO 149
<211> LENGTH: 40
<212> TYPE: DNA
<213> ORGANISM: Artificial
<220> FEATURE:
<223> OTHER INFORMATION: synthetic primer

<400> SEQUENCE: 149
ctgaagcctt tcaccggcga ctggggtcga ccgcagcggg          40

<210> SEQ ID NO 150
<211> LENGTH: 36
<212> TYPE: DNA
<213> ORGANISM: Artificial
<220> FEATURE:
<223> OTHER INFORMATION: synthetic primer

```
<400> SEQUENCE: 150
agtggctcat caacaacgas tatcagtcga ctgtgt                         36

<210> SEQ ID NO 151
<211> LENGTH: 36
<212> TYPE: DNA
<213> ORGANISM: Artificial
<220> FEATURE:
<223> OTHER INFORMATION: synthetic primer

<400> SEQUENCE: 151
agtggctcat caacaacacc tatcagtcga ctgtgt                         36

<210> SEQ ID NO 152
<211> LENGTH: 34
<212> TYPE: DNA
<213> ORGANISM: Artificial
<220> FEATURE:
<223> OTHER INFORMATION: synthetic primer

<400> SEQUENCE: 152
gtggctcatc aacaatggta tcagtcgact gtgt                           34

<210> SEQ ID NO 153
<211> LENGTH: 36
<212> TYPE: DNA
<213> ORGANISM: Artificial
<220> FEATURE:
<223> OTHER INFORMATION: synthetic primer

<400> SEQUENCE: 153
agtggctcat caacaacctg tatcagtcga ctgtgt                         36

<210> SEQ ID NO 154
<211> LENGTH: 36
<212> TYPE: DNA
<213> ORGANISM: Artificial
<220> FEATURE:
<223> OTHER INFORMATION: synthetic primer

<400> SEQUENCE: 154
agtggctcat caacaactcc tatcagtcga ctgtgt                         36

<210> SEQ ID NO 155
<211> LENGTH: 38
<212> TYPE: DNA
<213> ORGANISM: Artificial
<220> FEATURE:
<223> OTHER INFORMATION: synthetic primer

<400> SEQUENCE: 155
ttgcccagta ctggaacgas accggctttg acctctgg                       38

<210> SEQ ID NO 156
<211> LENGTH: 38
<212> TYPE: DNA
<213> ORGANISM: Artificial
<220> FEATURE:
<223> OTHER INFORMATION: synthetic primer

<400> SEQUENCE: 156
ttgcccagta ctggaacstg accggctttg acctctgg                       38
```

```
<210> SEQ ID NO 157
<211> LENGTH: 38
<212> TYPE: DNA
<213> ORGANISM: Artificial
<220> FEATURE:
<223> OTHER INFORMATION: synthetic primer

<400> SEQUENCE: 157
ttgcccagta ctggaacacc accggctttg acctctgg                             38

<210> SEQ ID NO 158
<211> LENGTH: 38
<212> TYPE: DNA
<213> ORGANISM: Artificial
<220> FEATURE:
<223> OTHER INFORMATION: synthetic primer

<400> SEQUENCE: 158
ttgcccagta ctggaaccga accggctttg acctctgg                             38

<210> SEQ ID NO 159
<211> LENGTH: 38
<212> TYPE: DNA
<213> ORGANISM: Artificial
<220> FEATURE:
<223> OTHER INFORMATION: synthetic primer

<400> SEQUENCE: 159
ttgcccagta ctggaactgc accggctttg acctctgg                             38

<210> SEQ ID NO 160
<211> LENGTH: 6
<212> TYPE: PRT
<213> ORGANISM: Trichoderma reesei

<400> SEQUENCE: 160

Ser Val Asp Asp Phe Ile
1               5
```